(12) United States Patent
Luo et al.

(10) Patent No.: US 11,319,303 B2
(45) Date of Patent: *May 3, 2022

(54) COMPOUND USED AS AUTOPHAGY REGULATOR, AND PREPARATION METHOD THEREFOR AND USES THEREOF

(71) Applicant: WIGEN BIOMEDICINE TECHNOLOGY (SHANGHAI) CO., LTD., Shanghai (CN)

(72) Inventors: Cheng Luo, Shanghai (CN); Yuli Xie, Shanghai (CN); Bing Zhou, Shanghai (CN); Zhiyi Yao, Shanghai (CN); Liyan Yue, Shanghai (CN); Wei Wan, Shanghai (CN); Bidong Zhang, Shanghai (CN); Yuanyuan Zhang, Shanghai (CN); Hualiang Jiang, Shanghai (CN); Kaixian Chen, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/614,465

(22) PCT Filed: May 18, 2018

(86) PCT No.: PCT/CN2018/087446
§ 371 (c)(1),
(2) Date: Nov. 18, 2019

(87) PCT Pub. No.: WO2018/214812
PCT Pub. Date: Nov. 29, 2018

(65) Prior Publication Data
US 2020/0190066 A1 Jun. 18, 2020

(30) Foreign Application Priority Data

May 22, 2017 (CN) .......................... 201710364986.4

(51) Int. Cl.
| | | |
|---|---|---|
| C07D 295/088 | (2006.01) | |
| C07D 295/185 | (2006.01) | |
| C07D 209/12 | (2006.01) | |
| C07D 213/50 | (2006.01) | |
| C07D 333/22 | (2006.01) | |
| C07D 471/04 | (2006.01) | |
| C07D 473/00 | (2006.01) | |
| C07D 495/04 | (2006.01) | |
| C07C 49/563 | (2006.01) | |
| C07C 49/573 | (2006.01) | |
| C07D 405/12 | (2006.01) | |
| C07C 49/407 | (2006.01) | |
| C07D 213/89 | (2006.01) | |
| C07D 241/04 | (2006.01) | |
| C07D 265/30 | (2006.01) | |
| C07D 403/12 | (2006.01) | |

(Continued)

(52) U.S. Cl.
CPC .......... *C07D 405/12* (2013.01); *C07C 49/407* (2013.01); *C07C 49/563* (2013.01); *C07C 49/573* (2013.01); *C07D 209/12* (2013.01); *C07D 213/50* (2013.01); *C07D 213/89* (2013.01); *C07D 241/04* (2013.01); *C07D 265/30* (2013.01); *C07D 295/088* (2013.01); *C07D 295/185* (2013.01); *C07D 333/22* (2013.01); *C07D 403/12* (2013.01); *C07D 403/14* (2013.01); *C07D 409/12* (2013.01); *C07D 417/12* (2013.01); *C07D 471/04* (2013.01); *C07D 473/00* (2013.01); *C07D 487/04* (2013.01); *C07D 495/04* (2013.01); *C07D 519/00* (2013.01)

(58) Field of Classification Search
CPC . C07C 49/563; C07C 49/573; C07D 295/088; C07D 295/185
See application file for complete search history.

(56) References Cited

U.S. PATENT DOCUMENTS

2009/0163545 A1* 6/2009 Goldfarb ................ A61K 31/47
514/312

FOREIGN PATENT DOCUMENTS

| GB | 2449293 A | 11/2008 |
|---|---|---|
| WO | 2011017809 A1 | 2/2011 |

(Continued)

OTHER PUBLICATIONS

ChemBridge Product Guide (2 pages) retrieved from the Internet at http://www./.chembridge.com/screening libraries/ on Aug. 9, 2015. (Year: 2015).*

(Continued)

*Primary Examiner* — Emily A Bernhardt
(74) *Attorney, Agent, or Firm* — SZDC Law P.C.

(57) ABSTRACT

It is related to compounds used as autophagy modulators and a method for preparing and using the same, specifically providing a compound of general formula (I), or pharmaceutically acceptable salts thereof, which is a type of autophagy modulators, particularly mammalian ATG8 homologues modulators.

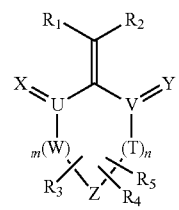

6 Claims, No Drawings
Specification includes a Sequence Listing.

(51) Int. Cl.
  *C07D 403/14* (2006.01)
  *C07D 409/12* (2006.01)
  *C07D 417/12* (2006.01)
  *C07D 487/04* (2006.01)
  *C07D 519/00* (2006.01)

(56) References Cited

FOREIGN PATENT DOCUMENTS

| | | |
|---|---|---|
| WO | 2011033389 A2 | 3/2011 |
| WO | 2017189553 A1 | 11/2017 |
| WO | 2018214813 A1 | 11/2018 |
| WO | 2018214814 A1 | 11/2018 |

OTHER PUBLICATIONS

Fukumoto et al. J.Med. Chem. 45, p. 3009-3021. (Year: 2002).*
Wolfbeis et al. Chemical Abstracts vol. 91:4692 (Abstract for Zeitschrift fuer Naturforschung, Teil B: Anorganische Chemie, Organische Chemie (1979), 34B(2), 283-9. (Year: 1979).*
Goldfarb et al. Chemical Abstract vol. 151, No. 92851 Abstract for US Pub 2009/0163545. (Year: 2009).*
Canela, M.D. et al., "Targeting the Colchicine Site in Tubulin through Cyclohexanedione Dervatives" RSC Advances, vol. 6, No. 23, Feb. 9, 2016.
Registry Database, "RN 441740-08-5" Enter STN: Aug. 1, 2002.
Maria-Dolores et al, "Targeting the colchicine site in tubulin through cyclohexanedione derivatives", RCS Advances, vol. 6, No. 23, Jan. 1, 2016, pp. 19492-19506.
Database Caplus [Online] Chemical Abstracts Services; Jan. 1, 1991, Kozlovskaya T.F. et al. "Reactions of 2-formyldimedone with some nitrogeneous nucleophiles", XP055772621, accession No. RN: 135655-32-2 Database accession No. 1991:535957, abstract.
Cook et al. "Chloroquine inhibits autophagy to potentiate antiestrogen responsiveness in ER + breast cancer", Clinical Cancer Research, vol. 20, No. 12, Jun. 12, 2014, pp. 3222-3232.
Maria-Dolores Canela et al. "Novel Colchicine-Site Binders with a Cyclohexanedione Scaffold Identified through a Ligand-Based Virtual Screening Approach" J. Med. Chem. 2014, 57, 3924-3938 (Apr. 28, 2014).

* cited by examiner

COMPOUND USED AS AUTOPHAGY REGULATOR, AND PREPARATION METHOD THEREFOR AND USES THEREOF

This application is the National Stage Application of PCT/CN2018/087446, filed on May 18, 2018, which claims priority to Chinese Patent Application No.: 201710364986.4, filed on May 22, 2017, which is incorporated by reference for all purposes as if fully set forth herein.

FIELD OF THE INVENTION

The present invention relates to bio-medicine technical field, specifically relating to a type of autophagy modulators, particularly relates to mammalian ATG8 homologues modulators and the use thereof.

BACKGROUND OF THE INVENTION

Autophagy is a cellular degradative pathway whereby dysfunctional proteins or organelles are transported to lysosome and then digested and degraded. It is a universal and conservative process amongst yeast, plants and mammals.

Current studies demonstrate that autophagy not only plays an important role in maintaining physiological functions, such as providing nutrients, eliminating cellular contents, and antigen presentation, but also has key functions in diseases such as cancer, infectious diseases and neurodegenerative disorders. During tumor development, autophagy functions as a double edged-sword: in the early stage of tumor development, autophagy defects may increase genomic instabilities and promote carcinogenesis; whereas when tumor is rapidly growing and metastasizes, autophagy helps tumor cells resist stress to inhibit anoikis and promote survival. Although precise roles of autophagy in tumor development are stage-dependent, the development of autophagy modulators will be of great value for advanced cancer and chemotherapy-resistant cancers, where tumor cells are under stress.

Currently, there are about 30 clinical trials involving autophagy modulation. For example, two autophagy inhibitors including hydroxychloroquine and chloroquine, which disrupt lysosomes, are tested in the clinical trial as single agents or in combination with other agents for the treatment of refractory or relapsed solid tumors. Relevant results can be retrieved on the clinicaltrial.gov website. However, because of the lack of defined molecular targets, side effects and challenges in guided chemical optimization may severely limit further development of these antilysosomal agents.

Small molecules modulators targeting autophagy are primarily mTOR or lysosome modulators at present. Small molecules modulators of autophagy related proteins, such as the enzymes ATG4 and ULK1, are still at an early development stage. Chemical modulators for the most key autophagy related proteins, ATG8 and its mammalian homologous families including LC3, GABARAP and GATE-16 subfamilies, still have not been reported. In human The LC3 family has three members including LC3A, LC3B and LC3C; the GABARAP family comprises GABARAP and GABARAPL1; and the GATE-16 family includes GABARAPL2. LC3B is undoubtedly the most thoroughly investigated among the ATG8 mammalian homologous proteins. LC3B often serves as a biomarker of autophagy. There has been no reports on modulators of LC3B at present. Therefore, there is an urgent need for developing LC3B modulators for treating autophagy related deceases.

SUMMARY OF THE INVENTION

The present invention provides a compound of general formula (I), or pharmaceutically acceptable salts thereof:

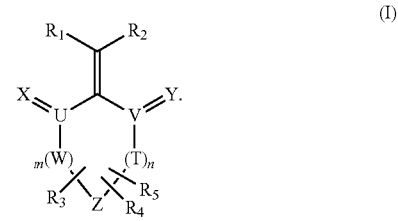

Wherein:
X and Y are each independently selected from the group consisting of O, S, $NR_a$, NOH, and $CH_2$;
U and V are each independently selected from the group consisting of C, S, SO, and $POR_a$;
W, Z, and T are each independently selected from the group consisting of O, S, SO, $SO_2$, N, $NR_a$, CO, C, $CR_a$, and $CH_2$;
m is 0, 1, 2, or 3, preferably 0 or 1;
n is 0, 1, 2, or 3, preferably 0 or 1;
$R_1$ is selected from the group consisting of H, deuterium, C1-6 alkyl, C1-6 hydroxyalkyl, C1-6 haloalkyl, substituted or unsubstituted phenyl;
$R_2$ is expressed as -J-K-M-Q, wherein:
J is $NR_a$, $NOR_a$, O, S or

wherein:

ring is a divalent 3-10 membered heterocycloalkyl group containing at least one nitrogen atom or a divalent 3-7 membered heterocycloalkenyl group containing at least one nitrogen atom;
K is a covalent bond, $NR_a$, $CR_cR_{c'}$ or $CR_cR_{c'}CR_cR_{c'}$;
M is a covalent bond, $CR_cR_{c'}$, a divalent 3-10 membered heterocycloalkyl group, a divalent 3-7 membered heterocycloalkenyl, or a divalent 5-10 membered heteroaryl group,
Q is H, C1-6 alkyl, C1-6 hydroxyalkyl, —$(CH_2)_p$—C(O)$R_b$, —$(CH_2)_p$—C(O)$NHR_b$, —$(CH_2)_p$—C(S)$R_b$, —$(CH_2)_p$—C(S)$NHR_b$, —$(CH_2)_p$—$SO_2R_b$, —$(CH_2)_p$—$SO_2NHR_b$;
p is 0, 1, 2 or 3, preferably 0 or 1;
$R_c$ and $R_c'$ are each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 heteroalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; preferably selected from the group consisting of H, hydroxyl, amino group, NRaRa', halogen, carboxyl, formyl, amide group, ester group, C1-6 haloalkyl, C1-6 hydroxyalkyl, C1-6 heteroalkyl, C1-6 alkoxyl, C3-10 cycloalkyl, 3-10 membered heterocycloalkyl, substituted or unsubstituted phenyl or pyridyl;

$R_3$, $R_4$, and $R_5$ are each independently selected from the group consisting of H, hydroxyl, amino group, halogen, cyano, nitro, carboxyl, formyl, amide group, —NH—$COR_b$, ester group, C1-6 alkyl, C1-6 haloalkyl, C1-6 hydroxyalkyl, C1-6 heteroalkyl, C1-6 alkoxy, C1-6 alkoxyalkyl, C2-6 alkenyl, C2-6 alkynyl, unsubstituted or substituted —CONH—(C6-10 aryl), unsubstituted or substituted —CH═CH—(C6-10 aryl), unsubstituted or substituted C6-10 aryl, unsubstituted or substituted 5-10 membered heteroaryl, unsubstituted or substituted C3-10 cycloalkyl, unsubstituted or substituted 3-10 membered heterocycloalkyl, unsubstituted or substituted 3-7 membered heterocycloalkenyl, unsubstituted or substituted C6-10 aryl C1-6 alkyl, unsubstituted or substituted C1-6 alkyl C6-10 aryl, unsubstituted or substituted 5-10 membered heteroaryl C1-6 alkyl, and unsubstituted or substituted C1-6 alkyl 5-10 membered heteroaryl;

or two adjacent groups in $R_3$, $R_4$ and $R_5$ may be bonded to form an unsubstituted or substituted C6-10 aryl group, an unsubstituted or substituted 5-10 membered heteroaryl group, an unsubstituted or substituted C3-10 cycloalkyl group, or an unsubstituted or substituted 3-10 membered heterocycloalkyl group;

wherein each $R_b$ is independently C1-6 alkyl, C2-6 alkenyl, $NHR_a$, $NR_aR_a'$, unsubstituted or substituted phenyl or 3-7 membered heterocyclic group;

$R_a$ and $R_a'$ are each independently H or C1-6 alkyl;

unsubstituted or substituted means that the group is unsubstituted or substituted by one or more substituents selected from the group consisting of hydroxyl, amino group, cyano, nitro, carboxyl, halogen, C1-6 alkyl, C1-6 haloalkyl or C1-6 hydroxyalkyl, or two adjacent substituents may be bonded to form a C6-10 aryl group, a C5-10 heteroaryl group, a C3-10 cycloalkyl group or a C3-10 heterocycloalkyl group;

and meets the following conditions:
(1) when W, Z or T is substituted by one group of $R_3$, $R_4$ and $R_5$, the W, Z or T is N or CH;
(2) when W, Z or T is substituted by one group of $R_3$, $R_4$ and $R_5$ and this group is bonded to another adjacent group of $R_3$, $R_4$ and $R_5$ to form an unsubstituted or substituted C6-10 aryl or unsubstituted or substituted 5-10 membered heteroaryl, the W, Z or T is C; for example, when W is substituted by $R_3$ and $R_3$ is bonded to the adjacent $R_4$ group to form an unsubstituted or substituted C6-10 aryl or unsubstituted or substituted 5-10 membered heteroaryl, the W is C;
(3) when W, Z or T is substituted by two of $R_3$, $R_4$ and $R_5$, the W, Z or T is C.

Preferably, in the general formula (I):
X and Y are each independently selected from the group consisting of O, S or NH;
U and V are each independently selected from the group consisting of C or S;
W, Z, and T are each independently selected from the group consisting of O, N, $NR_a$, CO, C, $CR_a$, and $CH_2$;
m is 0, 1 or 2;
n is 0, 1 or 2;
$R_1$ is selected from H and deuterium;

$R_2$ is expressed as -J-K-M-Q, wherein:
J is $NR_a$, $NOR_a$, O, S or

wherein:

is a divalent 3-10 membered heterocycloalkyl group containing at least one nitrogen atom or a divalent 3-7 membered heterocycloalkenyl group containing at least one nitrogen atom;

K is a covalent bond, $NR_a$, $CR_cR_c'$, or $CR_cR_c'CR_cR_c'$;

M is a covalent bond, $CR_cR_c'$, a divalent 3-10 membered heterocycloalkyl group, a divalent 3-7 membered heterocycloalkenyl, or a divalent 5-10 membered heteroaryl group, Q is H, C1-6 alkyl, C1-6 hydroxyalkyl, —$(CH_2)_p$—C(O)$R_b$, —$(CH_2)_p$—C(O)$NHR_b$, —$(CH_2)_p$—C(S)$R_b$, —$(CH_2)_p$—C(S)$NHR_b$, —$(CH_2)_p$—$SO_2R_b$, —$(CH_2)_p$—$SO_2NHR_b$; wherein p is 0, 1, 2 or 3, preferably 0 or 1;

$R_c$ and $R_c'$ are each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 heteroalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; preferably selected from the group consisting of H, hydroxyl, amino group, NRaRa', halogen, carboxyl, formyl, amide group, ester group, C1-6 haloalkyl, C1-6 hydroxyalkyl, C1-6 heteroalkyl, C1-6 alkoxyl, C3-10 cycloalkyl, 3-10 membered heterocycloalkyl, substituted or unsubstituted phenyl or pyridyl;

$R_3$, $R_4$, and $R_5$ are each independently selected from the group consisting of H, hydroxyl, amino group, halogen, cyano, nitro, carboxyl, formyl, amide group, —NH—$COR_b$, ester group, C1-6 alkyl, C1-6 haloalkyl, C1-6 hydroxyalkyl, C1-6 heteroalkyl, C1-6 alkoxy, C1-6 alkoxyalkyl, C2-6 alkenyl, C2-6 alkynyl, unsubstituted or substituted —CONH—(C6-10 aryl), unsubstituted or substituted —CH═CH—(C6-10 aryl), unsubstituted or substituted C6-10 aryl, unsubstituted or substituted 5-10 membered heteroaryl, unsubstituted or substituted C3-10 cycloalkyl, unsubstituted or substituted 3-10 membered heterocycloalkyl, unsubstituted or substituted 3-7 membered heterocycloalkenyl, unsubstituted or substituted C6-10 aryl C1-6 alkyl, unsubstituted or substituted C1-6 alkyl C6-10 aryl, unsubstituted or substituted 5-10 membered heteroaryl C1-6 alkyl, or unsubstituted or substituted C1-6 alkyl 5-10 membered heteroaryl;

or two adjacent groups in $R_3$, $R_4$ and $R_5$ may be bonded to form an unsubstituted or substituted C6-10 aryl group, an unsubstituted or substituted 5-10 membered heteroaryl group, an unsubstituted or substituted C3-10 cycloalkyl group, or an unsubstituted or substituted 3-10 membered heterocycloalkyl group;

wherein each $R_b$ is independently C1-6 alkyl, C2-6 alkenyl, $NHR_a$, $NR_aR_a'$, unsubstituted or substituted phenyl or 3-7 membered heterocyclic group;

$R_a$ and $R_a'$ are each independently H or C1-6 alkyl;

unsubstituted or substituted means that the group is unsubstituted or substituted by one or more substituents selected from the group consisting of hydroxyl, amino group, cyano, nitro, carboxyl, halogen, C1-6 alkyl, C1-6 haloalkyl and C1-6 hydroxyalkyl, or two adjacent substituents may be bonded to form a C6-10 aryl group, a 5-10 membered heteroaryl group, a C3-10 cycloalkyl group or a 3-10 membered heterocycloalkyl group;

and meets the following conditions:

(1) when W, Z or T is substituted by one group of $R_3$, $R_4$ and $R_5$, the W, Z or T is N or CH;

(2) when W, Z or T is substituted by one group of $R_3$, $R_4$ and $R_5$ and this group is bonded to another adjacent group of $R_3$, $R_4$ and $R_5$ to form an unsubstituted or substituted C6-10 aryl or unsubstituted or substituted 5-10 membered heteroaryl, the W, Z or T is C;

(3) when W, Z or T is substituted by two of $R_3$, $R_4$ and $R_5$, the W, Z or T is C.

In one embodiment of the invention, in the general formula (I), $R_2$ is selected from the group consisting of:

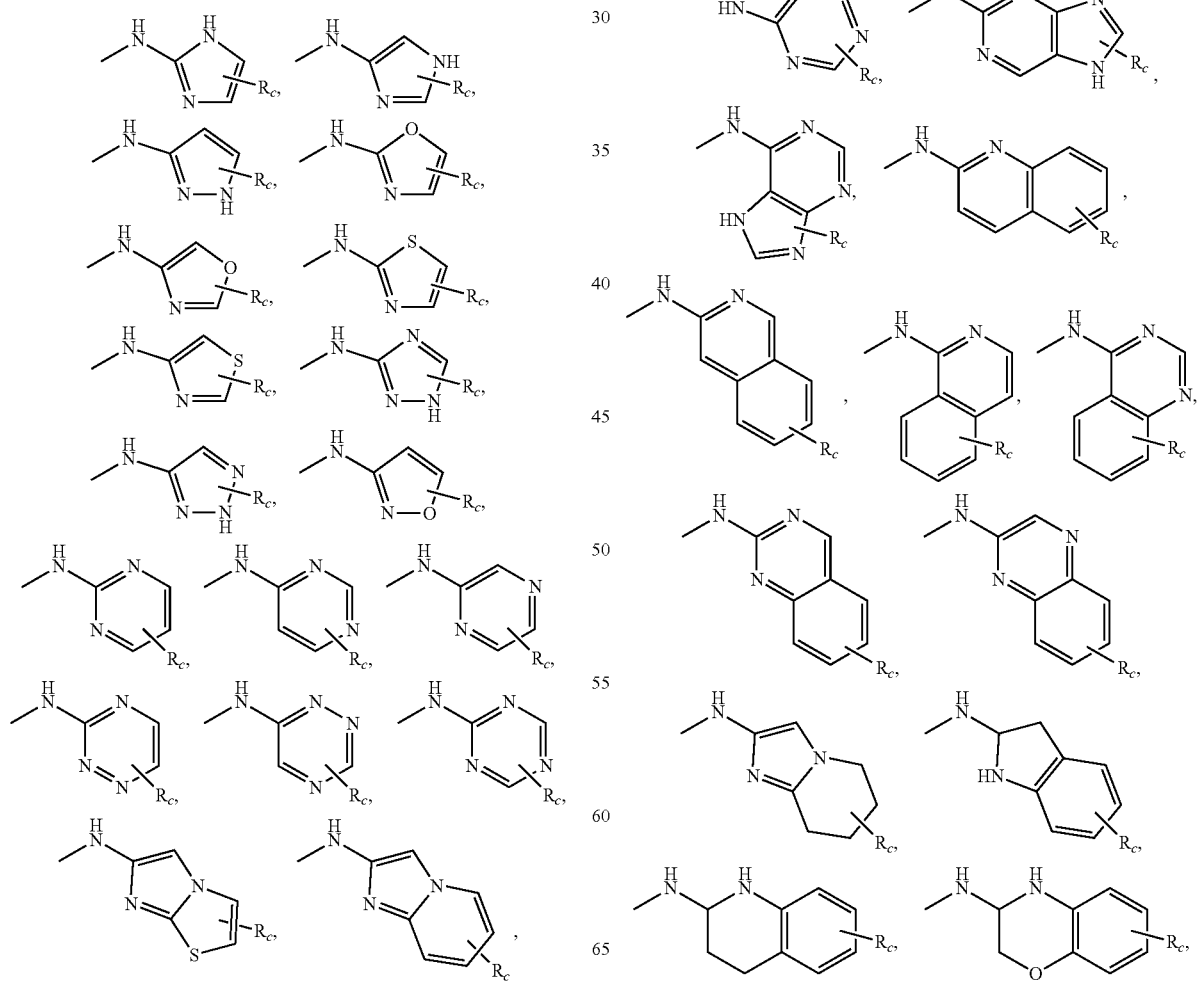
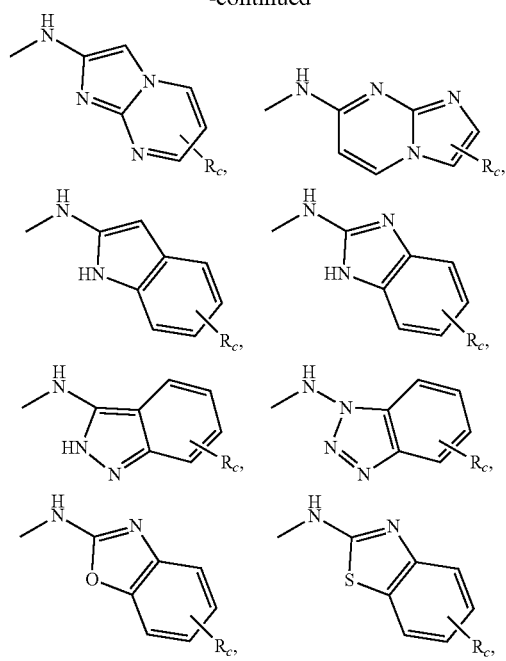
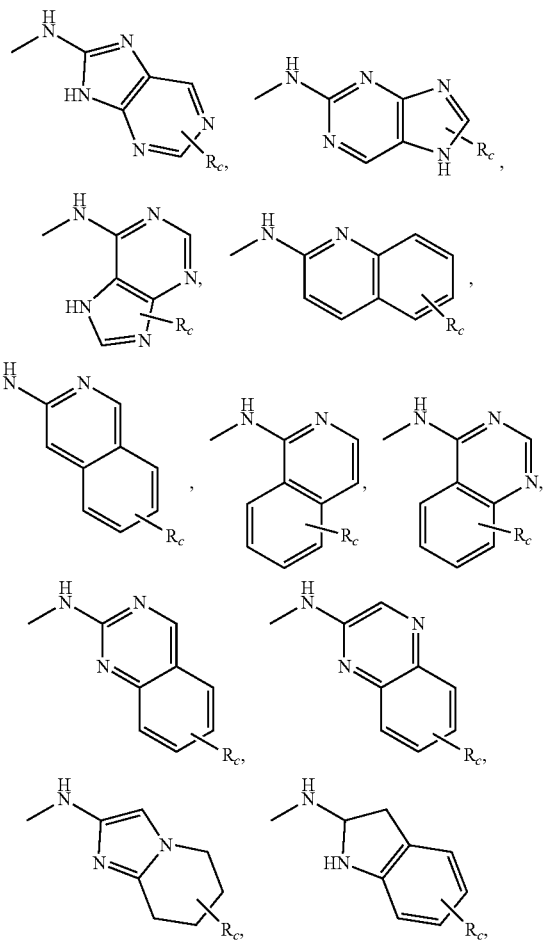
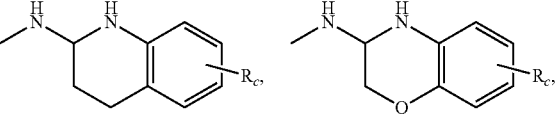

-continued

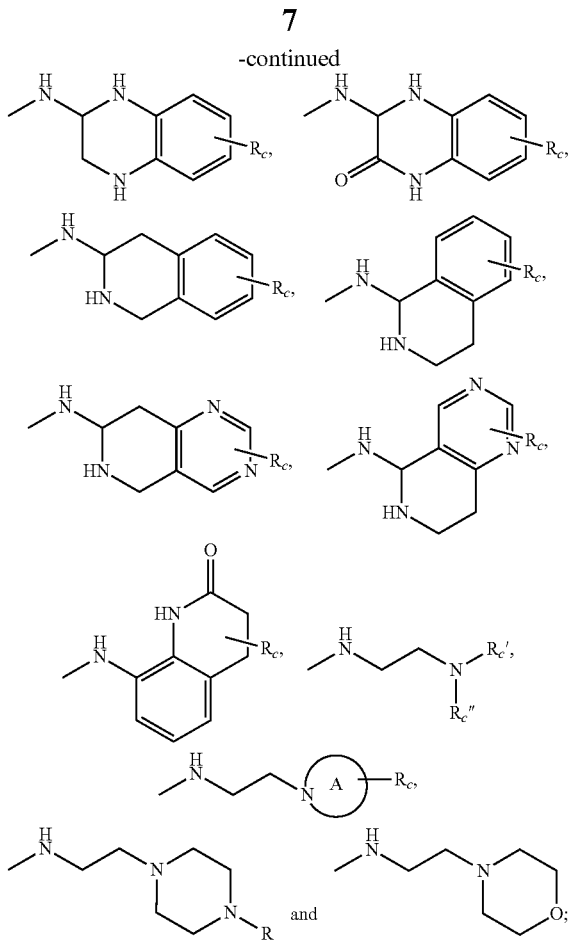

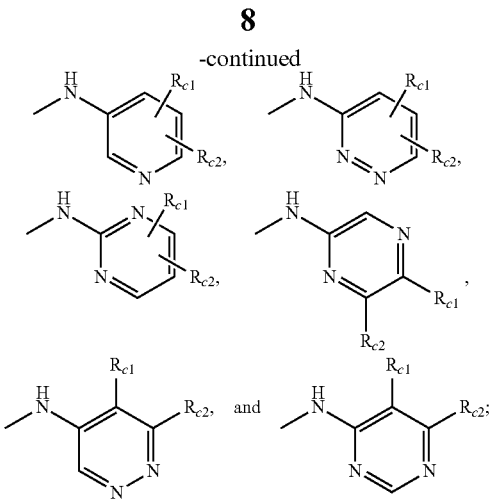

Wherein, A is a divalent 3-10 membered nitro-containing heterocycloalkyl or a divalent 3-7 membered nitro-containing heterocycloalkenyl;

$R_c$, $R_c'$ and $R_c''$ are each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 heteroalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl and C1-6 alkyl 5-10 membered heteroaryl; preferably selected from the group consisting of H, hydroxyl, amino group, NRaRa', halogen, carboxyl, formyl, amide group, ester group, C1-6 haloalkyl, C1-6 hydroxyalkyl, C1-6 heteroalkyl, C1-6 alkoxyl, C3-10 cycloalkyl, 3-10 membered heterocycloalkyl, substituted or unsubstituted phenyl or pyridyl;

$R_a$ and $R_a'$ are each independently H or C1-6 alkyl.

In another embodiment of the invention, in the general formula (I), $R_2$ is selected from the group consisting of:

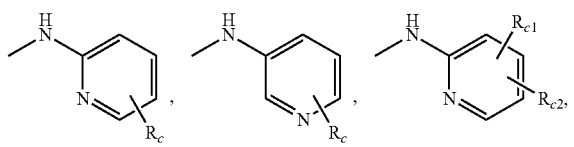

Wherein, $R_c$ is selected from the group consisting of H, hydroxyl, amino group, cyano, nitro, carboxyl, halogen, C1-6 alkyl, C1-6 haloalkyl, or C1-6 hydroxyalkyl;

$R_{c1}$ and $R_{c2}$ are each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 heteroalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; preferably selected from the group consisting of H, hydroxyl, amino group, NRaRa', halogen, carboxyl, formyl, amide group, ester group, C1-6 haloalkyl, C1-6 hydroxyalkyl, C1-6 heteroalkyl, C1-6 alkoxyl, C3-10 cycloalkyl, 3-10 membered heterocycloalkyl, substituted or unsubstituted phenyl or pyridyl;

or $R_{c1}$ and $R_{c2}$ may be bonded to form C6-10 aryl, 5-10 membered heteroaryl, C3-10 cycloalkyl, 3-10 membered heterocycloalkyl;

$R_a$ and $R_a'$ are each independently H or C1-6 alkyl.

In another embodiment of the invention, the compounds of general formula (I) are selected from the compounds expressed by the following general formula (Ia) or (Ib):

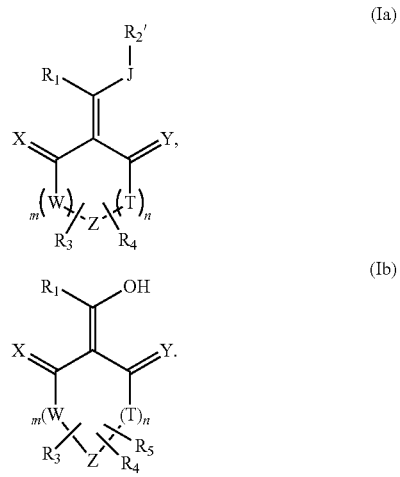

Wherein:
X and Y are each independently selected from the group consisting of O, S, or NH;

W, Z, and T are each independently selected from the group consisting of O, N, $NR_a$, CO, C, $CR_a$, or $CH_2$;

m is 0, 1, or 2;

n is 0, 1, or 2;

$R_1$ is selected from H and deuterium;

J is $NR_a$, $NOR_a$, O, S or

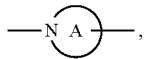

wherein:

is a divalent 3-10 membered heterocycloalkyl group containing at least one nitrogen atom or a divalent 3-7 membered heterocycloalkenyl group containing at least one nitrogen atom;

$R_2'$ is selected from the group consisting of H, C1-6 alkyl, C1-6 haloalkyl, C1-6 alkoxy, C1-6 alkylamine, C6-10 aryl or 5-10 membered heteroaryl, C3-10 cycloalkyl, 3-10 membered heterocycloalkyl, —$(CH_2)_m$-M-Q;

wherein M is a covalent bond, a divalent 3-10 membered heterocycloalkyl group, a divalent 3-7 membered heterocycloalkenyl, or a divalent 5-10 membered heteroaryl group;

Q is H, C1-6 alkyl, C1-6 hydroxyalkyl, —$(CH_2)_p$—C(O)$R_b$, —$(CH_2)_p$—C(O)$NHR_b$, —$(CH_2)_p$—C(S)$R_b$, —$(CH_2)_p$—C(S)$NHR_b$, —$(CH_2)_p$—$SO_2R_b$, —$(CH_2)_p$—$SO_2NHR_b$;

p is 0, 1, 2 or 3, preferably 0 or 1;

$R_3$, $R_4$, and $R_5$ are each independently selected from the group consisting of H, hydroxyl, amino group, halogen, cyano, nitro, carboxyl, formyl, amide group, NH—$COR_b$, ester group, C1-6 alkyl, C1-6 haloalkyl, C1-6 hydroxyalkyl, C1-6 heteroalkyl, C1-6 alkoxy, C1-6 alkoxyalkyl, C2-6 alkenyl, C2-6 alkynyl, unsubstituted or substituted —CONH—(C6-10 aryl), unsubstituted or substituted —CH=CH—(C6-10 aryl), unsubstituted or substituted C6-10 aryl, unsubstituted or substituted 5-10 membered heteroaryl, unsubstituted or substituted C3-10 cycloalkyl, unsubstituted or substituted 3-10 membered heterocycloalkyl, unsubstituted or substituted 3-7 membered heterocycloalkenyl, unsubstituted or substituted C6-10 aryl C1-6 alkyl, unsubstituted or substituted C1-6 alkyl C6-10 aryl, unsubstituted or substituted 5-10 membered heteroaryl C1-6 alkyl, or unsubstituted or substituted C1-6 alkyl 5-10 membered heteroaryl;

or two adjacent groups in $R_3$, $R_4$ and $R_5$ may be bonded to form an unsubstituted or substituted C6-10 aryl group, an unsubstituted or substituted 5-10 membered heteroaryl group, an unsubstituted or substituted C3-10 cycloalkyl group, or an unsubstituted or substituted 3-10 membered heterocycloalkyl group;

wherein each $R_b$ is independently C1-6 alkyl, C2-6 alkenyl, $NHR_a$, $NR_aR_a'$, unsubstituted or substituted phenyl or 3-7 membered heterocyclic group;

$R_a$ and $R_a'$ are each independently H or C1-6 alkyl;

unsubstituted or substituted means that the group is unsubstituted or substituted by one or more substituents selected from the group consisting of hydroxyl, amino group, cyano, nitro, carboxyl, halogen, C1-6 alkyl, C1-6 haloalkyl and C1-6 hydroxyalkyl, or two adjacent substituents may be bonded to form a C6-10 aryl group, a 5-10 membered heteroaryl group, a C3-10 cycloalkyl group or a 3-10 membered heterocycloalkyl group;

and meets the following conditions:

(1) when W, Z or T is substituted by one group of $R_3$, $R_4$ and $R_5$, the W, Z or T is N or CH;

(2) when W, Z or T is substituted by one group of $R_3$, $R_4$ and $R_5$ and this group is bonded to another adjacent group of $R_3$, $R_4$ and $R_5$ to form an unsubstituted or substituted C6-10 aryl or unsubstituted or substituted 5-10 membered heteroaryl, the W, Z or T is C;

(3) when W, Z or T is substituted by two of $R_3$, $R_4$ and $R_5$, the W, Z or T is C.

In another embodiment of the invention, the compounds of general formula (I) are selected from the compounds expressed by the following general formula (IIa), (IIb), (IIc) and (IId):

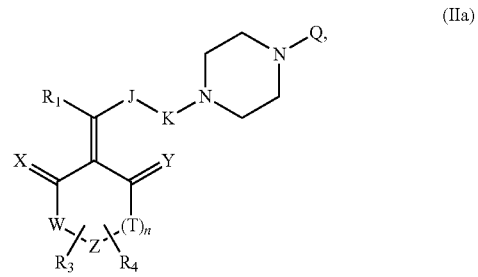

(IIa)

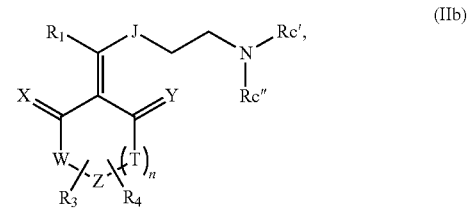

(IIb)

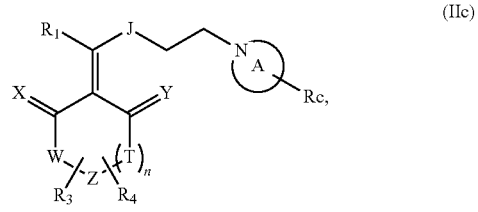

(IIc)

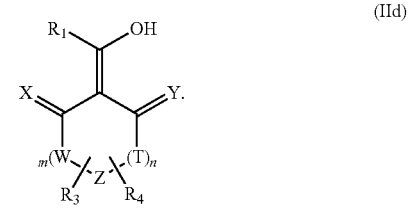

(IId)

Wherein,

X and Y are independently O, S or NH;

W, Z, and T are each independently selected from the group consisting of O, N, $NR_a$, CO, C, $CR_a$, or $CH_2$;

n is 0, 1, 2, or 3;

$R_1$ is selected from H and deuterium;

is a divalent 3-10 membered nitrogen-containing heterocycloalkyl group or a divalent 3-7 membered nitrogen-containing heterocycloalkenyl group;

J is selected from NR$_a$, NOR$_a$, O and S;

K is a covalent bond, NR$_a$, CR$_c$R$_c'$ or CR$_c$R$_c'$CR$_c$R$_c'$;

Q is H, C1-6 alkyl, C1-6 hydroxyalkyl, —(CH$_2$)$_p$—C(O)R$_b$, —(CH$_2$)$_p$—C(O)NHR$_b$, —(CH$_2$)$_p$—C(S)R$_b$, —(CH$_2$)$_p$—C(S)NHR$_b$, —(CH$_2$)$_p$—SO$_2$R$_b$, —(CH$_2$)$_p$—SO$_2$NHR$_b$;

p is 0, 1, 2 or 3, preferably 0 or 1;

R$_c$, R$_c'$ and R$_c''$ are each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 heteroalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; preferably selected from the group consisting of H, hydroxyl, amino group, NRaRa', halogen, carboxyl, formyl, amide group, ester group, C1-6 haloalkyl, C1-6 hydroxyalkyl, C1-6 heteroalkyl, C1-6 alkoxyl, C3-10 cycloalkyl, 3-10 membered heterocycloalkyl, substituted or unsubstituted phenyl or pyridyl;

R$_3$ and R$_4$ are each independently selected from the group consisting of H, hydroxyl, amino group, halogen, cyano, nitro, carboxyl, formyl, amide group, NH—COR$_b$, ester group, C1-6 alkyl, C1-6 haloalkyl, C1-6 hydroxyalkyl, C1-6 heteroalkyl, C1-6 alkoxy, C1-6 alkoxyalkyl, C2-6 alkenyl, C2-6 alkynyl, unsubstituted or substituted —CONH—(C6-10 aryl), unsubstituted or substituted —CH═CH—(C6-10 aryl), unsubstituted or substituted C6-10 aryl, unsubstituted or substituted 5-10 membered heteroaryl, unsubstituted or substituted C3-10 cycloalkyl, unsubstituted or substituted 3-10 membered heterocycloalkyl, unsubstituted or substituted 3-7 membered heterocycloalkenyl, unsubstituted or substituted C6-10 aryl C1-6 alkyl, unsubstituted or substituted C1-6 alkyl C6-10 aryl, unsubstituted or substituted 5-10 membered heteroaryl C1-6 alkyl, or unsubstituted or substituted C1-6 alkyl 5-10 membered heteroaryl;

or R$_3$ and R$_4$ may be bonded to form an unsubstituted or substituted C6-10 aryl group, an unsubstituted or substituted 5-10 membered heteroaryl group, an unsubstituted or substituted C3-10 membered cycloalkyl group, or an unsubstituted or substituted 3-10 membered heterocycloalkyl group;

wherein each R$_b$ is independently C1-6 alkyl, C2-6 alkenyl, NHR$_a$, NR$_a$R$_a'$, unsubstituted or substituted phenyl or 3-7 membered heterocyclic group;

R$_a$ and R$_a'$ are each independently H or C1-6 alkyl;

unsubstituted or substituted means that the group is unsubstituted or substituted by one or more substituents selected from the group consisting of hydroxyl, amino group, cyano, nitro, carboxyl, halogen, C1-6 alkyl, C1-6 haloalkyl and C1-6 hydroxyalkyl, or two adjacent substituents may be bonded to form a C6-10 aryl group, a 5-10 membered heteroaryl group, a C3-10 cycloalkyl group or a 3-10 membered heterocycloalkyl group;

and meets the following conditions:

(1) when W, Z or T is substituted by one group of R$_3$ and R$_4$, the W, Z or T is N or CH;

(2) when W, Z or T is substituted by one group of R$_3$ and R$_4$ and R$_3$ and R$_4$ are bonded to form C6-10 aryl or 5-10 membered heteroaryl, the W, Z or T is C;

(3) when W, Z or T is substituted by both of R$_3$ and R$_4$, the W, Z or T is C.

In another embodiment of the invention, the compounds of general formula (I) are selected from the compounds expressed by the following general formula (IIIa), (IIIb), (IIIc) and (IIId):

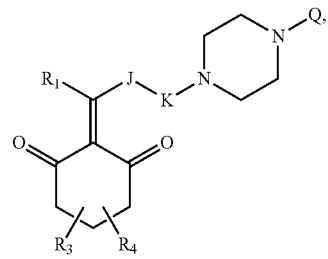

(IIIa)

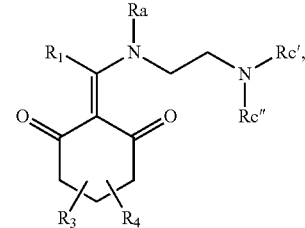

(IIIb)

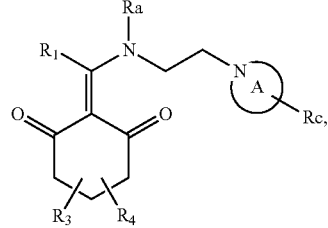

(IIIc)

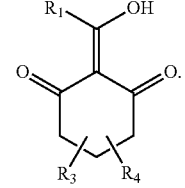

(IIId)

Wherein,

R$_1$ is selected from H, deuterium, C1-6 alkyl, C1-6 hydroxyalkyl, C1-6 haloalkyl, unsubstituted or substituted phenyl; preferably selected from H and deuterium; preferably is H;

J is NR$_a$, NOR$_a$, O or S;

K is a covalent bond, NR$_a$, CR$_c$R$_c'$, or CR$_c$R$_c'$CR$_c$R$_c'$;

is a divalent 3-10 membered nitrogen-containing heterocycloalkyl group or a divalent 3-7 membered nitrogen-containing heterocycloalkenyl group;

Q is H, C1-6 alkyl, C1-6 hydroxyalkyl, —(CH$_2$)$_p$—C(O)R$_b$, —(CH$_2$)$_p$—C(O)NHR$_b$, —(CH$_2$)$_p$—C(S)R$_b$, —(CH$_2$)$_p$—C(S)NHR$_b$, —(CH$_2$)$_p$—SO$_2$R$_b$, —(CH$_2$)$_p$—SO$_2$NHR$_b$;

p is 0, 1, 2 or 3, preferably 0 or 1;

R$_c$, R$_c'$ and R$_c''$ are each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 heteroalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; preferably selected from the group consisting of H, hydroxyl, amino group, NRaRa', halogen, carboxyl, formyl, amide group, ester group, C1-6 haloalkyl, C1-6 hydroxyalkyl, C1-6 heteroalkyl, C1-6 alkoxyl, C3-10 cycloalkyl, 3-10 membered heterocycloalkyl, substituted or unsubstituted phenyl or pyridyl;

$R_3$ and $R_4$ are each independently selected from the group consisting of H, hydroxyl, amino group, halogen, cyano, nitro, carboxyl, formyl, amide group, NH—$COR_b$, ester group, C1-6 alkyl, C1-6 haloalkyl, C1-6 hydroxyalkyl, C1-6 heteroalkyl, C1-6 alkoxy, C1-6 alkoxyalkyl, C2-6 alkenyl, C2-6 alkynyl, unsubstituted or substituted —CONH—(C6-10 aryl), unsubstituted or substituted —CH=CH—(C6-10 aryl), unsubstituted or substituted C6-10 aryl, unsubstituted or substituted 5-10 membered heteroaryl, unsubstituted or substituted C3-10 cycloalkyl, unsubstituted or substituted 3-10 membered heterocycloalkyl, unsubstituted or substituted 3-7 membered heterocycloalkenyl, unsubstituted or substituted C6-10 aryl C1-6 alkyl, unsubstituted or substituted C1-6 alkyl C6-10 aryl, unsubstituted or substituted 5-10 membered heteroaryl C1-6 alkyl, or unsubstituted or substituted C1-6 alkyl 5-10 membered heteroaryl;

or $R_3$ and $R_4$ may be bonded to form an unsubstituted or substituted C6-10 aryl group, an unsubstituted or substituted 5-10 membered heteroaryl group, an unsubstituted or substituted C3-10 membered cycloalkyl group, or an unsubstituted or substituted 3-10 membered heterocycloalkyl group;

wherein each $R_b$ is independently C1-6 alkyl, C2-6 alkenyl, $NHR_a$, $NR_aR_a'$, unsubstituted or substituted phenyl or 3-7 membered heterocyclic group;

$R_a$ and $R_a'$ are each independently H or C1-6 alkyl;

unsubstituted or substituted means that the group is unsubstituted or substituted by one or more substituents selected from the group consisting of hydroxyl, amino group, cyano, nitro, carboxyl, halogen, C1-6 alkyl, C1-6 haloalkyl and C1-6 hydroxyalkyl, or two adjacent substituents may be bonded to form a C6-10 aryl group, a 5-10 membered heteroaryl group, a C3-10 cycloalkyl group or a 3-10 membered heterocycloalkyl group.

In another embodiment of the invention, the compounds of general formula (I) are selected from the compounds expressed by the following general formula (IVa), (IVb), (IVc) and (IVd):

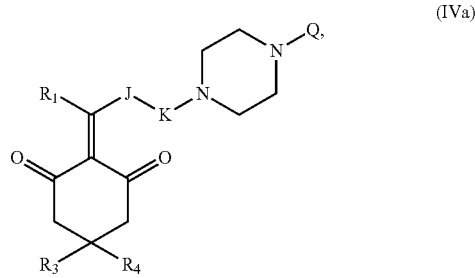
(IVa)

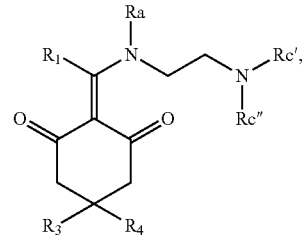
(IVb)

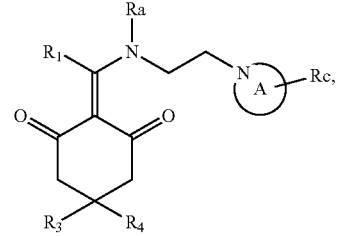
(IVc)

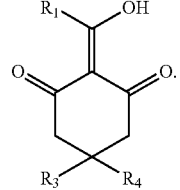
(IVd)

Wherein, $R_1$ is selected from H, deuterium, C1-6 alkyl, C1-6 hydroxyalkyl, C1-6 haloalkyl, unsubstituted or substituted phenyl; preferably selected from H and deuterium; preferably is H;

J is $NR_a$, $NOR_a$, O or S;

K is a covalent bond, $NR_a$, $CR_cR_c$, or $CR_cR_c CR_cR_c$;

is a divalent 3-10 membered nitrogen-containing heterocycloalkyl group or a divalent 3-7 membered nitrogen-containing heterocycloalkenyl group;

Q is H, C1-6 alkyl, C1-6 hydroxyalkyl, —$(CH_2)_p$—$C(O)R_b$, —$(CH_2)_p$—$C(O)NHR_b$, —$(CH_2)_p$—$C(S)R_b$, —$(CH_2)_p$—$C(S)NHR_b$, —$(CH_2)_p$—$SO_2R_b$, —$(CH_2)_p$—$SO_2NHR_b$;

p is 0, 1, 2 or 3, preferably 0 or 1;

$R_c$, $R_c'$ and $R_c''$ are each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 heteroalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; preferably selected from the group consisting of H, hydroxyl, amino group, NRaRa', halogen, carboxyl, formyl, amide group, ester group, C1-6 haloalkyl, C1-6 hydroxyalkyl, C1-6 heteroalkyl, C1-6 alkoxyl, C3-10 cycloalkyl, 3-10 membered heterocycloalkyl, substituted or unsubstituted phenyl or pyridyl;

R₃ is selected from the group consisting of H, hydroxyl, amino group, halogen, cyano, nitro, carboxyl, formyl, amide group, NH—COR$_b$, ester group, C1-6 alkyl, C1-6 haloalkyl, C1-6 hydroxyalkyl, C1-6 heteroalkyl, C1-6 alkoxy, C1-6 alkoxyalkyl, C2-6 alkenyl, C2-6 alkynyl, unsubstituted or substituted —CONH—(C6-10 aryl), unsubstituted or substituted —CH═CH—(C6-10 aryl), unsubstituted or substituted C6-10 aryl, unsubstituted or substituted 5-10 membered heteroaryl, unsubstituted or substituted C3-10 cycloalkyl, unsubstituted or substituted 3-10 membered heterocycloalkyl, unsubstituted or substituted 3-7 membered heterocycloalkenyl, unsubstituted or substituted C6-10 aryl C1-6 alkyl, unsubstituted or substituted C1-6 alkyl C6-10 aryl, unsubstituted or substituted 5-10 membered heteroaryl C1-6 alkyl, or unsubstituted or substituted C1-6 alkyl 5-10 membered heteroaryl;

wherein each R$_b$ is independently C1-6 alkyl, C2-6 alkenyl, NHR$_a$, NR$_a$R$_a$', unsubstituted or substituted phenyl or 3-7 membered heterocyclic group;

R$_a$ and R$_a$' are each independently H or C1-6 alkyl;

unsubstituted or substituted means that the group is unsubstituted or substituted by one or more substituents selected from the group consisting of hydroxyl, amino group, cyano, nitro, carboxyl, halogen, C1-6 alkyl, C1-6 haloalkyl and C1-6 hydroxyalkyl, or two adjacent substituents may be bonded to form a C6-10 aryl group, a 5-10 membered heteroaryl group, a C3-10 cycloalkyl group or a 3-10 membered heterocycloalkyl group;

R$_4$ is selected from H, hydroxyl, and C1-6 alkyl.

In another embodiment of the invention, R$_3$ in the general formula (I), (Ia), (Ib), (IIa), (IIb), (IIc), (IId), (IIIa), (IIIb), (IIIc), (IIId), (IVa), (IVb), (IVc), (IVd) is selected from the following groups:

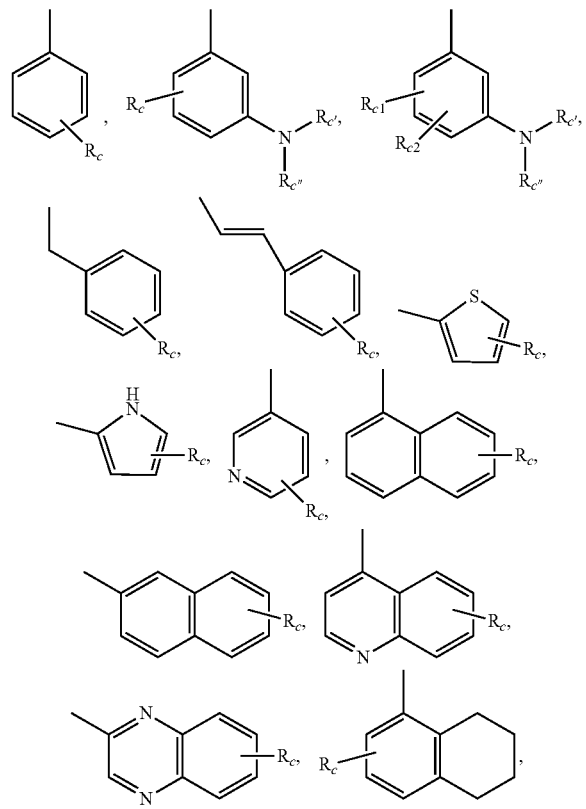

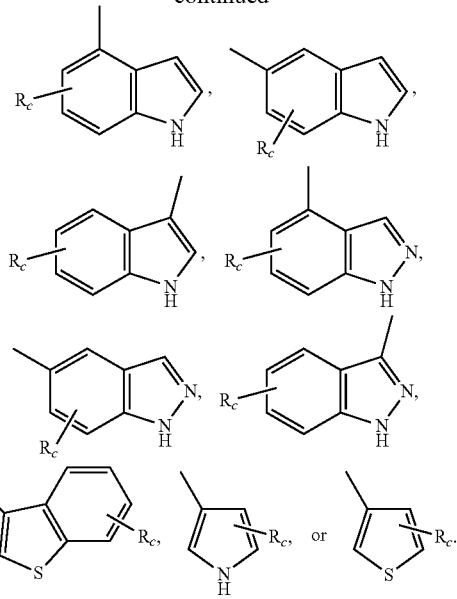

Wherein, R$_c$, R$_{c1}$, R$_{c2}$, R$_c$' and R$_c$" are independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 heteroalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; preferably selected from the group consisting of H, hydroxyl, amino group, NRaRa', halogen, carboxyl, formyl, amide group, ester group, C1-6 haloalkyl, C1-6 hydroxyalkyl, C1-6 heteroalkyl, C1-6 alkoxyl, C3-10 cycloalkyl, 3-10 membered heterocycloalkyl, substituted or unsubstituted phenyl or pyridyl;

R$_a$ and R$_a$' are each independently H or C1-6 alkyl;

or R$_{c1}$ and R$_{c2}$ may be bonded to form C6-10 aryl, 5-10 membered heteroaryl, C3-10 cycloalkyl, 3-10 membered heterocycloalkyl.

In another embodiment of the invention, R$_3$ in the general formula (I), (Ia), (Ib), (IIa), (IIb), (IIc), (IId), (IIIa), (IIIb), (IIIc), (IIId), (IVa), (IVb), (IVc), (IVd) is selected from the following groups:

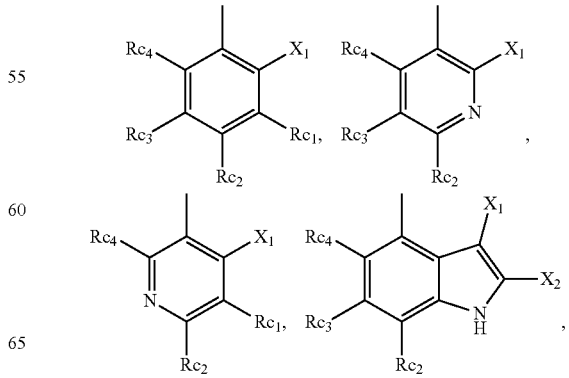

-continued

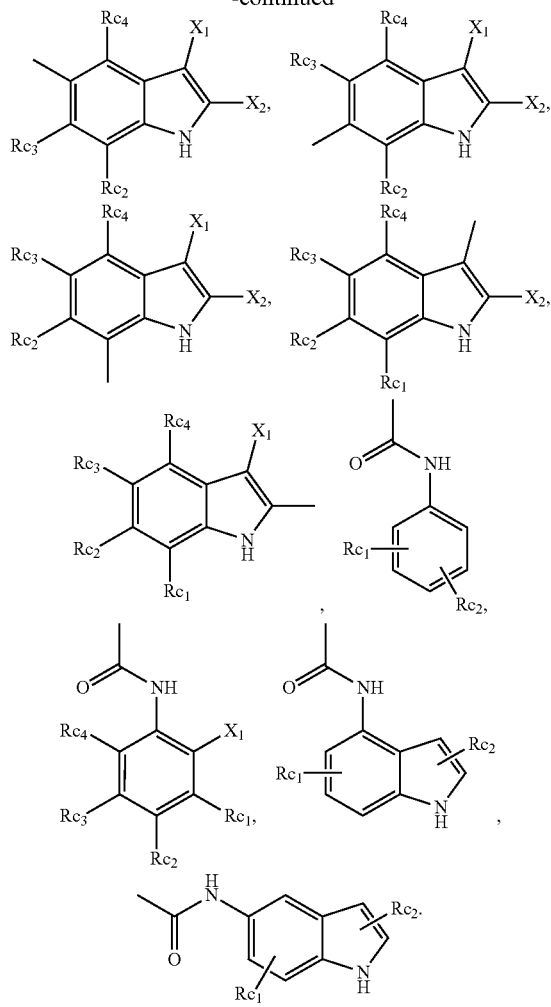

Wherein, $X_1$ is F, Cl, Br, I or trifluoromethyl;

$X_2$ is H, F, Cl, Br, or I;

$R_{c1}$, $R_{c2}$, $R_{c3}$, or $R_{c4}$ is each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 heteroalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; preferably selected from the group consisting of H, hydroxyl, amino group, NRaRa', halogen, carboxyl, formyl, amide group, ester group, C1-6 haloalkyl, C1-6 hydroxyalkyl, C1-6 heteroalkyl, C1-6 alkoxyl, C3-10 cycloalkyl, 3-10 membered heterocycloalkyl, substituted or unsubstituted phenyl or pyridyl;

or $R_{c1}$ and $R_{c2}$, or $R_{c2}$ and $R_{c3}$, or $R_{c3}$ and $R_{c4}$ may be bonded to form C6-10 aryl, 5-10 membered heteroaryl, C3-10 cycloalkyl, and 3-10 membered heterocycloalkyl;

$R_a$ and $R_a'$ are each independently H or C1-6 alkyl.

In another embodiment of the invention, $R_4$ and $R_5$ in the general formula (I) is H.

In another embodiment of the invention, the compounds of general formula (I) are selected from the compounds expressed by the following general formula (Va), (Vb) and (Vc):

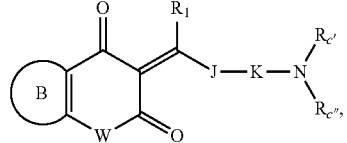
(Va)

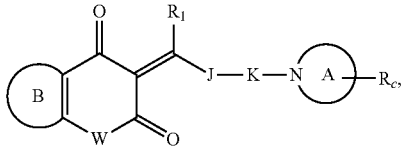
(Vb)

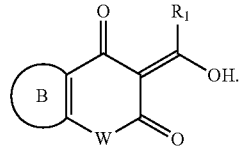
(Vc)

Wherein, W is selected from O, $NR_a$ and $CHR_a$;

J is $NR_a$, $NOR_a$, O or S;

K is a covalent bond, $NR_a$, $CR_cR_c'$, or $CR_cR_c'CR_cR_c'$;

$R_1$ is selected from the group consisting of H, deuterium, C1-6 alkyl, C1-6 hydroxyalkyl, C1-6 haloalkyl, unsubstituted or substituted phenyl; preferably selected from H and deuterium; preferably H;

A ring is a divalent 3-10 membered nitrogen-containing heterocycloalkyl group or a divalent 3-7 membered nitrogen-containing heterocycloalkenyl group;

B ring is unsubstituted or substituted C6-10 aryl, 5-10 membered heteroaryl; preferably, the B ring is unsubstituted or substituted C6-10 aryl; more preferably, the B ring is unsubstituted or substituted phenyl;

$R_c$, $R_c'$ and $R_c''$ are each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 heteroalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; preferably selected from the group consisting of H, hydroxyl, amino group, NRaRa', halogen, carboxyl, formyl, amide group, ester group, C1-6 haloalkyl, C1-6 hydroxyalkyl, C1-6 heteroalkyl, C1-6 alkoxyl, C3-10 cycloalkyl, 3-10 membered heterocycloalkyl, substituted or unsubstituted phenyl or pyridyl;

$R_a$ is independently selected from H and C1-6 alkyl.

In another embodiment of the invention, the compounds of the present invention are preferably selected from the following compounds:

| No. | Structures |
|---|---|
| 1 | 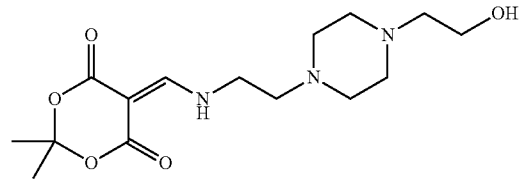 |
| 4A | 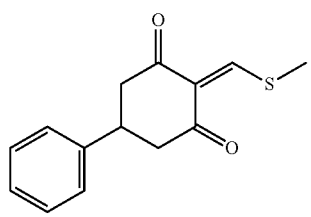 [SMILES: CSC=C1C(=O)CC(c2ccccc2)CC1=O] |
| 7 | 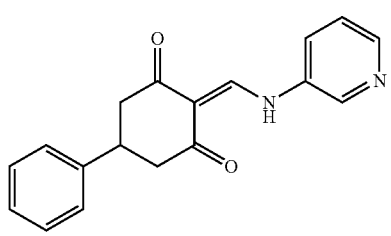 [SMILES: O=C1CC(c2ccccc2)CC(=O)C1=CNc1cccnc1] |
| 8 | 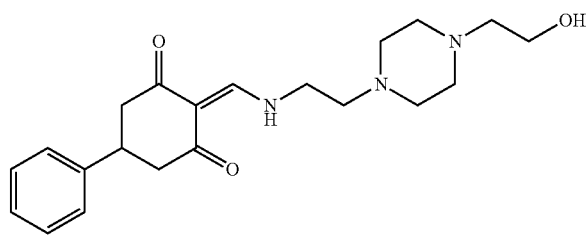 |
| 9 | 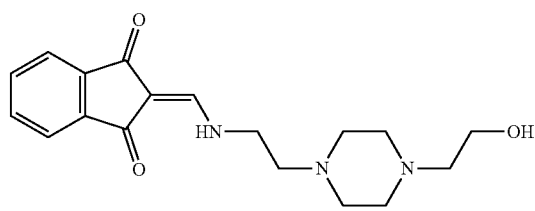 |
| 10 | 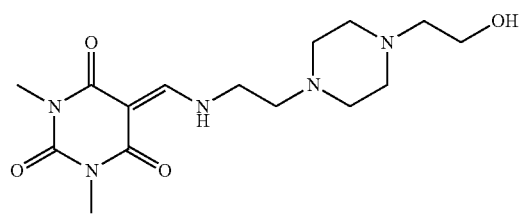 [SMILES: CN1C(=O)C(=CNCCN2CCN(CCO)CC2)C(=O)N(C)C1=O] |
| 11 | 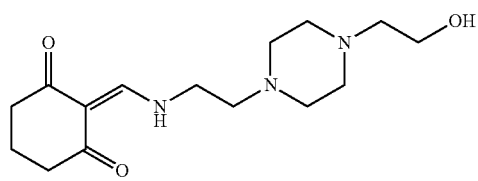 [SMILES: O=C1CCCC(=O)C1=CNCCN1CCN(CCO)CC1] |

-continued

| No. | Structures |
|-----|------------|
| 12  | (structure) |
| 14  | (structure) |
| 15  | (structure) |
| 17  | (structure) |
| 18  | (structure) |

-continued
| No. | Structures |
|---|---|
| 19 | 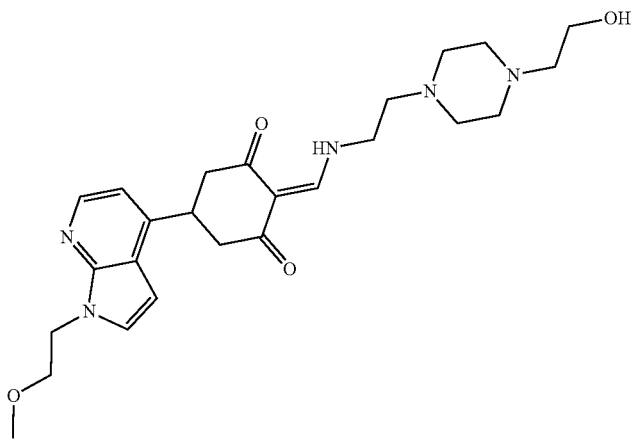 [SMILES: COCCn1ccc2c(C3CC(=O)C(=CNCCN4CCN(CCO)CC4)C(=O)C3)ccnc21] |
| 20 | 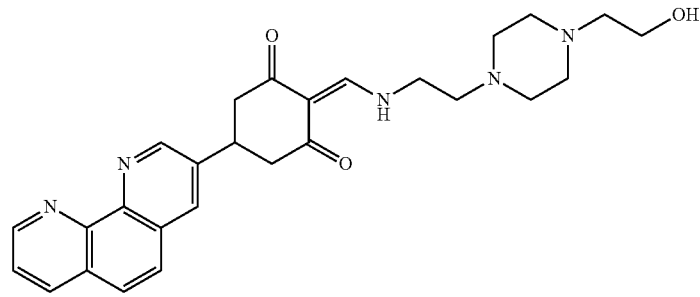 [SMILES: O=C1CC(c2cnc3c(ccc4cccnc43)c2)CC(=O)C1=CNCCN1CCN(CCO)CC1] |
| 21 | 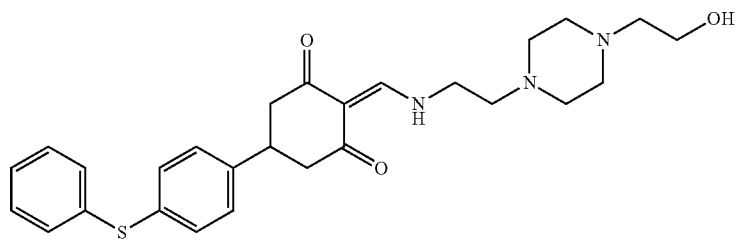 [SMILES: O=C1CC(c2ccc(Sc3ccccc3)cc2)CC(=O)C1=CNCCN1CCN(CCO)CC1] |
| 22 | 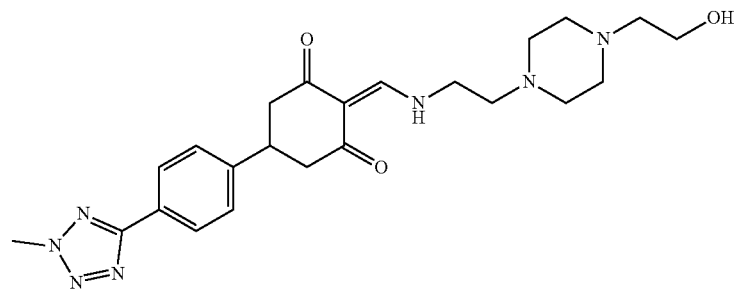 [SMILES: Cn1nnc(-c2ccc(C3CC(=O)C(=CNCCN4CCN(CCO)CC4)C(=O)C3)cc2)n1] |
| 23 | 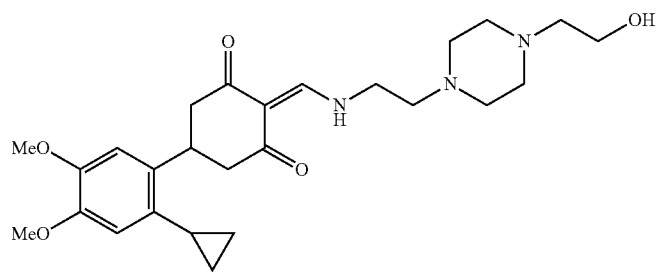 [SMILES: COc1cc(C2CC2)c(C2CC(=O)C(=CNCCN3CCN(CCO)CC3)C(=O)C2)cc1OC] |

| No. | Structures |
|---|---|
| 24 | 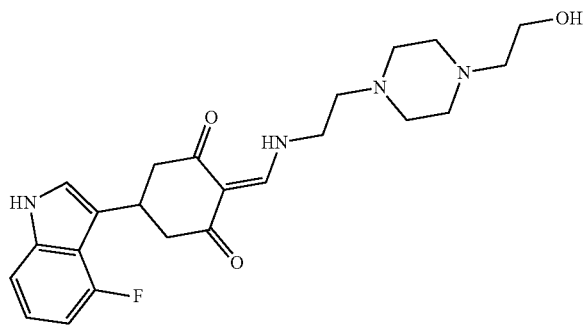 [SMILES: O=C1CC(c2c[nH]c3cccc(F)c23)CC(=O)C1=CNCCN1CCN(CCO)CC1] |
| 25 | 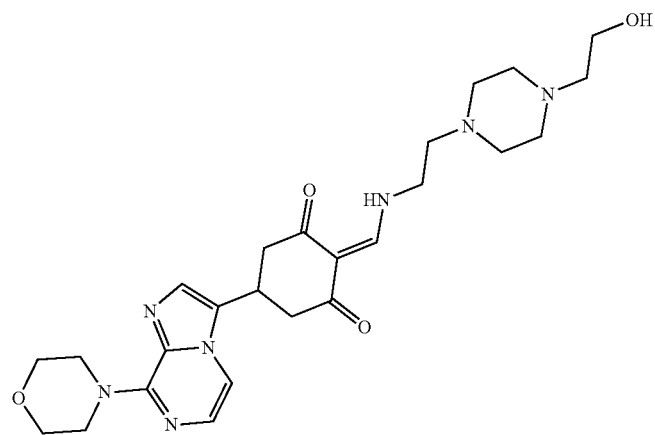 [SMILES: O=C1CC(c2cnc3c(N4CCOCC4)nccn23)CC(=O)C1=CNCCN1CCN(CCO)CC1] |
| 26 | 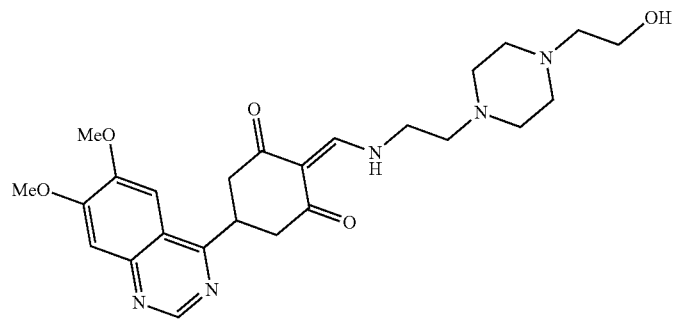 [SMILES: COc1cc2ncnc(C3CC(=O)C(=CNCCN4CCN(CCO)CC4)C(=O)C3)c2cc1OC] |
| 27 | 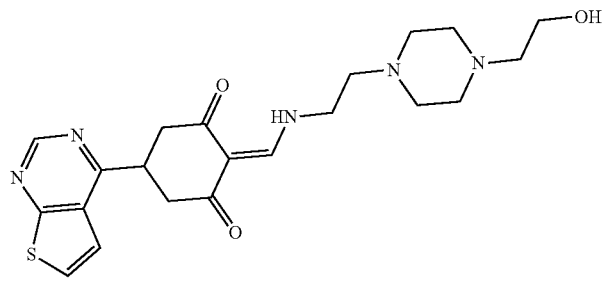 [SMILES: O=C1CC(c2ncnc3sccc23)CC(=O)C1=CNCCN1CCN(CCO)CC1] |
| 28 | 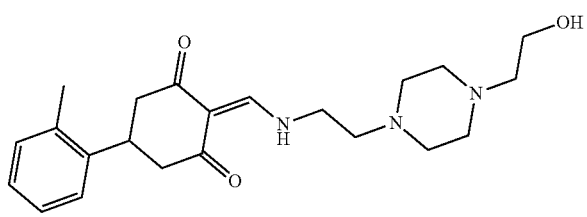 [SMILES: Cc1ccccc1C1CC(=O)C(=CNCCN2CCN(CCO)CC2)C(=O)C1] |

-continued
| No. | Structures |
|---|---|
| 29 | 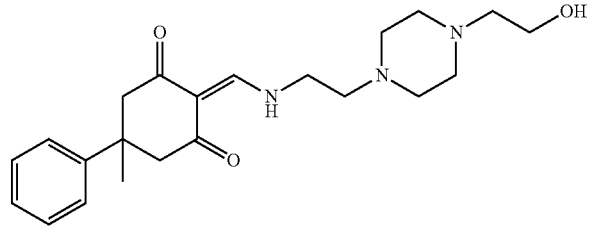 |
| 30 | 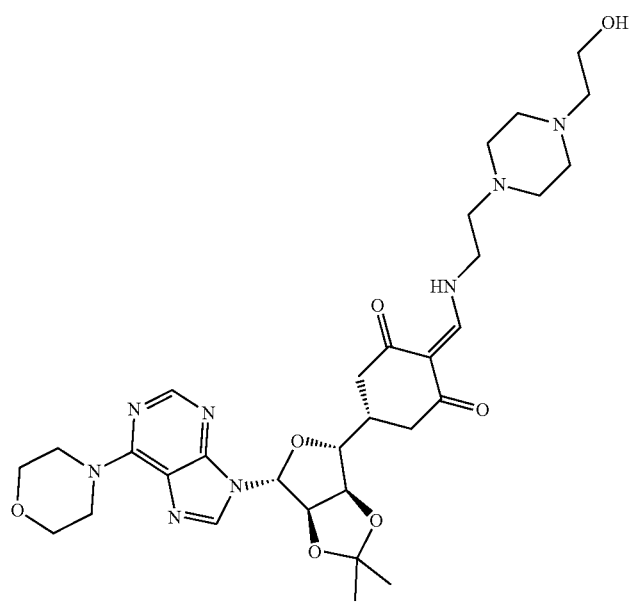 |
| 31 | 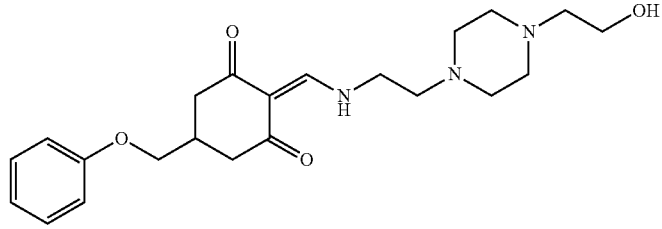 [SMILES: O=C1CC(COc2ccccc2)CC(=O)C1=CNCCN1CCN(CCO)CC1] |
| 32 | 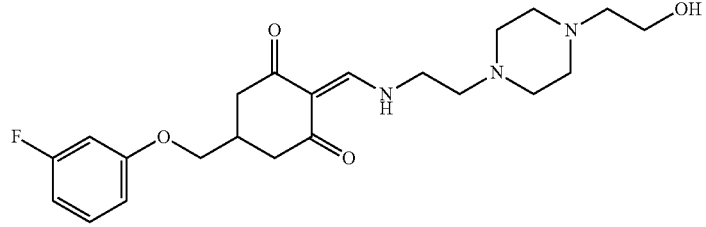 [SMILES: O=C1CC(COc2cccc(F)c2)CC(=O)C1=CNCCN1CCN(CCO)CC1] |

-continued
| No. | Structures |
|---|---|
| 33 | 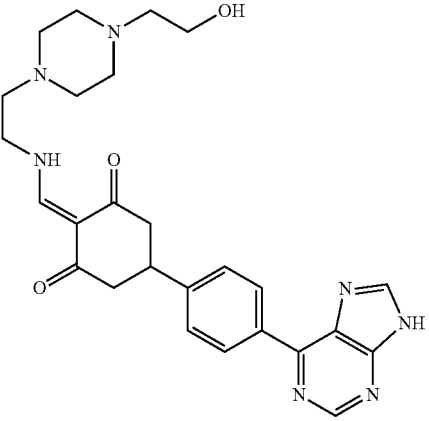 [SMILES: O=C1CC(c2ccc(-c3ncnc4[nH]cnc34)cc2)CC(=O)C1=CNCCN1CCN(CCO)CC1] |
| 34 | 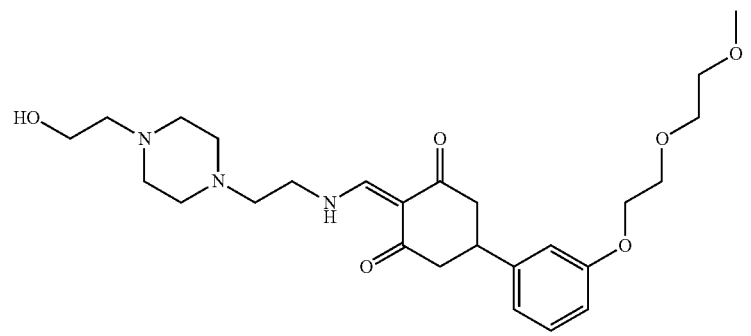 [SMILES: COCCOCCOc1cccc(C2CC(=O)C(=CNCCN3CCN(CCO)CC3)C(=O)C2)c1] |
| 35 | 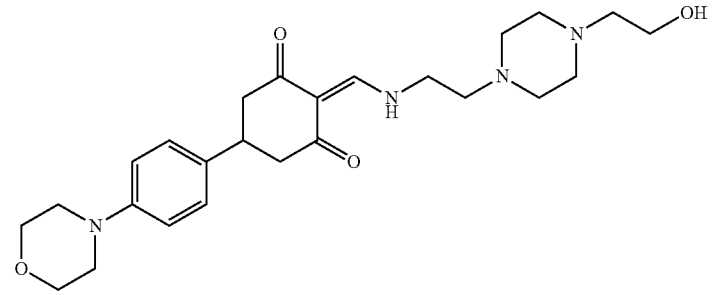 [SMILES: O=C1CC(c2ccc(N3CCOCC3)cc2)CC(=O)C1=CNCCN1CCN(CCO)CC1] |
| 36 | 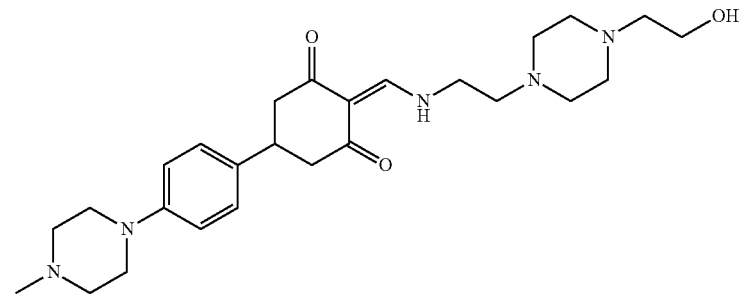 [SMILES: CN1CCN(c2ccc(C3CC(=O)C(=CNCCN4CCN(CCO)CC4)C(=O)C3)cc2)CC1] |
| 37 | 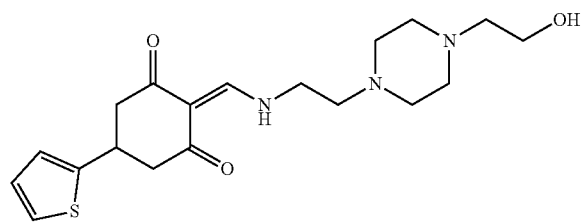 |

-continued
| No. | Structures |
|---|---|
| 39 | 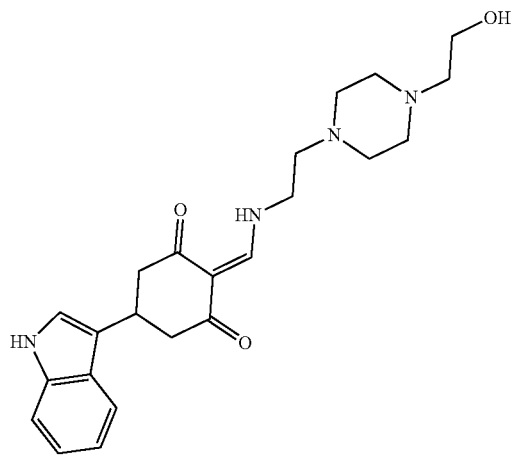 |
| 40 | 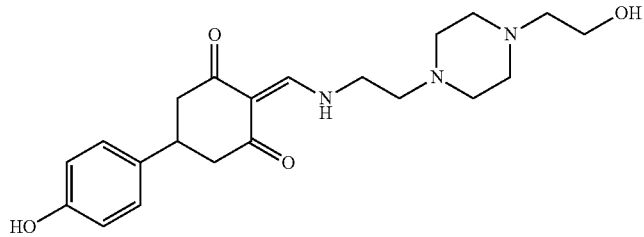 |
| 41 | 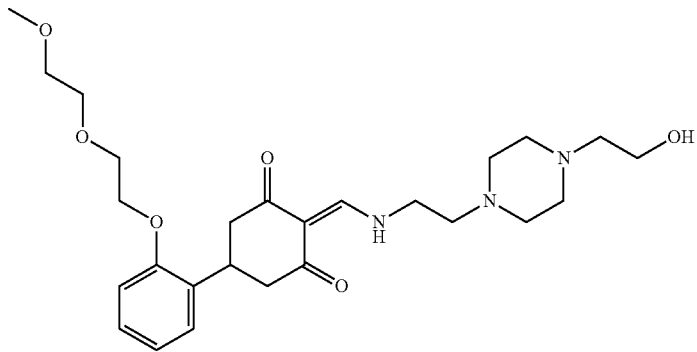 [SMILES: COCCOCCOc1ccccc1C1CC(=O)C(=CNCCN2CCN(CCO)CC2)C(=O)C1] |
| 42 | 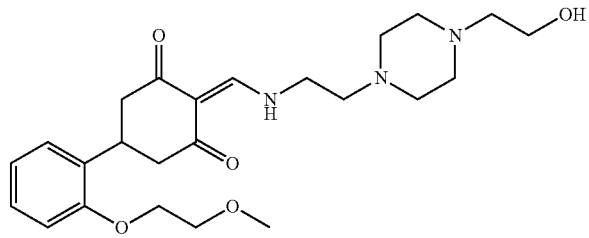 [SMILES: COCCOc1ccccc1C1CC(=O)C(=CNCCN2CCN(CCO)CC2)C(=O)C1] |
| 43 | 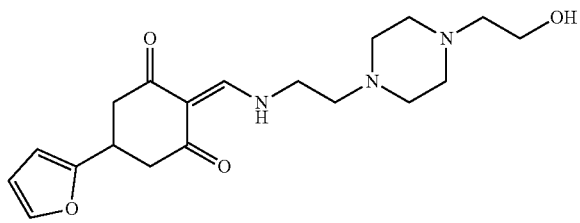 [SMILES: O=C1CC(c2ccco2)CC(=O)C1=CNCCN1CCN(CCO)CC1] |

-continued
| No. | Structures |
|---|---|
| 44 | 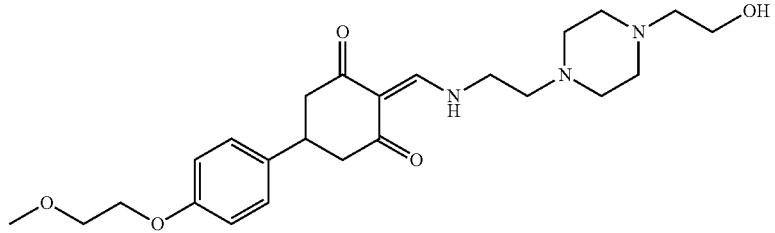 [SMILES: COCCOc1ccc(C2CC(=O)C(=CNCCN3CCN(CCO)CC3)C(=O)C2)cc1] |
| 45 | 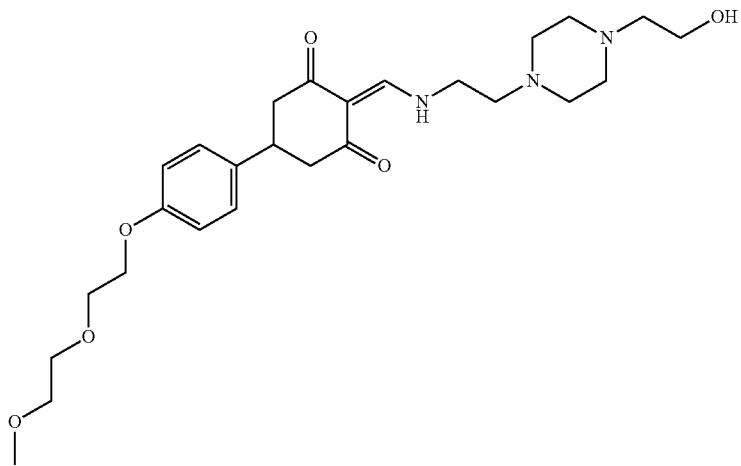 [SMILES: COCCOCCOc1ccc(C2CC(=O)C(=CNCCN3CCN(CCO)CC3)C(=O)C2)cc1] |
| 46 | 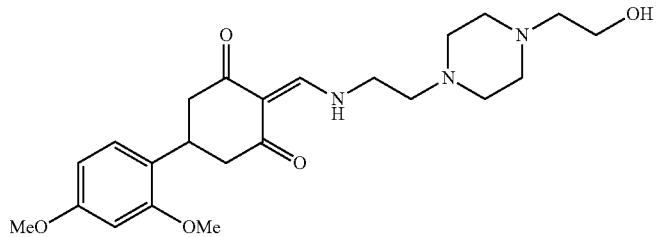 [SMILES: COc1ccc(C2CC(=O)C(=CNCCN3CCN(CCO)CC3)C(=O)C2)c(OC)c1] |
| 47 | 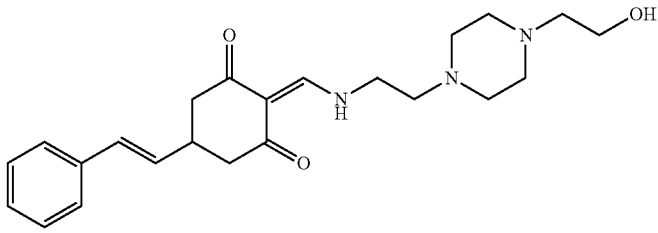 [SMILES: O=C1CC(/C=C/c2ccccc2)CC(=O)C1=CNCCN1CCN(CCO)CC1] |
| 48 | 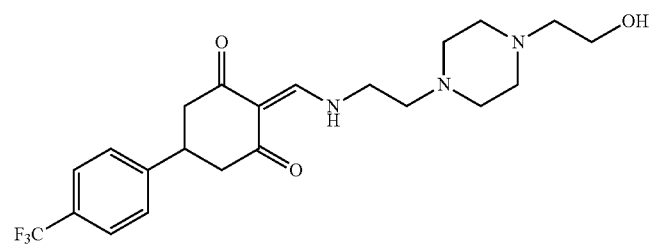 [SMILES: O=C1CC(c2ccc(C(F)(F)F)cc2)CC(=O)C1=CNCCN1CCN(CCO)CC1] |

US 11,319,303 B2
35                                                                36
-continued
| No. | Structures |
|-----|------------|
| 49  | 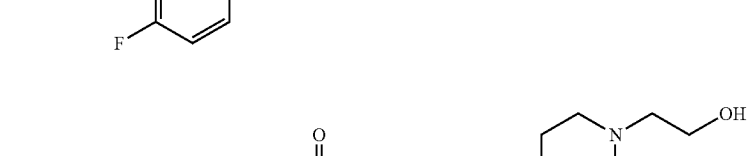 |
| 50  | 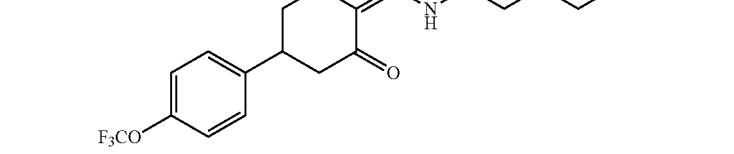 |
| 51  | 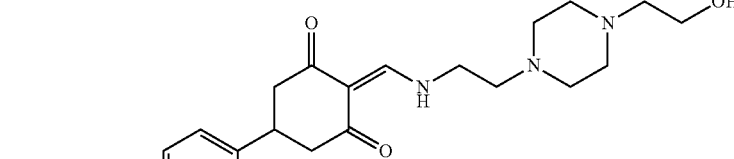 |
| 52  | 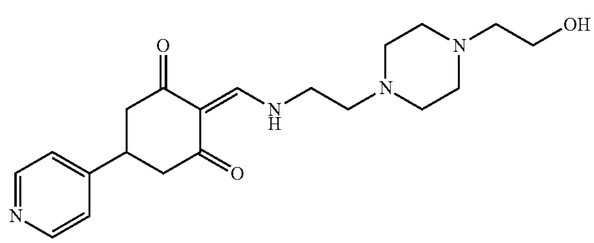 [SMILES: O=C1CC(c2ccncc2)CC(=O)C1=CNCCN1CCN(CCO)CC1] |
| 53  | 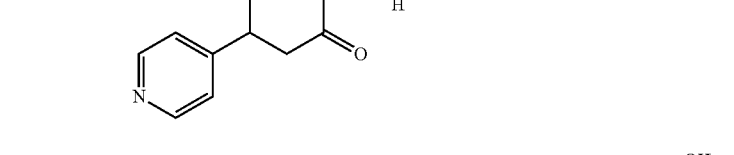 |
| 54  | 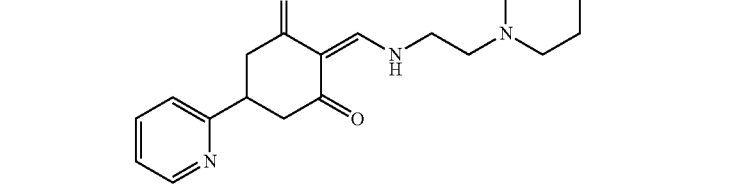 |

-continued

| No. | Structures |
|---|---|
| 55 | 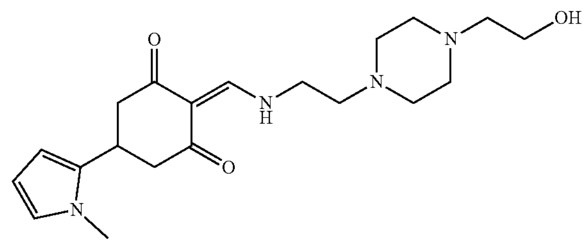 [SMILES: Cn1cccc1C1CC(=O)C(=CNCCN2CCN(CCO)CC2)C(=O)C1] |
| 56 | 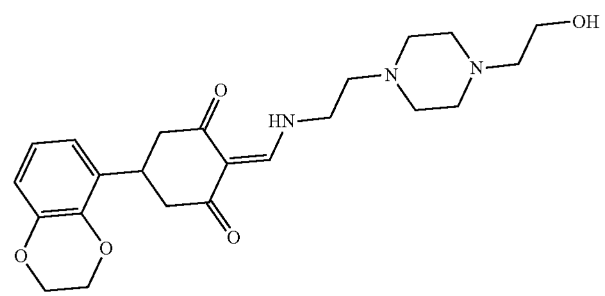 [SMILES: O=C1CC(c2cccc3c2OCCO3)CC(=O)C1=CNCCN1CCN(CCO)CC1] |
| 57 | 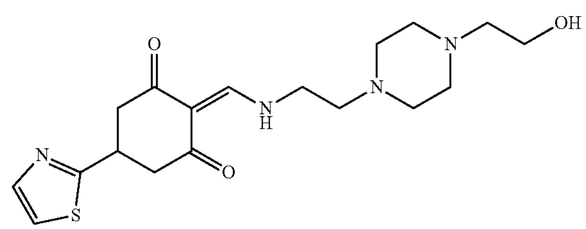 [SMILES: O=C1CC(c2nccs2)CC(=O)C1=CNCCN1CCN(CCO)CC1] |
| 58 | 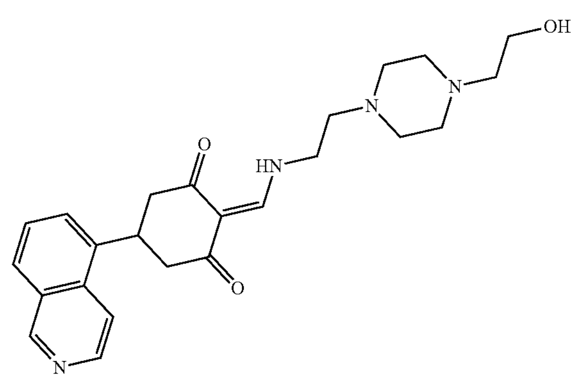 [SMILES: O=C1CC(c2cccc3cnccc23)CC(=O)C1=CNCCN1CCN(CCO)CC1] |
| 59 | 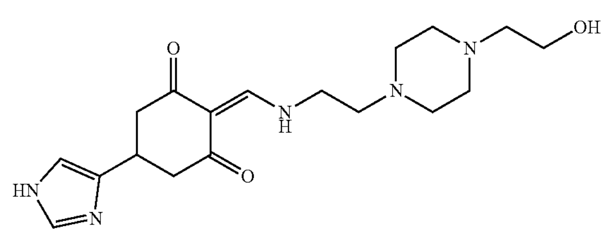 [SMILES: O=C1CC(c2c[nH]cn2)CC(=O)C1=CNCCN1CCN(CCO)CC1] |

-continued
| No. | Structures |
|---|---|
| 61 | 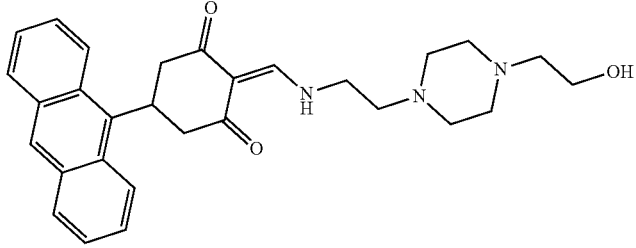 [SMILES: O=C1CC(c2c3ccccc3cc3ccccc23)CC(=O)C1=CNCCN1CCN(CCO)CC1] |
| 62 | 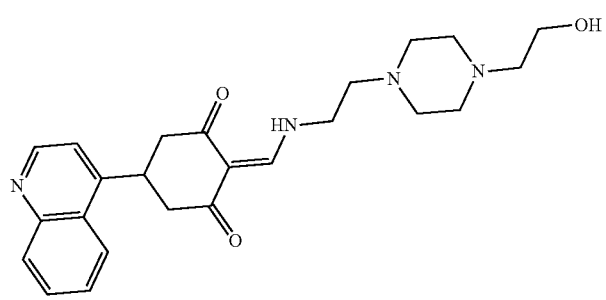 [SMILES: O=C1CC(c2ccnc3ccccc23)CC(=O)C1=CNCCN1CCN(CCO)CC1] |
| 63 | 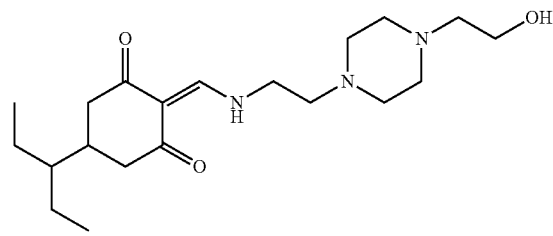 [SMILES: CCC(CC)C1CC(=O)C(=CNCCN2CCN(CCO)CC2)C(=O)C1] |
| 64 | 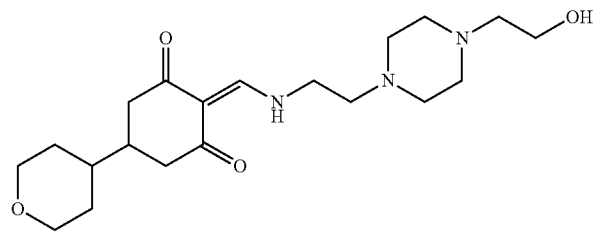 [SMILES: O=C1CC(C2CCOCC2)CC(=O)C1=CNCCN1CCN(CCO)CC1] |
| 65 | 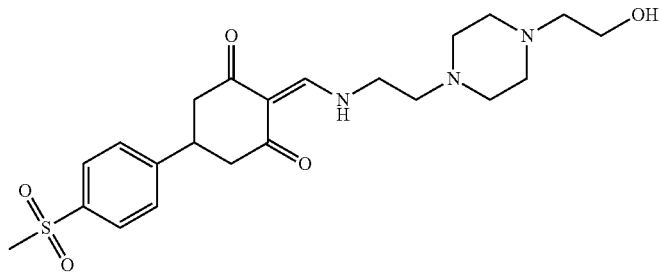 [SMILES: CS(=O)(=O)c1ccc(C2CC(=O)C(=CNCCN3CCN(CCO)CC3)C(=O)C2)cc1] |

-continued
| No. | Structures |
|-----|------------|
| 66 | 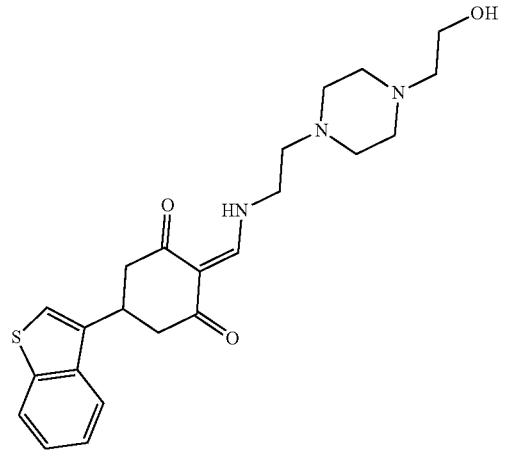 [SMILES: O=C1CC(c2csc3ccccc23)CC(=O)C1=CNCCN1CCN(CCO)CC1] |
| 67 | 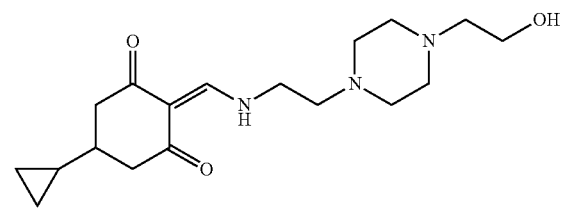 [SMILES: O=C1CC(C2CC2)CC(=O)C1=CNCCN1CCN(CCO)CC1] |
| 68 | 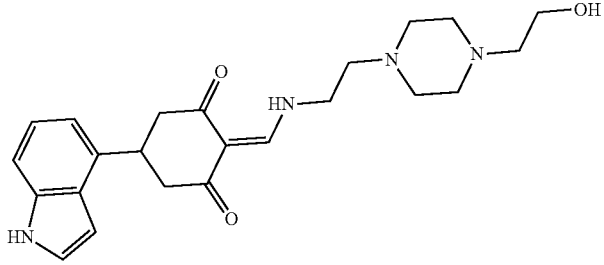 [SMILES: O=C1CC(c2cccc3[nH]ccc23)CC(=O)C1=CNCCN1CCN(CCO)CC1] |
| 69 | 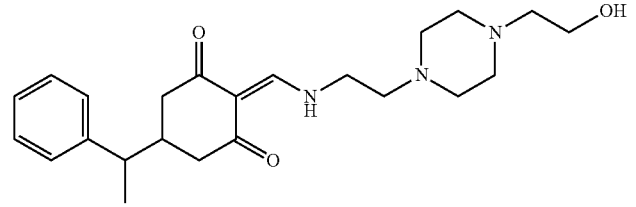 [SMILES: CC(c1ccccc1)C1CC(=O)C(=CNCCN2CCN(CCO)CC2)C(=O)C1] |
| 70 | 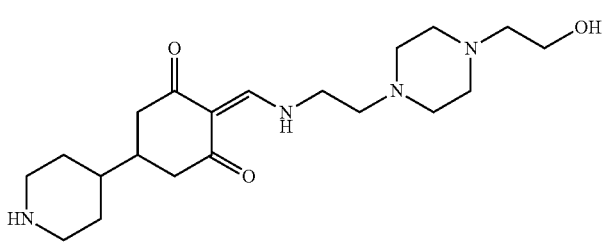 [SMILES: O=C1CC(C2CCNCC2)CC(=O)C1=CNCCN1CCN(CCO)CC1] |

-continued

| No. | Structures |
|---|---|
| 71 | (structure: 4-pyridyl-O-CH2CH2-O-phenyl-cyclohexane-1,3-dione with =CH-NH-CH2CH2-piperazine-N-CH2CH2OH) |
| 72 | (structure: 4-pyridyl-thiophene-cyclohexane-1,3-dione with =CH-NH-CH2CH2-piperazine-N-CH2CH2OH) |
| 73 | (structure: 4-(4-pyridyl)phenyl-cyclohexane-1,3-dione with =CH-NH-CH2CH2-piperazine-N-CH2CH2OH) |
| 74 | (structure: benzothiazole substituted with N=CH-N(CH3)2 and attached to cyclohexane-1,3-dione with =CH-NH-CH2CH2-piperazine-N-CH2CH2OH) |
| 75 | (structure: 3-(4-pyridyloxy)phenyl-cyclohexane-1,3-dione with =CH-NH-CH2CH2-piperazine-N-CH2CH2OH) |

| No. | Structures |
|---|---|
| 76 | 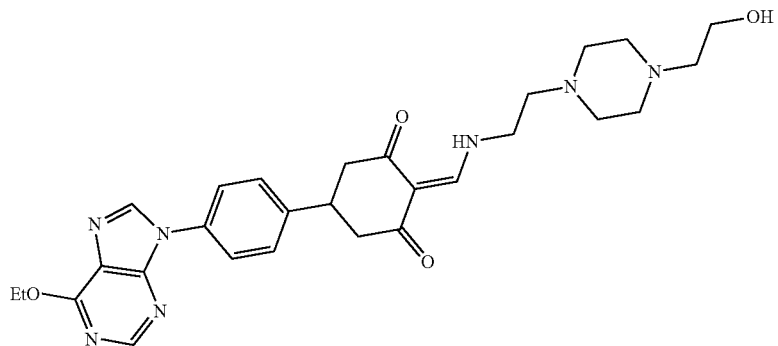 [SMILES: CCOc1ncnc2c1ncn2-c1ccc(C2CC(=O)C(=CNCCN3CCN(CCO)CC3)C(=O)C2)cc1] |
| 77 | 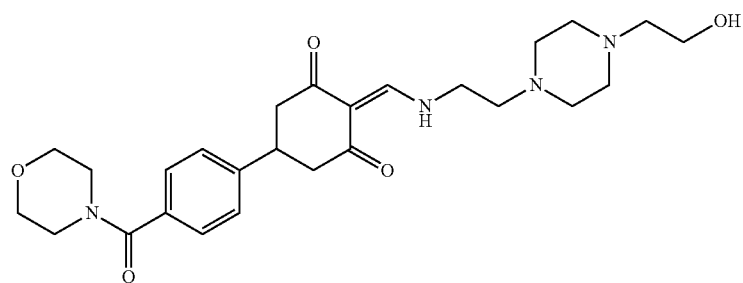 [SMILES: O=C1CC(c2ccc(C(=O)N3CCOCC3)cc2)CC(=O)C1=CNCCN1CCN(CCO)CC1] |
| 78 | 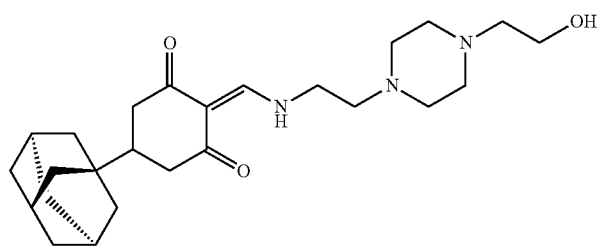 [SMILES: O=C1CC([C@]23C[C@H]4C[C@H](C[C@H](C4)C2)C3)CC(=O)C1=CNCCN1CCN(CCO)CC1] |
| 79 | 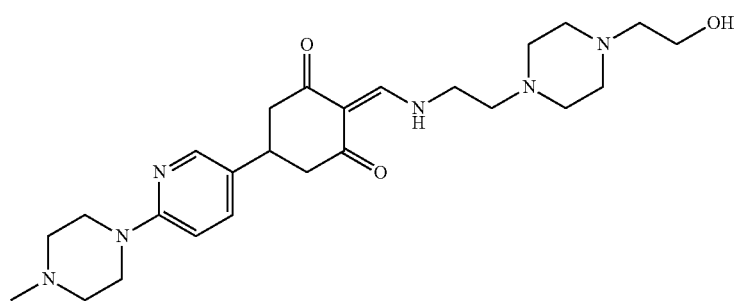 [SMILES: CN1CCN(c2ccc(C3CC(=O)C(=CNCCN4CCN(CCO)CC4)C(=O)C3)cn2)CC1] |
| 80 | 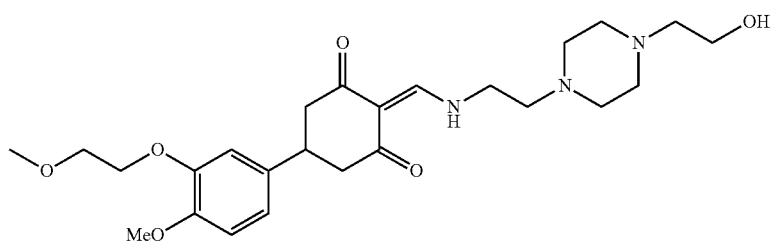 [SMILES: COCCOc1cc(C2CC(=O)C(=CNCCN3CCN(CCO)CC3)C(=O)C2)ccc1OC] |

| No. | Structures |
|---|---|
| 81 | 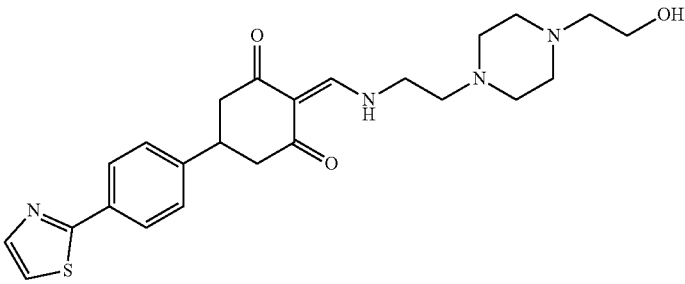 [SMILES: O=C1CC(c2ccc(-c3nccs3)cc2)CC(=O)C1=CNCCN1CCN(CCO)CC1] |
| 82 | 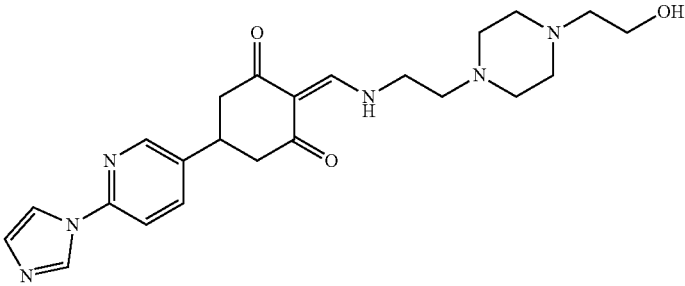 |
| 83 | 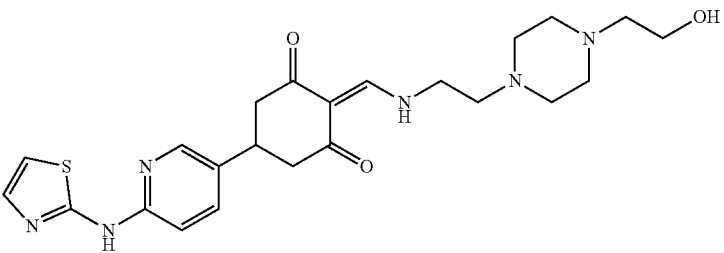 [SMILES: O=C1CC(c2ccc(Nc3nccs3)nc2)CC(=O)C1=CNCCN1CCN(CCO)CC1] |
| 84 | 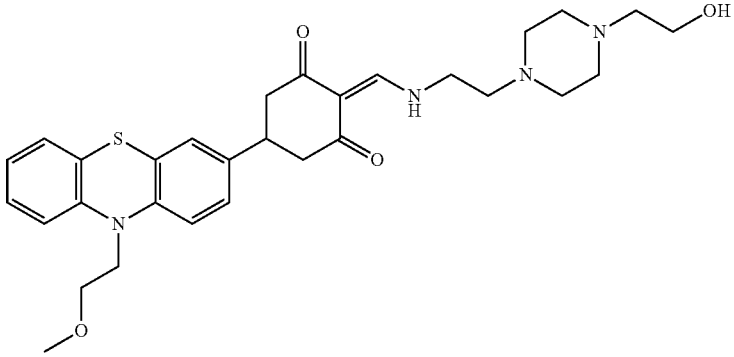 [SMILES: COCCN1c2ccccc2Sc2cc(C3CC(=O)C(=CNCCN4CCN(CCO)CC4)C(=O)C3)ccc21] |
| 85 | 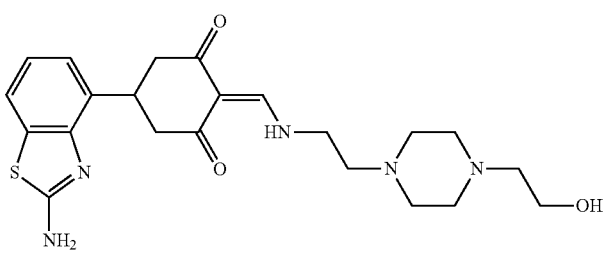 [SMILES: Nc1nc2c(C3CC(=O)C(=CNCCN4CCN(CCO)CC4)C(=O)C3)cccc2s1] |

| No. | Structures |
|---|---|
| 86 | 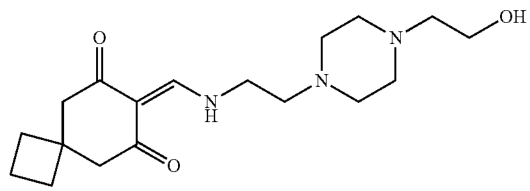 [SMILES: O=C1CC2(CCC2)CC(=O)C1=CNCCN1CCN(CCO)CC1] |
| 87 | 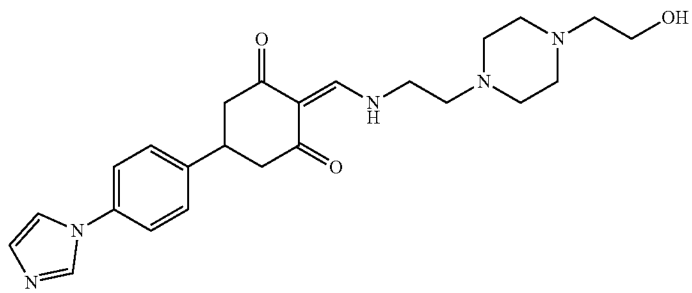 |
| 88 | 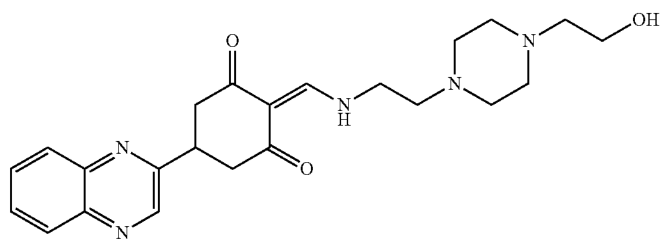 [SMILES: O=C1CC(c2cnc3ccccc3n2)CC(=O)C1=CNCCN1CCN(CCO)CC1] |
| 89 | 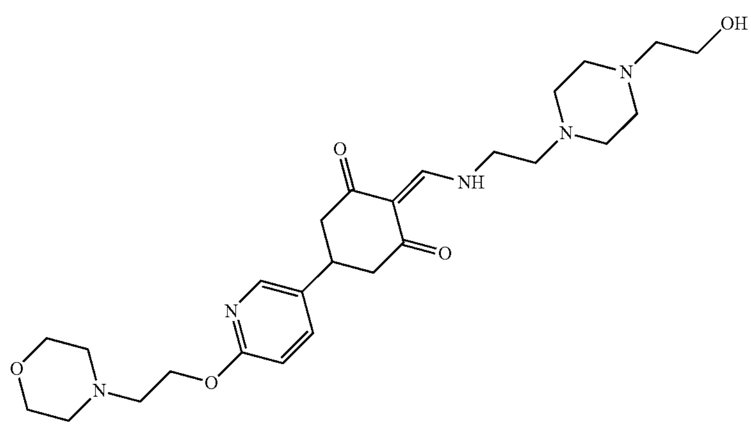 [SMILES: O=C1CC(c2ccc(OCCN3CCOCC3)nc2)CC(=O)C1=CNCCN1CCN(CCO)CC1] |
| 90 | 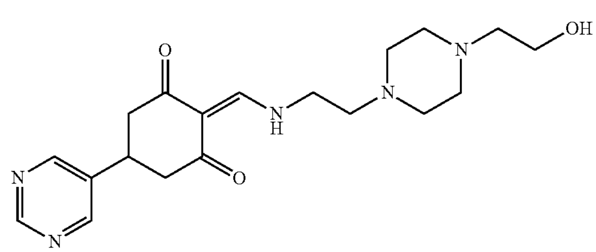 [SMILES: O=C1CC(c2cncnc2)CC(=O)C1=CNCCN1CCN(CCO)CC1] |

| No. | Structures |
|---|---|
| 91 | 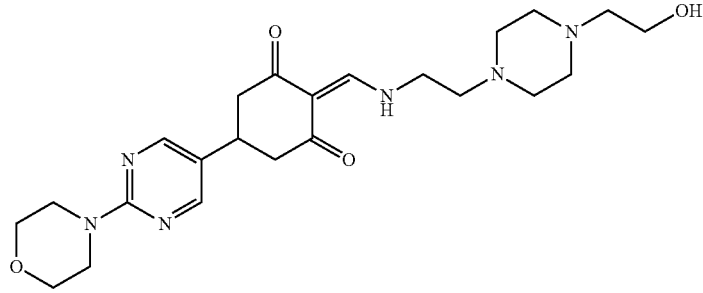 [SMILES: O=C1CC(c2cnc(N3CCOCC3)nc2)CC(=O)C1=CNCCN1CCN(CCO)CC1] |
| 92 | 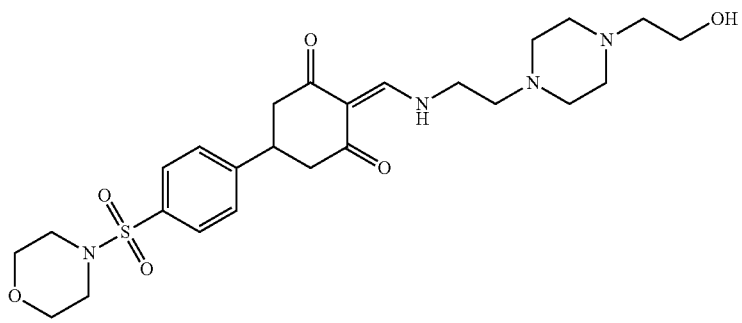 [SMILES: O=C1CC(c2ccc(S(=O)(=O)N3CCOCC3)cc2)CC(=O)C1=CNCCN1CCN(CCO)CC1] |
| 93 | 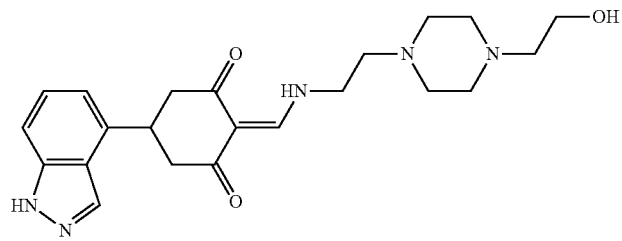 [SMILES: O=C1CC(c2cccc3[nH]ncc23)CC(=O)C1=CNCCN1CCN(CCO)CC1] |
| 94 | 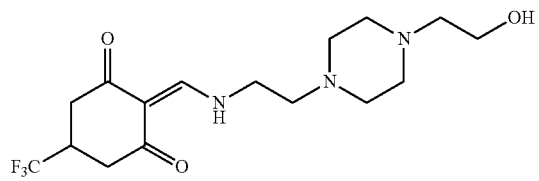 [SMILES: O=C1CC(C(F)(F)F)CC(=O)C1=CNCCN1CCN(CCO)CC1] |
| 95 | 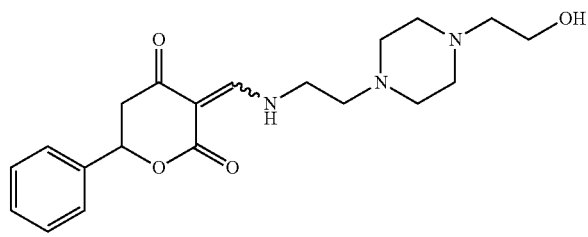 [SMILES: O=C1CC(c2ccccc2)OC(=O)C1=CNCCN1CCN(CCO)CC1] |
| 96 | 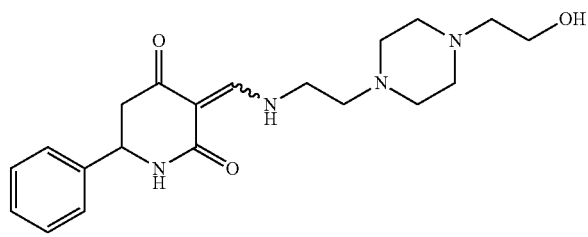 [SMILES: O=C1CC(c2ccccc2)NC(=O)C1=CNCCN1CCN(CCO)CC1] |

| No. | Structures |
| --- | --- |
| 97 | 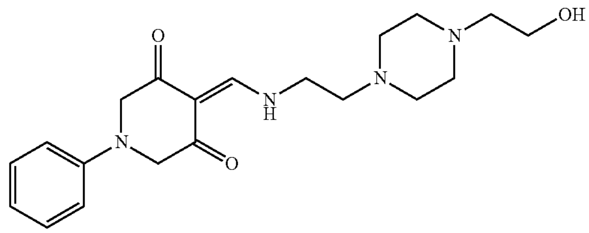 [SMILES: O=C1CN(c2ccccc2)CC(=O)C1=CNCCN1CCN(CCO)CC1] |
| 99 | 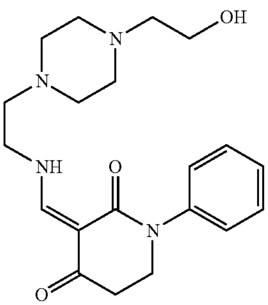 [SMILES: O=C1CCN(c2ccccc2)C(=O)/C1=C\NCCN1CCN(CCO)CC1] |
| 100 | 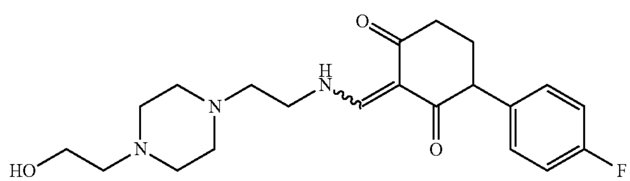 [SMILES: O=C1CCC(c2ccc(F)cc2)C(=O)C1=CNCCN1CCN(CCO)CC1] |
| 101 | 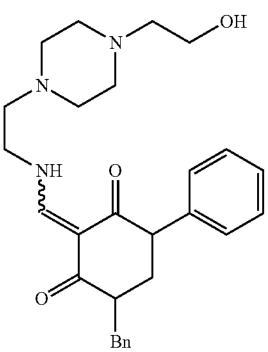 [SMILES: O=C1C(=CNCCN2CCN(CCO)CC2)C(=O)C(c2ccccc2)CC1Cc1ccccc1] |
| 102 | 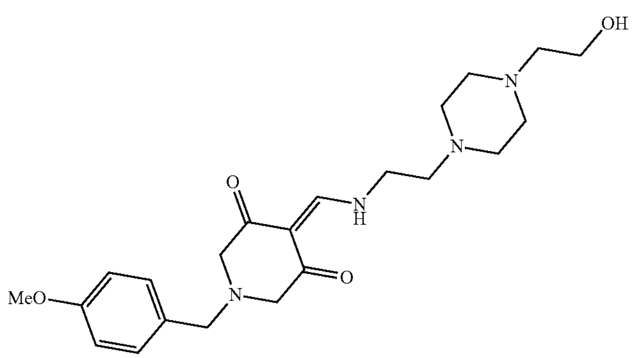 [SMILES: COc1ccc(CN2CC(=O)C(=CNCCN3CCN(CCO)CC3)C(=O)C2)cc1] |
| 103 | 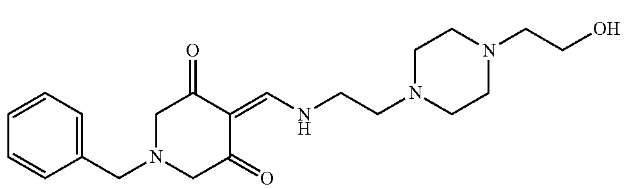 [SMILES: O=C1CN(Cc2ccccc2)CC(=O)C1=CNCCN1CCN(CCO)CC1] |

| No. | Structures |
|---|---|
| 104 | 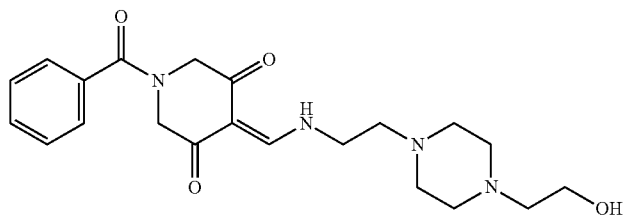 [SMILES: O=C1CN(C(=O)c2ccccc2)CC(=O)C1=CNCCN1CCN(CCO)CC1] |
| 106 | 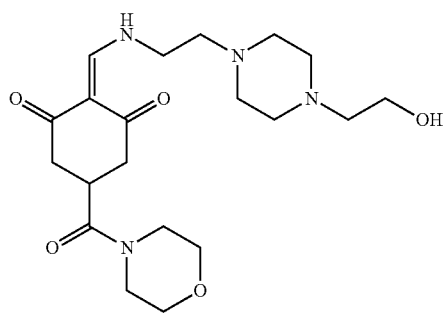 [SMILES: O=C1CC(C(=O)N2CCOCC2)CC(=O)C1=CNCCN1CCN(CCO)CC1] |
| 107 | 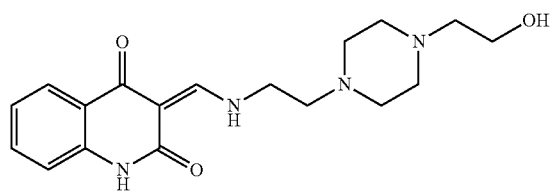 [SMILES: O=C1Nc2ccccc2C(=O)/C1=C/NCCN1CCN(CCO)CC1] |
| 108 | 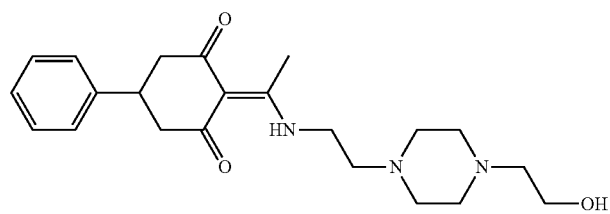 |
| 109 | 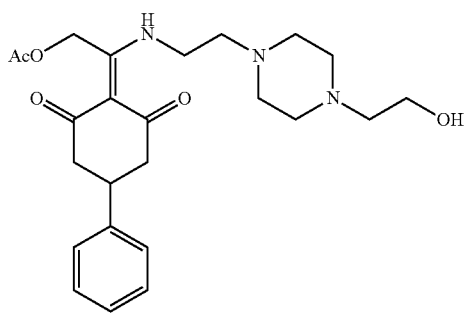 [SMILES: CC(=O)OCC(NCCN1CCN(CCO)CC1)=C1C(=O)CC(c2ccccc2)CC1=O] |
| 110 | 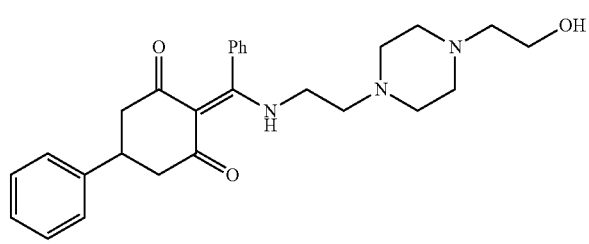 [SMILES: O=C1CC(c2ccccc2)CC(=O)C1=C(NCCN1CCN(CCO)CC1)c1ccccc1] |

-continued

| No. | Structures |
|---|---|
| 111 | 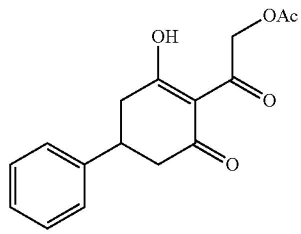 [SMILES: CC(=O)OCC(=O)C1=C(O)CC(c2ccccc2)CC1=O] |
| 112 | 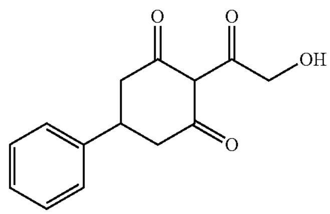 [SMILES: O=C(CO)C1C(=O)CC(c2ccccc2)CC1=O] |
| 113 | 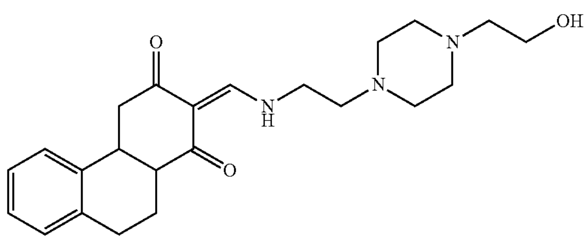 [SMILES: O=C1CC2c3ccccc3CCC2C(=O)/C1=C\NCCN1CCN(CCO)CC1] |
| 114 | 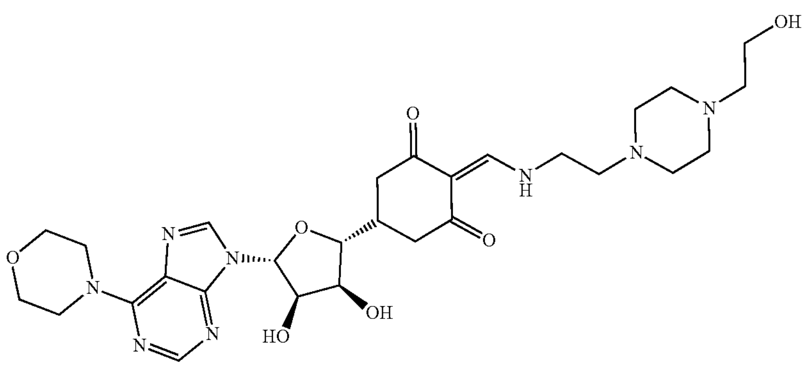 [SMILES: O=C1CC([C@H]2O[C@@H](n3cnc4c(N5CCOCC5)ncnc43)[C@H](O)[C@@H]2O)CC(=O)C1=CNCCN1CCN(CCO)CC1] |
| 115 | 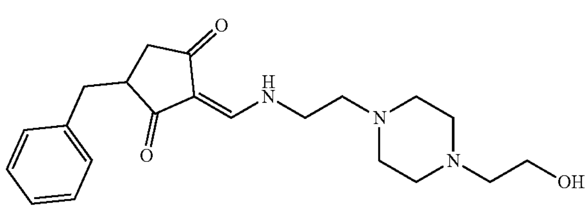 [SMILES: O=C1CC(Cc2ccccc2)C(=O)/C1=C/NCCN1CCN(CCO)CC1] |
| 116 | 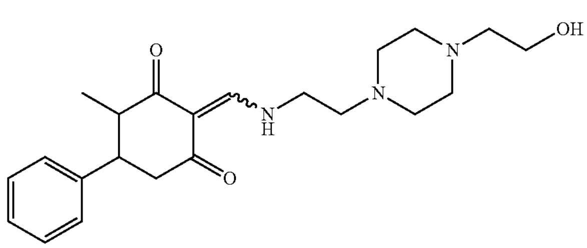 [SMILES: CC1C(=O)C(=CNCCN2CCN(CCO)CC2)C(=O)CC1c1ccccc1] |

| No. | Structures |
|---|---|
| 119 | 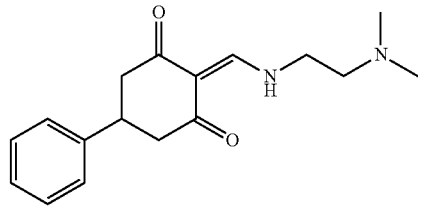 [SMILES: CN(C)CCNC=C1C(=O)CC(c2ccccc2)CC1=O] |
| 120 | 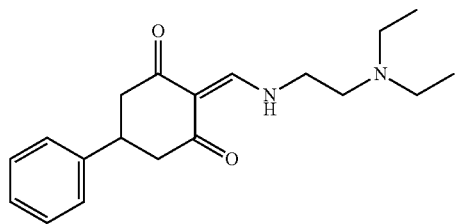 [SMILES: CCN(CC)CCNC=C1C(=O)CC(c2ccccc2)CC1=O] |
| 121 | 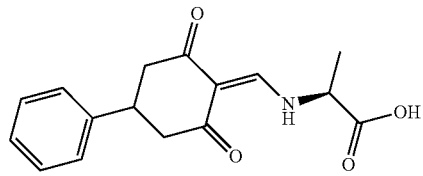 [SMILES: C[C@H](NC=C1C(=O)CC(c2ccccc2)CC1=O)C(=O)O] |
| 122 | 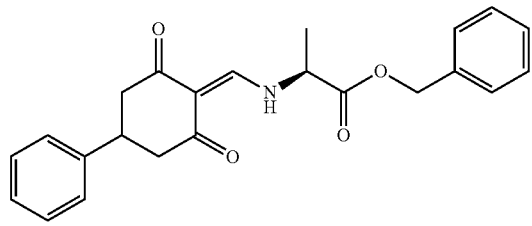 [SMILES: C[C@H](NC=C1C(=O)CC(c2ccccc2)CC1=O)C(=O)OCc1ccccc1] |
| 123 | 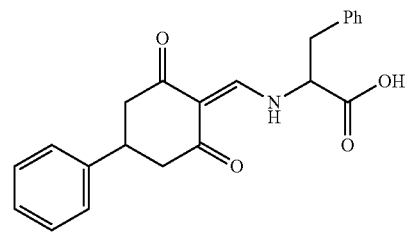 |
| 124 | 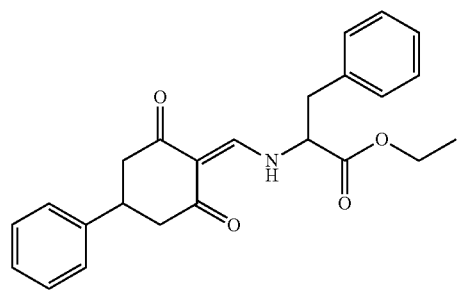 [SMILES: CCOC(=O)C(Cc1ccccc1)NC=C1C(=O)CC(c2ccccc2)CC1=O] |

-continued
| No. | Structures |
|---|---|
| 125 | 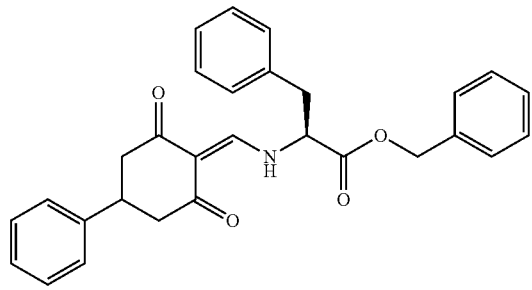 [SMILES: O=C1CC(c2ccccc2)CC(=O)C1=CN[C@@H](Cc1ccccc1)C(=O)OCc1ccccc1] |
| 126 | 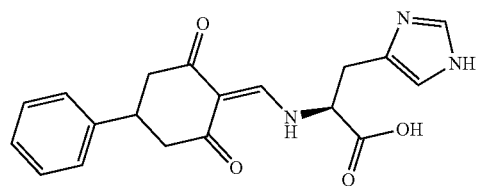 [SMILES: O=C1CC(c2ccccc2)CC(=O)C1=CN[C@@H](Cc1c[nH]cn1)C(=O)O] |
| 127 | 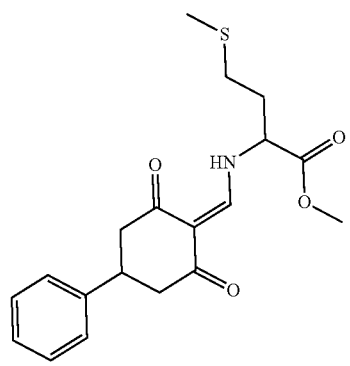 [SMILES: COC(=O)C(CCSC)NC=C1C(=O)CC(c2ccccc2)CC1=O] |
| 128 | 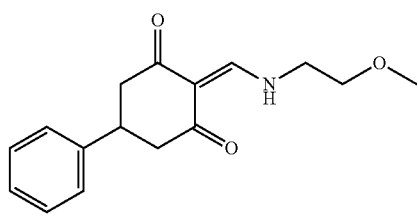 [SMILES: COCCNC=C1C(=O)CC(c2ccccc2)CC1=O] |
| 129 | 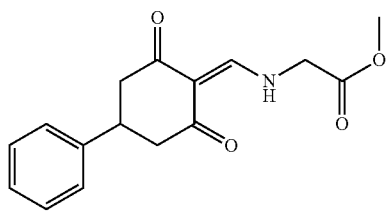 [SMILES: COC(=O)CNC=C1C(=O)CC(c2ccccc2)CC1=O] |
| 131 | 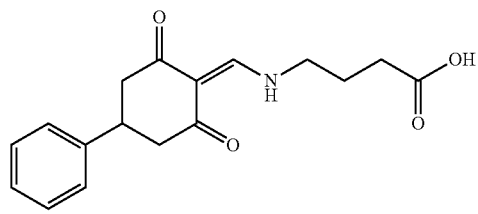 [SMILES: O=C(O)CCCNC=C1C(=O)CC(c2ccccc2)CC1=O] |

| No. | Structures |
|---|---|
| 132 | 2-{[(4-hydroxybutyl)amino]methylidene}-5-phenylcyclohexane-1,3-dione |
| 133 | 2-{[(3-chloropropyl)amino]methylidene}-5-phenylcyclohexane-1,3-dione |
| 134 | 2-({[2-(2-hydroxyethoxy)ethyl]amino}methylidene)-5-phenylcyclohexane-1,3-dione |
| 135 | 2-({[2-(1H-indol-3-yl)ethyl]amino}methylidene)-5-phenylcyclohexane-1,3-dione |
| 136 | 2-{[(4-hydroxycyclohexyl)amino]methylidene}-5-phenylcyclohexane-1,3-dione |
| 137 | 2-{[(2-oxothiolan-3-yl)amino]methylidene}-5-phenylcyclohexane-1,3-dione |

-continued
| No. | Structures |
|---|---|
| 138 | 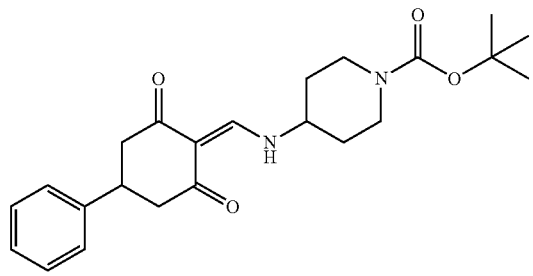 [SMILES: CC(C)(C)OC(=O)N1CCC(NC=C2C(=O)CC(c3ccccc3)CC2=O)CC1] |
| 139 | 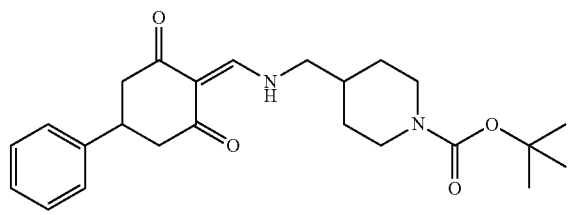 [SMILES: CC(C)(C)OC(=O)N1CCC(CNC=C2C(=O)CC(c3ccccc3)CC2=O)CC1] |
| 140 | 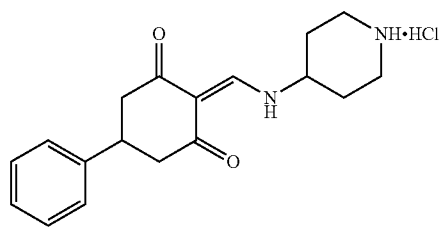 |
| 141 | 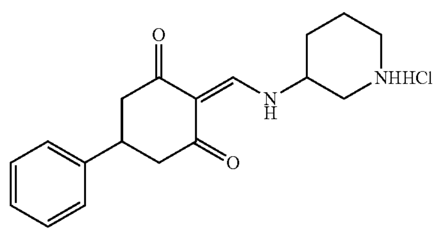 |
| 142 | 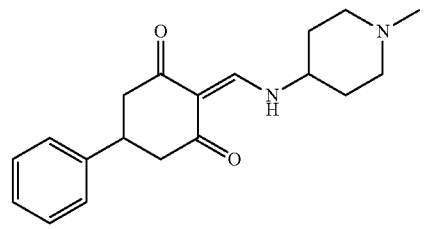 [SMILES: CN1CCC(NC=C2C(=O)CC(c3ccccc3)CC2=O)CC1] |
| 143 | 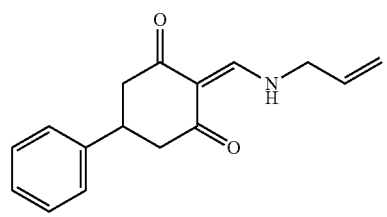 [SMILES: C=CCNC=C1C(=O)CC(c2ccccc2)CC1=O] |

| No. | Structures |
|---|---|
| 145 | 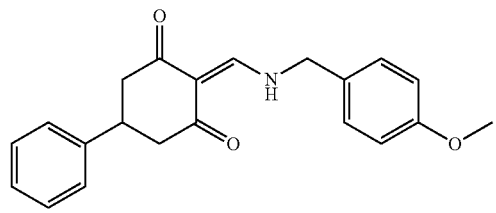 [SMILES: COc1ccc(CNC=C2C(=O)CC(c3ccccc3)CC2=O)cc1] |
| 146 | 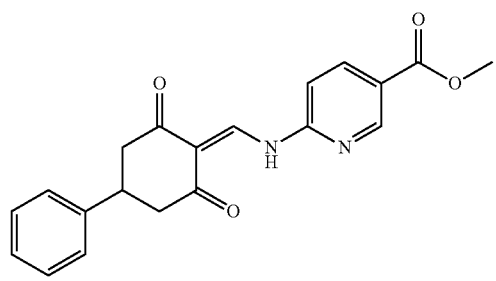 [SMILES: COC(=O)c1ccc(NC=C2C(=O)CC(c3ccccc3)CC2=O)nc1] |
| 147 | 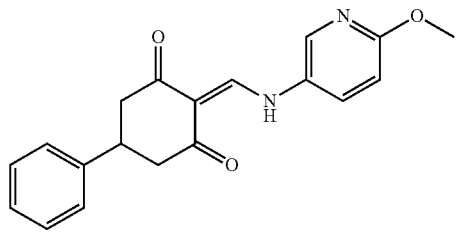 [SMILES: COc1ccc(NC=C2C(=O)CC(c3ccccc3)CC2=O)cn1] |
| 148 | 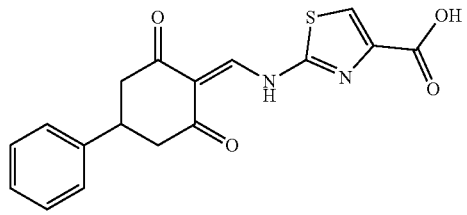 [SMILES: O=C1CC(c2ccccc2)CC(=O)C1=CNc1nc(C(=O)O)cs1] |
| 149 | 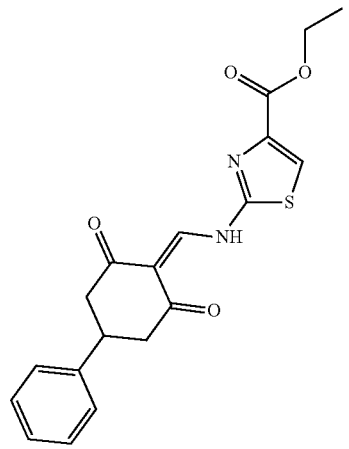 [SMILES: CCOC(=O)c1csc(NC=C2C(=O)CC(c3ccccc3)CC2=O)n1] |

| No. | Structures |
|---|---|
| 150 | 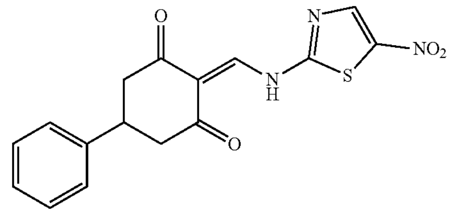 [SMILES: O=C1CC(c2ccccc2)CC(=O)C1=CNc1ncc([N+](=O)[O-])s1] |
| 155 | 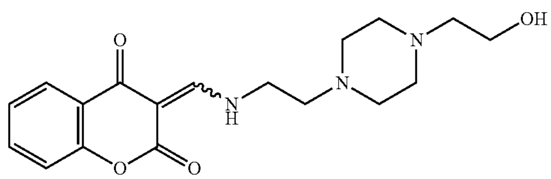 [SMILES: O=C1Oc2ccccc2C(=O)C1=CNCCN1CCN(CCO)CC1] |
| 156 | 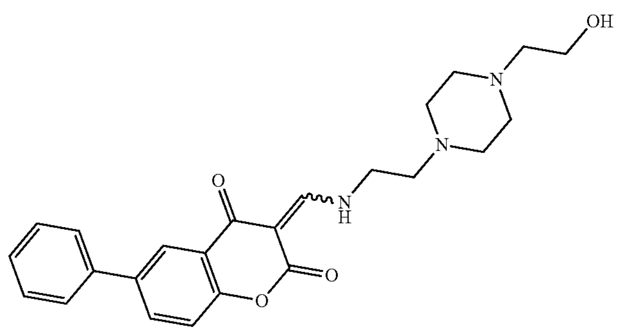 [SMILES: O=C1Oc2ccc(-c3ccccc3)cc2C(=O)C1=CNCCN1CCN(CCO)CC1] |
| 158 | 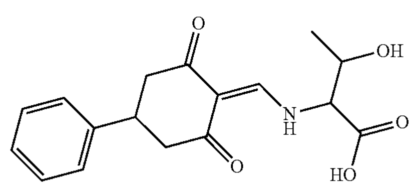 [SMILES: CC(O)C(NC=C1C(=O)CC(c2ccccc2)CC1=O)C(=O)O] |
| 160 | 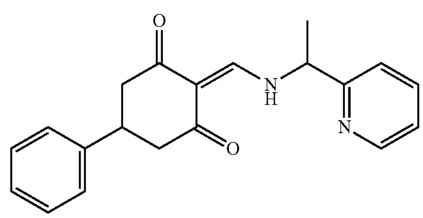 [SMILES: CC(NC=C1C(=O)CC(c2ccccc2)CC1=O)c1ccccn1] |
| 161 | 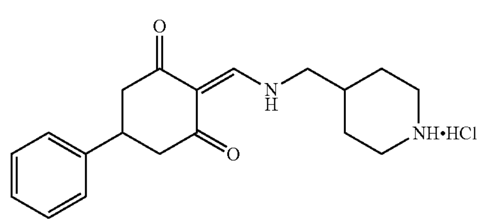 |
| 162 | 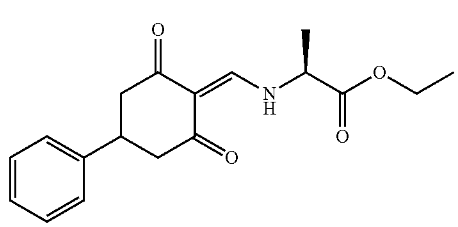 [SMILES: CCOC(=O)[C@H](C)NC=C1C(=O)CC(c2ccccc2)CC1=O] |

-continued

| No. | Structures |
|---|---|
| 163 | 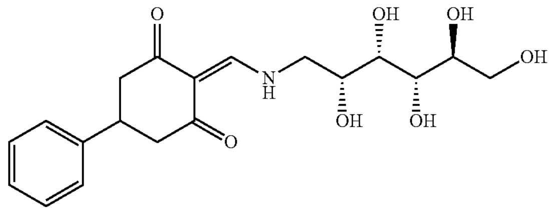 [SMILES: O=C1CC(c2ccccc2)CC(=O)C1=CNC[C@@H](O)[C@H](O)[C@@H](O)[C@@H](O)CO] |
| 164 | 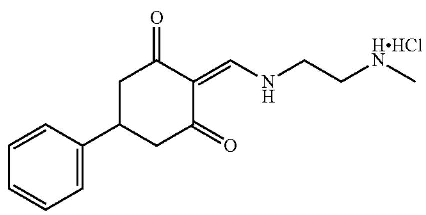 |
| 165 | 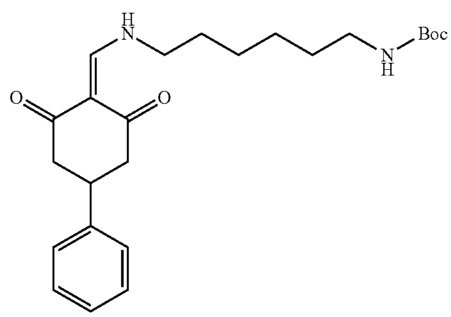 [SMILES: CC(C)(C)OC(=O)NCCCCCCNC=C1C(=O)CC(c2ccccc2)CC1=O] |
| 169 | 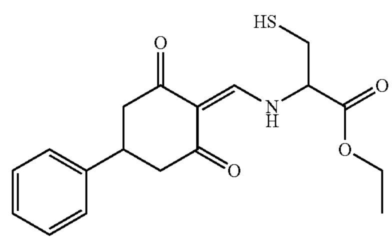 [SMILES: CCOC(=O)C(CS)NC=C1C(=O)CC(c2ccccc2)CC1=O] |
| 170 | 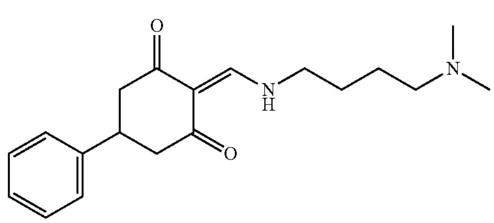 [SMILES: CN(C)CCCCNC=C1C(=O)CC(c2ccccc2)CC1=O] |
| 171 | 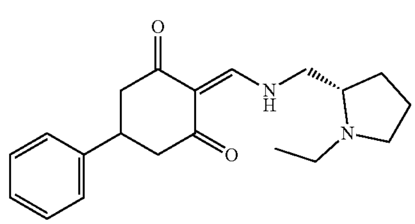 [SMILES: CCN1CCC[C@H]1CNC=C1C(=O)CC(c2ccccc2)CC1=O] |

-continued
| No. | Structures |
|---|---|
| 172 | 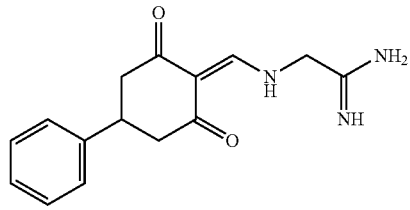 [SMILES: N=C(N)CNC=C1C(=O)CC(c2ccccc2)CC1=O] |
| 173 | 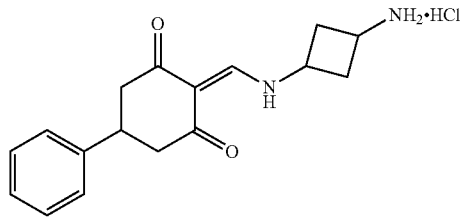 |
| 174 | 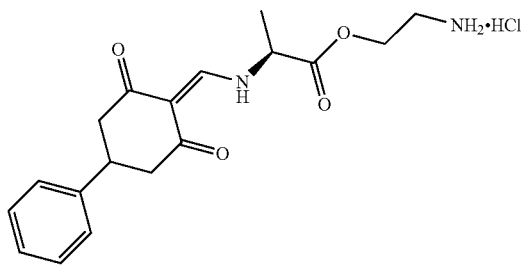 |
| 175 | 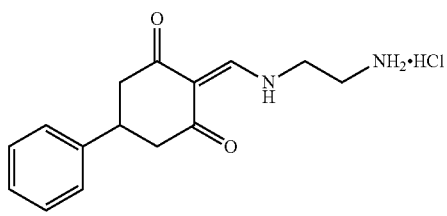 |
| 176 | 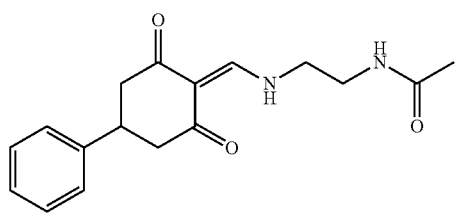 [SMILES: CC(=O)NCCNC=C1C(=O)CC(c2ccccc2)CC1=O] |
| 177 | 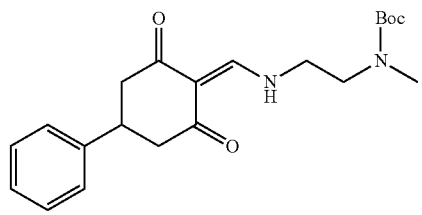 [SMILES: CN(CCNC=C1C(=O)CC(c2ccccc2)CC1=O)C(=O)OC(C)(C)C] |

-continued

| No. | Structures |
|---|---|
| 178 | 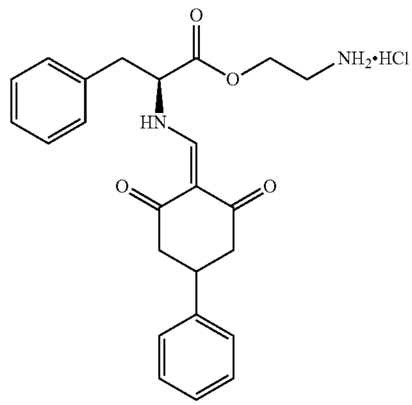 |
| 180 | 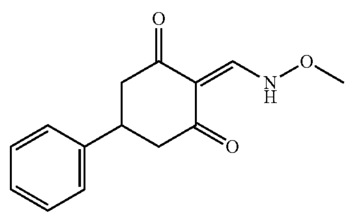 [SMILES: CONC=C1C(=O)CC(c2ccccc2)CC1=O] |
| 182 | 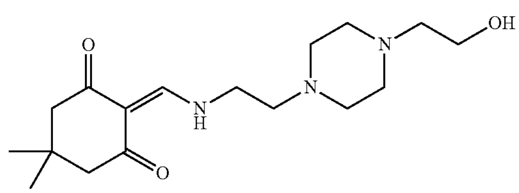 [SMILES: CC1(C)CC(=O)C(=CNCCN2CCN(CCO)CC2)C(=O)C1] |
| 183 | 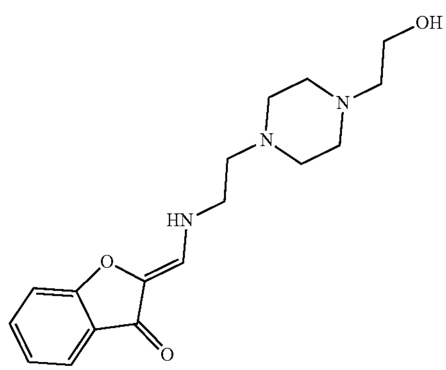 [SMILES: O=C1/C(=C/NCCN2CCN(CCO)CC2)Oc2ccccc21] |
| 184 | 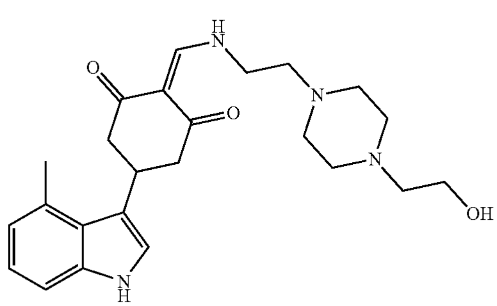 [SMILES: Cc1cccc2[nH]cc(C3CC(=O)C(=CNCCN4CCN(CCO)CC4)C(=O)C3)c12] |

| No. | Structures |
|---|---|
| 185 | 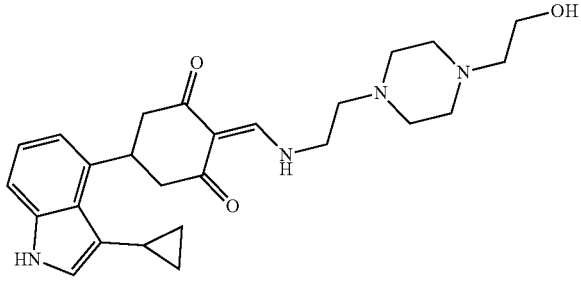 [SMILES: O=C1CC(c2cccc3[nH]cc(C4CC4)c23)CC(=O)C1=CNCCN1CCN(CCO)CC1] |
| 186 | 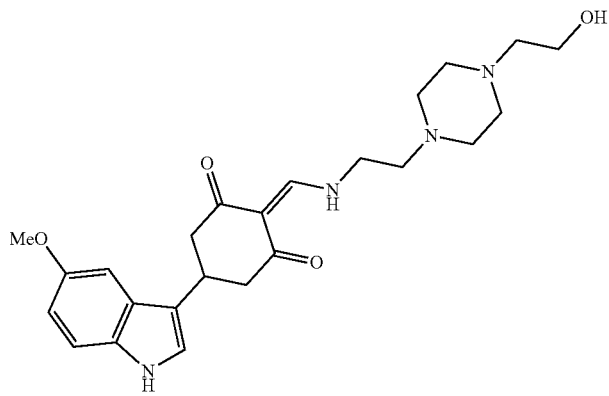 [SMILES: COc1ccc2[nH]cc(C3CC(=O)C(=CNCCN4CCN(CCO)CC4)C(=O)C3)c2c1] |
| 187 | 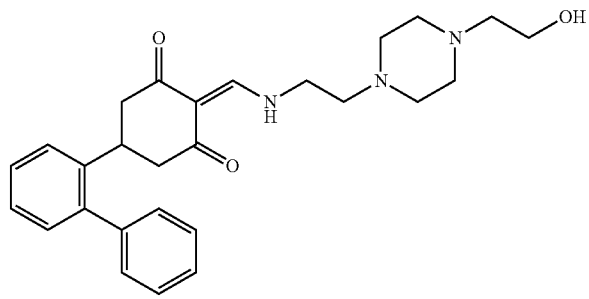 [SMILES: O=C1CC(c2ccccc2-c2ccccc2)CC(=O)C1=CNCCN1CCN(CCO)CC1] |
| 188 | 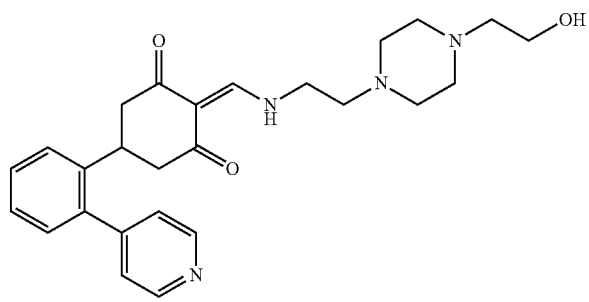 [SMILES: O=C1CC(c2ccccc2-c2ccncc2)CC(=O)C1=CNCCN1CCN(CCO)CC1] |
| 189 | 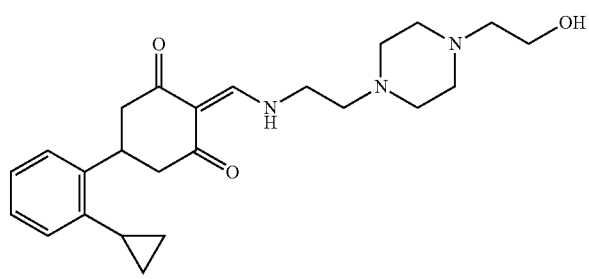 [SMILES: O=C1CC(c2ccccc2C2CC2)CC(=O)C1=CNCCN1CCN(CCO)CC1] |

| No. | Structures |
|---|---|
| 190 | 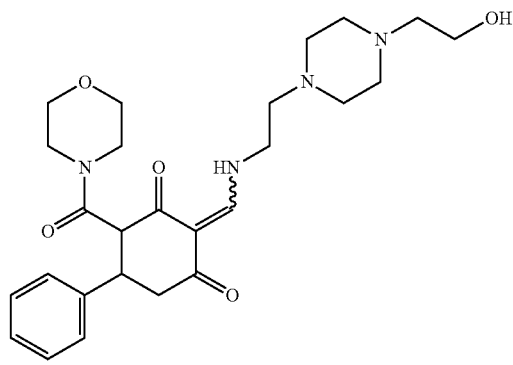 [SMILES: O=C1CC(c2ccccc2)C(C(=O)N2CCOCC2)C(=O)C1=CNCCN1CCN(CCO)CC1] |
| 191 | 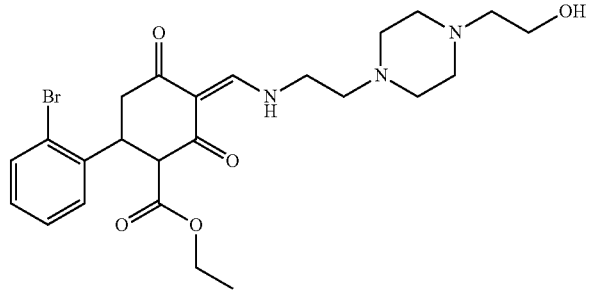 [SMILES: CCOC(=O)C1C(=O)/C(=C\NCCN2CCN(CCO)CC2)C(=O)CC1c1ccccc1Br] |
| 192 | 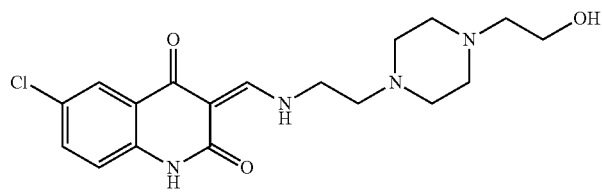 [SMILES: O=C1Nc2ccc(Cl)cc2C(=O)/C1=C/NCCN1CCN(CCO)CC1] |
| 193 | 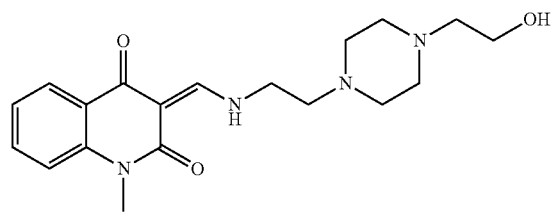 [SMILES: CN1C(=O)/C(=C\NCCN2CCN(CCO)CC2)C(=O)c2ccccc21] |
| 194 | 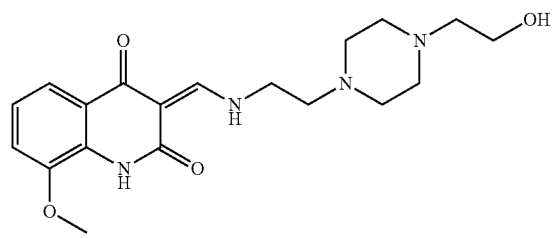 [SMILES: COc1cccc2c1NC(=O)/C(=C\NCCN1CCN(CCO)CC1)C2=O] |
| 195 | 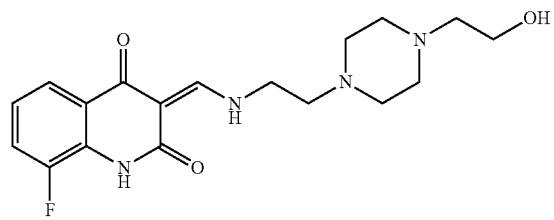 [SMILES: O=C1Nc2c(F)cccc2C(=O)/C1=C/NCCN1CCN(CCO)CC1] |

-continued

| No. | Structures |
|---|---|
| 196 | 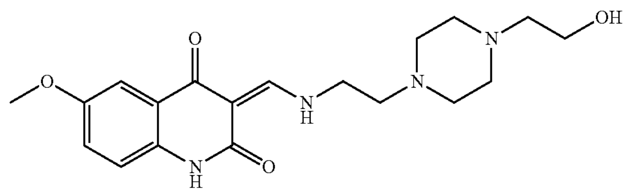 [SMILES: COc1ccc2c(c1)C(=O)/C(=C/NCCN1CCN(CCO)CC1)C(=O)N2] |
| 197 | 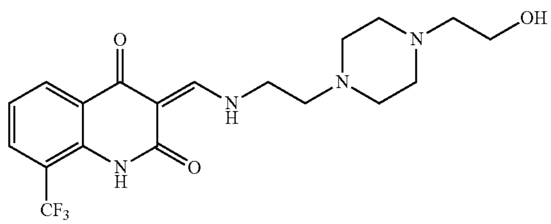 |
| 200 | 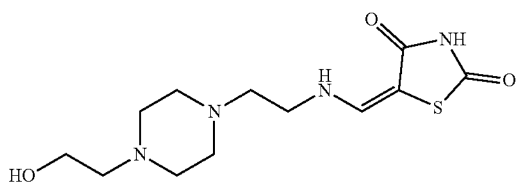 [SMILES: O=C1NC(=O)/C(=C\NCCN2CCN(CCO)CC2)S1] |
| 201 | 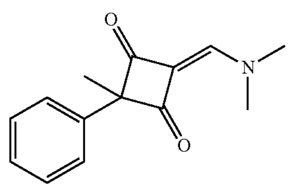 [SMILES: CN(C)C=C1C(=O)C(C)(c2ccccc2)C1=O] |
| 202 | 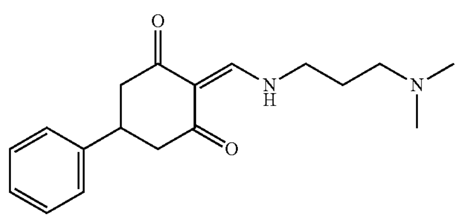 [SMILES: CN(C)CCCNC=C1C(=O)CC(c2ccccc2)CC1=O] |
| 203 | 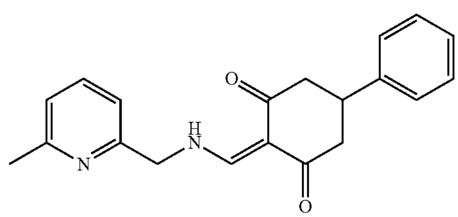 [SMILES: Cc1cccc(CNC=C2C(=O)CC(c3ccccc3)CC2=O)n1] |
| 204 | 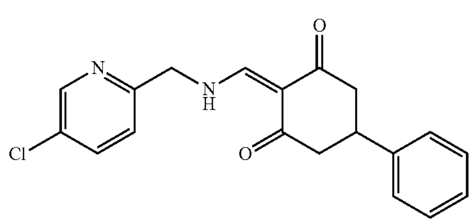 [SMILES: O=C1CC(c2ccccc2)CC(=O)C1=CNCc1ccc(Cl)cn1] |

| No. | Structures |
|---|---|
| 205 | 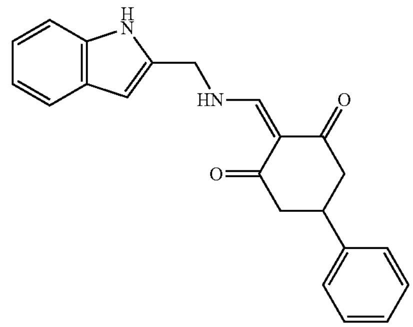 [SMILES: O=C1CC(c2ccccc2)CC(=O)C1=CNCc1cc2ccccc2[nH]1] |
| 206 | 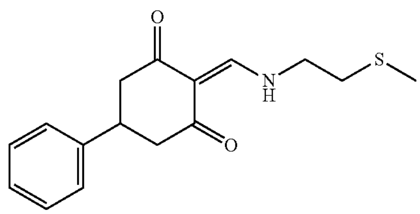 [SMILES: CSCCNC=C1C(=O)CC(c2ccccc2)CC1=O] |
| 207 | 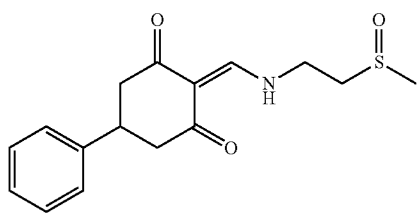 [SMILES: CS(=O)CCNC=C1C(=O)CC(c2ccccc2)CC1=O] |
| 208 | 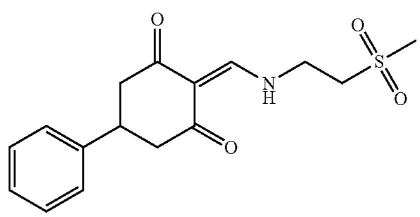 [SMILES: CS(=O)(=O)CCNC=C1C(=O)CC(c2ccccc2)CC1=O] |
| 209 | 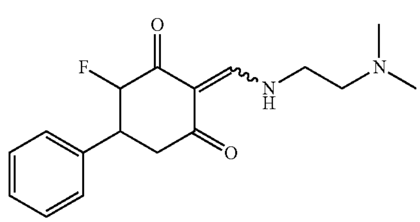 [SMILES: CN(C)CCNC=C1C(=O)CC(c2ccccc2)C(F)C1=O] |
| 210 | 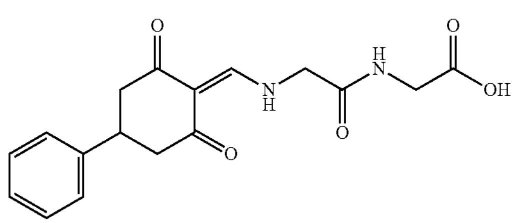 [SMILES: O=C(O)CNC(=O)CNC=C1C(=O)CC(c2ccccc2)CC1=O] |

| No. | Structures |
|---|---|
| 211 | 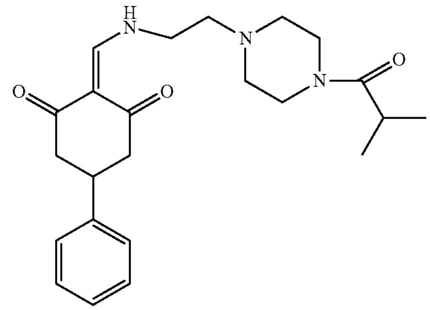 |
| 212 | 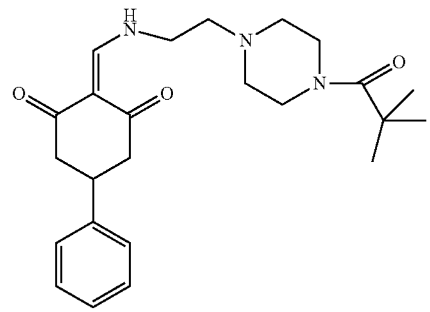 [SMILES: CC(C)(C)C(=O)N1CCN(CCNC=C2C(=O)CC(c3ccccc3)CC2=O)CC1] |
| 213 | 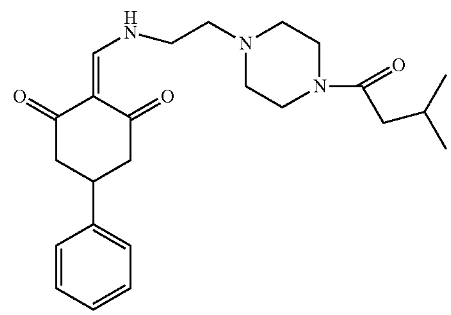 [SMILES: CC(C)CC(=O)N1CCN(CCNC=C2C(=O)CC(c3ccccc3)CC2=O)CC1] |
| 214 | 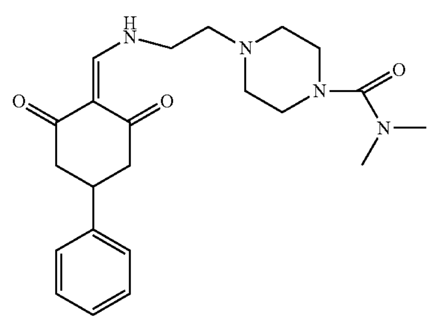 |
| 215 | 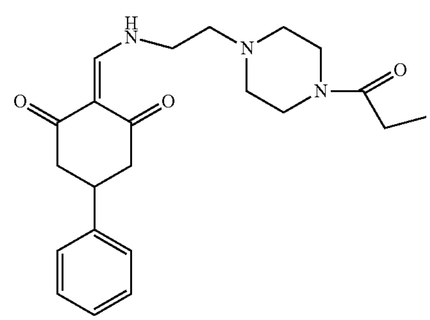 [SMILES: CCC(=O)N1CCN(CCNC=C2C(=O)CC(c3ccccc3)CC2=O)CC1] |

-continued
| No. | Structures |
|---|---|
| 216 | 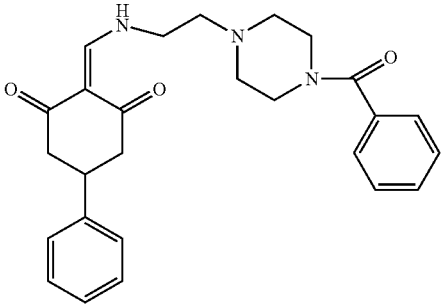 [SMILES: O=C1CC(c2ccccc2)CC(=O)C1=CNCCN1CCN(C(=O)c2ccccc2)CC1] |
| 217 | 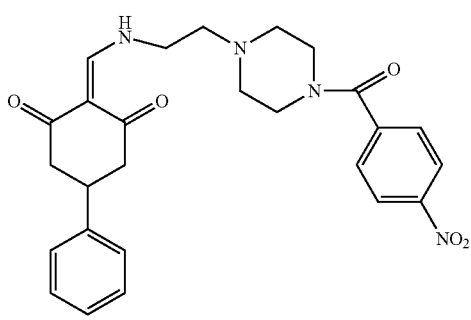 [SMILES: O=C1CC(c2ccccc2)CC(=O)C1=CNCCN1CCN(C(=O)c2ccc([N+](=O)[O-])cc2)CC1] |
| 218 | 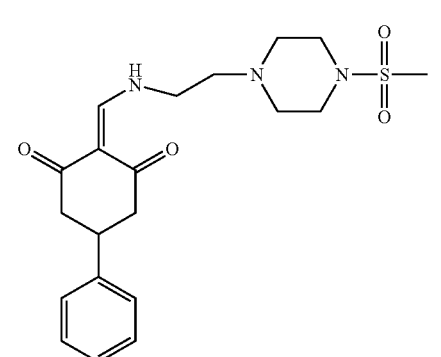 |
| 219 | 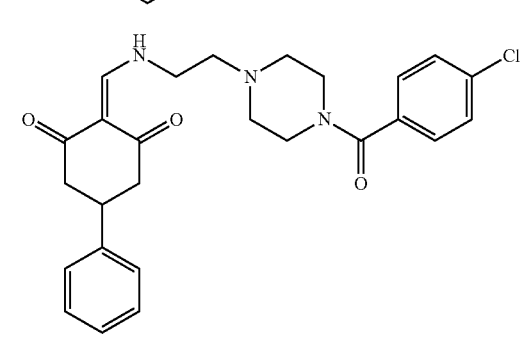 |
| 220 | 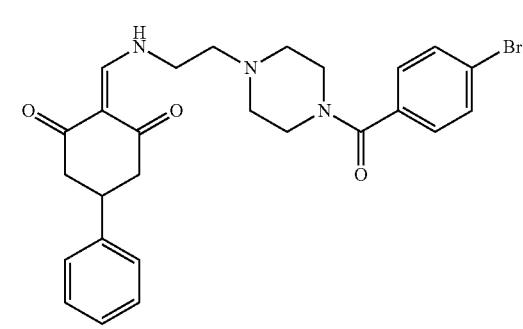 [SMILES: O=C1CC(c2ccccc2)CC(=O)C1=CNCCN1CCN(C(=O)c2ccc(Br)cc2)CC1] |

| No. | Structures |
|---|---|
| 221 | 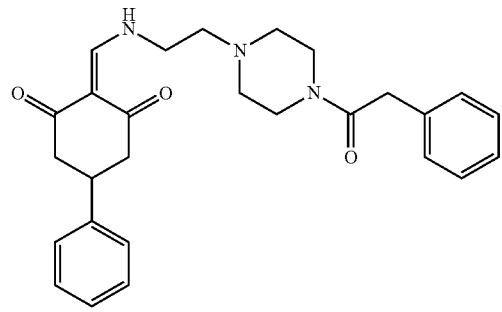 [SMILES: O=C1CC(c2ccccc2)CC(=O)C1=CNCCN1CCN(C(=O)Cc2ccccc2)CC1] |
| 222 | 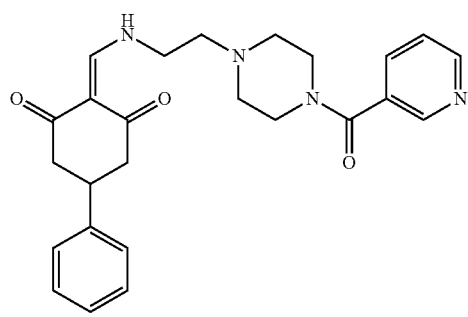 [SMILES: O=C1CC(c2ccccc2)CC(=O)C1=CNCCN1CCN(C(=O)c2cccnc2)CC1] |
| 223 | 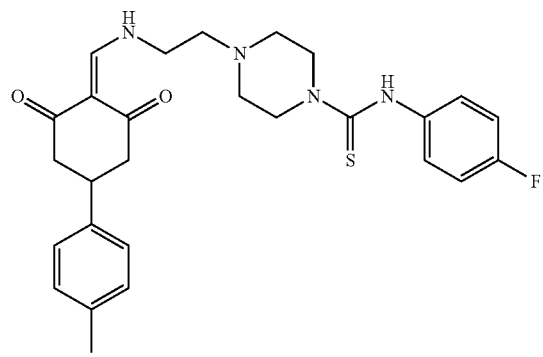 [SMILES: Cc1ccc(C2CC(=O)C(=CNCCN3CCN(C(=S)Nc4ccc(F)cc4)CC3)C(=O)C2)cc1] |
| 224 | 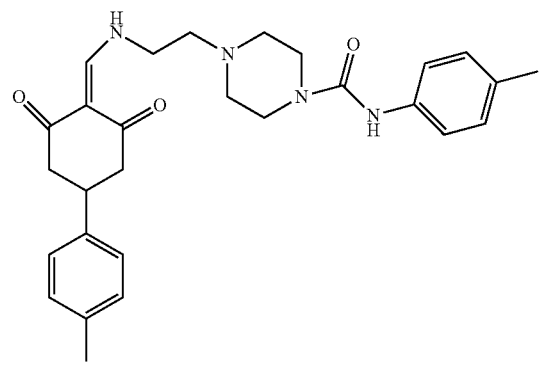 [SMILES: Cc1ccc(NC(=O)N2CCN(CCNC=C3C(=O)CC(c4ccc(C)cc4)CC3=O)CC2)cc1] |

| No. | Structures |
|---|---|
| 225 | 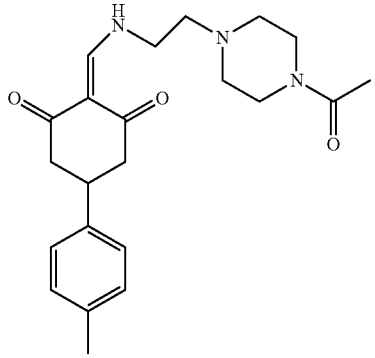 [SMILES: CC(=O)N1CCN(CCNC=C2C(=O)CC(c3ccc(C)cc3)CC2=O)CC1] |
| 226 | 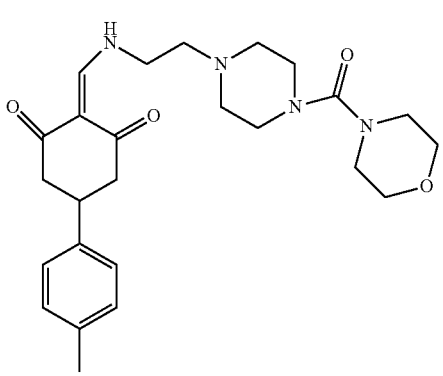 [SMILES: Cc1ccc(C2CC(=O)C(=CNCCN3CCN(C(=O)N4CCOCC4)CC3)C(=O)C2)cc1] |
| 227 | 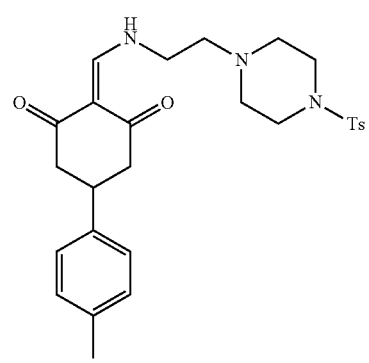 [SMILES: Cc1ccc(C2CC(=O)C(=CNCCN3CCN(S(=O)(=O)c4ccc(C)cc4)CC3)C(=O)C2)cc1] |
| 228 | 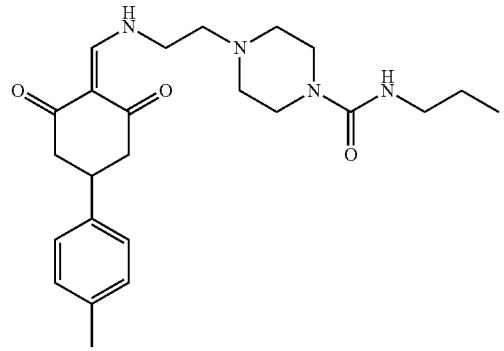 [SMILES: CCCNC(=O)N1CCN(CCNC=C2C(=O)CC(c3ccc(C)cc3)CC2=O)CC1] |

-continued
| No. | Structures |
|---|---|
| 229 | 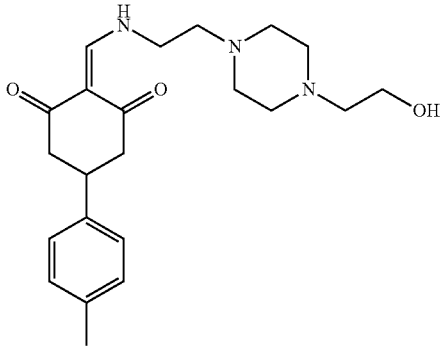 [SMILES: Cc1ccc(C2CC(=O)C(=CNCCN3CCN(CCO)CC3)C(=O)C2)cc1] |
| 230 | 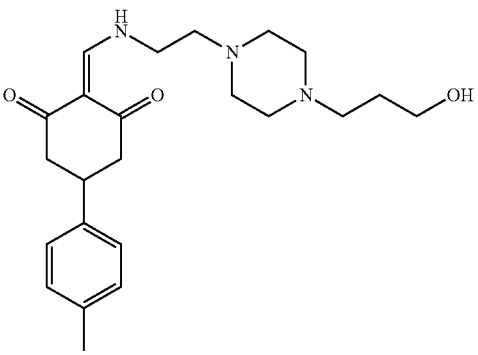 [SMILES: Cc1ccc(C2CC(=O)C(=CNCCN3CCN(CCCO)CC3)C(=O)C2)cc1] |
| 231 | 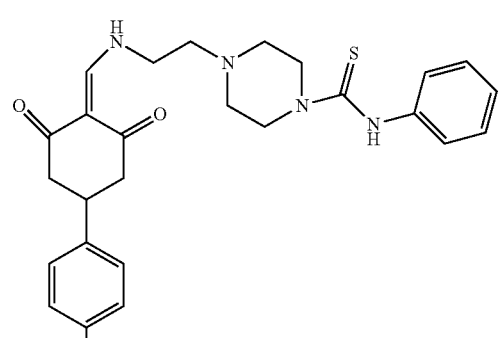 |
| 232 | 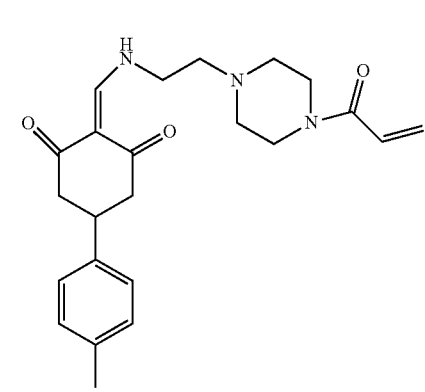 [SMILES: C=CC(=O)N1CCN(CCNC=C2C(=O)CC(c3ccc(C)cc3)CC2=O)CC1] |

| No. | Structures |
|---|---|
| 233 | 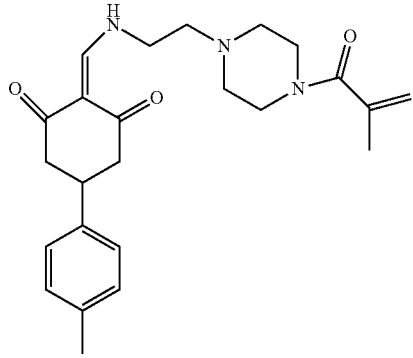 [SMILES: C=C(C)C(=O)N1CCN(CCNC=C2C(=O)CC(c3ccc(C)cc3)CC2=O)CC1] |
| 236 | 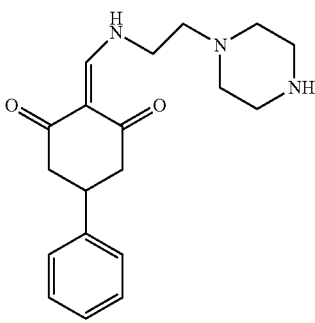 [SMILES: O=C1CC(c2ccccc2)CC(=O)C1=CNCCN1CCNCC1] |
| 237 | 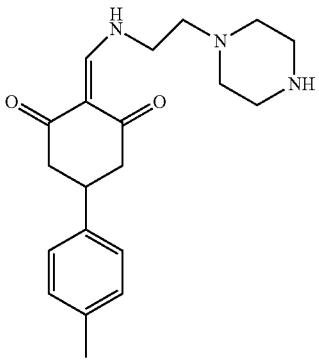 [SMILES: Cc1ccc(C2CC(=O)C(=CNCCN3CCNCC3)C(=O)C2)cc1] |
| 238 | 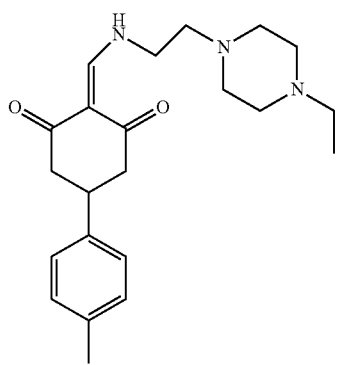 [SMILES: CCN1CCN(CCNC=C2C(=O)CC(c3ccc(C)cc3)CC2=O)CC1] |

| No. | Structures |
|---|---|
| 239 | 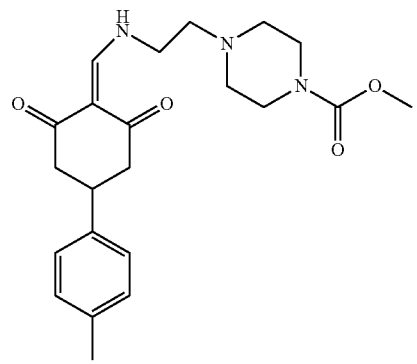 [SMILES: COC(=O)N1CCN(CCNC=C2C(=O)CC(c3ccc(C)cc3)CC2=O)CC1] |
| 240 | 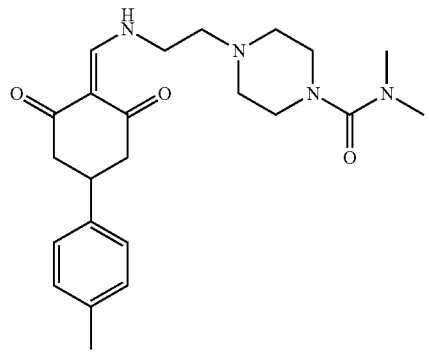 [SMILES: Cc1ccc(C2CC(=O)C(=CNCCN3CCN(C(=O)N(C)C)CC3)C(=O)C2)cc1] |
| 242 | 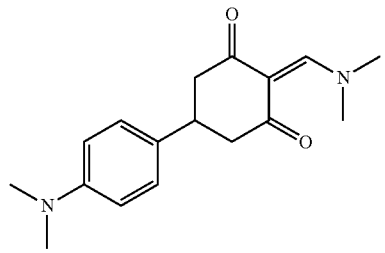 |
| 245 | 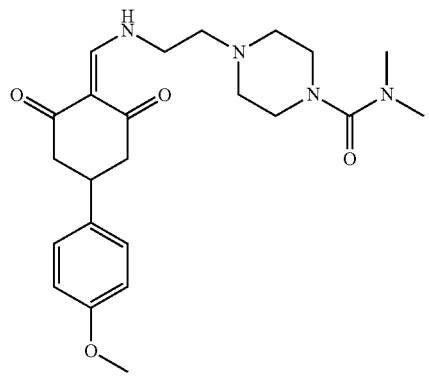 [SMILES: COc1ccc(C2CC(=O)C(=CNCCN3CCN(C(=O)N(C)C)CC3)C(=O)C2)cc1] |

-continued
| No. | Structures |
|---|---|
| 246 | 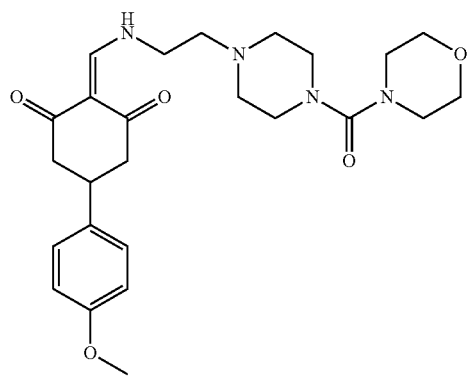 [SMILES: COc1ccc(C2CC(=O)C(=CNCCN3CCN(C(=O)N4CCOCC4)CC3)C(=O)C2)cc1] |
| 247 | 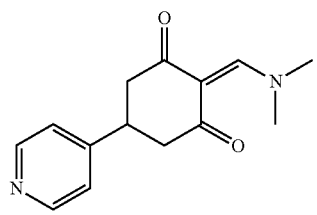 |
| 248 | 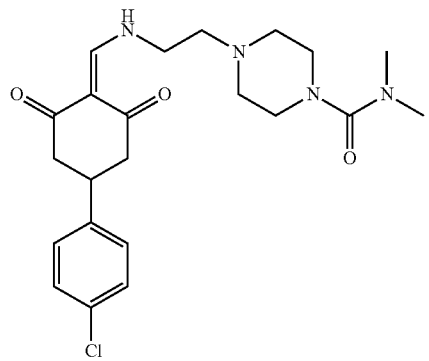 [SMILES: CN(C)C(=O)N1CCN(CCNC=C2C(=O)CC(c3ccc(Cl)cc3)CC2=O)CC1] |
| 249 | 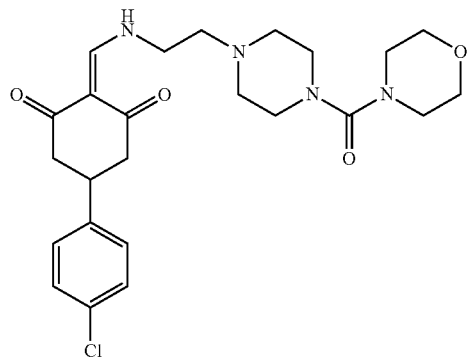 [SMILES: O=C1CC(c2ccc(Cl)cc2)CC(=O)C1=CNCCN1CCN(C(=O)N2CCOCC2)CC1] |
| 251 | 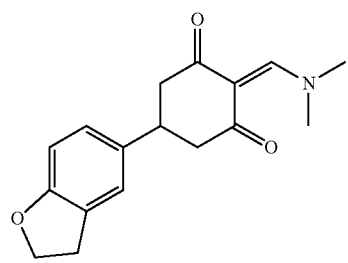 [SMILES: CN(C)C=C1C(=O)CC(c2ccc3c(c2)CCO3)CC1=O] |

-continued
| No. | Structures |
|---|---|
| 252 | 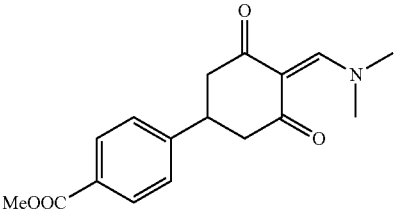 [SMILES: COC(=O)c1ccc(C2CC(=O)C(=CN(C)C)C(=O)C2)cc1] |
| 253 | 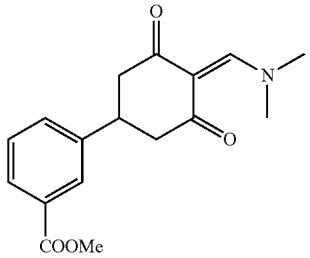 [SMILES: COC(=O)c1cccc(C2CC(=O)C(=CN(C)C)C(=O)C2)c1] |
| 254 | 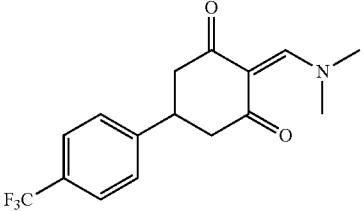 [SMILES: CN(C)C=C1C(=O)CC(c2ccc(C(F)(F)F)cc2)CC1=O] |
| 255 | 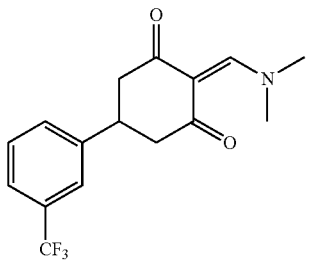 [SMILES: CN(C)C=C1C(=O)CC(c2cccc(C(F)(F)F)c2)CC1=O] |
| 256 | 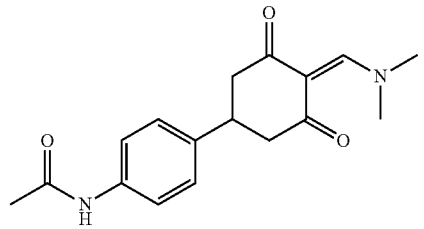 [SMILES: CC(=O)Nc1ccc(C2CC(=O)C(=CN(C)C)C(=O)C2)cc1] |
| 257 | 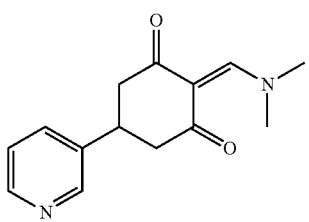 [SMILES: CN(C)C=C1C(=O)CC(c2cccnc2)CC1=O] |

-continued

| No. | Structures |
|---|---|
| 258 | (structure) |
| 259 | (structure) |
| 260 | (structure) |
| 262 | (structure) |
| 263 | (structure) |

| No. | Structures |
|---|---|
| 265 | 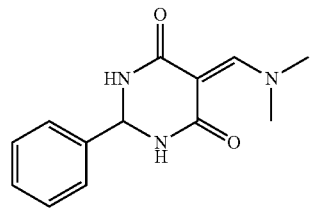 [SMILES: CN(C)C=C1C(=O)NC(c2ccccc2)NC1=O] |
| 266 | 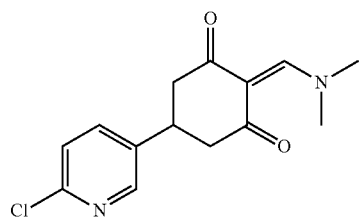 [SMILES: CN(C)C=C1C(=O)CC(c2ccc(Cl)nc2)CC1=O] |
| 267 | 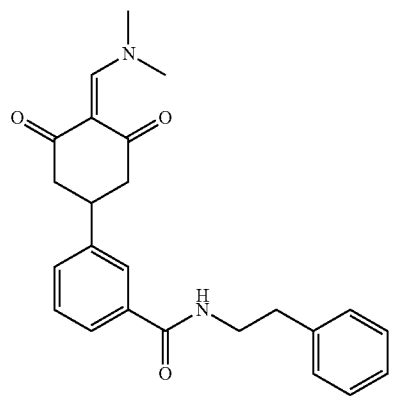 [SMILES: CN(C)C=C1C(=O)CC(c2cccc(C(=O)NCCc3ccccc3)c2)CC1=O] |
| 268 | 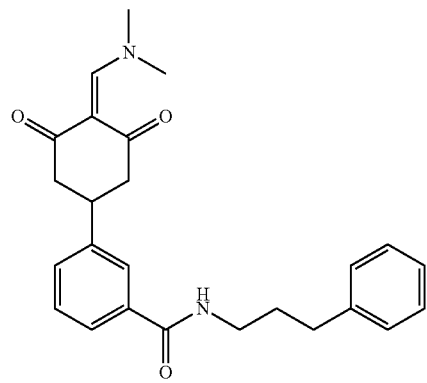 [SMILES: CN(C)C=C1C(=O)CC(c2cccc(C(=O)NCCCc3ccccc3)c2)CC1=O] |

| No. | Structures |
|---|---|
| 269 | 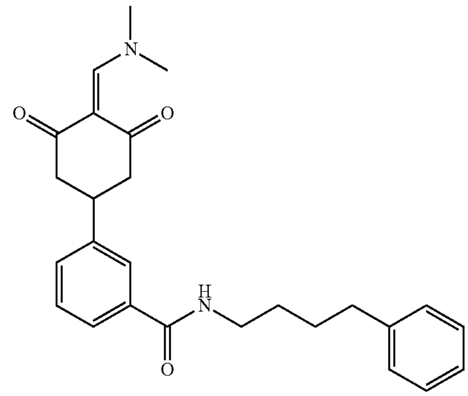 [SMILES: CN(C)C=C1C(=O)CC(c2cccc(C(=O)NCCCCc3ccccc3)c2)CC1=O] |
| 270 | 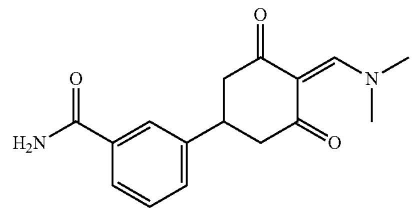 [SMILES: CN(C)C=C1C(=O)CC(c2cccc(C(N)=O)c2)CC1=O] |
| 271 | 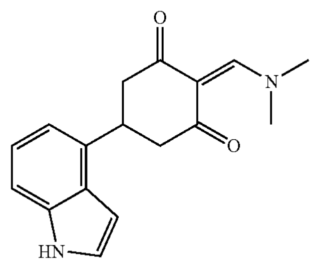 [SMILES: CN(C)C=C1C(=O)CC(c2cccc3[nH]ccc23)CC1=O] |
| 272 | 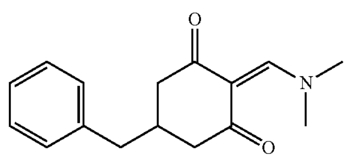 [SMILES: CN(C)C=C1C(=O)CC(Cc2ccccc2)CC1=O] |
| 273 | 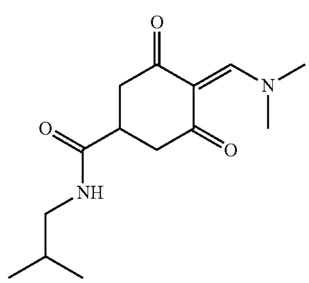 [SMILES: CC(C)CNC(=O)C1CC(=O)C(=CN(C)C)C(=O)C1] |
| 274 | 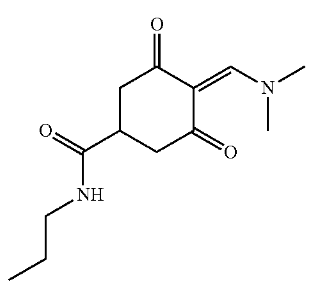 [SMILES: CCCNC(=O)C1CC(=O)C(=CN(C)C)C(=O)C1] |

-continued

| No. | Structures |
|-----|------------|
| 276 | 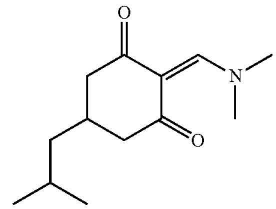 [SMILES: CC(C)CC1CC(=O)C(=CN(C)C)C(=O)C1] |
| 277 | 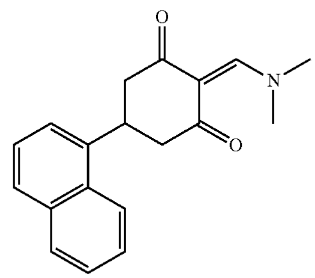 [SMILES: CN(C)C=C1C(=O)CC(c2cccc3ccccc23)CC1=O] |
| 278 | 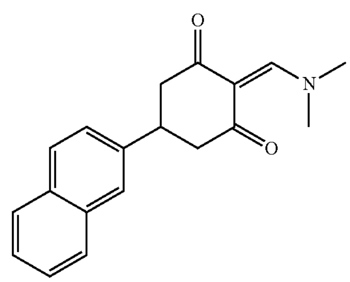 [SMILES: CN(C)C=C1C(=O)CC(c2ccc3ccccc3c2)CC1=O] |
| 279 | 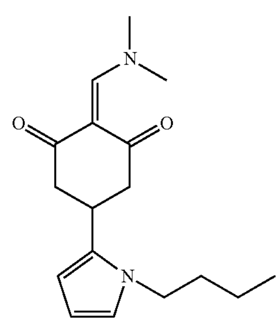 [SMILES: CCCCn1cccc1C1CC(=O)C(=CN(C)C)C(=O)C1] |
| 280 | 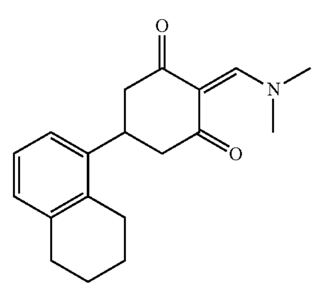 [SMILES: CN(C)C=C1C(=O)CC(c2cccc3c2CCCC3)CC1=O] |

-continued

| No. | Structures |
|---|---|
| 281 | (5-(1H-indol-5-yl)-2-((dimethylamino)methylene)cyclohexane-1,3-dione) |
| 282 | (5-(benzo[b]thiophen-3-yl)-2-((dimethylamino)methylene)cyclohexane-1,3-dione) |
| 283 | (2-((dimethylamino)methylene)-5-(1H-indol-3-yl)cyclohexane-1,3-dione) |
| 284 | (2-((dimethylamino)methylene)-5-(1-isobutyl-1H-pyrrol-2-yl)cyclohexane-1,3-dione) |
| 285 | (2-((dimethylamino)methylene)-5-(quinolin-4-yl)cyclohexane-1,3-dione) |

| No. | Structures |
|---|---|
| 286 | 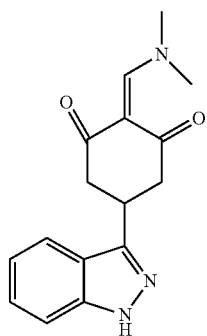 [SMILES: CN(C)C=C1C(=O)CC(c2n[nH]c3ccccc23)CC1=O] |
| 287 | 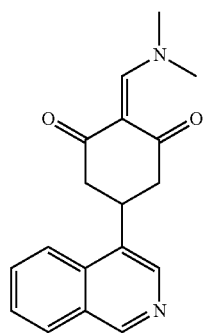 [SMILES: CN(C)C=C1C(=O)CC(c2cncc3ccccc23)CC1=O] |
| 288 | 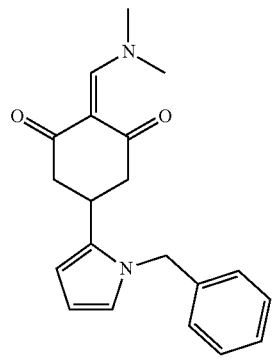 [SMILES: CN(C)C=C1C(=O)CC(c2cccn2Cc2ccccc2)CC1=O] |
| 289 | 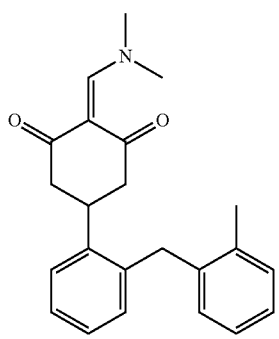 |

| No. | Structures |
|---|---|
| 290 | 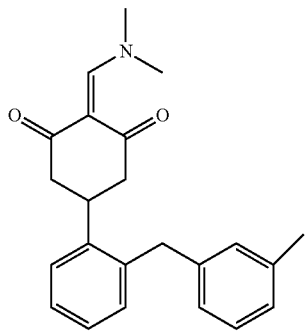 [SMILES: Cc1cccc(Cc2ccccc2C2CC(=O)C(=CN(C)C)C(=O)C2)c1] |
| 291 | 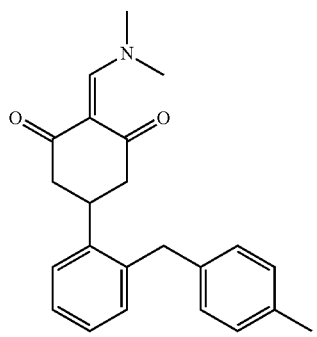 [SMILES: Cc1ccc(Cc2ccccc2C2CC(=O)C(=CN(C)C)C(=O)C2)cc1] |
| 293 | 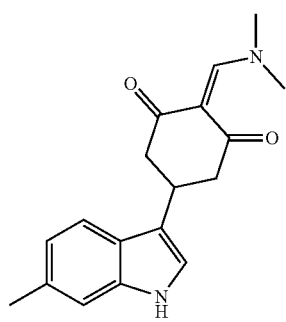 |
| 294 | 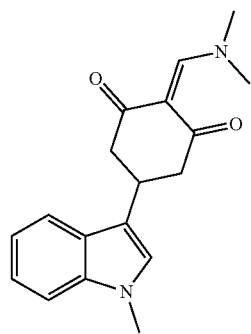 [SMILES: CN(C)C=C1C(=O)CC(c2cn(C)c3ccccc23)CC1=O] |

| No. | Structures |
|---|---|
| 295 | 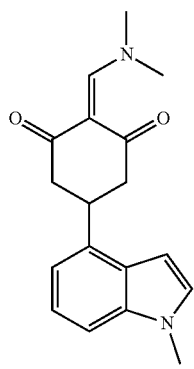 |
| 296 | 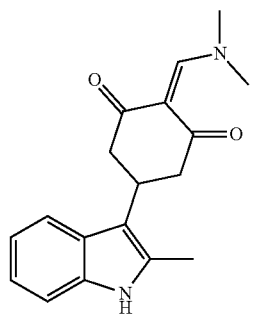 [SMILES: Cc1[nH]c2ccccc2c1C1CC(=O)C(=CN(C)C)C(=O)C1] |
| 297 | 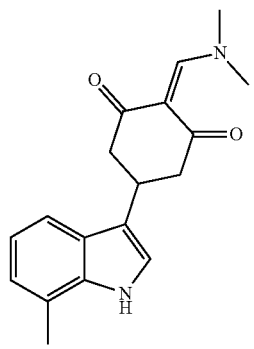 [SMILES: Cc1cccc2c(C3CC(=O)C(=CN(C)C)C(=O)C3)c[nH]c12] |
| 298 | 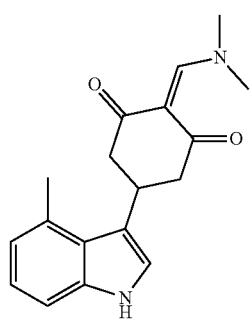 [SMILES: Cc1cccc2[nH]cc(C3CC(=O)C(=CN(C)C)C(=O)C3)c12] |

-continued
| No. | Structures |
|---|---|
| 299 | 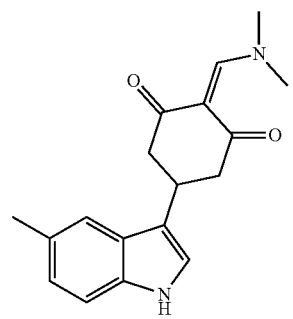 |
| 300 | 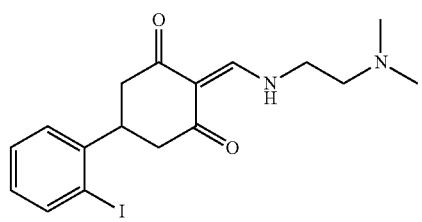 [SMILES: CN(C)CCNC=C1C(=O)CC(c2ccccc2I)CC1=O] |
| 301 | 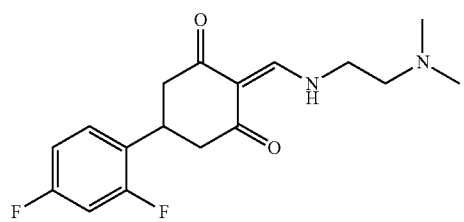 |
| 302 | 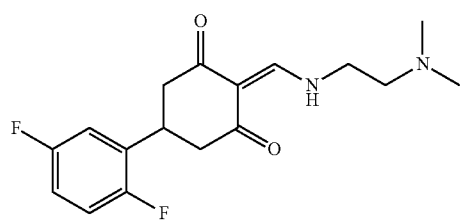 |
| 303 | 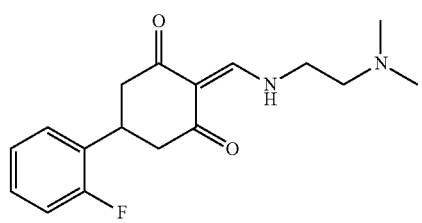 |
| 304 | 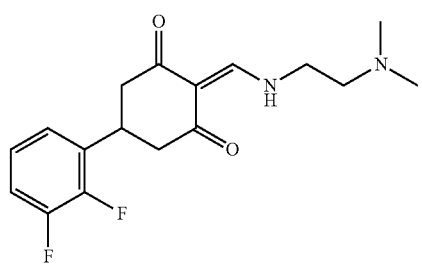 [SMILES: CN(C)CCNC=C1C(=O)CC(c2cccc(F)c2F)CC1=O] |

-continued

| No. | Structures |
|---|---|
| 305 | 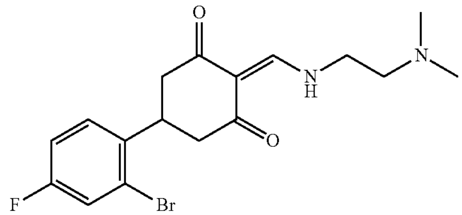 [SMILES: CN(C)CCNC=C1C(=O)CC(c2ccc(F)cc2Br)CC1=O] |
| 306 | 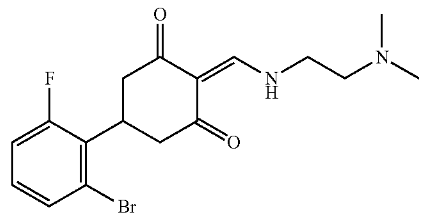 [SMILES: CN(C)CCNC=C1C(=O)CC(c2c(F)cccc2Br)CC1=O] |
| 307 | 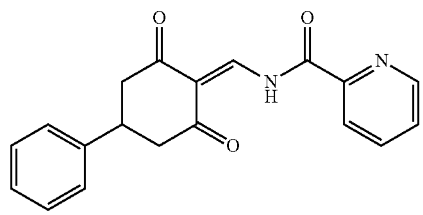 [SMILES: O=C1CC(c2ccccc2)CC(=O)C1=CNC(=O)c1ccccn1] |
| 308 | 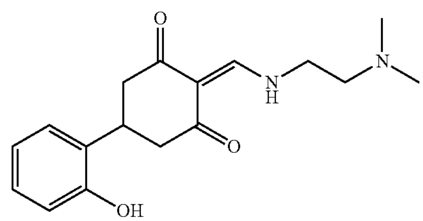 [SMILES: CN(C)CCNC=C1C(=O)CC(c2ccccc2Cl)CC1=O] |
| 309 | 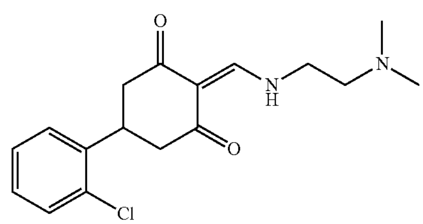 |
| 310 | 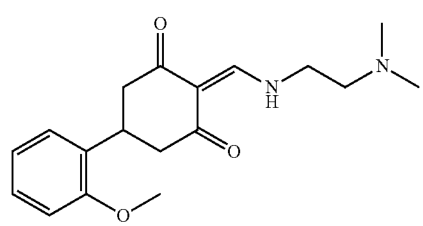 [SMILES: COc1ccccc1C1CC(=O)C(=CNCCN(C)C)C(=O)C1] |
| 311 | 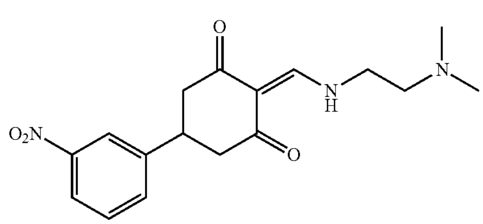 [SMILES: CN(C)CCNC=C1C(=O)CC(c2cccc([N+](=O)[O-])c2)CC1=O] |

-continued
| No. | Structures |
|---|---|
| 315 | 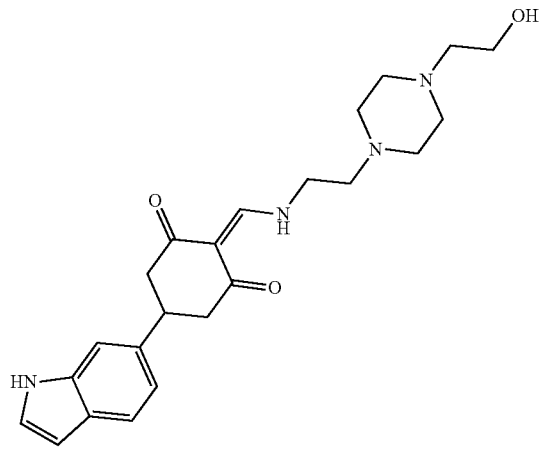 [SMILES: O=C1CC(c2ccc3cc[nH]c3c2)CC(=O)C1=CNCCN1CCN(CCO)CC1] |
| 317 | 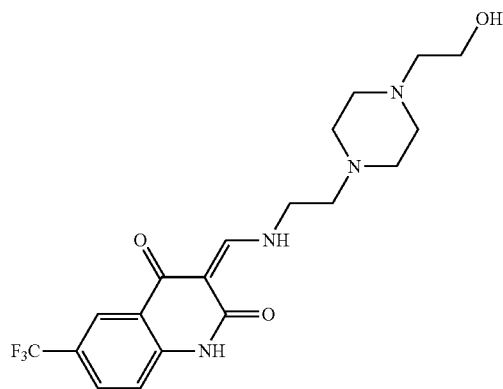 [SMILES: O=C1Nc2ccc(C(F)(F)F)cc2C(=O)/C1=C/NCCN1CCN(CCO)CC1] |
| 318 | 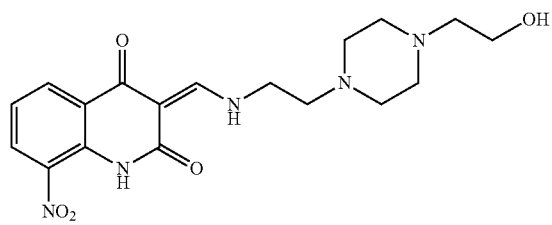 [SMILES: O=C1Nc2c(cccc2[N+](=O)[O-])C(=O)/C1=C/NCCN1CCN(CCO)CC1] |
| 320 | 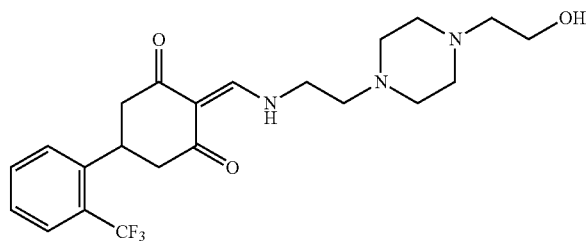 [SMILES: O=C1CC(c2ccccc2C(F)(F)F)CC(=O)C1=CNCCN1CCN(CCO)CC1] |
| 321 | 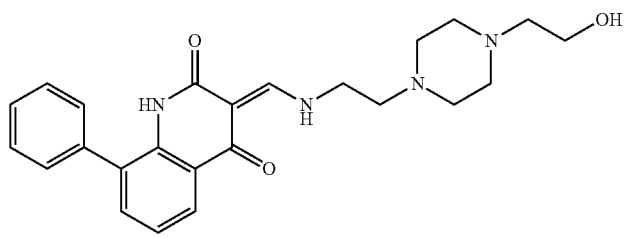 [SMILES: O=C1Nc2c(cccc2-c2ccccc2)C(=O)/C1=C\NCCN1CCN(CCO)CC1] |

| No. | Structures |
|---|---|
| 322 | 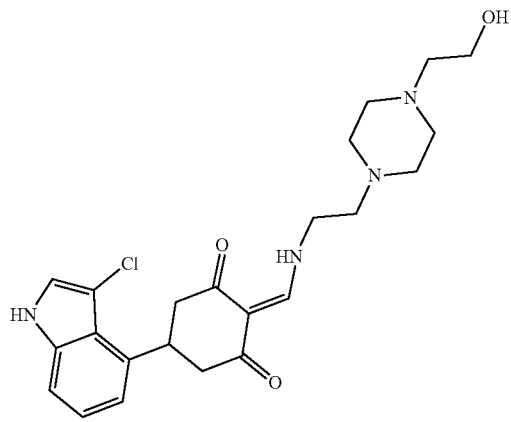 [SMILES: O=C1CC(c2cccc3[nH]cc(Cl)c23)CC(=O)C1=CNCCN1CCN(CCO)CC1] |
| 323 | 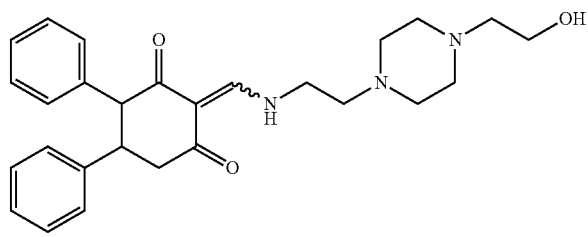 [SMILES: O=C1CC(c2ccccc2)C(c2ccccc2)C(=O)C1=CNCCN1CCN(CCO)CC1] |
| 324 | 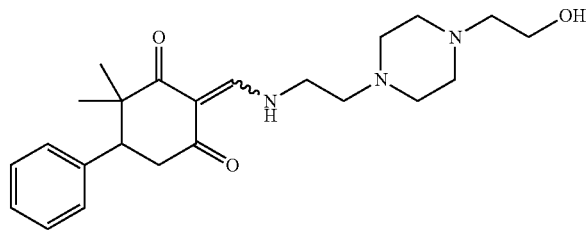 [SMILES: CC1(C)C(=O)C(=CNCCN2CCN(CCO)CC2)C(=O)CC1c1ccccc1] |
| 325 | 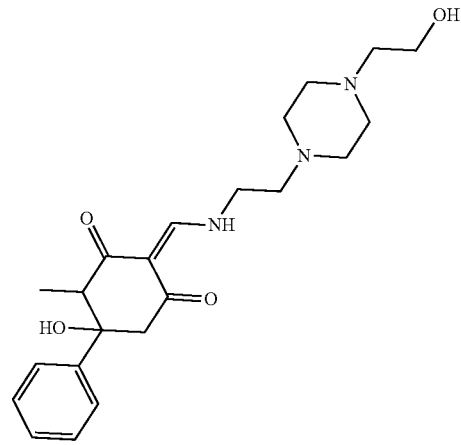 [SMILES: CC1C(=O)/C(=C/NCCN2CCN(CCO)CC2)C(=O)CC1(O)c1ccccc1] |

| No. | Structures |
|---|---|
| 326 | 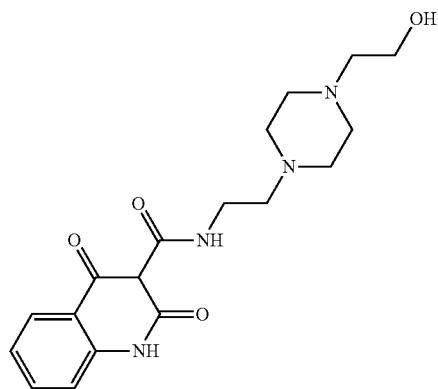 [SMILES: O=C(NCCN1CCN(CCO)CC1)C1C(=O)Nc2ccccc2C1=O] |
| 327 | 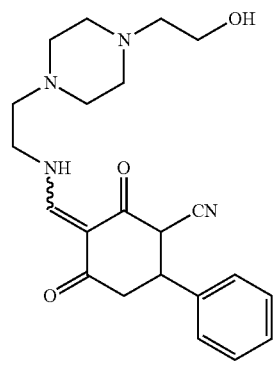 [SMILES: N#CC1C(=O)C(=CNCCN2CCN(CCO)CC2)C(=O)CC1c1ccccc1] |
| 328 | 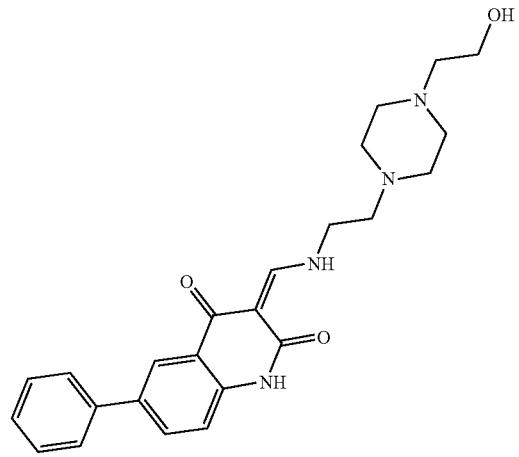 [SMILES: O=C1Nc2ccc(-c3ccccc3)cc2C(=O)/C1=C/NCCN1CCN(CCO)CC1] |

-continued
| No. | Structures |
|---|---|
| 329 | 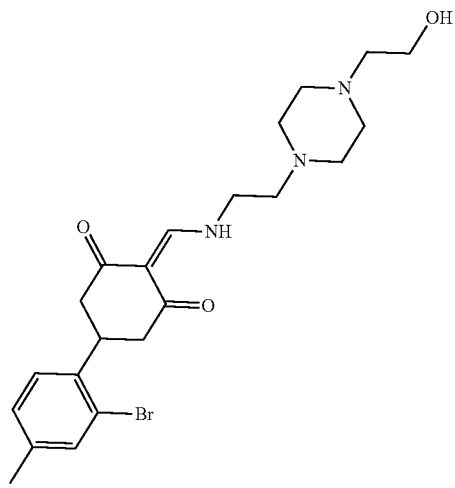 [SMILES: Cc1ccc(C2CC(=O)C(=CNCCN3CCN(CCO)CC3)C(=O)C2)c(Br)c1] |
| 330 | 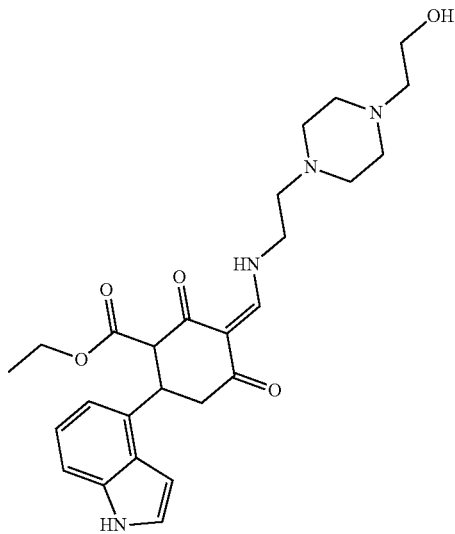 [SMILES: CCOC(=O)C1C(=O)/C(=C\NCCN2CCN(CCO)CC2)C(=O)CC1c1cccc2[nH]ccc12] |
| 331 | 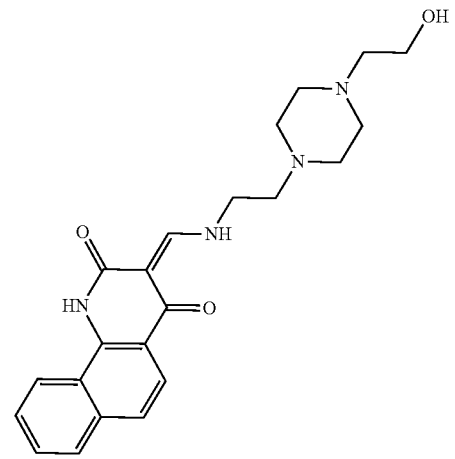 [SMILES: O=C1Nc2c(ccc3ccccc23)C(=O)/C1=C\NCCN1CCN(CCO)CC1] |

| No. | Structures |
|---|---|
| 332 | 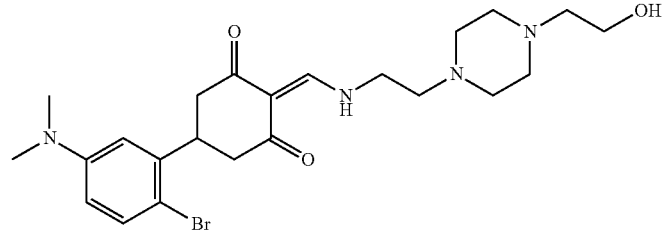 [SMILES: CN(C)c1ccc(Br)c(C2CC(=O)C(=CNCCN3CCN(CCO)CC3)C(=O)C2)c1] |
| 333 | 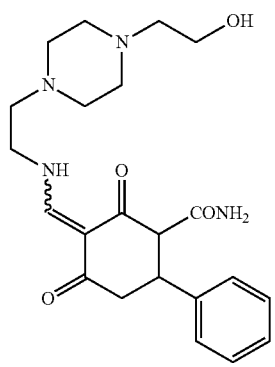 [SMILES: NC(=O)C1C(=O)C(=CNCCN2CCN(CCO)CC2)C(=O)CC1c1ccccc1] |
| 334 | 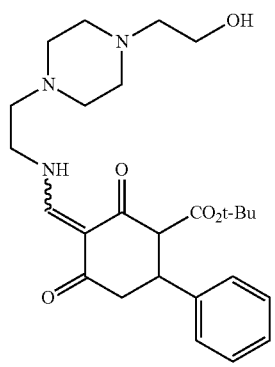 [SMILES: CC(C)(C)OC(=O)C1C(=O)C(=CNCCN2CCN(CCO)CC2)C(=O)CC1c1ccccc1] |
| 335 | 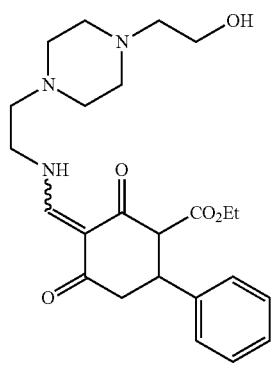 [SMILES: CCOC(=O)C1C(=O)C(=CNCCN2CCN(CCO)CC2)C(=O)CC1c1ccccc1] |

-continued
| No. | Structures |
|---|---|
| 336 | 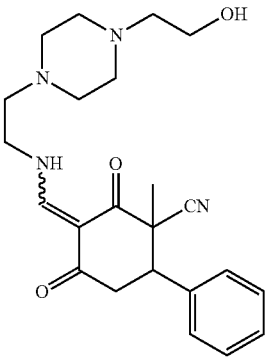 [SMILES: CC1(C#N)C(=O)C(=CNCCN2CCN(CCO)CC2)C(=O)CC1c1ccccc1] |
| 337 | 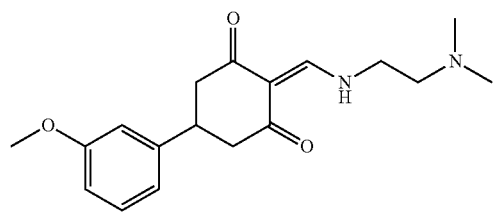 |
| 338 | 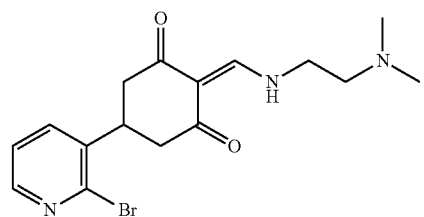 [SMILES: CN(C)CCNC=C1C(=O)CC(c2cccnc2Br)CC1=O] |
| 339 | 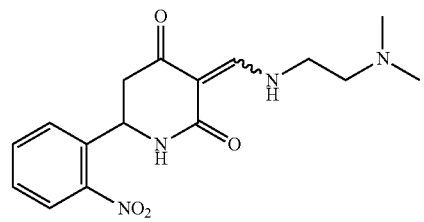 |
| 340 | 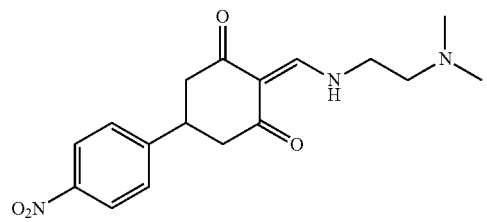 [SMILES: CN(C)CCNC=C1C(=O)CC(c2ccc([N+](=O)[O-])cc2)CC1=O] |
| 341 | 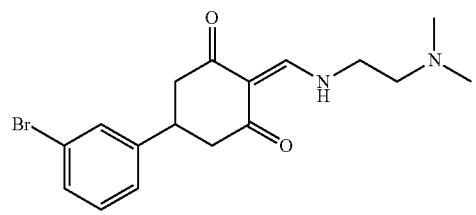 [SMILES: CN(C)CCNC=C1C(=O)CC(c2cccc(Br)c2)CC1=O] |

| No. | Structures |
|---|---|
| 342 | 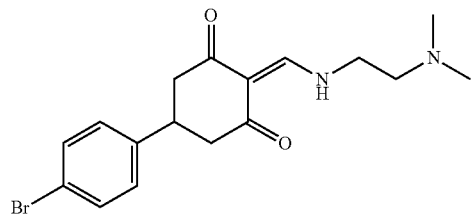 |
| 343 | 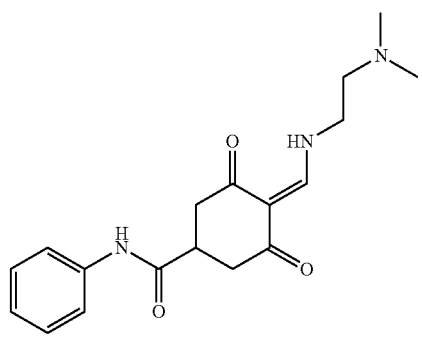 [SMILES: CN(C)CCNC=C1C(=O)CC(C(=O)Nc2ccccc2)CC1=O] |
| 344 | 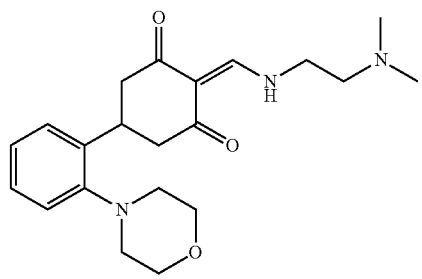 [SMILES: CN(C)CCNC=C1C(=O)CC(c2ccccc2N2CCOCC2)CC1=O] |
| 345 | 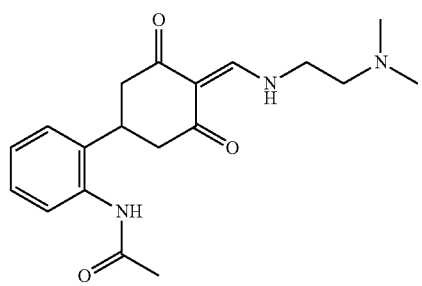 [SMILES: CC(=O)Nc1ccccc1C1CC(=O)C(=CNCCN(C)C)C(=O)C1] |
| 346 | 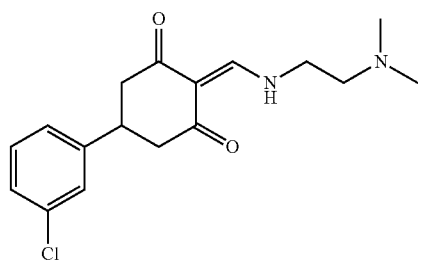 [SMILES: CN(C)CCNC=C1C(=O)CC(c2cccc(F)c2)CC1=O] |

-continued

| No. | Structures |
|---|---|
| 347 | 5-(3-fluorophenyl)-2-(((2-(dimethylamino)ethyl)amino)methylene)cyclohexane-1,3-dione |
| 349 | 5-(2-bromo-5-fluorophenyl)-2-(((2-(dimethylamino)ethyl)amino)methylene)cyclohexane-1,3-dione |
| 350 | 5-(2-bromo-3-fluorophenyl)-2-(((2-(dimethylamino)ethyl)amino)methylene)cyclohexane-1,3-dione |
| 351 | 5-(2-chloro-5-fluorophenyl)-2-(((2-(dimethylamino)ethyl)amino)methylene)cyclohexane-1,3-dione |
| 352 | 2-(((2-(4-(2-hydroxyethyl)piperazin-1-yl)ethyl)amino)methylene)cycloheptane-1,3-dione |
| 353 | 2-(((2-(4-(2-hydroxyethyl)piperazin-1-yl)ethyl)amino)methylene)-5-(3-phenyl-1H-indol-4-yl)cyclohexane-1,3-dione |

| No. | Structures |
|---|---|
| 354 | 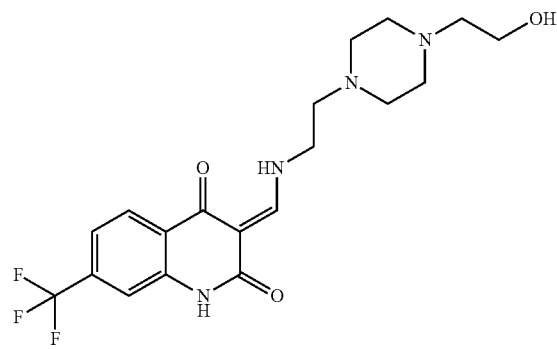 [SMILES: O=C1Nc2cc(C(F)(F)F)ccc2C(=O)/C1=C\NCCN1CCN(CCO)CC1] |
| 355 | 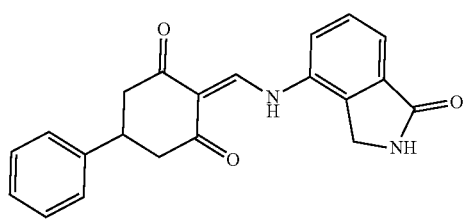 [SMILES: O=C1CC(c2ccccc2)CC(=O)C1=CNc1cccc2c1CNC2=O] |
| 356 | 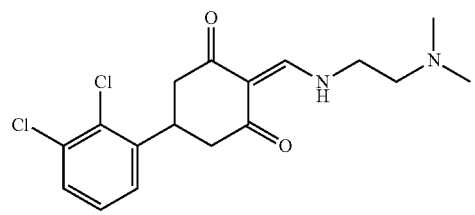 [SMILES: CN(C)CCNC=C1C(=O)CC(c2cccc(Cl)c2Cl)CC1=O] |
| 357 | 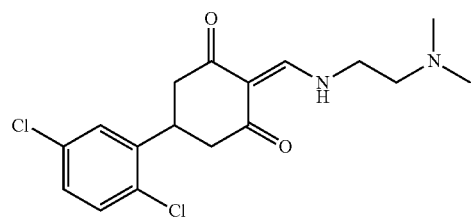 |
| 358 | 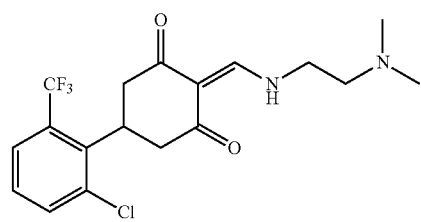 [SMILES: CN(C)CCNC=C1C(=O)CC(c2c(Cl)cccc2C(F)(F)F)CC1=O] |
| 359 | 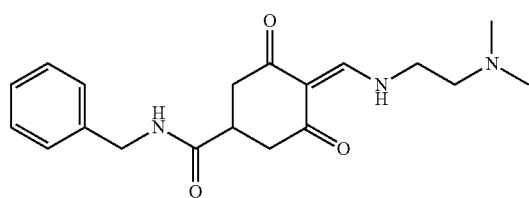 [SMILES: CN(C)CCNC=C1C(=O)CC(C(=O)NCc2ccccc2)CC1=O] |

| No. | Structures |
|---|---|
| 360 | 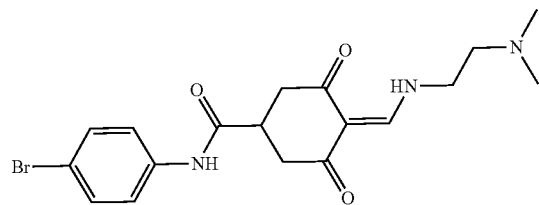 [SMILES: CN(C)CCNC=C1C(=O)CC(C(=O)Nc2ccc(Br)cc2)CC1=O] |
| 361 | 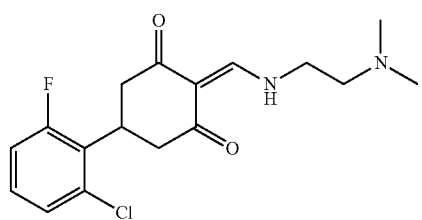 [SMILES: CN(C)CCNC=C1C(=O)CC(c2c(F)cccc2Cl)CC1=O] |
| 362 | 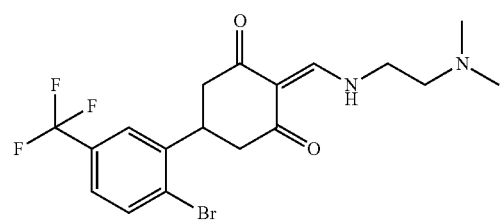 |
| 363 | 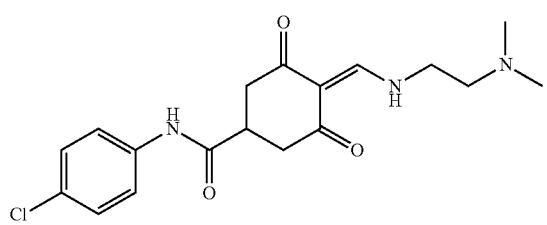 [SMILES: CN(C)CCNC=C1C(=O)CC(C(=O)Nc2ccc(Cl)cc2)CC1=O] |
| 364 | 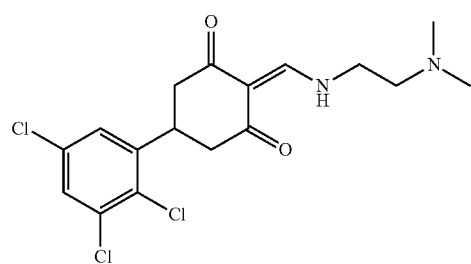 [SMILES: CN(C)CCNC=C1C(=O)CC(c2cc(Cl)cc(Cl)c2Cl)CC1=O] |
| 365 | 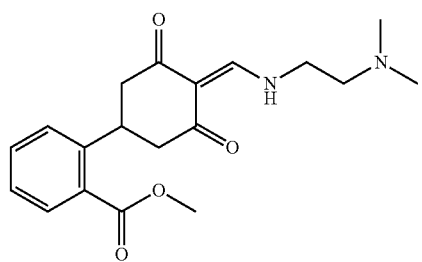 [SMILES: COC(=O)c1ccccc1C1CC(=O)C(=CNCCN(C)C)C(=O)C1] |

-continued
| No. | Structures |
|---|---|
| 366 | 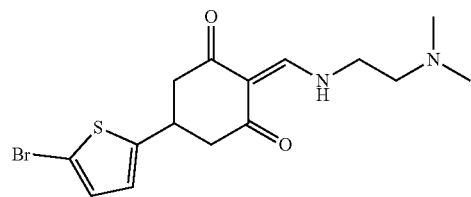 |
| 367 | 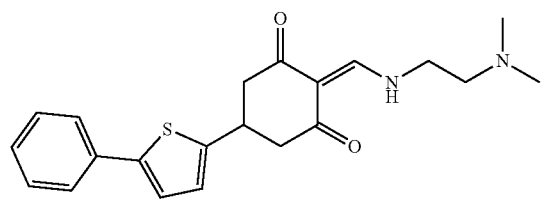 [SMILES: CN(C)CCNC=C1C(=O)CC(c2ccc(-c3ccccc3)s2)CC1=O] |
| 368 | 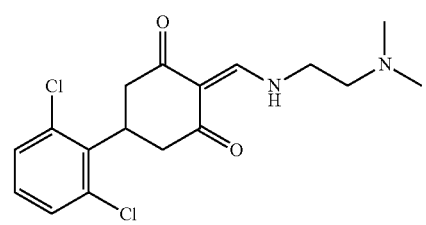 [SMILES: CN(C)CCNC=C1C(=O)CC(c2c(Cl)cccc2Cl)CC1=O] |
| 369 | 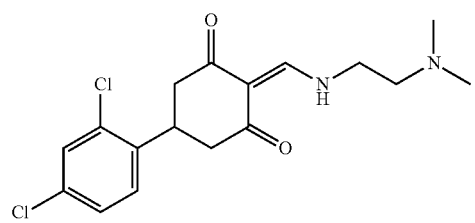 [SMILES: CN(C)CCNC=C1C(=O)CC(c2ccc(Cl)cc2Cl)CC1=O] |
| 370 | 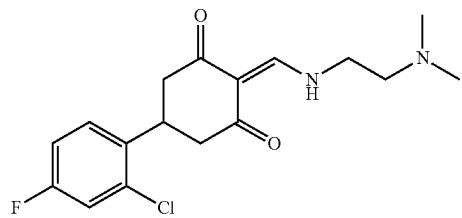 |
| 371 | 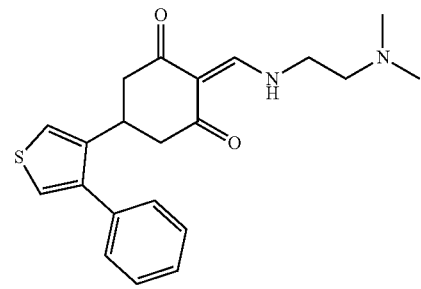 [SMILES: CN(C)CCNC=C1C(=O)CC(c2cscc2-c2ccccc2)CC1=O] |

-continued
| No. | Structures |
|---|---|
| 372 | 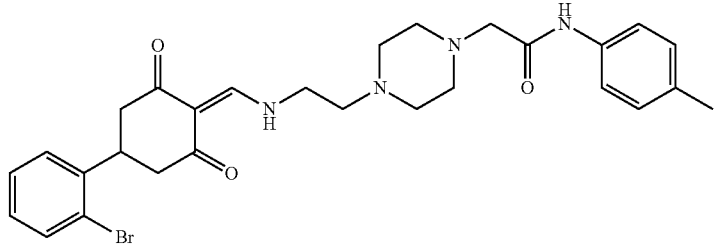 [SMILES: Cc1ccc(NC(=O)CN2CCN(CCNC=C3C(=O)CC(c4ccccc4Br)CC3=O)CC2)cc1] |
| 373 | 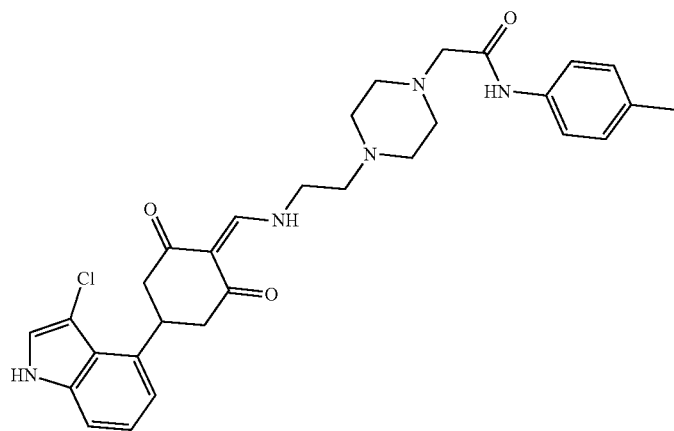 [SMILES: Cc1ccc(NC(=O)CN2CCN(CCNC=C3C(=O)CC(c4cccc5[nH]cc(Cl)c45)CC3=O)CC2)cc1] |
| 374 | 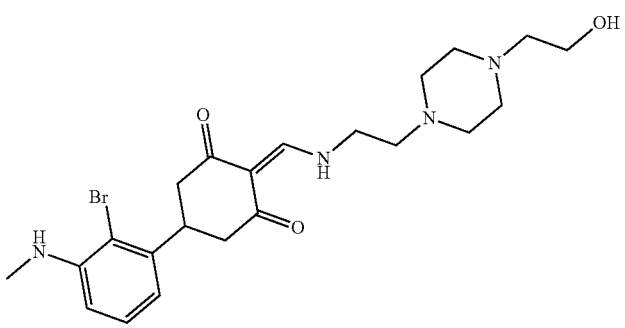 [SMILES: CNc1cccc(C2CC(=O)C(=CNCCN3CCN(CCO)CC3)C(=O)C2)c1Br] |
| 375 | 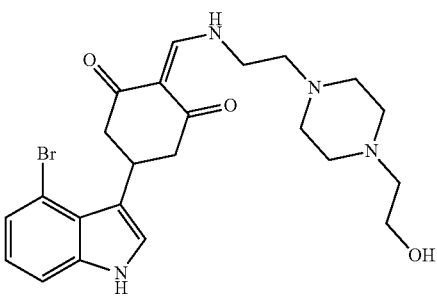 |
| 376 | 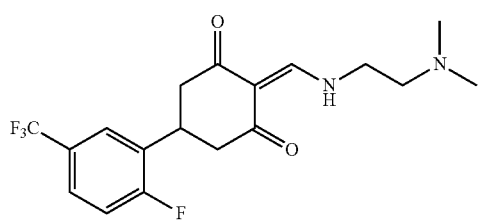 [SMILES: CN(C)CCNC=C1C(=O)CC(c2cc(C(F)(F)F)ccc2F)CC1=O] |

| No. | Structures |
|---|---|
| 377 | (2,3-dichloro-6-trifluoromethylphenyl)-substituted cyclohexane-1,3-dione with =CH-NH-CH₂CH₂-N(CH₃)₂ |
| 378 | (3-chloro-2-fluoro-6-trifluoromethylphenyl)-substituted cyclohexane-1,3-dione with =CH-NH-CH₂CH₂-N(CH₃)₂ |
| 379 | (2-bromo-4,5-dimethoxyphenyl)-substituted cyclohexane-1,3-dione with =CH-NH-CH₂CH₂-N(CH₃)₂ |
| 380 | N-(3-fluoro-4-methylphenyl)carboxamide-substituted cyclohexane-1,3-dione with =CH-NH-CH₂CH₂-N(CH₃)₂ |
| 381 | (2-chloro-5-trifluoromethylphenyl)-substituted cyclohexane-1,3-dione with =CH-NH-CH₂CH₂-N(CH₃)₂ |
| 382 | (4-chloro-2-fluorophenyl)-substituted cyclohexane-1,3-dione with =CH-NH-CH₂CH₂-N(CH₃)₂ |
| 383 | (2,6-difluorophenyl)-substituted cyclohexane-1,3-dione with =CH-NH-CH₂CH₂-N(CH₃)₂ |

| No. | Structures |
|---|---|
| 384 | 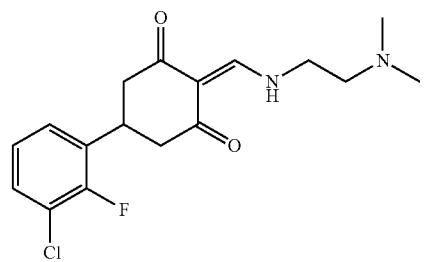 [SMILES: CN(C)CCNC=C1C(=O)CC(c2cccc(Cl)c2F)CC1=O] |
| 385 | 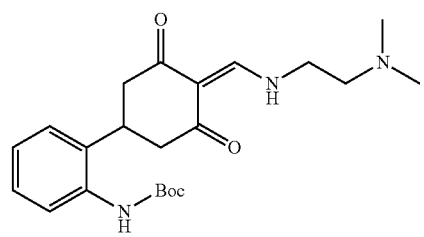 [SMILES: CN(C)CCNC=C1C(=O)CC(c2ccccc2NC(=O)OC(C)(C)C)CC1=O] |
| 386 | 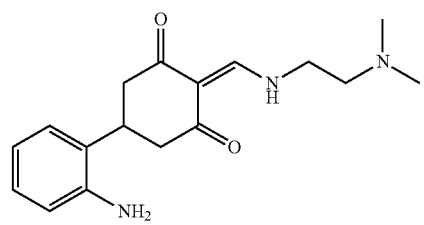 [SMILES: CN(C)CCNC=C1C(=O)CC(c2ccccc2N)CC1=O] |
| 387 | 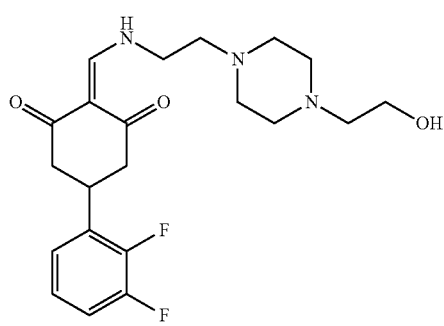 [SMILES: O=C1CC(c2cccc(F)c2F)CC(=O)C1=CNCCN1CCN(CCO)CC1] |
| 388 | 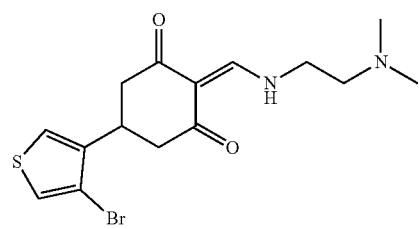 [SMILES: CN(C)CCNC=C1C(=O)CC(c2cscc2Br)CC1=O] |
| 389 | 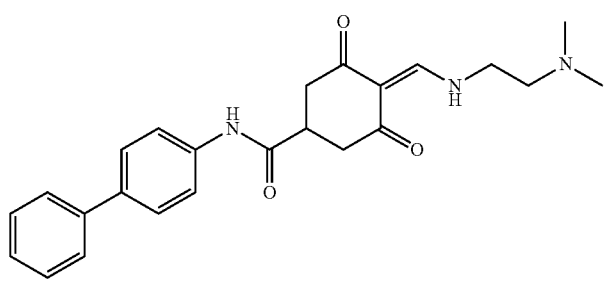 [SMILES: CN(C)CCNC=C1C(=O)CC(C(=O)Nc2ccc(-c3ccccc3)cc2)CC1=O] |

| No. | Structures |
|---|---|
| 390 | 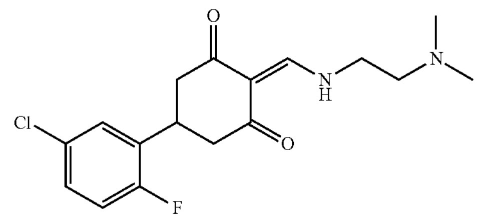 |
| 391 | 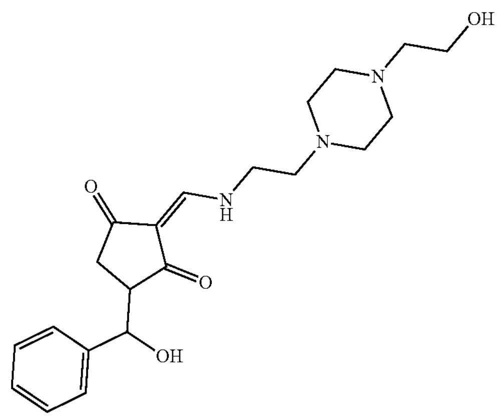 [SMILES: O=C1CC(C(O)c2ccccc2)C(=O)/C1=C\NCCN1CCN(CCO)CC1] |
| 392 | 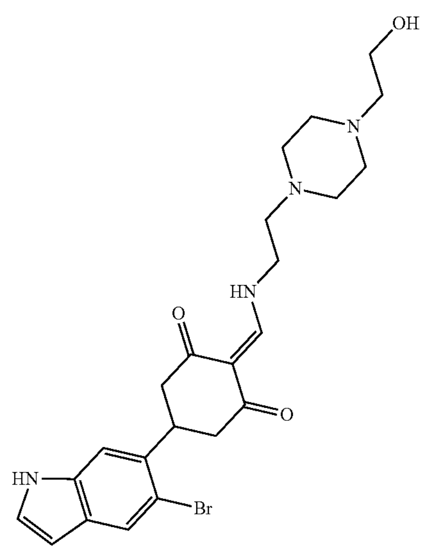 [SMILES: O=C1CC(c2cc3[nH]ccc3cc2Br)CC(=O)C1=CNCCN1CCN(CCO)CC1] |
| 393 | 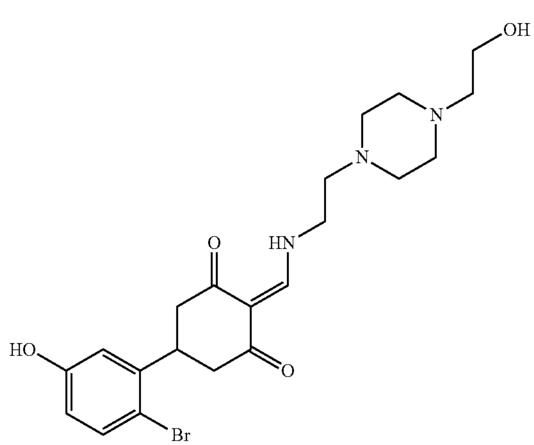 [SMILES: O=C1CC(c2cc(O)ccc2Br)CC(=O)C1=CNCCN1CCN(CCO)CC1] |

-continued
| No. | Structures |
|---|---|
| 394 | 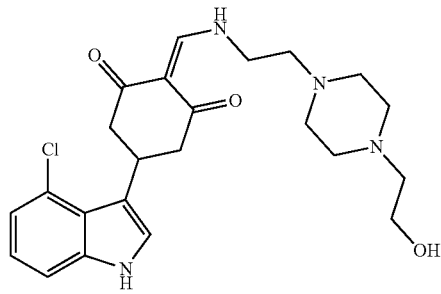 [SMILES: O=C1CC(c2c[nH]c3cccc(Cl)c23)CC(=O)C1=CNCCN1CCN(CCO)CC1] |
| 395 | 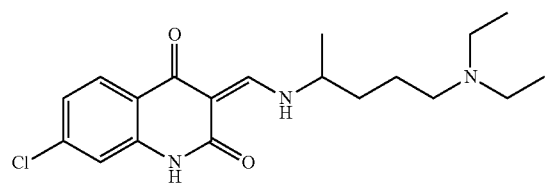 [SMILES: CCN(CC)CCCC(C)N/C=C1\C(=O)Nc2cc(Cl)ccc2C1=O] |
| 396 | 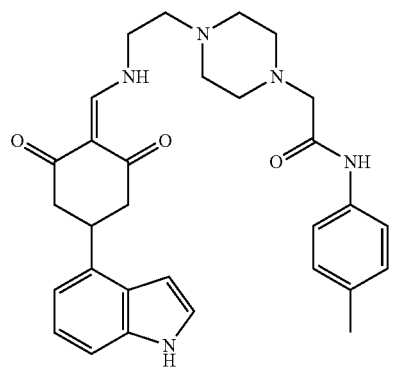 [SMILES: Cc1ccc(NC(=O)CN2CCN(CCNC=C3C(=O)CC(c4cccc5[nH]ccc45)CC3=O)CC2)cc1] |
| 397 | 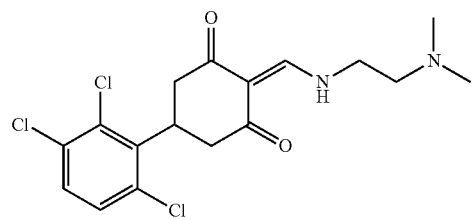 [SMILES: CN(C)CCNC=C1C(=O)CC(c2c(Cl)ccc(Cl)c2Cl)CC1=O] |
| 398 | 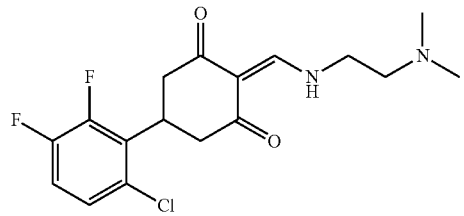 |
| 399 | 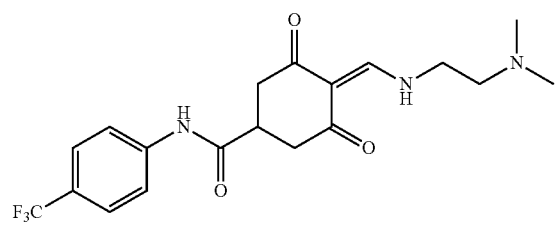 [SMILES: CN(C)CCNC=C1C(=O)CC(C(=O)Nc2ccc(C(F)(F)F)cc2)CC1=O] |

-continued
| No. | Structures |
|---|---|
| 400 | 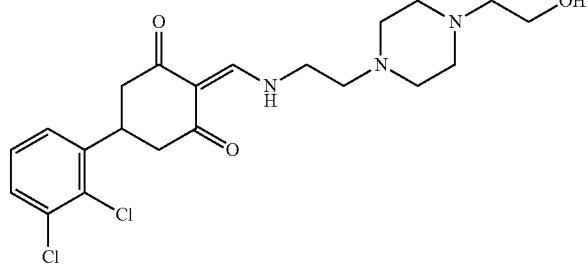 |
| 401 | 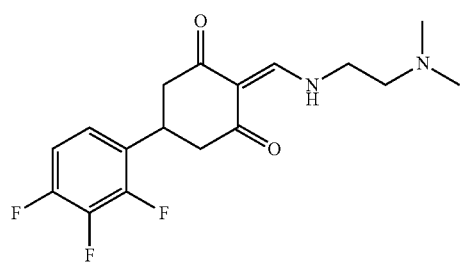 |
| 402 | 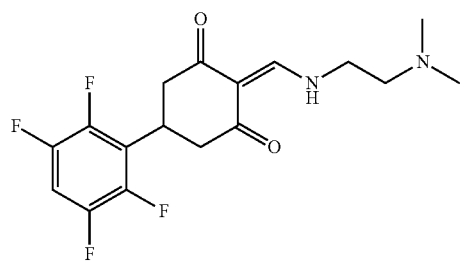 |
| 403 | 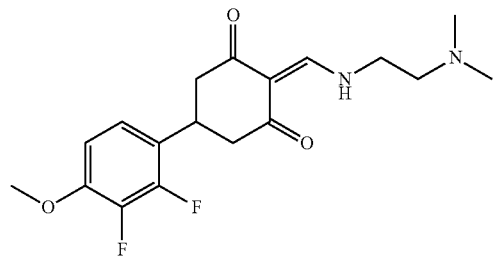 |
| 404 | 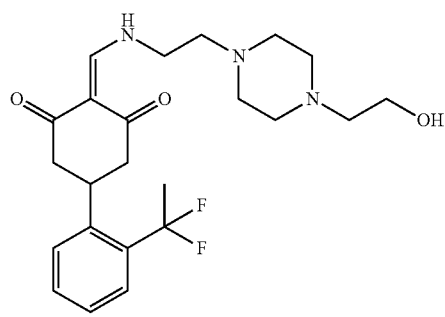 [SMILES: CC(F)(F)c1ccccc1C1CC(=O)C(=CNCCN2CCN(CCO)CC2)C(=O)C1] |

| No. | Structures |
|---|---|
| 405 | 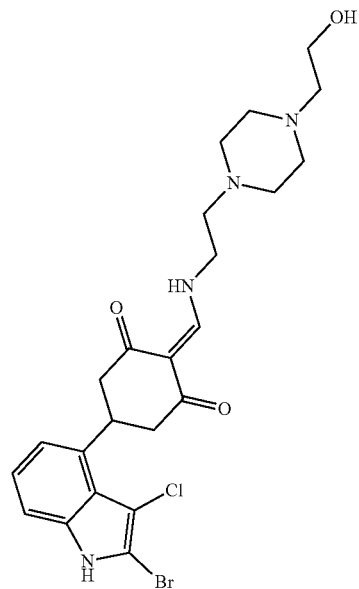 [SMILES: O=C1CC(c2cccc3[nH]c(Br)c(Cl)c23)CC(=O)C1=CNCCN1CCN(CCO)CC1] |
| 406 | 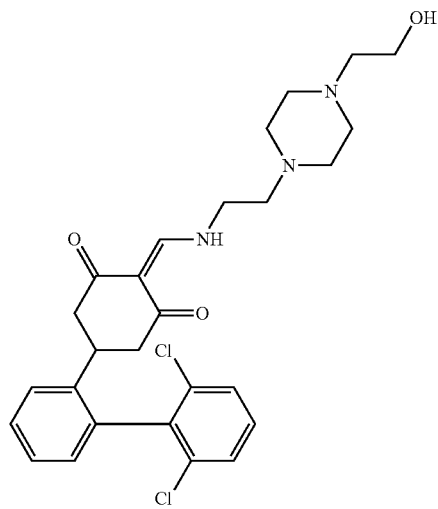 [SMILES: O=C1CC(c2ccccc2-c2c(Cl)cccc2Cl)CC(=O)C1=CNCCN1CCN(CCO)CC1] |
| 407 | 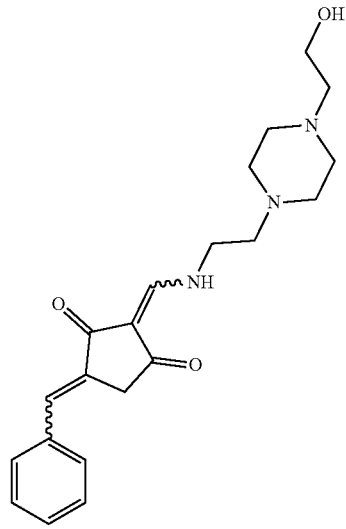 [SMILES: O=C1CC(=Cc2ccccc2)C(=O)C1=CNCCN1CCN(CCO)CC1] |

| No. | Structures |
|---|---|
| 408 | 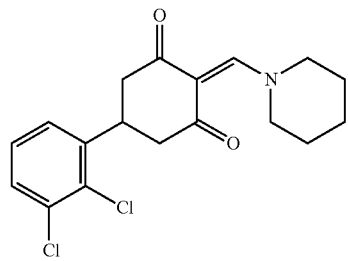 [SMILES: O=C1CC(c2cccc(Cl)c2Cl)CC(=O)C1=CN1CCCCC1] |
| 409 | 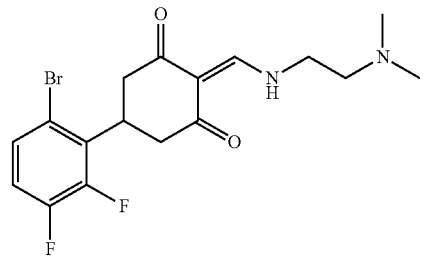 [SMILES: CN(C)CCNC=C1C(=O)CC(c2c(Br)ccc(F)c2F)CC1=O] |
| 410 | 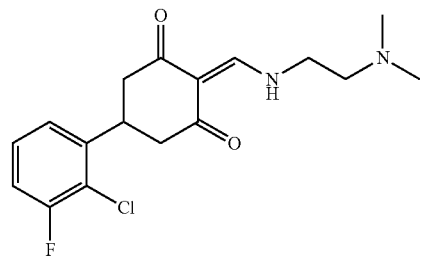 [SMILES: CN(C)CCNC=C1C(=O)CC(c2cccc(F)c2Cl)CC1=O] |
| 411 | 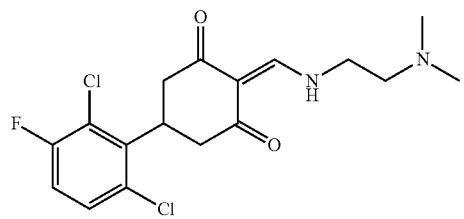 |
| 412 | 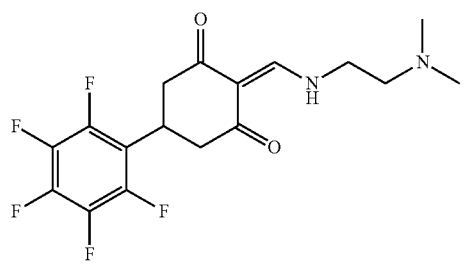 |
| 413 | 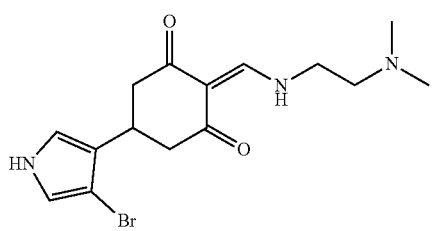 [SMILES: CN(C)CCNC=C1C(=O)CC(c2c[nH]cc2Br)CC1=O] |

-continued
| No. | Structures |
|---|---|
| 414 | 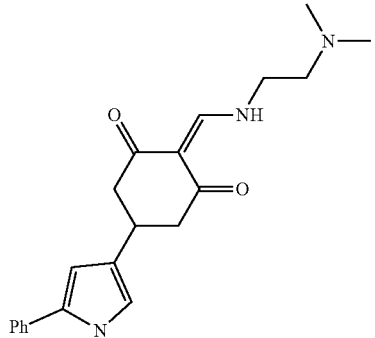 |
| 415 | 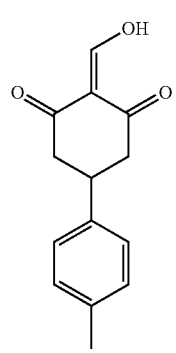 |
| 416 | 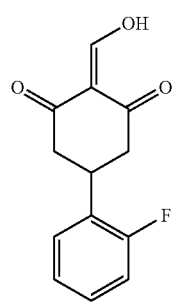 |
| 417 | 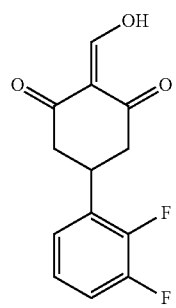 |
| 418 | 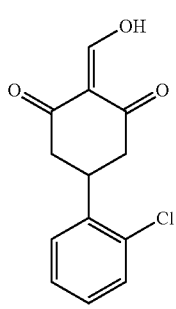 [SMILES: O=C1CC(c2ccccc2Cl)CC(=O)C1=CO] |

| No. | Structures |
|---|---|
| 419 | 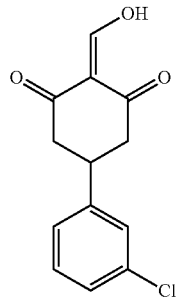 [SMILES: O=C1CC(c2cccc(Cl)c2)CC(=O)C1=CO] |
| 420 | 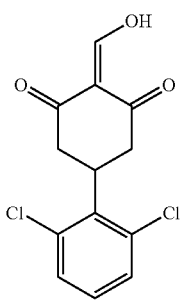 [SMILES: O=C1CC(c2c(Cl)cccc2Cl)CC(=O)C1=CO] |
| 421 | 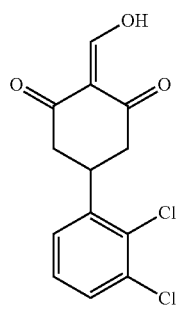 [SMILES: O=C1CC(c2cccc(Cl)c2Cl)CC(=O)C1=CO] |
| 422 | 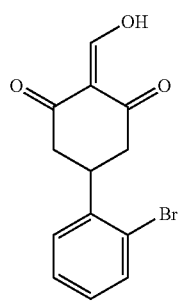 [SMILES: O=C1CC(c2ccccc2Br)CC(=O)C1=CO] |
| 423 | 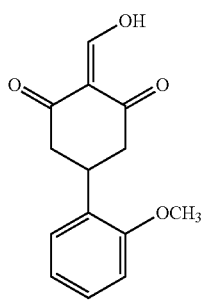 [SMILES: COc1ccccc1C1CC(=O)C(=CO)C(=O)C1] |

-continued

| No. | Structures |
|-----|------------|
| 424 | 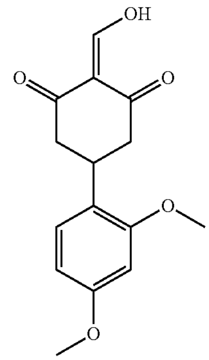 [SMILES: COc1ccc(C2CC(=O)C(=CO)C(=O)C2)c(OC)c1] |
| 425 | 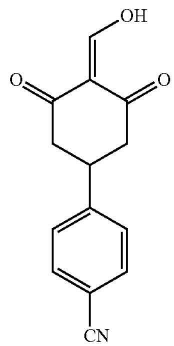 |
| 426 | 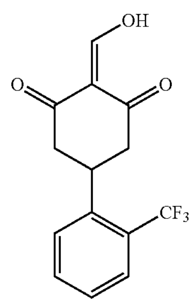 [SMILES: O=C1CC(c2ccccc2C(F)(F)F)CC(=O)C1=CO] |
| 427 | 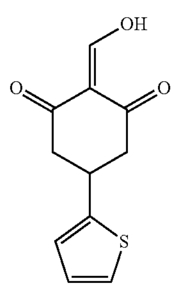 |
| 428 | 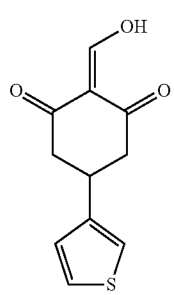 |

| No. | Structures |
|---|---|
| 429 | 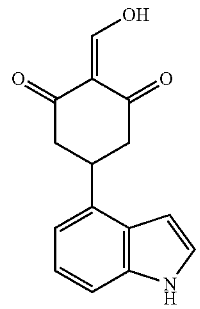 [SMILES: O=C1CC(c2cccc3[nH]ccc23)CC(=O)C1=CO] |
| 430 | 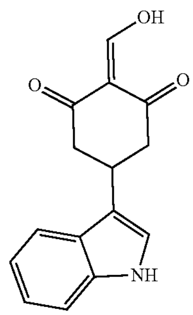 [SMILES: O=C1CC(c2c[nH]c3ccccc23)CC(=O)C1=CO] |
| 431 | 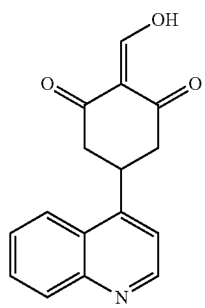 [SMILES: O=C1CC(c2ccnc3ccccc23)CC(=O)C1=CO] |
| 432 | 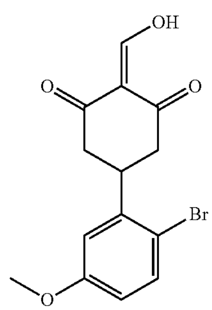 [SMILES: COc1ccc(Br)c(C2CC(=O)C(=CO)C(=O)C2)c1] |
| 433 | 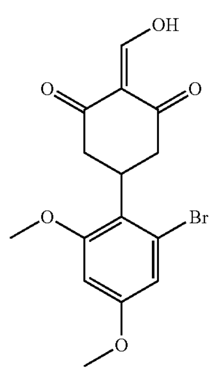 [SMILES: COc1cc(Br)c(C2CC(=O)C(=CO)C(=O)C2)c(OC)c1] |

| No. | Structures |
|---|---|
| 434 | 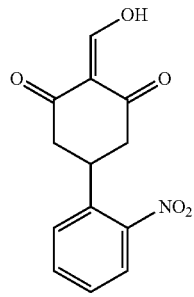 [SMILES: O=C1CC(c2ccccc2[N+](=O)[O-])CC(=O)C1=CO] |
| 435 | 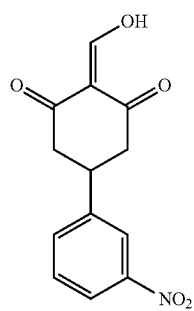 |
| 436 | 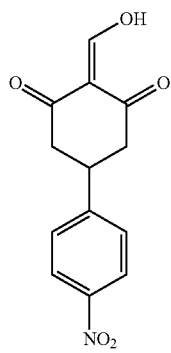 |
| 437 | 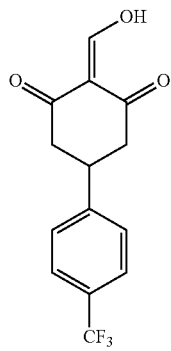 |

-continued
| No. | Structures |
|---|---|
| 438 | 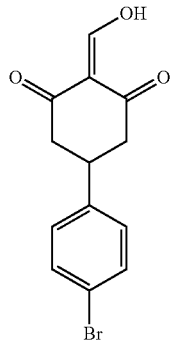 |
| 439 | 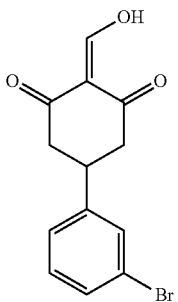 [SMILES: O=C1CC(c2cccc(Br)c2)CC(=O)C1=CO] |
| 440 | 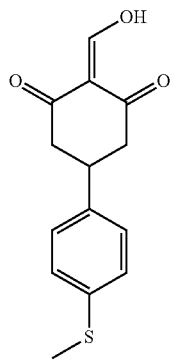 |
| 441 | 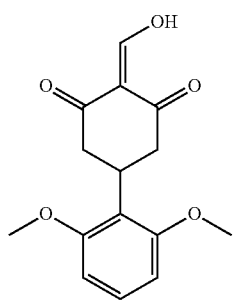 |

| No. | Structures |
|---|---|
| 442 | 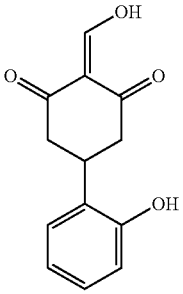 [SMILES: O=C1CC(c2ccccc2O)CC(=O)C1=CO] |
| 443 | 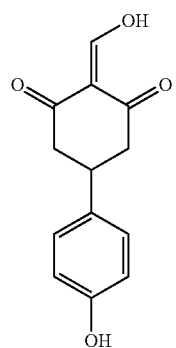 |
| 444 | 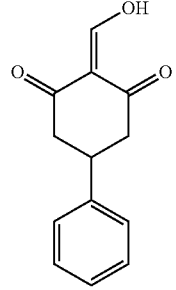 |
| 445 | 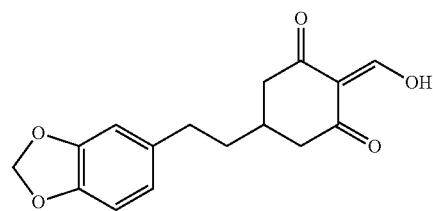 [SMILES: O=C1CC(CCc2ccc3c(c2)OCO3)CC(=O)C1=CO] |
| 446 | 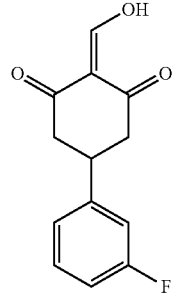 |

| No. | Structures |
|-----|------------|
| 447 | 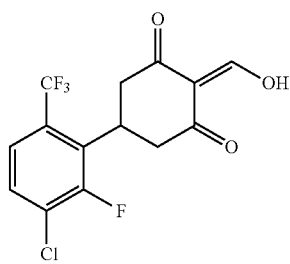 [SMILES: O=C1CC(c2c(C(F)(F)F)ccc(Cl)c2F)CC(=O)C1=CO] |
| 448 | 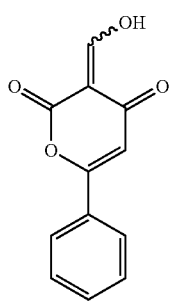 |
| 450 | 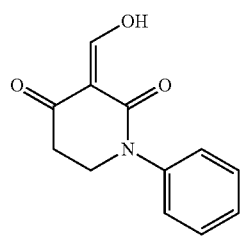 |
| 451 | 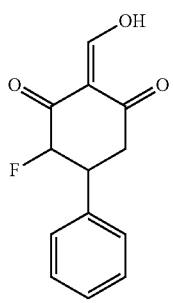 |
| 452 | 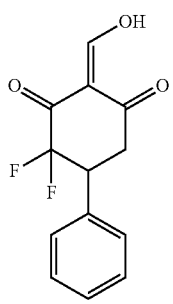 |

| No. | Structures |
|---|---|
| 453 | 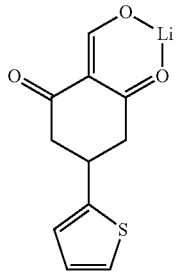 |
| 454 | 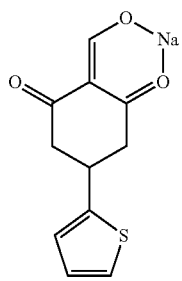 |
| 455 | 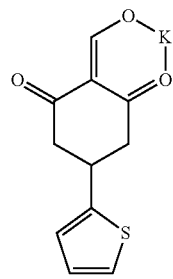 |
| 456 | 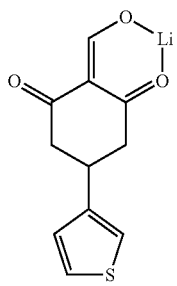 |
| 457 | 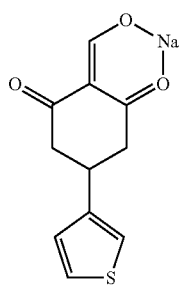 |

-continued

| No. | Structures |
|---|---|
| 458 | 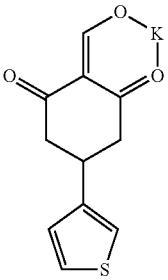 |
| 459 | 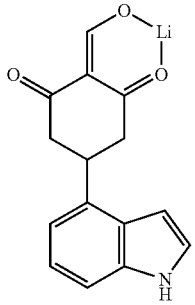 |
| 460 | 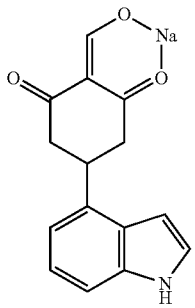 |
| 461 | 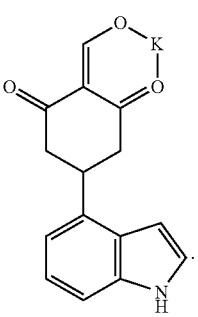 |

In another embodiment of the invention, the invention provides a pharmaceutical composition, comprising a compound or a pharmaceutical acceptable salt thereof according to the present invention. The pharmaceutical composition may also include a pharmaceutical excipient.

In another embodiment of the invention, the invention provides use of a compound or a pharmaceutically acceptable salt thereof according to the invention in manufacturing a medicant for regulating autophagy in a cell.

In another embodiment of the invention, the medicant for regulating autophagy in a cell is a medicant that can regulate a mammalian ATG8 homologue.

In another embodiment of the invention, the medicant for regulating autophagy in a cell is a medicant that can prevent or treat diseases associated with autophagy in a cell, particularly the diseases associated with mammalian ATG8 homologues.

In another embodiment of the invention, the invention provides a method for regulating autophagy in a cell, comprising administering a compound or a pharmaceutically acceptable salt thereof according to the invention, to a subject in need thereof.

In another embodiment of the invention, the method for regulating autophagy in a cell is a method for regulating a mammalian ATG8 homologue.

In another embodiment of the invention, the method for regulating autophagy in a cell is a method for preventing or treating diseases associated with autophagy in a cell, particularly the diseases associated with mammalian ATG8 homologues.

In another embodiment of the invention, the mammalian ATG8 homologue is LC3B.

In another embodiment of the present invention, the disease prevented or treated that is associated with autophagy in a cell, particularly associated with mammalian ATG8 homologues, is selected from the group consisting of tumor, cardiovascular diseases, autoimmune diseases, neurodegenerative diseases, hypertension, bone tissues and bone-related diseases, Crohn's diseases, acute kidney injury, brain ischemia, retinal diseases, bronchial asthma, Vici syndrome, and infectious diseases.

In another embodiment of the invention, said tumor is selected from the group consisting of liver cancer, lung cancer, pancreatic cancer, breast cancer, cervical cancer, endometrial cancer, colorectal cancer, gastric cancer, lung cancer, nasopharyngeal cancer, ovarian cancer, prostate cancer, leukemia, lymphoma, and myeloma.

In the use of the medicant prepared for regulating autophagy in a cell and the method for regulating autophagy in a cell according to the present invention, certain preferred compounds are selected from the group consisting of the compounds with general formula (Ib), general formula (IId), general formula (IIId), general formula (IVd), and general formula (Vc). Wherein, the general formula (Ib), general formula (IId), general formula (IIId), general formula (IVd), and general formula (Vc) are the same as described above; alternatively, certain preferred compounds are selected from the group consisting of the Compound 2, Compound 3, Compound 241, Compound 264, Compound 449, Compound 462, Compound 463 and Compound 464.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention, example of which is illustrated in the accompanying drawings.

The terms used herein have their ordinary meaning. Chemical names, common names and chemical structures may be used interchangeably to describe that same structure. These definitions apply regardless of whether a term is used by itself or in combination with other terms, unless otherwise indicated. Thus, the definition of "C1-6 alkyl" is applicable to "C1-6 alkyl" as well as the "C1-6 alkyl" portion of "C1-6 hydroxyalkyl", "C1-6 haloalkyl", "C6-10 aryl C1-6 alkyl", "C1-6 alkyl C6-10 aryl", "C1-6 alkoxy" and the like.

The term "pharmaceutical composition" refers to a composition suitable for administration to a patient. Such compositions may only contain the neat compound (or compounds) of the invention or mixtures thereof, or salts, solvates, prodrugs, isomers, or tautomers thereof, or they may contain one or more pharmaceutically acceptable carriers or excipients. The term "patient" includes both human and non-human animals. The pharmaceutical composition may be in various forms, such as tablet, capsule, powder, syrup, solution, suspension and aerosol and the like, and may be present in a suitable solid or liquid carrier or diluent and suitable sterilizing device used for injection or infusion.

Various dosage forms of the pharmaceutical composition of the present invention can be prepared by conventional preparation methods in the pharmaceutical field. A single unit dosage of the prepared formulation comprises 0.05 to 200 mg of the compound of formula (I), preferably comprising 0.1 mg to 100 mg of the compound of formula (I) per unit dosage of the formulation.

The compounds and pharmaceutical compositions of the present invention can be used clinically in mammals, including humans and animals, by administration routes of mouth, nose, skin, lungs, or gastrointestinal tract, etc. Most preferably is oral administration. The best preferred daily dose is 0.01-200 mg/kg body weight, taken at one time, or 0.01-100 mg/kg body weight taken by divided doses. Regardless of the administration route, optimal dosage for an individual should be determined according to particular treatment regime. In general, a small dose is taken at the beginning, then the dose is gradually increased until the most suitable dose is found.

"Halogen" (or "halo") refers to fluorine, chlorine, bromine, or iodine.

"C1-6 alkyl" refers to a straight or branched alkyl group having 1 to 6 carbon atoms, preferably a straight or branched alkyl group having 1 to 4 carbon atoms. "Branched" refers to one or more alkyl group having 1 to 4 carbon atoms, such as methy, ethyl or propyl and the like, is connected to a straight alkyl group. The preferred C1-6 alkyl group includes, but not limited to, methyl, ethyl, n-propyl, isopropyl, n-butyl, i-butyl, and t-butyl and the like.

"C1-6 haloalkyl" refers to an alkyl as defined above having one or more halo group substituent(s).

"C1-6 heteroalkyl" refers to an alkyl as defined above having one or more substituent(s) selected from the group consisting of O, S, N, —(S=O)—, —(O=S=O)—, etc.

"C2-6 alkenyl" refers to a straight or branched alkenyl group having 2 to 6 carbon atoms, preferably 2 to 4 carbon atoms. "Branched" refers to one or more lower C1-6 alkyl group is connected to a straight C2-6 alkenyl group chain. The preferred C2-6 alkenyl group includes, but not limited to, ethenyl, propenyl, n-butenyl, 3-methylbutenyl, n-pentenyl and the like.

"C1-6 alkylene" refers to a bivalent group obtained by removal of a hydrogen atom from an alkyl group as defined above. The preferred C1-6 alkylene group includes, but not limited to, methylene, ethylidene and propylidene, etc. Generally, it can be optionally and equivalently expressed herein as —(C1-6 alkyl)-, for example —CH$_2$CH$_2$— is an ethylidene.

"C2-6 alkynyl" refers to a straight or branched alkynyl group having 2 to 6 carbon atoms, preferably 2 to 6 carbon atoms, more preferably having 2 to 4 carbon atoms. "Branched" refers to one or more alkyl group having 2 to 4 carbon atoms is connected to a straight alkynyl group chain. The preferred C2-6 alkynyl group includes, but not limited to, ethynyl, propynyl, 2-butynyl and 3-methylbutynyl, etc.

"C2-6 alkenylene" refers to a difunctional group obtained by removal of hydrogen from a C2-6 alkenyl group as defined above. The preferred C2-6 alkenylene group includes, but not limited to, —CH=CH—, —C(CH$_3$)=CH—, —CH=CHCH$_2$—, etc.

"C6-10 aryl" refers to an aromatic monocyclic or multicyclic ring system having 6 to 10 carbon atoms. Preferably, the C6-10 aryl group includes, but not limited to, phenyl and naphthyl.

"C6-10 arylidene" refers to a bivalent group obtained by removal of a hydrogen atom from a C6-10 aryl group as defined above, for example

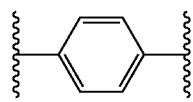 [SMILES: *c1ccc(*)cc1]

is p-phenylene.

"5-10 membered heteroaryl" refers to an aromatic monocyclic or multicyclic ring group having 5 to 10 ring atoms. The 5-10 membered heteroaryl group includes 1 to 4 hetero atoms selected from N, O and S. Preferred 5-10 membered heteroaryl group includes 5 to 6 ring atoms. The term "5-10 membered heteroaryl" also includes a C6-10 aryl fused ring as defined above. Preferred 5-10 membered heteroaryl group includes, but not limited to, pyridyl, pyrazinyl, furanyl, thienyl, pyrimidinyl, pyridone, oxazolyl, isothiazolyl, oxazolyl, oxadiazolyl, thiazolyl, thiadiazolyl, pyrazolyl, furazanyl, pyrrolyl, triazolyl, 1,2,4-thiadiazolyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the oxides thereof and the like. The term "5-10 membered heteroaryl" also refers to partially saturated 5-10 membered heteroaryl group, such as, for example, tetrahydroisoquinolyl, tetrahydroquinolyl and the like.

"C3-10 cycloalkyl" refers to a non-aromatic monocyclic or multicyclic ring group having 3 to 10 carbon atoms, preferably 3 to 6 carbon atoms. Preferred monocyclic C3-10 cycloalkyl includes, but not limited to, cyclopropyl, cyclopentyl, cyclohexyl, cycloheptyl and the like. Preferred multicyclic cycloalkyl includes, but not limited to, [1.1.1]-bicyclopentane, 1-capryl, norbornyl, adamantyl and the like.

"C3-10 cycloalkenyl" refers to a non-aromatic monocyclic or multicyclic ring group having 3 to 10 carbon atoms, preferably 3 to 7 ring atoms, most preferably 5 to 7 ring atoms, which contains at least one carbon-carbon double bond within the ring. Preferred C3-10 cycloalkenyl includes, but not limited to, cyclopropenyl, cyclobutenyl, cyclopentenyl, cyclohexenyl, cyclohetpenyl, cycloheptane-1,3-dienyl, norbornylenyl and the like.

"3-10 membered heterocycloalkyl" (or "3-10 membered heterocyclyl") refers to a non-aromatic saturated monocyclic or multicyclic ring group having 3 to 10 ring atoms, preferably 5 to 10 ring atoms, more preferably 5 to 6 ring atoms, in which the 3-10 membered heterocyclyl group includes 1 to 4 hetero atoms selected from N, O and S, and two of the hetero atoms in the ring system are not adjacent. The nitrogen or sulfur atom of the heterocyclyl can be optionally oxidized to the corresponding N-oxide, S-oxide or S,S-dioxide. Thus, the term "oxide" of the invention refers to the corresponding N-oxide, S-oxide, or S,S-dioxide. "3-10 membered heterocyclyl" also includes rings in which two available hydrogens on the same carbon atom are simultaneously replaced by one single group -ep(for example, a carbonyl group). Such —O group may be referred as "oxo-" in the present invention. Preferred monocyclic 3-10 membered heterocycloalkyl includes, but not limited to, piperidyl, oxetanyl, pyrrolyl, piperazinyl, morpholinyl, thiomorpholinyl, thiazolidinyl, 1,4-dioxin C1-6 alkyl, tetrahydrofuranyl, tetrahydrothiophenyl, lactamyl (such as pyrrolidinone), lactone group having 3 to 10 ring atoms and oxides thereof.

"3-7 membered heterocycloalkenyl" refers to a non-aromatic monocyclic or multicyclic ring group having 3 to 7 ring atoms, preferably 5 to 6 ring atoms, in which the 3-10 membered heterocycloalkenyl group includes 1 to 4 hetero atoms selected from N, O and S, and includes at least one carbon-carbon double bond or carbon-nitrogen double bond. There are no adjacent oxygen and/or sulfur atoms present in the ring system. The prefix aza, oxa or thia before the 3-7 membered heterocyclenyl group name refers to at least one nitrogen, oxygen or sulfur atom respectively presented as a ring atom. The nitrogen or sulfur atom in the 3-7 membered heterocyclenyl group can be optionally oxidized to the corresponding N-oxide, S-oxide or S,S-dioxide. Preferred 3-7 membered heterocyclenyl group includes, but not limited to, 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, and the oxides thereof, and the like. "3-7 membered heterocyclenyl" may also be rings in which two available hydrogens on the same carbon atom are simultaneously replaced by one single group =O (i.e., forming a carbonyl).

"C6-10 aryl C1-6 alkyl" (or "C6-10 aryl C1-6 alkyl") refers to a group formed by connecting the C6-10 aryl as defined above to the C1-6 alkyl as defined above. Preferred C6-10 aryl C1-6 alkyl includes, but not limited to, benzyl, 2-phenethyl and naphthalenylmethyl. The C6-10 aryl C1-6 alkyl is bonded to the parent moiety by a C1-6 alkyl group. Similarly, "5-10 membered heteroaryl C1-6 alkyl", "C3-10 cycloalkyl C1-6 alkyl", "C2-6 cycloalkenyl C1-6 alkyl", "3-10 membered heterocycloalkyl C1-6 alkyl", "3-7 membered heterocycloalkenyl C1-6 alkyl" and the like refer to the 5-10 membered heteroaryl, C2-6 cycloalkenyl, 3-10 membered heterocycloalkyl, 3-7 membered heterocycloalkenyl and the like as described herein are bonded to the parent moiety by a C1-6 alkyl group.

"C1-6 alkyl C6-10 aryl" refers to a group formed by connecting the C1-6 alkyl as defined above to the C6-10 aryl as defined above. Preferred C1-6 alkyl C6-10 aryl includes, but not limited to, tolyl. The C1-6 alkyl C6-10 aryl is boned to the parent moiety by a C6-10 aryl group.

"5-10 membered heteroaryl C1-6 alkyl" refers to a group formed by connecting the 5-10 membered heteroaryl as defined above to the C1-6 alkyl as defined above. Preferred C6-10 aryl C1-6 alkyl includes, but not limited to, pyridylmethyl and quinolin-3-ylmethyl. The 5-10 membered heteroaryl C1-6 alkyl is boned to the parent moiety by a C1-6 alkyl group.

"C1-6 hydroxyalkyl" refers to a hydroxyl-substituted C1-6 alkyl group, wherein the C1-6 alkyl group is described as above. Preferred C1-6 hydroxyalkyl includes, but not limited to, hydroxymethyl and 2-hydroxyethyl.

"C1-6 alkoxy" refers to a C1-6 alkyl-O— group, which is bonded to the parent moiety by —O—, wherein the C1-6 alkyl group is described as above. Preferred C1-6 alkoxy includes, but not limited to, methoxy, ethoxy, n-propoxy, isopropoxy and n-butoxy.

"C1-6 alkyoxyalkyl" refers to a group derived from a C1-6 alkoxy and C1-6 alkyl as defined herein, which is bonded to the parent moiety by a C1-6 alkyl group.

"Ester group" refers to —C(O)OR$_x$, wherein R$_x$ is C1-6 alkyl, C6-10 aryl, C6-10 aryl C1-6 alkyl and C3-10 cycloalkyl. Preferred ester group includes, but are not limited to, methoxycarbonyl, ethoxycarbonyl, isopropyl ester group, tert-butyl ester group, phenyl ester group.

"Amide group" refers to —C(O)NR$_y$R$_{y'}$, wherein R$_y$ and R$_{y'}$ are hydrogen, C1-6 alkyl, C6-10 aryl, C6-10 aryl C1-6 alkyl or C3-10 cycloalkyl.

Any of the foregoing functional groups may be unsubstituted or substituted as described herein. The term "substituted" (or substitute) refers to that one or more hydrogens on the designated atom is replaced with a group selected from the indicated groups, provided that not exceeding the designated atom's normal valency and the substitution forms a stable compound. Combinations of substituents and/or variables are permissible only if such combinations result in stable compounds. "Stable compound" or "stable structure" is meant a compound having a sufficient stablility that can be separated to a useful purity from a reaction mixture and can be formulated to an efficacious therapeutic agent.

The term "unsubstituted or substituted" refers to a particular group that is unsubstituted or substituted with one or more substituents. Substituents include, but not limited to, hydrogen, hydroxyl, amino, cyano, nitro, carboxy, halo, C1-6 alkyl, C1-6 haloalkyl or C1-6 hydroxyalkyl. Two adjacent substituents may be joined to form a C6-10 aryl group, a 5-10 membered heteroaryl group, a C3-10 cycloalkyl group or a 3-10 membered heterocycloalkyl group. Substitutions on the C6-10 aryl, 5-10 membered heteroaryl, C3-10 cycloalkyl, 3-10 membered heterocycloalkyl, 3-7 membered heterocycloalkenyl groups and the like include, but not limited to, substitution in any ring portion of the groups.

In the present application, if a group is a "covalent bond", it means that the group "does not exist" and the two linked groups are joined by a covalent bond. For example, in the substituent "-J-K-M-Q", if K is a covalent bond, then this substituent becomes "-J-M-Q".

Tautomers mean compounds produced by the phenomenon wherein a proton of one atom of a molecule shifts to another atom. Tautomers also refer to one of two or more structural isomers that exist in equilibrium and are readily converted from one isomeric form to another. One of ordinary skills in the art would recognize that other tautomeric ring atom arrangements are possible. All such isomeric forms of these compounds are expressly included in the present disclosure.

Specifically, the compounds of the present invention include all tautomers thereof, for example, keto-enol tautomers. For the sake of convenience, in the detailed description and claims of the present invention, partial structures of these tautomers and the mixtures thereof (Examples 11, 112 and 415) are shown below.

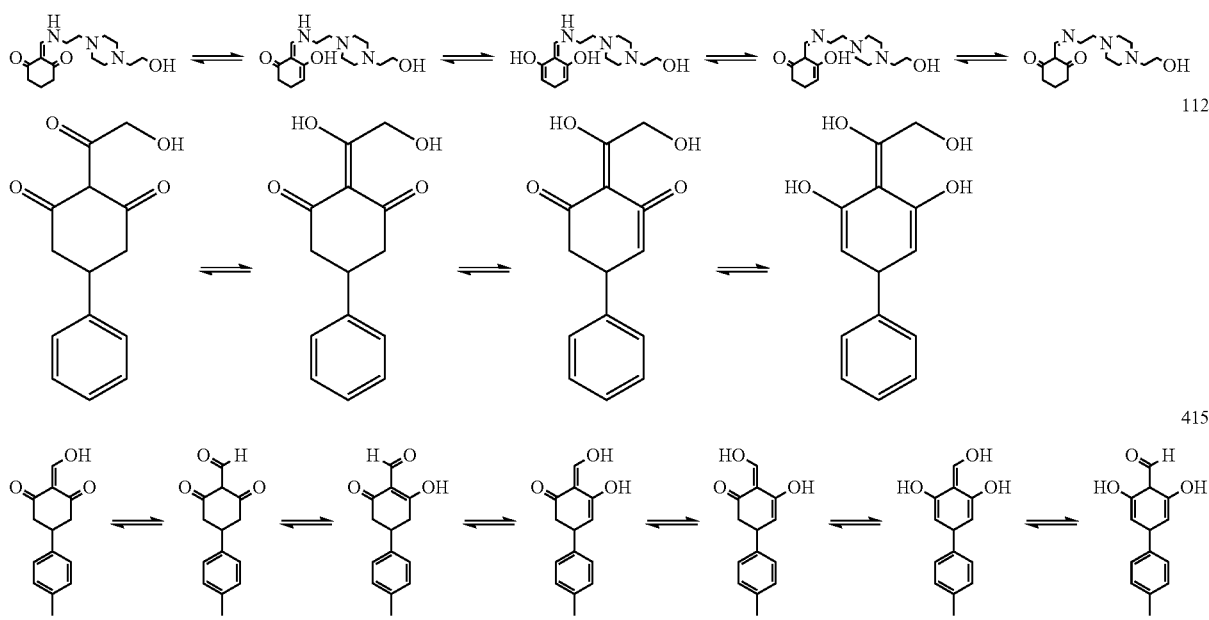

For convenience, only one tautomer for each compound is shown in the present invention. It should be noted the compounds of the present invention include all tautomers.

Stereoisomer refers to compounds having identical molecular formulae and identical order of atomic connectivity in molecular but different spatial arrangement of atoms which results the isomerization. Stereoisomers include cis-trans isomerization, conformational isomerization, enantiomeric isomerization and diastereomeric isomerization and so on. Wherein the cis-trans isomerization refers to such a cis-trans isomerization that is caused by two carbon atoms connected by a double bond cannot relatively freely rotate about a bond, generally referring to a double bond in an alkene, as well as the cis-trans isomer of compounds having C═N double bond, N═N double bond and cyclic structure and the like. The enantiomer refers to stereoisomers that are mirrored to each other; the diastereomer refers to stereoisomers in which the molecules have two or more chiral centers and the molecules are in a non-mirrored relationship. Unless otherwise indicated, the description is intended to include individual stereoisomers as well as mixtures thereof.

Specifically, the compounds of the present invention include all isomers thereof, for example, diastereomers and cis/trans (Z/E) isomers. Examples of the cis/trans isomers of compound 101 disclosed in the present invention are shown below.

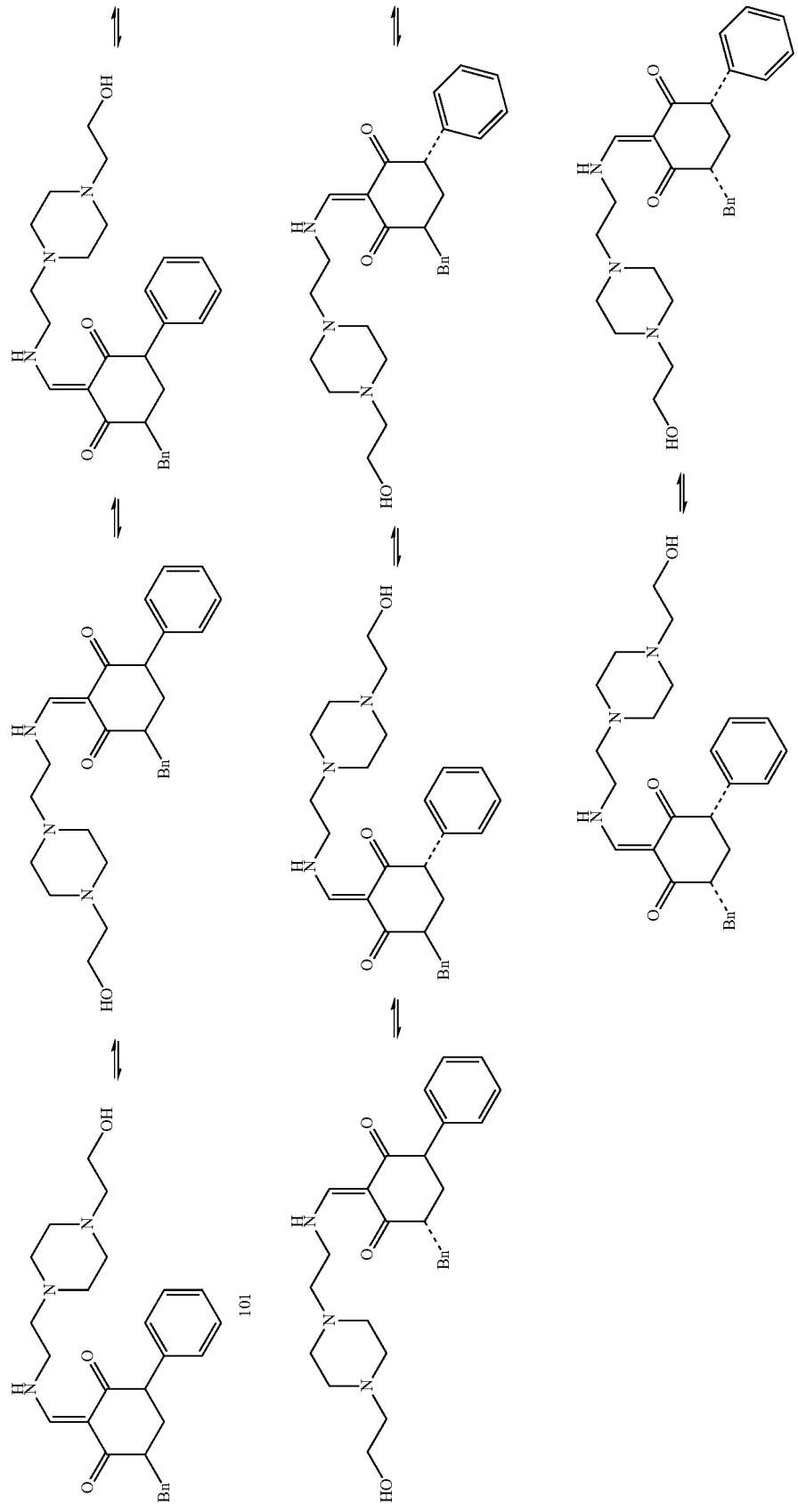

For convenience, only one isomer for each compound is shown in the present invention. It should be noted the compounds of the present invention include all isomers.

The compounds of the present invention may form metal chelates with one or more metal ions. The metal ions include, but not limited to, copper, iron, magnesium, calcium, zinc, nickel and platinum, etc. As described in the invention, one example of the metal chelates is provided in Example 38. It should be noted the compounds of the present invention include all metal chelates thereof.

The term "pharmaceutically acceptable salts" represent those salts which are suitable for humans and/or animals without undue adverse side effects, such as toxicity, irritation, allergic response and the like, also means materials having a reasonable benefit/risk ratio. The pharmaceutically acceptable salts may comprise inorganic and organic salts, which can be obtained during the final isolation and purification of the compounds of the invention, or formed by reacting the free acidic or alkali functional group with a suitable acid or alkali. Suitable acids for generating salts include, but not limited to, inorganic acids, such as hydrochloric acid, phosphoric acid, or sulfuric acid; or organic acids, such as citric acid, ascorbic acid, citric acid, tartaric acid, lactic acid, maleic acid, malonic acid, fumaric acid, glycolic acid, succinic acid, propionic acid, acetic acid or methanesulfonic acid, and the like. Suitable alkali for generating salts include, but not limited to, inorganic alkali, such as sodium carbonate, sodium hydroxide, potassium carbonate, potassium hydroxide, lithium hydroxide, calcium acetate, calcium chloride, magnesium chloride and the like; organic alkali, such as amino ethanol and the like.

The term "effective amount" refers to the amount of the compounds of the present invention contained in a composition administered is sufficient to regulate (e.g., inhibit or activate) mammalian ATG8 homologues.

The compounds of the invention can be prepared by various methods well known in the art, and the following reaction schemes are an optional solution for preparing the compounds of the invention.

General reaction scheme

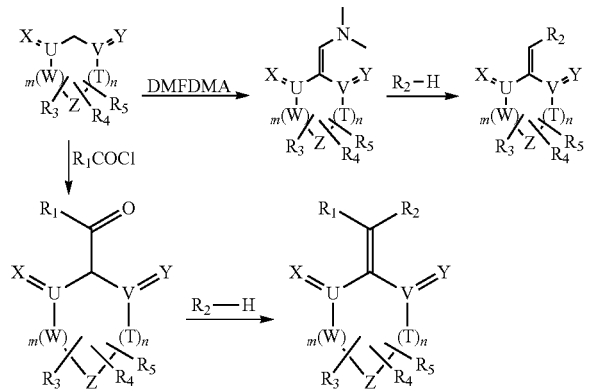

The groups and substituents in the general scheme have the same definitions as the general formula (I). The compounds can be prepared by the methods described in some references known to one of ordinary skills in the art. These references include, for example, Bioorganic & Medicinal Chemistry Letters, 24(16), 3764-3771, 2014; Chemistry—A European Journal, 20(9), 2445-2448, 2014; Bioorganic & Medicinal Chemistry, 20(2), 1029-1045, 2012; Journal of Organic Chemistry, 82(5), 2630-2640, 2017; Tetrahedron Letters, 49 (2008), 4725-4727; Journal of Organic Chemistry, 78(9), 4563-4567, 2013; Heterocycles, 28(2), 1015-35, 1989; Journal of Medicinal Chemistry, 57(10), 3924-3938, 2014; Journal of Organic Chemistry, 66(24), 8000-8009, 2001; and Tetrahedron Letters, 56(45), 6287-6289, 2015.

EXAMPLES

The invention is further described with reference to the following examples. It is to be appreciated that the invention is not limited to these examples. It is to be understood that the examples are not intended to limit the scope of the invention, and the invention is not limited thereto. Those skilled in die art will readily appreciate that these compounds can be prepared by using known variations in the conditions and procedures of the following preparation methods. The starting materials used in the present invention are commercially available unless otherwise specified, Abbreviations acetonitrile (MeCN, ACN); aqueous solution (aq.); benzyl bromide (BnBr); di-tert-butyl dicarbonate ($Boc_2O$); tert-Butyl methyl ether (t-BuOMe): potassium tert-butoxide (t-BuOK); sodium tert-butoxide (t-BuONa); ceric ammonium nitrate (CAN): concentrated/high concentration (con.); dichloromethane (DCM); diisobutylaluminum hydride (DIBAL-H); diisopropylethylamine (DI(P)EA); 4-dimethylaminopyridine (DMAP); N,N-dimethylformamide dimethyl acetal (DMFDMA); dimethylformamide (DMF); dimethylsulfoxide (DMSO); ethyl acetate (EA or EtOAc); equivalent (eq.): ethanol (EtOH); sodium ethoxide (EtONa); gram/milligram (g/mg); 2-(7-azabenzotriazol)-N,N,N'N'-tetramethyluronium hexafluorophosphate (HATU); hour(s) (h, hr, hrs); acetic acid (HOAc); liter/milliliter (L/mL) liquid chromatography-mass spectrometer (LCM S); lithium diisopropylamide (LDA); methanol (MeOH); mole/millimole (mol/mmol); mass spectroscopy (MS); methanesulfonyl chloride (MsCl); minute(s) (min(s)); sodium acetate (NaOAc); nitrogen ($N_2$); N-bromosuccinimide (NBS); 4-methylmorpholine N-oxide (NMO); nuclear magnetic resonance (NMR); palladium on carbon (Pd/C); petroleum ether (PE); benzoyl chloride (PhCOCl); toluene (PhMe); triphenylphosphine ($PPh_3$); pyridine (Py); 1H-benzotriazol-1-yloxytrispyrrolidinophosphonium hexafluorophosphate (PyBOP): preparative thin layer chromatography (Pre-TLC) room temperature (RT, rt) triethylamine (TEA); tetrahydrofuran (THF); thin layer chromatography (TLC); trimethylsilyl chloride (TMSCl); 1,1'-bis(diphenylphosphino)ferrocene]dichloropalladium ($Pd(dppf)_2Cl_2$).

General Preparation Process:

Unless otherwise specified, all reactions were carried out under inert atmosphere (e.g argon or nitrogen) using commercially available reagents and anhydrous solvents without further treatment.

Mass spectrometry was recorded by liquid chromatography-mass spectrometry (LC-MS) (Agilent 6120B single quadrupole liquid chromatography-mass spectrometer). Nuclear magnetic resonance spectroscopy (such as Proton NMR (-), carbon NMR (OC), phosphorus NMR ($^{31}P$) and fluorine NMR ($^{19}F$) and so on) was recorded by Bruker AMX400, Gemini-300 or AMX-600 nuclear magnetic resonance spectrometer. It is recorded in deuterated solvents, such as deuterated chloroform, deuterated methanol, deuterated water or deuterated dimethyl sulfoxide and the like, and the deuterated solvent peak is used as a reference standard. The unit of chemical shift δ is ppm, the unit of coupling constant (J or J) is Hertz (Hz, Hertz), and the coupling split peak in NMR spectrum is expressed as: broadened singlet (brs), singlet (s), doublet (d), doublet of doublets (dd), triplet (t), quartet (q) and multiplet (m).

Example 1: Synthesis of Compound 2-(4-(2-aminoethyl)piperazin-1-yl)ethan-1-ol

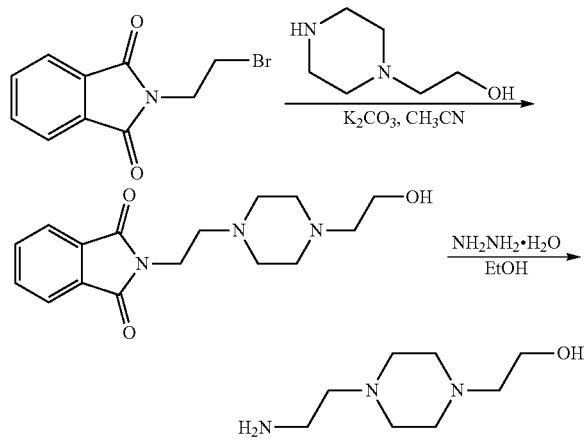

Step 1: Synthesis of Compound 2-(2-(4-(2-hydroxyethyl)piperazin-1-yl)ethyl)isoindoline-1,3-dione The compound 2-(2-bromoethyl)isoindoline-1,3-dione (20.0 g, 78 mmol), the compound 2-(piperazin-1-yl)ethan-1-ol (10.2 g, 78 mmol) and potassium carbonate (22.0 g, 156 mmol) were dissolved in 100 mL acetonitrile, the mixture of which was refluxed for 3 hours. After finishing the reaction, the mixture was cooled to room temperature, then filtered, and the residue was washed with acetonitrile (20 mL). The filtrate was collected, concentrated, and purified and separated by column chromatography to give 13.45 g of the desired compound with a yield of 57%.

Step 2: Synthesis of Compound 2-(4-(2-aminoethyl)piperazin-1-yl)ethan-1-ol

The compound 2-{2-[4-(2-Hydroxy-ethyl)-piperazin-1-yl]-ethyl}-isoindole-1,3-dione (13.45 g, 43.67 mmol) and hydrazine hydrate (80%, 6 mL) were dissolved in EtOH (130 mL) and then refluxed for 4 hours. After finishing the reaction, the mixture was cooled to room temperature, then filtered, and the residue was washed with cold EtOH (20 mL×2). The filtrate was collected, concentrated to give 6.5 g of crude product which can be directly used in the next following step without further purification.

Example 2: Synthesis of Compound 5-(((2-(4-(2-hydroxyethyl)piperazin-1-yl)ethyl)amino)methylene)-2,2-dimethyl-1,3-dioxane-4,6-dione (Compound 1)

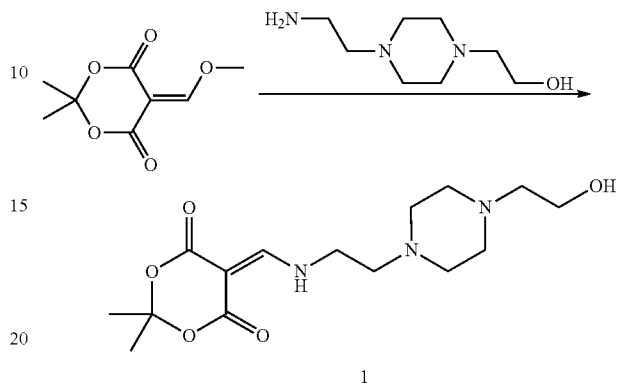

The compound 5-(methoxymethylene)-2,2-dimethyl-1,3-dioxane-4,6-dione (186 mg, 1 mmol) was dissolved in EtOH (5 mL) and 2-(4-(2-aminoethyl)piperazin-1-yl)ethan-1-ol (259.5 mg, 1.5 mmol) was added, then reacting at RT for 15 min. A crude product was obtained by concentration and then purified and separated by column chromatography to give 220 mg of the desired product with a yield of 67.2%. $^1$H NMR (400 MHz, CD$_3$OD) δ 8.22 (s, 1H), 3.67 (t, J=6.0 Hz, 1H), 3.58 (t, J=5.9 Hz, 1H), 2.57 (dt, J=24.7, 6.0 Hz, 1H), 1.66 (s, 1H); LCMS: 328.4 (M+1).

Example 3: Synthesis of Compound 2-(aminomethylene)-5-phenylcyclohexane-1,3-dione (Compound 2)

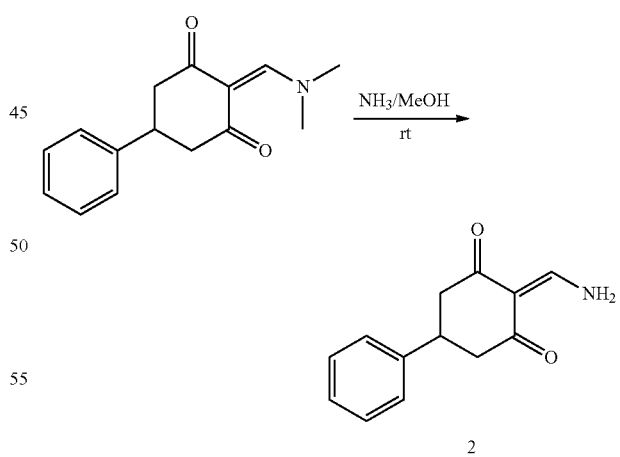

The compound 2-dimethylaminomethylene-5-phenyl-cyclohexane-1,3-dione (1.1 g, 4.52 mmol) was dissolved in ammonia-methanol solution (7 N, 50 mL), stirring at RT for 1 h. A crude product was obtained by concentration and then separated by column chromatography to give 900 mg of the desired product with a yield of 93%. Compound 2: $^1$H NMR (400 MHz, CD$_3$OD) δ 10.12 (br, 1H), 8.24 (br, 1H), 8.02 (q, J=8.8 Hz, 1H), 7.32-7.29 (m, 4H), 7.23-7.17 (m, 1H), 3.31-3.25 (m, 1H), 2.77-2.63 (m, 2H), 2.51-2.45 (m, 2H); MS: 216.1 [M+1].

Example 4: Synthesis of Compound 2-(hydroxymethylene)-5-phenylcyclohexane-1,3-dione (Compound 3)

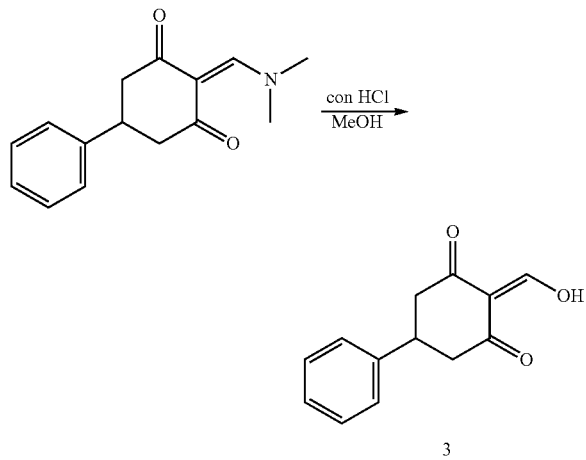

The compound 2-((dimethylamino)methylene)-5-phenyl-cyclohexane-1,3-dione (244 mg, 1 mmol) was dissolved in MeOH (5 mL) and concentrated HCl (1 mL) was added dropwise, then reacting at RT for 30 min. A crude product was obtained by concentration and then separated by column chromatography to give 162 mg of the desired product with a yield of 75%. Compound 3: ¹H NMR (400 MHz, DMSO-d6) δ 9.58 (s, 1H), 7.27-7.30 (m, 4H), 7.16-7.19 (m, 1H), 3.14-3.20 (m, 1H), 2.51 (d, J=16.8 Hz, 1H), 2.47 (d, J=9.2 Hz, 1H), 2.31 (dd, J=16.0, 4.0 Hz, 2H); LCMS: 217.1 [M+1].

Synthesis of Compound 5-(2-bromophenyl)-2-(hydroxymethylene)cyclohexane-1,3-dione (Compound 4)

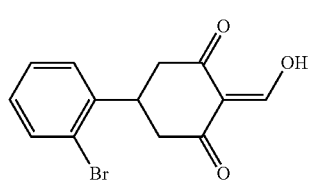 [SMILES: O=C1CC(c2ccccc2Br)CC(=O)C1=CO]

Compound 4 was synthesized by the same procedures as Compound 3. Compound 4: ¹H NMR (400 MHz, DMSO-d6) δ 9.34 (dd, J=9.1, 1.9 Hz, 1H), 7.60 (d, J=7.6 Hz, 1H), 7.49-7.29 (m, 2H), 7.16 (d, J=7.0 Hz, 1H), 3.57 (m, 2H), 2.82-2.56 (m, 2H), 2.41 (d, J=1.8 Hz, 1H); MS: 297.0 [M+1].

Example 5: Synthesis of Compound 2-((methylthio)methylene)-5-phenylcyclohexane-1,3-dione (Compound 4A)

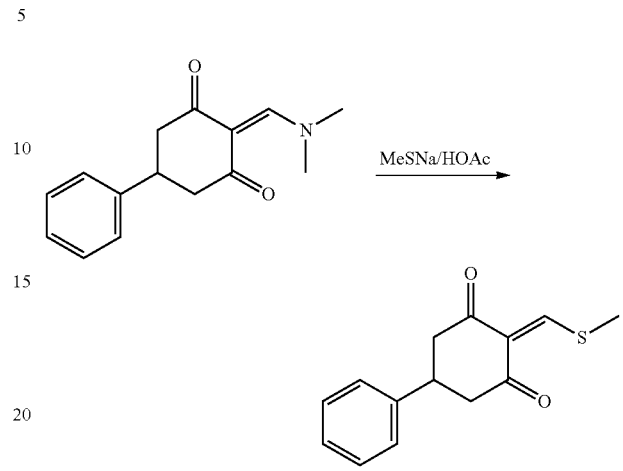

The compound 2-((dimethylamino)methylene)-5-phenyl-cyclohexane-1,3-dione (200 mg, 0.823 mmol) was dissolved in anhydrous EtOH (5 mL) and DCM (5 mL), followed by addition of HOAc (1 mL) and MeSNa (115 mg, 1.64 mmol) at RT. The reaction mixture was stirred at RT in sealed tube for 16 hs. Then HOAc (1 mL) and MeSNa (115 mg, 1.64 mmol) were added, the resulting mixture was stirred for additional 16 hs. After finishing the reaction, the reaction solution was poured into water, and extracted with dichloromethane (DCM). The organic phases were combined and washed successively with water and saturated brine, dried with anhydrous Na₂SO₄ and concentrated to give a crude product, which was separated by column chromatography to give the desired product (15 mg, yield 7%). Compound 4A: ¹H NMR (400 MHz, DMSO-d6) δ 8.75 (s, 1H), 7.33-7.19 (m, 5H), 3.46-3.37 (m, 1H), 2.95-2.86 (m, 2H), 2.72-2.64 (m, 2H), 2.60 (s, 3H); MS: 247.1 [M+1].

Example 6: Synthesis of Compound 5-phenyl-2-((phenylamino)methylene)cyclohexane-1,3-dione (Compound 5)

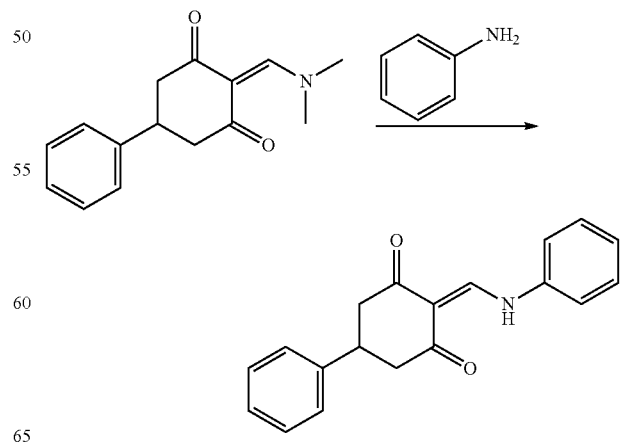

The compound 2-((dimethylamino)methylene)-5-phenyl-cyclohexane-1,3-dione (200 mg, 0.82 mmol), aniline (60 mg, 0.65 mmol) and HOAc (0.5 mL) were dissolved in EtOH (10 mL) and refluxed for 1 hour. The reaction mixture was cooled to RT and concentrated to give a crude product, which was separated by column chromatography to give the desired product (150 mg, yield 79%). Compound 5: ¹H NMR (400 MHz, DMSO-d6) δ 8.72 (s, 1H), 7.49-7.41 (m, 4H), 7.35-7.28 (m, 5H), 7.25-7.22 (m, 1H), 3.46-3.40 (m, 1H), 2.95-2.70 (m, 4H); MS: 292.1 [M+1].

Example 7: Synthesis of Compounds 6 and 7

Compounds 6 and 7 were synthesized by the same procedures as Compound 5, as shown in Table 1.

-continued

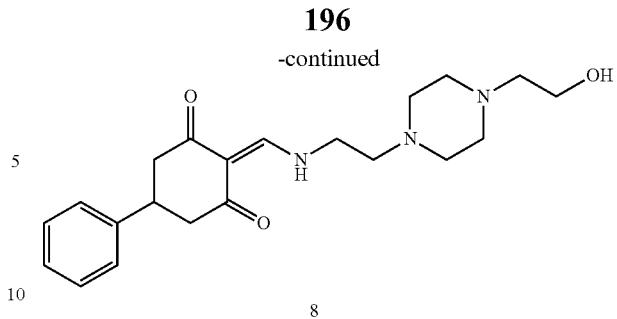

8

Step 1: Synthesis of Compound 2-((dimethylamino)methylene)-5-phenylcyclohexane-1,3-dione The compound 5-phenylcyclohexane-1,3-dione (5.0 g, 26.6 mmol) was dissolved in CHCl₃ (25 mL) and then

TABLE 1

Compound 6 and 7

| # | Structure | Name | Proton NMR (¹HNMR), Mass Spectrum (MS) |
|---|---|---|---|
| 6 | 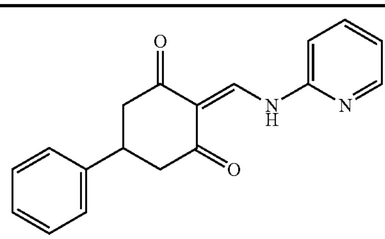 | 5-phenyl-2-((pyridin-2-ylamino)methylene)cyclohexane-1,3-dione | ¹H NMR (400 MHz, CD₃OD) δ 9.27 (s, 1H), 8.43 (dd, J = 4.8, 1.2 Hz, 1H), 7.88-7.84 (m, 1H), 7.35-7.21 (m, 8H), 3.50-3.40 (m, 1H), 2.96-2.72 (m, 4H); MS: 293.1 [M + 1] |
| 7 | 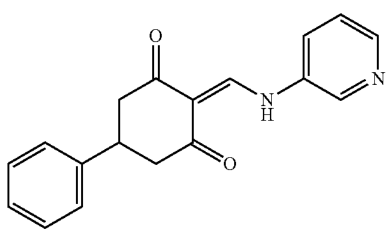 [SMILES: O=C1CC(c2ccccc2)CC(=O)C1=CNc1cccnc1] | 5-phenyl-2-((pyridin-3-ylamino)methylene)cyclohexane-1,3-dione | ¹H NMR (400 MHz, CD₃OD) δ 8.72 (s, 1H), 8.68 (d, J = 3.2 Hz, 1H), 8.45 (d, J = 4.4 Hz, 1H), 7.99-7.96 (m, 1H), 7.55-7.51 (m, 1H), 7.63-7.31 (m, 4H), 7.26-7.22 (m, 1H), 3.47-3.41 (m, 1H), 2.97-2.76 (m, 4H); MS: 293.1 [M + 1] |

Example 8: Synthesis of Compound 2-(((2-(4-(2-hydroxyethyl)piperazin-1-yl)ethyl)amino)methylene)-5-phenylcyclohexane-1,3-dione (Compound 8)

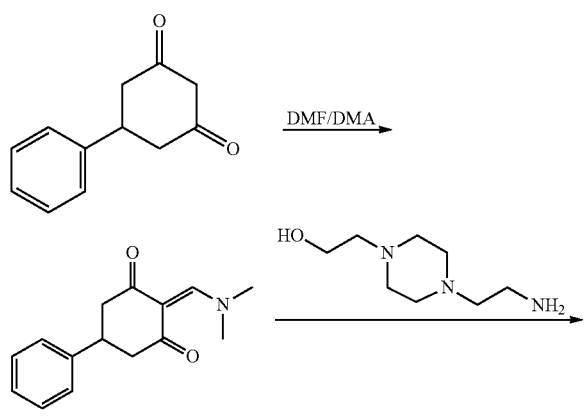

N,N-dimethylformamide dimethyl acetal (DMFDMA) (5 mL) was added. The mixture was reacted at RT for 1 h. After the reaction was completed, the reaction solution was concentrated, and the condensed concentrate was homogenized and precipitated by using 10% ethyl acetate (EA)/petroleum ether (PE), the resulting precipitate was filtered to give a residue, which was dried to give the desired product (4.81 g, yield 74%).

Step 2: Synthesis of Compound 2-(((2-(4-(2-hydroxyethyl)piperazin-1-yl)ethyl)amino)methylene)-5-phenylcyclohexane-1,3-dione (Compound 8)

The compound 2-(4-(2-aminoethyl)piperazin-1-yl)ethan-1-ol (200 mg, 1.15 mmol) was dissolved in EtOH (5 mL) and then 2-((dimethylamino)methylene)-5-phenylcyclohexane-1,3-dione (365 mg, 1.5 mmol) was added. The mixture was reacted at room temperature for 30 min to produce a solid, then filtered. The residue was washed by EtOH, then collected and dried to give the desired product (312 mg, yield 73%). Compound 8: ¹HNMR (400 MHz, CD₃OD) δ 8.25 (s, 1H), 7.34-7.20 (m, 5H), 3.80 (t, J=5.6 Hz, 2H), 3.61 (t, J=5.6 Hz, 2H), 3.40-3.30 (m, 1H), 3.06 (br, 4H), 2.98 (t, J=4.4 Hz, 2H), 2.85-2.64 (m, 10H); MS: 372.3 [M+1].

Example 9: Synthesis of Compounds 9-12, 14-15

Compounds 9-16 were synthesized by the same procedures as Compound 8 using corresponding substituted cyclohexane-1,3-dione, or other ketones with active methylene (see, e.g, Example 9-1), and are shown in Table 2.

TABLE 2

Compounds 9-12 and 14-15

| # | Structure | Name | Proton NMR ($^1$HNMR), Mass Spectrum (MS) |
|---|---|---|---|
| 9 | 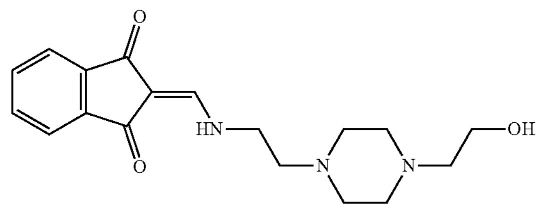 [SMILES: O=C1C(=CNCCN2CCN(CCO)CC2)C(=O)c2ccccc21] | 2-(((2-(4-(2-hydroxyethyl)piperazin-1-yl)ethyl)amino)methylene)-1H-indene-1,3(2H)-dione | $^1$H NMR (400 MHz, CD$_3$OD) δ 7.85 (s, 1H), 7.66 (d, J = 2.4 Hz, 4H), 3.72 (t, J = 5.9 Hz, 2H), 3.59 (t, J = 5.9 Hz, 2H), 2.78-2.60 (m, 12H); MS: 330.3 [M + 1]. |
| 10 | 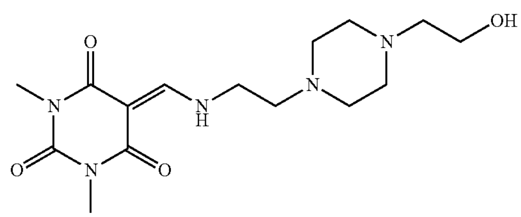 | 5-(((2-(4-(2-hydroxyethyl)piperazin-1-yl)ethyl)amino)methylene)-1,3-dimethylpyrimidine-2,4,6(1H,3H,5H)-trione | $^1$H NMR (400 MHz, CD$_3$OD) δ 8.25 (s, 1H), 3.72 (t, J = 5.9 Hz, 2H), 3.62 (t, J = 5.8 Hz, 2H), 3.39-3.08 (m, 6H), 2.97 2.31 (m, 12H); MS: 400.2 [M + 1]. |
| 11 | 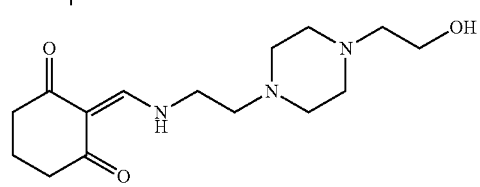 | 2-(((2-(4-(2-hydroxyethyl)piperazin-1-yl)ethyl)amino)methylene)cyclohexane-1,3-dione | $^1$H NMR (400 MHz, CD$_3$OD) δ 8.21 (s, 1H), 3.68 (t, J = 6.0 Hz, 2H), 3.57 (t, J = 5.9 Hz, 2H), 2.61 (dd, J = 15.9, 10.1 Hz, 12H), 2.44 (dd, J = 9.5, 6.6 Hz, 4H), 2.04-1.85 (m, 2H); MS: 296.2 [M + 1]. |
| 12 | 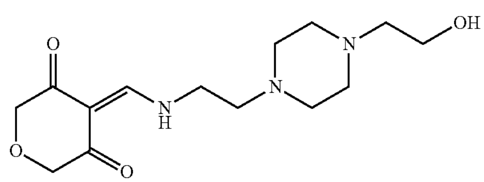 [SMILES: O=C1COCC(=O)C1=CNCCN1CCN(CCO)CC1] | 4-(((2-(4-(2-hydroxyethyl)piperazin-1-yl)ethyl)amino)methylene)-2H-pyran-3,5(4H,6H)-dione | $^1$H NMR (400 MHz, CD$_3$OD) δ 8.24 (s, 1H), 4.17 (s, 4H), 3.74 (t, J = 5.9 Hz, 2H), 3.64 (t, J = 5.9 Hz, 2H), 2.96-2.41 (m, 12H); MS: 298.2 [M + 1]. |
| 14 | 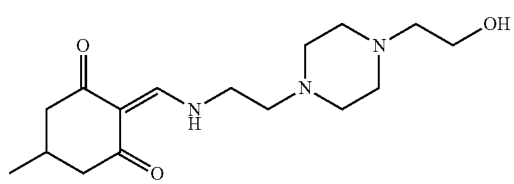 [SMILES: CC1CC(=O)C(=CNCCN2CCN(CCO)CC2)C(=O)C1] | 2-(((2-(4-(2-hydroxyethyl)piperazin-1-yl)ethyl)amino)methylene)-5-methylcyclohexane-1,3-dione | $^1$H NMR (400 MHz, CD$_3$OD) δ 8.19 (s, 1H), 3.71 (t, J = 5.9 Hz, 2H), 3.57 (t, J = 5.9 Hz, 2H), 2.84-2.54 (m, 12H), 2.49 (d, J = 15.5 Hz, 2H), 2.24-2.02 (m, 3H), 1.05 (d, J = 5.6 Hz, 3H); MS: 310.3 [M + 1]. |
| 15 | 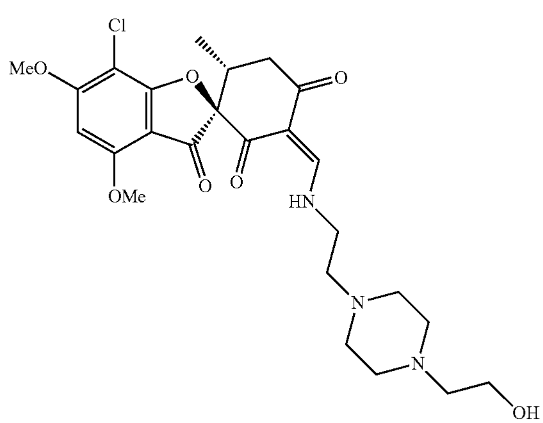 [SMILES: COc1cc(OC)c2c(c1Cl)O[C@@]1(C(=O)/C(=C\NCCN3CCN(CCO)CC3)C(=O)C[C@H]1C)C2=O] | (2R,6'R)-7-chloro-3'-(((2-(4-(2-hydroxyethyl)piperazin-1-yl)ethyl)amino)methylene)-4,6-dimethoxy-6'-methyl-3H-spiro[benzofuran-2,1'-cyclohexane]-2',3,4'-trione | $^1$HNMR (400 MHz, CD$_3$OD) δ 8.25 (d, J = 13.6 Hz, 1H), 6.39 (s, 1H), 4.05 (s, 3H), 3.95 (s, 3H), 3.71 (t, J = 6.0 Hz, 2H), 3.61 (d, J = 4.8 Hz, 2H), 3.17-3.06 (m, 1H), 2.84-2.49 (m, 14H), 0.94 (d, J = 6.8 Hz, 3H); MS: 522.2 [M + 1]. |

Example 9-1: Synthesis of Intermediate 3-1: (2S, 2'R)-7-chloro-4,6-dimethoxy-2'-methyl-3H-spiro[benzofuran-2,1'-cyclohexane]-3,4',6'-trione

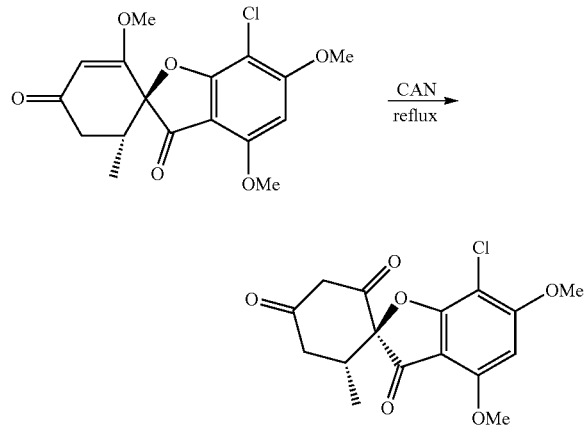

The compound (2S, 6'R)-7-chloro-2',4,6-trimethoxy-6'-methyl-3H-spiro[benzofuran-2,1'-cyclohexan]-2'-ene-3,4'-dione (1.0 g, 2.84 mmol) and ceric ammonium nitrate (1.55 g, 2.84 mmol) were dissolved in the mixed solvent of CH₃CN (40 mL)/H₂O (40 mL), then heated to reflux for 6 hours. After the reaction was completed, the reaction mixture was cooled to RT and poured into water, extracted with EA. The organic phase was washed successively with water, and saturated brine, dried with anhydrous Na₂SO₄ and concentrated to give a crude product, which was separated by column chromatography to give the desired product (880 mg, yield 91%).

Example 10: Synthesis of Compound 2-(((2-(4-(2-hydroxyethyl)piperazin-1-yl)ethyl)amino)methylene)-5-(1H-pyrrolo[2,3-b]pyridin-4-yl)cyclohexane-1,3-dione (Compound 17)

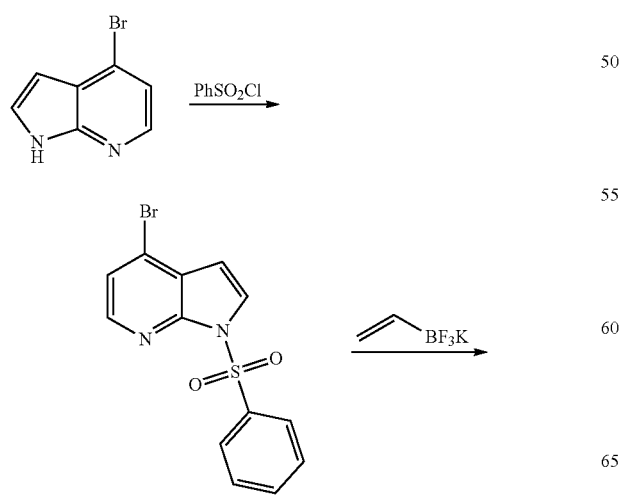

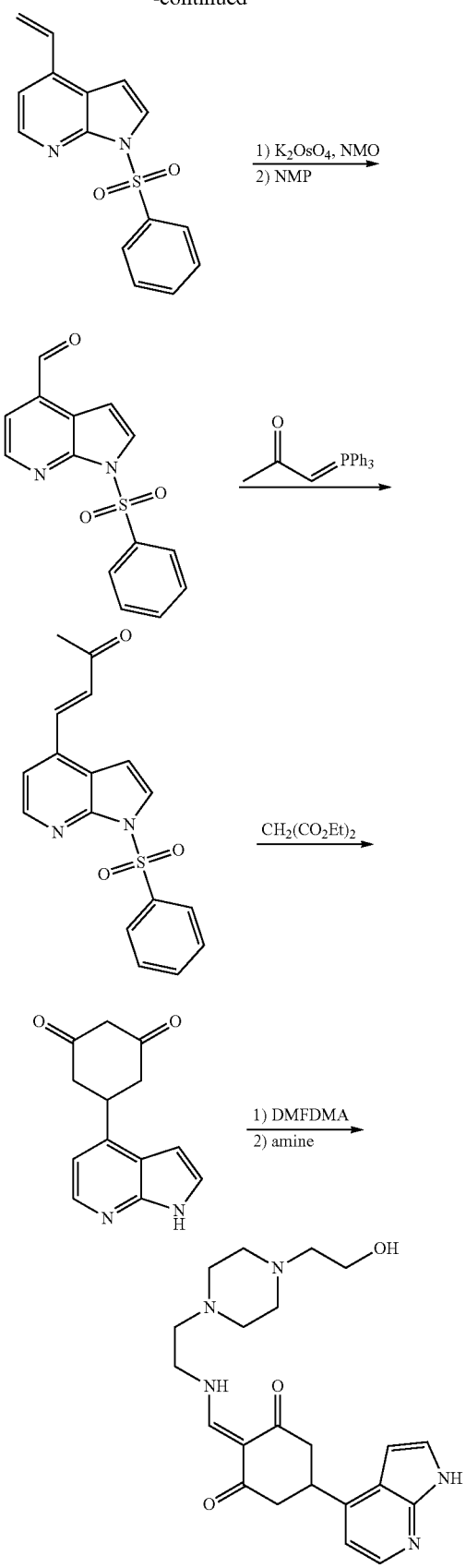

Step 1: Synthesis of Compound 4-bromo-1-(phenylsulfonyl)-1H-pyrrolo[2,3-b]pyridine Under the protection of nitrogen atmosphere, the compound 4-bromo-1H-pyrrolo[2,3-b]pyridine (3.0 g, 15.23 mmol) was dissolved in anhydrous tetrahydrofuran (THF) (50 mL), then 60% NaH (800 mg, 20 mmol) was added portionwise into the above mixed solution at 0° C. After stirring at this temperature for 30 min, benzenesulfonyl chloride (3.53 g, 20 mmol) was added, the resulting mixture was reacted at RT for 1 h. After the reaction was completed, the reaction mixture was carefully quenched by ice-water at 0° C. and extracted with EA. The organic phase was washed with water, dried with anhydrous $Na_2SO_4$ and concentrated to give a crude product, which was separated by column chromatography to give the desired product (4.3 g, yield 84%).

Step 2: Synthesis of Compound 1-(phenylsulfonyl)-4-C2-6 vinyl-1H-pyrrolo[2,3-b]pyridine Under the protection of nitrogen atmosphere, the compound 4-bromo-1-(phenylsulfonyl)-1H-pyrrolo[2,3-b]pyridine (4.3 g, 12.8 mmol) was dissolved in dioxane (50 mL) and $H_2O$ (10 mL), then Pd(dppf)$Cl_2$ (470 mg, 0.64 mmol), potassium vinyltrifluoroborate (2.57 g, 19.2 mmol) and N,N-diisopropylethylamine (DIPEA) (3.23 g, 25 mmol) were added successively. The above mixture was reacted and refluxed for 2 hours. After the reaction was completed, the reaction mixture was cooled to RT, poured into ice-water, extracted with EA. The organic phase was washed with water and saturated brine, then dried and concentrated to give a crude product, which was separated by column chromatography to give the desired product (2.52 g, yield 70%).

Step 3: Synthesis of Compound 1-(phenylsulfonyl)-1H-pyrrolo[2,3-b]pyridine-4-carbaldehyde The compound 1-(phenylsulfonyl)-4-C2-6 vinyl-1H-pyrrolo[2,3-b]pyridine (2.52 g, 8.86 mmol) was dissolved in acetone (50 mL) and $H_2O$ (10 mL), then NMO (1.56 g, 13.3 mmol) and $K_2OsO_4 \cdot 2H_2O$ (100 mg) were added and reacted at RT for 2 hours. Then NaIO4 (7.56 g, 35.44 mmol) was added portionwise into the above reaction solution at RT, then reacted continuously at RT for 1 hour. After the reaction was completed, the reaction mixture was poured into water and extracted with EA. The organic phase was washed with water and saturated brine, then dried and concentrated to give a crude product, which was separated by column chromatography to give the desired product (1.52 g, yield 60%).

Step 4: Synthesis of Compound 4-(1-(phenylsulfonyl)-1H-pyrrolo[2,3-b]pyridin-4-yl)but-3-en-2-one The compounds 1-(phenylsulfonyl)-1H-pyrrolo[2,3-b]pyridine-4-carbaldehyde (1.52 g, 5.3 mmol) and (acetylmethyene)triphenylphosphorane (2.55 g, 8 mmol) were respectively added into anhydrous THE (30 mL), then reacted and refluxed for 2 hours. After the reaction was completed, the reaction mixture was cooled to RT and concentrated to give a crude product, which was separated by column chromatography to give the desired product (1.52 g, yield 88%).

Step 5: Synthesis of Compound 5-(1H-pyrrolo[2,3-b]pyridin-4-yl)cyclohexane-1,3-dione The compound diethyl malonate (970 mg, 6.06 mmol) was added into the solution of EtONa (412 mg, 6.06 mmol) in EtOH (20 mL). After stirring at RT for 10 min, the solution of 4-(1-(phenylsulfonyl)-1H-pyrrolo[2,3-b]pyridin-4-yl)but-3-en-2-one (1.52 g, 4.66 mmol) in anhydrous EtOH (10 mL) was added, the resulting mixture was heated and refluxed for 1 hour. The reaction mixture was cooled to room temperature and added with $H_2O$ (50 mL) and then extracted with EA (50 mL). The aqueous phase was acidified with 3N HCl to pH 2-3 and then heated to reflux for 30 min. The reaction mixture was cooled to RT an extracted with EA The combined organic phase was washed successively with water and saturated brine, then dried and concentrated. The crude product was separated by column chromatography to give the desired product (620 mg, yield 58.3%).

Step 6: Synthesis of Compound 2-(((2-(4-(2-hydroxyethyl)piperazin-1-yl)ethyl)amino)methylene)-5-(1H-pyrrolo[2,3-b]pyridin-4-yl)cyclohexane-1,3-dione The operation procedure was the same as that of Example 2. Compound 17: $^1$H NMR (400 MHz, CDCl$_3$) δ 11.31-11.15 (m, 1H), 9.81 (s, 1H), 8.27 (dd, J=18.6, 9.6 Hz, 2H), 7.35 (d, J=3.4 Hz, 1H), 6.95 (d, J=5.0 Hz, 1H), 6.56 (d, J=3.5 Hz, 1H), 3.92-3.77 (m, 1H), 3.73-3.64 (m, 2H), 3.60-3.46 (m, 2H), 3.07-2.53 (m, 17H); MS: 412.4 [M+1].

Example 11: Compounds 18-32

Compounds 18-32 were synthesized by the same procedures as Compound 17 except for using corresponding bromine-substituted C6-10 aryl or aldehyde (see, e.g, Examples 11-1 to 11-5), the results are shown in Table 3.

TABLE 3

Compounds 18-32

| # | Structure | Name | Proton NMR (¹HNMR), Mass Spectrum (MS) |
|---|---|---|---|
| 18 | 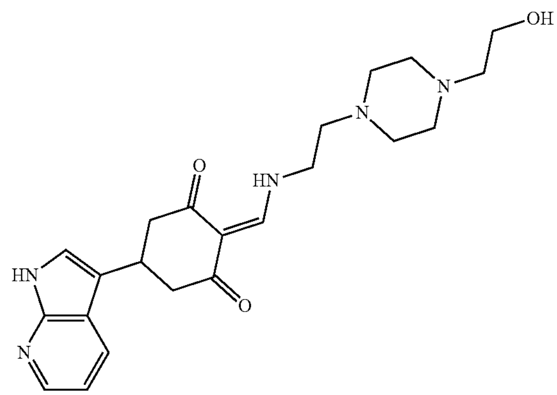 [SMILES: O=C1CC(c2c[nH]c3ncccc23)CC(=O)C1=CNCCN1CCN(CCO)CC1] | 2-(((2-(4-(2-hydroxyethyl)piperazin-1-yl)ethyl)amino)methylene)-5-(1H-pyrrolo[2,3-b]pyridin-3-yl)cyclohexane-1,3-dione | ¹H NMR (400 MHz, CDCl$_3$) δ 11.28-11.08 (m, 1H), 9.50 (s, 1H), 8.32 (dd, J = 4.6, 0.6 Hz, 1H), 8.20 (d, J = 14.3 Hz, 1H), 7.97 (dd, J = 7.9, 1.3 Hz, 1H), δ 7.14-7.07 (m, 1H), 3.85-3.62 (m, 2H), 3.52 (d, J = 5.9 Hz, 3H), 3.12-2.51 (m, 2H): MS: 412.2 [M + 1]. |
| 19 | 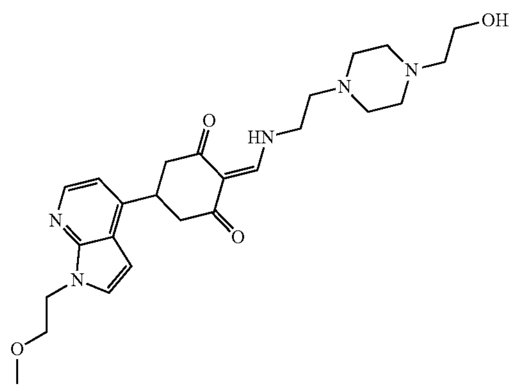 [SMILES: COCCn1ccc2c(C3CC(=O)C(=CNCCN4CCN(CCO)CC4)C(=O)C3)ccnc21] | 2-(((2-(4-(2-hydroxyethyl)piperazin-1-yl)ethyl)amino)methylene)-5-(1-(2-methoxyethyl)-1H-pyrrolo[2,3-b]pyridin-4-yl)cyclohexane-1,3-dione | ¹H NMR (400 MHz, DMSO-d$_6$) δ 11.03-10.91 (m, 1H), 8.34-8.01 (m, 2H), 7.51 (d, J = 3.5 Hz, 1H), 7.00 (d, J = 5.0 Hz, 1H), 6.64 (d, J = 3.5 Hz, 1H), 4.40 (t, J = 5.4 Hz, 3H), 3.83-3.65 (m, 3H), 3.58 (dd, J = 11.6, 5.8 Hz, 4H), 3.49 (dd, J = 11.4, 5.9 Hz, 3H), 3.23 (s, 2H), 2.97-2.76 (m, 2H), 2.69-2.23 (m, 12H); MS: 470.1 [M + 1]. |
| 20 | 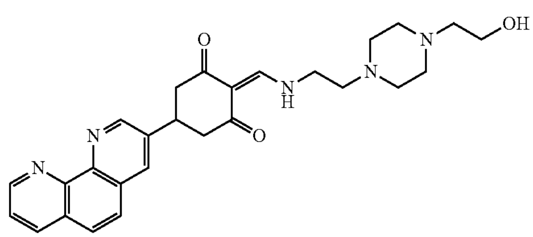 [SMILES: O=C1CC(c2cnc3c(ccc4cccnc43)c2)CC(=O)C1=CNCCN1CCN(CCO)CC1] | 2-(((2-(4-(2-hydroxyethyl)piperazin-1-yl)ethyl)amino)methylene)-5-(1,10-phenanthrolin-3-yl)cyclohexane-1,3-dione | ¹H NMR (400 MHz, DMSO-d$_6$) δ 11.09-10.83 (m, 1H), 9.09 (dd, J = 2.0, 1.0 Hz, 1H), 8.47 (dd, J = 12.3, 4.7 Hz, 2H), 8.17 (d, J = 14.6 Hz, 1H), 7.95 (s, 2H), 7.77 (dd, J = 7.6, 6.9 Hz, 2H), 5.20-4.90 (m, 1H), 3.94-3.52 (m, 6H), 3.14-2.83 (m, 7H), 2.85-2.62 (m, 4H), 2.57 (s, 4H); MS: 474.3 [M + 1]. |
| 21 | 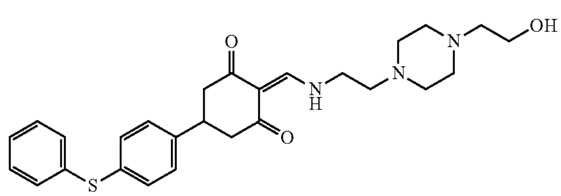 [SMILES: O=C1CC(c2ccc(Sc3ccccc3)cc2)CC(=O)C1=CNCCN1CCN(CCO)CC1] | 2-(((2-(4-(2-hydroxyethyl)piperazin-1-yl)ethyl)amino)methylene)-5-(4-(phenylthio)phenyl)cyclohexane-1,3-dione | ¹H NMR (400 MHz, CD$_3$OD) δ 8.24 (s, 1H), 7.49-6.95 (m, 9H), 3.79 (t, J = 5.4 Hz, 2H), 3.61 (t, J = 5.3 Hz, 2H), 3.43-3.32 (m, 1H), 3.11-2.87 (m, 6H), 2.85-2.58 (m, 10H); MS: 480.2 [M + 1]. |
| 22 | 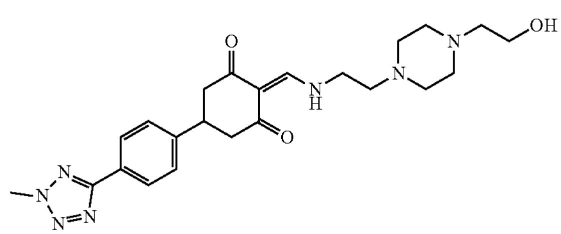 [SMILES: Cn1nnc(-c2ccc(C3CC(=O)C(=CNCCN4CCN(CCO)CC4)C(=O)C3)cc2)n1] | 2-(((2-(4-(2-hydroxyethyl)piperazin-1-yl)ethyl)amino)methylene)-5-(4-(2-methyl-2H-tetrazol-5-yl)phenyl)cyclohexane-1,3-dione | ¹H NMR (400 MHz, DMSO-d$_6$) δ 11.01-10.86 (m, 1H), 8.12 (d, J = 14.6 Hz, 1H), 7.98 (d, J = 8.3 Hz, 2H), 7.49 (d, J = 8.3 Hz, 2H), 4.40 (s, 4H), 3.63-3.51 (m, 2H), 3.51-3.42 (m, 2H), 3.43-3.34 (m, 1H), 2.86-2.62 (m, 3H), 2.60-2.51 (m, 3H), 2.51-2.24 (m, 10H); MS: 454.3 [M + 1]. |

TABLE 3-continued

Compounds 18-32

| # | Structure | Name | Proton NMR ($^1$HNMR), Mass Spectrum (MS) |
|---|---|---|---|
| 23 | 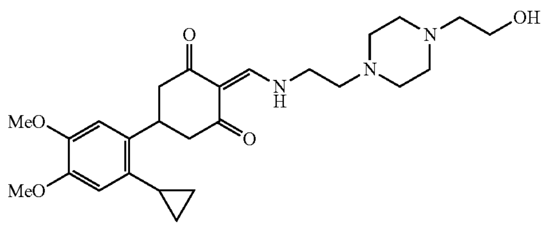 [SMILES: COc1cc(C2CC2)c(C2CC(=O)C(=CNCCN3CCN(CCO)CC3)C(=O)C2)cc1OC] | 5-(2-cyclopropyl-4,5-dimethoxyphenyl)-2-(((2-(4-(2-hydroxyethyl)piperazin-1-yl)ethyl)amino)methylene)cyclohexane-1,3-dione | $^1$H NMR (400 MHz, CD$_3$OD) δ 8.28 (s, 1H), 6.88 (s, 1H), 6.67 (s, 1H), 3.99 (dd, J = 10.1, 6.2 Hz, 1H), 3.80 (t, J = 4.0 Hz, 8H), 3.63 (t, J = 5.7 Hz, 2H), 3.18-2.39 (m, 16H), 2.01-1.78 (m, 1H), 0.90 (dd, J = 8.3, 1.5 Hz, 2H), 0.61 (d, J = 4.0 Hz, 2H); MS: 472.2 [M + 1]. |
| 24 | 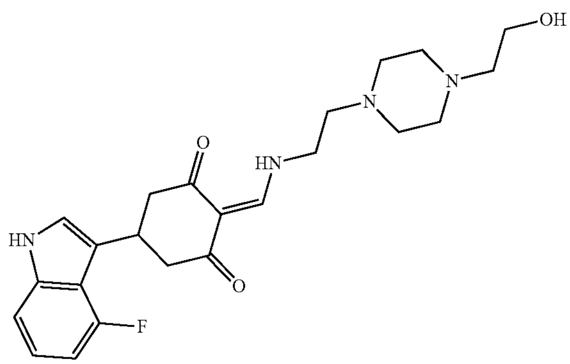 [SMILES: O=C1CC(c2c[nH]c3cccc(F)c23)CC(=O)C1=CNCCN1CCN(CCO)CC1] | 5-(4-fluoro-1H-indol-3-yl)-2-(((2-(4-(2-hydroxyethyl)piperazin-1-yl)ethyl)amino)methylene)cyclohexane-1,3-dione | $^1$H NMR (400 MHz, CD$_3$OD) δ 8.29 (s, 1H), 7.18 (d, J = 8.1 Hz, 1H), 7.11-6.99 (m, 2H), 6.71 (dd, J = 11.7, 7.8 Hz, 1H), 3.85-3.69 (m, 3H), 3.64 (t, J = 5.7 Hz, 2H), 3.03-2.52 (m, 16H); MS: 430.4 [M + 1]. |
| 25 | 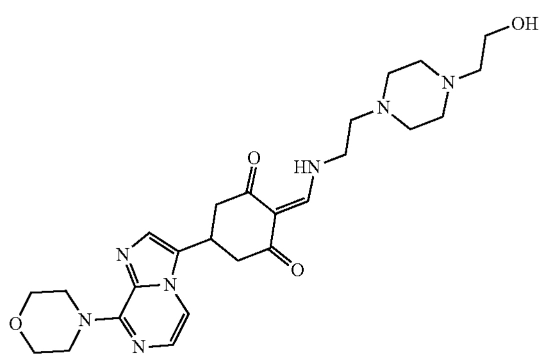 [SMILES: O=C1CC(c2cnc3c(N4CCOCC4)nccn23)CC(=O)C1=CNCCN1CCN(CCO)CC1] | 2-(((2-(4-(2-hydroxyethyl)piperazin-1-yl)ethyl)amino)methylene)-5-(8-morpholinoimidazo[1,2-a]pyrazin-3-yl)cyclohexane-1,3-dione | $^1$HNMR (400 MHz, CD$_3$OD) δ 8.28 (s, 1H), 7.77 (d, J = 4.7 Hz, 1H), 7.43 (d, J = 4.6 Hz, 1H), 7.37 (s, 1H), 4.18-4.06 (m, 4H), 3.90-3.78 (m, 5H), 3.69 (t, J = 6.0 Hz, 2H), 3.62 (t, J = 5.8 Hz, 2H), 3.01-2.73 (m, 5H), 2.59 (m, 11H). |
| 26 | 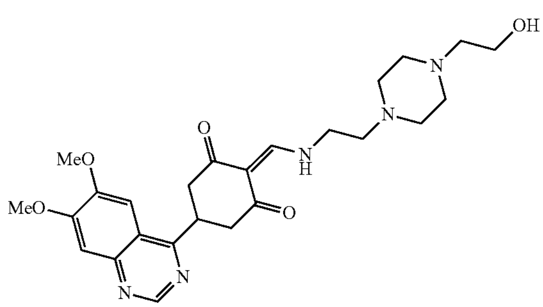 [SMILES: COc1cc2ncnc(C3CC(=O)C(=CNCCN4CCN(CCO)CC4)C(=O)C3)c2cc1OC] | 5-(6,7-dimethoxyquinazolin-4-yl)-2-(((2-(4-(2-hydroxyethyl)piperazin-1-yl)ethyl)amino)methylene)cyclohexane-1,3-dione | $^1$HNMR (400 MHz, DMSO-d6) δ 11.00-10.90 (m, 1H), 9.00 (s, 1H), 8.17 (d, J = 14.6 Hz, 1H), 7.59 (s, 1H), 7.35 (s, 1H), 4.59-4.45 (m, 1H), 3.97 (d, J = 4.0 Hz, 6H), 3.74-3.52 (m, 4H), 2.85 (ddd, J = 22.8, 16.8, 10.8 Hz, 7H), 2.71-2.53 (m, 6H). |
| 27 | 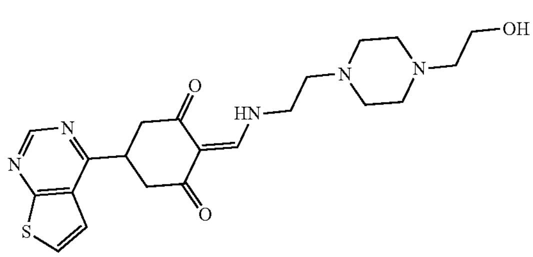 [SMILES: O=C1CC(c2ncnc3sccc23)CC(=O)C1=CNCCN1CCN(CCO)CC1] | 2-(((2-(4-(2-hydroxyethyl)piperazin-1-yl)ethyl)amino)methylene)-5-(thieno[2,3-d]pyrimidin-4-yl)cyclohexane-1,3-dione | $^1$HNMR (400 MHz, CD$_3$OD) δ 8.96 (s, 1H), 8.28 (s, 1H), 7.83 (d, J = 6.1 Hz, 1H), 7.68 (d, J = 6.1 Hz, 1H), 4.22 (td, J = 10.5, 5.2 Hz, 1H), 3.84-3.76 (m, 2H), 3.63 (t, J = 5.7 Hz, 2H), 3.15 2.87 (m, 8H), 2.85-2.59 (m, 8H). |

TABLE 3-continued

Compounds 18-32

| # | Structure | Name | Proton NMR (¹HNMR), Mass Spectrum (MS) |
|---|---|---|---|
| 28 | 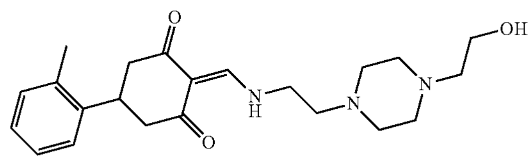 [SMILES: Cc1ccccc1C1CC(=O)C(=CNCCN2CCN(CCO)CC2)C(=O)C1] | 2-(((2-(4-(2-hydroxyethyl)piperazin-1-yl)ethyl)amino)methylene)-5-(o-tolyl)cyclohexane-1,3-dione | ¹HNMR (400 MHz, CD$_3$OD) δ 8.27 (s, 1H), 7.27-7.11 (m, 4H), 3.69 (t, J = 6.0 Hz, 2H), 3.63-3.55 (m, 3H), 2.78-2.56 (m, 16H), 3.34 (s, 3H); MS: 386.2 [M + 1]. |
| 29 | 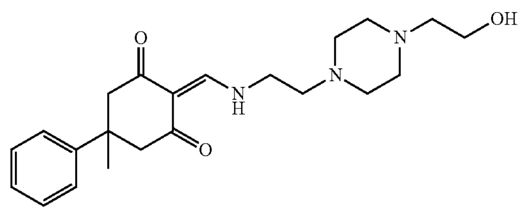 [SMILES: CC1(c2ccccc2)CC(=O)C(=CNCCN2CCN(CCO)CC2)C(=O)C1] | 2-(((2-(4-(2-hydroxyethyl)piperazin-1-yl)ethyl)amino)methylene)-5-methyl-5-phenylcyclohexane-1,3-dione | ¹H NMR (400 MHz, CD$_3$OD) δ 8.07 (s, 1H), 7.34-7.25 (m, 4H), 7.18-7.14 (m, 1H), 3.79 (t, J = 5.6 Hz, 2H), 3.53-3.49 (m, 2H), 3.06-2.96 (m, 8H), 2.77-2.58 (m, 8H), 1.36 (s, 3H) |
| 30 | 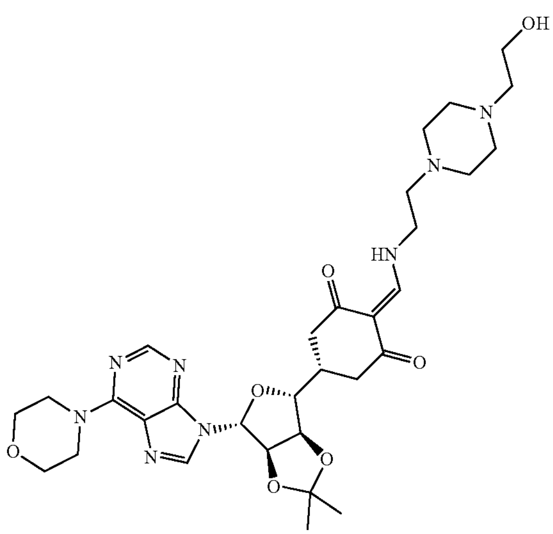 | 5-((3aR,4R,6R,6aR)-2,2-dimethyl-6-(6-morpholino-9H-purin-9-yl)tetrahydrofuro[3,4-d][1,3]dioxol-4-yl)-2-(((2-(4-(2-hydroxyethyl)piperazin-1-yl)ethyl)amino)methylene)cyclohexane-1,3-dione | ¹HNMR (400 MHz, CD$_3$OD) δ 8.25 (s, 1H), 8.17 (m, 2H), 6.14 (d, J = 2.6 Hz, 1H), 5.42-5.31 (m, 1H), 5.08-4.99 (m, 1H), 4.26 (s, 4H), 3.95 (m, 1H), 3.84-3.68 (m, 6H), 3.57 (m, 2H), 2.90-2.70 (m, 6H), 2.61 (s, 7H), 2.46 (m, 5H), 1.57 (s, 3H), 1.37 (s, 3H) |
| 31 | 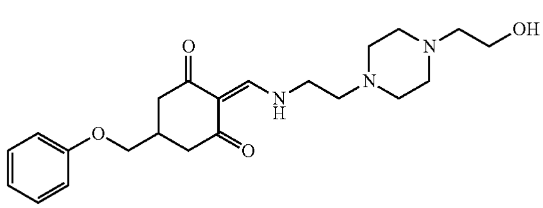 [SMILES: O=C1CC(COc2ccccc2)CC(=O)C1=CNCCN1CCN(CCO)CC1] | 2-(((2-(4-(2-hydroxyethyl)piperazin-1-yl)ethyl)amino)methylene)-5-(phenoxymethyl)cyclohexane-1,3-dione | ¹HNMR (400 MHz, CD$_3$OD) δ 8.26 (s, 1H), 7.41-7.14 (m, 2H), 7.03-6.88 (m, 3H), 3.97 (d, J = 5.1 Hz, 2H), 3.75 (t, J = 5.8 Hz, 2H), 3.63 (t, J = 5.8 Hz, 2H), 2.92-2.41 (m, 17H); MS: 402.4 [M + 1]. |
| 32 | 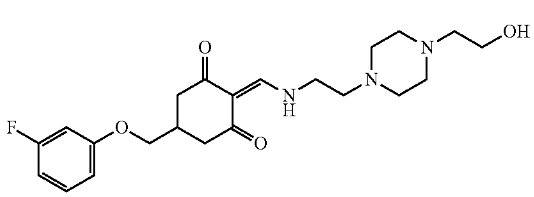 [SMILES: O=C1CC(COc2cccc(F)c2)CC(=O)C1=CNCCN1CCN(CCO)CC1] | 5-((3-fluorophenoxy)methyl)-2-(((2-(4-(2-hydroxyethyl)piperazin-1-yl)ethyl)amino)methylene)cyclohexane-1,3-dione | ¹HNMR (400 MHz, CD$_3$OD) δ 8.22 (s, 1H), 7.24 (dd, J = 15.2, 8.1 Hz, 1H), 6.73 (d, J = 8.2 Hz, 1H), 6.70-6.59 (m, 2H), 3.94 (d, J = 5.1 Hz, 2H), 3.77 (t, J = 5.6 Hz, 2H), 3.59 (t, J = 5.7 Hz, 2H), 2.98-2.91 (m, 5H), 2.79-2.32 (m, 12H); MS: 420.4 [M + 1]. |

Example 11-1: Synthesis of Intermediate 11-1: 4-bromo-1-(2-methoxyethyl)-1H-pyrrolo[2,3-b]pyridine

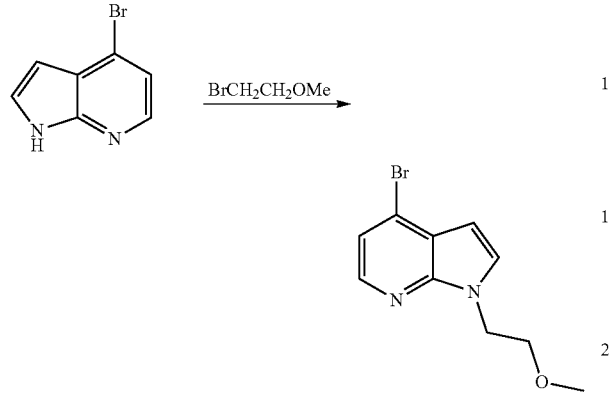

4-bromo-1H-pyrrolo[2,3-b]pyridine (3.0 g, 15.2 mmol) was dissolved in anhydrous N,N-dimethylformamide (DMF) (30 mL), into which was slowly added NaH (60%, 800 mg, 20 mmol) at 0° C. and was reacted at this temperature for 30 min. Then 1-bromo-2-methoxyethane (2.78 g, 20 mmol) was added and the reaction was warmed to RT and reacted for additional 4 hours. After the reaction was completed, the reaction mixture was carefully poured into ice-water and extracted with EA. The organic phase was successively washed with water and saturated brine, then dried and concentrated. The crude product was separated by column chromatography to give the desired product (3.12 g, yield 80%).

Example 11-2: Synthesis of Intermediate 11-2: 2-cyclopropyl-4,5-dimethoxybenzaldehyde

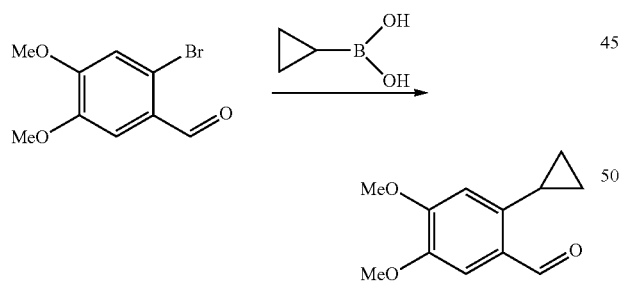

Under the protection of nitrogen atmosphere, 6-bromoveratraldehyde (1.0 g, 4.08 mmol), cyclopropylboronic acid (515 mg, 6 mmol), $Na_2CO_3$ (1.06 g, 10 mmol) and $Pd(PPh_3)_4$ (100 mg, 0.086 mmol) were added into dioxane (15 mL)/$H_2O$ (5 mL), then refluxed and reacted overnight. After the reaction was completed, the reaction mixture was cooled to RT, poured into ice-water and extracted with EA. The organic phase was successively washed with water and saturated brine, then dried and concentrated. The crude product was separated by column chromatography to give the product (560 mg, yield 66%).

Example 11-3: Synthesis of Intermediate 11-3: 4-(3-bromoimidazo-[1,2-a]pyrazin-8-yl)morpholine

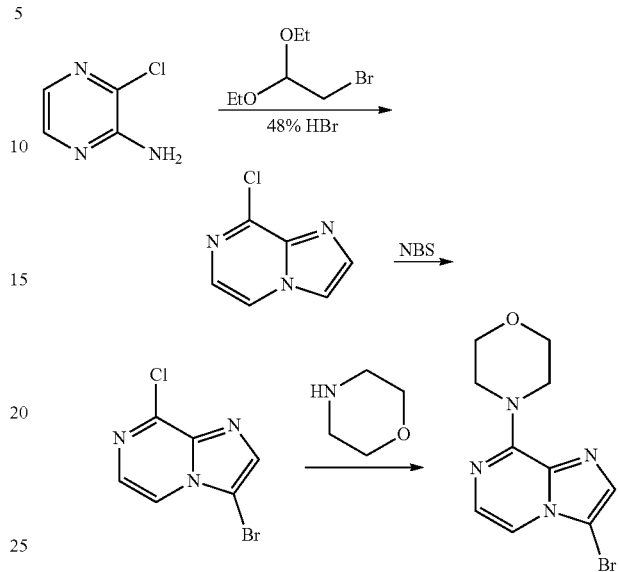

Step 1: Synthesis of Compound 8-chloroimidazo[1,2-a]pyrazine

A aqueous solution of 2-bromo-1,1-diethoxyethane (22.7 g, 0.115 mol) in 48% hydrogen bromide (4.45 mL) was heated under reflux for 2 hours and then poured into a solution of $NaHCO_3$ (74.5 g) in isopropanol (200 mL). The mixture was stirred for 30 minutes and then filtered. 3-Chloropyrazin-2-amine (5.0 g, 38.6 mmol) was added into the filtrate and the mixture was stirred at 85dded rred for and then concentrated. The resulted product was added into a saturated solution of $Na_2CO_3$ and extracted with DCM. The combined organic layers were dried and concentrated. The crude product was recrystallized with ether to give the desired product (5.7 g, crude) which was used in next step without further purification.

Step 2: Synthesis of Compound 3-bromo-8-chloroimidazo[1,2-a]pyrazine

NBS (6.6 g, 37 mmol) was added portionwise to a solution of 8-chloroimidazo[1,2-a]pyrazine (5.7 g) in DCM (100 mL) at RT and reacted for 2 hours, After the reaction was completed, the reaction mixture was poured into water and extracted with DCM. The organic phase was washed with water, brine, then dried and concentrated to give the crude product (8.0 g) which was used in next step without further purification.

Step 3: Synthesis of Compound 4-(3-bromoimidazo [1,2-a]pyrazin-8-yl)morpholine The mixture of 3-bromo-8-chloroimidazo[1,2-a]pyrazine (8.0 g), DIPEA (5.7 g, 44 mmol) and morpholine (6.44 g, 74 mmol) was reacted at 80° C. for 4 hours. After the reaction was completed, the reaction mixture was poured into water and extracted with DCM. The organic phase was washed with water, brine, then dried, concentrated and separated by column chromatography to give the desired product (5.71 g, yield 52%).

Example 11-4: Synthesis of Intermediate 11-4: (3aS,4S,6R,6aR)-2,2-dimethyl-6-(6-morpholino-9H-purin-9-yl)tetrahydrofuro[3,4-D][1,3]dioxole-4-carbaldehyde

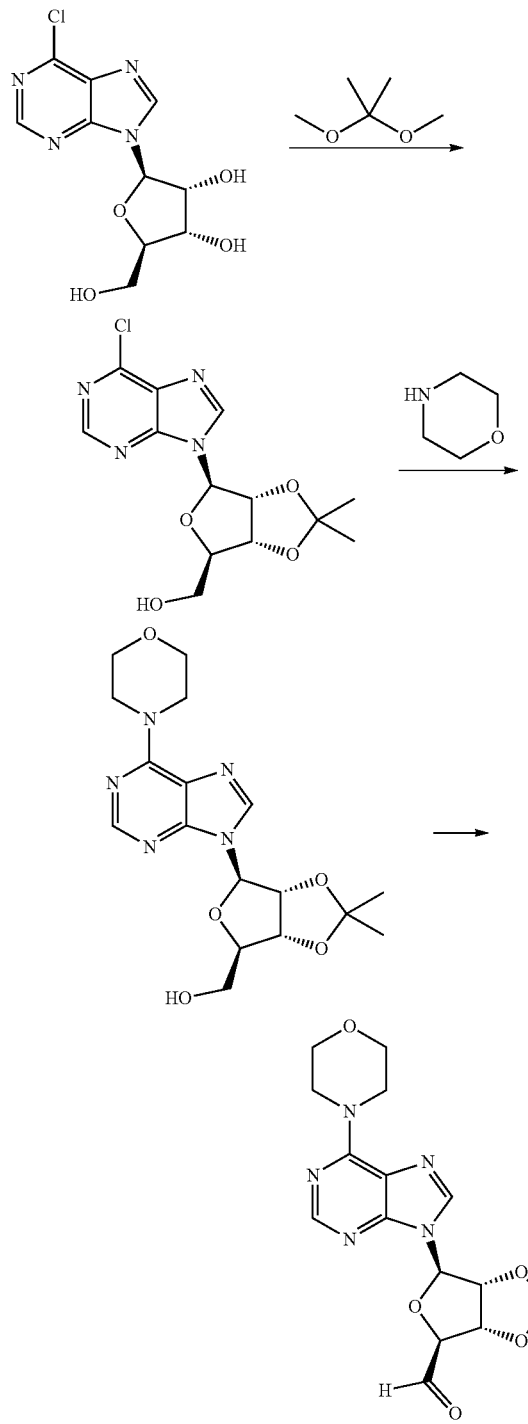

Step 1: Synthesis of Compound ((3aR,4R,6R,6aR)-2,2-dimethyl-6-(6-morpholino-9H-purin-9-yl)tetrahydrofuro[3,4-d][1,3]dioxol-4-yl)methanol The solution of 6-chloropurine riboside (3.0 g, 10.46 mmol), 2,2-dimethoxypropane (5.2 g, 50 mmol) and TsOH-H$_2$O (1.99 g, 10.46 mmol) in acetone (120 ml) was refluxed for 2 hours. After the reaction was completed, the reaction mixture was poured into ice-water and adjusted pH to 8-9, then extracted with DCM. The organic phase was washed with water, dried with Na$_2$SO$_4$ and concentrated to give the desired product (3.31 g, yield 96%).

Step 2: Synthesis of Compound ((3aR,4R,6R,6aR)-2,2-dimethyl-6-(6-morpholino-9H-purin-9-yl)tetrahydrofuro[3,4-d][1,3]dioxol-4-yl)methanol The compounds ((3aR,4R,6R,6aR)-6-(6-chloro-9H-purin-9-yl)-2,2-dimethyl-tetrahydrofuro[3,4-D][1,3]dioxol-4-yl)methanol (1.00 g, 3.06 mmol), morpholine (610 mg, 7.0 mmol) and DIPEA (900 mg, 7.0 mmol) were dissolved in CH$_3$CN (20 mL), then refluxed and reacted for 2 hours. After the reaction was completed, the reaction mixture was cooled to RT, poured into ice-water and extracted with EA. The organic phase was washed with water, dried with Na$_2$SO$_4$ and concentrated. The crude product was purified and separated by column chromatography to give the desired product (912 mg, yield 80%).

Step 3: Synthesis of Compound (3aS,4S,6R,6aR)-2,2-dimethyl-6-(6-morpholino-9H-purin-9-yl)tetrahydrofuro[3,4-d][1,3]dioxole-4-carbaldehyde ((3aR,4R,6R,6aR)-2,2-dimethyl-6-(6-morpholino-9H-purin-9-yl)-tetrahydrofuro[3,4-d][1,3]dioxol-4-yl)methanol (700 mg, 1.85 mmol) was dissolved in DCM, Dess-Martin reagent (2.5 mmol) was slowly added at 0° C. The reaction solution was then heated to RT and stirred at RT for 2 hours, then diluted by adding water and extracted with DCM. The organic phase was washed with saturated brine, dried and concentrated. The crude product was separated by column chromatography to give the desired product (508 mg, yield 73%).

Example 11-5: Synthesis of Intermediate 11-5: 2-phenoxyacetaldehyde

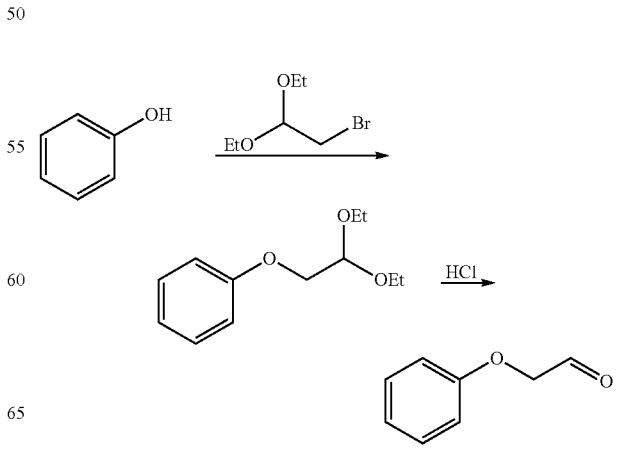

Step 1: Synthesis of Compound (2,2-diethoxyethoxy)benzene

Phenol (0.94 g, 10 mmol), chloroacetaldehyde diethyl acetal (1.52 g, 10 mmol), K₂CO₃ (2.77 g, 20 mmol) and KI (500 mg) were dissolved in DMF (15 mL). The above mixture was stirred at 100° C. overnight. After the reaction was completed, the reaction mixture was cooled to RT, poured into ice-water and extracted with EA. The organic phase was washed with water, dried with Na₂SO₄ and concentrated. The crude product was separated by column chromatography to give the desired product (1.21 g, yield 58%).

Step 2: Synthesis of Compound 2-phenoxyacetaldehyde (2,2-diethoxyethoxy)benzene (0.84 g, 4 mmol) was dissolved in the mixed solution of HOAc (5 mL), 1N aqeuous HCl (2.5 mL) and EtOH (20 mL), then heated and refluxed for 3 hours. After the reaction was completed, the reaction mixture was cooled to RT, poured into ice-water and extracted with EA. The organic phase was washed with water, dried with Na₂SO₄ and concentrated. The crude product was separated by column chromatography to give the desired product (468 mg, yield 86%).

Example 12: Synthesis of Compound 5-(4-(9H-purin-6-yl)phenyl)-2-(((2-(4-(2-hydroxyethyl)piperazin-1-yl)ethyl)amino)methylene)cyclohexane-1,3-dione (Compound 33)

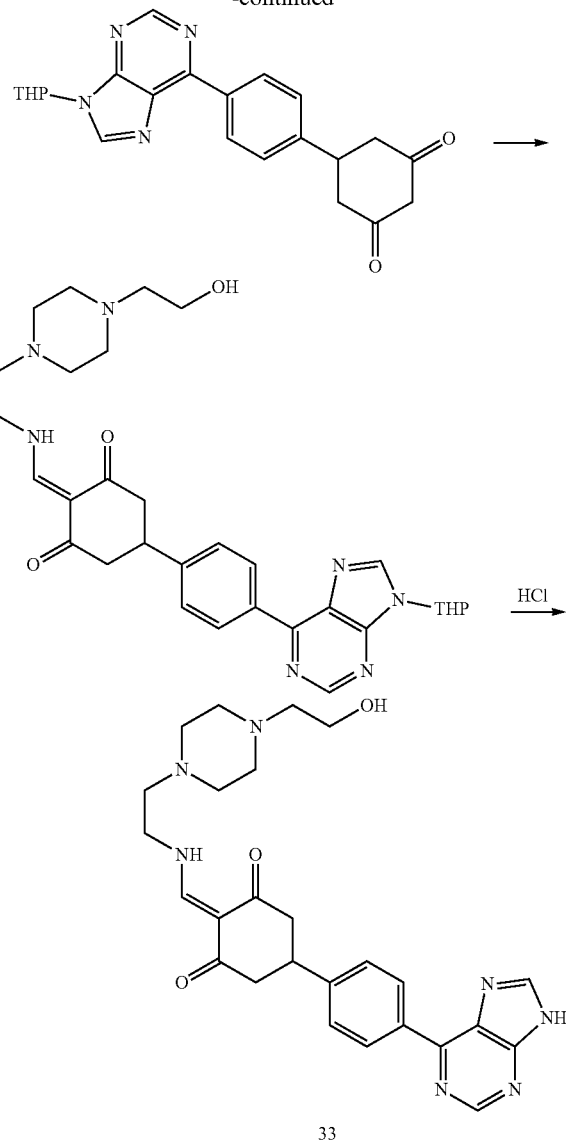

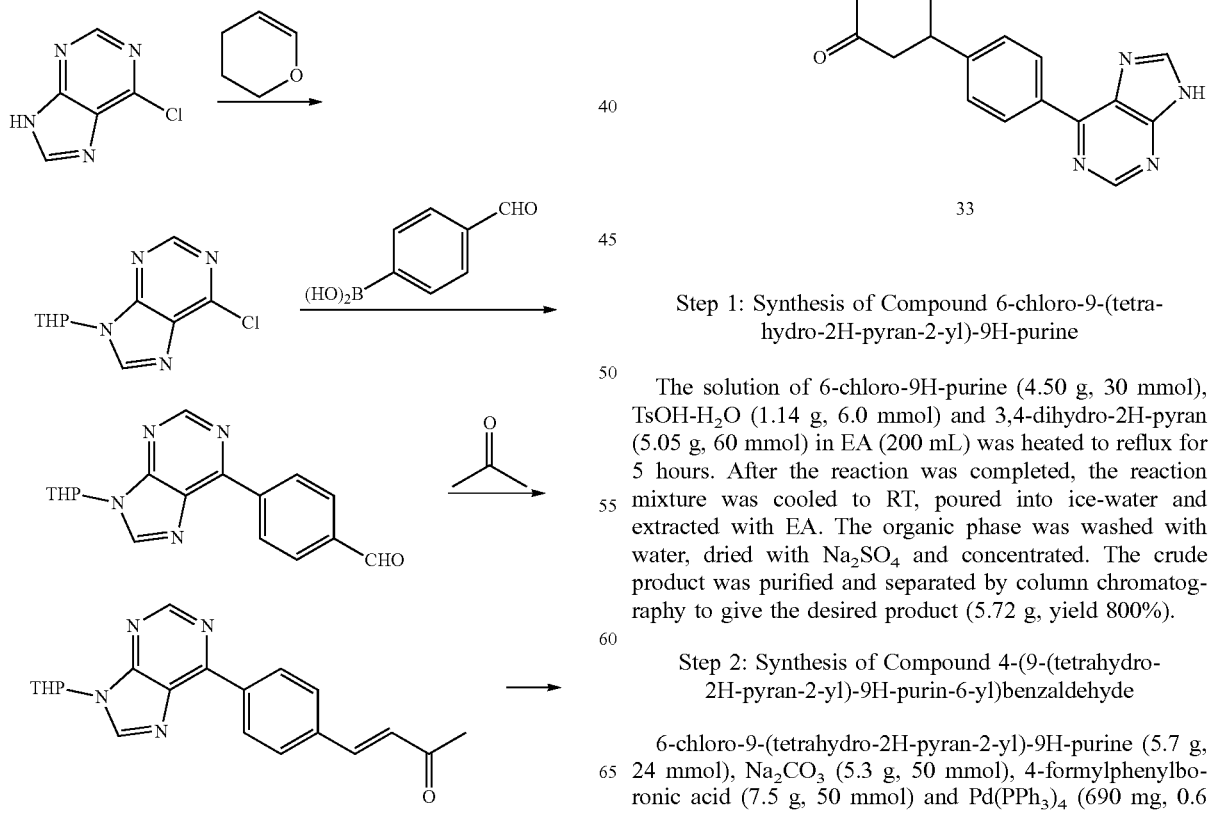

Step 1: Synthesis of Compound 6-chloro-9-(tetrahydro-2H-pyran-2-yl)-9H-purine The solution of 6-chloro-9H-purine (4.50 g, 30 mmol), TsOH-H₂O (1.14 g, 6.0 mmol) and 3,4-dihydro-2H-pyran (5.05 g, 60 mmol) in EA (200 mL) was heated to reflux for 5 hours. After the reaction was completed, the reaction mixture was cooled to RT, poured into ice-water and extracted with EA. The organic phase was washed with water, dried with Na₂SO₄ and concentrated. The crude product was purified and separated by column chromatography to give the desired product (5.72 g, yield 800%).

Step 2: Synthesis of Compound 4-(9-(tetrahydro-2H-pyran-2-yl)-9H-purin-6-yl)benzaldehyde 6-chloro-9-(tetrahydro-2H-pyran-2-yl)-9H-purine (5.7 g, 24 mmol), Na₂CO₃ (5.3 g, 50 mmol), 4-formylphenylboronic acid (7.5 g, 50 mmol) and Pd(PPh₃)₄ (690 mg, 0.6 mmol) were dissolved in the mixed solution of dioxane (200 mL) and water (20 mL), then refluxed and reacted overnight. After the reaction was completed, the reaction mixture was cooled to RT, poured into ice-water and extracted with EA. The organic phase was washed with water, dried with $Na_2SO_4$ and concentrated. The crude product was purified and separated by column chromatography to give the desired product (5.51 g, yield 740%).

Step 3, 4, & 5: The operation procedures were the same as Example 9.

Step 6: Synthesis of Compound 5-(4-(9H-purin-6-yl)phenyl)-2-(((2-(4-(2-hydroxyethyl)piperazin-1-yl)ethyl)amino)methylene)cyclohexane-1,3-dione 2-(((2-(4-(2-hydroxyethyl)piperazin-1-yl)ethyl)amino)methylene)-5-(4-(9-(tetrahydro-2H-pyran-2-yl)-9H-purin-6-yl)phenyl)cyclohexane-1,3-dione (160.0 mg, 0.28 mmol) was dissolved in EtOH (3 mL)/DCM (5 mL), into which aqeuous HCl (1M, 2.0 mL) was added dropwise at RT. After the dropwise addition, the reaction solution was stirred at RT for 6 hours. After the reaction was completed, the pH was adjusted to basicity with aqeuous $NaHCO_3$ solution and extracted with DCM. The organic phase was washed with saturated brine, dried and concentrated. The crude product was separated by preparation plate to give the desired product (46 mg, yield 33%). Compound 33: $^1$H NMR (400 MHz, DMSO-$d_6$) δ 13.59 (s, 1H), 11.20-10.79 (m, 1H), 9.08-8.52 (m, 4H), 8.13 (d, J=14.6 Hz, 1H), 7.53 (d, J=8.0 Hz, 2H), 4.55-4.21 (m, 1H), 3.70-3.12 (m, 8H), 2.95-2.66 (m, 2H), 2.62-2.10 (m, 11H); MS: 490.3 [M+1].

Example 12A: Synthesis of Compound 2-(((2-(4-(2-hydroxyethyl)piperazin-yl)ethyl)amino) methylene)-5-(3-(2-(2-methoxyethoxy)ethoxy)phenyl)cyclohexane-1,3-dione (Compound 34)

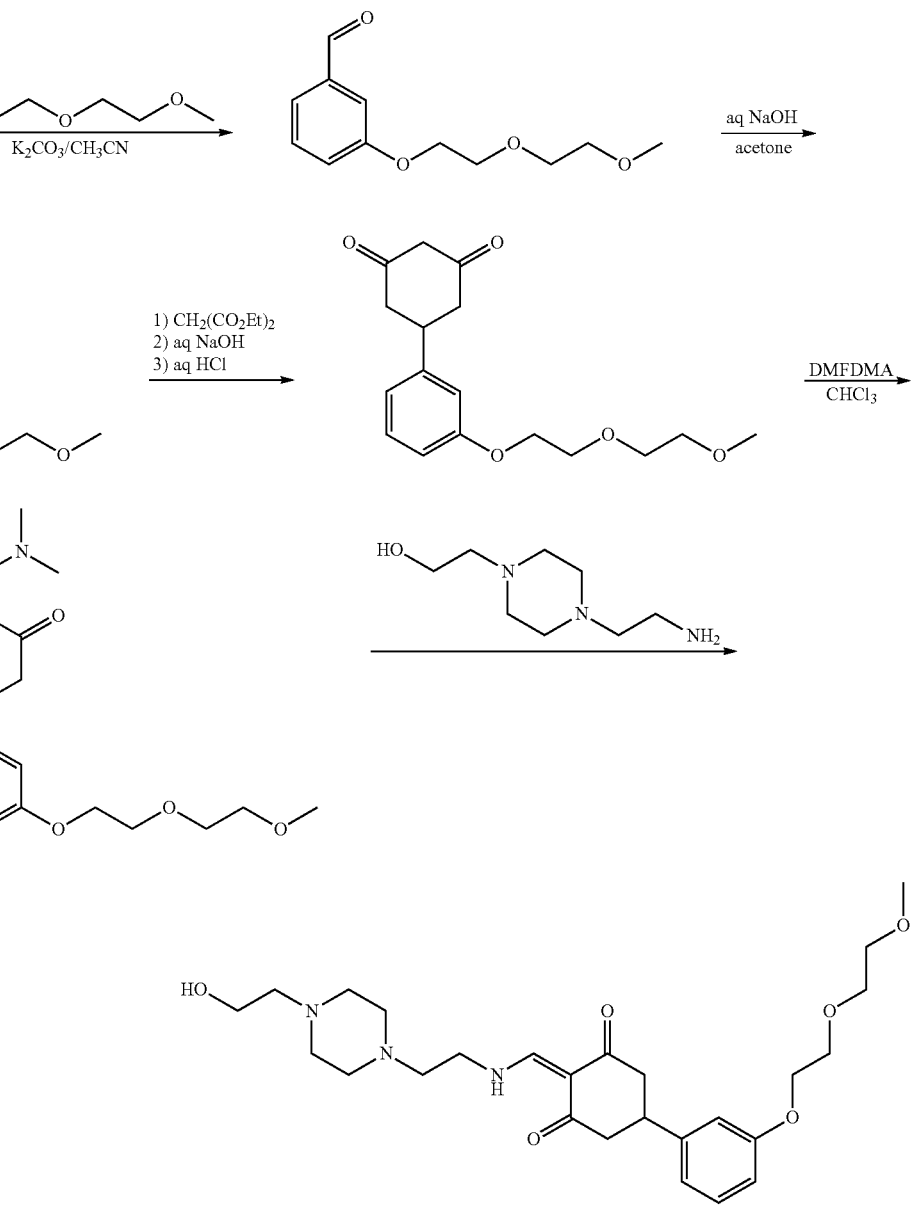

Step 1: Synthesis of Compound 3-(2-(2-methoxyethoxy)ethoxy)benzaldehyde 3-hydroxybenzaldehyde (2.00 g, 16.4 mmol), 2-(2-methoxyethoxy)ethyl 4-methylbenzenesulfonate (4.94 g, 18 mmol) and $K_2CO_3$ (4.53 g, 32.8 mmol) were dissolved in $CH_3CN$ (50 mL), refluxed and reacted for 3 hours. After the reaction was completed, the reaction mixture was cooled to RT, poured into ice-water and extracted with EA. The organic phase was washed with water, dried with $Na_2SO_4$, and concentrated. The crude product was separated by column chromatography to give the desired product (1.7 g, yield 46%).

Step 3: Synthesis of Compound 4-(3-(2-(2-methoxyethoxy)ethoxy)phenyl)but-3-en-2-one 3-(2-(2-methoxyethoxy)ethoxy)benzaldehyde (7.0 g, 31.21 mmol) was dissolved in acetone (20 mL) and water (10 mL) to which 1% NaOH solution (20 mL) was added. Then the above mixture was heated to reflux for 2 hours, then cooled to RT, poured into ice-water and extracted with EA. The combined organic phase was washed with water and saturated brine, dried, and concentrated. The crude product was separated by column chromatography to give the desired product (6.16 g, yield 75%).

Step 4,5,6: Synthesis of Compound 2-(((2-(4-(2-hydroxyethyl)piperazin-yl)ethyl)amino) methylene)-5-(3-(2-(2-methoxyethoxy)ethoxy)phenyl)cyclohexane-1,3-dione Step 4,5,6: the operation procedures were the same as Example 9. Compound 34: $^1$HNMR (400 MHz, $CD_3OD$): δ 8.24 (s, 1H), 7.23 (t, J=8.0 Hz, 1H), 6.88-6.80 (i, 3H), 4.11 (t, J 4.8 Hz, 2H), 3.82 (t, J 4.8 Hz, 2H), 3.74 (t, J=5.6 Hz, 2H), 3.70-3.67 (m, 2H), 3.60 (t, J° 5.6 Hz, 2H), 3.57-3.55 (m, 2H), 3.36 (m, 3H), 3.35-3.34 (m, 1H), 2.81-2.61 (m, 16H); MS: 491.6 [M+1].

Example 13: Synthesis of Compounds 35-59, 61-84

Compounds 35-84 were synthesized by the same procedures as Compound 34 except for using corresponding benzaldehyde, aromatic aldehyde, or substituted cyclohexane-1,3-dione (see, e.g., Examples 13-1 to 13-11), as shown in Table 4.

TABLE 4

Compounds 35-59 and 61-84

| # | Structure | Name | Proton NMR ($^1$HNMR), Mass Spectrum (MS) |
|---|---|---|---|
| 35 | 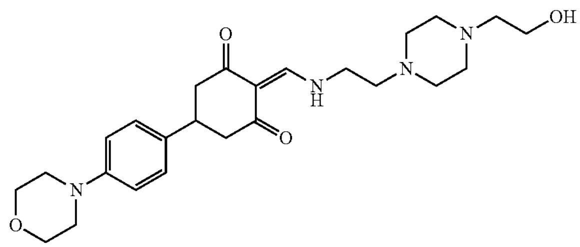 [SMILES: O=C1CC(c2ccc(N3CCOCC3)cc2)CC(=O)C1=CNCCN1CCN(CCO)CC1] | 2-(((2-(4-(2-hydroxyethyl)piperazin-1-yl)ethyl)amino)methylene)-5-(4-morpholinophenyl)cyclohexane-1,3-dione | $^1$HNMR (400 MHz, $CD_3OD$) δ 8.27 (s, 1H), 7.21 (d, J = 8.1 Hz, 2H), 6.97 (d, J = 8.2 Hz, 2H), 3.86 (s, 4H), 3.75 (t, J = 5.5 Hz, 2H), 3.64 (s, 2H), 3.14 (s, 4H), 2.88-2.49 (m, 17H); MS: 457.4 [M + 1]. |
| 36 | 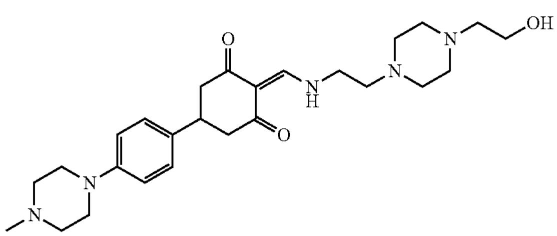 [SMILES: CN1CCN(c2ccc(C3CC(=O)C(=CNCCN4CCN(CCO)CC4)C(=O)C3)cc2)CC1] | 2-(((2-(4-(2-hydroxyethyl)piperazin-1-yl)ethyl)amino)methylene)-5-(4-(4-methylpiperazin-1-yl)phenyl)cyclohexane-1,3-dione | $^1$HNMR (400 MHz, $CD_3OD$) δ 8.27 (s, 1H), 7.21 (d, J = 8.6 Hz, 2H), 6.98 (d, J = 8.7 Hz, 2H), 3.79 (t, J = 5.7 Hz, 2H), 3.63 (t, J = 5.7 Hz, 2H), 2.92 (s, 4H), 2.89-2.59 (m, 21H), 2.52 (s, 3H); MS: 470.2 [M + 1]. |
| 37 | 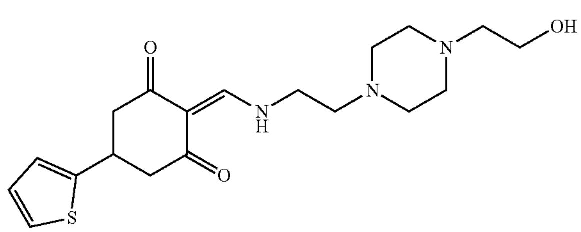 | 2-(((2-(4-(2-hydroxyethyl)piperazin-1-yl)ethyl)amino)methylene)-5-(thiophen-2-yl)cyclohexane-1,3-dione | $^1$HNMR (400 MHz, $CD_3OD$): δ 8.26 (d, J = 14.4 Hz, 1H), 7.27 (br, 1H), 6.95 (br, 1H), 4.09-3.30 (m, 7H), 2.50-2.84 (m, 14H); MS: 378.5 [M + 1]. |

TABLE 4-continued

Compounds 35-59 and 61-84

| # | Structure | Name | Proton NMR ($^1$HNMR), Mass Spectrum (MS) |
|---|---|---|---|
| 38 | 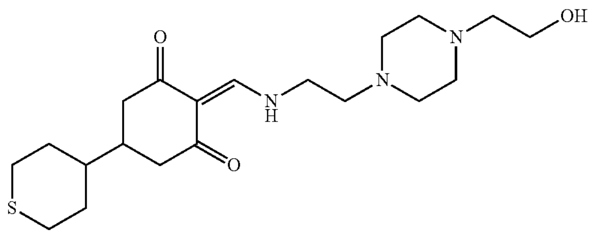 [SMILES: O=C1CC(C2CCSCC2)CC(=O)C1=CNCCN1CCN(CCO)CC1] | 2-(((2-(4-(2-hydroxyethyl)piperazin-1-yl)ethyl)amino)methylene)-5-(tetrahydro-2H-thiopyran-4-yl)cyclohexane-1,3-dione | 1H NMR (400 MHz, CD$_3$OD) δ 8.10 (s, 1H), 3.70 (t, J = 5.5 Hz, 2H), 3.50 (t, J = 5.7 Hz, 2H), 2.92 (d, J = 29.8 Hz, 5H), 2.69-2.42 (m, 8H), 2.44-2.12 (m, 4H), 2.05-1.72 (m, 3H), 1.52-1.07 (m, 6H); MS: 396.1 [M + 1]. |
| 39 | 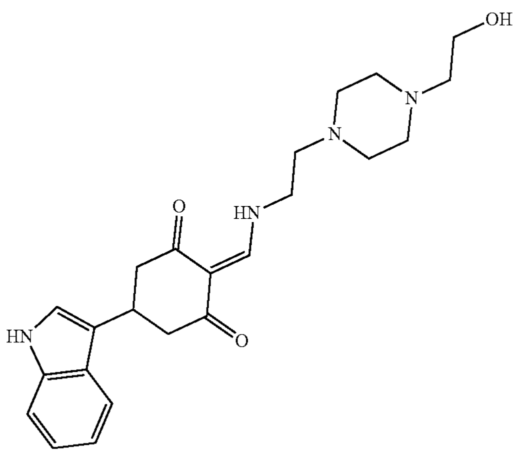 [SMILES: O=C1CC(c2c[nH]c3ccccc23)CC(=O)C1=CNCCN1CCN(CCO)CC1] | 2-(((2-(4-(2-hydroxyethyl)piperazin-1-yl)ethyl)amino)methylene)-5-(1H-indol-3-yl)cyclohexane-1,3-dione | $^1$H NMR (400 MHz, CD$_3$OD): δ 8.23 (s, 1H), 7.56 (d, J = 7.8 Hz, 1H), 7.32 (d, J = 8.1 Hz, 1H), 7.08 (t, J = 7.1 Hz, 1H), 7.03-6.94 (m, 2H), 3.78-3.61 (m, 3H), 3.57 (t, J = 5.7 Hz, 2H), 2.95-2.49 (m, 16H); MS: 411.4 [M + 1]. |
| 40 | 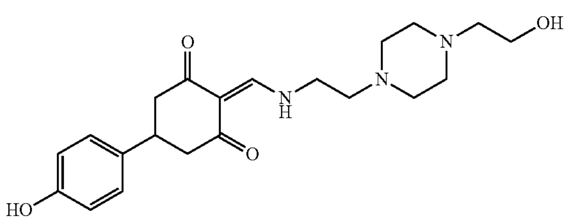 | 2-(((2-(4-(2-hydroxyethyl)piperazin-1-yl)ethyl)amino)methylene)-5-(4-hydroxyphenyl)cyclohexane-1,3-dione | $^1$HNMR (400 MHz, CD$_3$OD): δ 8.27 (s, 1H), 7.13 (d, J = 8.5 Hz, 2H), 6.77 (d, J = 8.6 Hz, 2H), 3.81 (t, J = 5.6 Hz, 2H), 3.64 (t, J = 5.7 Hz, 2H), 3.14-2.57 (m, 16H) |
| 41 | 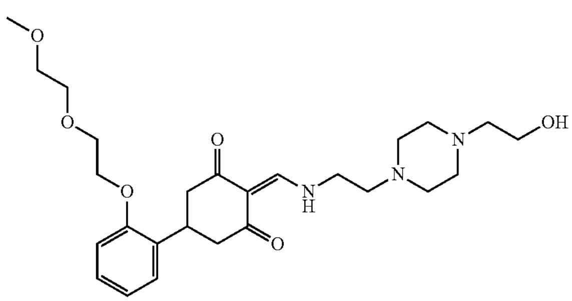 [SMILES: COCCOCCOc1ccccc1C1CC(=O)C(=CNCCN2CCN(CCO)CC2)C(=O)C1] | 2-(((2-(4-(2-hydroxyethyl)piperazin-1-yl)ethyl)amino)methylene)-5-(3-(2-(2-methoxyethoxy)ethoxy)phenyl)cyclohexane-1,3-dione | $^1$HNMR (400 MHz, CD$_3$OD): δ 8.26 (s, 1H), 7.23-7.17 (m, 2H), 6.97 (d, J = 8.0 Hz, 1H), 6.92 (t, J = 7.2 Hz, 1H), 4.16 (t, J = 4.4 Hz, 2H), 3.84 (q, J = 4.8 Hz, 4H), 3.73-3.61 (m, 5H), 3.54-3.52 (m, 2H), 3.32-3.26 (m, 9H), 2.93-2.61 (m, 10H); MS: 490.2 [M + 1]. |
| 42 | 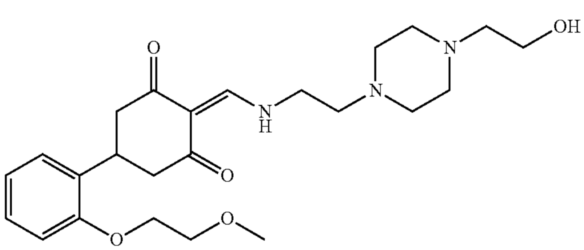 [SMILES: COCCOc1ccccc1C1CC(=O)C(=CNCCN2CCN(CCO)CC2)C(=O)C1] | 2-(((2-(4-(2-hydroxyethyl)piperazin-1-yl)ethyl)amino)methylene)-5-(2-(2-methoxyethoxy)phenyl)cyclohexane-1,3-dione | $^1$HNMR (400 MHz, CD$_3$OD): δ 8.27 (s, 1H), 7.24-7.19 (m, 2H), 7.00-6.92 (m, 2H), 4.17 (t, J = 4.0 Hz, 2H), 3.78-3.70 (m, 5H), 3.63 (t, J = 5.2 Hz, 2H), 3.32 (s, 3H), 2.88-2.64 (m, 16H); MS: 446.9 [M + 1] |

TABLE 4-continued

Compounds 35-59 and 61-84

| # | Structure | Name | Proton NMR ($^1$HNMR), Mass Spectrum (MS) |
|---|---|---|---|
| 43 | 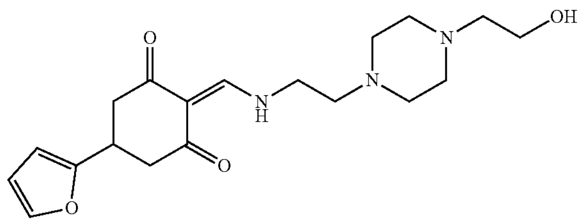 | 5-(furan-2-yl)-2-(((2-(4-(2-hydroxyethyl)piperazin-1-yl)ethyl)amino)methylene)cyclohexane-1,3-dione | $^1$HNMR (400 MHz, CD$_3$OD): δ 8.20 (s, 1H), 7.38 (s, 1H), 7.29 (s, 1H), 6.08 (d, J = 3.2 Hz, 1H), 3.76 (t, J = 6.4 Hz, 2H), 3.58 (t, J = 6.4 Hz, 2H), 3.50-3.44 (m, 1H), 2.94-2.62 (m, 16H). MS: 362.5 [M + 1] |
| 44 | 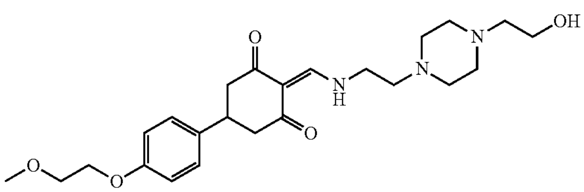 [SMILES: COCCOc1ccc(C2CC(=O)C(=CNCCN3CCN(CCO)CC3)C(=O)C2)cc1] | 2-(((2-(4-(2-hydroxyethyl)piperazin-1-yl)ethyl)amino)methylene)-5-(4-(2-methoxyethoxy)phenyl)cyclohexane-1,3-dione | $^1$HNMR (400 MHz, CD$_3$OD): δ 8.23 (s, 1H), 7.19 (t, J = 8.4 Hz, 2H), 6.89 (t, J = 8.8 Hz, 2H), 4.09-4.06 (m, 2H), 3.60 (t, J = 5.6 Hz, 2H), 3.40 (s, 3H), 3.30-3.27 (m, 1H), 3.07 (br, 4H), 2.99 (t, J = 5.6 Hz, 2H), 2.82-2.61 (m, 16H); MS: 446.6 [M + 1]. |
| 45 | 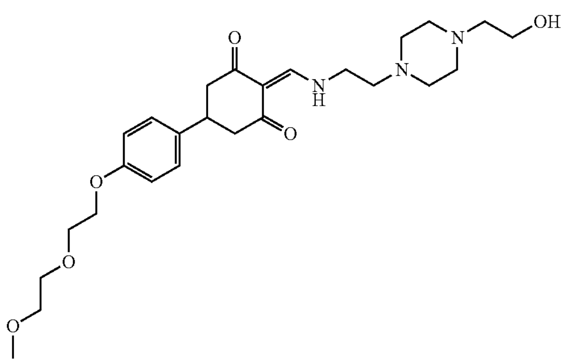 [SMILES: COCCOCCOc1ccc(C2CC(=O)C(=CNCCN3CCN(CCO)CC3)C(=O)C2)cc1] | 2-(((2-(4-(2-hydroxyethyl)piperazin-1-yl)ethyl)amino)methylene)-5-(4-(2-(2-methoxyethoxy)ethoxy)phenyl)cyclohexane-1,3-dione | $^1$HNMR (400 MHz, CD$_3$OD): δ 8.27 (s, 1H), 7.23 (t, J = 8.8 Hz, 2H), 6.93 (t, J = 8.8 Hz, 2H), 4.14-4.12 (m, 2H), 3.86-3.83 (m, 2H), 3.73-3.70 (m, 4H), 3.39 (s, 3H), 3.33-3.27 (m, 1H), 3.07 (br, 4H), 2.99 (t, J = 5.6 Hz, 2H), 2.83-2.56 (m, 16H). MS: 490.6 [M + 1]. |
| 46 | 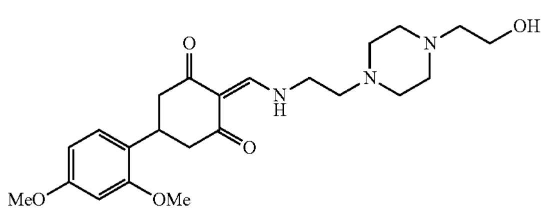 [SMILES: COc1ccc(C2CC(=O)C(=CNCCN3CCN(CCO)CC3)C(=O)C2)c(OC)c1] | 5-(2,4-dimethoxyphenyl)-2-(((2-(4-(2-hydroxyethyl)piperazin-1-yl)ethyl)amino)methylene)cyclohexane-1,3-dione | $^1$H NMR (400 MHz, CD$_3$OD) δ 8.12 (d, J = 14.6 Hz, 1H), 7.08 (d, J = 8.4 Hz, 1H), 6.54 (d, J = 2.3 Hz, 1H), 6.48 (dd, J = 8.4, 2.3 Hz, 1H), 4.77 (s, 1H), 3.78 (s, 3H), 3.74 (s, 3H), 3.64-3.52 (m, 4H), 3.52-3.41 (m, 1H), 2.74-2.52 (m, 12H), 2.49-2.37 (m, 4H); MS: 432.5 [M + 1]. |
| 47 | 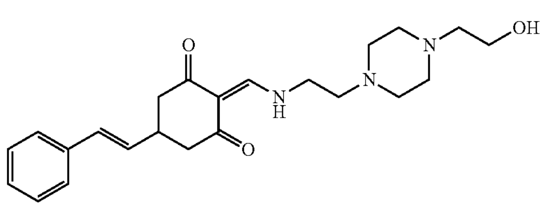 [SMILES: O=C1CC(/C=C/c2ccccc2)CC(=O)C1=CNCCN1CCN(CCO)CC1] | 2-(((2-(4-(2-hydroxyethyl)piperazin-1-yl)ethyl)amino)methylene)-5-C2-6 styrylcyclohexane-1,3-dione | $^1$H NMR (400 MHz, CD$_3$OD) δ 8.21 (s, 1H), 7.35 (d, J = 7.3 Hz, 2H), 7.26 (t, J = 7.5 Hz, 2H), 7.18 (t, J = 7.3 Hz, 1H), 6.46 (d, J = 15.9 Hz, 1H), 6.23 (dd, J = 15.9, 6.8 Hz, 1H), 3.74-3.65 (m, 3H), 3.63-3.53 (m, 2H), 3.04-2.90 (m, 1H), 2.88 (s, 1H), 2.77-2.39 (m, 14H); MS: 398.3 [M + 1]. |
| 48 | 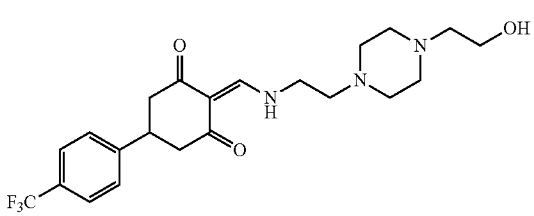 [SMILES: O=C1CC(c2ccc(C(F)(F)F)cc2)CC(=O)C1=CNCCN1CCN(CCO)CC1] | 2-(((2-(4-(2-hydroxyethyl)piperazin-1-yl)ethyl)amino)methylene)-5-(4-(trifluoromethyl)phenyl)cyclohexane-1,3-dione | $^1$HNMR (400 MHz, CD$_3$OD): δ 9.29 (s, 1H), 7.66 (d, J = 8.0 Hz, 2H), 7.54 (d, J = 8.0 Hz, 2H), 3.73 (t, J = 5.6 Hz, 2H), 3.64 (t, J = 5.6 Hz, 2H), 3.55-3.47 (m, 1H), 2.91-2.83 (m, 16H); MS: 440.6 [M + 1]. |

TABLE 4-continued

Compounds 35-59 and 61-84

| # | Structure | Name | Proton NMR (¹HNMR), Mass Spectrum (MS) |
|---|---|---|---|
| 49 | 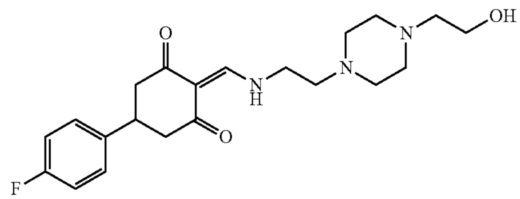 [SMILES: O=C1CC(c2ccc(F)cc2)CC(=O)C1=CNCCN1CCN(CCO)CC1] | 5-(4-fluorophenyl)-2-(((2-(4-(2-hydroxyethyl)piperazin-1-yl)ethyl)amino)methylene)cyclohexane-1,3-dione | ¹HNMR (400 MHz, CD$_3$OD): δ 8.28 (s, 1H), 7.36-7.32 (m, 2H), 7.10-7.01 (m, 2H), 3.75 (t, J = 5.6 Hz, 2H), 3.64 (t, J = 5.6 Hz, 2H), 3.44-3.36 (m, 1H), 2.87-2.65 (m, 16H); MS: 390.5 [M + 1]. |
| 50 | 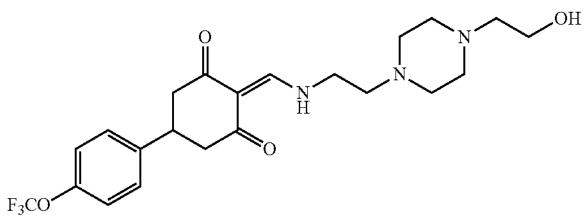 [SMILES: O=C1CC(c2ccc(OC(F)(F)F)cc2)CC(=O)C1=CNCCN1CCN(CCO)CC1] | 2-(((2-(4-(2-hydroxyethyl)piperazin-1-yl)ethyl)amino)methylene)-5-(4-(trifluoromethoxy)phenyl)cyclohexane-1,3-dione | ¹H NMR (400 MHz, CD$_3$OD) δ 8.24 (s, 1H), 7.39 (d, J = 8.6 Hz, 2H), 7.22 (d, J = 8.1 Hz, 2H), 3.67 (t, J = 6.0 Hz, 2H), 3.59 (t, J = 5.8 Hz, 2H), 3.49-3.33 (m, 1H), 2.93-2.39 (m, 16H); MS: 456.2 [M + 1]. |
| 51 | 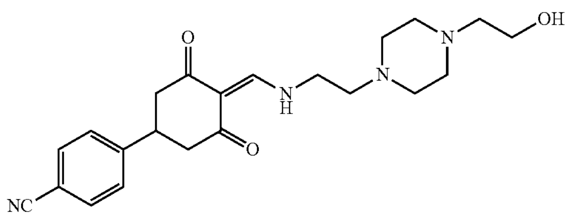 [SMILES: N#Cc1ccc(C2CC(=O)C(=CNCCN3CCN(CCO)CC3)C(=O)C2)cc1] | 2-(((2-(4-(2-hydroxyethyl)piperazin-1-yl)ethyl)amino)methylene)-5-(4-(cyano)phenyl)cyclohexane-1,3-dione | ¹H NMR (400 MHz, CD$_3$OD) δ 8.28 (s, 1H), 7.72 (d, J = 8.3 Hz, 2H), 7.53 (d, J = 8.2 Hz, 2H), 3.75 (t, J = 5.8 Hz, 2H), 3.63 (t, J = 5.8 Hz, 2H), 3.56-3.40 (m, 1H), 3.00-2.49 (m, 16H); MS: 397.2 [M + 1]. |
| 52 | 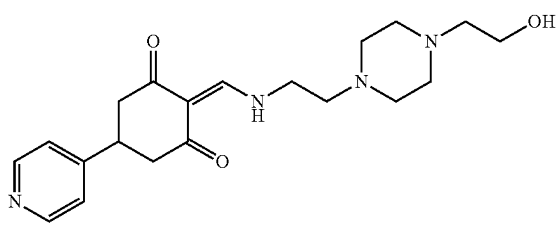 [SMILES: O=C1CC(c2ccncc2)CC(=O)C1=CNCCN1CCN(CCO)CC1] | 2-(((2-(4-(2-hydroxyethyl)piperazin-1-yl)ethyl)amino)methylene)-5-(4-(trifluoromethoxy)phenyl)cyclohexane-1,3-dione | ¹HNMR (400 MHz, CD$_3$OD) δ 8.742 (d, J = 6.0 Hz, 2H), 8.253 (s, 1H), 7.396 (d, J = 6.0 Hz, 2H), 3.712 (t, J = 6.0 Hz, 2H), 3.606 (d, J = 5.6 Hz, 2H), 3.419-3.496 (m, 1H), 2.873-2.610 (m, 16H); MS: 373.2 [M + 1]. |
| 53 | 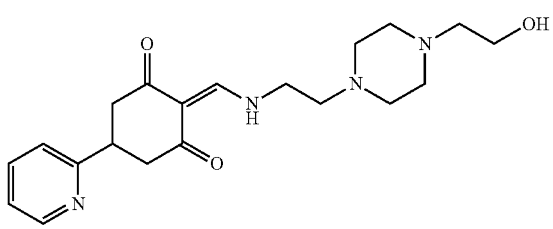 [SMILES: O=C1CC(c2ccccn2)CC(=O)C1=CNCCN1CCN(CCO)CC1] | 2-(((2-(4-(2-hydroxyethyl)piperazin-1-yl)ethyl)amino)methylene)-5-(pyridin-2-yl)cyclohexane-1,3-dione | ¹HNMR (400 MHz, CD$_3$OD): δ 8.49 (d, J = 4.0 Hz, 1H), 8.25 (s, 1H), 7.80-7.76 (m, 1H), 7.37 (d, J = 7.2 Hz, 1H), 7.29-7.26 (m, 1H), 3.68 (t, J = 6.0 Hz, 2H), 3.60 (t, J = 6.4 Hz, 2H), 3.56-3.49 (m, 1H), 2.93-2.82 (m, 2H), 2.71-2.54 (m, 14H); MS: 373.5 [M + 1]. |
| 54 | 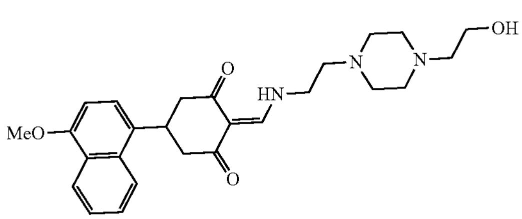 [SMILES: COc1ccc(C2CC(=O)C(=CNCCN3CCN(CCO)CC3)C(=O)C2)c2ccccc12] | 2-(((2-(4-(2-hydroxyethyl)piperazin-1-yl)ethyl)amino)methylene)-5-(4-methoxy-naphthalen-1-yl)cyclohexane-1,3-dione | ¹H NMR (400 MHz, CD$_3$OD) δ 8.27 (d, J = 6.9 Hz, 2H), 8.02 (d, J = 8.5 Hz, 1H), 7.54 (t, J = 7.0 Hz, 1H), 7.49-7.40 (m, 1H), 7.31 (d, J = 8.0 Hz, 1H), 6.86 (d, J = 8.1 Hz, 1H), 4.19-4.05 (m, 1H), 3.98 (s, 3H), 3.67 (t, J = 6.0 Hz, 2H), 3.64-3.53 (m, 2H), 2.92-2.47 (m, 16H); MS: 452.3 [M + 1]. |

TABLE 4-continued

Compounds 35-59 and 61-84

| # | Structure | Name | Proton NMR (¹HNMR), Mass Spectrum (MS) |
|---|---|---|---|
| 55 | 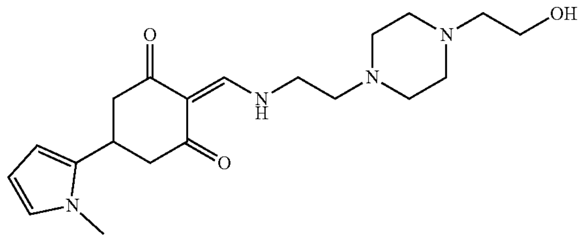 [SMILES: Cn1cccc1C1CC(=O)C(=CNCCN2CCN(CCO)CC2)C(=O)C1] | 2-(((2-(4-(2-hydroxyethyl)piperazin-1-yl)ethyl)amino)methylene)-5-(1-methyl-1H-pyrrol-2-yl)cyclohexane-1,3-dione | ¹H NMR (400 MHz, CD$_3$OD) δ 8.22 (s, 1H), 6.77-6.27 (m, 1H), 6.05-5.83 (m, 1H), 5.85-5.76 (m, 1H), 3.74 (t, J = 5.7 Hz, 2H), 3.64-3.53 (m, 5H), 3.50-3.37 (m, 1H), 3.06-2.45 (m, 16H); MS: 375.3 [M + 1]. |
| 56 | 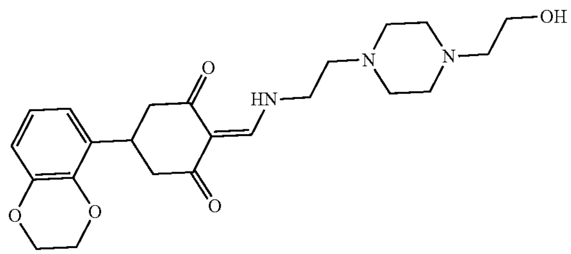 [SMILES: O=C1CC(c2cccc3c2OCCO3)CC(=O)C1=CNCCN1CCN(CCO)CC1] | 5-(2,3-dihydrobenzo[b][1,4]dioxin-5-yl)-2-(((2-(4-(2-hydroxyethyl)piperazin-1-yl)ethyl)amino)methylene)cyclohexane-1,3-dione | ¹H NMR (400 MHz, CD$_3$OD) δ 8.24 (s, 1H), 6.83-6.51 (m, 3H), 4.24 (dd, J = 16.6, 5.0 Hz, 4H), 3.73 (t, J = 5.8 Hz, 2H), 3.64-3.47 (m, 3H), 3.05-2.32 (m, 16H); MS: 430.2 [M + 1]. |
| 57 | 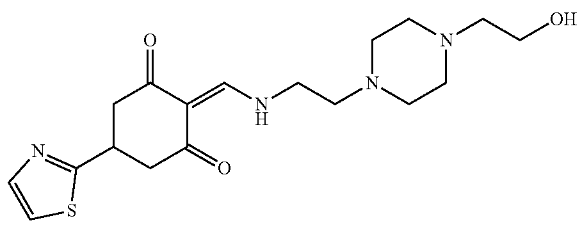 [SMILES: O=C1CC(c2nccs2)CC(=O)C1=CNCCN1CCN(CCO)CC1] | 2-(((2-(4-(2-hydroxyethyl)piperazin-1-yl)ethyl)amino)methylene)-5-(thiazol-2-yl)cyclohexane-1,3-dione | ¹H NMR (400 MHz, CD$_3$OD) δ 8.26 (s, 1H), 7.74 (d, J = 3.3 Hz, 1H), 7.53 (d, J = 3.3 Hz, 1H), 3.97-3.83 (m, 2H), 3.74 (t, J = 5.9 Hz, 2H), 3.62 (t, J = 5.8 Hz, 2H), 2.95 (dd, J = 14.4, 6.0 Hz, 4H), 2.80-2.54 (m, 12H); MS: 379.3 [M + 1]. |
| 58 | 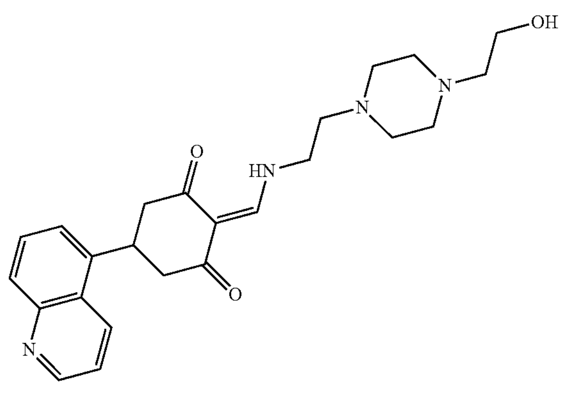 [SMILES: O=C1CC(c2cccc3ncccc23)CC(=O)C1=CNCCN1CCN(CCO)CC1] | 2-(((2-(4-(2-hydroxyethyl)piperazin-1-yl)ethyl)amino)methylene)-5-(isoquinolin-5-yl)cyclohexane-1,3-dione | ¹H NMR (400 MHz, CD$_3$OD) δ 9.25 (s, 1H), 8.49 (d, J = 6.1 Hz, 1H), 8.31 (s, 1H), 8.06 (d, J = 6.2 Hz, 1H), 8.03 (d, J = 8.1 Hz, 1H), 7.77 (d, J = 7.2 Hz, 1H), 7.72-7.64 (m, 1H), 4.30-4.19 (m, 1H), 3.72 (t, J = 5.9 Hz, 2H), 3.64 (t, J = 5.8 Hz, 2H), 2.98-2.58 (m, 16H); MS: 423.4 [M + 1]. |
| 59 | 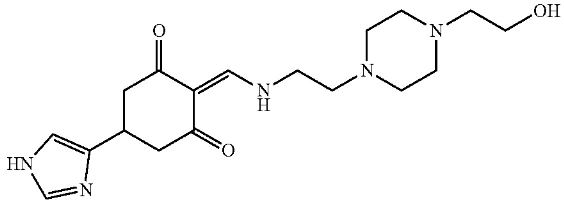 [SMILES: O=C1CC(c2c[nH]cn2)CC(=O)C1=CNCCN1CCN(CCO)CC1] | 2-(((2-(4-(2-hydroxyethyl)piperazin-1-yl)ethyl)amino)methylene)-5-(1H-imidazol-4-yl)cyclohexane-1,3-dione | ¹H NMR (400 MHz, CDCl$_3$) δ 11.39-10.87 (m, 1H), 9.33-8.87 (m, 1H), 8.15 (d, J = 14.4 Hz, 1H), 7.60 (s, 1H), 6.80 (s, 1H), 3.61 (t, J = 5.3 Hz, 2H), 3.55-3.47 (m, 3H), 3.05-2.30 (m, 17H); MS: 362.3 [M + 1]. |
| 61 | 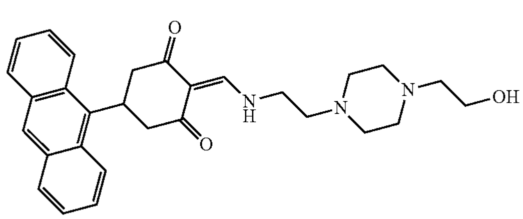 [SMILES: O=C1CC(c2c3ccccc3cc3ccccc23)CC(=O)C1=CNCCN1CCN(CCO)CC1] | 5-(anthracen-9-yl)-2-(((2-(4-(2-hydroxyethyl)piperazin-1-yl)ethyl)amino)methylene)cyclohexane-1,3-dione | ¹H NMR (400 MHz, CD$_3$OD) δ 8.54-8.42 (m, 3H), 8.40 (s, 1H), 8.06 (d, J = 8.0 Hz, 2H), 7.57-7.39 (m, 4H), 5.09-4.94 (m, 1H), 3.90-3.59 (m, 6H), 2.73-2.52 (m, 14H); MS: 472.2 [M + 1]. |

TABLE 4-continued

Compounds 35-59 and 61-84

| # | Structure | Name | Proton NMR (¹HNMR), Mass Spectrum (MS) |
|---|---|---|---|
| 62 | 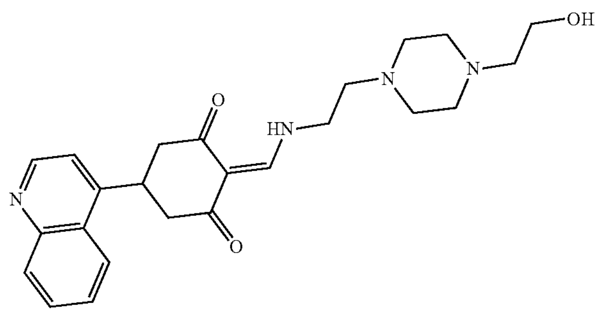 [SMILES: O=C1CC(c2ccnc3ccccc23)CC(=O)C1=CNCCN1CCN(CCO)CC1] | 2-(((2-(4-(2-hydroxyethyl)piperazin-1-yl)ethyl)amino)methylene)-5-(quinolin-4-yl)cyclohexane-1,3-dione | ¹H NMR (400 MHz, CD$_3$OD) δ 8.80 (d, J = 4.7 Hz, 1H), 8.30 (s, 1H), 8.23 (d, J = 8.4 Hz, 1H), 8.06 (d, J = 8.4 Hz, 1H), 7.78 (d, J = 7.3 Hz, 1H), 7.73-7.62 (m, 1H), 7.49 (d, J = 4.8 Hz, 1H), 4.34 (s, 1H), 3.72 (t, J = 5.8 Hz, 2H), 3.63 (t, J = 5.7 Hz, 2H), 3.01-2.51 (m, 16H); MS: 423.3 [M + 1]. |
| 63 | 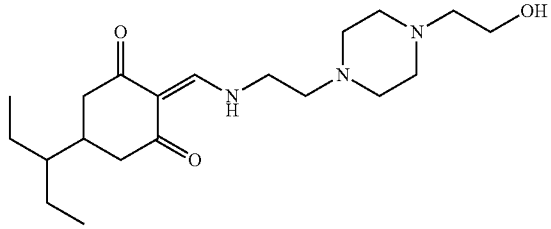 [SMILES: CCC(CC)C1CC(=O)C(=CNCCN2CCN(CCO)CC2)C(=O)C1] | 2-(((2-(4-(2-hydroxyethyl)piperazin-1-yl)ethyl)amino)methylene)-5-(pentan-3-yl)cyclohexane-1,3-dione | ¹H NMR (400 MHz, DMSO-d$_6$) δ 11.17-10.13 (m, 1H), 8.06 (d, J = 14.6 Hz, 1H), 4.82 (s, 1H), 3.74-3.46 (m, 5H), 3.38 (dd, J = 14.0, 7.0 Hz, 2H), 2.74 (s, 5H), 2.57 (s, 3H), 2.36-2.09 (m, 4H), 2.01 (s, 1H), 1.91 (s, 1H), 1.46-1.13 (m, 4H), 1.05 (t, J = 21.2 Hz, 1H), 0.83 (t, J = 7.3 Hz, 6H); MS: 366.2 [M + 1]. |
| 64 | 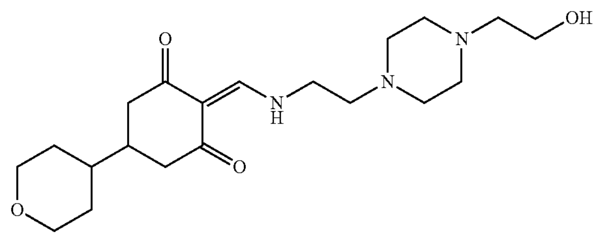 [SMILES: O=C1CC(C2CCOCC2)CC(=O)C1=CNCCN1CCN(CCO)CC1] | 2-(((2-(4-(2-hydroxyethyl)piperazin-1-yl)ethyl)amino)methylene)-5-(tetrahydro-2H-pyran-4-yl)cyclohexane-1,3-dione | ¹H NMR (400 MHz, CD$_3$OD) δ 8.18 (s, 1H), 3.95 (dd, J = 11.1, 3.8 Hz, 2H), 3.69 (t, J = 5.9 Hz, 2H), 3.57 (t, J = 5.8 Hz, 2H), 3.37 (t, J = 11.0 Hz, 2H), 2.90-2.43 (m, 13H), 2.41-2.15 (m, 2H), 1.89-1.78 (m, 1H), 1.65 (d, J = 12.2 Hz, 2H), 1.59-1.10 (m, 4H); MS 380.2 [M + 1]. |
| 65 | 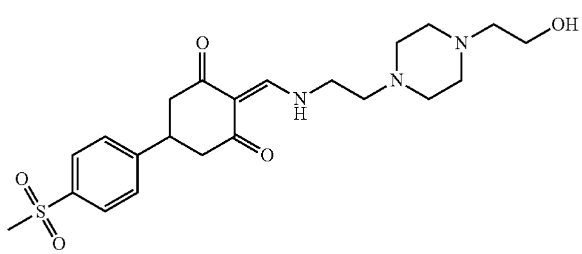 [SMILES: CS(=O)(=O)c1ccc(C2CC(=O)C(=CNCCN3CCN(CCO)CC3)C(=O)C2)cc1] | 2-(((2-(4-(2-hydroxyethyl)piperazin-1-yl)ethyl)amino)methylene)-5-(4-(methylsulfonyl)phenyl)cyclohexane-1,3-dione | ¹H NMR (400 MHz, CD$_3$OD) δ 8.29 (s, 1H), 7.95 (d, J = 8.4 Hz, 2H), 7.62 (d, J = 8.4 Hz, 2H), 3.71 (t, J = 6.1 Hz, 2H), 3.64 (t, J = 5.9 Hz, 2H), 3.61-3.47 (m, 1H), 3.14 (s, 3H), 3.00-2.44 (m, 16H); MS: 450.2 [M + 1]. |
| 66 | 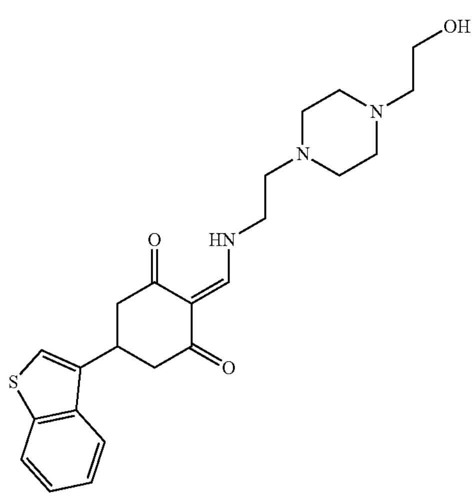 [SMILES: O=C1CC(c2csc3ccccc23)CC(=O)C1=CNCCN1CCN(CCO)CC1] | 5-(benzo[b]thiophen-3-yl)-2-(((2-(4-(2-hydroxyethyl)piperazin-1-yl)ethyl)amino)methylene)cyclohexane-1,3-dione | ¹H NMR (400 MHz, CD$_3$OD) δ 8.27 (s, 1H), 7.95-7.78 (m, 2H), 7.37 (dt, J = 19.3, 7.1 Hz, 2H), 7.30 (s, 1H), 3.89-3.79 (m, 1H), 3.77 (t, J = 5.6 Hz, 2H), 3.61 (t, J = 5.8 Hz, 2H), 3.09-2.57 (m, 16H); MS: 428.2 [M + 1]. |

TABLE 4-continued

Compounds 35-59 and 61-84

| # | Structure | Name | Proton NMR (¹HNMR), Mass Spectrum (MS) |
|---|---|---|---|
| 67 | 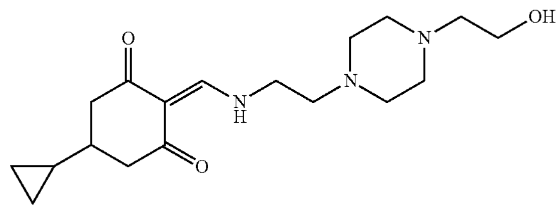 [SMILES: O=C1CC(C2CC2)CC(=O)C1=CNCCN1CCN(CCO)CC1] | 5-cyclopropyl-2-(((2-(4-(2-hydroxyethyl)piperazin-1-yl)ethyl)amino)methylene)cyclohexane-1,3-dione | ¹H NMR (400 MHz, CD$_3$OD) δ 8.19 (s, 1H), 3.70 (t, J = 5.9 Hz, 2H), 3.57 (t, J = 5.8 Hz, 2H), 2.76-2.51 (m, 13H), 2.49-2.30 (m, 2H), 1.31-1.18 (m, 2H), 0.77-0.59 (m, 1H), 0.47 (dd, J = 5.1, 2.7 Hz, 2H), 0.14 (d, J = 4.9 Hz, 2H); MS: 336.2 [M + 1]. |
| 68 | 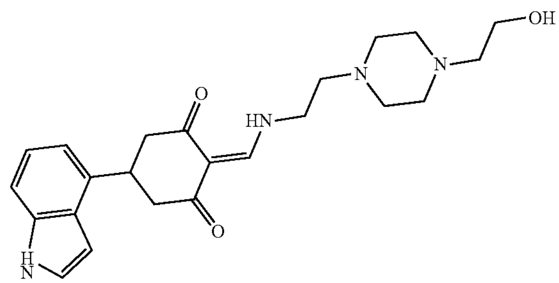 [SMILES: O=C1CC(c2cccc3[nH]ccc23)CC(=O)C1=CNCCN1CCN(CCO)CC1] | 2-(((2-(4-(2-hydroxyethyl)piperazin-1-yl)ethyl)amino)methylene)-5-(1H-indol-4-yl)cyclohexane-1,3-dione | ¹H NMR (400 MHz, CD$_3$OD) δ 8.26 (s, 1H), 7.25 (dd, J = 14.5, 5.7 Hz, 2H), 7.05 (t, J = 7.7 Hz, 1H), 6.87 (d, J = 7.2 Hz, 1H), 6.52 (d, J = 2.5 Hz, 1H), 3.85-3.74 (m, 1H), 3.71 (t, J = 5.8 Hz, 2H), 3.59 (t, J = 5.8 Hz, 2H), 3.05-2.38 (m, 16H): MS: 411.4 [M + 1]. |
| 69 | 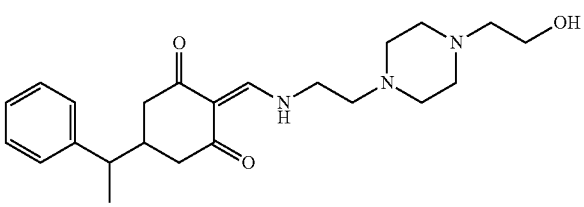 [SMILES: CC(c1ccccc1)C1CC(=O)C(=CNCCN2CCN(CCO)CC2)C(=O)C1] | 2-(((2-(4-(2-hydroxyethyl)piperazin-1-yl)ethyl)amino)methylene)-5-(1-phenylethyl)cyclohexane-1,3-dione | ¹H NMR (400 MHz, CD$_3$OD) δ 8.16 (d, J = 10.5 Hz, 1H), 7.28 (t, J = 7.4 Hz, 2H), 7.18 (t, J = 8.3 Hz, 3H), 3.78 (t, J = 5.4 Hz, 2H), 3.57 (t, J = 5.6 Hz, 2H), 3.15-2.85 (m, 5H), 2.82-2.52 (m, 8H), 2.46-1.90 (m, 5H), 1.29 (d, J = 7.0 Hz, 3H); MS: 400.2 [M + 1]. |
| 70 | 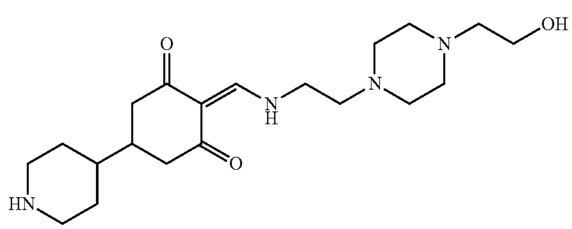 [SMILES: O=C1CC(C2CCNCC2)CC(=O)C1=CNCCN1CCN(CCO)CC1] | 2-(((2-(4-(2-hydroxyethyl)piperazin-1-yl)ethyl)amino)methylene)-5-(piperidin-4-yl)cyclohexane-1,3-dione HCl salt | ¹H NMR (400 MHz, D$_2$O) δ 8.09 (s, 1H), 3.88-3.74 (m, 3H), 3.68-3.26 (m, 15H), 2.91-2.74 (m, 2H), 2.45 (dd, J = 17.1, 3.9 Hz, 2H), 2.27 (s, 2H), 2.02-1.75 (m, 3H), 1.59-1.44 (m, 1H), 1.43-1.21 (m, 2H); MS: 379.2 [M + 1]. |
| 71 | 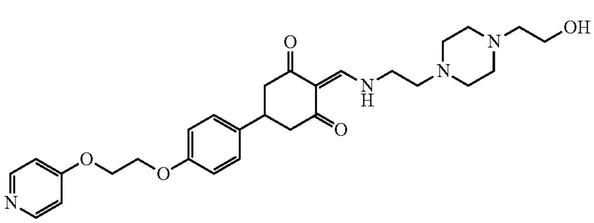 [SMILES: O=C1CC(c2ccc(OCCOc3ccncc3)cc2)CC(=O)C1=CNCCN1CCN(CCO)CC1] | 2-(((2-(4-(2-hydroxyethyl)piperazin-1-yl)ethyl)amino)methylene)-5-(4-(2-(pyridin-4-yloxy)ethoxy)phenyl)cyclohexane-1,3-dione | ¹H NMR (400 MHz, DMSO-d$_6$) δ 10.92 (d, J = 14.7 Hz, 1H), 8.38 (d, J = 6.2 Hz, 2H), 8.11 (d, J = 14.6 Hz, 1H), 7.21 (d, J = 8.7 Hz, 2H), 7.00 (dd, J = 4.8, 1.5 Hz, 2H), 6.91 (d, J = 8.7 Hz, 2H), 4.69 (s, 1H), 4.38 (dd, J = 5.6, 2.9 Hz, 2H), 4.29 (dd, J = 5.5, 3.1 Hz, 2H), 3.55 (d, J = 5.4 Hz, 4H), 3.28-2.31 (m, 17H); MS: 510.2 [M + 1]. |
| 72 | 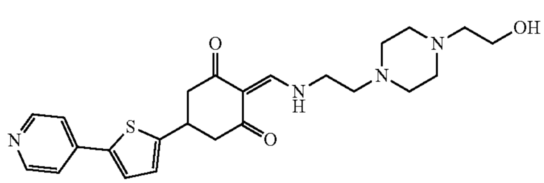 [SMILES: O=C1CC(c2ccc(-c3ccncc3)s2)CC(=O)C1=CNCCN1CCN(CCO)CC1] | 2-(((2-(4-(2-hydroxyethyl)piperazin-1-yl)ethyl)amino)methylene)-5-(5-(pyridin-4-yl)thiophen-2-yl)cyclohexane-1,3-dione | ¹H NMR (400 MHz, CD$_3$OD) δ 8.47 (dd, J = 4.8, 1.5 Hz, 2H), 8.23 (s, 1H), 7.61 (dd, J = 4.7, 1.6 Hz, 2H), 7.55 (d, J = 3.8 Hz, 1H), 7.00 (d, J = 3.1 Hz, 1H), 3.83-3.69 (m, 1H), 3.66 (t, J = 6.0 Hz, 2H), 3.59 (t, J = 5.8 Hz, 2H), 3.00-2.71 (m, 4H), 2.66-2.42 (m, 12H); MS: 455.3 [M + 1]. |

TABLE 4-continued

Compounds 35-59 and 61-84

| # | Structure | Name | Proton NMR (¹HNMR), Mass Spectrum (MS) |
|---|---|---|---|
| 73 | 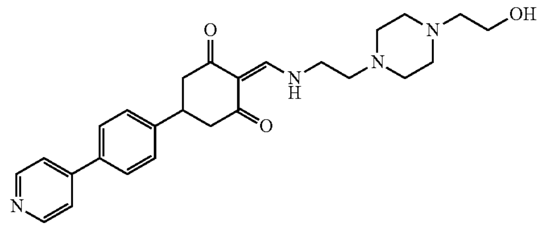 [SMILES: O=C1CC(c2ccc(-c3ccncc3)cc2)CC(=O)C1=CNCCN1CCN(CCO)CC1] | 2-(((2-(4-(2-hydroxyethyl)piperazin-1-yl)ethyl)amino)methylene)-5-(4-(pyridin-4-yl)phenyl)cyclohexane-1,3-dione | 1H NMR (400 MHz, CD$_3$OD) δ 8.55 (dd, J = 4.7, 1.6 Hz, 2H), 8.25 (s, 1H), 7.77-7.66 (m, 4H), 7.46 (d, J = 8.3 Hz, 2H), 3.67 (t, J = 6.0 Hz, 2H), 3.60 (t, J = 6.0 Hz, 2H), 3.45 (m, 1H), 2.67 (m, 16H); MS: 449.5 [M + 1]. |
| 74 | 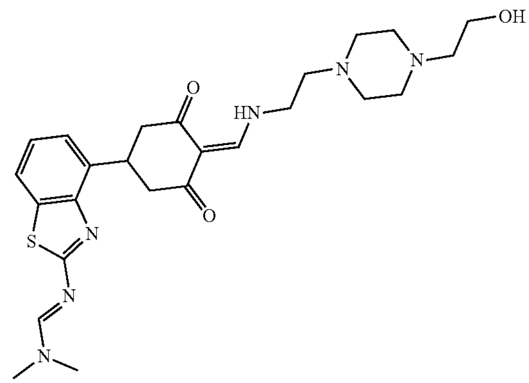 [SMILES: CN(C)/C=N/c1nc2c(C3CC(=O)C(=CNCCN4CCN(CCO)CC4)C(=O)C3)cccc2s1] | N'-(4-(4-(((2-(4-(2-hydroxyethyl)piperazin-1-yl)ethyl)amino)methylene)-3,5-dioxocyclohexyl)benzo[d]thiazol-2-yl)-N,N-dimethylformimidamide | ¹HNMR (400 MHz, CD$_3$OD) δ 8.35 (s, 1H), 8.26 (s, 1H), 7.64-7.52 (m, 1H), 7.21 (d, J = 6.8 Hz, 1H), 7.15 (t, J = 7.7 Hz, 1H), 4.06 (t, J = 11.6 Hz, 1H), 3.74 (t, J = 5.7 Hz, 2H), 3.61 (t, J = 5.6 Hz, 2H), 3.19 (s, 3H), 3.11 (s, 3H), 3.09-2.54 (m, 16H).; MS: 499.3 [M + 1]. |
| 75 | 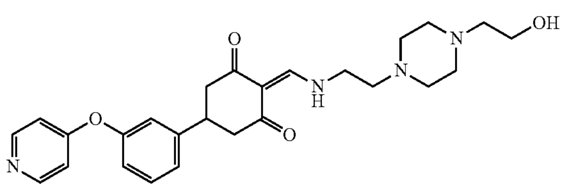 [SMILES: O=C1CC(c2cccc(Oc3ccncc3)c2)CC(=O)C1=CNCCN1CCN(CCO)CC1] | 2-(((2-(4-(2-hydroxyethyl)piperazin-1-yl)ethyl)amino)methylene)-5-(3-(pyridin-4-yloxy)phenyl)cyclohexane-1,3-dione | ¹HNMR (400 MHz, CD$_3$OD) δ 8.41 (dd, J = 5.0, 1.4 Hz, 2H), 8.26 (s, 1H), 7.47 (t, J = 7.9 Hz, 1H), 7.28 (d, J = 7.8 Hz, 1H), 7.14 (s, 1H), 7.04 (dd, J = 8.1, 1.5 Hz, 1H), 6.95 (dd, J = 4.9, 1.5 Hz, 2H), 3.70 (t, J = 6.0 Hz, 2H), 3.62 (t, J = 5.9 Hz, 2H), 3.52-3.39 (m, 1H), 2.91-2.47 (m, 16H); MS: 465.4 [M + 1]. |
| 76 | 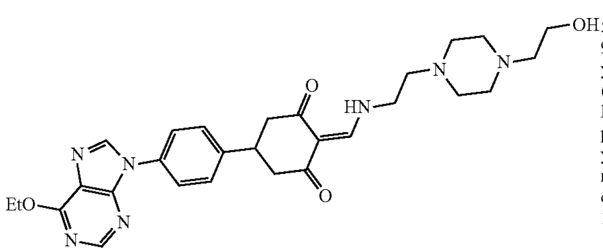 [SMILES: CCOc1ncnc2c1ncn2-c1ccc(C2CC(=O)C(=CNCCN3CCN(CCO)CC3)C(=O)C2)cc1] | 5-(4-(6-ethoxy-9H-purin-9-yl)phenyl)-2-(((2-(4-(2-hydroxyethyl)piperazin-1-yl)ethyl)amino)methylene)cyclohexane-1,3-dione | ¹HNMR (400 MHz, CD$_3$OD) δ 8.48 (s, 1H), 8.43 (s, 1H), 8.18 (s, 1H), 7.69 (d, J = 8.5 Hz, 2H), 7.47 (d, J = 8.5 Hz, 2H), 4.60 (q, J = 7.1 Hz, 2H), 3.67 (t, J = 5.6 Hz, 2H), 3.53 (t, J = 5.7 Hz, 2H), 3.46-3.37 (m, 1H), 2.89-2.52 (m, 16H), 1.42 (t, J = 7.1 Hz, 3H); MS: 534.3 [M + 1]. |
| 77 | 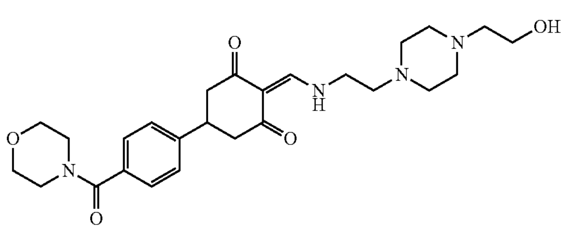 [SMILES: O=C1CC(c2ccc(C(=O)N3CCOCC3)cc2)CC(=O)C1=CNCCN1CCN(CCO)CC1] | 2-(((2-(4-(2-hydroxyethyl)piperazin-1-yl)ethyl)amino)methylene)-5-(4-(morpholine-4-carbonyl)phenyl)cyclohexane-1,3-dione | ¹HNMR (400 MHz, CD$_3$OD) δ 8.29 (s, 1H), 7.45 (s, 4H), 3.84-3.38 (m, 13H), 2.93-2.50 (m, 16H); MS: 485.3 [M + 1]. |
| 78 | 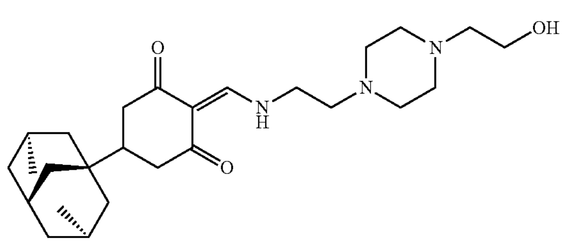 | 5-adamantan-1-yl)-2-(((2-(4-(2-hydroxyethyl)piperazin-1-yl)ethyl)amino)methylene)cyclohexane-1,3-dione | ¹HNMR (400 MHz, CD$_3$OD) δ 8.21 (s, 1H), 3.73 (t, J = 5.9 Hz, 2H), 3.61 (t, J = 5.8 Hz, 2H), 3.37 (d, J = 5.3 Hz, 2H), 2.84-2.47 (m, 12H), 2.40-2.19 (m, 2H), 2.09-1.88 (m, 4H), 1.86-1.54 (m, 12H): MS: 430.2 [M + 1]. |

TABLE 4-continued

Compounds 35-59 and 61-84

| # | Structure | Name | Proton NMR (¹HNMR), Mass Spectrum (MS) |
|---|---|---|---|
| 79 | 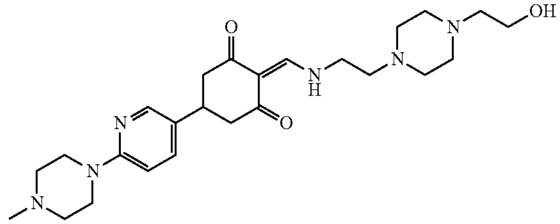 [SMILES: CN1CCN(c2ccc(C3CC(=O)C(=CNCCN4CCN(CCO)CC4)C(=O)C3)cn2)CC1] | 2-(((2-(4-(2-hydroxyethyl)piperazin-1-yl)ethyl)amino)methylene)-5-(6-(4-methylpiperazin-1-yl)pyridin-3-yl)cyclohexane-1,3-dione | ¹HNMR (400 MHz, CD₃OD) δ 8.24 (s, 1H), 8.02 (d, J = 2.2 Hz, 1H), 7.55 (dd, J = 8.8, 2.4 Hz, 1H), 6.82 (d, J = 8.9 Hz, 1H), 3.68 (t, J = 6.0 Hz, 2H), 3.60 (t, J = 5.8 Hz, 2H), 3.53-3.49 (m, 4H), 2.76-2.50 (m, 21H), 2.34 (s, 3H); MS: 471.3 [M + 1]. |
| 80 | 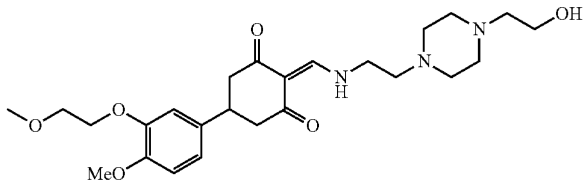 [SMILES: COCCOc1cc(C2CC(=O)C(=CNCCN3CCN(CCO)CC3)C(=O)C2)ccc1OC] | 2-(((2-(4-(2-hydroxyethyl)piperazin-1-yl)ethyl)amino)methylene)-5-(4-methoxy-3-(2-methoxyethoxy)phenyl)cyclohexane-1,3-dione | ¹H NMR (400 MHz, CD₃OD) δ 8.24 (s, 1H), 6.92-6.83 (m, 3H), 4.13-4.11 (m, 2H), 3.82 (s, 3H), 3.76-3.72 (m, 4H), 3.60 (t, J = 5.6 Hz, 2H), 3.42 (s, 3H), 2.87-2.61 (m, 17H); MS: 476.2 [M + 1]. |
| 81 | 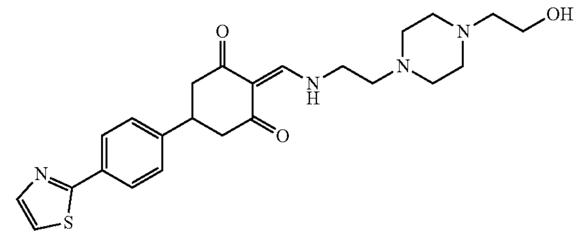 [SMILES: O=C1CC(c2ccc(-c3nccs3)cc2)CC(=O)C1=CNCCN1CCN(CCO)CC1] | 2-(((2-(4-(2-hydroxyethyl)piperazin-1-yl)ethyl)amino)methylene)-5-(4-(thiazol-2-yl)phenyl)cyclohexane-1,3-dione | ¹H NMR (400 MHz, CD₃OD) δ 8.26 (s, 1H), 7.92 (d, J = 8.3 Hz, 2H), 7.85 (d, J = 3.2 Hz, 1H), 7.59 (d, J = 3.3 Hz, 1H), 7.44 (d, J = 8.2 Hz, 2H), 3.68 (t, J = 6.2 Hz, 2H), 3.61 (t, J = 9.1 Hz, 2H), 3.45 (m, 2H), 2.62 (m, 15H). |
| 82 | 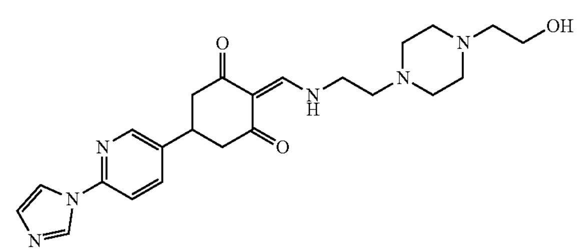 [SMILES: O=C1CC(c2ccc(-n3ccnc3)nc2)CC(=O)C1=CNCCN1CCN(CCO)CC1] | 5-(6-(1H-imidazol-1-yl)pyridin-3-yl)-2-(((2-(4-(2-hydroxyethyl)piperazin-1-yl)ethyl)amino)methylene)cyclohexane-1,3-dione | ¹H NMR (400 MHz, CD₃OD) δ 8.50 (s, 1H), 8.44 (d, J = 1.8 Hz, 1H), 8.26 (s, 1H), 7.94 (dd, J = 8.5, 2.1 Hz, 1H), 7.87 (s, 1H), 7.66 (d, J = 8.4 Hz, 1H), 7.14 (s, 1H), 3.67 (t, J = 6.0 Hz, 2H), 3.61 (t, J = 5.9 Hz, 2H), 3.52 (m, 1H), 2.94-2.67 (m, 5H), 2.66-2.43 (m, 11H) |
| 83 | 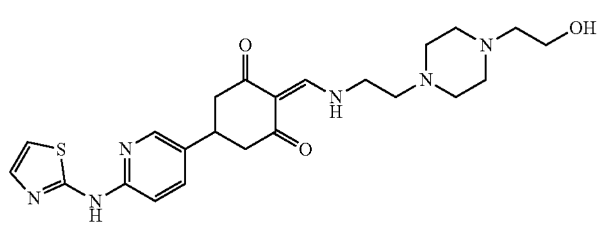 [SMILES: O=C1CC(c2ccc(Nc3nccs3)nc2)CC(=O)C1=CNCCN1CCN(CCO)CC1] | 2-(((2-(4-(2-hydroxyethyl)piperazin-1-yl)ethyl)amino)methylene)-5-(6-(thiazol-2-ylamino)pyridin-3-yl)cyclohexane-1,3-dione | ¹HNMR (400 MHz, CD₃OD) δ 8.28-8.20 (m, 2H), 7.66 (dd, J = 8.6, 2.4 Hz, 1H), 7.31 (d, J = 3.7 Hz, 1H), 7.00 (d, J = 8.6 Hz, 1H), 6.89 (d, J = 3.7 Hz, 1H), 3.82-3.77 (m, 2H), 3.60-3.63 (m, 2H), 3.39 (m, 1H), 3.14-2.89 (m, 6H), 2.87-2.61 (m, 10H). |
| 84 | 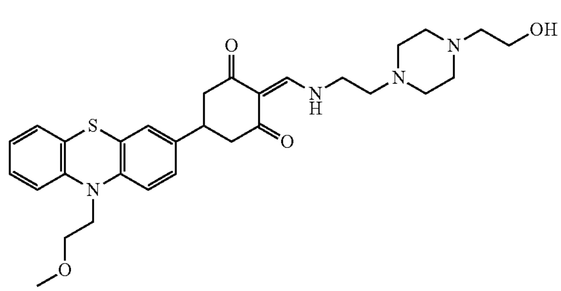 [SMILES: COCCN1c2ccccc2Sc2cc(C3CC(=O)C(=CNCCN4CCN(CCO)CC4)C(=O)C3)ccc21] | 2-(((2-(4-(2-hydroxyethyl)piperazin-1-yl)ethyl)amino)methylene)-5-(10-(2-methoxyethyl)-10H-phenothiazin-3-yl)cyclohexane-1,3-dione | ¹HNMR (400 MHz, CD₃OD) δ 8.24 (s, 1H), 7.16 (m, 1H), 7.10 (d, J = 7.9 Hz, 2H), 7.05 (s, 1H), 7.00-6.88 (m, 3H), 4.08 (t, J = 5.7 Hz, 2H), 3.72 (q, J = 5.8 Hz, 4H), 3.60 (t, J = 5.7 Hz, 2H), 3.32 (s, 5H), 2.83-2.49 (m, 15H) |

Example 13-1: Synthesis of Intermediate 13-1: (6-(4-methylpiperazin-1-yl)pyridine)

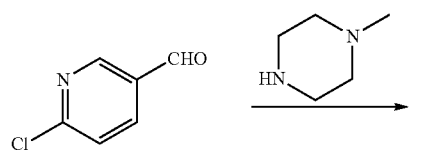

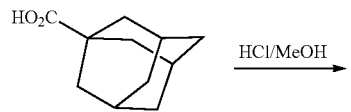

The solution of 6-chloronicotinaldehyde (5.00 g, 35.32 mmol) and N-methylpiperazine (15.68 mL, 141.28 mmol) in DMF (20 mL) was heated to 100° C. and reacted for 1 h. After the reaction was completed, the reaction mixture was cooled to room temperature, poured into ice-water and extracted with EA. The combined organic phase was washed successively with water and saturated brine, then dried and concentrated. The crude product was separated by column chromatography to give the desired product (6.32 g, yield 870%).

Example 13-2: Synthesis of Intermediate 13-2: 1-Adamantanecarbaldehyde

Step 1: Synthesis of Methyl 1-Adamantanecarboxylate

1-Adamantanecarboxylic acid (5.00 g, 27.74 mmol) and concentrated $H_2SO_4$ (0.5 ml) were dissolved in MeOH (50 ml), refluxed and reacted overnight. After the reaction was completed, the reaction mixture was cooled to room temperature, poured into ice-water and extracted with DCM. The organic phase was washed with saturated $NaHCO_3$, water, brine, dried with $Na_2SO_4$ and concentrated to give the crude desired product (4.8 g, yield 89%).

Step 2: 1-Adamantanecarbaldehyde

Under the protection of nitrogen atmosphere, methyl 1-Adamantanecarboxylate (3 g, 15.5 mmol) was dissolved in PhMe (80 mL), then cooled down to −78° C. and DIBAL-H (1.5M of toluene solution, 10.3 mL) was added dropwise. 4N HCl was carefully added dropwise to carry out a quench reaction, then poured into ice-water and extracted with EA. The combined organic phase was washed with saturated brine, dried and concentrated. The crude product was separated by column chromatography to give the desired product (2.1 g, yield 82%).

Example 13-3: Synthesis of Intermediate 13-3: 4-(morpholine-4-carbonyl)benzaldehyde

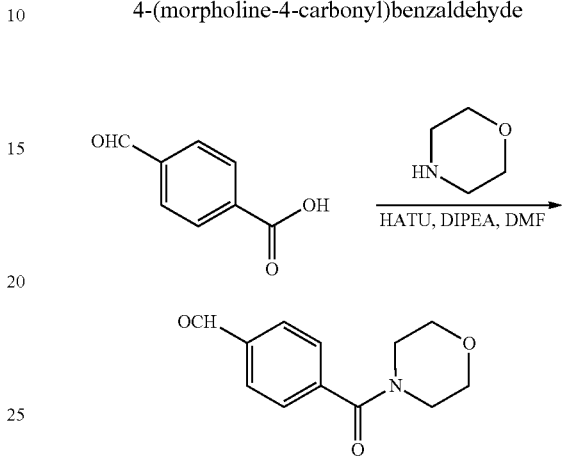

4-formylbenzoic acid (5.0 g, 33.3 mmol) was dissolved in anhydrous DMF (10 mL), to which 2-(7~azabenzotriazol) N,N,N',N'-tetramethyluronium hexafluorophosphate (HATU) (17.12 g, 45 mmol) and DIPEA (6.45 g, 50 mmol) were added sequentially and reacted at RT for 30 min. Then morpholine (3.92 g, 45 mmol) was added and the above mixture was continuously reacted at RT for additional 1 hour. After the reaction was completed, the reaction mixture was poured into ice-water and extracted with EA. The organic phase was washed with water, dried with $Na_2SO_4$ and concentrated. The crude product was separated by column chromatography to give the desired product (5.0 g, yield 68%).

Example 13-4: Synthesis of Intermediate 13-4: 3-(pyridin-4-yloxy)benzaldehyde

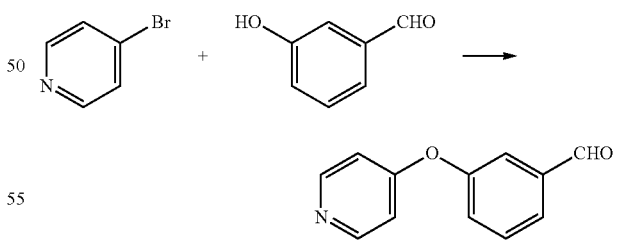

4-bromopyridine (3.1 g, 40 mmol), 3-hydroxybenzaldehyde (40 mmol) and $Cs_2CO_3$ (26.1 g, 80 mmol) were dissolved in DMF (80 mL) and reacted at 100° C. overnight. After the reaction was completed, the reaction mixture was cooled to RT, poured into ice-water and extracted with EA. The organic phase was successively washed with water, brine, then dried and concentrated. The crude product was separated by column chromatography to give the desired product (1.99 g, yield 25%).

Example 13-5: Synthesis of Intermediate 13-5: 5-(pyridin-4-yl)thiophene-2-carbaldehyde

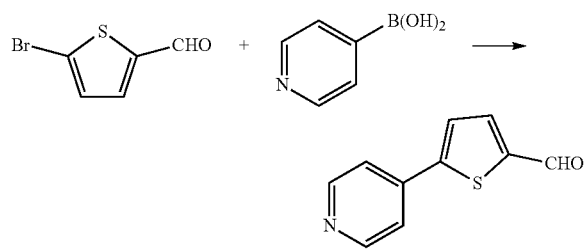

Under the protection of nitrogen atmosphere, 5-bromo-2-thiophenecarboxaldehyde (3.80 g, 20.0 mmol), pyridine-4-boronic acid (3.0 g, 24.0 mmol), Na$_2$CO$_3$ (3.18 g, 30.0 mmol), Pd(OAc)$_2$ (224.0 mg, 1.0 mmol) and PPh$_3$ (520.0 mg, 2.0 mmol) were dissolved in the mixed solvent of dioxane and water (v/v=3:1, 80 mL), then refluxed and reacted overnight. After the reaction was completed, the reaction mixture was cooled to RT, poured into ice-water and extracted with EA. The combined organic phase was washed with water, dried with Na$_2$SO$_4$. The crude product was separated by column chromatography to give the desired product (3.2 g, yield 85.0%).

Example 13-6: Synthesis of Intermediate 13-6: 4-(pyridin-4-yl)benzaldehyde

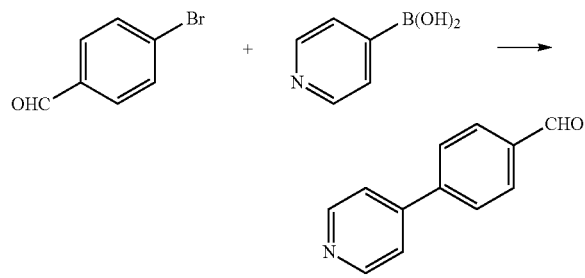

Under the protection of nitrogen atmosphere, 4-bromobenzaldehyde (2.78 g, 15 mmol), pyridine-4-boronic acid (2.46 g, 20 mmol), Na$_2$CO$_3$ (3.18 g, 30 mmol) and Pd(PPh$_3$)$_4$ (722 mg, 0.62 mmol) were dissolved in dioxane (40 mL) and water (10 mL). The mixture was refluxed and reacted overnight. After the reaction was completed, the reaction mixture was cooled to RT, poured into ice-water and extracted with EA. The organic phase was washed with water, dried and concentrated. The crude product was separated by column chromatography to give the desired product (2.23 g, yield 81%).

Example 13-7: Synthesis of Intermediate 13-7: compound 4-(thiazol-2-yl)benzaldehyde

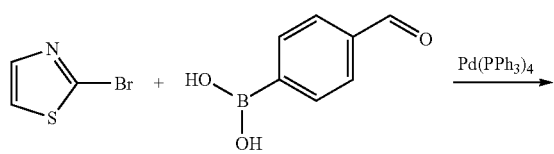

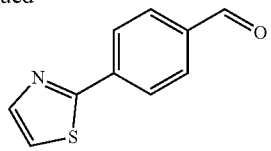

Under the protection of nitrogen atmosphere, 2-bromothiazole (3.0 g, 18.3 mmol), (4-formylphenyl)boronic acid (3.3 g, 22 mmol), sodium carbonate (3.88 g, 36.6 mmol) and tetrakis(triphenylphosphine)palladium (1.0 g, 0.865 mmol) were dissolved in the mixed solvent of toluene/ethanol/water (50 mL, v:v=3:1:1), then refluxed and reacted overnight. After the reaction was completed, the reaction mixture was cooled to room temperature, poured into water and extracted with EA. The organic layers were dried with sodium sulfate, concentrated and separated by column chromatography to give the desired compound (2.24 g, yield 65%).

Example 13-8: Synthesis of Intermediate 13-8: 10-(2-methoxyethyl)-10H-phenothiazine-3-carbaldehyde

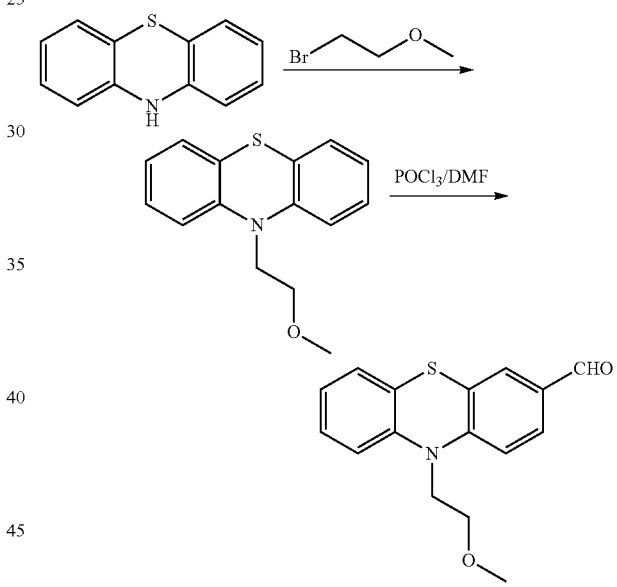

Step 1: Synthesis of Compound 10-(2-methoxyethyl)-10H-phenothiazine

Under the protection of nitrogen atmosphere, NaH (2.4 g, 2 eq.) was added portionwise into a solution of 10H-phenothiazine (6 g, 1 eq.) in DMF (60 mL) at 0° C. and the resulting mixture was stirred for 30 minutes. 1-bromo-2-methoxyethane (6.3 g, 1.5 eq.) was added and the mixture was stirred at RT for 2 hours. Water was added to quench the reaction, extracted with DCM. The organic layers were dried with Na$_2$SO$_4$ and concentrated. The crude product was separated by column chromatography to give 9 g of the desired compound.

Step 2: Synthesis of Compound 10-(2-methoxyethyl)-10H-phenothiazine-3-carbaldehyde Under the protection of nitrogen atmosphere, POCl$_3$ (10.2 mL, 5 eq.) was added dropwise into anhydrous DMF (8 g, 5 eq.) at 0 e-3-carbaldehydetion, the mixture was stirred until a colorless solid formed. 1,2-dichloroethane (50 mL) was added to dissolve the solid and stirring was continued for 1 hour. A solution of 10-(2-methoxyethyl)-10H-phenothiazine (5.6 g, 1 eq.) in 1,2-dichloroethane was added dropwise and stirred at 90° C. for 2 hours. After the reaction was completed, the reaction mixture was cooled to room temperature. An aqueous solution of 20% NaOH was added to adjust to pH 7 and the aqueous phase was extracted with DCM. The combined organic phase was dried with $Na_2SO_4$ and concentrated. The crude product was separated by column chromatography to give 5.3 g of the desired compound.

Example 13-9: Synthesis of Intermediate 13-9: tert-butyl (4-formylbenzo[d]thiazol-2-yl)carbamate

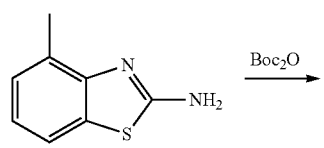

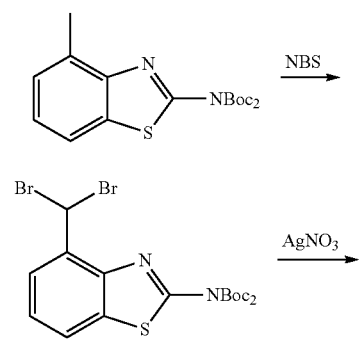

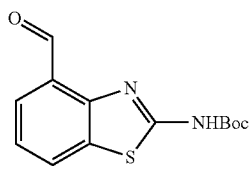

Step 1: Synthesis of Compound Di-Tert-Butyl (4-methylbenzo[d]thiazol-2-yl)carbamate 4-methylbenzo[d]thiazol-2-amine (3.0 g, 18.3 mmol), di-tert-butyl dicarbonate (10.0 g, 45.7 mmol) and DMAP (0.67 g, 5.5 mmol) were dissolved in DCM (80 mL) and reacted at RT overnight. After the reaction was completed, the reaction mixture was poured into ice-water and extracted with DCM. The combined organic phase was washed with water, dried with $Na_2SO_4$ and concentrated. The crude product was separated by column chromatography to give the desired product (5.2 g, yield 78%).

Step 2: Synthesis of Compound Di-Tert-Butyl (4-(dibromomethyl)benzo[d]thiazol-2-yl)carbamate Di-tert-butyl (4-methylbenzo[d]thiazol-2-yl)carbamate (5.2 g, 14.3 mmol), NBS (5.08 g, 28.5 mmol) and AIBN (330 mg, 2 mmol) were dissolved in $CCl_4$ (30 mL), then refluxed and reacted overnight. After the reaction was completed, the reaction mixture was poured into ice-water and extracted with DCM. The combined organic phase was washed with water, dried with sulfate and concentrated to give the crude product (4.5 g), which can be used directly in next step without further purification.

Step 3: Synthesis of Compound Tert-Butyl (4-formylbenzo[d]thiazol-2-yl)carbamate Tert-butyl (4-(dibromomethyl)benzo[d]thiazol-2-yl)carbamate (4.5 g, crude) and $AgNO_3$ (12.2 g, 71.5 mmol) in the mixed solvent of PhMe (50 mL) and DMSO (5 mL), reacted at 60° C. for 2 hs. After the reaction was completed, the reaction mixture was poured into ice-water and extracted with EA. The combined organic phase was washed with water, dried with $Na_2SO_4$ and concentrated. The crude product was separated by column chromatography to give the desired product (1.8 g, yield 45.2%).

Example 13-10: Synthesis of Intermediate 13-10: (E)-4-(4-(6-ethoxy-9H-purin-9-yl)phenyl)but-3-en-2-one

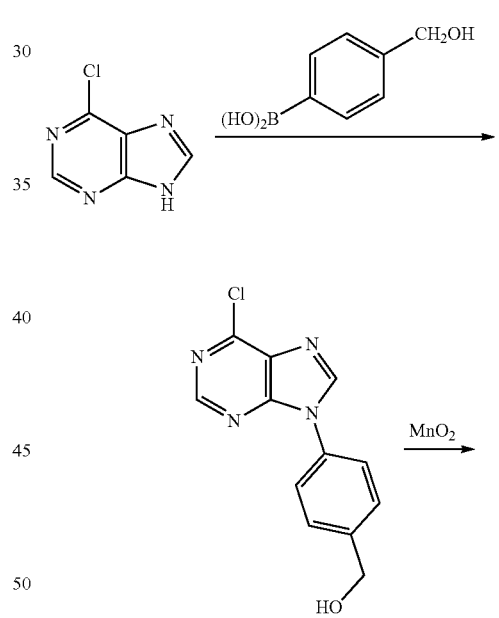

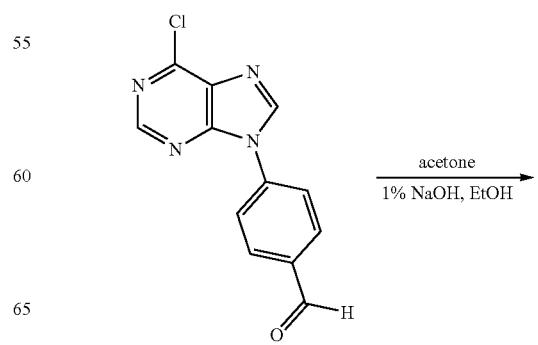

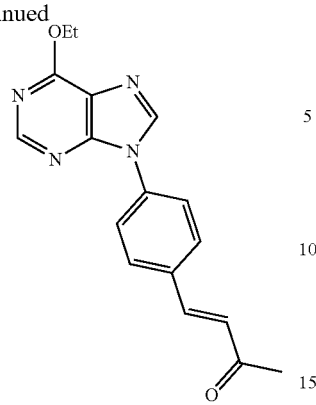

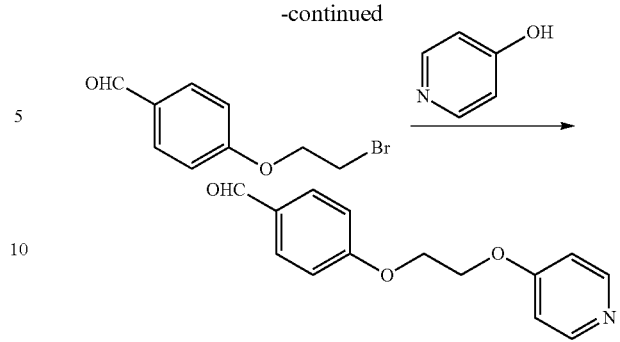

Step 1: Synthesis of Compound 4-(2-bromoethoxy)benzaldehyde 4-hydroxybenzaldehyde (3.0 g, 24.6 mmol), $K_2CO_3$ (6.90 g, 50 mmol) and 1,2-dibromoethane (9.4 g, 50 mmol) were dissolved in EtOH (85 mL), then refluxed and reacted overnight. After the reaction was completed, the reaction mixture was poured into ice-water and extracted with EA. The combined organic phase was washed with water, dried with $Na_2SO_4$ and concentrated. The crude product was separated by column chromatography to give the desired product (1.8 g, yield 32%).

Step 1: Synthesis of Compound (4-(6-chloro-9H-purin-9-yl)phenyl)methanol 6-chloro-9H-purine (1.54 g, 10.0 mmol), $Cu(OAc)_2$ (3.63 g, 20 mmol), (4-(hydroxymethyl)phenyl)boronic acid (3.63 g, 20 mmol), 1,10-phenanthroline (3.60 g, 20 mmol) and 4A molecular sieve (1.0 g) were placed in dried DMF (50 mL) solution, reacted at 40° C. overnight. After the reaction was completed, the reaction mixture was poured into ice-water and extracted with EA. The organic phase was washed with water, dried with $Na_2SO_4$ and concentrated. The crude product was separated by column chromatography to give the desired product (1.49 g, yield 57%).

Step 2: Synthesis of Compound 4-(2-(pyridin-4-yloxy)ethoxy)benzaldehyde 4-(2-bromoethoxy)benzaldehyde (1.80 g, 7.86 mmol), $Cs_2CO_3$ (4.89 g, 15 mmol) and 4-hydroxypyridine (950 mg, 10 mmol) were dissolved in EtOH (125 mL), then refluxed and reacted overnight. After the reaction was completed, the reaction mixture was cooled to RT, poured into ice-water and extracted with EA. The combined organic phase was dried with $Na_2SO_4$ and concentrated. The crude product was separated by column chromatography to give the desired product (400 mg, yield 21%).

Step 2: Synthesis of Compound 4-(6-chloro-9H-purin-9-yl)benzaldehyde (4-(6-chloro-9H-purin-9-yl)phenyl)methanol (900 mg, 3.5 mmol) and $MnO_2$ (6.1 g, 70 mmol) were placed in DCM (80 ml) and stirred at RT for 1 h, then filtered, the residue was washed with DCM. The filtrate was collected and concentrated to give the crude product (900 mg), which can be directly used in next step without further purification.

Step 3: Synthesis of Compound 4-(4-(6-ethoxy-9H-purin-9-yl)phenyl)but-3-en-2-one 4-(6-chloro-9H-purin-9-yl)benzaldehyde (900 mg, 3.5 mmol) and saturated $NaHCO_3$ (5 mL) were added into acetone (30 mL) and EtOH (20 mL), then heated to reflux for 5 hours. After the reaction was completed, the reaction mixture was cooled to RT, poured into ice-water and extracted with DCM. The combined organic phase was dried with $Na_2SO_4$ and concentrated. The crude product was separated by column chromatography to give the desired product (490 mg, yield 46%).

Example 14: Synthesis of Compound 5-(2-amino-benzo[d]thiazol-4-yl)-2-(((2-(4-(2-hydroxyethyl)piperazin-1-yl)ethyl)amino)methylene)cyclohexane-1,3-dione (Compound 85)

Example 13-11: Synthesis of Intermediate 13-11: 4-(2-(pyridin-4-yloxy)ethoxy)benzaldehyde

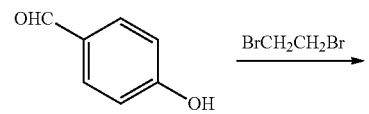

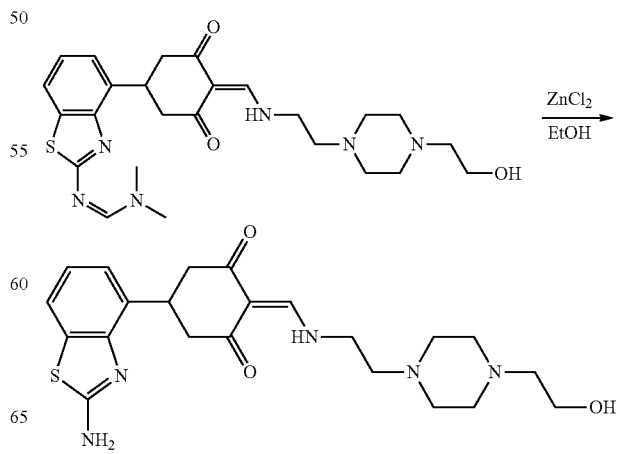

N'-(4-(4-(((2-(4-(2-hydroxyethyl)piperazin-1-yl)ethyl) amino)methylene)-3,5-dioxocyclohexyl)benzo[d]thiazol-2-yl)-N,N-dimethylformimidamide (100 mg, 2 mmol) and ZnCl$_2$ (1.36 g, 10 mmol) were dissolved in anhydrous EtOH (5 mL), then refluxed and reacted overnight. After the reaction was completed, the reaction mixture was cooled to RT, poured into ice-water and extracted with EA. The combined organic phase was dried with Na$_2$SO$_4$ and concentrated. The crude product was separated by column chromatography to give the desired product (40 mg, yield 45%). Compound 85: $^1$H NMR (400 MHz, CD$_3$OD) δ 8.27 (s, 1H), 7.48 (d, J=7.7 Hz, 1H), 7.14 (d, J=7.4 Hz, 1H), 7.03 (t, J=7.7 Hz, 1H), 3.92 (s, 1H), 3.75 (t, J=5.6 Hz, 2H), 3.62 (t, J=5.8 Hz, 2H), 3.10-2.49 (m, 16H); MS: 444.2 [M+1].

Example 15: Preparation of Compound 7-(((2-(4-(2-hydroxyethyl)piperazin-1-yl)ethyl)amino)methylene)-spiro[3.5]nonane-6,8-dione (Compound 86)

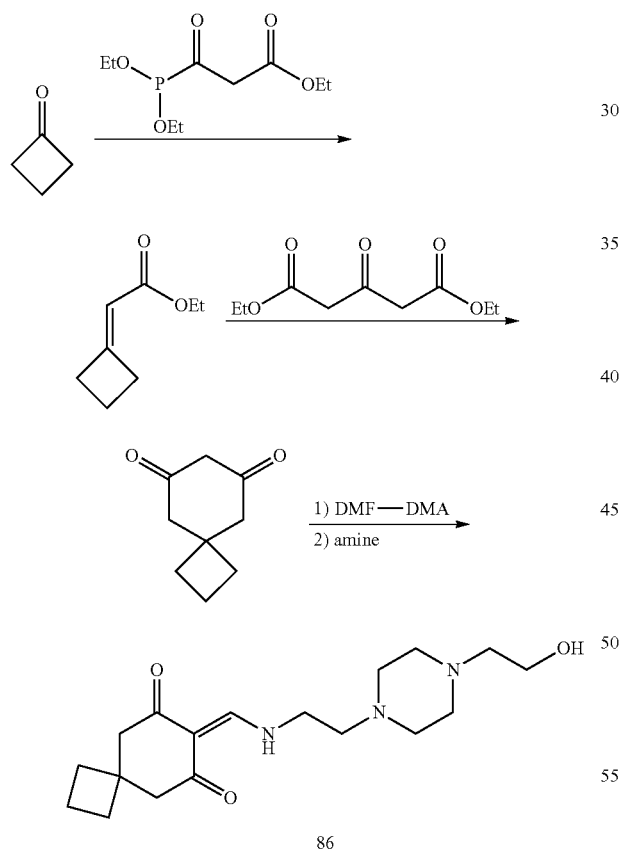

86

Step 1: Synthesis of Compound Ethyl 2-Cyclobutylideneacetate

Under the protection of nitrogen atmosphere, NaH (60%, 1.60 g, 40 mmol) was added portionwise at 0° C. to a solution of ethyl 3-(diethoxyphosphanyl)-3-oxopropanoate (8.96 g, 40 mmol) in anhydrous THF (50 mL) and stirred at this temperature for 30 mins, cyclobutanone (2.8 g, 40 mmol) in anhydrous THF (10 mL) solution was then added. The above mixture was stirred at this temperature for 2 hs, then water (10 mL) was added carefully, the resulting mixture was stirred at RT for additional 30 min. After the reaction was completed, the reaction mixture was poured into ice-water and extracted with EA. The combined organic phase was washed with water, dried with Na$_2$SO$_4$ and concentrated. The crude product was separated by column chromatography to give the desired product (4.62 g, yield 82.5%).

Step 2: Synthesis of Compound Spiro[3.5]nonane-6,8-dione

Under the protection of nitrogen atmosphere, NaH (60%, 960 mg, 24 mmol) was added portionwise at 0° C. to a solution of diethyl 3-oxopentanedioate (2.53 g, 12.5 mmol) in anhydrous THF (50 mL) and stirred at this temperature for 30 mins, ethyl 2-cyclobutylideneacetate (1.4 g, 10 mmol) in anhydrous THF (10 mL) solution was then added, reacted at RT for 2 hours, then EtONa (816 mg, 12 mmol) in anhydrous EtOH (5 mL) solution was added. The above mixture was refluxed and reacted for 5 hours, then cooled to 50° C., 20% KOH solution (10 mL) was added. The resulting mixture was stirred at this temperature overnight. After the reaction was completed, the reaction mixture was cooled to RT and extracted with EA, the aqueous phase was adjusted to 1-2 and stirred at 70° C. for 2 hours. The reaction mixture was cooled to RT and extracted with DCM. The combined organic phase was washed with water, dried with sulfate and concentrated. The crude product was separated and purified by column chromatography to give the desired product (483 mg, yield 32%).

Step 3: Synthesis of Compound 7-(((2-(4-(2-hydroxyethyl)piperazin-1-yl)ethyl)amino)methylene) spiro[3.5]nonane-6,8-dione The operation procedures were the same as Example 2. Compound 86: $^1$HNMR (CD$_3$OD, 400 MHz) δ 8.16 (s, 1H), 3.67 (t, J=6.0 Hz, 2H), 3.56 (t, J=6.0 Hz, 2H), 2.59-2.53 (m, 16H), 1.95-1.82 (m, 6H); MS: 336.5 [M+1].

Example 16: Compounds 87-94

Compounds 87-94 were synthesized by the same procedures as Compound 86 except for using corresponding aldehyde, ketone or substituted acrylate ester (see, e.g, Examples 16-1 and 16-2), as shown in Table 5.

TABLE 5

Compounds 87-94

| # | Structure | Name | Proton NMR ($^1$HNMR), Mass Spectrum (MS) |
|---|---|---|---|
| 87 | 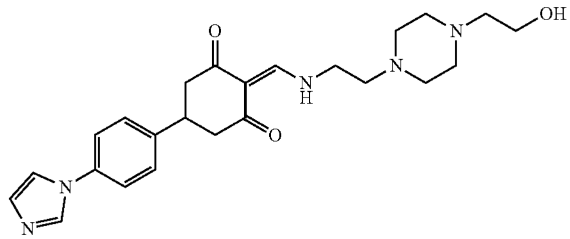 [SMILES: O=C1CC(c2ccc(-n3ccnc3)cc2)CC(=O)C1=CNCCN1CCN(CCO)CC1] | 5-(4-(1H-imidazol-1-yl)phenyl)-2-(((2-(4-(2-hydroxyethyl)piperazin-1-yl)ethyl)amino)methylene)cyclohexane-1,3-dione | $^1$HNMR (CD$_3$OD, 400 MHz) δ 8.25 (s, 1H), 8.10 (s, 1H), 7.54-7.45 (m, 5H), 7.13 (s, 1H), 3.67 (t, J = 6.0 Hz, 2H), 3.60 (t, J = 6.0 Hz, 2H), 3.49-3.41 (m, 1H), 2.87-2.52 (m, 16H); MS: 438.6 [M + 1]. |
| 88 | 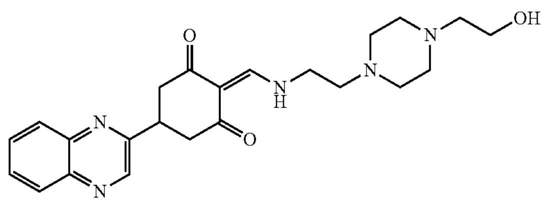 [SMILES: O=C1CC(c2cnc3ccccc3n2)CC(=O)C1=CNCCN1CCN(CCO)CC1] | 2-(((2-(4-(2-hydroxyethyl)piperazin-1-yl)ethyl)amino)methylene)-5-(quinoxalin-2-yl)cyclohexane-1,3-dione | $^1$HNMR (CD$_3$OD, 400 MHz) δ 8.89 (s, 1H), 8.24 (s, 1H), 8.07-8.05 (m, 2H), 7.83-7.76 (m, 2H), 3.93-3.88 (m, 1H), 3.67-3.57 (m, 2H), 3.30-3.28 (m, 2H), 3.11-2.91 (m, 2H), 2.88-2.81 (m, 2H), 2.61-2.50 (m, 12H). |
| 89 | 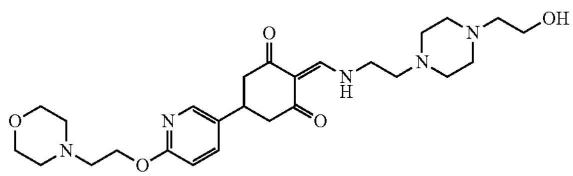 [SMILES: O=C1CC(c2ccc(OCCN3CCOCC3)nc2)CC(=O)C1=CNCCN1CCN(CCO)CC1] | 2-(((2-(4-(2-hydroxyethyl)piperazin-1-yl)ethyl)amino)methylene)-5-(6-(2-morpholinoethoxy)pyridin-3-yl)cyclohexane-1,3-dione | $^1$HNMR (400 MHz, CD$_3$OD) δ 8.25 (s, 1H), 7.57 (d, J = 9.2 Hz, 1H), 7.52 (s, 1H), 6.53 (d, J = 9.3 Hz, 1H), 4.09 (t, J = 6.4 Hz, 2H), 3.72 (t, J = 5.5 Hz, 2H), 3.67-3.56 (m, 6H), 3.26-3.17 (m, 1H), 2.93-2.43 (m, 22H); MS: 502.3 [M + 1] |
| 90 | 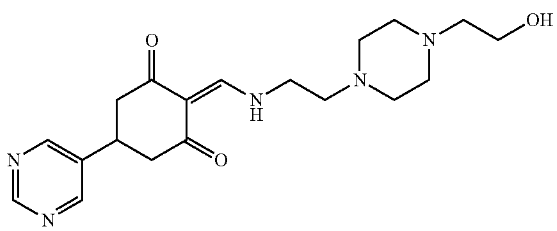 [SMILES: O=C1CC(c2cncnc2)CC(=O)C1=CNCCN1CCN(CCO)CC1] | 2-(((2-(4-(2-hydroxyethyl)piperazin-1-yl)ethyl)amino)methylene)-5-(pyrimidin-5-yl)cyclohexane-1,3-dione | $^1$HNMR (400 MHz, DMSO-d6) δ 10.97 (dd, J = 7.9, 6.7 Hz, 1H), 9.07 (s, 1H), 8.80 (s, 2H), 8.15 (d, J = 14.7 Hz, 1H), 4.35 (t, J = 5.3 Hz, 1H), 3.57 (d, J = 5.7 Hz, 2H), 3.53-3.35 (m, 3H), 2.93-2.67 (m, 2H), 2.65-2.23 (m, 14H); MS: 374.2 [M + 1]. |
| 91 | 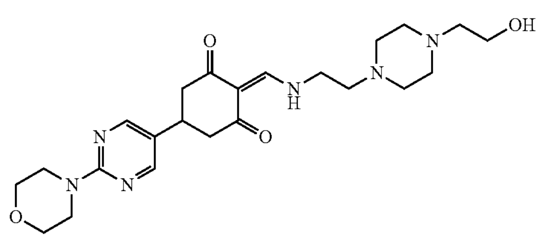 [SMILES: O=C1CC(c2cnc(N3CCOCC3)nc2)CC(=O)C1=CNCCN1CCN(CCO)CC1] | 2-(((2-(4-(2-hydroxyethyl)piperazin-1-yl)ethyl)amino)methylene)-5-(2-morpholino-pyrimidin-5-yl)cyclohexane-1,3-dione | $^1$HNMR (400 MHz, CD$_3$OD) δ 8.29 (s, 2H), 8.23 (s, 1H), 3.67 (t, J = 6.1 Hz, 11H), 3.59 (t, J = 5.9 Hz, 2H), 2.95-2.45 (m, 16H); MS: 459.3 [M + 1]. |
| 92 | 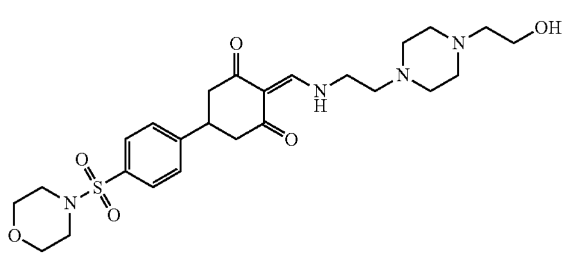 [SMILES: O=C1CC(c2ccc(S(=O)(=O)N3CCOCC3)cc2)CC(=O)C1=CNCCN1CCN(CCO)CC1] | 2-(((2-(4-(2-hydroxyethyl)piperazin-1-yl)ethyl)amino)methylene)-5-(4-(morpholino)phenyl)cyclohexane-1,3-dione | $^1$HNMR (400 MHz, CD$_3$OD) δ 8.32 (s, 1H), 7.80 (d, J = 8.3 Hz, 2H), 7.64 (d, J = 8.4 Hz, 2H), 3.83 (t, J = 5.6 Hz, 2H), 3.77-3.72 (m, 4H), 3.67 (t, J = 5.8 Hz, 2H), 3.63-3.51 (m, 1H), 3.05-2.97 (m, 6H), 2.97-2.67 (m, 14H); MS: 521.3 [M + 1]. |

TABLE 5-continued

Compounds 87-94

| # | Structure | Name | Proton NMR (¹HNMR), Mass Spectrum (MS) |
|---|---|---|---|
| 93 | 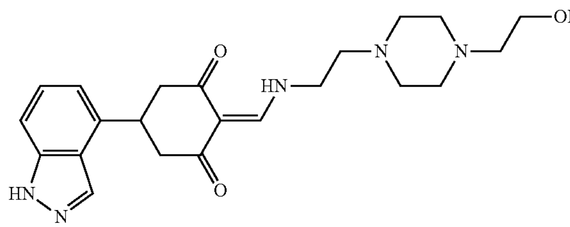 | 2-(((2-(4-(2-hydroxyethyl)piperazin-1-yl)ethyl)amino)methylene)-5-(1H-indazol-4-yl)cyclohexane-1,3-dione | ¹H NMR (400 MHz, CD₃OD) δ 8.32 (s, 1H), 8.23 (s, 1H), 7.47 (d, J = 8.4 Hz, 1H), 7.41-7.33 (m, 1H), 7.06 (d, J = 7.1 Hz, 1H), 3.92 (t, J = 11.0 Hz, 1H), 3.82 (t, J = 5.4 Hz, 2H), 3.66 (t, J = 5.7 Hz, 2H), 3.17-2.62 (m, 16H); MS: 412.4 [M + 1]. |
| 94 | 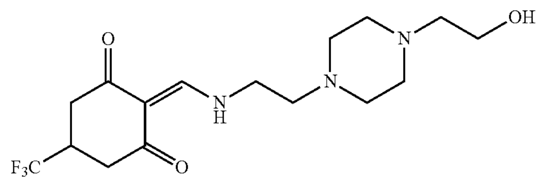 [SMILES: O=C1CC(C(F)(F)F)CC(=O)C1=CNCCN1CCN(CCO)CC1] | 2-(((2-(4-(2-hydroxyethyl)piperazin-1-yl)ethyl)amino)methylene)-5-(trifluoromethyl)cyclohexane-1,3-dione | ¹H NMR (400 MHz, CD₃OD) δ 8.22 (s, 1H), 3.69 (t, J = 5.9 Hz, 2H), 3.59 (t, J = 5.8 Hz, 2H), 3.02 (d, J = 8.2 Hz, 1H), 2.77-2.51 (m, 16H); MS: 364.0 [M + 1]. |

Example 16-1: Synthesis of Intermediate 16-1: ethyl 3-(4-(morpholinosulfonyl)phenyl)-acrylate

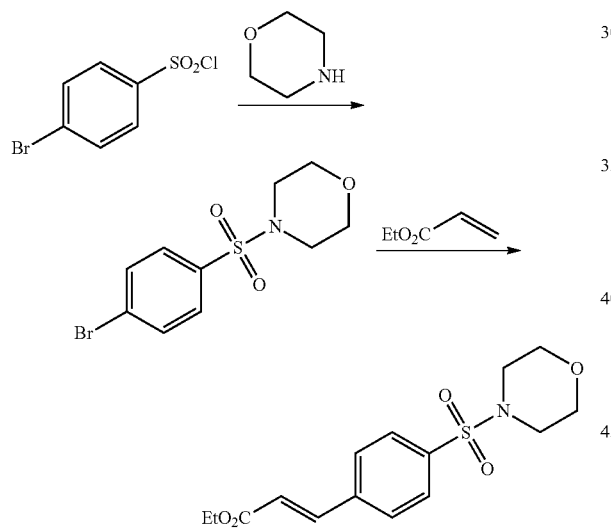

Step 1: Synthesis of Compound 4-((4-bromophenyl)sulfonyl)morpholine 4-bromobenzenesulfonyl chloride (5.0 g, 19.6 mmol), triethylamine (TEA) (2.98 mL) and morpholine (1.88 g, 21.53 mmol) were dissolved in DCM (50 mL) and reacted at RT for 30 min. After the reaction was completed, the reaction mixture was poured into water and extracted with DCM. The combined organic phase was washed with 1N HCl, water, brine, dried and concentrated to give 5.21 g of the desired product, which can be directly used in next step without further purification.

Step 2: Synthesis of Compound Ethyl 3-(4-(morpholinosulfonyl)phenyl)acrylate

Under the protection of nitrogen atmosphere, 4-((4-bromophenyl)sulfonyl)morpholine (2.0 g, 6.53 mmol), ethyl acrylate (849 mg, 8.49 mmol), Pd(OAc)₂ (43.88 mg, 0.2 mmol) and PPh₃ (68.89 mg, 0.26 mmol) were added in TEA (3 mL) and stirred at 150° C. for 6 hours in sealed tube. The reaction mixture was cooled, poured into ice-water and extracted with EA. The combined organic phase was dried with Na₂SO₄ and concentrated. The crude product was separated by column chromatography to give the desired product (1.8 g, yield 85%).

Example 16-2: Synthesis of Intermediate 16-3: 6-(2-morpholinoethoxy)nicotinaldehyde

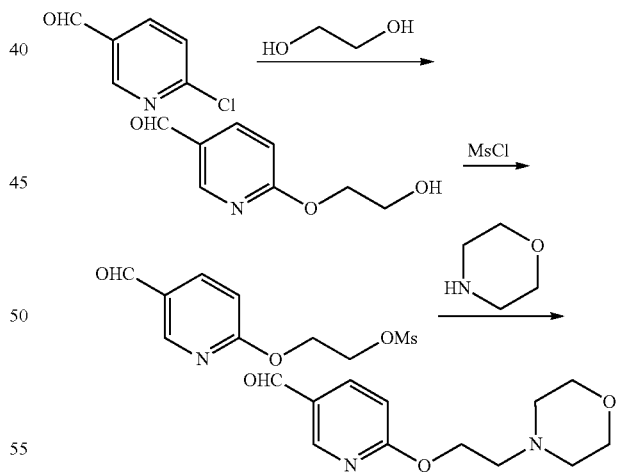

Step 1: Synthesis of Compound 6-(2-hydroxyethoxy)nicotinaldehyde t-BuONa (3.49 g, 36.3 mmol) was added to ethane-1,2-diol (30 mL) at RT. After stirring for 30 min, 6-chloronicotinaldehyde (4.0 g, 28.3 mmol) was added and the resulting mixture was stirred at RT overnight, then it was heated to 80° C. and stirred for additional 2 hours. After the reaction was completed, the reaction mixture was cooled to RT, poured into ice-water and extracted with EA. The organic phase was washed with water, dried and concentrated. The crude product was separated by column chromatography to give the desired product (4.01 g, yield 85%).

Step 2: Synthesis of Compound 2-((5-formylpyridin-2-yl)oxy)ethyl methanesulfonate 6-(2-hydroxyethoxy)nicotinaldehyde (4.0 g, 24 mmol) and TEA (4.0 mL) were added into DCM (90 mL), then MsCl (3.66 g, 32 mmol) in dichloromethane solution was added dropwise at 0° C. After the addition, the resulting mixture was stirred at 0° C. for 30 min. After the reaction was completed, the reaction solution was poured into water and extracted with EA. The combined organic phase was dried with $Na_2SO_4$ and concentrated to give 5.21 g of the desired product, which can be directly used in next step without further purification.

Step 3: Synthesis of Compound 6-(2-morpholinoethoxy)nicotinaldehyde 2-((5-formylpyridin-2-yl)oxy)ethyl methanesulfonate (5.21 g, crude), morpholine (4.35 g, 50 mmol) and $K_2CO_3$ (6.91 g, 50 mmol) were added into $CH_3CN$ (80 mL), then refluxed and reacted overnight. The reaction mixture was cooled, poured into ice-water and extracted with EA. The organic phase was dried with $Na_2SO_4$ and concentrated. The crude product was separated by column chromatography to give the desired product (2.92 g, yield 51%).

Example 17: Synthesis of Compound (3-(((2-(4-(2-hydroxyethyl)piperazin-1-yl)ethyl)amino)methylene)-6-phenyldihydro-2H-pyran-2,4(3H)-dione) (Compound 95)

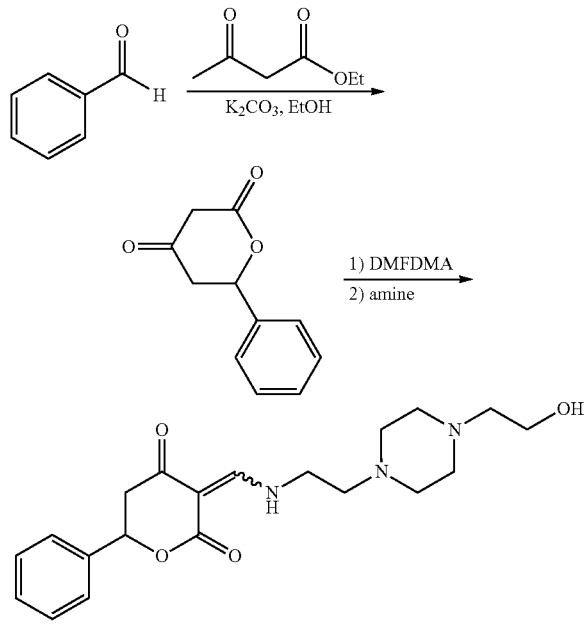

95

Step 1: Preparation of Compound 6-phenyldihydro-2H-pyran-2,4(3H)-dione

Ethyl acetoacetate (13.01 g, 0.1 mol), $K_2CO_3$ (27.64 g, 0.2 mol) and benzaldehyde (10.1 mL, 0.1 mol) were dissolved in EtOH (100 mL) and stirred at 45° C. for 22 hrs, then it was filtered and the residue was washed with EtOH. The collected filtrate was poured into water and washed with PE. The aqueous phase was collected, acidified to pH 2-3 by 6N HCl and extracted with EA. The organic phase was washed with water, dried with $Na_2SO_4$ and concentrated. The crude product was separated and purified by column chromatography to give the desired product (8.87 g, yield 46.7%).

Step 2: Synthesis of Compound 3-(((2-(4-(2-hydroxyethyl)piperazin-1-yl)ethyl)amino)methylene)-6-phenyldihydro-2H-pyran-2,4(3H)-dione The synthesis procedure was the same as example 2. Compound 95: $^1$HNMR (400 MHz, $CD_3OD$) δ 8.31 (s, 0.33H), 8.18 (s, 0.67H), 7.46-7.32 (m, 5H), 5.53 (dd, J=7.2 Hz, 2.4 Hz, 1H), 3.68 (t, J=6.0 Hz, 2H), 3.61-3.58 (m, 2H), 2.98-2.86 (m, 1H), 2.72-2.54 (m, 14H); MS: 374.4 [M+1].

Example 17A: Synthesis of Compound 3-(((2-(4-(2-hydroxyethyl)piperazin-1-yl)ethyl)amino)methylene)-6-phenylpiperidine-2,4-dione (Compound 96)

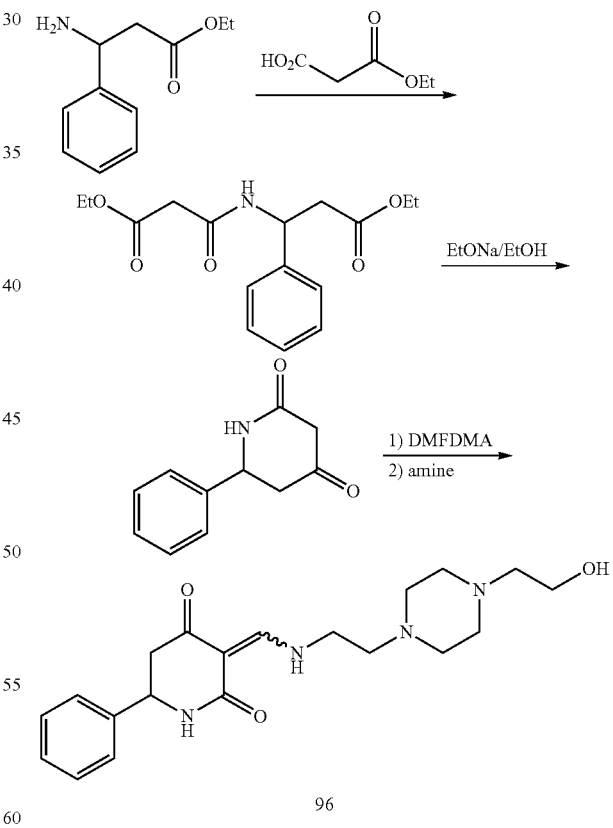

96

Step 1: Synthesis of Compound Ethyl 3-((3-ethoxy-3-oxo-1-phenylpropyl)amino)-3-oxopropanoate Ethyl 3-amino-3-phenylpropanoate (4.31 g, 22.23 mmol), 3-ethoxy-3-oxopropanoic acid (4.47 g, 33.84 mmol), DIPEA (7.7 g, 55.8 mmol) and (benzotriazol-1-yloxy)tripyrrolidinophosphonium hexafluorophosphate (PyBOP) (17.42 g, 33.84 mmol) were added into DMF (30 mL) and reacted at RT for 2 hours. After the reaction was completed, the reaction mixture was poured into water and extracted with EA. The organic phase was dried with Na$_2$SO$_4$ and concentrated. The crude product was separated by column chromatography to give the desired product (6.05 g, yield 88%).

Step 2: Synthesis of Compound 6-phenylpiperidine-2,4-dione

The solution of compound ethyl 3-((3-ethoxy-3-oxo-1-phenylpropyl)amino)-3-oxopropanoate (2.0 g, 6.51 mmol) in toluene (16 mL) was added dropwise at 0° C. into the solution of EtONa (0.66 g, 9.77 mmol) in anhydrous EtOH (16 mL), then refluxed and reacted for 1 hour. After the reaction was completed, the reaction mixture was poured into water, adjusted to pH 1-2 and extracted with EA. The organic phase was washed with water and brine, then dried and concentrated. The resulting residue was dissolved in the mixed solvent of CH$_3$CN/H$_2$O (v/v=100:1, 16 mL) and refluxed overnight. After the reaction was completed, the reaction mixture was cooled to RT, poured into ice-water and extracted with EA. The organic phase was washed with water, dried with Na$_2$SO$_4$ and concentrated. The resulting crude product was separated and purified by column chromatography to give the desired product (622 mg, yield 50%). Compound 96: $^1$HNMR (400 MHz, CD$_3$OD) δ 8.09 (s, 0.3H), 8.04 (s, 0.7H), 7.34-7.24 (m, 5H), 4.75-4.72 (m, 1H), 3.72 (t, J=5.6 Hz, 2H), 3.55-3.52 (m, 2H), 2.87-2.57 (m, 15H), MS: 373.3 [M+1].

Example 18: Synthesis of Compound 4-(((2-(4-(2-hydroxyethyl)piperazin-1-yl)ethyl)amino)methylene)-1-phenylpiperidine-3,5-dione (Compound 97)

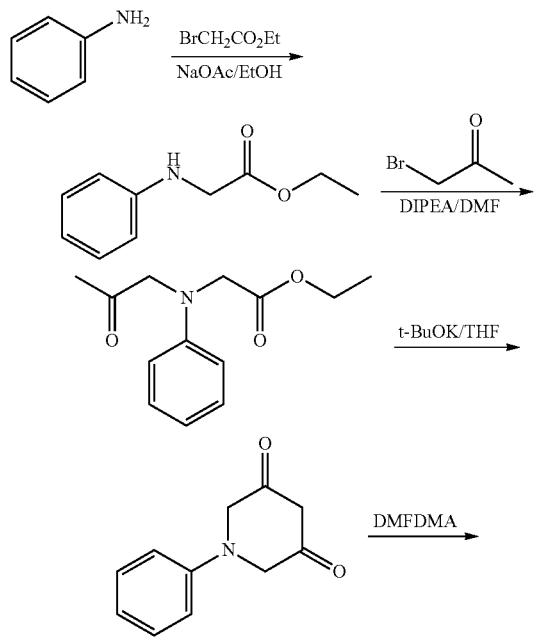

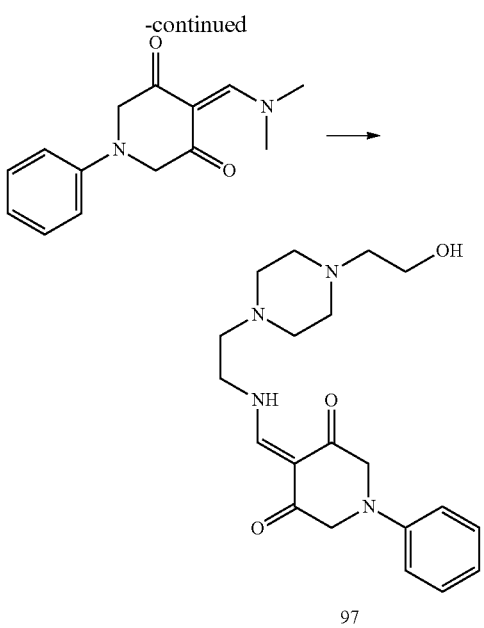

97

Step 1: Synthesis of Ethyl Phenylglycinate

Phenylamine (5.0 g, 53.69 mmol), ethyl bromoacetate (10.76 g, 64.43 mmol) and NaOAc (5.29 g, 64.43 mmol) were dissolved in anhydrous EtOH (120 mL), refluxed and reacted for 2 hours. After the reaction was completed, the reaction mixture was concentrated. The crude product was separated and purified by column chromatography to give the desired product (7.4 g, yield 77%).

Step 2: Synthesis of Compound Ethyl N-(2-oxopropyl)-N-phenylglycinate

Ethyl phenylglycinate (2.30 g, 12.83 mmol), 1-bromopropan-2-one (2.11 g, 25.67 mmol) and DIPEA (4.57 mL, 25.67 mmol) were added into DMF (50 mL) and reacted at 110° C. for 4 hours, then 1-bromopropan-2-one (1.06 g, 12.8 mmol) was additionally added and further reacted at 110° C. for 4 hours. The reaction mixture was cooled to RT, poured into water and extracted with EA. The combined organic phase was dried with Na$_2$SO$_4$ and concentrated. The crude product was separated by column chromatography to give the desired product (1.30 g, yield 43%).

Step 3: Synthesis of Compound 1-phenylpiperidine-3,5-dione

The solution of t-BuOK in THF (2 mol/L, 3.8 mL) was added dropwise at 0° C. into the solution of compound ethyl N-(2-oxopropyl)-N-phenylglycinate (1.2 g, 5.1 mmol) in anhydrous THF (50 mL). The above reaction solution was stirred at room temperature for 3 hours. After the reaction was completed, the reaction mixture was added dropwise with 20% HOAc to quench the reaction, then poured into ice-water and extracted with EA. The organic phase was dried with Na$_2$SO$_4$. The crude product was separated by column chromatography to give the desired product (600 mg, yield 62%).

Step 4 & step 5

The operation procedures were the same as example 2. Compound 97: $^1$HNMR (400 MHz, CD$_3$OD) δ 8.22 (s, 1H), 7.26 (t, J=8.0 Hz, 2H), 6.98 (d, J=8.0 Hz, 2H), 6.88 (t, J=7.3 Hz, 1H), 4.03 (d, J=10.9 Hz, 4H), 3.75 (t, J=5.8 Hz, 2H), 3.61 (t, J=5.7 Hz, 2H), 2.66 (dd, J=23.9, 18.2 Hz, 12H); MS: 373.3 [M+1].

Example 19: Synthesis of Compound 3-(((2-(4-(2-hydroxyethyl)piperazin-1-yl)ethyl)amino)methylene)-1-phenylpiperidine-2,4-dione (Compound 99)

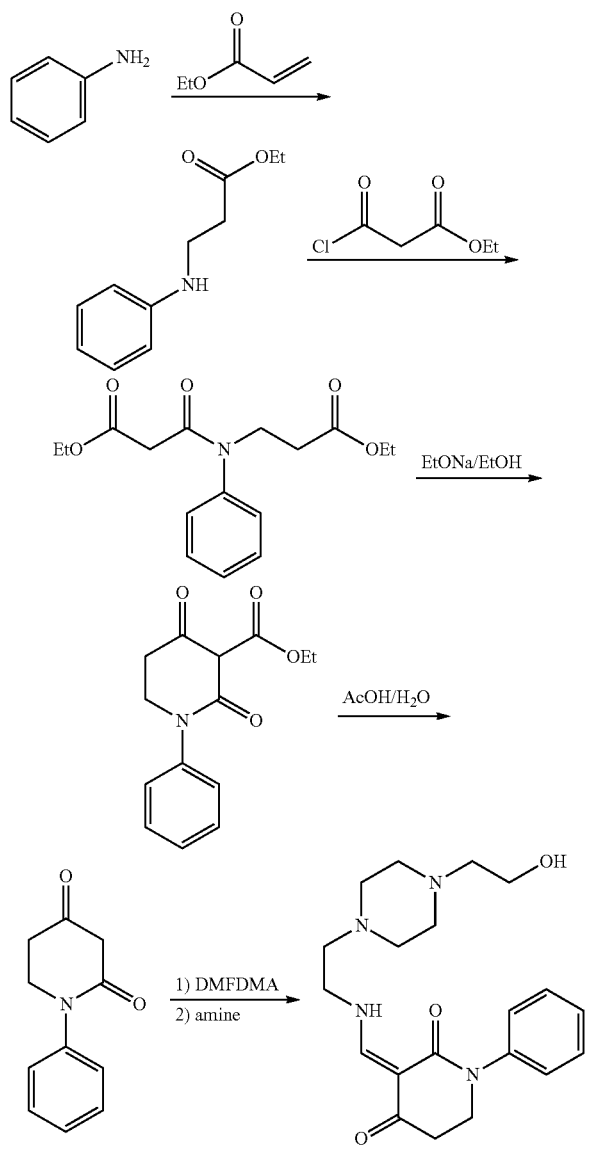

Step 1: Synthesis of Compound Ethyl 3-(phenylamino)propanoate

Phenylamine (2.8 g, 30 mmol) and ethyl acrylate (3.6 g, 36 mmol) were dissolved in HOAc (2 mL), reacted at 95° C. overnight. After the reaction was completed, the reaction mixture was cooled to RT, poured into ice-water, adjusted pH to 9-10 with saturated $Na_2CO_3$ solution and extracted with EA. The organic phase was washed with water, dried and concentrated. The crude product was separated by column chromatography to give the desired product (5.3 g, yield 91%).

Step 2: Synthesis of Compound Ethyl 3-((3-ethoxy-3-oxopropyl)(phenyl)amino)-3-oxopropanoate Ethyl 3-(phenylamino)propanoate (5.3 g, 27.4 mmol), ethyl 3-chloro-3-oxopropanoate (5.35 g, 35.6 mmol) and DIPEA (7.09 g, 54.8 mmol) were dissolved in DCM (35 mL), reacted at RT for 1 hour. After the reaction was completed, the reaction mixture was poured into ice-water and extracted with EA. The organic phase was washed with water, dried and concentrated. The crude product was separated by column chromatography to give the desired product (2.1 g, yield 25%).

Step 3: Synthesis of Compound Ethyl 2,4-dioxo-1-phenylpiperidine-3-carboxylate

The compound ethyl 3-((3-ethoxy-3-oxopropyl)(phenyl)amino)-3-oxopropanoate (2.00 g, 6.5 mmol) and EtONa (0.88 g, 13 mmol) were dissolved in anhydrous EtOH (15 mL), reacted at RT for 2 hours. After the reaction was completed, the reaction mixture was poured into ice-water and the aqueous phase was adjusted to pH 3-4 by 2N HCl and extracted with EA. The organic phase was washed with water, dried with $Na_2SO_4$ and concentrated. The crude product was separated and purified by column chromatography to give the desired product (780 mg, yield 46%).

Step 4: Synthesis of Compound 1-phenylpiperidine-2,4-dione

The aqueous solution (7 mL) of ethyl 2,4-dioxo-1-phenylpiperidine-3-carboxylate (780 mg, 3.0 mmol) and HOAc (0.7 mL) was reacted at 90° C. for 18 hours. After the reaction was completed, the reaction mixture was poured into ice-water and extracted with EA. The organic phase was washed with water, dried and concentrated. The crude product was separated by column chromatography to give the desired product (510 mg, yield 90%).

Step 5: Synthesis of Compound 3-(((2-(4-(2-hydroxyethyl)piperazin-1-yl)ethyl)amino)methylene)-1-phenylpiperidine-2,4-dione The operation procedures in this step were the same as Example 2. Compound 99: $^1$H NMR (400 MHz, $CD_3OD$) δ 8.13 (d, J=7.1 Hz, 1H), 7.48-7.33 (m, 2H), 7.34-7.15 (m, 3H), 3.90-3.72 (m, 2H), 3.71-3.61 (m, 2H), 3.60-3.46 (m, 2H), 2.83-2.38 (m, 14H); MS: 373.3 [M+1].

Example 20: Synthesis of Compound 4-(4-fluorophenyl)-2-(((2-(4-(2-hydroxyethyl)piperazin-1-yl)ethyl)amino)methylene)cyclohexane-1,3-dione (Compound 100)

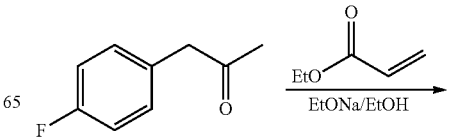

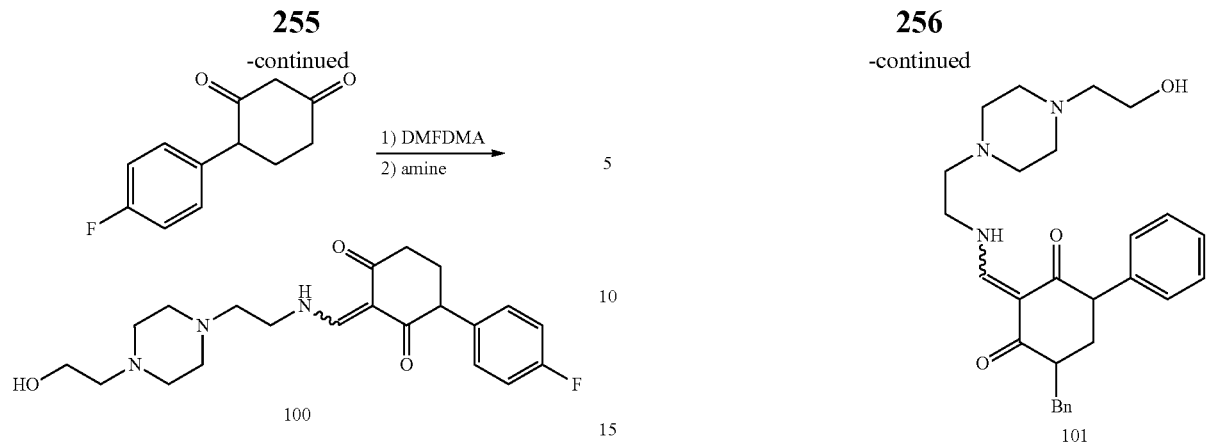

Step 1: Synthesis of Compound 4-(4-fluorophenyl)cyclohexane-1,3-dione

The compound 1-(4-fluorophenyl)propan-2-one (2.0 g, 13.14 mmol), ethyl acrylate (1.45 g, 14.46 mmol) and EtONa (893.5 mg, 13.14 mmol) were dissolved in anhydrous EtOH (20 mL), refluxed and reacted overnight. After the reaction was completed, the reaction mixture was cooled to RT and poured into ice-water, then adjusted to pH 3-4 with 2N HCl and extracted with EA. The organic phase was washed with water, dried with $Na_2SO_4$ and concentrated. The crude product was separated and purified by column chromatography to give the desired product (620 mg, yield 23%).

Step 2: Synthesis of Compound 4-(4-fluorophenyl)-2-(((2-(4-(2-hydroxyethyl)piperazin-1-yl)ethyl)amino)methylene)cyclohexane-1,3-dione The operation procedures were the same as Example 2. Compound 100: $^1$H NMR (400 MHz, $CD_3OD$) δ 8.30 (d, J=8.8 Hz, 1H), 7.28-7.16 (m, 2H), 7.06 (t, J=8.0 Hz, 2H), 3.81-3.66 (m, 3H), 3.62 (t, J=5.8 Hz, 2H), 2.86-2.43 (m, 14H), 2.27-2.15 (m, 2H). MS: 390.4 [M+1].

Example 21: Synthesis of Compound 4-benzyl-2-(((2-(4-(2-hydroxyethyl)piperazin-1-yl)ethyl)amino)methylene)-6-phenylcyclohexane-1,3-dione (Compound 101)

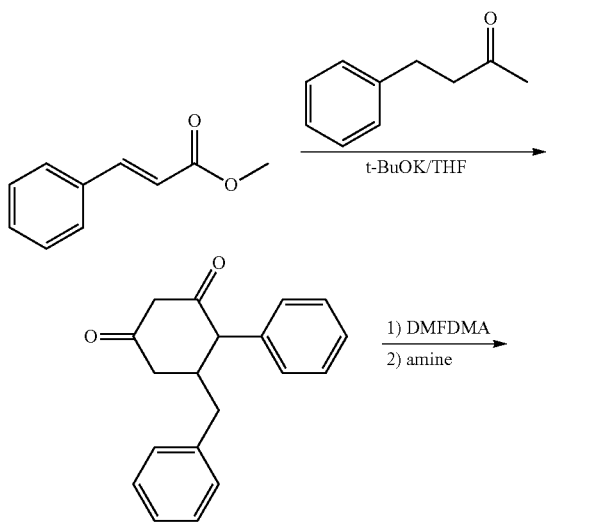

Step 1: Synthesis of Compound 5-benzyl-4-phenylcyclohexane-1,3-dione

Under the protection of nitrogen atmosphere, t-BuOK (1.61 g, 14.3 mmol) was added at 0° C. into a solution of 4-phenylbutan-2-one (2.5 mL, 15.5 mmol) in anhydrous THF (20 mL). After stirring for 10 min, methyl cinnamate (2.0 g, 12.3 mmol) was added, then keep stirring for 30 min. After the reaction was completed, the reaction mixture was poured into water, adjusted to pH 6-7 with 2N HCl and extracted with EA. The organic phase was dried and concentrated to give 3.61 g of the desired product, which can be directly used in the following reactions.

Step 2: Synthesis of Compound 4-benzyl-2-(((2-(4-(2-hydroxyethyl)piperazin-1-yl)ethyl)amino)methylene)-6-phenylcyclohexane-1,3-dione The operation procedures were the same as Example 2. Compound 101: $^1$H NMR (400 MHz, $CD_3OD$) δ 8.24 (d, J=5.6 Hz, 1H), 7.39-6.98 (m, 9H), 6.91 (d, J=7.4 Hz, 1H), 3.72 (t, J=5.8 Hz, 2H), 3.60 (t, J=5.7 Hz, 2H), 3.46-3.40 (m, 1H), 3.24-3.01 (m, 3H), 2.95-2.56 (m, 13H), 2.49 (dd, J=13.8, 7.6 Hz, 1H); MS: 462.3 [M+1].

Example 22: Synthesis of Compound 4-(((2-(4-(2-hydroxyethyl)piperazin-1-yl)ethyl)amino)methylene)-1-(4-methoxybenzyl)piperidine-3,5-dione (Compound 102)

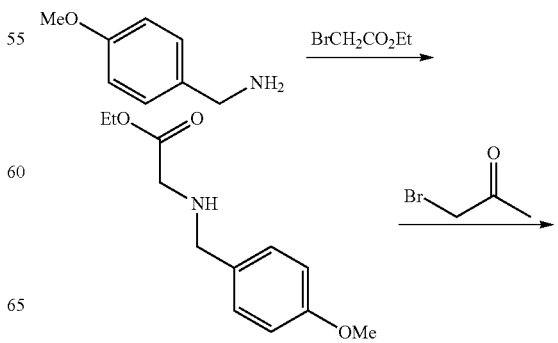

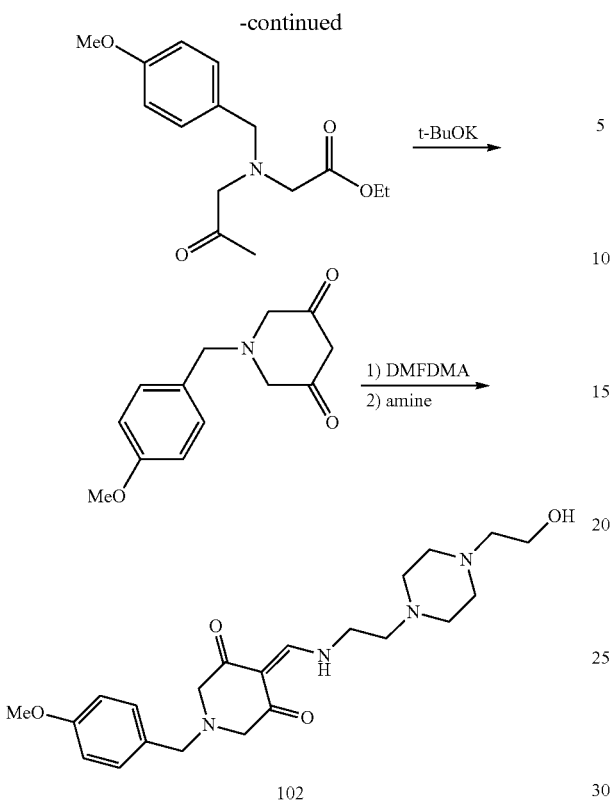

102

Step 1: Synthesis of Compound Ethyl (4-methoxybenzyl)glycinate

The solution of ethyl 2-bromoacetate (5.00 g, 29.94 mmol) in anhydrous THE (20 mL) was added dropwise at RT into the solution of (4-methoxyphenyl)methanamine (9.04 g, 66 mmol) in anhydrous THE (120 mL), reacted at RT overnight. After the reaction was completed, the reaction mixture was poured into water, adjusted to pH 9-10 with saturated NaHCO$_3$ and extracted with EA. The organic phase was washed with water, dried with Na$_2$SO$_4$ and concentrated. The crude product was separated and purified by column chromatography to give the desired product (3.12 g, yield 47%).

Step 2: Synthesis of Compound Ethyl N-(4-methoxybenzyl)-N-(2-oxopropyl)glycinate Ethyl (4-methoxybenzyl)glycinate (3 g, 13.44 mmol), 1-bromopropan-2-one (7.36 g, 53.75 mmol) and NaHCO$_3$ (2.26 g, 26.87 mmol) were added into anhydrous EtOH (50 mL), heated to reflux for 4 hours. The reaction mixture was cooled to RT and concentrated. The crude product was separated by column chromatography to give the desired product (700 mg, yield 19%).

Step 3: Synthesis of Compound 1-(4-methoxybenzyl)piperidine-3,5-dione

The solution of t-BuOK in THE (1 mol/L, 4 mL) was added dropwise at 0° C. into the solution of ethyl N-(4-methoxybenzyl)-N-(2-oxopropyl)glycinate (700 mg, 2.51 mmol) in anhydrous THE (30 ml), reacted at RT for 3 hours. After the reaction was completed, the reaction solution was poured into 10% aqueous HOAc solution and extracted with EA. The organic phase was dried with Na$_2$SO$_4$ and concentrated. The crude product was separated by column chromatography to give the desired product (220 mg, yield 38%).

Step 4: Synthesis of Compound 4-(((2-(4-(2-hydroxyethyl)piperazin-1-yl)ethyl)amino)methylene)-1-(4-methoxybenzyl)piperidine-3,5-dione The operation procedures were the same as Example 2. Compound 102: $^1$H NMR (400 MHz, CD$_3$OD) δ 8.19 (s, 1H), 7.24 (d, J=8.2 Hz, 2H), 6.89 (d, J=8.3 Hz, 2H), 3.86-3.73 (m, 5H), 3.60 (s, 4H), 3.31 (s, 2H), 3.14 (d, J=33.6 Hz, 8H), 2.72 (m, 6H); MS: 417.4 [M+1].

Example 23: Synthesis of Compound 1-benzyl-4-(((2-(4-(2-hydroxyethyl)piperazin-1-yl)ethyl)amino)methylene)-piperidine-3,5-dione (Compound 103)

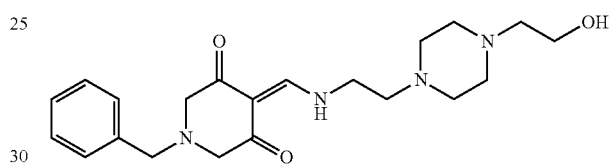

Compound 103 was prepared by the same procedures as Example 22 (Compound 102) except for using BnNH$_2$. Compound 103: $^1$H NMR (400 MHz, CD$_3$OD) δ 8.22 (s, 1H), 7.40-7.26 (m, 5H), 3.72 (t, J=5.9 Hz, 2H), 3.69 (s, 2H), 3.62 (t, J=5.8 Hz, 2H), 3.34 (s, 2H), 3.23 (d, J=6.6 Hz, 1H), 2.80-2.54 (m, 10H); MS: 387.4 [M+1].

Example 24: Synthesis of Compound 1-benzoyl-4-(((2-(4-(2-hydroxyethyl)piperazin-1-yl)ethyl)amino)methylene)-piperidine-3,5-dione (Compound 104)

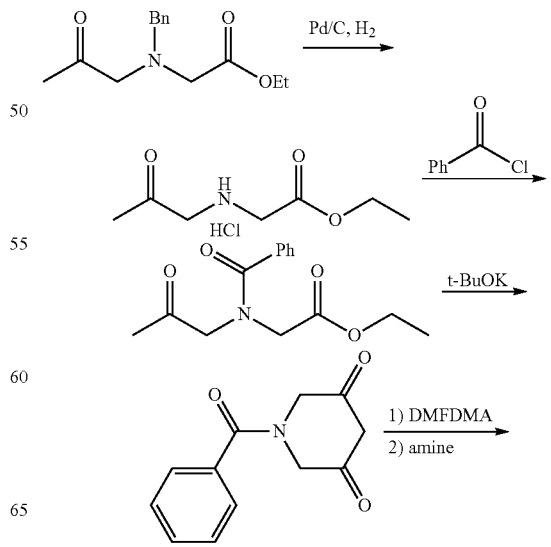

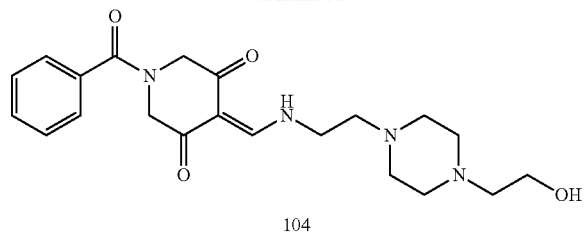

104

Step 1: Synthesis of Compound Ethyl (2-oxopropyl)glycinate hydrochloride salt Ethyl N-benzyl-N-(2-oxopropyl)glycinate (4.00 g, 16.04 mmol), 10% Pd/C (500 mg) and HCl (5 mL) were dissolved in EtOH (100 mL) to replace hydrogen gas, then reacted at RT for 4 hours. After the reaction was completed, Pd/C was removed by filtration and the filtrated residue was washed with EtOH. The filtrate was collected and concentrated to give 3.4 g of the desired product, which can be directly used in next step.

Step 2: Synthesis of Compound Ethyl N-benzoyl-N-(2-oxopropyl)glycinate

TEA (4 mL, 29 mmol) was added at RT into the solution of ethyl (2-oxopropyl)glycinate hydrochloride salt (2.78 g, crude) in DCM (100 mL), followed by adding PhCOCl (1.65 mL, 14.23 mmol) to the above mixed solution, then reacted at RT for 4 hours. After the reaction was completed, the reaction mixture was poured into water and extracted with DCM. The organic phase was washed with water, dried with $Na_2SO_4$ and concentrated. The crude product was separated and purified by column chromatography to give the desired product (1.92 g, yield 56%).

Step 3: Synthesis of Compound 1-benzoyl-3,5-dione

The solution of t-BuOK in THF (1 mol/L, 11 mL) was added dropwise at 0° C. into the solution of ethyl N-benzoyl-N-(2-oxopropyl)glycinate (1.90 g, 7.22 mmol) in anhydrous THF (60 mL), reacting at RT for 3 hours. After the reaction was completed, the reaction solution was poured into 10% aqueous HOAc solution and extracted with EA. The organic phase was dried with $Na_2SO_4$ and concentrated. The crude product was separated by column chromatography to give the desired product (1.03 g, yield 66%).

Step 4: Synthesis of Compound 1-benzoyl-4-(((2-(4-(2-hydroxyethyl)piperazin-1yl)ethyl)amino)methylene)piperidine-3,5-dione The operation procedures in the final step were the same as Example 8. Compound 104: $^1$H NMR (400 MHz, $CD_3OD$) δ 8.25 (s, 1H), 7.57-7.45 (m, 3H), 7.42 (dd, J=8.0, 1.5 Hz, 2H), 4.47 (s, 2H), 4.18 (s, 2H), 3.73 (t, J=5.8 Hz, 2H), 3.62 (t, J=5.8 Hz, 2H), 2.83-2.58 (m, 12H); MS: 401.4 [M+1].

Example 26: Synthesis of Compound 2-(((2-(4-(2-hydroxyethyl)piperazin-1-yl)ethyl)amino)methylene)-5-(morpholine-4-carbonyl)cyclohexane-1,3-dione (Compound 106)

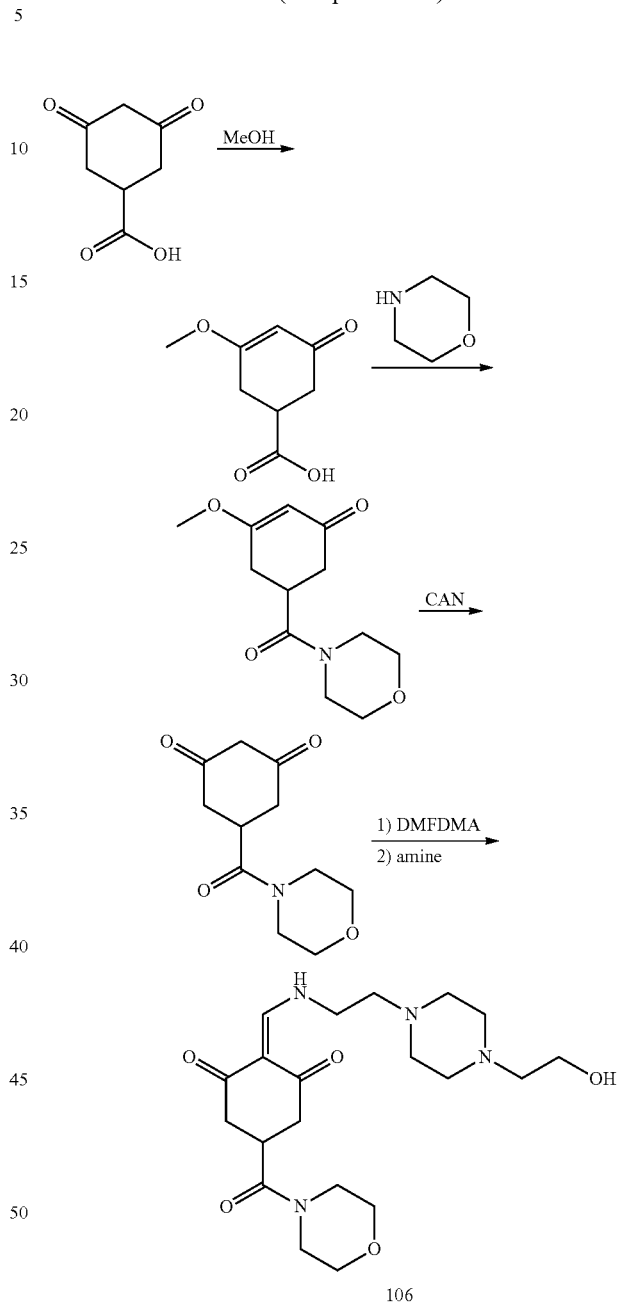

106

Step 1: Synthesis of Compound 3-methoxy-5-oxocyclohex-3-ene-1-carboxylic acid The compounds 3,5-dioxocyclohexane-1-carboxylic acid (780 mg, 5 mmol) and $TsOH \cdot H_2O$ (95 mg, 0.5 mmol) were dissolved in MeOH (6 mL), then refluxed and reacted for 2 hours. After the reaction was completed, the reaction mixture was cooled to RT and added with EA, then precipitated and filtrated to give 420 mg of crude product, which was directly used in next step without further purification.

Step 2: Synthesis of Compound 3-methoxy-5-(morpholine-4-carbonyl)cyclohex-2-en-1-one 3-methoxy-5-oxocyclohex-3-ene-1-carboxylic acid (340 mg, crude), morpholine (310 mg, 2.4 mmol), DIPEA (390 mg, 3 mmol) and HATU (1.14 g, 3 mmol) were added into anhydrous DMF (12 mL), stirring at RT overnight. After the reaction was completed, the reaction mixture was poured into water and extracted with EA. The organic phase was dried with $Na_2SO_4$ and concentrated. The crude product was separated by column chromatography to give the desired product (140 mg, yield 15%).

Step 3: Synthesis of Compound 5-(morpholine-4-carbonyl)cyclohexane-1,3-dione 3-methoxy-5-(morpholine-4-carbonyl)cyclohex-2-en-1-one (132 mg, 0.55 mmol) and ceric ammonium nitrate (110 mg, 0.2 mmol) were added into acetonitrile (4 mL) and water (4 mL), then heated to reflux for 3 hours. After the reaction was completed, the reaction solution was cooled to RT, poured into water and extracted with EA. The combined organic phase was dried with $Na_2SO_4$ and concentrated. The crude product was separated by column chromatography to give the desired product (112 mg, yield 90%).

Step 4: Synthesis of Compound 2-(((2-(4-(2-hydroxyethyl)piperazin-1-yl)ethyl)amino)methylene)-5-(morpholine-4-carbonyl)cyclohexane-1,3-dione The operation procedures were the same as Example 2. Compound 106: $^1$H NMR (400 MHz, CD3OD) δ 8.19 (s, 1H), 3.75 (t, J=5.7 Hz, 2H), 3.65 (dd, J=13.9, 4.5 Hz, 4H), 3.61-3.47 (m, 7H), 2.88 (s, 3H), 2.81 (t, J=5.8 Hz, 2H), 2.75-2.42 (m, 10H).

Example 27: Synthesis of Compound 3-(((2-(4-(2-hydroxyethyl)piperazin-1-yl)ethyl)amino)methylene)quinoline-2,4(1H,3H)-dione (Compound 107)

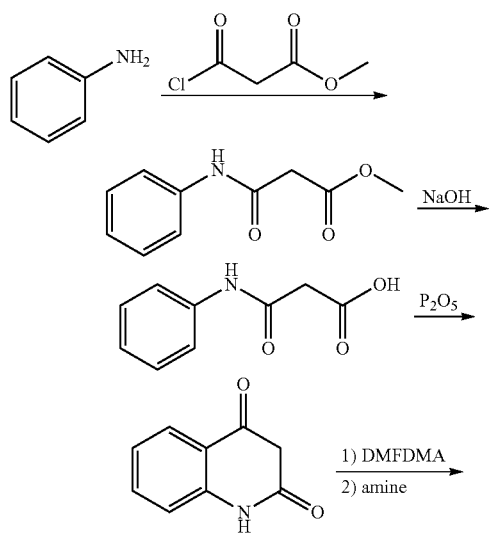

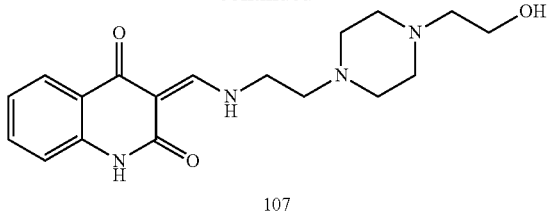

107

Step 1: Synthesis of Compound Methyl 3-oxo-3-(phenylamino)propanoate

Methyl 3-chloro-3-oxopropanoate (1.84 g, 13.5 mmol) was added dropwise at 0° C. into the solution of phenylamine (1.00 g, 10.74 mmol) and TEA (1.42 g, 14 mmol) in EtOAc, stirred at RT for 30 min, After the reaction was completed, the reaction mixture was poured into water and extracted with EA. The organic phase was washed with water, dried with $Na_2SO_4$ and concentrated. The crude product was separated by column chromatograph to give the desired product (1.75 g, yield 85%).

Step 2: Synthesis of Compound 3-oxo-3-(phenylamino)propanoic acid

The mixed solution of methyl 3-oxo-3-(phenylamino)propanoate (1.00 g, 5.18 mmol) and NaOH (415 mg, 10.37 mmol) in MeOH/$H_2O$ (v/v=3/1, 20 mL) was stirred at RT for 1 hour. After the reaction was completed, the reaction mixture was poured into water and extracted with EA. The aqueous phase was adjusted to pH 5-6 and extracted with DCM. The combined organic phase was washed with water, dried with $Na_2SO_4$ and concentrated to give 820 mg of the crude product, which was directly used in next step.

Step 3: Synthesis of Compound Quinoline-2,4(1H,3H)-dione 3-oxo-3-(phenylamino)propanoic acid (537 mg, crude) was added into $MeSO_3H$ (6 mL) and heated to 50° C., then $P_2O_5$ (852 mg) was added portionwise. The reaction solution was then heated to 75° C. and stirred for 2 hours. After cooling to RT, the reaction mixture was carefully poured into ice-water, the aqueous phase was adjusted to pH 7-8 with aq $Na_2CO_3$. The precipitated solid was collected by filtration and concentrated to give the crude product (220 mg, yield 40%), which can be directly used in next step without further purification.

Step 4: Synthesis of Compound 3-(((2-(4-(2-hydroxyethyl)piperazin-1-yl)ethyl)amino)methylene)quinoline-2,4(1H,3H)-dione The operation procedures were the same as Example 2. Compound 107: $^1$H NMR (400 MHz, CD$_3$OD) δ 8.57 (d, J=36.5 Hz, 1H), 8.04 (d, J=7.5 Hz, 1H), 7.53 (t, J=6.9 Hz, 1H), 7.16 (t, J=8.7 Hz, 2H), 3.73 (m, 4H), 2.69 (m, 11H).

Example 28: Synthesis of Compound 2-(1-((2-(4-(2-hydroxyethyl)piperazin-1-yl)ethyl)amino)ethylidene)-5-phenylcyclohexane-1,3-dione (Compound 108)

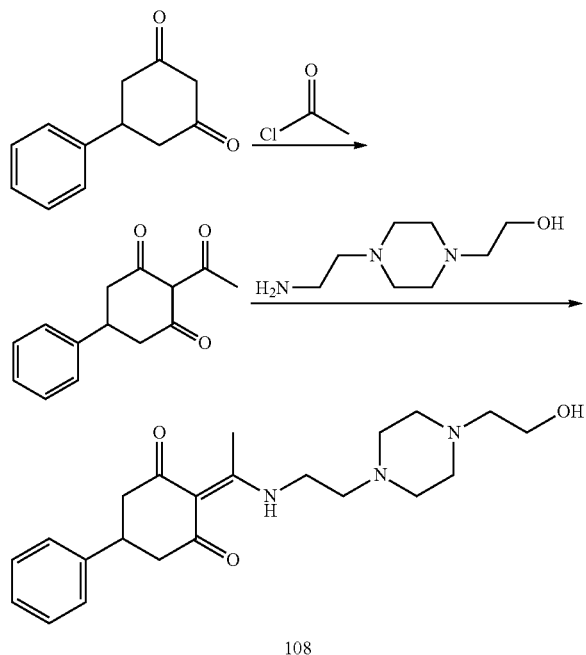

108

Step 1: Synthesis of Compound 2-acetyl-5-phenylcyclohexane-1,3-dione

Acetyl chloride (4.2 g, 53.5 mmol) was added dropwise at RT into the mixture of 5-phenylcyclohexane-1,3-dione (10.0 g, 53.1 mmol), DMAP (2.00 g, 16.4 mmol) and DIPEA (7.75 g, 60 mmol), then refluxed to react for 2 hours. After the reaction was completed, the reaction mixture was cooled to RT, poured into ice-water and extracted with DCM. The organic phase was washed with water, dried with $Na_2SO_4$ and concentrated. The crude product was separated and purified by column chromatography to give the desired product (8.51 g, yield 70%).

Step 2: Synthesis of Compound 2-(1-((2-(4-(2-hydroxyethyl)piperazin-1-yl)ethyl)amino)ethylidene)-5-phenylcyclohexane-1,3-dione 2-acetyl-5-phenylcyclohexane-1,3-dione (90 mg, 0.39 mmol) and 2-(4-(2-aminoethyl)piperazin-1-yl)ethan-1-ol (81 mg, 0.47 mmol) were dissolved in EtOH (5 mL), then heated to reflux for 1 hour, cooled and concentrated. The crude product was separated by preparation plate to give the desired product (80 mg, yield 44%). Compound 108: $^1$H NMR (400 MHz, DMSO-d6) δ 13.18 (s, 1H), 7.37-7.26 (m, 4H), 7.26-7.19 (m, 1H), 5.00 (s, 1H), 3.68 (s, 2H), 3.57 (d, J=5.4 Hz, 2H), 3.31-3.18 (m, 2H), 2.91 (s, 4H), 2.77-2.58 (m, 7H), 2.56 (d, J=4.1 Hz, 2H), 2.53 (s, 3H).

Compounds 109-112 were synthesized by the same procedures as Compound 107, as shown in Table 6.

TABLE 6

Compounds 109-112

| # | Structure | Name | Proton NMR ($^1$HNMR), Mass Spectrum (MS) |
|---|---|---|---|
| 109 | 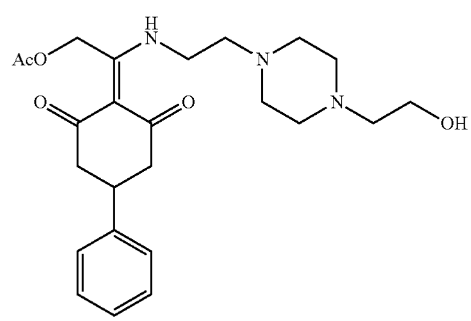 [SMILES: CC(=O)OCC(NCCN1CCN(CCO)CC1)=C1C(=O)CC(c2ccccc2)CC1=O] | 2-(2,6-dioxo-4-phenylcyclohexylidene)-2((2-(4-(2-hydroxyethyl)piperazin-1-yl)ethyl)amino)ethyl acetate | $^1$HNMR (400 MHz, DMSO-d6) δ 13.13 (s, 1H), 7.29 (s, 4H), 7.20 (s, 1H), 5.33 (s, 2H), 4.82 (s, 1H), 3.60 (d, J = 5.0 Hz, 4H), 3.24 (d, J = 11.9 Hz, 2H), 2.98-2.66 (m, 8H), 2.66-2.52 (m, 7H), 2.04 (s, 3H). |
| 110 | 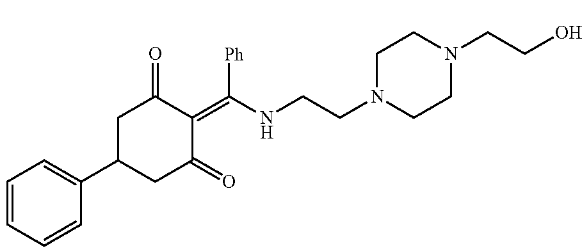 [SMILES: O=C1CC(c2ccccc2)CC(=O)C1=C(NCCN1CCN(CCO)CC1)c1ccccc1] | 2-(((2-(4-(2-hydroxyethyl)piperazin-1-yl)ethyl)amino)(phenyl)methylene)-5-phenylcyclohexane-1,3-dione | $^1$HNMR (400 MHz, DMSO-d6) δ 13.07 (s, 1H), 7.42 (m, 3H), 7.31 (m, 4H), 7.26-7.14 (m, 3H), 4.91 (s, 1H), 3.62 (s, 2H), 3.32 (m, 5H), 3.12-2.57 (m, 10H), 2.43 (m, 4H). |

TABLE 6-continued

Compounds 109-112

| # | Structure | Name | Proton NMR ($^1$HNMR), Mass Spectrum (MS) |
|---|---|---|---|
| 111 | 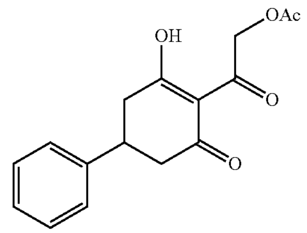 [SMILES: CC(=O)OCC(=O)C1=C(O)CC(c2ccccc2)CC1=O] | 2-(5-hydroxy-3-oxo-1,2,3,6-tetrahydro-[1,1'-biphenyl]-4-yl)-2-oxoethyl acetate | $^1$HNMR (DMSO-d6) δ 16.58 (s, 1H), 7.22-7.34 (m, 5H), 5.20 (s, 2H), 3.32-3.46 (m, 1H), 2.68-3.10 (m, 4H), 2.11 (s, 3H); LCMS: 289.1 [M + 1]. |
| 112 | 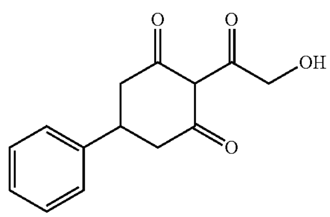 [SMILES: O=C(CO)C1C(=O)CC(c2ccccc2)CC1=O] | 2-(hydroacetyl)-5-pheyl-cyclohexane-1,3-dione | $^1$HNMR (CD$_3$OD) δ 7.24-7.36 (m, 6H), 4.73 (s, 2H), 3.35-3.44 (m, 1H), 2.66-2.95 (m, 4H); LCMS: 247.2 [M + 1]. |

Example 30: Synthesis of Compound 2-(((2-(4-(2-hydroxyethyl)piperazin-1-yl)ethyl)amino)methylene)-4a,9,10,10a-tetrahydrophenanthrene-1,3(2H,4H)-dione (Compound 113)

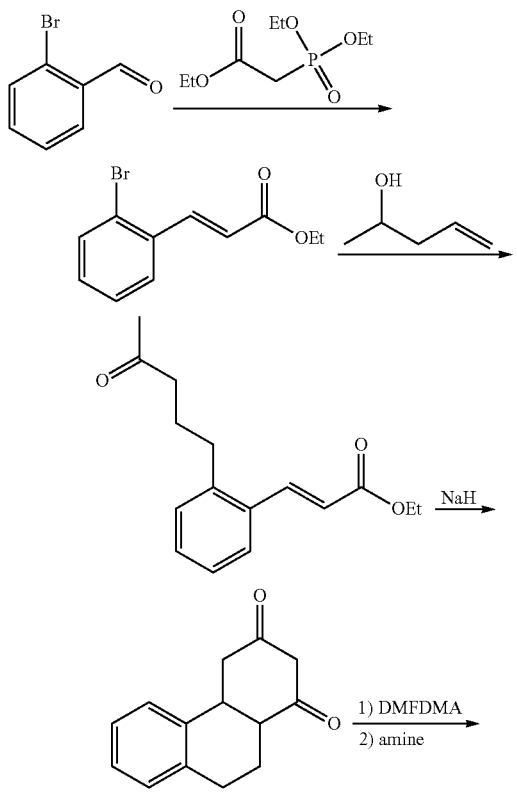

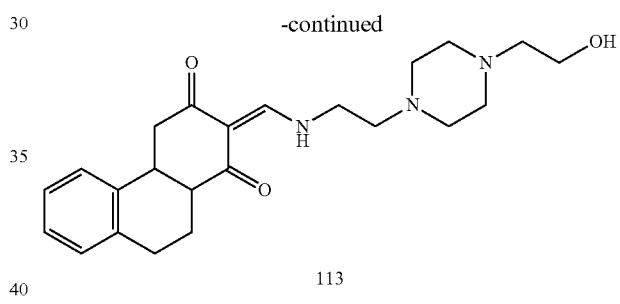

113

Step 1: Synthesis of Compound Ethyl 3-(2-bromophenyl)acrylate 2-bromobenzaldehyde (2.0 g, 10.8 mmol), ethyl 2-(diethoxyphosphoryl)acetate (2.66 g, 11.9 mmol) and LiOH (285 mg, 11.9 mmol) were dissolved in anhydrous THF solution (14 mL), reacted at RT for 3.5 hours. After the reaction was completed, the reaction mixture was poured into ice-water and extracted with DCM. The organic phase was washed with water, dried with Na$_2$SO$_4$ and concentrated. The crude product was separated and purified by column chromatography to give the desired product (2.59 g, yield 940%).

Step 2: Synthesis of Compound Ethyl 3-(2-(4-oxopentyl)phenyl)acrylate

Under the protection of nitrogen atmosphere, the compound ethyl 3-(2-bromophenyl)acrylate (1.00 g, 3.92 mmol), pent-4-en-2-ol (843 mg, 9.8 mmol), Pd(OAc)2 (44 mg, 0.2 mmol), DIPEA (4.00 g, 31 mmol) and LiCl (167 mg, 3.94 mmol) were dissolved in anhydrous DMF solution (100 mL), reacted at 80° C. for 48 hours. After the reaction was completed, the reaction mixture was cooled to RT, poured into ice-water and extracted with t-BuOMe. The organic phase was washed with water, dried with Na$_2$SO$_4$ and concentrated. The crude product was separated and purified by column chromatography to give the desired product (612 mg, yield 60%).

Step 3: Synthesis of Compound 4a,9,10,10a-tetrahydrophenanthrene-1,3(2H,4H)-dione Ethyl 3-(2-(4-oxopentyl)phenyl)acrylate (195 mg, 0.75 mmol) and NaH (60%, 100 mg, 2.5 mmol) were dissolved in anhydrous THE solution (12 mL), reacted at RT overnight. After the reaction was completed, the reaction mixture was carefully poured into 1N HCl (20 mL) at 0° C. and extracted with EA. The organic phase was washed with water, dried with Na$_2$SO$_4$ and concentrated. The crude product was separated and purified by column chromatography to give the desired product (74 mg, yield 46%).

Step 4: Synthesis of Compound 2-(((2-(4-(2-hydroxyethyl)piperazin-1-yl)ethyl)amino)methylene)-4a,9,10,10a-tetrahydrophenanthrene-1,3(2H,4H)-dione The operation procedures were the same as Example 2. Compound 113: $^1$H NMR (400 MHz, CD$_3$OD) δ 8.26 (s, 1H), 7.30 (d, J=7.6 Hz, 1H), 7.13 (m, 3H), 3.88-3.77 (m, 2H), 3.63 (t, J=5.7 Hz, 2H), 3.28-2.72 (m, 12H), 2.72-2.64 (m, 2H), 2.61-2.35 (m, 3H), 1.62-1.47 (m, 1H).

Example 30B: Synthesis of Compound 5-((2R, 3S, 4R, 5R)-3,4-dihydroxy-5-(6-morpholino-9H-purin-9-yl) tetrahydrofuran-2-yl)-2-(((2-(4-(2-hydroxyethyl)piperazin-1-yl)ethyl)amino)methylene)cyclohexane-1,3-dione (Compound 114)

5-((3AR, 4R, 6R, 6AR)-2,2-dimethyl-6-(6-morpholino-9H-purin-9-yl)tetrahydrofuro[3,4-D][1,3]dioxol-4-yl)-2-(((2-(4-(2-hydroxyethyl)piperazin-1-yl)ethyl)amino)methylene)cyclohexane-1,3-dione (120 mg, 0.187 mmol) was dissolved in HCO$_2$H (1 mL) and water (1 mL), reacted at 50° C. for 4 hours. After the reaction was completed, the reaction mixture was cooled to RT and poured into ice-water, then adjusted to pH 9-10 and extracted with DCM. The organic phase was dried with Na$_2$SO$_4$ and concentrated. The crude product was separated by preparation plate to give the desired product (73 mg, yield 65%). Compound 114: $^1$H NMR (400 MHz, CD$_3$OD) δ 8.24 (s, 1H), 8.19 (s, 1H), 8.15 (s, 1H), 5.94 (d, J=4.9 Hz, 1H), 4.72 (t, J=5.3 Hz, 1H), 4.38 (s, 1H), 4.26 (s, 4H), 3.88 (t, J=5.7 Hz, 1H), 3.82-3.75 (m, 4H), 3.70 (t, J=5.9 Hz, 2H), 3.57 (t, J=5.8 Hz, 2H), 2.71-2.36 (m, 17H).

Example 31: Synthesis of Compound 4-benzyl-2-(((2-(4-(2-hydroxyethyl)piperazin-1-yl)ethyl)amino)methylene)cyclopentane-1,3-dione (Compound 115)

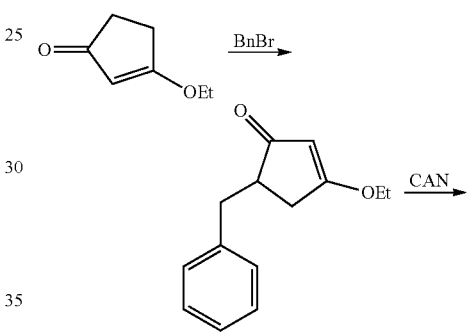

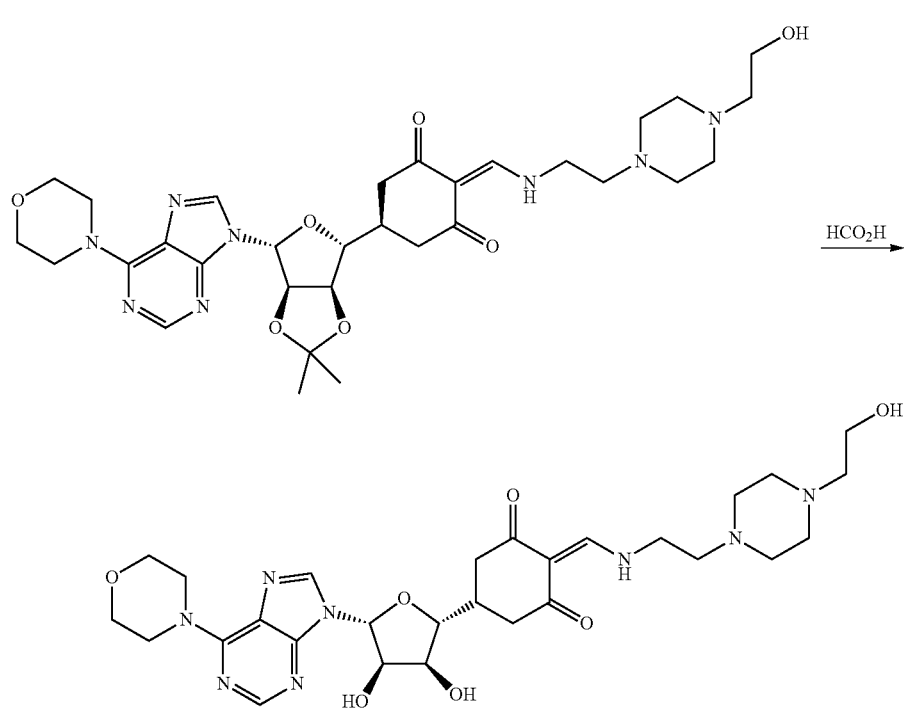

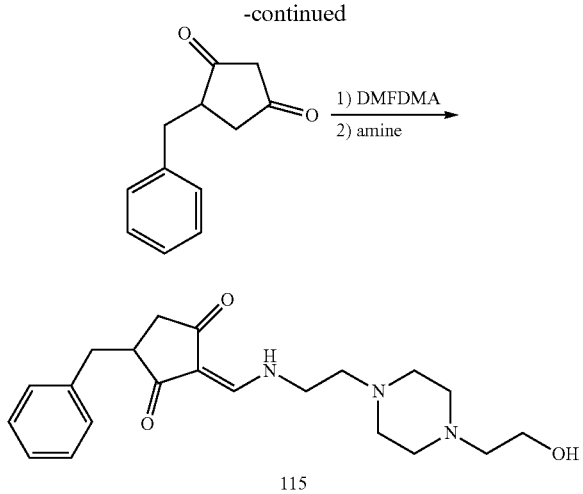

Step 1: Synthesis of Compound 5-benzyl-3-ethoxycyclopent-2-en-1-one

Under the protection of nitrogen atmosphere, LDA (1 mol/L THF solution, 5 mL, 5 mmol) was added dropwise at −60° C. into a solution of 3-ethoxycyclopent-2-en-1-one (500 mg, 4 mmol) in anhydrous THF (15 mL), the mixture was stirred at this temperature for 30 min and then added with BnBr (855 mg, 5 mmol) to further react for 3 hrs. After the reaction was completed, the reaction mixture was poured into saturated NH$_4$Cl aqueous solution and extracted with DCM. The organic phase was washed with water, dried with Na$_2$SO$_4$ and concentrated. The crude product was separated and purified by column chromatography to give the desired product (540 mg, yield 63%).

Step 2: Synthesis of Compound 4-benzylcyclopentane-1,3-dione 5-benzyl-3-ethoxycyclopent-2-en-1-one (300 mg, 1.38 mmol) and CAN (152 mg, 0.27 mmol) were added into CH$_3$CN (5 mL) and water (5 mL), then heated to reflux for 4 hours. After the reaction was completed, the reaction mixture was cooled to RT, poured into water and extracted with DCM. The organic phase was dried and concentrated. The crude product was separated by column chromatography to give the desired product (160 mg, yield 62%).

Step 3: Synthesis of Compound 4-benzyl-2-(((2-(4-(2-hydroxyethyl)piperazin-1-yl)ethyl)amino)methylene)-cyclopentane-1,3-dione The operation procedures were the same as Example 2. Compound 115: $^1$H NMR (400 MHz, CD$_3$OD) δ 7.86 (s, 1H), 7.27-7.17 (m, 5H), 3.71 (t, J=6.0 Hz, 2H), 3.59 (t, J=6.0 Hz, 2H), 3.18-3.14 (m, 1H), 2.94-2.88 (m, 1H), 2.74-2.60 (m, 13H), 2.51-2.45 (m, 1H), 2.24-2.18 (m, 1H); MS: 372.2 [M+1].

Example 32: Synthesis of Compound 2-(((2-(4-(2-hydroxyethyl)piperazin-1-yl)ethyl)amino)methylene)-4-methyl-5-phenylcyclohexane-1,3-dione (Compound 116)

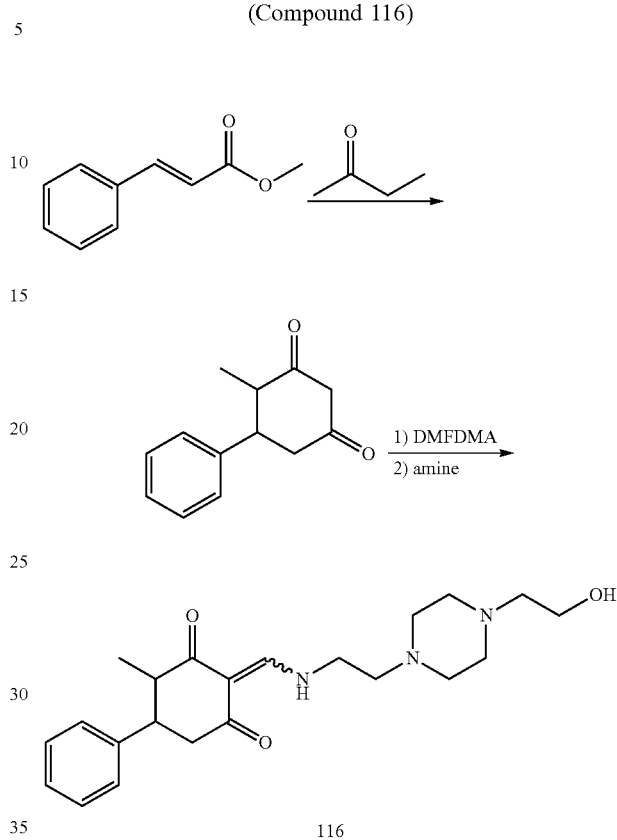

Step 1: Synthesis of Compound 4-methyl-5-phenylcyclohexane-1,3-dione

Under the protection of nitrogen atmosphere, t-BuOK (831 mg, 7.4 mmol) was added portionwise to butan-2-one (5 mL) at 0° C. After stirring at this temperature for 10 min, methyl cinnamate (1.00 g, 6.17 mmol) was added. The reaction mixture was heated to RT to react for 30 min. After the reaction was completed, the reaction mixture was poured into ice-water, adjusted to pH 7 with 1N HCl, and extracted with EA. The organic phase was washed with water, dried and concentrated. The crude product was separated by column chromatography to give the desired product (510 mg, yield 41%).

Step 2: Synthesis of Compound 2-(((2-(4-(2-hydroxyethyl)piperazin-1-yl)ethyl)amino)methylene)-4-methyl-5-phenylcyclohexane-1,3-dione The operation procedures were the same as Example 2. Compound 116: $^1$H NMR (400 MHz, CD$_3$OD) δ 8.35-8.13 (m, 1H), 7.44-7.08 (m, 5H), 3.67 (t, J=6.0 Hz, 2H), 3.63-3.55 (m, 2H), 3.06-2.43 (m, 16H), 0.97 (dd, J=12.6, 6.6 Hz, 3H); MS: 386.2 [M+1].

Example 33: Synthesis of Compound 1-(hydroxymethyl)-4-phenylpiperidine-2,6-dione (Compound 117)

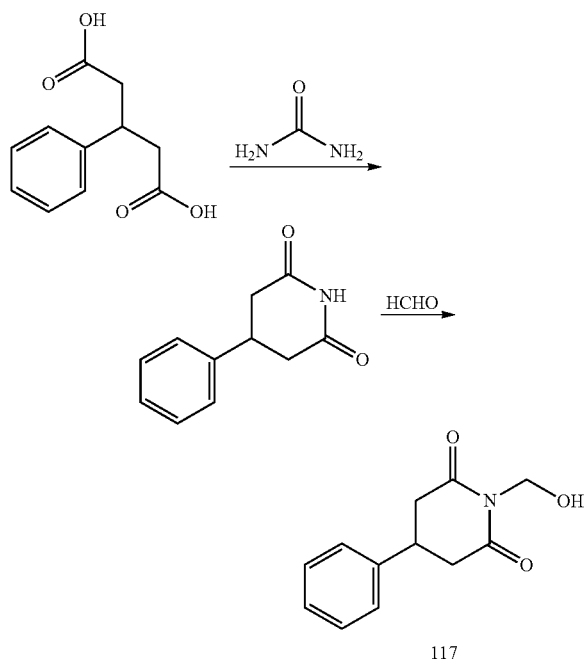

Step 1: Synthesis of Compound 4-phenylpiperidine-2,6-dione

The mixture of 3-phenylpentanedioic acid (5.0 g, 24 mmol) and urea (25 g) was reacted at 160° C. for 3 hours. After the reaction was completed, the reaction mixture was carefully poured into ice-water and extracted with EA. The organic phase was washed with water, dried with $Na_2SO_4$ and concentrated. The crude product was separated by column chromatography to give the desired product (3.6 g, yield 79%).

Step 2: Synthesis of Compound 1-(hydroxymethyl)-4-phenylpiperidine-2,6-dione The mixture of 4-phenylpiperidine-2,6-dione (800 mg, 4.22 mmol) and 35% HCHO solution (10 mL) was heated to 100° C. until all solids were dissolved. After the reaction was completed, the reaction mixture was cooled to RT, poured into water and extracted with EA. The combined organic phase was dried with $Na_2SO_4$ and concentrated. The crude product was separated by column chromatography to give the desired product (513 mg, yield 55%). Compound 117: $^1$HNMR (DMSO-d6) δ 7.31-7.34 (m, 5H), 6.10 (t, J=7.6 Hz, 1H), 5.06 (d, J=7.6 Hz, 2H), 3.41-3.33 (m, 1H), 2.97-2.90 (m, 2H), 2.82-2.77 (m, 2H); MS: 220.1 [M+1]. Example 34: Synthesis of compounds 119-129, 131-143, 145-150, 155-156, 158, 160-165, 169-180, 182-197, 200-233, 236-243, 245-260, 262-274, 276-291, 293-311, 315, 317-318, 320-347 and 349-414.

The compounds listed below were synthesized by the same procedures as the compounds above (e.g., Compound 8) except for using corresponding substituted cyclohexane-1,3-dione, or other similar compounds having active methylene (e.g., Example 9-1), as shown in Table 7.

TABLE 7

Compounds 119-355

| # | Structure | Name | Proton NMR($^1$HNMR), Mass Spectrum(MS) |
|---|-----------|------|-----------------------------------------|
| 119 | 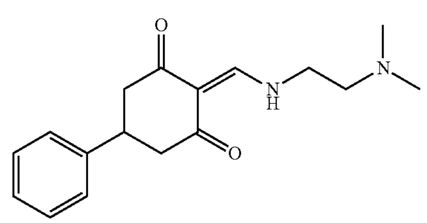 [SMILES: CN(C)CCNC=C1C(=O)CC(c2ccccc2)CC1=O] | 2-(((2-(dimethylamino)ethyl)amino)methylene)-5-phenylcyclohexane-1,3-dione | $^1$H NMR (400 MHz, CDCl$_3$) δ 11.20 (s, 1H), 8.17 (d, J = 14.3 Hz, 1H), 7.34 (t, J = 7.5 Hz, 2H), 7.23 (d, J = 8.3 Hz, 3H), 3.51 (q, J = 6.1 Hz, 2H), 3.36 (ddd, J = 15.7, 10.4, 5.1 Hz, 1H), 2.80-2.60 (m, 4H), 2.55 (t, J = 6.2 Hz, 2H), 2.29 (s, 6H). |
| 120 | 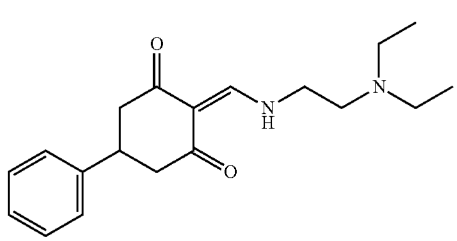 [SMILES: CCN(CC)CCNC=C1C(=O)CC(c2ccccc2)CC1=O] | 2-(((2-(diethylamino)ethyl)amino)methylene)-5-phenylcyclohexane-1,3-dione | $^1$H NMR (400 MHz, CDCl$_3$) δ 11.19 (s, 1H), 8.17 (d, J = 14.4 Hz, 1H), 7.33 (t, J = 7.6 Hz, 2H), 7.23 (d, J = 8.0 Hz, 3H), 3.48 (q, J = 6.0 Hz, 2H), 3.36 (ddd, J = 15.7, 10.3, 5.1 Hz, 1H), 2.80-2.52 (m, 10H), 1.04 (t, J = 7.1 Hz, 6H). |

TABLE 7-continued

Compounds 119-355

| # | Structure | Name | Proton NMR($^1$HNMR), Mass Spectrum(MS) |
|---|---|---|---|
| 121 | 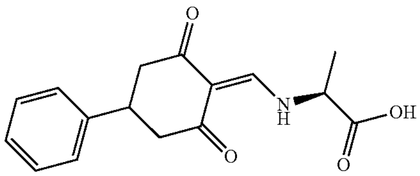 [SMILES: C[C@H](NC=C1C(=O)CC(c2ccccc2)CC1=O)C(=O)O] | ((2,6-dioxo-4-phenylcyclohexylidene)methyl)-L-alanine | $^1$H NMR (400 MHz, DMSO-d6) δ 11.34 (s, 1H), 9.35 (s, 1H), 8.07 (s, 1H), 7.35-7.24 (m, 4H), 7.20 (dd, J = 8.1, 3.8 Hz, 1H), 3.93 (q, J = 6.8 Hz, 1H), 3.34-3.22 (m, 1H), 2.77-2.58 (m, 2H), 2.47-2.40 (m, 2H), 1.32 (d, J = 7.1 Hz, 3H). |
| 122 | 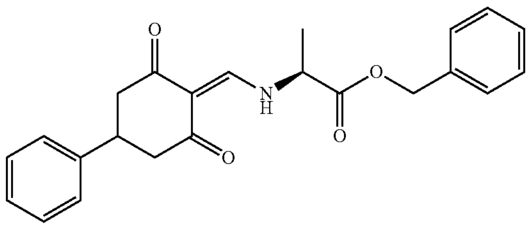 [SMILES: C[C@H](NC=C1C(=O)CC(c2ccccc2)CC1=O)C(=O)OCc1ccccc1] | benzyl ((2,6-dioxo-4-phenylcyclohexylidene)methyl)-L-alaninate | $^1$HNMR (400 MHz, DMSO-d6) δ 11.27-11.19 (m, 1H), 8.21 (d, J = 14.1 Hz, 1H), 7.48-7.26 (m, 9H), 7.22 (dt, J = 8.5, 4.1 Hz, 1H), 5.22 (d, J = 13.0 Hz, 2H), 4.79-4.69 (m, 1H), 2.84-2.68 (m, 2H), 2.60-2.51 (m, 2H), 1.50 (d, J = 7.2 Hz, 3H). |
| 123 | 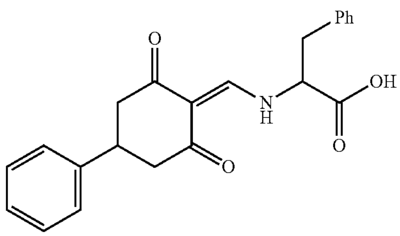 [SMILES: O=C1CC(c2ccccc2)CC(=O)C1=CNC(Cc1ccccc1)C(=O)O] | ((2,6-dioxo-4-phenylcyclohexylidene)methyl) phenylalanine | $^1$HNMR (400 MHz, CD$_3$OD) δ 7.87 (d, J = 5.7 Hz, 1H), 7.34-7.15 (m, 10H), 4.60-4.52 (m, 1H), 3.39-3.31 (m, 2H), 3.16-3.06 (m, 1H), 2.76 (dt, J = 8.9, 5.0 Hz, 1H), 2.70-2.56 (m, 3H). |
| 124 | 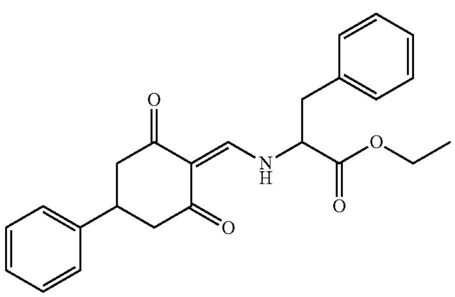 [SMILES: CCOC(=O)C(Cc1ccccc1)NC=C1C(=O)CC(c2ccccc2)CC1=O] | (l)-ethyl ((2,6-dioxo-4-phenylcyclohexylidene)methyl) phenylalaninate | $^1$HNMR (400 MHz, CDCl$_3$) δ 11.38 (s, 1H), 7.84 (dd, J = 13.8, 4.7 Hz, 1H), 7.38-7.27 (m, 5H), 7 19 (d, J = 31.7 Hz, 5H), 4.24 (d, J = 6.1 Hz, 3H), 3.30 (dd, J = 18.9, 8.0 Hz, 2H), 3.15-3.06 (m, 1H), 2.80-2.57 (m, 4H), 1.27 (td, J = 7.1, 3.5 Hz, 3H). |
| 125 | 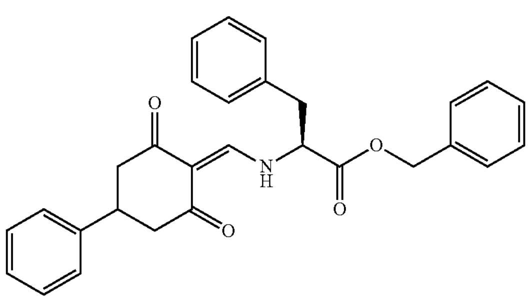 [SMILES: O=C1CC(c2ccccc2)CC(=O)C1=CN[C@@H](Cc1ccccc1)C(=O)OCc1ccccc1] | benzyl ((2,6-dioxo-4-phenylcyclohexylidene)methyl)-L-phenylalaninate | $^1$HNMR (400 MHz, DMSO-d6) δ 11.12 (dd, J = 13.7, 9.1 Hz, 1H), 8.03 (d, J = 14.0 Hz, 1H), 7.40-7.30 (m, 5H), 7.31-7.16 (m, 8H), 7.11 (t, J = 6.4 Hz, 2H), 5.18 (d, J = 3.0 Hz, 2H), 4.99 (dd, J = 14.3, 8.0 Hz, 1H), 3.28-3.14 (m, 3H), 2.78-2.61 (m, 2H), 2.52 (s, 1H). |
| 126 | 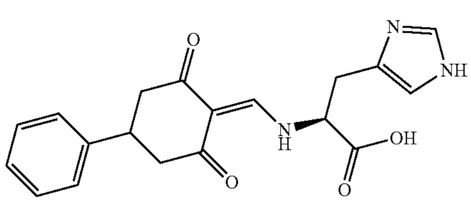 [SMILES: O=C1CC(c2ccccc2)CC(=O)C1=CN[C@@H](Cc1c[nH]cn1)C(=O)O] | ((2,6-dioxo-4-phenylcyclohexylidene)methyl)-L-histidine | $^1$HNMR (400 MHz, DMSO-d6) δ 11.27-11.09 (m, 1H), 7.95 (d, J = 14.6 Hz, 1H), 7.69 (s, 1H), 7.24 (d, J = 34.3 Hz, 4H), 6.86 (s, 1H), 4.67 (s, 1H), 3.27 (s, 1H), 3.08 (s, 2H), 2.81-2.56 (m, 2H), 2.41 (s, 2H). |

TABLE 7-continued

Compounds 119-355

| # | Structure | Name | Proton NMR(¹HNMR), Mass Spectrum(MS) |
|---|---|---|---|
| 127 | 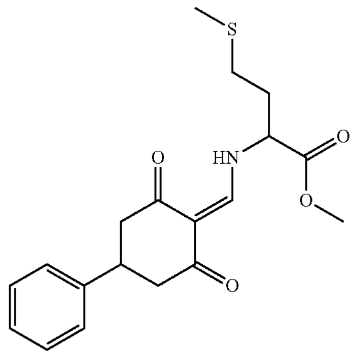 [SMILES: COC(=O)C(CCSC)NC=C1C(=O)CC(c2ccccc2)CC1=O] | methyl ((2,6-dioxo-4-phenylcyclo-hexylidene)methyl)methioninate | ¹HNMR (400 MHz, CDCl₃) δ 11.37 (s, 1H), 8.14 (d, J = 13.6 Hz, 1H), 7.35 (t, J = 7.4 Hz, 2H), 7.23 (d, J = 7.1 Hz, 3H), 4.35 (td, J = 8.9, 4.9 Hz, 1H), 3.81 (d, J = 1.8 Hz, 3H), 3.44-3.31 (m, 1H), 2.85-2.57 (m, 5H), 2.50 (dd, J = 7.2, 3.5 Hz, 1H), 2.27 (dt, J = 13.2, 7.5 Hz, 1H), 2.19-2.02 (m, 4H). |
| 128 | 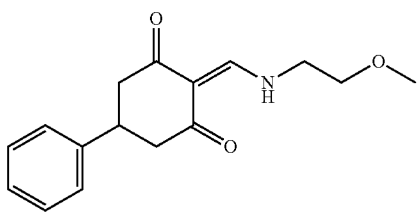 [SMILES: COCCNC=C1C(=O)CC(c2ccccc2)CC1=O] | 2-(((2-methoxyethyl)amino)methylene)-5-phenylcyclohexane-1,3-dione | ¹HNMR (400 MHz, CDCl₃) δ 11.23 (s, 1H), 8.18 (d, J = 14.2 Hz, 1H), 7.34 (t, J = 7.4 Hz, 2H), 7.23 (d, J = 8.3 Hz, 3H), 3.62-3.51 (m, 4H), 3.42-3.30 (m, 4H), 2.81-2.60 (m, 4H). |
| 129 | 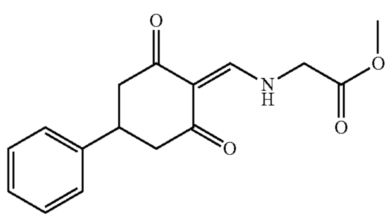 [SMILES: COC(=O)CNC=C1C(=O)CC(c2ccccc2)CC1=O] | methyl ((2,6-dioxo-4-phenylcyclo-hexylidene)methyl)glycinate | ¹HNMR (400 MHz, CDCl₃) δ 11.27 (s, 1H), 8.10 (d, J = 13.8 Hz, 1H), 7.35 (t, J = 7.4 Hz, 2H), 7.24 (dd, J = 6.5, 5.1 Hz, 3H), 4.20 (d, J = 6.1 Hz, 2H), 3.82 (s, 3H), 3.38 (dd, J = 14.4, 8.2 Hz, 1H), 2.82-2.65 (m, 4H). |
| 131 | 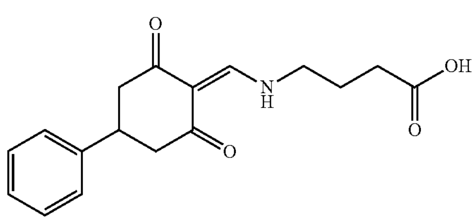 [SMILES: O=C(O)CCCNC=C1C(=O)CC(c2ccccc2)CC1=O] | 4-(((2,6-dioxo-4-phenylcyclo-hexylidene)methyl)amino)butanoic acid | ¹H NMR (400 MHz, DMSO-d6) δ 12.17 (s, 1H), 10.91 (d, J = 14.6 Hz, 1H), 8.08 (d, J = 14.6 Hz, 1H), 7.34-7.14 (m, 5H), 3.46 (q, J = 6.7 Hz, 2H), 3.31-3.22 (m, 1H), 2.70 (ddd, J = 33.3, 16.6, 11.8 Hz, 2H), 2.51 (d, J = 3.9 Hz, 1H), 2.44 (s, 1H), 2.21 (t, J = 7.4 Hz, 2H), 1.78 (dd, J = 14.2, 7.0 Hz, 2H). |
| 132 | 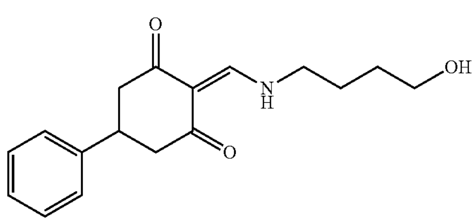 [SMILES: O=C1CC(c2ccccc2)CC(=O)C1=CNCCCCO] | 2-(((4-hydroxybutyl)amino)methylene)-5-phenylcyclohexane-1,3-dione | ¹HNMR (400 MHz, CDCl₃) δ 11.23 (s, 1H), 8.17 (d, J = 14.2 Hz, 1H), 7.33 (t, J = 7.4 Hz, 2H), 7.23 (d, J = 8.2 Hz, 3H), 3.70 (t, J = 6.1 Hz, 2H), 3.50 (q, J = 6.7 Hz, 2H), 3.35 (td, J = 10.8, 5.7 Hz, 1H), 2.82-2.58 (m, 4H), 1.84-1.71 (m, 2H), 1.68-1.56 (m, 2H). |
| 133 | 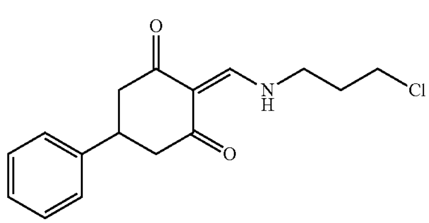 [SMILES: O=C1CC(c2ccccc2)CC(=O)C1=CNCCCCl] | 2-(((3-chloropropyl)amino)methylene)-5-phenylcyclohexane-1,3-dione | ¹HNMR (400 MHz, CDCl₃) δ 11.22 (s, 1H), 8.19 (d, J = 14.0 Hz, 1H), 7.34 (t, J = 7.4 Hz, 2H), 7.26-7.20 (m, 3H), 3.63 (dt, J = 12.1, 6.3 Hz, 4H), 3.42-3.30 (m, 1H), 2.82-2.60 (m, 4H), 2.18-2.06 (m, 2H). |

TABLE 7-continued

Compounds 119-355

| # | Structure | Name | Proton NMR($^1$HNMR), Mass Spectrum(MS) |
|---|---|---|---|
| 134 | 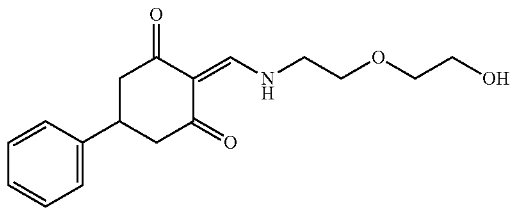 [SMILES: O=C1CC(c2ccccc2)CC(=O)C1=CNCCOCCO] | 2-(((2-(2-hydroxyethoxy)ethyl)amino)methylene)-5-phenylcyclohexane-1,3-dione | $^1$HNMR (400 MHz, CDCl$_3$) δ 11.32 (s, 1H), 8.24 (d, J = 14.2 Hz, 1H), 7.34 (t, J = 7.4 Hz, 2H), 7.23 (dd, J = 5.9, 4.7 Hz, 3H), 3.80-3.73 (m, 2H), 3.69 (t, J = 4.7 Hz, 2H), 3.61 (dd, J = 8.7, 4.4 Hz, 4H), 3.36 (ddd, J = 15.8, 10.6, 5.3 Hz, 1H), 2.82-2.58 (m, 4H). |
| 135 | 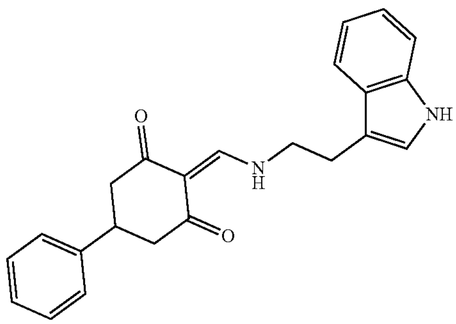 [SMILES: O=C1CC(c2ccccc2)CC(=O)C1=CNCCc1c[nH]c2ccccc12] | 2-(((2-(1H-indol-3-yl)ethyl)amino)methylene)-5-phenylcyclohexane-1,3-dione | $^1$HNMR (400 MHz, DMSO-d6) δ 11.01 (d, J = 14.2 Hz, 1H), 10.87 (s, 1H), 8.03 (d, J = 14.6 Hz, 1H), 7.58 (d, J = 7.8 Hz, 1H), 7.35-7.25 (m, 5H), 7.22-7.17 (m, 1H), 7.15 (d, J = 2.1 Hz, 1H), 7.06 (t, J = 7.5 Hz, 1H), 6.96 (t, J = 7.5 Hz, 1H), 3.74 (dd, J = 13.4, 6.8 Hz, 2H), 3.25 (dd, J = 13.7, 9.9 Hz, 1H), 2.98 (t, J = 7.0 Hz, 2H), 2.74-2.58 (m, 2H), 2.46-2.38 (m, 2H). |
| 136 | 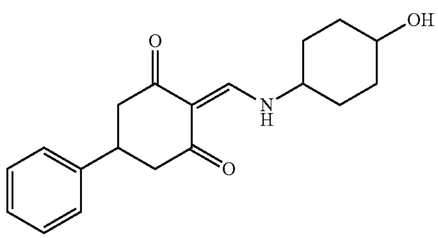 [SMILES: O=C1CC(c2ccccc2)CC(=O)C1=CNC1CCC(O)CC1] | 2-(((4-hydroxycyclohexyl)amino)methylene)-5-phenylcyclohexane-1,3-dione | $^1$HNMR (400 MHz, DMSO-d6) δ 11.03 (dd, J = 14.4, 8.1 Hz, 1H), 8.16 (d, J = 14.3 Hz, 1H), 7.35-7.25 (m, 4H), 7.24-7.16 (m, 1H), 4.60 (d, J = 4.4 Hz, 1H), 3.57-3.35 (m, 2H), 3.28 (dt, J = 11.7, 4.0 Hz, 1H), 2.69 (ddd, J = 33.9, 16.6, 11.8 Hz, 2H), 2.54-2.50 (m, 1H), 2.47-2.41 (m, 1H), 1.82 (t, J = 13.1 Hz, 4H), 1.55-1.38 (m, 2H), 1.22 (dd, J = 21.5, 11.0 Hz, 2H). |
| 137 | 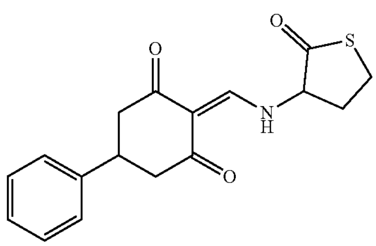 [SMILES: O=C1CC(c2ccccc2)CC(=O)C1=CNC1CCSC1=O] | 2-(((2-oxotetrahydrothiophen-3-yl)amino)methylene)-5-phenylcyclohexane-1,3-dione | $^1$HNMR (400 MHz, DMSO-d6) δ 10.86-10.73 (m, 1H), 8.05 (d, J = 14.5 Hz, 1H), 7.36-7.25 (m, 4H), 7.21 (dd, J = 8.3, 4.0 Hz, 1H), 4.74 (dt, J = 12.9, 6.6 Hz, 1H), 3.35-3.25 (m, 2H), 2.87-2.58 (m, 3H), 2.58-2.50 (m, 1H), 2.45-2.37 (m, 1H). |
| 138 | 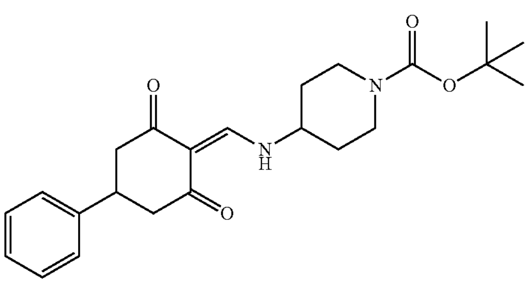 [SMILES: CC(C)(C)OC(=O)N1CCC(NC=C2C(=O)CC(c3ccccc3)CC2=O)CC1] | tert-butyl 4-(((2,6-dioxo-4-phenylcyclohexylidene)methyl)amino)piperidine-1-carboxylate | $^1$HNMR (400 MHz, CDCl$_3$) δ 11.29 (s, 1H), 8.23 (d, J = 14.0 Hz, 1H), 7.34 (t, J = 7.5 Hz, 2H), 7.25-7.20 (m, 3H), 4.08 (s, 2H), 3.48 (d, J = 7.1 Hz, 1H), 3.35 (dd, J = 13.5, 8.2 Hz, 1H), 2.91 (t, J = 11.7 Hz, 2H), 2.79-2.61 (m, 4H), 1.97 (d, J = 11.0 Hz, 2H), 1.61 (d, J = 8.1 Hz, 2H), 1.46 (s, 9H). |
| 139 | 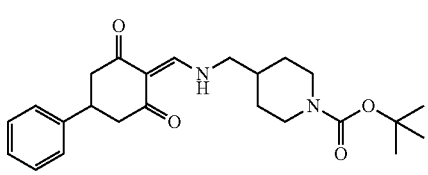 [SMILES: CC(C)(C)OC(=O)N1CCC(CNC=C2C(=O)CC(c3ccccc3)CC2=O)CC1] | tert-butyl 4-((((2,6-dioxo-4-phenylcyclohexylidene)methyl)amino)methyl)piperidine-1-carboxylate | $^1$HNMR (400 MHz, DMSO-d6) δ 11.01-10.91 (m, 1H), 8.08 (d, J = 14.4 Hz, 1H), 7.30 (dd, J = 7.0, 6.1 Hz, 4H), 7.23-7.16 (m, 1H), 3.92 (d, J = 12.4 Hz, 2H), 3.38 (t, J = 6.5 Hz, 2H), 3.30-3.25 (m, 1H), 2.70 (ddd, J = 34.4, 16.6, 11.8 Hz, 4H), 2.44 (s, 1H), 1.70 (s, 1H), 1.53 (d, J = 11.4 Hz, 2H), 1.37 (s, 9H), 0.99 (dt, J = 12.0, 8.1 Hz, 2H). |

TABLE 7-continued

Compounds 119-355

| # | Structure | Name | Proton NMR($^1$HNMR), Mass Spectrum(MS) |
|---|---|---|---|
| 140 | 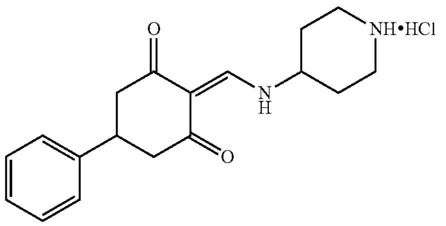 | 5-phenyl-2-((piperidin-4-ylamino)methylene)cyclohexane-1,3-dione hydrochloride | $^1$HNMR (400 MHz, CD$_3$OD) δ 8.32 (s, 1H), 7.35-7.26 (m, 4H), 7.23 (dd, J = 11.2, 4.3 Hz, 1H), 3.84 (t, J = 11.3 Hz, 1H), 3.49 (d, J = 13.3 Hz, 2H), 3.40-3.32 (m, 1H), 3.13 (t, J = 11.6 Hz, 2H), 2.85-2.74 (m, 2H), 2.67 (dd, J = 16.7, 4.1 Hz, 2H), 2.25 (d, J = 11.9 Hz, 2H), 1.90 (td, J = 14.1, 4.2 Hz, 2H). |
| 141 | 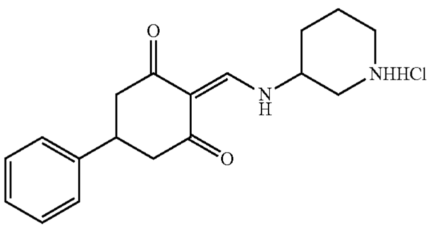 | 5-phenyl-2-((piperidin-3-ylamino)methylene)cyclohexane-1,3-dione hydrochloride | $^1$HNMR (400 MHz, DMSO-d6) δ 10.88 (dd, J = 14.1, 8.4 Hz, 1H), 9.54 (s, 1H), 9.35 (d, J = 10.1 Hz, 1H), 8.14 (d, J = 14.2 Hz, 1H), 7.33 (dd, J = 7.2, 6.1 Hz, 3H), 7.27-7.18 (m, 1H), 5.92 (s, 3H), 3.89 (s, 1H), 3.34 (d, J = 11.7 Hz, 1H), 3.19-3.05 (m, 2H), 2.72 (d, J = 12.7 Hz, 3H), 2.55 (s, 1H), 1.98 (s, 1H), 1.79 (m, 3H). |
| 142 | 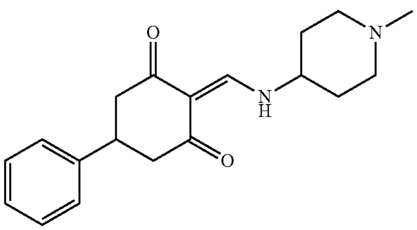 [SMILES: CN1CCC(NC=C2C(=O)CC(c3ccccc3)CC2=O)CC1] | 2-(((1-methylpiperidin-4-yl)amino)methylene)-5-phenylcyclohexane-1,3-dione | $^1$HNMR (400 MHz, CDCl$_3$) δ 11.30 (s, 1H), 8.23 (d, J = 14.1 Hz, 1H), 7.34 (t, J = 7.4 Hz, 2H), 7.23 (d, J = 8.2 Hz, 3H), 3.36 (dd, J = 19.1, 13.2 Hz, 2H), 2.87-2.61 (m, 6H), 2.30 (s, 3H), 2.16 (t, J = 10.6 Hz, 2H), 2.00 (d, J = 13.2 Hz, 2H), 1.76 (q, J = 13.7 Hz, 2H). |
| 143 | 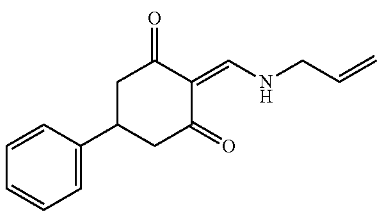 [SMILES: C=CCNC=C1C(=O)CC(c2ccccc2)CC1=O] | 2-((allylamino)methylene)-5-phenylcyclohexane-1,3-dione | $^1$HNMR (400 MHz, CDCl$_3$) δ 11.21 (s, 1H), 8.17 (d, J = 14.1 Hz, 1H), 7.34 (t, J = 7.4 Hz, 2H), 7.26-7.20 (m, 3H), 5.89 (ddd, J = 22.2, 11.0, 5.6 Hz, 1H), 5.34-5.26 (m, 2H), 4.04 (t, J = 5.7 Hz, 2H), 3.44-3.28 (m, 1H), 2.83-2.59 (m, 4H). |
| 145 | 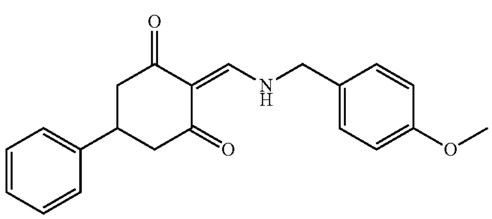 [SMILES: COc1ccc(CNC=C2C(=O)CC(c3ccccc3)CC2=O)cc1] | 2-(((4-methoxybenzyl)amino)methylene)-5-phenylcyclohexane-1,3-dione | $^1$HNMR (400 MHz, CDCl$_3$) δ 11.39 (s, 1H), 8.24 (d, J = 14.1 Hz, 1H), 7.34 (t, J = 7.4 Hz, 2H), 7.26-7.14 (m, 5H), 6.93-6.86 (m, 2H), 4.53 (d, J = 6.0 Hz, 2H), 3.81 (s, 3H), 3.41-3.31 (m, 1H), 2.82-2.60 (m, 4H). |
| 146 | 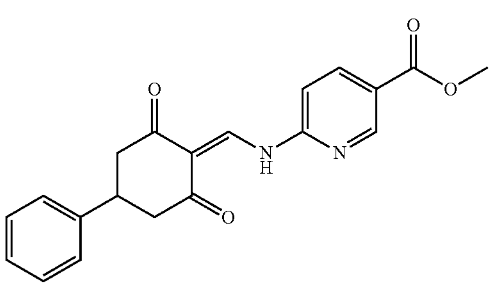 [SMILES: COC(=O)c1ccc(NC=C2C(=O)CC(c3ccccc3)CC2=O)nc1] | methyl 6-(((2,6-dioxo-4-phenylcyclohexylidene)methyl)amino)nicotinate | $^1$HNMR (400 MHz, DMSO-d6) δ 12.44 (d, J = 10.9 Hz, 1H), 9.07 (d, J = 10.8 Hz, 1H), 8.93 (d, J= 2.0 Hz, 1H), 8.30 (dd, J = 8.6, 2.1 Hz, 1H), 7.68 (d, J = 8.6 Hz, 1H), 7.37-7.16 (m, 5H), 3.86 (s, 3H), 3.44 (t, J = 11.4 Hz, 1H), 3.03-2.79 (m, 2H), 2.67 (t, J = 16.8 Hz, 2H). |

TABLE 7-continued

Compounds 119-355

| # | Structure | Name | Proton NMR(¹HNMR), Mass Spectrum(MS) |
|---|---|---|---|
| 147 | 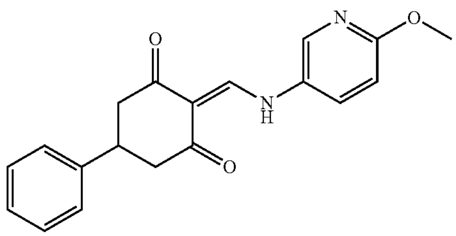 [SMILES: COc1ccc(NC=C2C(=O)CC(c3ccccc3)CC2=O)cn1] | 2-(((6-methoxypyridin-3-yl)amino)methylene)-5-phenylcyclohexane-1,3-dione | ¹HNMR (400 MHz, DMSO-d6) δ 12.63 (d, J = 13.6 Hz, 1H), 8.40 (d, J = 13.7 Hz, 1H), 8.33 (d, J = 2.8 Hz, 1H), 7.96 (dd, J = 9.0, 2.9 Hz, 1H), 7.38-7.25 (m, 4H), 7.25-7.18 (m, 1H), 6.87 (d, J = 8.9 Hz, 1H), 3.84 (s, 3H), 3.38 (ddd, J = 15.4, 7.6, 3.9 Hz, 1H), 2.82 (ddd, J = 41.2, 16.4, 11.6 Hz, 2H), 2.61 (dd, J = 20.6, 16.8 Hz, 2H). |
| 148 | 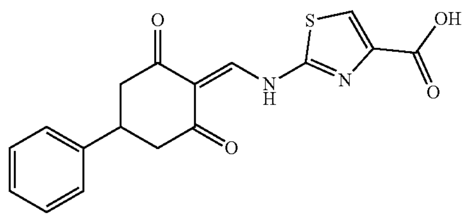 [SMILES: O=C1CC(c2ccccc2)CC(=O)C1=CNc1nc(C(=O)O)cs1] | 2-(((2,6-dioxo-4-phenylcyclohexylidene)methyl)amino)thiazole-4-carboxylic acid | ¹HNMR (400 MHz, DMSO-d6) δ 8.71 (s, 1H), 7.87 (s, 1H), 7.28 (t, J = 21.9 Hz, 5H), 3.40 (s, 1H), 2.92-2.76 (m, 2H), 2.61 (d, J = 17.2 Hz, 2H). |
| 149 | 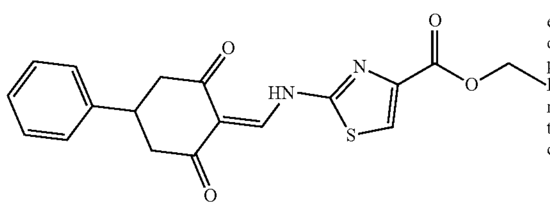 [SMILES: CCOC(=O)c1csc(NC=C2C(=O)CC(c3ccccc3)CC2=O)n1] | ethyl 2-(((2,6-dioxo-4-phenylcyclohexylidene)methyl)amino)thiazole-4-carboxylate | ¹HNMR (400 MHz, CDCl₃) δ 13.15 (d, J = 12.3 Hz, 1H), 8.71 (d, J = 12.4 Hz, 1H), 7.89 (s, 1H), 7.36 (t, J = 7.4 Hz, 2H), 7.31-7.18 (m, 3H), 4.42 (q, J = 7.1 Hz, 2H), 3.43 (s, 1H), 2.82 (m, 4H), 1.42 (t, J = 7.1 Hz, 3H). |
| 150 | 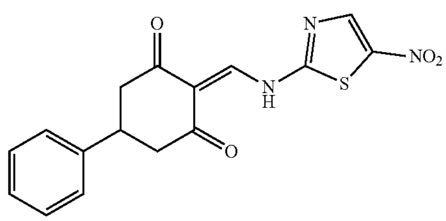 [SMILES: O=C1CC(c2ccccc2)CC(=O)C1=CNc1ncc([N+](=O)[O-])s1] | 2-(((5-nitrothiazol-2-yl)amino)methylene)-5-phenylcyclohexane-1,3-dione | ¹HNMR (400 MHz, DMSO-d6) δ 12.88 (s, 1H), 8.71 (s, 1H), 8.62 (s, 1H), 7.38-7.15 (m, 5H), 3.46 (t, J = 11.6 Hz, 1H), 3.03-2.82 (m, 2H), 2.71 (s, 2H). |
| 155 | 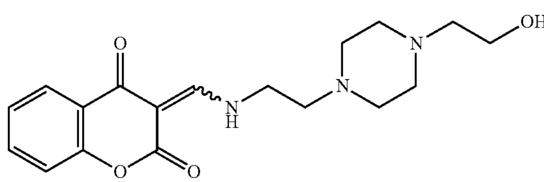 | 3-(((2-(4-(2-hydroxyethyl)piperazin-1-yl)ethyl)amino)methylene)chromanone-2,4-dione | ¹HNMR (400 MHz, DMSO-d6) δ 11.54 (s, 1H), 10.29 (s, 1H), 8.49 (dd, J = 8.2, 5.7 Hz, 1H), 7.92 (t, J = 7.5 Hz, 1H), 7.63 (t, J = 6.9 Hz, 1H), 7.28 (dd, 8.4, 5.2 Hz, 2H), 4.60 (s, 1H), 3.68 (d, J = 5.5 Hz, 2H), 3.53 (s, 2H), 3.32 (s, 2H), 2.57-2.31 (m, 10H). |
| 156 | 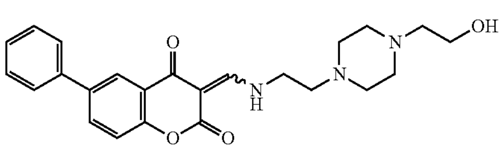 [SMILES: O=C1Oc2ccc(-c3ccccc3)cc2C(=O)C1=CNCCN1CCN(CCO)CC1] | 3-(((2-(4-(2-hydroxyethyl)piperazin-1-yl)ethyl)amino)methylene)-6-phenylchromane-2,4-dione | ¹HNMR (400 MHz, DMSO-d6) δ 11.57 (s, 1H), 10.33 (s, 1H), 8.52 (dd, J = 53.2, 15.2 Hz, 1H), 8.16-8.07 (m, 1H), 7.93 (d, J = 8.4 Hz, 1H), 7.68 (d, J = 7.3 Hz, 2H), 7.48 (t, J = 7.6 Hz, 2H), 7.38 (t, J = 8.6 Hz, 2H), 4.55 (s, 1H), 3.69 (d, J = 5.5 Hz, 2H), 3.52 (s, 2H), 2.56 (s, 8H). |
| 158 | 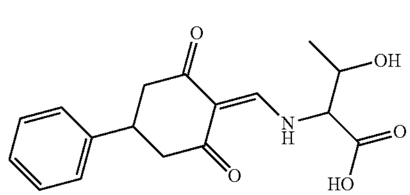 [SMILES: CC(O)C(NC=C1C(=O)CC(c2ccccc2)CC1=O)C(=O)O] | 2-(((2,6-dioxo-4-phenylcyclohexylidene)methyl)amino)-3-hydroxybutanoic acid | ¹HNMR (400 MHz, DMSO-d6) δ 11.57 (dd, J = 14.6, 8.6 Hz, 1H), 9.29 (s, 1H), 8.02 (d, J = 15.0 Hz, 1H), 7.39-7.11 (m,5H),3.87 (d, J = 5.1 Hz, 1H), 3.71 (s, 1H), 3.33-3.24 (m, 1H), 2.77-2.59 (m, 2H), 2.46 (s, 2H), 1.02 (dd, J = 6.1, 2.6 Hz, 3H). |

TABLE 7-continued

Compounds 119-355

| # | Structure | Name | Proton NMR(¹HNMR), Mass Spectrum(MS) |
|---|---|---|---|
| 160 | 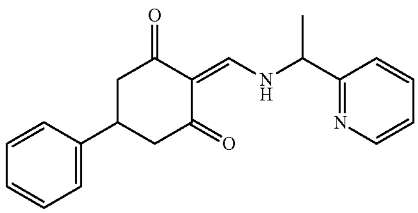 [SMILES: CC(NC=C1C(=O)CC(c2ccccc2)CC1=O)c1ccccn1] | 5-phenyl-2-(((1-(pyridin-2-yl)ethyl)amino)methylene)cyclohexane-1,3-dione | ¹HNMR (400 MHz, DMSO-d6) δ 11.59 (s, 1H), 8.59 (d, J = 4.0 Hz, 1H), 8.31 (d, J = 14.4 Hz, 1H), 7.82 (t, J = 7.7 Hz, 1H), 7.41 (d, J = 7.6 Hz, 1H), 7.37-7.31 (m, 1H), 7.28 (s, 4H), 7.21 (d, J = 3.3 Hz, 1H), 5.13-5.03 (m, 1H), 3.27 (d, J = 11.7 Hz, 1H), 2.80-2.62 (m, 2H), 2.52 (s, 1H), 1.54 (d, J = 6.8 Hz, 3H). |
| 161 | 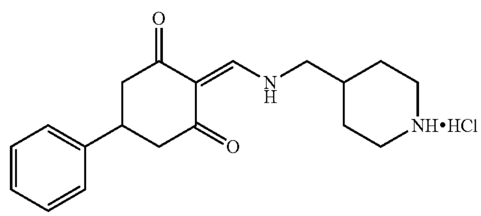 | 5-phenyl-2-((((piperidin-4-ylmethyl)amino)methylene)cyclohexane-1,3-dione hydrochloride | ¹HNMR (400 MHz, CD₃OD) δ 8.21 (s, 1H), 7.35-7.19 (m, 5H), 3.50-3.32 (m, 5H), 3.00 (td, J = 12.9, 2.8 Hz, 2H), 2.74 (dtd, J = 22.9, 17.0, 12.0 Hz, 4H), 1.96 (t, J = 10.0 Hz, 3H), 1.47 (dd, J = 23.9, 10.8 Hz, 2H). |
| 162 | 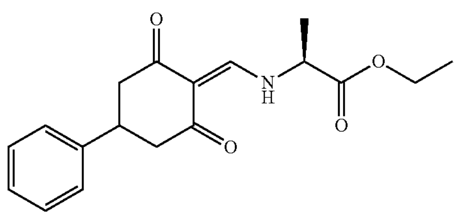 [SMILES: CCOC(=O)[C@H](C)NC=C1C(=O)CC(c2ccccc2)CC1=O] | ethyl ((2,6-dioxo-4-phenylcyclohexylidene)methyl)-L-alaninate | ¹HNMR (400 MHz, CDCl₃) δ 11.45 (s, 1H), 8.16 (d, J = 13.9 Hz, 1H), 7.34 (t, J = 7.4 Hz, 2H), 7.24 (d, J = 8.2 Hz, 3H), 4.30-4.15 (m, 3H), 3.42-3.32 (m, 1H), 2.82-2.64 (m, 4H), 1.61 (dd, J = 7.2, 1.1 Hz, 3H), 1.31 (td, J = 7.1, 1.5 Hz, 3H). |
| 163 | 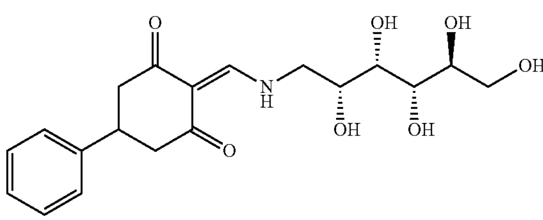 [SMILES: O=C1CC(c2ccccc2)CC(=O)C1=CNC[C@@H](O)[C@H](O)[C@@H](O)[C@@H](O)CO] | 2-(((((2R,3S,4S,5S)-2,3,4,5,6-OHpentahydroxyhexyl)amino)methylene)-5-phenylcyclohexane-1,3-dione | ¹HNMR (400 MHz, DMSO-d6) δ 11.05-10.96 (m, 1H), 8.08 (d, J = 14.4 Hz, 1H), 7.30 (d, J = 4.4 Hz, 4H), 7.23-7.17 (m, 1H), 5.02 (d, J = 4.2 Hz, 1H), 4.50 (d, J = 5.3 Hz, 1H), 4.44 (dd, J = 12.3, 6.3 Hz, 2H), 4.34 (t, J = 5.4 Hz, 1H), 3.68-3.53 (m, 4H), 3.50-3.36 (m, 4H), 3.28 (d, J = 11.5 Hz, 1H), 2.69 (ddd, J = 31.9, 16.6, 11.8 Hz, 2H). |
| 164 | 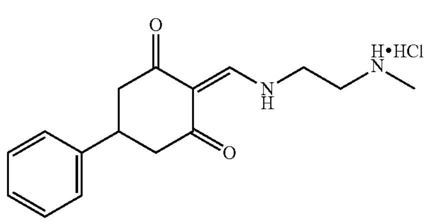 | 2-(((2-(methylamino)ethyl)amino)methylene)-5-phenylcyclohexane-1,3-dione hydrochloride | ¹HNMR (400 MHz, D₂O) δ 8.23 (s, 1H), 7.40 (t, J = 7.4 Hz, 2H), 7.31 (dd, J = 15.6, 7.6 Hz, 3H), 3.88 (t, J = 5.8 Hz, 2H), 3.46 (td, J = 9.8, 4.5 Hz, 1H), 3.37 (t, J = 5.9 Hz, 2H), 2.92-2.64 (m, 7H). |
| 165 | 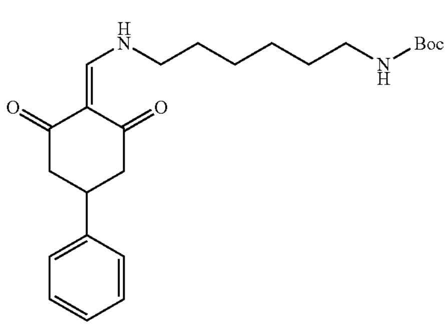 [SMILES: CC(C)(C)OC(=O)NCCCCCCNC=C1C(=O)CC(c2ccccc2)CC1=O] | tert-butyl (6-(((2,6-dioxo-4-phenylcyclohexylidene)methyl)amino)hexyl)carbamate | ¹HNMR (400 MHz, CDCl₃) δ 11.21 (s, 1H), 8.16 (d, J = 14.1 Hz, 1H), 7.34 (t, J = 7.4 Hz, 2H), 7.26-7.20 (m, 3H), 4.53 (s, 1H), 3.43 (dd, J = 13.4, 6.8 Hz, 2H), 3.39-3.31 (m, 1H), 3.11 (d, J = 6.7 Hz, 2H), 2.81-2.61 (m, 4H), 1.66 (dd, J = 13.9, 6.4 Hz, 3H), 1.55-1.23 (m, 14H). |

TABLE 7-continued

Compounds 119-355

| # | Structure | Name | Proton NMR($^1$HNMR), Mass Spectrum(MS) |
|---|---|---|---|
| 169 | 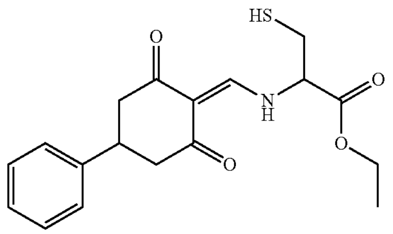 [SMILES: CCOC(=O)C(CS)NC=C1C(=O)CC(c2ccccc2)CC1=O] | ethyl ((2,6-dioxo-4-phenylcyclo-hexylidene)methyl) cysteinate | $^1$HNMR (400 MHz, CDCl$_3$) δ 11.52 (s, 1H), 8.16 (dd, J = 13.7, 0.7 Hz, 1H), 7.35 (t, J = 7.4 Hz, 2H), 7.25 (dd, J = 6.3, 4.9 Hz, 3H), 4.34-4.20 (m, 3H), 3.44-3.33 (m, 1H), 3.13-2.98 (m, 2H), 2.85-2.74 (m, 3H), 2.69 (dd, J = 16.9, 12.1 Hz, 1H), 1.56 (td, J = 9.1, 2.7 Hz, 1H), 1.33 (td, J = 7.1, 2.6 Hz, 3H). |
| 170 | 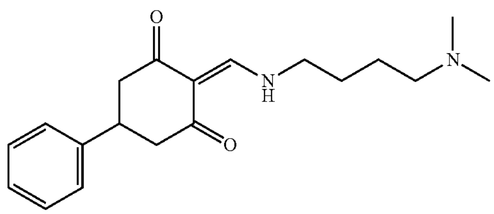 [SMILES: CN(C)CCCCNC=C1C(=O)CC(c2ccccc2)CC1=O] | 2-(((4-(dimethylamino)butyl)amino)methylene)-5-phenylcyclohexane-1,3-dione | $^1$HNMR (400 MHz, CD$_3$OD) δ 8.24 (s, 1H), 7.35-7.18 (m, 5H), 3.53 (t, J = 6.9 Hz, 2H), 3.35 (ddd, J = 11.6, 8.0, 4.3 Hz, 1H), 2.75 (d, J = 12.0 Hz, 2H), 2.64 (dd, J = 16.8, 4.2 Hz, 2H), 2.42-2.34 (m, 2H), 2.26 (s, 6H), 1.68 (dt, J = 14.1, 6.9 Hz, 2H), 1.59-1.51 (m, 2H). |
| 171 | 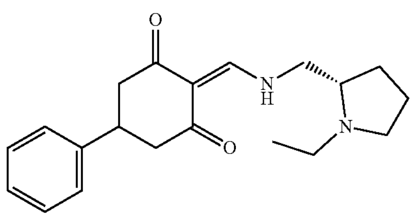 [SMILES: CCN1CCC[C@H]1CNC=C1C(=O)CC(c2ccccc2)CC1=O] | 2-(((((S)-1-ethylpyrrolidin-2-yl)methyl)amino)methylene)-5-phenylcyclohexane-1,3-dione | $^1$HNMR (400 MHz, CDCl$_3$) δ 11.19 (s, 1H), 8.17 (d, J = 14.3 Hz, 1H), 7.34 (t, J = 7.5 Hz, 2H), 7.24 (d, J = 8.0 Hz, 3H), 3.54-3.46 (m, 1H), 3.37 (dt, J = 15.7, 5.4 Hz, 2H), 3.24-3.17 (m, 1H), 2.85-2.61 (m, 6H), 2.35 (dq, J = 13.8, 7.0 Hz, 1H), 2.23 (dt, J = 16.4, 8.3 Hz, 1H), 1.93 (ddd, J = 17.2, 12.5, 8.6 Hz, 1H), 1.79-1.63 (m, 2H), 1.60-1.49 (m, 1H), 1.13 (t, J = 7.2 Hz, 3H). |
| 172 | 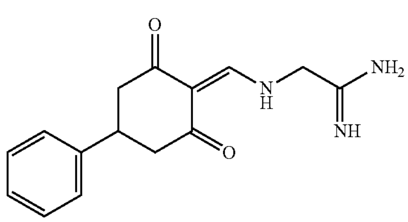 [SMILES: N=C(N)CNC=C1C(=O)CC(c2ccccc2)CC1=O] | 2-(((2,6-dioxo-4-phenylcyclo-hexylidene)methyl) amino) acetimidamide | $^1$HNMR (400 MHz, DMSO-d6) δ 10.83 (s, 1H), 8.89 (s, 4H), 8.16 (s, 1H), 7.33 (d, J = 4.4 Hz, 4H), 7.27-7.20 (m, 1H), 4.44 (s, 2H), 3.34-3.27 (m, 1H), 2.84-2.67 (m, 2H), 2.56 (d, J = 16.3 Hz, 2H). |
| 173 | 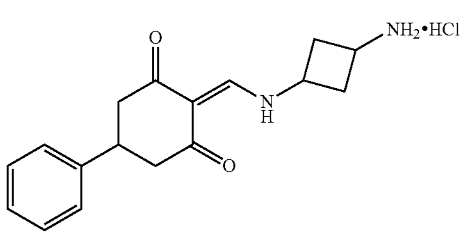 | 2-(((3-aminocyclobutyl)amino)methylene)-5-phenylcyclohexane-1,3-dione hydrochloride | $^1$HNMR (400 MHz, D$_2$O) δ 8.01 (s, 1H), 7.27-7.20 (m, 2H), 7.19-7.11 (m, 3H), 4.32 (dt, J= 15.1, 7.4 Hz, 1H), 3.82 (td, J = 8.6, 4.5 Hz, 1H), 3.28 (ddd, J = 15.0, 10.2, 4.6 Hz, 1H), 2.71-2.46 (m, 8H). |

TABLE 7-continued

Compounds 119-355

| # | Structure | Name | Proton NMR($^1$HNMR), Mass Spectrum(MS) |
|---|---|---|---|
| 174 | 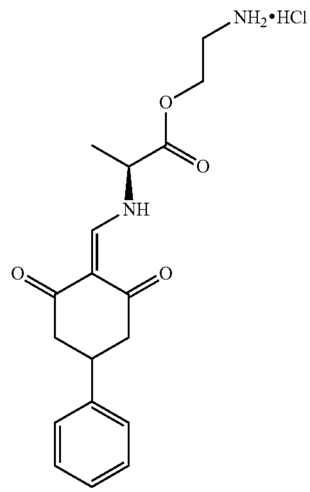 | ((2,6-dioxo-4-phenylcyclo-hexylidene)methyl)-L-alaninate hydrochloride | $^1$HNMR (400 MHz, DMSO-d6) δ 11.24-11.13 (m, 1H), 8.31 (s, 2H), 8.21 (d, J = 14.2 Hz, 1H), 8.00 (s, 1H), 7.32 (d, J = 4.4 Hz, 4H), 7.27-7.19 (m, 1H), 4.70 (p, J = 7.2 Hz, 1H), 4.45-4.35 (m, 1H), 4.33-4.24 (m, 1H), 3.58 (dd, J = 9.2, 3.7 Hz, 1H), 3.35-3.30 (m, 1H), 3.10 (d, J = 4.5 Hz, 2H), 2.93-2.66 (m, 3H), 2.59-2.53 (m, 1H), 1.53 (d, J = 7.1 Hz, 3H). |
| 175 | 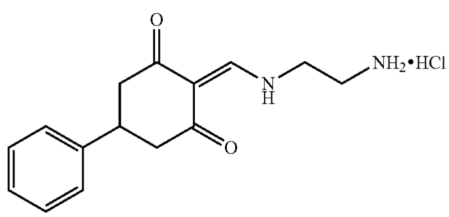 | 2-(((2-aminoethyl)amino)methylene)-5-phenylcyclo-hexane-1,3-dione hydrochloride | $^1$HNMR (400 MHz, DMSO-d6) δ 10.88-10.77 (m, 1H), 8.32 (s, 3H), 8.10 (d, J = 14.4 Hz, 1H), 7.32 (d, J = 4.3 Hz, 4H), 7.28 (dd, J = 37.6, 4.3 Hz, 5H), 7.23 (d, J = 4.3 Hz, 1H), 3.73 (d, J = 6.1 Hz, 2H), 3.31 (tt, J = 11.5, 4.0 Hz, 1H), 3.06 (dd, J = 11.4, 5.6 Hz, 2H), 2.73 (dt, J = 28.6, 14.1 Hz, 2H), 2.53 (d, J = 13.3 Hz, 2H). |
| 176 | 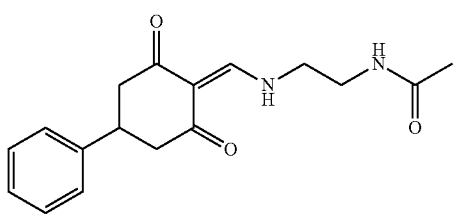 [SMILES: CC(=O)NCCNC=C1C(=O)CC(c2ccccc2)CC1=O] | N-(2-(((2,6-dioxo-4-phenylcyclo-hexylidene)methyl)amino)ethyl)acetamide | $^1$HNMR (400 MHz, CDCl$_3$) δ 11.21 (s, 1H), 8.14 (d, J = 14.0 Hz, 1H), 7.35 (t, J = 7.4 Hz, 2H), 7.24 (t, J = 6.7 Hz, 3H), 6.03 (s, 1H), 3.59 (dd, J = 11.7, 5.8 Hz, 2H), 3.49 (dd, J = 11.5, 5.7 Hz, 2H), 3.42-3.30 (m, 1H), 2.82-2.59 (m, 4H), 2.02 (s, 3H). |
| 177 | 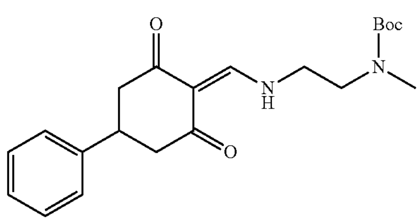 [SMILES: CN(CCNC=C1C(=O)CC(c2ccccc2)CC1=O)C(=O)OC(C)(C)C] | tert-butyl (2-(((2,6-dioxo-4-phenylcyclo-hexylidene)methyl)amino)ethyl)(methyl)carbamate | $^1$HNMR (400 MHz, CDCl$_3$) δ 11.22 (s, 1H), 8.12 (d, J = 13.9 Hz, 1H), 7.34 (t, J = 7.4 Hz, 2H), 7.27-7.20 (m, 3H), 3.58 (s, 2H), 3.46 (t, J = 5.7 Hz, 2H), 3.41-3.29 (m, 1H), 2.89 (s, 3H), 2.81-2.60 (m, 4H), 1.46 (s, 9H). |
| 178 | 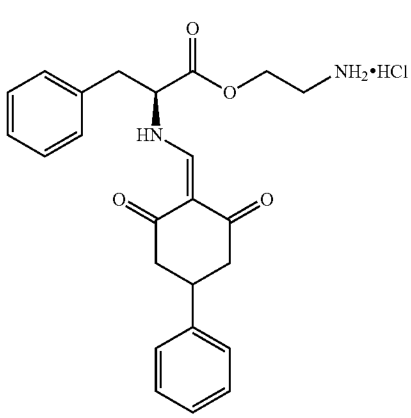 | 2-aminoethyl ((2,6-dioxo-4-phenylcyclo-hexylidene)methyl)-L-phenylalaninate hydrochloride | $^1$HNMR (400 MHz, DMSO-d6) δ 11.14-11.02 (m, 1H), 8.31 (s, 3H), 7.97 (d, J = 14.0 Hz, 1H), 7.40-7.06 (m, 10H), 4.94 (td, J = 8.9, 4.6 Hz, 1H), 4.41 (dd, J = 12.1, 3.2 Hz, 1H), 4.29 (dd, J = 12.1, 2.6 Hz, 1H), 3.26 (ddd, J = 19.7, 11.0, 3.5 Hz, 2H), 3.13 (s, 2H), 2.82-2.61 (m, 2H), 2.54 (s, 1H), 2.44 (s, 2H). |

TABLE 7-continued

Compounds 119-355

| # | Structure | Name | Proton NMR(¹HNMR), Mass Spectrum(MS) |
|---|---|---|---|
| 180 | 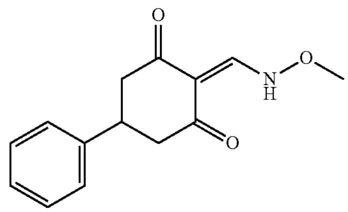 [SMILES: CONC=C1C(=O)CC(c2ccccc2)CC1=O] | 2-((methoxyamino)methylene)-5-phenylcyclohexane-1,3-dione | ¹H NMR (400 MHz, DMSO_d6) δ 12.36 (br, 1H), 8.16 (s, 1H), 7.32-7.20 (m, 5H), 3.83 (s, 3H), 3.41-3.33 (m, 1H), 2.84-2.77 (m, 2H), 2.61-2.57 (m, 2H); MS: 246.1 [M + 1]. |
| 182 | 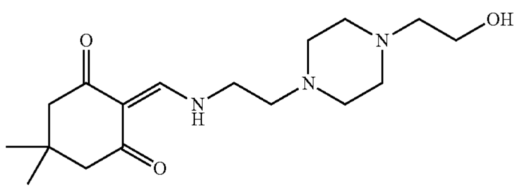 [SMILES: CC1(C)CC(=O)C(=CNCCN2CCN(CCO)CC2)C(=O)C1] | 2-(((2-(4-(2-hydroxyethyl)piperazin-1-yl)ethyl)amino)methylene)-5,5-dimethyl-cyclohexane-1,3-dione | ¹H NMR (400 MHz, CD₃OD) δ 8.19 (s, 1H), 3.68 (t, J = 6.1 Hz, 2H), 3.58 ((t, J = 5.9 Hz, 2H), 2.94 (m, 1H), 2.67-2.47 (m, 11H), 2.35 (d, J = 14.8 Hz, 4H) 1.04 (s, 6H); MS: 324.2 [M + 1]. |
| 183 | 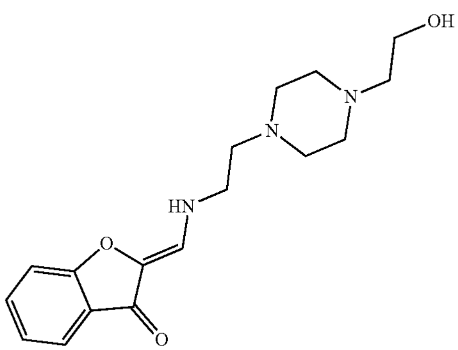 [SMILES: O=C1/C(=C/NCCN2CCN(CCO)CC2)Oc2ccccc21] | 2-(((2-(4-(2-hydroxyethyl)piperazin-1-yl)ethyl)amino)methylene)benzofuran-3(2H)-one | ¹HNMR (400 MHz, CD₃OD) δ 7.73 (d, J = 7.4 Hz, 1H), 7.57 (m, 2H), 7.31 (d, J = 8.8 Hz, 1H), 7.20 (t, J = 7.3 Hz, 1H), 3.77 (t, J = 5.5 Hz, 2H), 3.53 (t, 2H), 2.81 (m, 11H). |
| 184 | 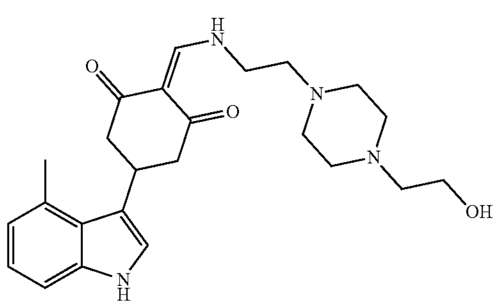 [SMILES: Cc1cccc2[nH]cc(C3CC(=O)C(=CNCCN4CCN(CCO)CC4)C(=O)C3)c12] | 2-(((2-(4-(2-hydroxyethyl)piperazin-1-yl)ethyl)amino)methylene)-5-(4-methyl-1H-indol-3-yl)cyclohexane-1,3-dione | ¹HNMR (400 MHz, CD₃OD) δ 8.26 (s, 1H), 7.16 (d, J = 8.0 Hz, 1H), 7.03 (s, 1H), 6.99-6.91 (m, 1H), 6.74 (d, J = 7.2 Hz, 1H), 3.94 (m, 1H), 3.73 (t, J = 5.8 Hz, 2H), 3.61 (t, J = 5.6 Hz, 2H), 2.95-2.55 (m, 19H). MS: 426.2 [M + 1]. |
| 185 | 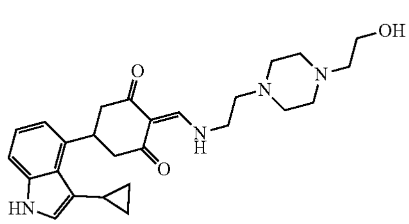 [SMILES: O=C1CC(c2cccc3[nH]cc(C4CC4)c23)CC(=O)C1=CNCCN1CCN(CCO)CC1] | 5-(3-cyclopropyl-1H-indol-4-yl)-2-(((2-(4-(2-hydroxyethyl)piperazin-1-yl)ethyl)amino)methylene)cyclohexane-1,3-dione | ¹H NMR (400 MHz, CD₃OD) δ 8.28 (s, 1H), 7.20 (d, J = 8.0 Hz, 1H), 7.05 (t, J = 7.6 Hz, 1H), 6.96-6.87 (m, 2H), 4.65 (s, 1H), 3.71 (dt, J = 25.1, 5.8 Hz, 2H), 3.61 (t, J = 5.7 Hz, 2H), 3.50 (m, 1H), 2.96-2.44 (m, 16H), 1.94 (m, 1H), 0.77 (d, J = 7.9 Hz, 2H), 0.61 (d, J = 3.5 Hz, 2H): MS: 451.2 [M + 1]. |

TABLE 7-continued

Compounds 119-355

| # | Structure | Name | Proton NMR(¹HNMR), Mass Spectrum(MS) |
|---|---|---|---|
| 186 | 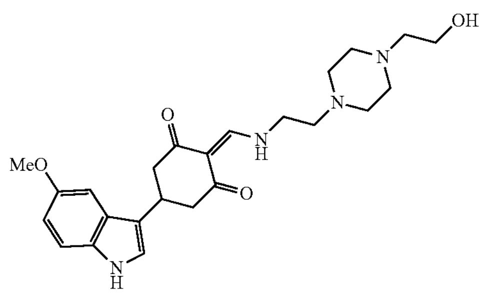 [SMILES: COc1ccc2[nH]cc(C3CC(=O)C(=CNCCN4CCN(CCO)CC4)C(=O)C3)c2c1] | 2-(((2-(4-(2-hydroxyethyl)piperazin-1-yl)ethyl)amino)methylene)-5-(5-methoxy-1H-indol-3-yl)cyclohexane-1,3-dione | ¹H NMR (400 MHz, CD₃OD) δ 8.24 (s, 1H), 7.23 (d, J = 8.8 Hz, 1H), 7.04 (s, 1H), 6.98 (s, 1H), 6.77 (d, J = 8.8 Hz, 1H), 3.81-3.76 (m, 5H), 3.66-3.59 (m, 3H), 3.05-2.65 (m, 16H); MS: 441.2 [M + 1]. |
| 187 | 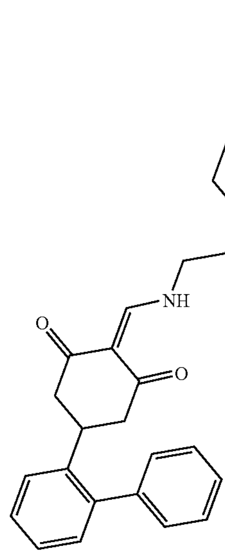 | 5-([1,1'-biphenyl]-2-yl)-2-(((2-(4-(2-hydroxyethyl)piperazin-1-yl)ethyl)amino)methylene)cyclohexane-1,3-dione | ¹H NMR (400 MHz, DMSO-d6) δ 10.93-10.77 (m, 1H), 8.03 (d, J = 14.7 Hz, 1H), 7.54 (d, J = 7.9 Hz, 1H), 7.44-7.23 (m, 6H), 7.14 (d, J = 7.5 Hz, 1H), 3.60 (s, 2H), 3.51 (d, J = 5.8 Hz, 2H), 3.30 (m, 4H), 2.73 (m, 5H), 2.28 (d, J = 14.1 Hz, 2H); MS: 448.2 [M + 1]. |
| 188 | 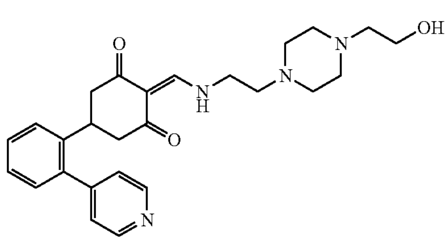 [SMILES: O=C1CC(c2ccccc2-c2ccncc2)CC(=O)C1=CNCCN1CCN(CCO)CC1] | 2-(((2-(4-(2-hydroxyethyl)piperazin-1-yl)ethyl)amino)methylene)-5-(2-(pyridin-4-yl)phenyl)cyclohexane-1,3-dione | ¹H NMR (400 MHz, DMSO-d6) δ 10.87 (m, 1H), 8.60 (d, J = 5.5 Hz, 2H), 8.03 (d, J = 14.7 Hz, 1H), 7.59 (d, J = 7.7 Hz, 1H), 7.44 (t, J = 7.1 Hz, 1H), 7.33 (m, 3H), 7.16 (dd, J = 7.5, 0.7 Hz, 1H), 4.35 (ds, 1H), 3.45 (m, 5H), 3.20 (m, 1H), 2.86-2.58 (m, 3H), 2.34 (m, 12H); MS: 449.2 [M + 1]. |
| 189 | 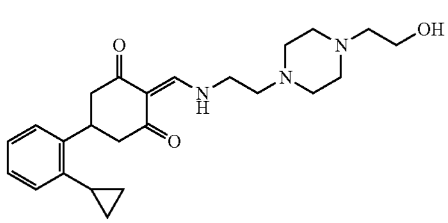 [SMILES: O=C1CC(c2ccccc2C2CC2)CC(=O)C1=CNCCN1CCN(CCO)CC1] | 5-(2-cyclopropylphenyl)-2-(((2-(4-(2-hydroxyethyl)piperazin-1-yl)ethyl)amino)methylene)cyclohexane-1,3-dione | ¹HNMR (400 MHz, DMSO-d6) δ 10.94 (d, J = 14.6 Hz, 1H), 8.13 (d, J = 14.6 Hz, 1H), 7.30 (d, J = 7.5 Hz, 1H), 7.13 (dt, J = 18.7, 7.2 Hz, 2H), 6.98 (d, J = 7.0 Hz, 1H), 4.39 (s, 1H), 3.87 (t, J = 12.3 Hz, 1H), 3.56 (d, J = 5.5 Hz, 2H), 3.46 (d, J = 5.9 Hz, 2H), 3.35 (s, 1H), 2.81-2.57 (m, 3H), 2.46-2.26 (m, 12H), 1.96 (m, 1H), 0.86 (m, 2H), 0.58 (m, 2H). |

TABLE 7-continued

Compounds 119-355

| # | Structure | Name | Proton NMR(¹HNMR), Mass Spectrum(MS) |
|---|---|---|---|
| 190 | 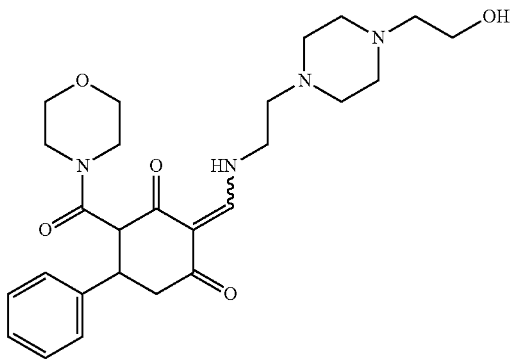 [SMILES: O=C1CC(c2ccccc2)C(C(=O)N2CCOCC2)C(=O)C1=CNCCN1CCN(CCO)CC1] | 2-(((2-(4-(2-hydroxyethyl)piperazin-1-yl)ethyl)amino)methylene)-4-(morpholine-4-carbonyl)-5-phenylcyclohexane-1,3-dione | ¹HNMR (400 MHz, CDCl₃) δ 8.29, 8.23 (two singles, 1H), 7.38-7.22 (m, 5H), 4.46-4.35 (m, 1H), 3.78-3.35 (m, 10H), 3.20-2.55 (m, 16H); MS: 485.3 [M + 1]. |
| 191 | 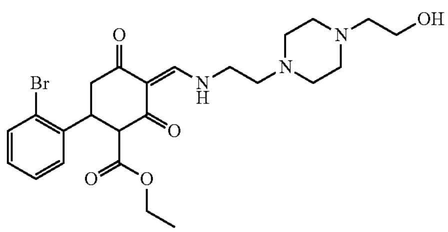 [SMILES: CCOC(=O)C1C(=O)/C(=C\NCCN2CCN(CCO)CC2)C(=O)CC1c1ccccc1Br] | ethyl-6-(2-bromophenyl)-3-(((2-(4-(2-hydroxyethyl)piperazin-1-yl)ethyl)amino)methylene)-2,4-dioxocyclohexane-1-carboxylate | ¹HNMR (400 MHz, DMSO-d6) δ 11.08-10.77 (m, 1H), 8.16 (dd, J = 15.0, 6.9 Hz, 1H), 7.60-7.51 (m, 2H), 7.37 (t, J = 7.5 Hz, 1H), 7.18-7.09 (m, 1H), 4.41-4.13 (m, 2H), 4.04-3.76 (m, 3H), 3.64-3.52 (m, 2H), 3.45 (d, J = 5.0 Hz, 2H), 2.78-2.54 (m, 2H), 2.46-2.29 (m, 9H), 1.31-1.03 (m, 2H), 0.90 (m, 3H); MS: 524.1 [M + 1] |
| 192 | 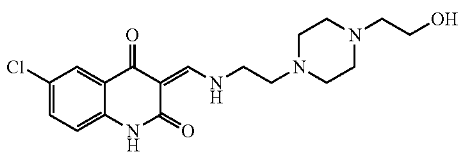 [SMILES: O=C1Nc2ccc(Cl)cc2C(=O)/C1=C/NCCN1CCN(CCO)CC1] | 6-chloro-3-(((2-(4-(2-hydroxyethyl)piperazin-1-yl)ethyl)amino)methylene)quinoline-2,4(1H,3H)-dione | ¹HNMR (400 MHz, CD₃OD) δ 8.55 (d, J = 32.6 Hz, 1H), 7.97 (d, J = 2.5 Hz, 1H), 7.49 (d, J = 6.5 Hz, 1H), 7.16 (d, J = 8.7 Hz, 1H), 3.71 (t, J = 5.4 Hz, 4H), 2.67 (m, 12H); MS: 379.1 [M + 1]. |
| 193 | 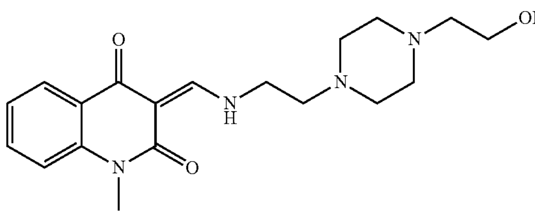 | 3-(((2-(4-(2-hydroxyethyl)piperazin-1-yl)ethyl)amino)methylene)-1-methylquinoline-2,4(1H,3H)-dione | ¹HNMR (400 MHz, CD₃OD) δ 8.59 (d, J = 18.0 Hz, 1H), 8.14 (m, 1H), 7.65 (t, J = 7.1 Hz, 1H), 7.42 (d, J = 8.5 Hz, 1H), 7.23 (t, J = 7.6 Hz, 1H), 3.82-3.76 (m, 2H), 3.73 (m, 2H), 3.57 (d, J = 3.4 Hz, 3H), 3.02 (m, 6H), 2.84-2.61 (m, 6H); MS: 359.2 [M + 1]. |
| 194 | 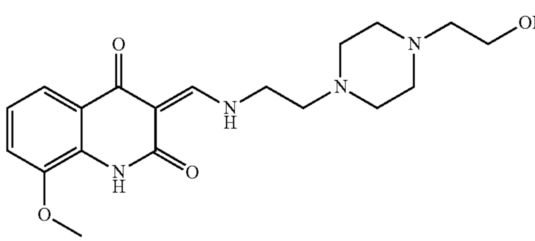 | 3-(((2-(4-(2-hydroxyethyl)piperazin-1-yl)ethyl)amino)methylene)-8-methoxyquinoline-2,4(1H,3H)-dione | ¹HNMR (400 MHz, CD₃OD) δ 8.56 (d, J = 32.3 Hz, 1H), 7.61 (d, J = 7.7 Hz, 1H), 7.23-7.06 (m, 2H), 3.97 (s, 3H), 3.81-3.66 (m, 4H), 2.99-2.57 (m, 12H); MS: 375.2 [M + 1]. |
| 195 | 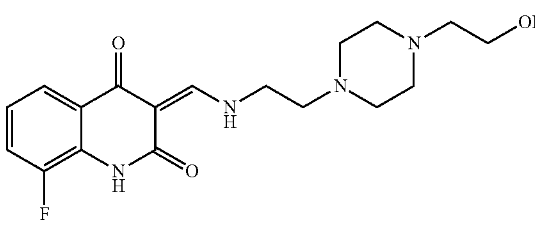 | 8-fluoro-3-(((2-(4-(2-hydroxyethyl)piperazin-1-yl)ethyl)amino)methylene)quinoline-2,4(1H,3H)-dione | ¹H NMR (400 MHz, CD₃OD) δ 8.57 (d, J = 30.8 Hz, 1H), 7.88-7.78 (m, 1H), 7.42-7.30 (m, 1H), 7.12 (m, 1H), 3.81 (m, 2H), 3.73 (m, 2H), 3.35 (s, 1H), 3.24 (s, 1H), 3.07 (d, J = 43.1 Hz, 5H), 2.75 (m, 5H); MS: 363.1 [M + 1] |

TABLE 7-continued

Compounds 119-355

| # | Structure | Name | Proton NMR(¹HNMR), Mass Spectrum(MS) |
|---|---|---|---|
| 196 | 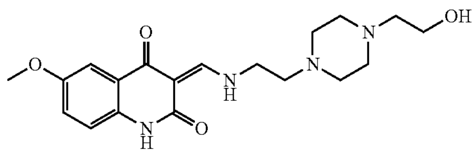 [SMILES: COc1ccc2c(c1)C(=O)/C(=C/NCCN1CCN(CCO)CC1)C(=O)N2] | 3-(((2-(4-(2-hydroxyethyl)piperazin-1-yl)ethyl)amino)methylene)-6-methoxyquinoline-2,4(1H,3H)-dione | ¹H NMR (400 MHz, DMSO-d6) δ 11.68-10.99 (m, 1H), 10.52 (d, J = 29.2 Hz, 1H), 8.43 (t, J = 14.5 Hz, 1H), 7.33 (t, J = 9.2 Hz, 1H), 7.23-7.01 (m, 2H), 4.66 (s, 1H), 3.77 (d, J = 19.5 Hz, 3H), 3.65 (m, 2H), 3.55 (s, 2H), 3.35 (s, 4H), 2.55 (m, 8H); MS: 375.2 [M + 1]. |
| 197 | 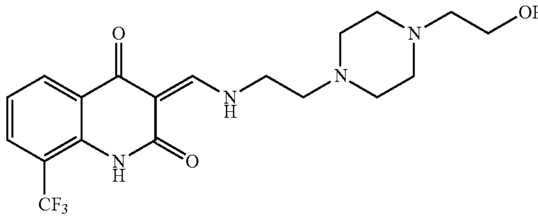 | 3-(((2-(4-(2-hydroxyethyl)piperazin-1-yl)ethyl)amino)methylene)-8-(trifluoromethyl)quinoline-2,4(1H,3H)-dione | ¹HNMR (400 MHz, CD₃OD) δ 8.54 (m, 1H), 8.35 (d, J = 7.1 Hz, 1H), 7.89 (d, J = 7.4 Hz, 1H), 7.31 (t, J = 7.9 Hz, 1H), 3.73 (m, 4H), 2.93-2.58 (m, 12H). |
| 202 | 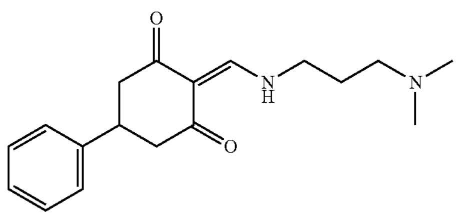 [SMILES: CN(C)CCCNC=C1C(=O)CC(c2ccccc2)CC1=O] | 2-(((3-(dimethylamino)propyl)amino)methylene)-5-phenylcyclohexane-1,3-dione | ¹HNMR (400 MHz, CDCl₃) δ 11.28 (s, 1H), 8.17 (s, 1H), 7.34 (t, J = 7.5 Hz, 2H), 7.24 (dd, J = 8.5, 7.1 Hz, 3H), 3.52 (t, J = 6.6 Hz, 2H), 3.43-3.30 (m, 1H), 2.81-2.61 (m, 4H), 2.43 (t, J = 6.9 Hz, 2H), 2.28 (s, 6H), 1.84 (p, J = 6.8 Hz, 2H). |
| 203 | 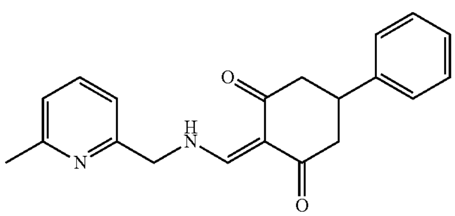 [SMILES: Cc1cccc(CNC=C2C(=O)CC(c3ccccc3)CC2=O)n1] | 2-((((6-methylpyridin-2-yl)methyl)amino)methylene)-5-phenylcyclohexane-1,3-dione | ¹HNMR (400 MHz, CDCl₃) δ 11.58 (s, 1H), 8.31 (d, J = 14.2 Hz, 1H), 7.59 (t, J = 7.7 Hz, 1H), 7.34 (t, J = 7.4 Hz, 2H), 7.27-7.18 (m, 3H), 7.11 (d, J = 7.7 Hz, 1H), 7.04 (d, J = 7.6 Hz, 1H), 4.68 (d, J = 6.1 Hz, 2H), 3.43-3.32 (m, 1H), 2.82-2.63 (m, 4H), 2.57 (s, 3H). |
| 204 | 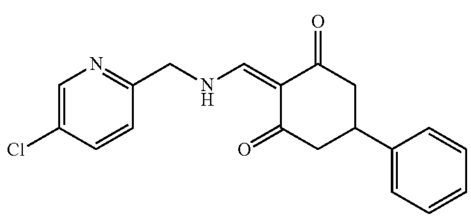 [SMILES: O=C1CC(c2ccccc2)CC(=O)C1=CNCc1ccc(Cl)cn1] | 2-((((5-chloropyridin-2-yl)methyl)amino)methylene)-5-phenylcyclohexane-1,3-dione | ¹HNMR (400 MHz, CDCl₃) δ 11.59 (s, 1H), 8.58 (d, J = 2.2 Hz, 1H), 8.30 (d, J = 14.0 Hz, 1H), 7.70 (dd, J = 8.3, 2.5 Hz, 1H), 7.35 (t, J = 7.4 Hz, 2H), 7.27-7.19 (m, 4H), 4.71 (d, J = 6.2 Hz, 2H), 3.42-3.33 (m, 1H), 2.83-2.64 (m, 4H) |
| 205 | 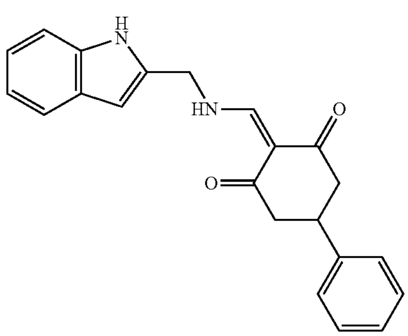 [SMILES: O=C1CC(c2ccccc2)CC(=O)C1=CNCc1cc2ccccc2[nH]1] | 2-((((1H-indol-2-yl)methyl)amino)methylene)-5-phenylcyclohexane-1,3-dione | ¹HNMR (400 MHz, DMSO-d6) δ 11.22 (s, 2H), 8.27 (d, J = 14.1 Hz, 1H), 7.51 (d, J = 7.8 Hz, 1H), 7.39-7.35 (m, 1H), 7.33-7.28 (m, 4H), 7.24-7.17 (m, 1H), 7.13-7.05 (m, 1H), 7.01-6.96 (m, 1H), 6.39 (d, J = 1.1 Hz, 1H), 4.81 (d, J = 4.7 Hz, 2H), 3.31 (td, J = 7.6, 3.8 Hz, 1H), 2.72 (ddd, J = 31.1, 16.6, 11.7 Hz, 2H), 2.55-2.50 (m, 2H) |

TABLE 7-continued

Compounds 119-355

| # | Structure | Name | Proton NMR($^1$HNMR), Mass Spectrum(MS) |
|---|---|---|---|
| 206 | 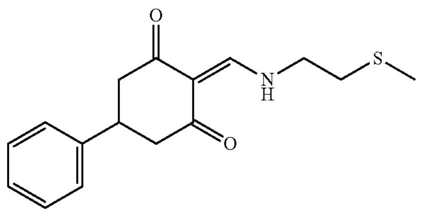 [SMILES: CSCCNC=C1C(=O)CC(c2ccccc2)CC1=O] | 2-(((2-(methylthio)ethyl)amino)methylene)-5-phenylcyclohexane-1,3-dione | $^1$HNMR (400 MHz, CDCl$_3$) δ 11.32 (s, 1H), 8.19 (d, J = 14.0 Hz, 1H), 7.34 (t, J = 7.4 Hz, 2H), 7.24 (d, J = 8.1 Hz, 3H), 3.63 (q, J = 6.4 Hz, 2H), 3.42-3.31 (m, 1H), 2.81-2.62 (m, 6H), 2.15 (s, 3H) |
| 207 | 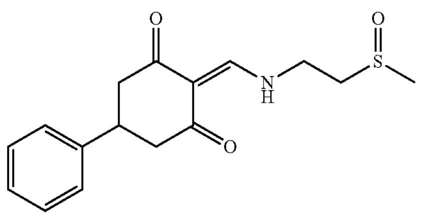 [SMILES: CS(=O)CCNC=C1C(=O)CC(c2ccccc2)CC1=O] | 2-(((2-(methylsulfinyl)ethyl)amino)methylene)-5-phenylcyclohexane-1,3-dione | $^1$HNMR (400 MHz, CDCl$_3$) δ 11.35 (s, 1H), 8.21 (d, J = 13.8 Hz, 1H), 7.34 (t, J = 7.4 Hz, 2H), 7.24 (t, J = 6.4 Hz, 3H), 4.06-3.89 (m, 2H), 3.36 (dd, J = 11.8, 8.7 Hz, 1H), 3.08-2.94 (m, 2H), 2.82-2.61 (m, 7H). |
| 208 | 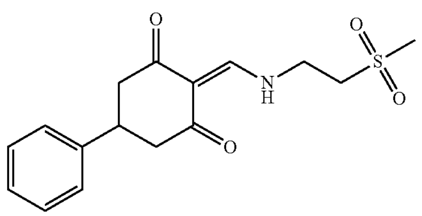 [SMILES: CS(=O)(=O)CCNC=C1C(=O)CC(c2ccccc2)CC1=O] | 2-(((2-(methylsulfonyl)ethyl)amino)methylene)-5-phenylcyclohexane-1,3-dione | $^1$HNMR (400 MHz, CDCl$_3$) δ 11.37 (s, 1H), 8.18 (d, J = 13.7 Hz, 1H), 7.34 (t, J = 7.4 Hz, 2H), 7.23 (d, J = 7.2 Hz, 3H), 3.98 (dd, J = 12.8, 6.4 Hz, 2H), 3.36 (dd, J = 14.2, 8.1 Hz, 3H), 3.00 (s, 3H), 2.83-2.63 (m, 4H) |
| 209 | 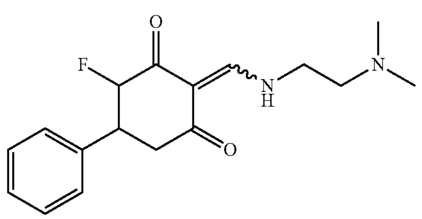 [SMILES: CN(C)CCNC=C1C(=O)CC(c2ccccc2)C(F)C1=O] | 2-(((2-(dimethylamino)ethyl)amino)methylene)-4-fluoro-5-phenylcyclohexane-1,3-dione | $^1$H NMR (400 MHz, cdcl$_3$) δ 11.31, 11.13 (2s, 1H), 8.24, 8.17 (2d, J = 14.7 Hz, 1H), 7.37-7.27 (m, 5H), 5.08, 4.96 (2dd, J = 8.6, 2.8 Hz, 1H), 3.65-3.48 (m, 3H), 3.18-3.07 (m, 1H), 2.81-2.69 (m, 1H), 2.55 (t, J = 6.1 Hz, 2H), 2.28 (d, J = 2.1 Hz, 6H) |
| 210 | 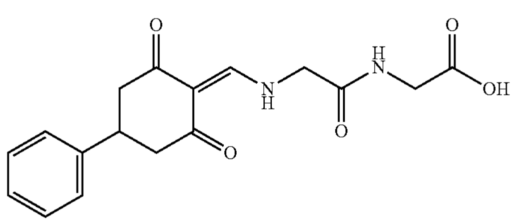 [SMILES: O=C(O)CNC(=O)CNC=C1C(=O)CC(c2ccccc2)CC1=O] | ((2,6-dioxo-4-phenylcyclohexylidene)methyl)glycylglycine | $^1$HNMR (400 MHz, CD$_3$OD) δ 8.22 (s, 1H), 7.37-7.26 (m, 4H), 7.26-7.19 (m, 1H), 4.29 (s, 2H), 3.96 (s, 2H), 3.42-3.33 (m, 1H), 2.80 (ddd, J = 23.7, 16.8, 11.6 Hz, 2H), 2.71-2.63 (m, 2H) |
| 211 | 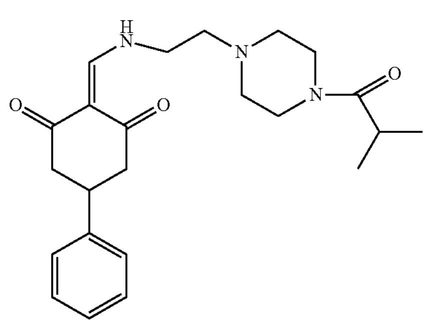 [SMILES: CC(C)C(=O)N1CCN(CCNC=C2C(=O)CC(c3ccccc3)CC2=O)CC1] | 2-(((2-(4-isobutyrylpiperazin-1-yl)ethyl)amino)methylene)-5-phenylcyclohexane-1,3-dione | $^1$HNMR (300 MHz, CDCl$_3$) δ 11.24 (s, 1H), 8.19 (d, J = 14.4 Hz, 1H), 7.38-7.29 (m, 2H), 7.26 (s, 1H), 7.23 (d, J = 8.0 Hz, 2H), 3.67 (s, 2H), 3.60-3.47 (m, 4H), 3.35 (s, 1H), 2.83-2.70 (m, 4H), 2.64 (dd, J = 11.8, 5.7 Hz, 2H), 2.49 (s, 4H), 1.12 (d, J = 6.7 Hz, 6H) |

TABLE 7-continued

Compounds 119-355

| # | Structure | Name | Proton NMR($^1$HNMR), Mass Spectrum(MS) |
|---|---|---|---|
| 212 | 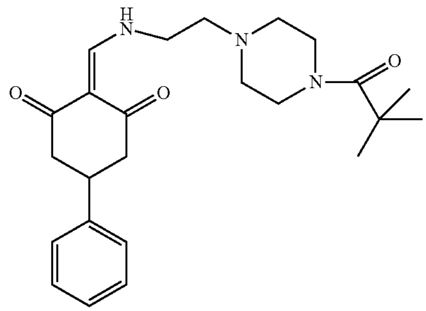 [SMILES: CC(C)(C)C(=O)N1CCN(CCNC=C2C(=O)CC(c3ccccc3)CC2=O)CC1] | 5-phenyl-2-(((2-(4-pivaloylpiperazin-1-yl)ethyl)amino) methylene) cyclohexane-1,3-dione | $^1$HNMR (300 MHz, CDCl$_3$) δ 11.26 (s, 1H), 8.19 (d, J = 14.4 Hz, 1H), 7.34 (t, J = 7.3 Hz, 2H), 7.23 (d, J = 8.4 Hz, 3H), 3.69 (s, 4H), 3.52 (d, J = 5.9 Hz, 2H), 3.35 (s, 1H), 2.75 (q, J = 8.6 Hz, 4H), 2.63 (dd, J = 13.9, 7.8 Hz, 2H), 2.49 (s, 4H), 1.27 (s, 9H). |
| 213 | 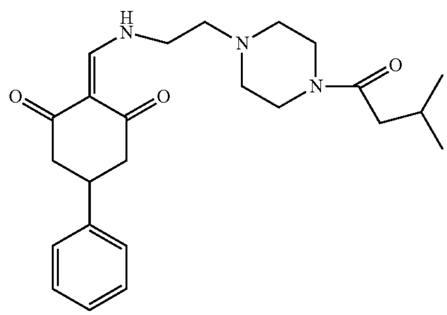 [SMILES: CC(C)CC(=O)N1CCN(CCNC=C2C(=O)CC(c3ccccc3)CC2=O)CC1] | 2-(((2-(4-(3-methylbutanoyl) piperazin-1-yl)ethyl)amino) methylene)-5-phenylcyclohexane-1,3-dione | $^1$HNMR (300 MHz, CDCl$_3$) δ 11.39 (s, 1H), 8.19 (d, J = 14.7 Hz, 1H), 7.33 (d, J = 7.3 Hz, 2H), 7.26 (s, 1H), 7.23 (d, J = 7.8 Hz, 2H), 3.67 (s, 2H), 3.53 (s, 4H), 3.36 (s, 1H), 2.77-2.69 (m, 2H), 2.69-2.58 (m, 2H), 2.49 (s, 4H), 2.20 (d, J = 6.7 Hz, 2H), 2.15-2.03 (m, 1H), 1.77-1.51 (m, 2H), 0.96 (d, J = 6.3 Hz, 6H) |
| 214 | 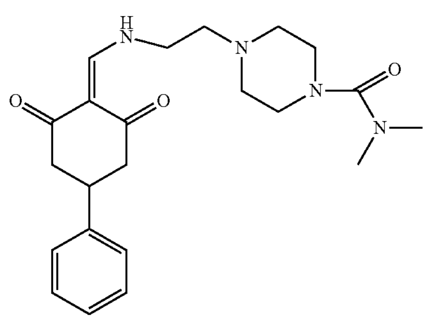 [SMILES: CN(C)C(=O)N1CCN(CCNC=C2C(=O)CC(c3ccccc3)CC2=O)CC1] | 4-(2-(((2,6-dioxo-4-phenylcyclo-hexylidene) methyl)amino)e thyl)-N,N-dimethylpiperazine-1-carboxamide | $^1$HNMR (300 MHz, CDCl$_3$) δ 11.30 (m, 1H), 8.17 (d, J = 14.9 Hz, 1H), 7.26-7.24 (m, 1H), 7.13 (s, 4H), 3.51 (d, J = 6.0 Hz, 2H), 3.30 (s, 5H), 2.81 (s, 6H), 2.72 (d, J = 6.8 Hz, 3H), 2.66-2.57 (m, 2H), 2.49 (s, 4H), 2.33 (s, 2H) |
| 215 | 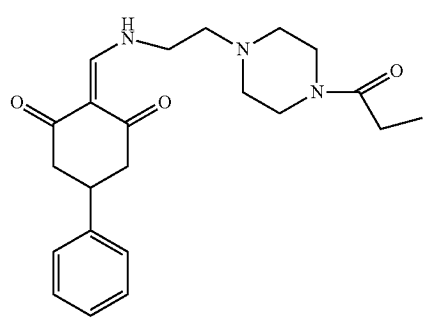 [SMILES: CCC(=O)N1CCN(CCNC=C2C(=O)CC(c3ccccc3)CC2=O)CC1] | 5-phenyl-2-(((2-(4-propionylpiperazin-1-yl)ethyl)amino) methylene) cyclohexane-1,3-dione | $^1$HNMR (300 MHz, CDCl$_3$) δ 11.25 (s, 1H), 8.19 (d, J = 14.3 Hz, 1H), 7.40-7.29 (m, 2H), 7.23 (d, J = 8.2 Hz, 3H), 3.66 (s, 2H), 3.51 (s, 4H), 3.36 (s, 1H), 2.75 (d, J = 7.3 Hz, 2H), 2.64 (dd, J = 12.2, 6.2 Hz, 2H), 2.49 (s, 4H), 2.34 (q, J = 7.5 Hz, 2H), 1.25 (s, 2H), 1.14 (t, J = 7.4 Hz, 3H) |

TABLE 7-continued

Compounds 119-355

| # | Structure | Name | Proton NMR($^1$HNMR), Mass Spectrum(MS) |
|---|---|---|---|
| 216 | 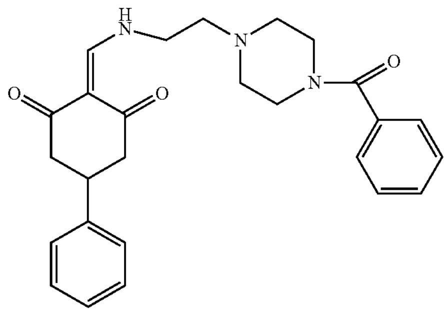 [SMILES: O=C1CC(c2ccccc2)CC(=O)C1=CNCCN1CCN(C(=O)c2ccccc2)CC1] | 2-(((2-(4-benzoylpiperazin-1-yl)ethyl)amino)methylene)-5-phenylcyclohexane-1,3-dione | $^1$HNMR (300 MHz, CDCl$_3$) δ 11.25 (s, 1H), 8.21 (d, J = 14.7 Hz, 1H), 8.10 (d, J = 7.6 Hz, 2H), 7.48 (d, J = 7.7 Hz, 1H), 7.40 (s, 4H), 7.32 (d, J = 7.1 Hz, 1H), 7.23 (d, J = 7.7 Hz, 2H), 3.85 (s, 2H), 3.54 (d, J = 5.8 Hz, 4H), 3.36 (s, 1H), 2.84-2.69 (m, 4H), 2.64 (d, J = 13.3 Hz, 4H), 2.48 (s, 2H) |
| 217 | 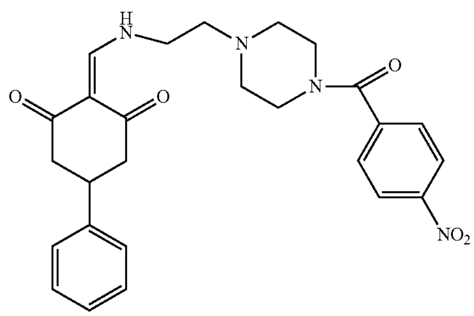 [SMILES: O=C1CC(c2ccccc2)CC(=O)C1=CNCCN1CCN(C(=O)c2ccc([N+](=O)[O-])cc2)CC1] | 2-(((2-(4-(4-nitrobenzoyl)piperazin-1-yl)ethyl)amino)methylene)-5-phenylcyclohexane-1,3-dione | $^1$HNMR (300 MHz, CDCl$_3$) δ 11.26 (s, 1H), 8.29 (d, J = 8.4 Hz, 2H), 8.19 (d, J = 14.3 Hz, 1H), 7.57 (d, J = 8.5 Hz, 2H), 7.33 (d, J = 7.1 Hz, 2H), 7.22 (s, 3H), 3.86 (s, 2H), 3.53 (d, J = 5.8 Hz, 4H), 3.42 (s, 2H), 3.38-3.28 (m, 1H), 2.83-2.69 (m, 4H), 2.65 (d, J = 6.0 Hz, 4H), 2.47 (s, 2H) |
| 218 | 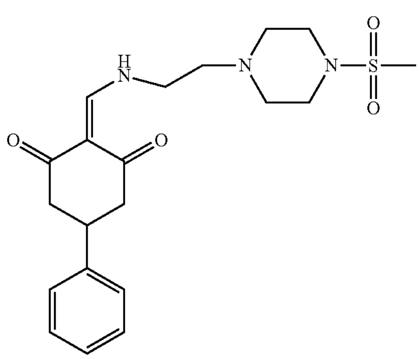 [SMILES: CS(=O)(=O)N1CCN(CCNC=C2C(=O)CC(c3ccccc3)CC2=O)CC1] | 2-(((2-(4-(methylsulfonyl)piperazin-1-yl)ethyl)amino)methylene)-5-phenylcyclohexane-1,3-dione | $^1$HNMR (300 MHz, CDCl$_3$) δ 11.22 (s, 1H), 8.18 (d, J = 14.3 Hz, 1H), 7.37-7.30 (m, 2H), 7.23 (d, J = 7.9 Hz, 3H), 3.60-3.46 (m, 2H), 3.36 (d, J = 5.5 Hz, 1H), 3.28 (s, 4H), 2.79 (s, 3H), 2.75 (d, J = 7.5 Hz, 2H), 2.72-2.63 (m, 4H), 2.67-2.59 (m, 4H) |
| 219 | 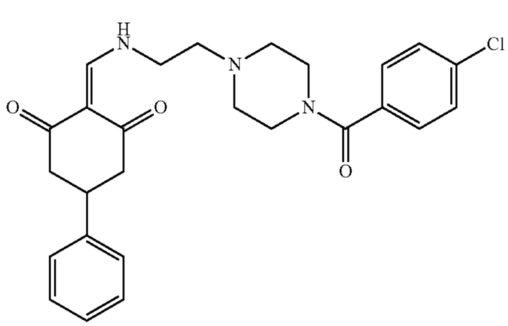 [SMILES: O=C1CC(c2ccccc2)CC(=O)C1=CNCCN1CCN(C(=O)c2ccc(Cl)cc2)CC1] | 2-(((2-(4-(4-chlorobenzoyl)piperazin-1-yl)ethyl)amino)methylene)-5-phenylcyclohexane-1,3-dione | $^1$HNMR (300 MHz, CDCl$_3$) δ 11.25 (s, 1H), 8.18 (d, J = 14.3 Hz, 1H), 7.37 (d, J = 6.6 Hz, 5H), 7.24 (d, J = 12.4 Hz, 4H), 3.81 (s, 2H), 3.51 (s, 4H), 3.40-3.29 (m, 1H), 2.83-2.67 (m, 4H), 2.65 (s, 2H), 2.62-2.35 (m, 4H) |

TABLE 7-continued

Compounds 119-355

| # | Structure | Name | Proton NMR(¹HNMR), Mass Spectrum(MS) |
|---|---|---|---|
| 220 | 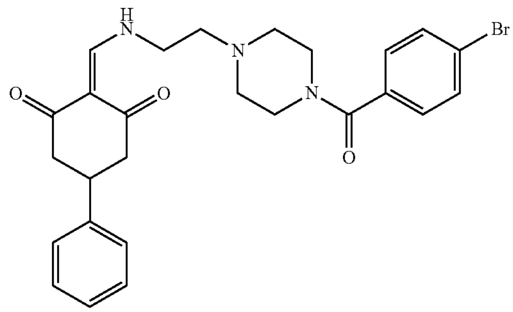 [SMILES: O=C1CC(c2ccccc2)CC(=O)C1=CNCCN1CCN(C(=O)c2ccc(Br)cc2)CC1] | 2-(((2-(4-(4-bromobenzoyl)piperazin-1-yl)ethyl)amino)methylene)-5-phenylcyclohexane-1,3-dione | ¹HNMR (300 MHz, CDCl₃) δ 11.26 (s, 1H), 8.18 (d, J = 14.1 Hz, 1H), 7.55 (d, J = 7.7 Hz, 2H), 7.38-7.27 (m, 4H), 7.23 (d, J = 7.4 Hz, 3H), 3.81 (s, 2H), 3.52 (d, J = 5.7 Hz, 4H), 3.36 (s, 1H), 2.82-2.68 (m, 4H), 2.65 (d, J = 6.4 Hz, 2H), 2.51 (d, J = 29.1 Hz, 4H) |
| 221 | 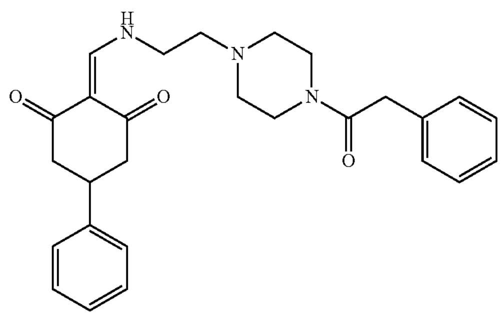 [SMILES: O=C1CC(c2ccccc2)CC(=O)C1=CNCCN1CCN(C(=O)Cc2ccccc2)CC1] | 5-phenyl-2-(((2-(4-(2-phenylacetyl)piperazin-1-yl)ethyl)amino)methylene)cyclohexane-1,3-dione | ¹HNMR (300 MHz, CDCl₃) δ 11.19 (s, 1H), 8.16 (d, J = 14.4 Hz, 1H), 7.38-7.28 (m, 5H), 7.23 (d, J = 7.7 Hz, 5H), 3.73 (s, 2H), 3.69 (s, 2H), 3.48 (d, J = 5.4 Hz, 4H), 3.35 (s, 1H), 2.81-2.63 (m, 4H), 2.57 (t, J = 5.6 Hz, 2H), 2.45 (s, 2H), 2.30 (s, 2H) |
| 222 | 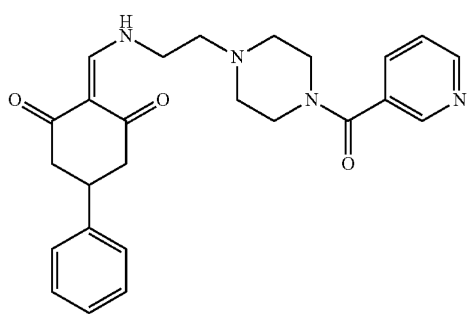 [SMILES: O=C1CC(c2ccccc2)CC(=O)C1=CNCCN1CCN(C(=O)c2cccnc2)CC1] | 2-(((2-(4-nicotinoylpiperazin-1-yl)ethyl)amino)methylene)-5-phenylcyclohexane-1,3-dione | ¹HNMR (300 MHz, CDCl₃) δ 11.26 (s, 1H), 8.66 (s, 2H), 8.18 (d, J = 14.4 Hz, 1H), 7.75 (d, J = 7.9 Hz, 1H), 7.35 (dd, J = 15.1, 7.6 Hz, 4H), 7.25-7.19 (m, 2H), 3.86 (s, 2H), 3.52 (d, J = 5.4 Hz, 4H), 3.38 (s, 1H), 2.85-2.70 (m, 4H), 2.65 (d, J = 6.0 Hz, 4H), 2.51 (t, J = 29.8 Hz, 2H) |
| 223 | 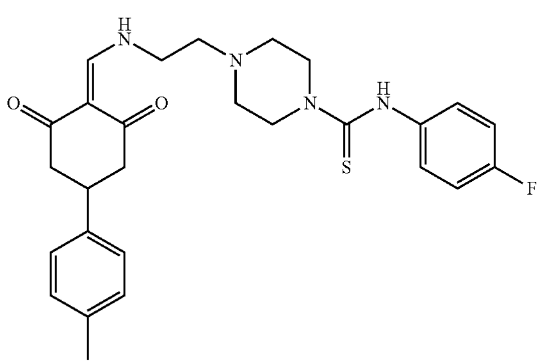 [SMILES: Cc1ccc(C2CC(=O)C(=CNCCN3CCN(C(=S)Nc4ccc(F)cc4)CC3)C(=O)C2)cc1] | 4-(2-(((2,6-dioxo-4-(p-tolyl)cyclohexylidene)methyl)amino)ethyl)-N-(4-fluorophenyl)piperazine-1-carbothioamide | ¹HNMR (300 MHz, DMSO) δ 10.93 (s, 1H), 9.28 (s, 1H), 8.14 (d, J = 14.5 Hz, 1H), 7.30-7.22 (m, 2H), 7.17 (d, J = 7.8 Hz, 2H), 7.11 (t, J = 7.2 Hz, 4H), 3.85 (s, 2H), 3.59 (s, 4H), 3.31 (s, 3H), 3.27-3.17 (m, 1H), 2.79 (m, 4H), 2.65 (d, J = 6.4 Hz, 2H), 2.22 (d, J = 13.5 Hz, 4H) |

TABLE 7-continued

Compounds 119-355

| # | Structure | Name | Proton NMR($^1$HNMR), Mass Spectrum(MS) |
|---|-----------|------|-----------------------------------------|
| 224 | 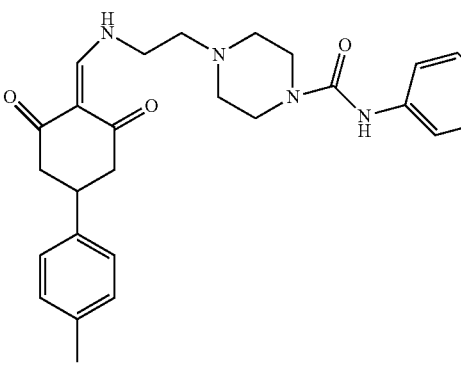 | 4-(2-(((2,6-dioxo-4-(p-tolyl)cyclohexylidene)methyl)amino)ethyl)-N-(p-tolyl)piperazine-1-carboxamide | $^1$HNMR (300 MHz, CDCl$_3$) δ 11.43-10.70 (m, 2H), 8.18 (d, J = 14.1 Hz, 1H), 7.26 (s, 1H), 7.21 (d, J = 8.4 Hz, 1H), 7.17-7.05 (m, 3H), 6.26 (s, 1H), 3.54 (s, 2H), 3.40-3.26 (m, 1H), 2.70 (dd, J = 18.3, 9.0 Hz, 3H), 2.55 (s, 2H), 2.31 (d, J = 11.6 Hz, 3H) |
| 225 | 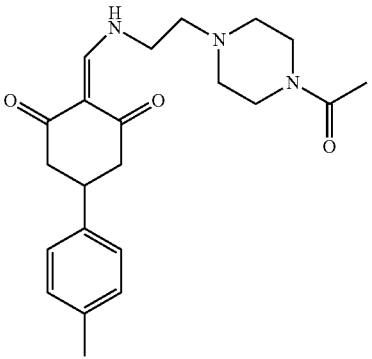 [SMILES: CC(=O)N1CCN(CCNC=C2C(=O)CC(c3ccc(C)cc3)CC2=O)CC1] | 2-(((2-(4-acetylpiperazin-1-yl)ethyl)amino)methylene)-5-(p-tolyl)cyclohexane-1,3-dione | $^1$HNMR (300 MHz, CDCl$_3$) δ 11.31-11.12 (m, 1H), 8.18 (d, J = 14.2 Hz, 1H), 7.13 (d, J = 2.6 Hz, 4H), 3.65 (s, 2H), 3.50 (d, J = 5.7 Hz, 3H), 3.42 (m, 2H), 3.33 (s, 1H), 2.73 (q, J = 9.0 Hz, 4H), 2.62 (d, J = 5.1 Hz, 2H), 2.55-2.42 (m, 4H), 2.30 (d, J = 13.6 Hz, 2H), 2.08 (s, 3H) |
| 226 | 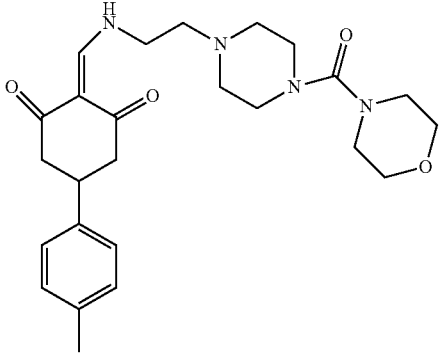 [SMILES: Cc1ccc(C2CC(=O)C(=CNCCN3CCN(C(=O)N4CCOCC4)CC3)C(=O)C2)cc1] | 2-(((2-(4-(morpholine-4-carbonyl)piperazin-1-yl)ethyl)amino)methylene)-5-(p-tolyl)cyclohexane-1,3-dione | $^1$HNMR (300 MHz, CDCl$_3$) δ 11.25 (m, 1H), 8.17 (d, J = 14.3 Hz, 1H), 7.18-6.89 (m, 4H), 3.69-3.62 (m, 5H), 3.51 (d, J = 5.8 Hz, 2H), 3.34 (s, 4H), 3.28-3.20 (m, 4H), 2.77-2.58 (m, 6H), 2.49 (s, 4H), 2.32 (s, 3H) |
| 227 | 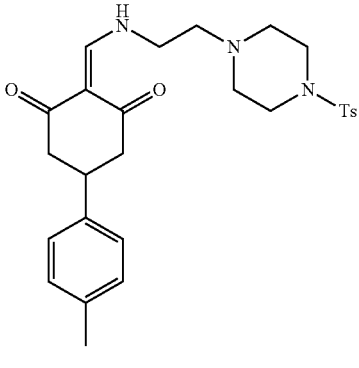 [SMILES: Cc1ccc(C2CC(=O)C(=CNCCN3CCN(S(=O)(=O)c4ccc(C)cc4)CC3)C(=O)C2)cc1] | 5-(p-tolyl)-2-(((2-(4-tosylpiperazin-1-yl)ethyl)amino)methylene)cyclohexane-1,3-dione | $^1$HNMR (300 MHz, CDCl$_3$) δ 11.05 (s, 1H), 8.09 (d, J = 14.2 Hz, 1H), 7.62 (d, J = 7.5 Hz, 2H), 7.44-7.24 (m, 2H), 7.11 (d, J = 6.1 Hz, 4H), 3.45 (d, J = 4.5 Hz, 2H), 3.27 (s, 1H), 3.05 (s, 4H), 2.73-2.53 (m, 8H), 2.37 (d, J = 31.3 Hz, 6H) |

TABLE 7-continued

Compounds 119-355

| # | Structure | Name | Proton NMR(¹HNMR), Mass Spectrum(MS) |
|---|---|---|---|
| 228 | 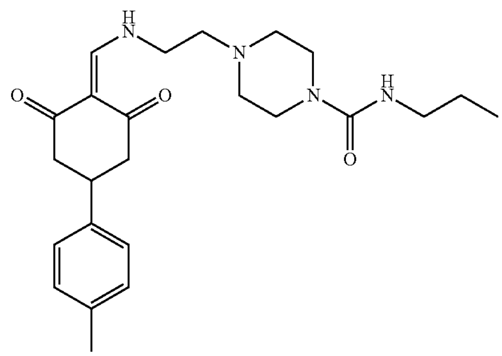 [SMILES: CCCNC(=O)N1CCN(CCNC=C2C(=O)CC(c3ccc(C)cc3)CC2=O)CC1] | 4-(2-(((2,6-dioxo-4-(p-tolyl)cyclohexylidene)methyl)amino)ethyl)-N-propylpiperazine-1-carboxamide | ¹HNMR (300 MHz, CDCl₃) δ 11.23 (s, 1H), 8.17 (d, J = 14.3 Hz, 1H), 7.20-7.07 (m, 4H), 4.47 (s, 1H), 3.49 (dd, J = 13.7, 8.2 Hz, 2H), 3.46-3.34 (m, 4H), 3.36-3.22 (m, 1H), 3.18 (dd, J = 13.0, 6.6 Hz, 2H), 2.79-2.60 (m, 6H), 2.46 (t, J = 16.1 Hz, 4H), 2.32 (s, 3H), 1.62-1.38 (m, 2H), 0.89 (dd, J = 16.1, 8.7 Hz, 3H) |
| 229 | 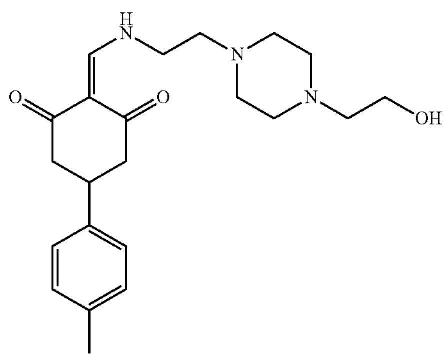 [SMILES: Cc1ccc(C2CC(=O)C(=CNCCN3CCN(CCO)CC3)C(=O)C2)cc1] | 2-(((2-(4-(2-hydroxyethyl)piperazin-1-yl)ethyl)amino)methylene)-5-(p-tolyl)cyclohexane-1,3-dione | ¹HNMR (300 MHz, CDCl₃) δ 11.20 (s, 1H), 8.17 (d, J = 14.3 Hz, 1H), 7.14 (d, J = 8.6 Hz, 4H), 3.71-3.63 (m, 2H), 3.55-3.29 (m, 5H), 2.73-2.59 (m, 14H), 2.32 (s, 3H) |
| 230 | 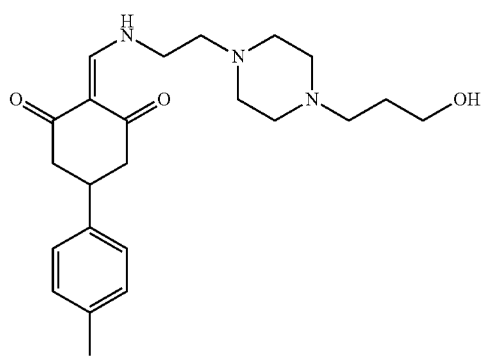 [SMILES: Cc1ccc(C2CC(=O)C(=CNCCN3CCN(CCCO)CC3)C(=O)C2)cc1] | 2-(((2-(4-(3-hydroxypropyl)piperazin-1-yl)ethyl)amino)methylene)-5-(p-tolyl)cyclohexane-1,3-dione | ¹HNMR (300 MHz, CDCl₃) δ 11.20 (s, 2H), 8.16 (d, J = 14.4 Hz, 1H), 7.18-7.06 (m, 4H), 3.84-3.72 (m, 2H), 3.49 (dd, J = 11.6, 5.8 Hz, 2H), 3.31 (d, J = 5.9 Hz, 1H), 2.87-2.50 (m, 14H), 2.33 (s, 3H), 1.85-1.72 (m, 2H) |
| 231 | 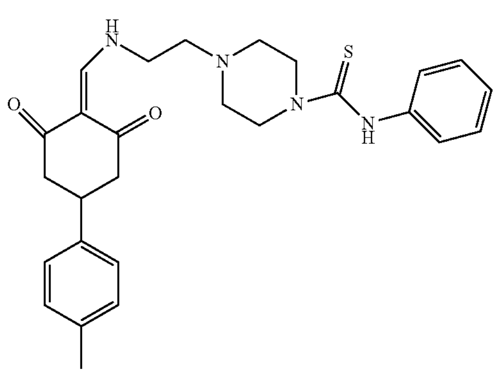 [SMILES: Cc1ccc(C2CC(=O)C(=CNCCN3CCN(C(=S)Nc4ccccc4)CC3)C(=O)C2)cc1] | 4-(2-(((2,6-dioxo-4-(p-tolyl)cyclohexylidene)methyl)amino)ethyl)-N-phenylpiperazine-1-carbothioamide | ¹HNMR (300 MHz, CDCl₃) δ 11.28 (m, 1H), 8.17 (d, J = 14.2 Hz, 1H), 7.32 (d, J = 7.8 Hz, 3H), 7.13 (d, J = 3.2 Hz, 6H), 3.87 (s, 4H), 3.50 (s, 2H), 3.36-3.26 (m, 1H), 2.81-2.65 (m, 4H), 2.64 (s, 2H), 2.57 (s, 4H), 2.33 (s, 3H) |

TABLE 7-continued

Compounds 119-355

| # | Structure | Name | Proton NMR(¹HNMR), Mass Spectrum(MS) |
|---|---|---|---|
| 232 | 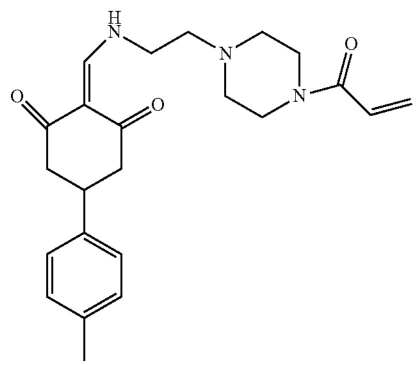 [SMILES: C=CC(=O)N1CCN(CCNC=C2C(=O)CC(c3ccc(C)cc3)CC2=O)CC1] | 2-(((2-(4-acryloylpiperazin-1-yl)ethyl)amino)methylene)-5-(p-tolyl)cyclohexane-1,3-dione | ¹HNMR (300 MHz, CDCl₃) δ 11.21 (s, 1H), 8.18 (d, J = 14.4 Hz, 1H), 7.14 (d, J = 10.6 Hz, 4H), 6.55 (dd, J = 16.4, 10.9 Hz, 1H), 6.28 (d, J = 16.8 Hz, 1H), 5.69 (d, J = 10.5 Hz, 1H), 3.73 (s, 2H), 3.57 (d, J = 22.5 Hz, 2H), 3.57-3.43 (m, 1H), 3.30 (d, J = 6.0 Hz, 2H), 2.83-2.65 (m, 4H), 2.63 (t, J = 5.4 Hz, 2H), 2.55-2.42 (m, 4H), 2.33 (s, 3H) |
| 233 | 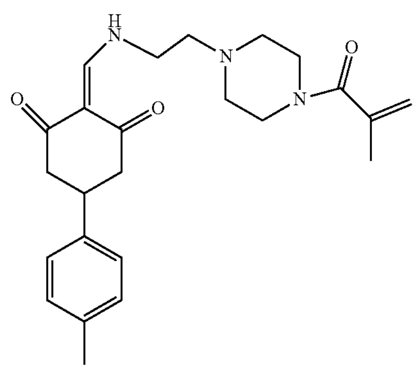 [SMILES: C=C(C)C(=O)N1CCN(CCNC=C2C(=O)CC(c3ccc(C)cc3)CC2=O)CC1] | 2-(((2-(4-methacryloyl-piperazin-1-yl)ethyl)amino)methylene)-5-(p-tolyl)cyclohexane-1,3-dione | ¹H NMR (300 MHz, CDCl₃) δ 11.28 (m, 1H), 8.18 (d, J = 14.0 Hz, 1H), 7.15 (d, J = 10.7 Hz, 4H), 5.19 (s, 1H), 5.02 (s, 1H), 3.63 (s, 4H), 3.52 (d, J = 5.8 Hz, 2H), 3.31 (s, 1H), 2.80-2.69 (m, 4H), 2.62 (d, J = 5.6 Hz, 2H), 2.49 (s, 4H), 2.33 (s, 3H), 1.94 (s, 3H) |
| 236 | 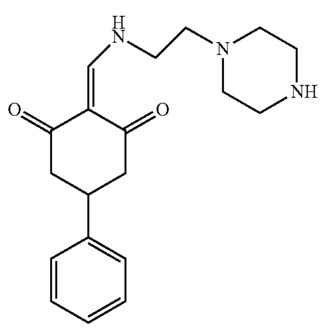 [SMILES: O=C1CC(c2ccccc2)CC(=O)C1=CNCCN1CCNCC1] | 5-phenyl-2-(((2-(piperazin-1-yl)ethyl)amino)methylene)cyclohexane-1,3-dione | ¹HNMR (300 MHz, CDCl₃) δ 11.20 (s, 1H), 8.17 (d, J = 14.0 Hz, 1H), 7.32 (d, J = 7.3 Hz, 2H), 7.24 (t, J = 6.7 Hz, 3H), 3.48 (d, J = 7.0 Hz, 2H), 3.41 (s, 4H), 3.41 (s, 2H), 3.08 (s, 2H), 2.74 (d, J = 7.1 Hz, 2H), 2.64 (s, 4H), 2.52 (s, 1H) |
| 237 | 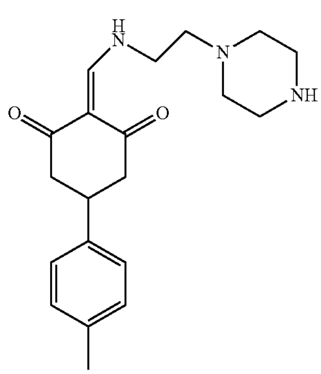 [SMILES: Cc1ccc(C2CC(=O)C(=CNCCN3CCNCC3)C(=O)C2)cc1] | 2-(((2-(piperazin-1-yl)ethyl)amino)methylene)-5-(p-tolyl)cyclohexane-1,3-dione | ¹HNMR (300 MHz, CDCl₃) δ 11.31-11.16 (m, 2H), 8.14 (s, 1H), 7.13 (s, 4H), 3.51 (s, 3H), 3.38-3.27 (m, 2H), 3.12 (s, 4H), 2.71 (s, 4H), 2.43 (s, 6H), 2.33 (s, 3H) |

TABLE 7-continued

Compounds 119-355

| # | Structure | Name | Proton NMR(¹HNMR), Mass Spectrum(MS) |
|---|---|---|---|
| 238 | 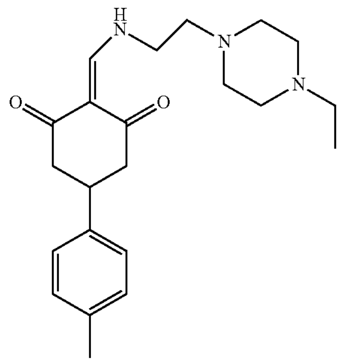 [SMILES: CCN1CCN(CCNC=C2C(=O)CC(c3ccc(C)cc3)CC2=O)CC1] | 2-(((2-(4-ethylpiperazin-1-yl)ethyl)amino)methylene)-5-(p-tolyl)cyclohexane-1,3-dione | ¹HNMR (300 MHz, CDCl₃) δ 11.20 (s, 1H), 8.16 (d, J = 14.3 Hz, 1H), 7.13 (s, 4H), 3.45 (t, J = 23.7 Hz, 2H), 3.31 (d, J = 5.3 Hz, 1H), 2.83-2.53 (m, 16H), 2.32 (s, 3H), 1.20 (t, J = 7.2 Hz, 3H) |
| 239 | 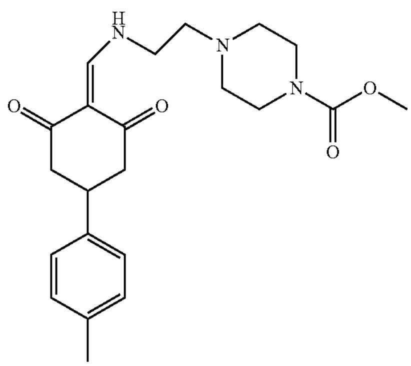 [SMILES: COC(=O)N1CCN(CCNC=C2C(=O)CC(c3ccc(C)cc3)CC2=O)CC1] | methyl 4-(2-(((2,6-dioxo-4-(p-tolyl)cyclohexylidene)methyl)amino)ethyl)piperazine-1-carboxylate | ¹HNMR (300 MHz, CDCl₃) δ 11.22 (s, 1H), 8.17 (d, J = 14.3 Hz, 1H), 7.13 (s, 4H), 3.69 (s, 3H), 3.50 (d, J = 4.2 Hz, 6H), 3.29 (d, J = 5.0 Hz, 1H), 2.77-2.53 (m, 6H), 2.45 (s, 4H), 2.32 (s, 3H) |
| 240 | 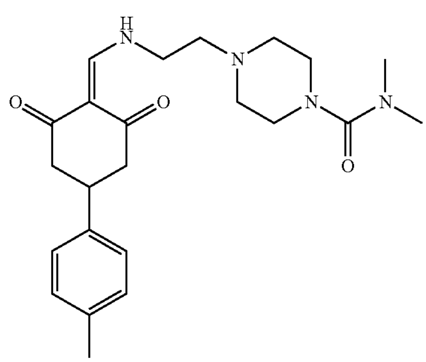 [SMILES: Cc1ccc(C2CC(=O)C(=CNCCN3CCN(C(=O)N(C)C)CC3)C(=O)C2)cc1] | 4-(2-(((2,6-dioxo-4-(p-tolyl)cyclohexylidene)methyl)amino)ethyl)-N,N-dimethyl-piperazine-1-carboxamide | ¹HNMR (300 MHz, CDCl₃) δ 11.26 (m, 1H), 8.17 (d, J = 14.2 Hz, 1H), 7.13 (s, 4H), 3.51 (d, J = 6.0 Hz, 2H), 3.30 (s, 5H), 2.81 (s, 4H), 2.72 (d, J = 6.8 Hz, 6H), 2.66-2.56 (m, 4H), 2.49 (s, 4H), 2.33 (s, 3H) |
| 241 | 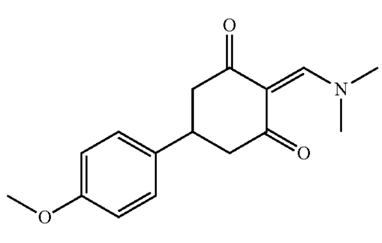 | 2-((dimethylamino)methylene)-5-(4-methoxyphenyl)cyclohexane-1,3-dione | ¹HNMR (300 MHz, CDCl₃) δ 8.04 (d, J = 16.8 Hz, 1H), 7.16 (d, J = 8.4 Hz, 2H), 6.86 (d, J = 8.5 Hz, 2H), 3.79 (s, 3H), 3.41 (s, 3H), 3.30 (td, J = 11.3, 5.7 Hz, 1H), 3.19 (d, J = 11.1 Hz, 3H), 2.69 (qd, J = 16.7, 8.1 Hz, 4H) |

TABLE 7-continued

Compounds 119-355

| # | Structure | Name | Proton NMR(¹HNMR), Mass Spectrum(MS) |
|---|---|---|---|
| 242 | 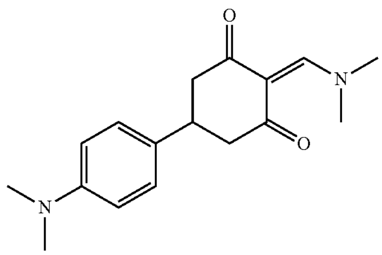 | 2-((dimethylamino)methylene)-5-(4-(dimethylamino)phenyl)cyclohexane-1,3-dione | ¹HNMR (300 MHz, CDCl₃) δ 8.07 (s, 1H), 7.12 (d, J = 8.4 Hz, 2H), 6.72 (d, J = 8.6 Hz, 2H), 3.41 (s, 3H), 3.27 (s, 1H), 3.21 (s, 3H), 2.93 (s, 6H), 2.78-2.59 (m, 4H) |
| 245 | 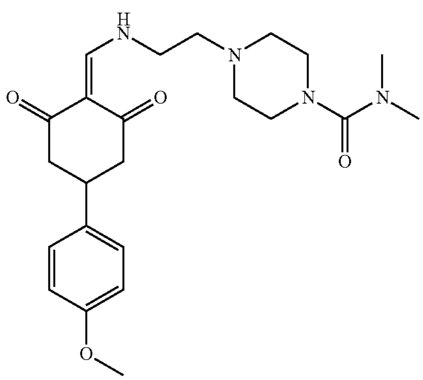 [SMILES: COc1ccc(C2CC(=O)C(=CNCCN3CCN(C(=O)N(C)C)CC3)C(=O)C2)cc1] | 4-(2-(((4-(4-methoxyphenyl)-2,6-dioxocyclohexylidene)methyl)amino)ethyl)-N,N-dimethylpiperazine-1-carboxamide | ¹HNMR (300 MHz, CDCl₃) δ 11.27 (m, 1H), 8.17 (d, J = 14.4 Hz, 1H), 7.13 (s, 4H), 3.51 (d, J = 5.1 Hz, 2H), 3.30 (s, 5H), 3.10 (q, J = 7.2 Hz, 4H), 2.81 (s, 6H), 2.65 (dd, J = 32.5, 10.9 Hz, 6H), 2.49 (s, 4H), 2.33 (s, 3H) |
| 246 | 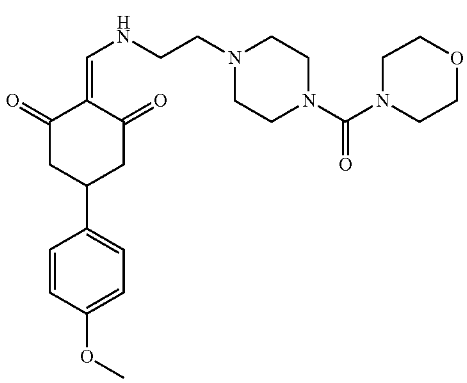 [SMILES: COc1ccc(C2CC(=O)C(=CNCCN3CCN(C(=O)N4CCOCC4)CC3)C(=O)C2)cc1] | 5-(4-methoxyphenyl)-2-(((2-(4-(morpholine-4-carbonyl)piperazin-1-yl)ethyl)amino)methylene)cyclohexane-1,3-dione | ¹HNMR (300 MHz, CDCl₃) δ 11.26 (m, 1H), 8.17 (d, J = 14.4 Hz, 1H), 7.13 (s, 4H), 3.72 (s, 2H), 3.67 (t, 8H), 3.52 (s, 1H), 3.35 (s, 4H), 3.27 (d, J = 11.8 Hz, 4H), 2.79-2.67 (m, 2H), 2.63 (d, J = 6.2 Hz, 2H), 2.50 (s, 4H), 2.33 (s, 3H) |
| 247 | 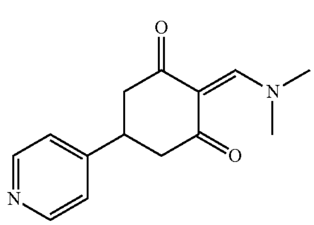 [SMILES: CN(C)C=C1C(=O)CC(c2ccncc2)CC1=O] | 2-((dimethylamino)methylene)-5-(pyridin-4-yl)cyclohexane-1,3-dione | ¹HNMR (300 MHz, CDCl₃) δ 8.18 (s, 1H), 7.35 (d, J = 8.3 Hz, 2H), 7.21 (d, J = 8.3 Hz, 2H), 3.38 (s, 3H), 3.39-3.28 (m, 1H), 3.11 (s, 3H), 2.63 (qd, J = 16.5, 8.0 Hz, 4H) |

TABLE 7-continued

Compounds 119-355

| # | Structure | Name | Proton NMR(¹HNMR), Mass Spectrum(MS) |
|---|---|---|---|
| 248 | 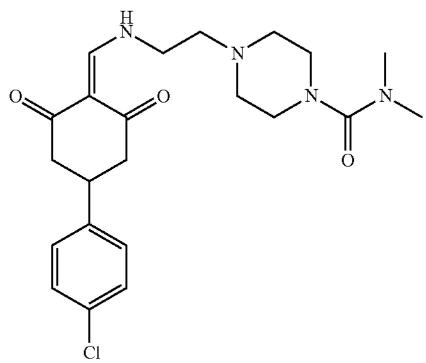 [SMILES: CN(C)C(=O)N1CCN(CCNC=C2C(=O)CC(c3ccc(Cl)cc3)CC2=O)CC1] | 4-(2-(((4-(4-chlorophenyl)-2,6-dioxocyclohexylidene)methyl)amino)ethyl)-N,N-dimethylpiperazine-1-carboxamide | ¹HNMR (300 MHz, CDCl₃) δ 11.26 (m, 1H), 8.17 (d, J = 14.3 Hz, 1H), 7.29 (t, J = 7.2 Hz, 2H), 7.16 (d, J = 8.1 Hz, 2H), 3.52 (d, J = 6.1 Hz, 2H), 3.30 (s, 5H), 2.81 (s, 6H), 2.78-2.64 (m, 4H), 2.64-2.58 (m, 2H), 2.49 (s, 4H) |
| 249 | 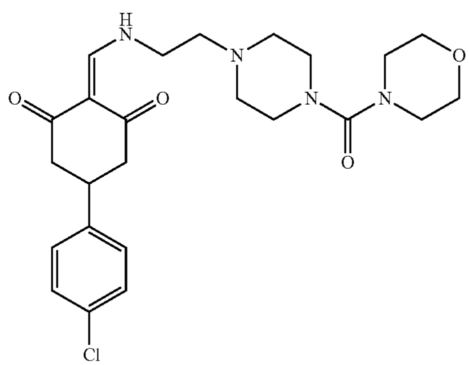 [SMILES: O=C1CC(c2ccc(Cl)cc2)CC(=O)C1=CNCCN1CCN(C(=O)N2CCOCC2)CC1] | 5-(4-chlorophenyl)-2-(((2-(4-(morpholine-4-carbonyl)piperazin-1-yl)ethyl)amino)methylene)cyclohexane-1,3-dione | ¹HNMR (300 MHz, CDCl₃) δ 11.22 (s, 1H), 8.17 (d, J = 14.5 Hz, 1H), 7.29 (t, J = 7.7 Hz, 2H), 7.15 (d, J = 8.4 Hz, 2H), 3.66 (d, J = 4.4 Hz, 4H), 3.51 (d, J = 6.0 Hz, 2H), 3.34 (s, 5H), 3.25 (d, J = 4.3 Hz, 4H), 2.79-2.55 (m, 6H), 2.49 (s, 4H) |
| 251 | 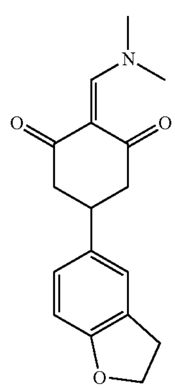 [SMILES: CN(C)C=C1C(=O)CC(c2ccc3c(c2)CCO3)CC1=O] | 5-(2,3-dihydrobenzofuran-5-yl)-2-((dimethylamino)methylene)cyclohexane-1,3-dione | ¹HNMR (400 MHz, CDCl₃) δ 8.09 (s, 1H), 7.09 (s, 1H), 6.99 (d, J = 8.1 Hz, 1H), 6.75 (d, J = 8.2 Hz, 1H), 4.58 (t, J = 8.7 Hz, 2H), 3.44 (d, J = 5.0 Hz, 3H), 3.31 (ddd, J = 16.2, 11.6, 4.4 Hz, 1H), 3.26-3.16 (m, 5H), 2.70 (qd, J = 16.6, 8.1 Hz, 4H) |
| 252 | 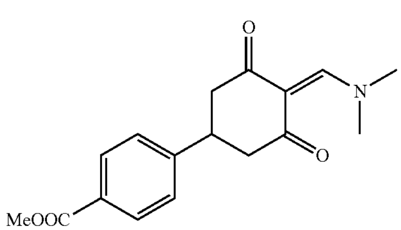 [SMILES: COC(=O)c1ccc(C2CC(=O)C(=CN(C)C)C(=O)C2)cc1] | methyl 4-(4-((dimethylamino)methylene)-3,5-dioxocyclohexyl)benzoate | ¹HNMR (400 MHz, CDCl₃) δ 8.10 (d, J = 5.5 Hz, 1H), 8.02 (d, J = 7.9, 6.1 Hz, 2H), 7.37-7.30 (d, 2H), 3.96-3.84 (s, 3H), 3.44 (t, J = 8.5 Hz, 4H), 3.24 (s, J = 5.6 Hz, 3H), 2.74 (m, J = 16.9, 5.3 Hz, 4H) |

TABLE 7-continued

Compounds 119-355

| # | Structure | Name | Proton NMR(¹HNMR), Mass Spectrum(MS) |
|---|---|---|---|
| 253 | 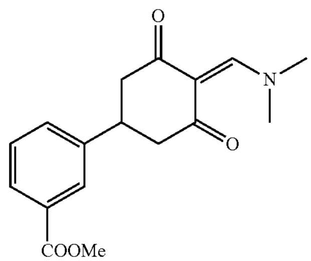 [SMILES: COC(=O)c1cccc(C2CC(=O)C(=CN(C)C)C(=O)C2)c1] | methyl 3-(4-((dimethylamino)methylene)-3,5-dioxocyclohexyl)benzoate | ¹HNMR (400 MHz, CDCl₃) δ 8.11 (s, 1H), 7.97 (s, 1H), 7.94 (d, J = 7.1 Hz, 1H), 7.49-7.40 (m, 2H), 3.94 (s, 3H), 3.52-3.35 (m, 4H), 3.25 (s, 3H), 2.84-2.63 (m, 4H) |
| 254 | 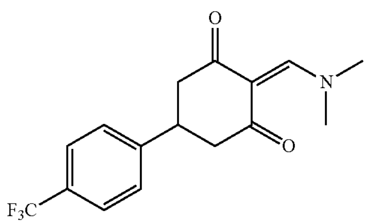 [SMILES: CN(C)C=C1C(=O)CC(c2ccc(C(F)(F)F)cc2)CC1=O] | 2-((dimethylamino)methylene)-5-(4-(trifluoromethyl)phenyl)cyclohexane-1,3-dione | ¹HNMR (400 MHz, CDCl₃) δ 8.10 (s, 1H), 7.61 (d, J = 8.0 Hz, 2H), 7.38 (d, J = 7.9 Hz, 2H), 3.45 (s, 4H), 3.24 (s, 3H), 2.84-2.62 (m, 5H) |
| 255 | 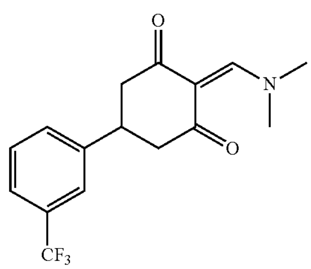 [SMILES: CN(C)C=C1C(=O)CC(c2cccc(C(F)(F)F)c2)CC1=O] | 2-((dimethylamino)methylene)-5-(3-(trifluoromethyl)phenyl)cyclohexane-1,3-dione | ¹HNMR (400 MHz, CDCl₃) δ 8.10 (s, 1H), 7.54-7.49 (m, 2H), 7.48 (d, J = 7.8 Hz, 1H), 7.46 (s, 1H), 3.51-3.35 (m, 4H), 3.24 (s, 3H), 2.75 (qd, J = 16.5, 8.1 Hz, 4H) |
| 256 | 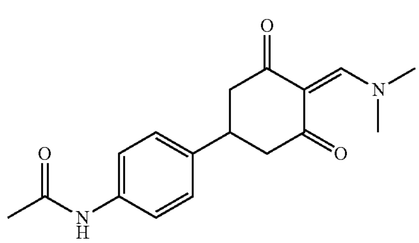 [SMILES: CC(=O)Nc1ccc(C2CC(=O)C(=CN(C)C)C(=O)C2)cc1] | N-(4-(4-((dimethylamino)methylene)-3,5-dioxocyclohexyl)phenyl)acetamide | ¹HNMR (400 MHz, CDCl₃) δ 8.07 (s, 1H), 7.94 (s, 1H), 7.47 (d, J = 6.8 Hz, 2H), 7.18 (d, J = 6.1 Hz, 2H), 3.40 (s, 3H), 3.33 (m, 1H), 3.21 (s, 3H), 2.69 (q, J = 15.7 Hz, 4H), 2.16 (s, 3H) |
| 257 | 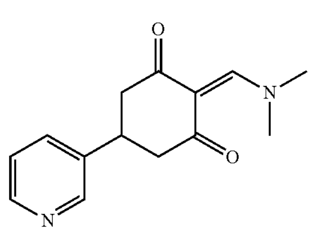 [SMILES: CN(C)C=C1C(=O)CC(c2cccnc2)CC1=O] | 2-((dimethylamino)methylene)-5-(pyridin-3-yl)cyclohexane-1,3-dione | ¹HNMR (400 MHz, CDCl₃) δ 8.56 (s, 1H), 8.53 (d, J = 4.5 Hz, 1H), 8.11 (s, 1H), 7.59 (d, J = 7.9 Hz, 1H), 7.32-7.29 (m, 1H), 3.46 (s, 3H), 3.41 (dd, J = 11.2, 4.8 Hz, 1H), 3.25 (s, 3H), 2.82-2.71 (m, 4H) |

TABLE 7-continued

Compounds 119-355

| # | Structure | Name | Proton NMR(¹HNMR), Mass Spectrum(MS) |
|---|---|---|---|
| 258 | 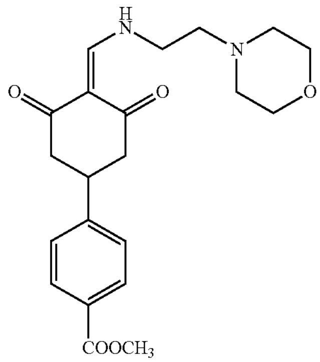 [SMILES: COC(=O)c1ccc(C2CC(=O)C(=CNCCN3CCOCC3)C(=O)C2)cc1] | methyl 4-(4-(((2-morpholinoethyl)amino)methylene)-3,5-dioxocyclohexyl)benzoate | ¹HNMR (400 MHz, CDCl₃) δ 11.26 (s, 1H), 8.21 (d, J = 14.4 Hz, 1H), 8.03 (d, J = 8.2 Hz, 2H), 7.33 (d, J = 8.2 Hz, 2H), 3.93 (s, 3H), 3.80-3.72 (m, 4H), 3.55 (dd, J = 11.9, 6.0 Hz, 2H), 3.46 (dd, J = 10.8, 5.8 Hz, 1H), 2.84-2.66 (m, 4H), 2.63 (t, J = 5.9 Hz, 2H), 2.53 (d, J = 4.1 Hz, 4H) |
| 259 | 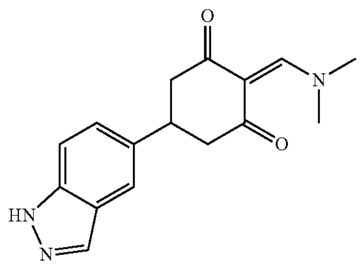 [SMILES: CN(C)C=C1C(=O)CC(c2ccc3[nH]ncc3c2)CC1=O] | 2-((dimethylamino)methylene)-5-(1H-indazol-5-yl)cyclohexane-1,3-dione | ¹HNMR (400 MHz, CDCl₃) δ 10.85-10.35 (m, 1H), 8.14 (s, 1H), 8.06 (s, 1H), 7.74 (d, J = 8.5 Hz, 1H), 7.38 (s, 1H), 7.11 (d, J = 8.0 Hz, 1H), 3.52 (s, 1H), 3.46 (s, 2H), 3.26 (s, 2H), 2.93-2.73 (m, 3H) |
| 260 | 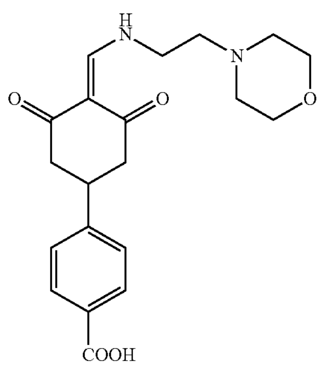 [SMILES: O=C1CC(c2ccc(C(=O)O)cc2)CC(=O)C1=CNCCN1CCOCC1] | 4-(4-(((2-morpholinoethyl)amino)methylene)-3,5-dioxocyclohexyl)benzoic acid | ¹HNMR (400 MHz, CDCl₃) δ 11.23 (s, 1H), 9.09-8.95 (m, 1H), 8.26 (d, J = 14.4 Hz, 1H), 8.06 (d, J = 8.2 Hz, 2H), 7.33 (d, J = 8.0 Hz, 2H), 3.79 (s, 3H), 3.79 (s, 3H), 3.61 (d, J = 5.9 Hz, 2H), 3.42 (s, 1H), 2.84-2.62 (m, 5H), 2.60 (s, 3H) |
| 262 | 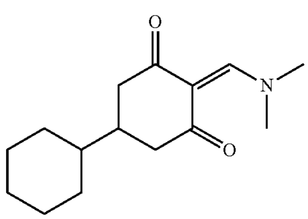 [SMILES: CN(C)C=C1C(=O)CC(C2CCCCC2)CC1=O] | 4-((dimethylamino)methylene)-[1,1'-bi(cyclohexane)]-3,5-dione | ¹HNMR (400 MHz, CDCl₃) δ 8.02 (s, 1H), 3.39 (s, 3H), 3.19 (s, 3H), 2.55 (dd, J = 16.7, 3.8 Hz, 2H), 2.25 (dd, J = 16.6, 12.1 Hz, 2H), 1.94-1.83 (m, 1H), 1.75 (d, J = 10.1 Hz, 4H), 1.67 (d, J = 12.0 Hz, 1H), 1.28-1.13 (m, 4H), 0.98 (dd, J = 23.2, 12.7 Hz, 2H) |
| 263 | 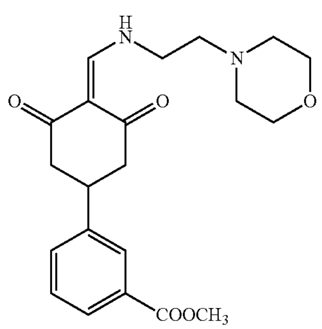 [SMILES: COC(=O)c1cccc(C2CC(=O)C(=CNCCN3CCOCC3)C(=O)C2)c1] | methyl 3-(4-(((2-morpholinoethyl)amino)methylene)-3,5-dioxocyclohexyl)benzoate | ¹HNMR (400 MHz, CDCl₃) δ 11.26 (s, 1H), 8.21 (d, J = 14.4 Hz, 1H), 8.03 (d, J = 8.2 Hz 2H), 7.33 (d, J = 8.2 Hz, 2H), 3.93 (s, 3H), 3.76 (dd, J = 9.4, 4.8 Hz, 4H), 3.55 (dd, J = 11.9, 6.0 Hz, 2H), 3.49-3.39 (m, 1H), 2.87-2.68 (m, 4H), 2.63 (t, J = 5.9 Hz, 2H), 2.52 (dd, J = 10.3, 5.9 Hz, 4H) |

TABLE 7-continued

Compounds 119-355

| # | Structure | Name | Proton NMR (¹HNMR), Mass Spectrum(MS) |
|---|---|---|---|
| 264 | 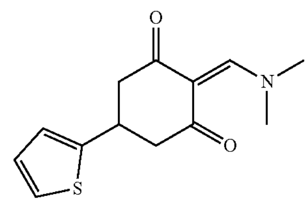 [SMILES: CN(C)C=C1C(=O)CC(c2cccs2)CC1=O] | 2-((dimethylamino)methylene)-5-(thiophen-2-yl)cyclohexane-1,3-dione | ¹HNMR (400 MHz, CDCl₃) δ 8.08 (s, 1H), 7.19 (d, J = 5.1 Hz, 1H), 6.99-6.92 (m, 1H), 6.88 (d, J = 3.4 Hz, 1H), 3.71-3.59 (m, 1H), 3.43 (s, 3H), 3.22 (s, 3H), 2.92 (dd, J = 16.8, 4.2 Hz, 2H), 2.74 (dd, J = 16.8, 10.9 Hz, 2H) |
| 265 | 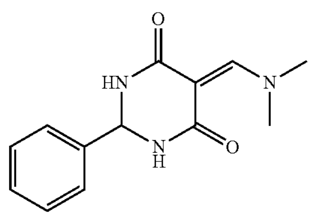 [SMILES: CN(C)C=C1C(=O)NC(c2ccccc2)NC1=O] | 5-((dimethylamino)methylene)-2-phenyldihydropyrimidine-4,6(1H,5H)-dione | ¹HNMR (400 MHz, DMSO) δ 11.53 (s, 2H), 8.34 (s, 1H), 8.06 (t, J = 9.1 Hz, 2H), 7.59 (t, J = 7.1 Hz, 1H), 7.51 (t, J = 7.3 Hz, 2H), 3.51 (s, 3H), 3.29 (s, 3H) |
| 266 | 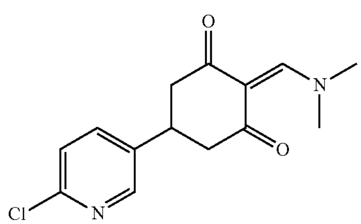 [SMILES: CN(C)C=C1C(=O)CC(c2ccc(Cl)nc2)CC1=O] | 5-(6-chloropyridin-3-yl)-2-((dimethylamino)methylene)cyclohexane-1,3-dione | ¹HNMR (400 MHz, CDCl₃) δ 8.32 (d, J = 2.2 Hz, 1H), 8.10 (s, 1H), 7.56 (dd, J = 8.2, 2.2 Hz, 1H), 7.32 (d, J = 8.3 Hz, 1H), 3.45 (s, 3H), 3.44-3.37 (m, 1H), 3.24 (s, 3H), 2.73 (qd, J = 16.6, 7.9 Hz, 4H) |
| 267 | 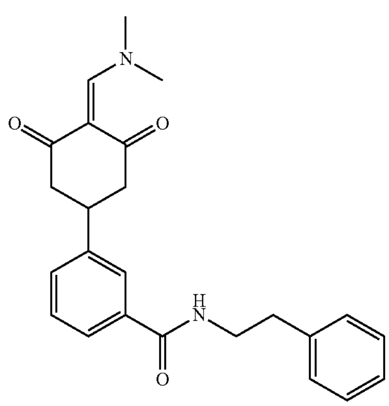 [SMILES: CN(C)C=C1C(=O)CC(c2cccc(C(=O)NCCc3ccccc3)c2)CC1=O] | 3-(4-((dimethylamino)methylene)-3,5-dioxocyclohexyl)-N-phenethylbenzamide | ¹HNMR (400 MHz, CDCl₃) δ 8.09 (s, 1H), 7.64 (s, 1H), 7.56-7.48 (m, 1H), 7.39-7.32 (m, 4H), 7.28-7.23 (m, 3H), 3.73 (dd, J = 12.9, 6.9 Hz, 2H), 3.44 (d, J = 5.0 Hz, 3H), 3.41-3.35 (m, 1H), 3.24 (s, 3H), 2.97 (t, J = 3.4 Hz, 2H), 2.78-2.68 (m, 4H) |
| 268 | 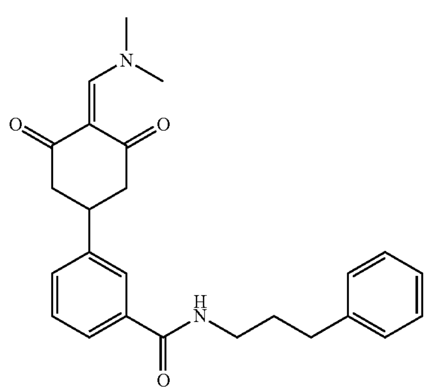 [SMILES: CN(C)C=C1C(=O)CC(c2cccc(C(=O)NCCCc3ccccc3)c2)CC1=O] | 3-(4-((dimethylamino)methylene)-3,5-dioxocyclohexyl)-N-(3-phenylpropyl)benzamide | ¹HNMR (400 MHz, CDCl₃) δ 8.09 (s, 1H), 7.61 (s, 1H), 7.53-7.48 (m, 1H), 7.40-7.34 (m, 2H), 7.31 (dd, J = 12.5, 5.2 Hz, 2H), 7.25-7.21 (m, 3H), 3.52 (dd, J = 12.9, 6.8 Hz, 2H), 3.43 (s, 3H), 3.38 (dd, J = 10.7, 5.5 Hz, 1H), 3.23 (s, 4H), 2.74 (dd, J = 13.9, 9.1 Hz, 6H), 1.99 (dd, J = 14.5, 7.3 Hz, 2H) |

TABLE 7-continued

Compounds 119-355

| # | Structure | Name | Proton NMR(¹HNMR), Mass Spectrum(MS) |
|---|---|---|---|
| 269 | 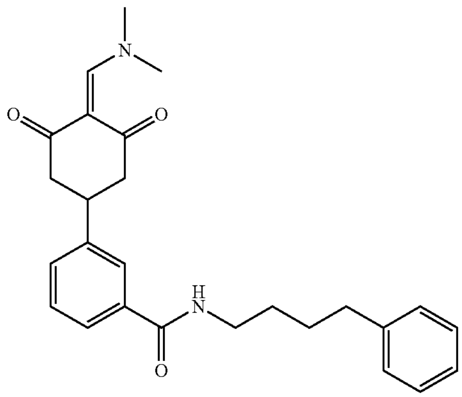 [SMILES: CN(C)C=C1C(=O)CC(c2cccc(C(=O)NCCCCc3ccccc3)c2)CC1=O] | 3-(4-((dimethylamino)methylene)-3,5-dioxocyclohexyl)-N-(4-phenylbutyl)-benzamide | ¹HNMR (400 MHz, CDCl₃) δ 8.10 (s, 1H), 7.68 (s, 1H), 7.61-7.57 (m, 1H), 7.41 (dd, J = 8.7, 5.0 Hz, 2H), 7.31 (d, J = 7.5 Hz, 1H), 7.23-7.17 (m, 4H), 3.53-3.48 (m, 2H), 3.46-3.43 (m, 3H), 3.42-3.35 (m, 1H), 3.24 (s, 3H), 2.82-2.64 (m, 8H), 1.73 (dd, J = 8.7, 5.8 Hz, 2H) |
| 270 | 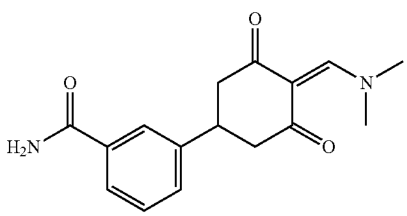 [SMILES: CN(C)C=C1C(=O)CC(c2cccc(C(N)=O)c2)CC1=O] | 3-(4-((dimethylamino)methylene)-3,5-dioxocyclohexyl)benzamide | ¹HNMR (400 MHz, CDCl₃) δ 8.66 (d, J = 5.1 Hz, 1H), 8.22-8.12 (m, 1H), 8.11 (s, 1H), 7.41 (dd, J = 12.1, 6.1 Hz, 3H), 3.44 (s, 4H), 3.20 (d, J = 15.1 Hz, 3H), 2.80-2.75 (m, 4H) |
| 271 | 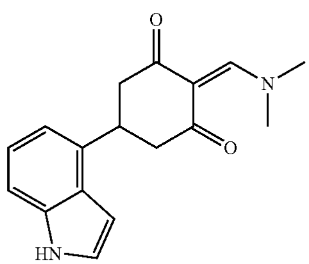 [SMILES: CN(C)C=C1C(=O)CC(c2cccc3[nH]ccc23)CC1=O] | 2-((dimethylamino)methylene)-5-(1H-indol-4-yl)cyclohexane-1,3-dione | ¹HNMR (400 MHz, CDCl₃) δ 8.35 (s, 1H), 8.14 (s, 1H), 7.33 (d, J = 8.2 Hz, 1H), 7.26-7.23 (m, 1H), 7.22-7.17 (m, 1H), 7.00 (d, J = 7.3 Hz, 1H), 6.63 (ddd, J = 3.1, 2.0, 0.9 Hz, 1H), 3.84 (ddd, J = 16.6, 10.8, 5.8 Hz, 1H), 3.44 (s, 3H), 3.27 (s, 3H), 2.95-2.85 (m, 4H) |
| 272 | 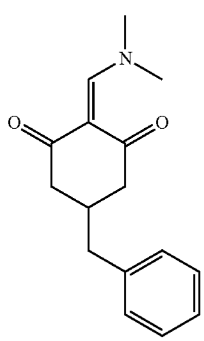 [SMILES: CN(C)C=C1C(=O)CC(Cc2ccccc2)CC1=O] | 5-benzyl-2-((dimethylamino)methylene)cyclohexane-1,3-dione | ¹HNMR (400 MHz, CDCl₃) δ 8.03 (s, 1H), 7.33-7.29 (m, 2H), 7.22 (ddd, J = 7.4, 3.9, 1.3 Hz, 1H), 7.16 (dd, J = 5.2, 3.1 Hz, 2H), 3.40 (s, 3H), 3.18 (s, 3H), 2.68 (d, J = 6.8 Hz, 2H), 2.55 (dt, J = 16.3, 2.7 Hz, 2H), 2.36 (tdd, J = 9.9, 7.1, 3.3 Hz, 1H), 2.30-2.20 (m, 2H) |
| 273 | 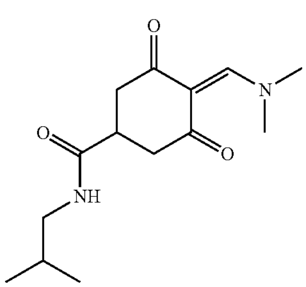 [SMILES: CC(C)CNC(=O)C1CC(=O)C(=CN(C)C)C(=O)C1] | 4-((dimethylamino)methylene)-N-isobutyl-3,5-dioxocyclohexane-1-carboxamide | ¹HNMR (400 MHz, CDCl₃) δ 8.05 (s, 1H), 3.42 (s, 3H), 3.21 (s, 3H), 3.16-3.06 (m, 2H), 2.88-2.73 (m, 3H), 2.70-2.55 (m, 2H), 1.79 (dt, J = 13.5, 6.8 Hz, 1H), 0.92 (t, J = 6.9 Hz, 6H) |

TABLE 7-continued

Compounds 119-355

| # | Structure | Name | Proton NMR($^1$HNMR), Mass Spectrum(MS) |
|---|---|---|---|
| 274 | 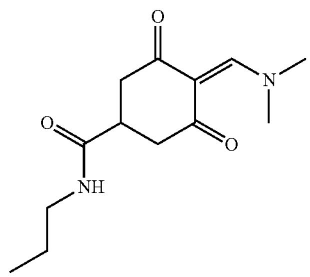 [SMILES: CCCNC(=O)C1CC(=O)C(=CN(C)C)C(=O)C1] | 4-((dimethylamino)methylene)-3,5-dioxo-N-propylcyclohexane-1-carboxamide | $^1$HNMR (400 MHz, CDCl$_3$) δ 8.05 (s, 1H), 3.42 (s, 3H), 3.26 (dd, J = 13.0, 7.1 Hz, 2H), 3.21 (s, 3H), 2.85-2.74 (m, 3H), 2.67-2.57 (m, 2H), 1.59-1.47 (m, 2H), 0.94 (t, J = 7.4 Hz, 3H) |
| 276 | 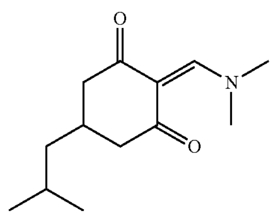 [SMILES: CC(C)CC1CC(=O)C(=CN(C)C)C(=O)C1] | 2-((dimethylamino)methylene)-5-isobutylcyclohexane-1,3-dione | $^1$HNMR (400 MHz, CDCl$_3$) δ 8.03 (s, 1H), 3.40 (s, 3H), 3.20 (s, 3H), 2.61-2.43 (m, 2H), 2.21-2.07 (m, 3H), 1.69 (td, J = 13.5, 6.8 Hz, 1H), 1.24 (dd, J = 12.4, 5.7 Hz, 3H), 0.90 (d, J = 6.6 Hz, 6H) |
| 277 | 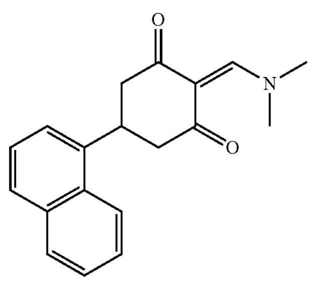 [SMILES: CN(C)C=C1C(=O)CC(c2cccc3ccccc23)CC1=O] | 2-((dimethylamino)methylene)-5-(naphthalen-1-yl)cyclohexane-1,3-dione | $^1$HNMR (400 MHz, CDCl$_3$) δ 8.15 (s, 1H), 8.09 (d, J = 8.1 Hz, 1H), 7.92-7.88 (m, 1H), 7.78 (d, J = 8.1 Hz, 1H), 7.58-7.45 (m, 3H), 7.41 (d, J = 7.0 Hz, 1H), 4.21 (tt, J = 11.9, 4.2 Hz, 1H), 3.46 (d, J = 8.5 Hz, 3H), 3.30 (s, 3H), 2.89 (ddd, J = 28.4, 16.7, 12.3 Hz, 4H) |
| 278 | 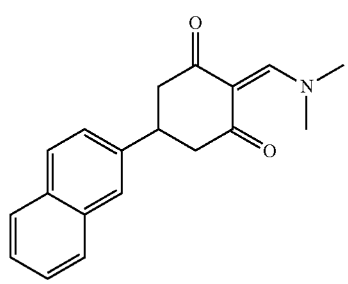 [SMILES: CN(C)C=C1C(=O)CC(c2ccc3ccccc3c2)CC1=O] | 2-((dimethylamino)methylene)-5-(naphthalen-2-yl)cyclohexane-1,3-dione | $^1$HNMR (400 MHz, CDCl$_3$) δ 8.12 (s, 1H), 7.87-7.80 (m, 3H), 7.69 (s, 1H), 7.53-7.45 (m, 2H), 7.42 (dd, J = 8.5, 1.8 Hz, 1H), 3.64-3.49 (m, 1H), 3.45 (s, 3H), 3.26 (s, 3H), 2.90-2.78 (m, 4H) |
| 279 | 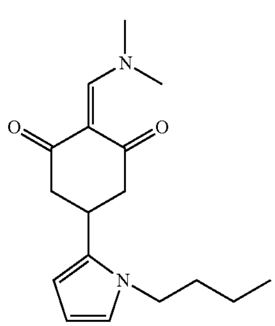 [SMILES: CCCCn1cccc1C1CC(=O)C(=CN(C)C)C(=O)C1] | 5-(1-butyl-1H-pyrrol-2-yl)-2-((dimethylamino)methylene)cyclohexane-1,3-dione | $^1$HNMR (400 MHz, CDCl$_3$) δ 8.10 (d, J = 10.7 Hz, 1H), 6.67-6.53 (m, 1H), 6.11 (dd, J = 6.8, 3.6 Hz, 1H), 6.00 (d, J = 37.2 Hz, 1H), 3.87-3.79 (m, 2H), 3.41 (d, J = 24.1 Hz, 3H), 3.39-3.31 (m, 1H), 3.26 (s, 3H), 2.92-2.73 (m, 2H), 2.66 (ddd, J = 23.2, 11.9, 6.0 Hz, 2H), 1.80-1.64 (m, 2H), 1.41-1.32 (m, 2H), 0.99-0.87 (m, 3H) |

TABLE 7-continued

Compounds 119-355

| # | Structure | Name | Proton NMR($^1$HNMR), Mass Spectrum(MS) |
|---|---|---|---|
| 280 | 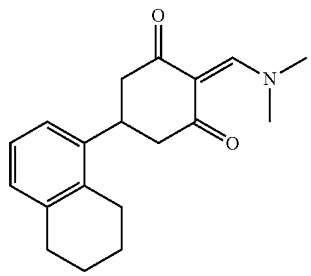 [SMILES: CN(C)C=C1C(=O)CC(c2cccc3c2CCCC3)CC1=O] | 2-((dimethylamino)methylene)-5-(5,6,7,8-tetrahydronaphthalen-1-yl)cyclohexane-1,3-dione | $^1$HNMR (400 MHz, CDCl$_3$) δ 8.10 (s, 1H), 7.15 (t, J = 7.5 Hz, 1H), 7.08 (d, J = 6.7 Hz, 1H), 7.00 (d, J = 7.3 Hz, 1H), 3.59 (p, J = 8.3 Hz, 1H), 3.44 (s, 3H), 3.26 (s, 3H), 2.82 (t, J = 6.2 Hz, 2H), 2.77 (t, J = 6.2 Hz, 2H), 2.67 (d, J = 8.2 Hz, 4H), 1.86-1.76 (m, 4H) |
| 281 | 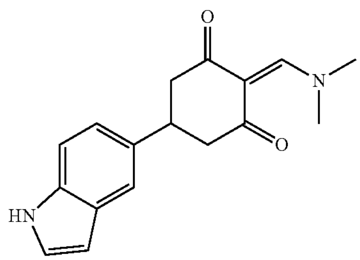 [SMILES: CN(C)C=C1C(=O)CC(c2ccc3[nH]ccc3c2)CC1=O] | 2-((dimethylamino)methylene)-5-(1H-indol-5-yl)cyclohexane-1,3-dione | $^1$HNMR (400 MHz, CDCl$_3$) δ 8.20 (s, 1H), 8.11 (s, 1H), 7.53 (s, 1H), 7.39 (d, J = 8.6 Hz, 1H), 7.26-7.21 (m, 1H), 7.12 (d, J = 8.6 Hz, 1H), 6.55 (s, 1H), 3.47 (dd, J = 11.1, 5.6 Hz, 1H), 3.44 (s, 3H), 3.25 (s, 3H), 2.83 (dd, J = 16.4, 11.2 Hz, 4H) |
| 282 | 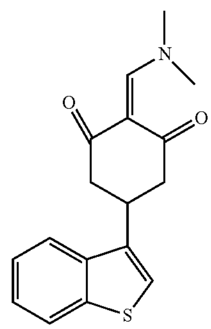 [SMILES: CN(C)C=C1C(=O)CC(c2csc3ccccc23)CC1=O] | 5-(benzo[b]thiophen-3-yl)-2-((dimethylamino)methylene)cyclohexane-1,3-dione | $^1$HNMR (400 MHz, CDCl$_3$) δ 8.13 (s, 1H), 7.89 (dd, J = 7.2, 1.9 Hz, 1H), 7.80 (dd, J = 7.0, 1.6 Hz, 1H), 7.45-7.33 (m, 2H), 7.18 (s, 1H), 3.85-3.74 (m, 1H), 3.46 (s, 3H), 3.27 (s, 3H), 2.99 (dd, J = 16.9, 4.1 Hz, 2H), 2.79 (dd, J = 16.8, 11.1 Hz, 2H) |
| 283 | 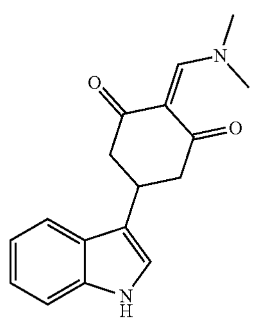 [SMILES: CN(C)C=C1C(=O)CC(c2c[nH]c3ccccc23)CC1=O] | 2-((dimethylamino)methylene)-5-(1H-indol-3-yl)cyclohexane-1,3-dione | $^1$HNMR (400 MHz, DMSO) δ 10.85 (s, 1H), 8.04 (s, 1H), 7.57 (d, J = 7.8 Hz, 1H), 7.35 (d, J = 8.1 Hz, 1H), 7.15-7.03 (m, 2H), 7.03-6.89 (m, 1H), 3.61-3.49 (m, 1H), 3.42 (s, 3H), 3.10 (s, 3H), 2.68 (qd, J = 16.2, 7.4 Hz, 4H) |
| 284 | 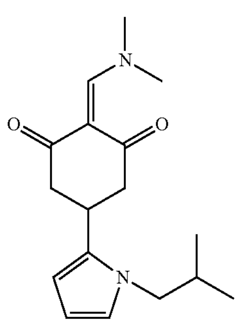 [SMILES: CC(C)Cn1cccc1C1CC(=O)C(=CN(C)C)C(=O)C1] | 2-((dimethylamino)methylene)-5-(1-isobutyl-1H-pyrrol-2-yl)cyclohexane-1,3-dione | $^1$HNMR (400 MHz, CDCl$_3$) δ 8.08 (s, 1H), 6.66-6.51 (m, 1H), 6.10 (t, J = 3.1 Hz, 1H), 6.02-5.85 (m, 1H), 3.63 (d, J = 7.5 Hz, 2H), 3.43 (s, 3H), 3.32 (ddd, J = 15.7, 7.8, 4.0 Hz, 1H), 3.25 (s, 3H), 2.76 (dd, J = 16.9, 4.1 Hz, 2H), 2.68-2.58 (m, 2H), 2.02-1.98 (m, 1H), 0.96 (dd, J = 15.8, 5.9 Hz, 2H), 0.90 (d, J = 6.6 Hz, 6H) |

TABLE 7-continued

Compounds 119-355

| # | Structure | Name | Proton NMR(¹HNMR), Mass Spectrum(MS) |
|---|---|---|---|
| 285 | 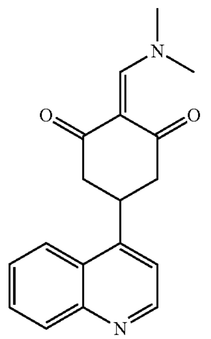 [SMILES: CN(C)C=C1C(=O)CC(c2ccnc3ccccc23)CC1=O] | 2-((dimethylamino)methylene)-5-(quinolin-4-yl)cyclohexane-1,3-dione | ¹HNMR (400 MHz, CDCl₃) δ 8.92 (dd, J = 10.6, 4.4 Hz, 1H), 8.22-8.15 (m, 2H), 8.08 (d, J = 8.3 Hz, 1H), 7.76 (dd, J = 16.9, 8.7 Hz, 1H), 7.69-7.57 (m, 1H), 4.25-4.16 (m, 1H), 3.48 (s, 3H), 3.29 (s, 3H), 2.94 (dd, J = 16.7, 4.1 Hz, 2H), 2.82 (dd, J = 16.6, 11.5 Hz, 2H) |
| 286 | 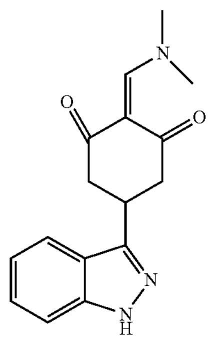 [SMILES: CN(C)C=C1C(=O)CC(c2n[nH]c3ccccc23)CC1=O] | 2-((dimethylamino)methylene)-5-(1H-indazol-3-yl)cyclohexane-1,3-dione | ¹HNMR (400 MHz, CDCl₃) δ 10.35 (s, 1H), 8.12 (s, 1H), 7.76 (d, J = 8.1 Hz, 1H), 7.50 (d, J = 8.3 Hz, 1H), 7.42-7.35 (m, 1H), 7.16 (t, J = 7.5 Hz, 1H), 3.91 (dt, J = 14.7, 4.8 Hz, 1H), 3.41 (s, 3H), 3.23 (s, 3H), 3.05-2.95 (m, 4H) |
| 287 | 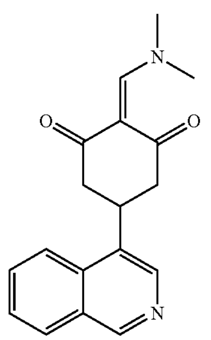 [SMILES: CN(C)C=C1C(=O)CC(c2cncc3ccccc23)CC1=O] | 2-((dimethylamino)methylene)-5-(isoquinolin-4-yl)cyclohexane-1,3-dione | ¹HNMR (400 MHz, CDCl₃) δ 9.29 (d, J = 4.3 Hz, 1H), 8.58 (t, J = 6.4 Hz, 1H), 8.16 (s, 1H), 7.91 (dd, J = 8.4, 4.6 Hz, 1H), 7.84 (d, J = 6.1 Hz, 1H), 7.63 (s, 1H), 7.61 (t, J = 2.6 Hz, 1H), 4.14 (tt, J = 11.4, 4.1 Hz, 1H), 3.48 (s, 3H), 3.30 (s, 3H), 2.92 (dd, J = 16.6, 4.2 Hz, 2H), 2.83 (dt, J = 16.6, 8.5 Hz, 2H) |
| 288 | 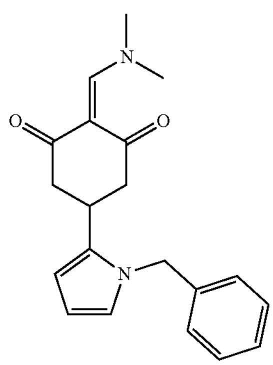 [SMILES: CN(C)C=C1C(=O)CC(c2cccn2Cc2ccccc2)CC1=O] | 5-(1-benzyl-1H-pyrrol-2-yl)-2-((dimethylamino)methylene)cyclohexane-1,3-dione | ¹HNMR (400 MHz, CDCl₃) δ 8.03 (d, J = 6.4 Hz, 1H), 7.31 (dd, J = 13.0, 5.6 Hz, 1H), 7.29-7.23 (m, 1H), 6.96 (d, J = 6.9 Hz, 2H), 6.69-6.60 (m, 1H), 6.22-6.12 (m, 1H), 6.05 (dd, J = 3.4, 1.5 Hz, 1H), 5.10 (d, J = 6.7 Hz, 1H), 3.41 (s, 3H), 3.27-3.21 (m, 1H), 3.20 (s, 3H), 2.64 (dd, J = 17.9, 5.9 Hz, 4H) |

TABLE 7-continued

Compounds 119-355

| # | Structure | Name | Proton NMR($^1$HNMR), Mass Spectrum(MS) |
|---|---|---|---|
| 289 | 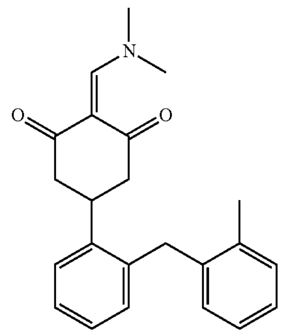 [SMILES: Cc1ccccc1Cc1ccccc1C1CC(=O)C(=CN(C)C)C(=O)C1] | 2-((dimethylamino)methylene)-5-(2-(2-methylbenzyl)phenyl)cyclohexane-1,3-dione | $^1$HNMR (400 MHz, CDCl$_3$) δ 8.07 (s, 1H), 7.33-7.29 (m, 2H), 7.25-7.19 (m, 1H), 7.15 (t, J = 7.3 Hz, 2H), 7.01 (d, J = 7.5 Hz, 1H), 6.91-6.83 (m, 2H), 4.04 (s, 2H), 3.60 (tt, J = 12.5, 4.0 Hz, 1H), 3.41 (d, J = 14.6 Hz, 3H), 3.21 (s, 3H), 2.64 (dt, J = 27.4, 13.7 Hz, 2H), 2.52 (dd, J = 16.9, 4.0 Hz, 2H), 2.29 (s, 3H) |
| 290 | 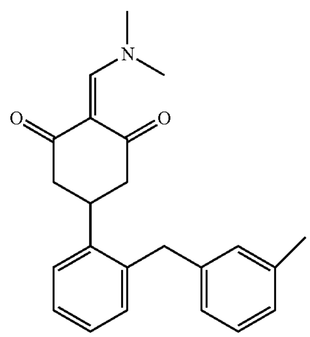 [SMILES: Cc1cccc(Cc2ccccc2C2CC(=O)C(=CN(C)C)C(=O)C2)c1] | 2-((dimethylamino)methylene)-5-(2-(3-methylbenzyl)phenyl)cyclohexane-1,3-dione | $^1$HNMR (400 MHz, CDCl$_3$) δ 8.09 (d, J = 11.8 Hz, 1H), 7.41-7.30 (m, 2H), 7.18 (t, J = 7.6 Hz, 2H), 7.14-7.06 (m, 1H), 6.96 (d, J = 7.5 Hz, 1H), 6.85 (d, J = 7.1 Hz, 1H), 4.01 (s, 2H), 3.59-3.50 (m, 2H), 3.44 (d, J = 4.8 Hz, 3H), 3.22 (s, 3H), 2.72 (dd, J = 16.7, 12.1 Hz, 2H), 2.65-2.58 (m, 2H), 2.27 (s, 3H) |
| 291 | 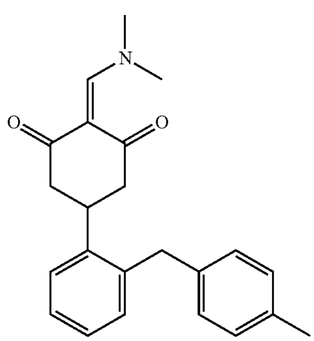 [SMILES: Cc1ccc(Cc2ccccc2C2CC(=O)C(=CN(C)C)C(=O)C2)cc1] | 2-((dimethylamino)methylene)-5-(2-(4-methylbenzyl)phenyl)cyclohexane-1,3-dione | $^1$HNMR (400 MHz, CDCl$_3$) δ 8.07 (s, 1H), 7.30 (t, J = 6.1 Hz, 2H), 7.24-7.18 (m, 1H), 7.16 (d, J = 7.2 Hz, 1H), 7.07 (d, J = 7.9 Hz, 2H), 6.96 (d, J = 8.0 Hz, 2H), 4.04 (s, 2H), 3.60 (tt, J = 12.5, 4.2 Hz, 1H), 3.43 (s, 3H), 3.22 (s, 3H), 2.66 (dd, J = 16.8, 12.5 Hz, 2H), 2.53 (dd, J = 17.0, 4.1 Hz, 2H), 2.31 (s, 3H) |
| 293 | 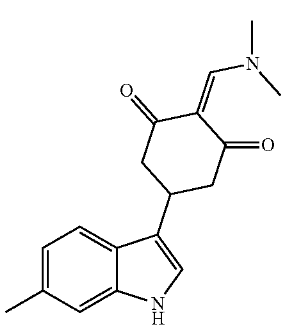 | 2-((dimethylamino)methylene)-5-(6-methyl-1H-indol-3-yl)cyclohexane-1,3-dione | $^1$HNMR (400 MHz, CDCl$_3$) δ 8.11 (s, 1H), 8.03 (s, 1H), 7.54 (d, J = 8.1 Hz, 1H), 7.18 (s, 1H), 6.98 (d, J = 8.2 Hz, 1H), 6.94 (d, J = 2.0 Hz, 1H), 3.67 (td, J = 11.0, 5.4 Hz, 1H), 3.41 (s, 3H), 3.24 (s, 3H), 2.99 (dd, J = 16.9, 4.0 Hz, 2H), 2.77 (dd, J = 16.8, 11.1 Hz, 2H), 2.48 (s, 3H) |

TABLE 7-continued

Compounds 119-355

| # | Structure | Name | Proton NMR (¹HNMR), Mass Spectrum(MS) |
|---|---|---|---|
| 294 | 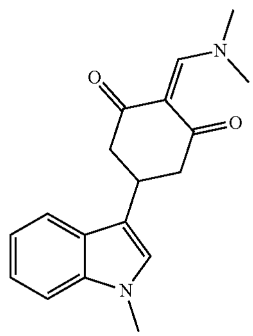 [SMILES: CN(C)C=C1C(=O)CC(c2cn(C)c3ccccc23)CC1=O] | 2-((dimethylamino)methylene)-5-(1-methyl-1H-indol-3-yl)cyclohexane-1,3-dione | ¹HNMR (400 MHz, CDCl₃) δ 8.12 (s, 1H), 7.67-7.63 (m, 1H), 7.32 (dt, J = 8.2, 0.9 Hz, 1H), 7.27-7.23 (m, 1H), 7.13 (ddd, J = 8.0, 6.9, 1.1 Hz, 1H), 6.87 (d, J = 0.7 Hz, 1H), 3.77 (s, 3H), 3.70 (ddt, J = 8.5, 4.3, 3.4 Hz, 1H), 3.43 (t, J = 2.1 Hz, 3H), 3.25 (d, J = 0.6 Hz, 3H), 3.02-2.94 (m, 2H), 2.77 (dd, J = 16.9, 11.0 Hz, 2H) |
| 295 | 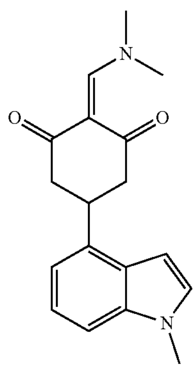 [SMILES: CN(C)C=C1C(=O)CC(c2cccc3c2ccn3C)CC1=O] | 2-((dimethylamino)methylene)-5-(1-methyl-1H-indol-4-yl)cyclohexane-1,3-dione | ¹HNMR (400 MHz, CDCl₃) δ 8.14 (s, 1H), 7.28-7.21 (m, 2H), 7.09 (d, J = 3.2 Hz, 1H), 7.00 (dd, J = 6.6, 1.0 Hz, 1H), 6.55 (dd, J = 3.2, 0.7 Hz, 1H), 3.87-3.76 (m, 4H), 3.47-3.41 (m, 3H), 3.27 (t, J = 4.2 Hz, 3H), 2.88 (dd, J = 15.1, 11.4 Hz, 4H). |
| 296 | 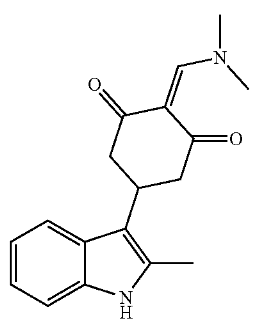 [SMILES: Cc1[nH]c2ccccc2c1C1CC(=O)C(=CN(C)C)C(=O)C1] | 2-((dimethylamino)methylene)-5-(2-methyl-1H-indol-3-yl)cyclohexane-1,3-dione | ¹HNMR (400 MHz, CDCl₃) δ 8.14 (s, 1H), 7.98 (s, 1H), 7.63 (d, J = 7.9 Hz, 1H), 7.35-7.29 (m, 1H), 7.13 (tt, J = 6.4, 1.8 Hz, 1H), 7.07 (ddd, J = 9.2, 5.2, 1.6 Hz, 1H), 3.63-3.54 (m, 1H), 3.41 (s, 3H), 3.26 (d, J = 0.5 Hz, 3H), 3.19 (dd, J = 17.2, 13.4 Hz, 2H), 2.72-2.65 (m, 2H), 2.40 (d, J = 6.1 Hz, 3H). |
| 297 | 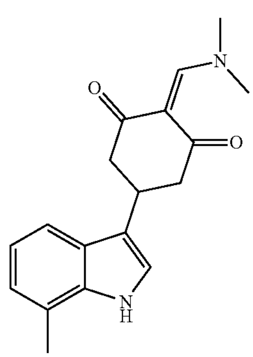 [SMILES: Cc1cccc2c(C3CC(=O)C(=CN(C)C)C(=O)C3)c[nH]c12] | 2-((dimethylamino)methylene)-5-(7-methyl-1H-indol-3-yl)cyclohexane-1,3-dione | ¹HNMR (400 MHz, CDCl₃) δ 8.12 (s, 1H), 8.07 (s, 1H), 7.52 (d, J = 7.7 Hz, 1H), 7.10-7.05 (m, 1H), 7.05-7.01 (m, 2H), 3.79-3.64 (m, 1H), 3.42 (s, 3H), 3.25 (s, 3H), 3.00 (dd, J = 16.9, 4.2 Hz, 2H), 2.79 (dd, J = 16.9, 11.2 Hz, 2H), 2.50 (s, 3H) |

TABLE 7-continued

Compounds 119-355

| # | Structure | Name | Proton NMR(¹HNMR), Mass Spectrum(MS) |
|---|---|---|---|
| 298 | 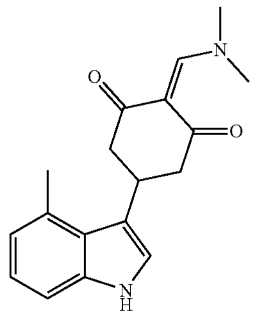 [SMILES: Cc1cccc2[nH]cc(C3CC(=O)C(=CN(C)C)C(=O)C3)c12] | 2-((dimethylamino)methylene)-5-(4-methyl-1H-indol-3-yl)cyclohexane-1,3-dione | ¹HNMR (400 MHz, CDCl₃) δ 8.11 (s, 2H), 7.23 (d, J = 7.9 Hz, 1H), 7.13-7.06 (m, 1H), 7.03 (d, J = 2.0 Hz, 1H), 6.91-6.86 (m, 1H), 3.97 (tt, J = 11.2, 3.7 Hz, 1H), 3.43 (d, J = 0.4 Hz, 3H), 3.26 (d, J = 0.5 Hz, 3H), 3.02-2.95 (m, 2H), 2.79-2.64 (m, 6H) |
| 299 | 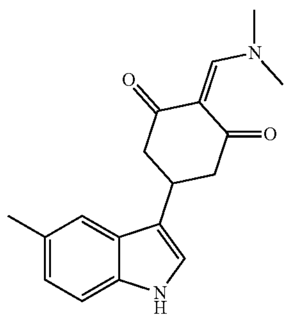 | 2-((dimethylamino)methylene)-5-(5-methyl-1H-indol-3-yl)cyclohexane-1,3-dione | ¹HNMR (400 MHz, CDCl₃) δ 8.11 (d, J = 5.2 Hz, 2H), 7.45 (d, J = 0.7 Hz, 1H), 7.28 (d, J = 6.6 Hz, 1H), 7.05 (dd, J = 8.3, 1.4 Hz, 1H), 6.97 (d, J = 1.8 Hz, 1H), 3.67 (tt, J = 11.1, 4.2 Hz, 1H), 3.42 (s, 3H), 3.30-3.23 (m, 3H), 3.00 (dd, J = 17.0, 4.2 Hz, 2H), 2.77 (dd, J = 16.9, 11.2 Hz, 2H), 2.48 (d, J = 5.1 Hz, 3H) |
| 300 | 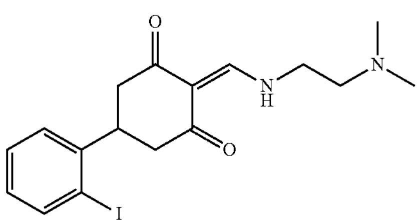 [SMILES: CN(C)CCNC=C1C(=O)CC(c2ccccc2I)CC1=O] | 2-(((2-(dimethylamino)ethyl)amino)methylene)-5-(2-iodophenyl)cyclohexane-1,3-dione | ¹H NMR (400 MHz, CDCl₃) δ 11.22 (s, 1H), 8.20 (d, J = 14.4 Hz, 1H), 7.86 (dd, J = 7.9, 1.0 Hz, 1H), 7.35 (t, J = 7.6 Hz, 1H), 7.21 (dd, J = 7.8, 1.3 Hz, 1H), 6.98-6.91 (m, 1H), 3.66 (tt, J = 12.1, 4.1 Hz, 1H), 3.51 (q, J = 6.0 Hz, 2H), 2.77 (dd, J = 16.7, 4.0 Hz, 2H), 2.69-2.52 (m, 4H), 2.29 (s, 6H). |
| 301 | 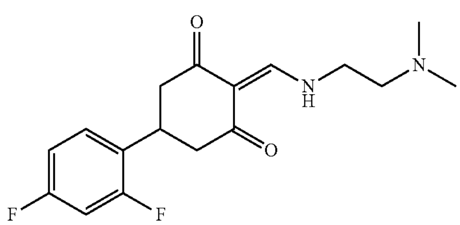 [SMILES: CN(C)CCNC=C1C(=O)CC(c2ccc(F)cc2F)CC1=O] | 5-(2,4-difluorophenyl)-2-(((2-(dimethylamino)ethyl)amino)methylene)cyclohexane-1,3-dione | ¹H NMR (400 MHz, CDCl₃) δ 11.22 (s, 1H), 8.18 (d, J = 14.4 Hz, 1H), 7.16 (dd, J = 14.8, 8.5 Hz, 1H), 6.88-6.77 (m, 2H), 3.60 (d, J = 9.8 Hz, 1H), 3.51 (q, J = 6.1 Hz, 2H), 2.71 (dd, J = 14.9, 9.7 Hz, 4H), 2.55 (t, J = 6.1 Hz, 2H), 2.29 (s, 6H). |
| 302 | 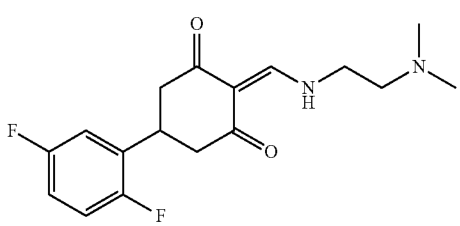 [SMILES: CN(C)CCNC=C1C(=O)CC(c2cc(F)ccc2F)CC1=O] | 5-(2,5-difluorophenyl)-2-(((2-(dimethylamino)ethyl)amino)methylene)cyclohexane-1,3-dione | 1H NMR (400 MHz, cdcl₃) δ 11.22 (s, 1H), 8.19 (d, J = 14.4 Hz, 1H), 7.01 (td, J = 9.6, 4.5 Hz, 1H), 6.95-6.87 (m, 2H), 3.64 (ddd, J = 15.7, 10.7, 5.2 Hz, 1H), 3.51 (q, J = 6.0 Hz, 2H), 2.77-2.61 (m, 4H), 2.55 (t, J = 6.1 Hz, 2H), 2.29 (s, 6H). |
| 303 | 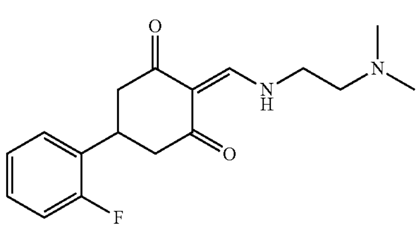 | 2-(((2-(dimethylamino)ethyl)amino)methylene)-5-(2-fluorophenyl)cyclohexane-1,3-dione | ¹H NMR (400 MHz, DMSO-d6) δ 10.99-10.88 (m, 1H), 8.13 (d, J = 14.7 Hz, 1H), 7.35 (t, J = 7.7 Hz, 1H), 7.32-7.23 (m, 1H), 7.16 (d, J = 7.2 Hz, 1H), 7.13 (d, J = 8.2 Hz, 1H), 3.54 (dt, J = 9.1, 4.6 Hz, 3H), 2.70 (ddd, J = 31.8, 16.5, 11.7 Hz, 2H), 2.54-2.49 (m, 1H), 2.45 (dd, J = 5.7, 3.7 Hz, 1H), 2.40 (t, J = 5.9 Hz, 2H), 2.15 (s, 6H). |

TABLE 7-continued

Compounds 119-355

| # | Structure | Name | Proton NMR(¹HNMR), Mass Spectrum(MS) |
|---|---|---|---|
| 304 | 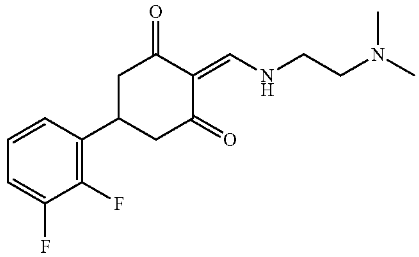 [SMILES: CN(C)CCNC=C1C(=O)CC(c2cccc(F)c2F)CC1=O] | 5-(2,3-difluorophenyl)-2-(((2-(dimethylamino)ethyl)amino)methylene)cyclohexane-1,3-dione | ¹H NMR (400 MHz, CDCl₃) δ 11.22 (s, 1H), 8.19 (d, J = 14.4 Hz, 1H), 7.06 (t, J = 6.2 Hz, 2H), 6.97 (dd, J = 5.4, 3.2 Hz, 1H), 3.75-3.63 (m, 1H), 3.51 (q, J = 6.0 Hz, 2H), 2.79-2.67 (m, 4H), 2.55 (t, J = 6.1 Hz, 2H), 2.29 (s, 6H). |
| 305 | 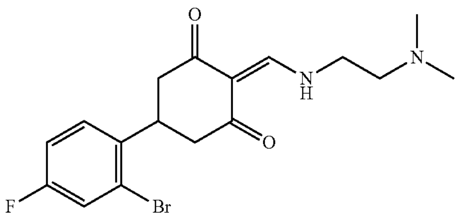 [SMILES: CN(C)CCNC=C1C(=O)CC(c2ccc(F)cc2Br)CC1=O] | 5-(2-bromo-4-fluorophenyl)-2-(((2-(dimethylamino)ethyl)amino)methylene)cyclohexane-1,3-dione | ¹H NMR (400 MHz, CDCl₃) δ 11.21 (s, 1H), 8.19 (d, J = 14.4 Hz, 1H), 7.33 (dd, J = 8.2, 2.6 Hz, 1H), 7.21 (dd, J = 8.7, 5.9 Hz, 1H), 7.04 (td, J = 8.3, 2.6 Hz, 1H), 3.77 (dd, J = 10.0, 5.9 Hz, 1H), 3.51 (q, J = 6.0 Hz, 2H), 2.77 (d, J = 2.6 Hz, 1H), 2.73 (d, J = 3.1 Hz, 1H), 2.68-2.56 (m, 2H), 2.55 (dd, J = 11.4, 5.3 Hz, 2H), 2.29 (s, 6H). |
| 306 | 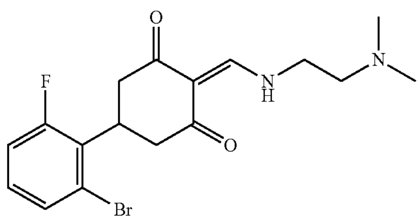 [SMILES: CN(C)CCNC=C1C(=O)CC(c2c(F)cccc2Br)CC1=O] | 5-(2-bromo-6-fluorophenyl)-2-(((2-(dimethylamino)ethyl)amino)methylene)cyclohexane-1,3-dione | ¹H NMR (400 MHz, CDCl₃) δ 11.24 (s, 1H), 8.22 (d, J = 14.4 Hz, 1H), 7.38 (d, J = 7.9 Hz, 1H), 7.10 (td, J = 8.1, 5.9 Hz, 1H), 7.06-6.98 (m, 1H), 4.00 (tt, J = 13.5, 3.5 Hz, 1H), 3.56-3.47 (m, 2H), 3.10 (ddd, J = 30.3, 16.6, 13.7 Hz, 2H), 2.60 (ddd, J = 14.7, 3.9, 2.0 Hz, 2H), 2.54 (t, J = 6.1 Hz, 2H), 2.29 (s, 6H). |
| 307 | 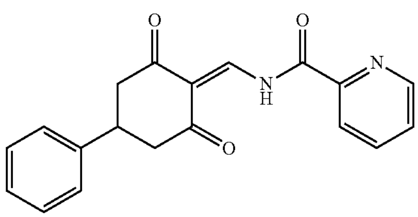 [SMILES: O=C1CC(c2ccccc2)CC(=O)C1=CNC(=O)c1ccccn1] | N-((2,6-dioxo-4-phenylcyclohexylidene)methyl)picolinamide | ¹H NMR (400 MHz, CDCl₃) δ 13.92 (d, J = 12.5 Hz, 1H), 8.88 (d, J = 12.9 Hz, 1H), 8.79 (d, J = 4.7 Hz, 1H), 8.29 (d, J = 7.8 Hz, 1H), 7.95 (td, J = 7.7, 1.6 Hz, 1H), 7.62-7.55 (m, 1H), 7.36 (t, J = 7.4 Hz, 2H), 7.28 (d, J = 7.3 Hz, 1H), 7.24 (s, 2H), 3.50-3.40 (m, 1H), 3.01-2.77 (m, 4H). |
| 308 | 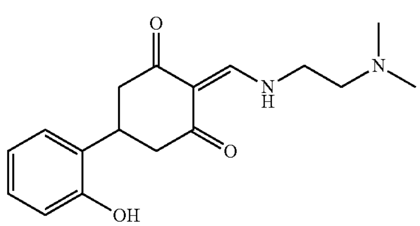 [SMILES: CN(C)CCNC=C1C(=O)CC(c2ccccc2O)CC1=O] | 2-(((2-(dimethylamino)ethyl)amino)methylene)-5-(2-hydroxyphenyl)cyclohexane-1,3-dione | ¹H NMR (400 MHz, CDCl₃) δ 11.25 (d, J = 14.2 Hz, 1H), 8.23 (d, J = 14.5 Hz, 1H), 7.07 (t, J = 6.9 Hz, 2H), 6.88-6.81 (m, 2H), 3.69 (s, 1H), 3.53 (q, J = 6.0 Hz, 2H), 2.95-2.85 (m, 2H), 2.81-2.62 (m, 2H), 2.57 (t, J = 6.1 Hz, 2H), 2.30 (s, 6H). |
| 309 | 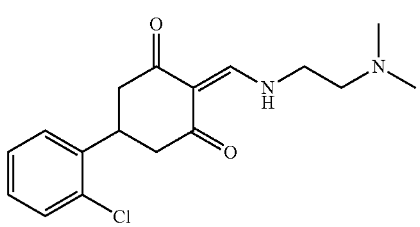 [SMILES: CN(C)CCNC=C1C(=O)CC(c2ccccc2Cl)CC1=O] | 5-(2-chlorophenyl)-2-(((2-(dimethylamino)ethyl)amino)methylene)cyclohexane-1,3-dione | ¹H NMR (400 MHz, CDCl₃) δ 11.20 (s, 1H), 8.19 (d, J = 14.3 Hz, 1H), 7.38 (d, J = 7.7 Hz, 1H), 7.25 (s, 2H), 7.21-7.14 (m, 1H), 3.85 (s, 1H), 3.51 (d, J = 6.0 Hz, 2H), 2.70 (ddd, J = 23.0, 16.8, 9.6 Hz, 4H), 2.55 (t, J = 5.9 Hz, 2H), 2.29 (s, 6H). |

TABLE 7-continued

Compounds 119-355

| # | Structure | Name | Proton NMR(¹HNMR), Mass Spectrum(MS) |
|---|---|---|---|
| 310 | 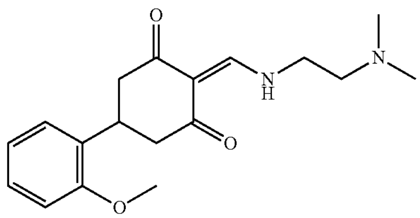 [SMILES: COc1ccccc1C1CC(=O)C(=CNCCN(C)C)C(=O)C1] | 2-(((2-(dimethylamino)ethyl)amino)methylene)-5-(2-methoxyphenyl)cyclohexane-1,3-dione | ¹H NMR (400 MHz, CDCl₃) δ 11.21 (s, 1H), 8.18 (d, J = 14.3 Hz, 1H), 7.23 (td, J = 8.2, 1.6 Hz, 1H), 7.15 (dd, J = 7.6, 1.3 Hz, 1H), 6.94 (td, J = 7.5, 0.9 Hz, 1H), 6.87 (d, J = 8.2 Hz, 1H), 3.82 (s, 3H), 3.77- 3.67 (m, 1H), 3.49 (q, J = 6.1 Hz, 2H), 2.77-2.66 (m, 4H), 2.53 (t, J = 6.2 Hz, 2H), 2.28 (s, 6H). |
| 311 | 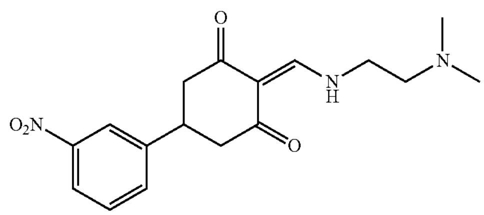 [SMILES: CN(C)CCNC=C1C(=O)CC(c2cccc([N+](=O)[O-])c2)CC1=O] | 2-(((2-(dimethylamino)ethyl)amino)methylene)-5-(3-nitrophenyl)cyclohexane-1,3-dione | ¹H NMR (400 MHz, CDCl₃) δ 11.21 (s, 1H), 8.20 (d, J = 14.5 Hz, 1H), 8.12 (dd, J = 4.3, 2.0 Hz, 2H), 7.61-7.48 (m, 2H), 3.55-3.44 (m, 3H), 2.80-2.76 (m, 2H), 2.74 (d, J = 12.4 Hz, 1H), 2.71-2.65 (m, 1H), 2.55 (t, J = 6.1 Hz, 2H), 2.29 (s, 6H). |
| 315 | 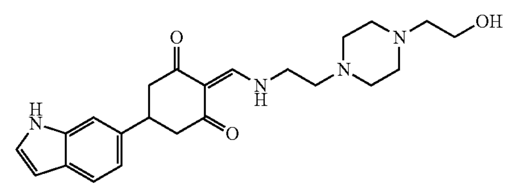 [SMILES: O=C1CC(c2ccc3cc[nH]c3c2)CC(=O)C1=CNCCN1CCN(CCO)CC1] | 2-(((2-(4-(2-hydroxyethyl)piperazin-1-yl)ethyl)amino)methylene)-5-(1H-indol-6-yl)cyclohexane-1,3-dione | ¹H NMR (400 MHz, CD₃OD) δ 8.24 (s, 1H), 7.49 (d, J = 8.2 Hz, 1H), 7.27 (s, 1H), 7.19 (d, J = 3.1 Hz, 1H), 6.96 (dd, 1H), 6.39 (dd, 1H), 3.81 (t, J = 5.4 Hz, 2H), 3.61 (m, 2H), 3.45 (m, 1H), 3.34 (s, 2H), 3.06 (m, 4H), 2.93-2.62 (m, 10H); MS: 411.2 [M + 1]. |
| 317 | 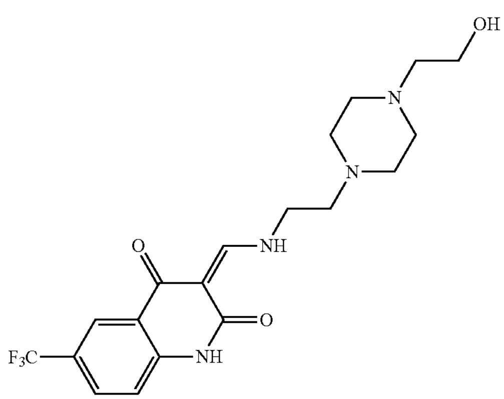 [SMILES: O=C1Nc2ccc(C(F)(F)F)cc2C(=O)/C1=C/NCCN1CCN(CCO)CC1] | 3-(((2-(4-(2-hydroxyethyl)piperazin-1-yl)ethyl)amino)methylene)-6-(trifluoromethyl)quinoline-2,4(1H,3H)-dione | ¹H NMR (400 MHz, CD₃OD) δ 8.58 (d, J = 32.5 Hz, 1H), 8.31 (s, 1H), 7.77 (d, J = 8.3 Hz, 1H), 7.32 (d, J = 8.6 Hz, 1H), 3.87-3.67 (m, 4H), 3.02 (d, J = 40.0 Hz, 6H), 2.74 (m, 6H). |
| 318 | 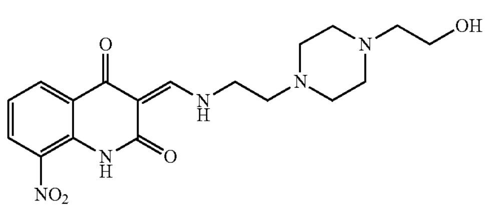 [SMILES: O=C1Nc2c(cccc2[N+](=O)[O-])C(=O)/C1=C/NCCN1CCN(CCO)CC1] | 3-(((2-(4-(2-hydroxyethyl)piperazin-1-yl)ethyl)amino)methylene)-8-nitroquinoline-2,4(1H,3H)-dione | ¹H NMR (400 MHz, CD₃OD) δ 8.47 (m, 3H), 7.27 (m, 1H), 3.81 (m, 4H), 3.10 (d, J = 45.3 Hz, 6H), 2.89-2.66 (m, 6H). |
| 320 | 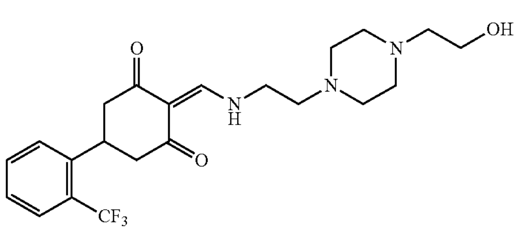 [SMILES: O=C1CC(c2ccccc2C(F)(F)F)CC(=O)C1=CNCCN1CCN(CCO)CC1] | 2-(((2-(4-(2-hydroxyethyl)piperazin-1-yl)ethyl)amino)methylene)-5-(2-(trifluoromethyl)phenyl)cyclohexane-1,3-dione | ¹H NMR (400 MHz, DMSO-d6) δ 11.05-10.84 (m, 1H), 8.15 (d, J = 14.8 Hz, 1H), 7.81 (d, J = 8.2 Hz, 1H), 7.67 (t, J = 7.2 Hz, 2H), 7.44 (t, J = 7.6 Hz, 1H), 4.80 (s, 1H), 3.58-3.12 (m, 9H), 3.00-2.50 (m, 10H), 2.34 (d, J = 16.5 Hz, 2H). |

TABLE 7-continued

Compounds 119-355

| # | Structure | Name | Proton NMR(¹HNMR), Mass Spectrum(MS) |
|---|---|---|---|
| 321 | 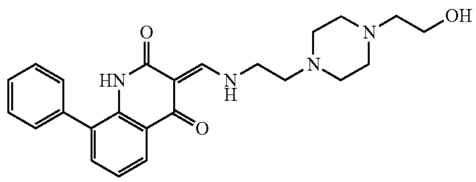 [SMILES: O=C1Nc2c(cccc2-c2ccccc2)C(=O)/C1=C\NCCN1CCN(CCO)CC1] | 3-(((2-(4-(2-hydroxyethyl)piperazin-1-yl)ethyl)amino)methylene)-8-phenylquinoline-2,4(1H,3H)-dione | ¹H NMR (400 MHz, CD₃OD) δ 8.54 (d, J = 47.0 Hz, 1H), 8.09 (d, J = 7.8 Hz, 1H), 7.63-7.37 (m, 6H), 7.25 (t, J = 7.7 Hz, 1H), 3.74 (m, 4H), 3.04-2.57 (m, 12H). |
| 322 | 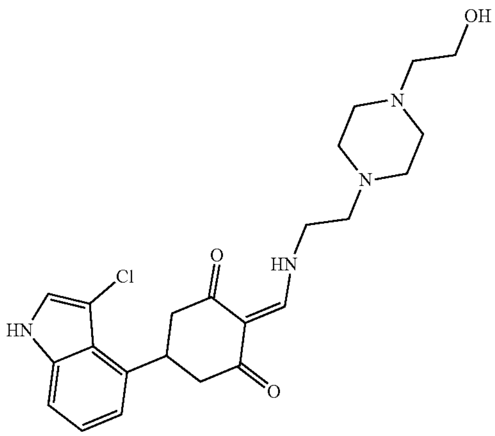 [SMILES: O=C1CC(c2cccc3[nH]cc(Cl)c23)CC(=O)C1=CNCCN1CCN(CCO)CC1] | 5-(3-chloro-1H-indol-4-yl)-2-(((2-(4-(2-hydroxyethyl)piperazin-1-yl)ethyl)amino)methylene)cyclohexane-1,3-dione | ¹H NMR (400 MHz, CD₃OD) δ 8.27 (s, 1H), 7.32-7.19 (m, 2H), 7.12 (t, J = 7.8 Hz, 1H), 6.96 (d, J = 7.2 Hz, 1H), 3.71 (t, J = 5.9 Hz, 2H), 3.61 (t, J = 5.9 Hz, 2H), 2.92-2.48 (m, 17H). |
| 323 | 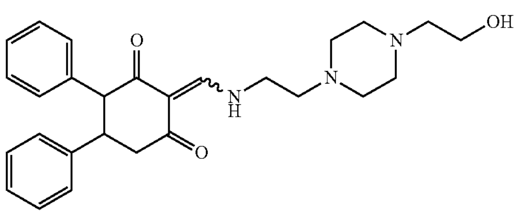 [SMILES: O=C1CC(c2ccccc2)C(c2ccccc2)C(=O)C1=CNCCN1CCN(CCO)CC1] | 2-(((2-(4-(2-hydroxyethyl)piperazin-1-yl)ethyl)amino)methylene)-4,5-diphenylcyclohexane-1,3-dione | ¹H NMR (400 MHz, CD₃OD) δ 8.30 (d, J = 24.8 Hz, 1H), 7.16-7.05 (m, 10H), 4.04-3.93 (m, 1H), 3.70-3.56 (m, 5H), 3.04-2.99 (m, 1H), 2.69-2.61 (m, 1H); MS: 448.2 [M + 1]. |
| 324 | 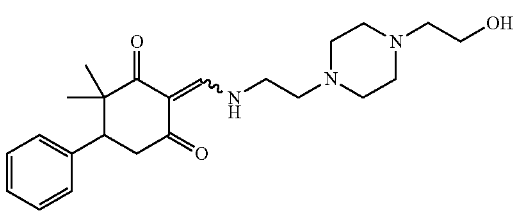 [SMILES: CC1(C)C(=O)C(=CNCCN2CCN(CCO)CC2)C(=O)CC1c1ccccc1] | 2-(((2-(4-(2-hydroxyethyl)piperazin-1-yl)ethyl)amino)methylene)-4,4-dimethyl-5-phenylcyclohexane-1,3-dione | ¹H NMR (400 MHz, CD₃OD) δ 8.27 (d, J = 20.4 Hz, 7.29-7.21 (m, 5H), 3.72 (t, J = 5.6 Hz, 2H), 3.62 (t, J = 5.6 Hz, 2H), 3.22-3.17 (m, 1H), 3.09-3.00 (m, 1H), 2.77-2.56 (m, 12H); MS: 400.2 [M + 1]. |
| 325 | 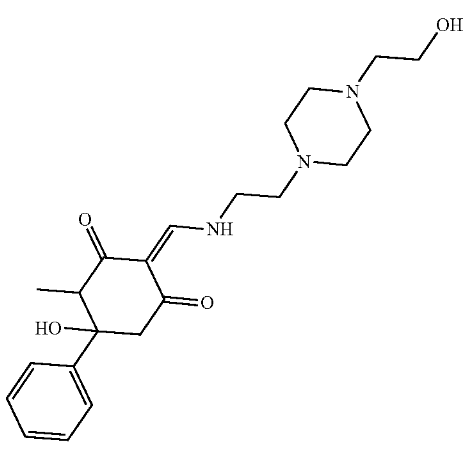 [SMILES: CC1C(=O)/C(=C/NCCN2CCN(CCO)CC2)C(=O)CC1(O)c1ccccc1] | 5-hydroxy-2-(((2-(4-(2-hydroxyethyl)piperazin-1-yl)ethyl)amino)methylene)-4-methyl-5-phenylcyclohexane-1,3-dione | ¹H NMR (400 MHz, DMSO-d6) δ 10.76 (s, 1H), 8.08 (d, J = 14.8 Hz, 1H), 7.71 (s, 1H), 7.47 (d, J = 7.7 Hz, 2H), 7.32 (t, J = 7.5 Hz, 2H), 7.20 (t, J = 7.2 Hz, 1H), 3.72 (s, 3H), 3.60 (s, 2H), 3.22-2.85 (m, 10H), 2.71 (s, 2H), 2.56 (m, 1H), 2.43 (s, 1H), 1.92 (d, J = 12.3 Hz, 1H), 1.07-0.71 (m, 3H). |

TABLE 7-continued

Compounds 119-355

| # | Structure | Name | Proton NMR(¹HNMR), Mass Spectrum(MS) |
|---|---|---|---|
| 326 | 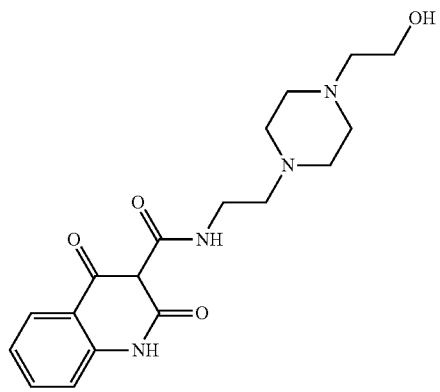 [SMILES: O=C(NCCN1CCN(CCO)CC1)C1C(=O)Nc2ccccc2C1=O] | N-(2-(4-(2-hydroxyethyl)piperazin-1-yl)ethyl)-2,4-dioxo-1,2,3,4-tetrahydroquinoline-3-carboxamide | ¹H NMR (400 MHz, CD₃OD) δ 8.06 (d, J = 8.0 Hz, 1H), 7.64 (t, J = 7.3 Hz, 1H), 7.29 (dd, J = 14.9, 7.7 Hz, 2H), 3.68 (t, J = 6.0 Hz, 2H), 3.57 (t, J = 6.4 Hz, 2H), 2.59 m, 12H). |
| 327 | 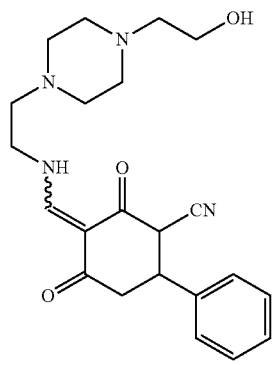 [SMILES: N#CC1C(=O)C(=CNCCN2CCN(CCO)CC2)C(=O)CC1c1ccccc1] | 2-(((2-(4-(2-hydroxyethyl)piperazin-1-yl)ethyl)amino)methylene)-4-cyano-5-phenylcyclohexane-1,3-dione | ¹H NMR (400 MHz, CD₃OD) δ 8.35-8.32 (m, 1H), 7.40-7.31 (m, 5H), 3.84-3.82 (m, 2H), 3.66-3.53 (m, 3H), 3.28-3.12 (m, 6H), 2.88-2.63 (m, 10H); MS: 397.2 [M + 1]. |
| 328 | 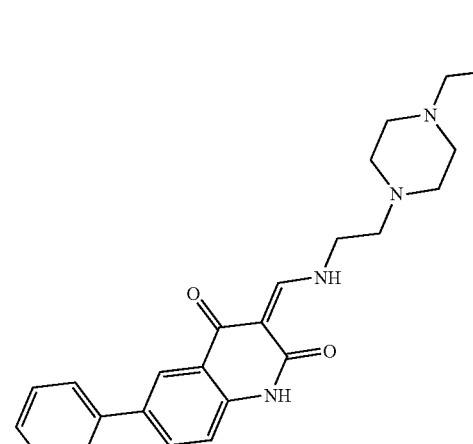 | 3-(((2-(4-(2-hydroxyethyl)piperazin-1-yl)ethyl)amino)methylene)-6-phenylquinoline-2,4(1H,3H)-dione | ¹H NMR (400 MHz, DMSO-d6) δ 11.93-11.64 (m, 1H), 10.72-10.02 (m, 2H), 8.48 (m, 1H), 8.23-7.16 (m, 7H), 3.67-3.31 (m, 10H), 2.94 (m, 6H). |

TABLE 7-continued

Compounds 119-355

| # | Structure | Name | Proton NMR($^1$HNMR), Mass Spectrum(MS) |
|---|---|---|---|
| 329 | 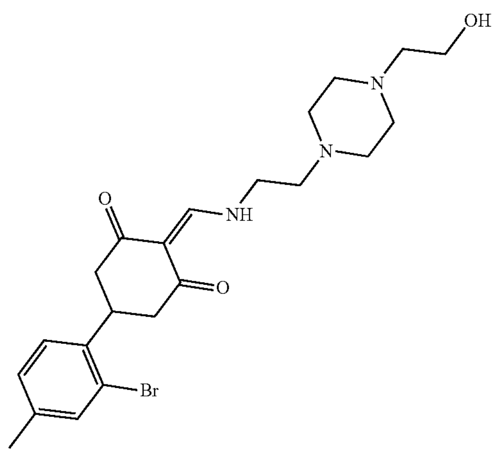 [SMILES: Cc1ccc(C2CC(=O)C(=CNCCN3CCN(CCO)CC3)C(=O)C2)c(Br)c1] | 5-(2-bromo-4-methylphenyl)-2-(((2-(4-(2-hydroxyethyl)piperazin-1-yl)ethyl)amino)methylene)cyclohexane-1,3-dione | $^1$H NMR (400 MHz, CD$_3$OD) δ 8.26 (s, 1H), 7.43 (s, 1H), 7.24 (d, J = 8.0 Hz, 1H), 7.17 (d, J = 8.0 Hz, 1H), 3.71 (m, 3H), 3.61 (t, J = 5.9 Hz, 2H), 2.81-2.52 (m, 16H), 2.30 (s, 3H). |
| 330 | 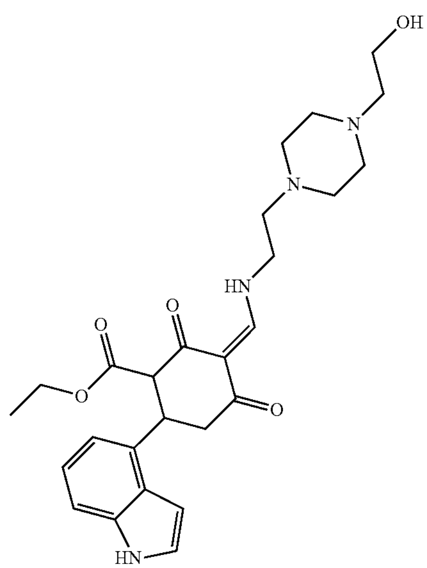 [SMILES: CCOC(=O)C1C(=O)/C(=C\NCCN2CCN(CCO)CC2)C(=O)CC1c1cccc2[nH]ccc12] | ethyl 3-(((2-(4-(2-hydroxyethyl)piperazin-1-yl)ethyl)amino)methylene)-6-(1H-indol-4-yl)-2,4-dioxocyclohexane-1-carboxylate | $^1$H NMR (400 MHz, CD$_3$OD) δ 8.30 (d, J = 18.1 Hz, 1H), 7.26 (dd, J = 14.0, 5.6 Hz, 2H), 7.05 (t, J = 7.8 Hz, 1H), 6.94 (d, J = 7.3 Hz, 1H), 6.56 (d, J = 3.1 Hz, 1H), 4.09 (m, 2H), 3.96-3.83 (m, 2H), 3.77 (t, J = 5.6 Hz, 2H), 3.62 (m, 2H), 2.92 (m, 6H), 2.80-2.45 (m, 8H), 0.90 (t, J = 7.1 Hz, 3H). |
| 331 | 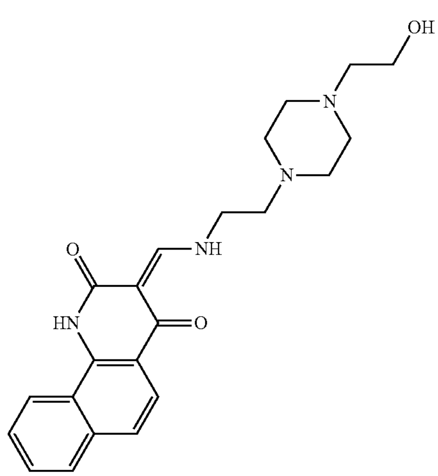 [SMILES: O=C1Nc2c(ccc3ccccc23)C(=O)/C1=C\NCCN1CCN(CCO)CC1] | 3-(((2-(4-(2-hydroxyethyl)piperazin-1-yl)ethyl)amino)methylene)benzo[h]quinoline-2,4(1H,3H)-dione | $^1$H NMR (400 MHz, CD$_3$OD) δ 8.61 (d, J = 34.9 Hz, 1H), 8.47 (d, J = 8.1 Hz, 1H), 8.06 (d, J = 8.7 Hz, 1H), 7.91 (d, J = 7.4 Hz, 1H), 7.71-7.54 (m, 3H), 3.73 (m, 4H), 2.92-2.53 (m, 12H). |

TABLE 7-continued

Compounds 119-355

| # | Structure | Name | Proton NMR(¹HNMR), Mass Spectrum(MS) |
|---|---|---|---|
| 332 | 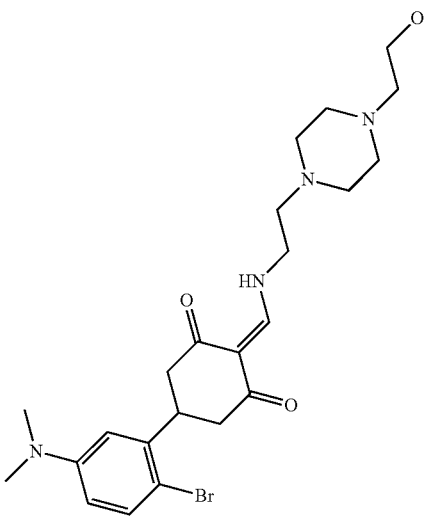 | 5-(2-bromo-5-(dimethylamino)phenyl)-2-(((2-(4-(2-hydroxyethyl)piperazin-1-yl)ethyl)amino)methylene)cyclohexane-1,3-dione | ¹H NMR (400 MHz, CD₃OD) δ 8.26 (s, 1H), 7.34 (d, J = 8.9 Hz, 1H), 6.66 (d, J = 3.0 Hz, 1H), 6.56 (dd, J = 8.9, 3.0 Hz, 1H), 3.76 (t, J = 5.7 Hz, 2H), 3.70 (m, 1H), 3.62 (t, J = 5.8 Hz, 2H), 2.99-2.56 (m, 22H). |
| 333 | 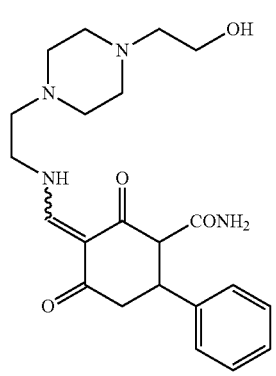 [SMILES: NC(=O)C1C(=O)C(=CNCCN2CCN(CCO)CC2)C(=O)CC1c1ccccc1] | 3-(((2-(4-(2-hydroxyethyl)piperazin-1-yl)ethyl)amino)methylene)-2,4-dioxo-6-phenylcyclohexane-1-carboxamide | ¹H NMR (400 MHz, CD₃OD) δ 8.27 (d, J = 16.8 Hz 1H), 7.31-7.25 (m, 5H), 3.84-3.72 (m, 3H), 3.66-3.59 (m, 3H), 3.16-3.04 (m, 6H), 2.86-2.59 (m, 12H); MS: 415.2 [M + 1]. |
| 334 | 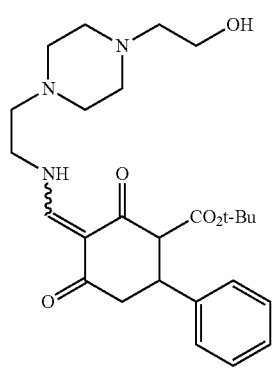 [SMILES: CC(C)(C)OC(=O)C1C(=O)C(=CNCCN2CCN(CCO)CC2)C(=O)CC1c1ccccc1] | tert-butyl 3-(((2-(4-(2-hydroxyethyl)piperazin-1-yl)ethyl)amino)methylene)-2,4-dioxo-6-phenylcyclohexane-1-carboxylate | ¹H NMR (400 MHz, CD₃OD) δ 8.28-8.24 (m, 1H), 7.31-7.20 (m, 5H), 3.89-3.27 (m, 12H), 2.90-2.55 (m, 8H), 1.20-1.17 (m, 9H); MS: 472.2 [M + 1]. |

TABLE 7-continued

Compounds 119-355

| # | Structure | Name | Proton NMR(¹HNMR), Mass Spectrum(MS) |
|---|---|---|---|
| 335 | 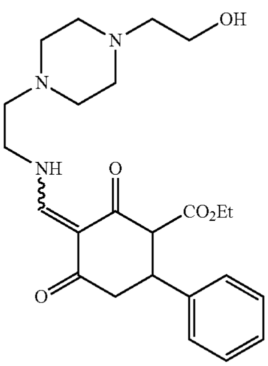 [SMILES: CCOC(=O)C1C(=O)C(=CNCCN2CCN(CCO)CC2)C(=O)CC1c1ccccc1] | ethyl 3-(((2-(4-(2-hydroxyethyl)piperazin-1-yl)ethyl)amino)methylene)-2,4-dioxo-6-phenylcyclohexane-1-carboxylate | ¹H NMR (400 MHz, CD₃OD) δ 8.30-8.25 (m, 1H), 7.46-7.12 (m, 5H), 4.00-3.87 (m, 5H), 3.86-3.11 (m, 9H), 2.87-2.57 (m, 8H), 1.01-0.90 (m, 3H); MS: 444.2 [M + 1]. |
| 336 | 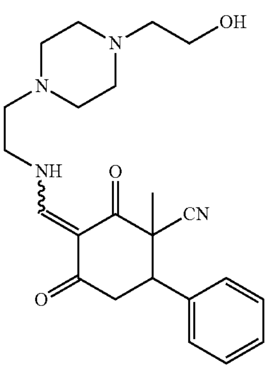 [SMILES: CC1(C#N)C(=O)C(=CNCCN2CCN(CCO)CC2)C(=O)CC1c1ccccc1] | 3-(((2-(4-(2-hydroxyethyl)piperazin-1-yl)ethyl)amino)methylene)-1-methyl-2,4-dioxo-6-phenylcyclohexane-1-carbonitrile | ¹H NMR (400 MHz, CD₃OD) δ 8.37-8.31 (m, 1H), 7.43-7.33 (m, 5H), 3.70 (t, J = 6.0 Hz, 2H), 3.64 (t, J = 5.6 Hz, 2H), 3.11-3.33 (m, 2H), 2.77-2.60 (m, 13H), 1.37 (br, 3H); MS: 411.2 [M + 1]. |
| 337 | 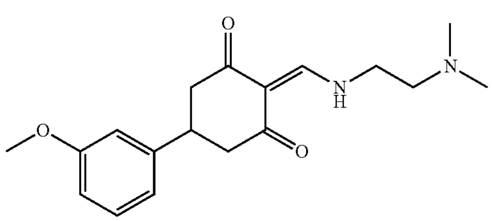 | 2-(((2-(dimethylamino)ethyl)amino)methylene)-5-(3-methoxyphenyl)cyclohexane-1,3-dione | ¹H NMR (400 MHz, CDCl₃) δ 11.21 (s, 1H), 8.18 (d, J = 14.3 Hz, 1H), 7.24 (d, J = 7.6 Hz, 1H), 6.80 (dd, J = 15.9, 7.6 Hz, 3H), 3.80 (s, 3H), 3.52 (dd, J = 12.1, 6.0 Hz, 2H), 3.38-3.27 (m, 1H), 2.80-2.69 (m, 3H), 2.70-2.61 (m, 1H), 2.57 (t, J = 6.1 Hz, 2H), 2.30 (s, 6H). |
| 338 | 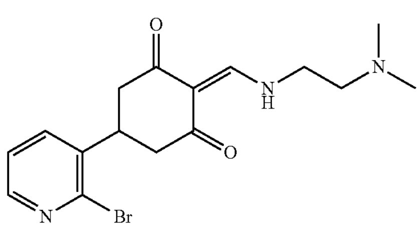 [SMILES: CN(C)CCNC=C1C(=O)CC(c2cccnc2Br)CC1=O] | 5-(2-bromopyridin-3-yl)-2-(((2-(dimethylamino)ethyl)amino)methylene)cyclohexane-1,3-dione | ¹H NMR (400 MHz, CDCl₃) δ 11.22 (s, 1H), 8.28 (d, J = 3.0 Hz, 1H), 8.20 (d, J = 14.4 Hz, 1H), 7.54 (d, J = 7.6 Hz, 1H), 7.29 (s, 1H), 3.84-3.74 (m, 1H), 3.57-3.47 (m, 2H), 2.81 (d, J = 6.7 Hz, 2H), 2.70-2.59 (m, 2H), 2.56 (d, J = 6.0 Hz, 2H), 2.31 (s, 6H). |
| 339 | 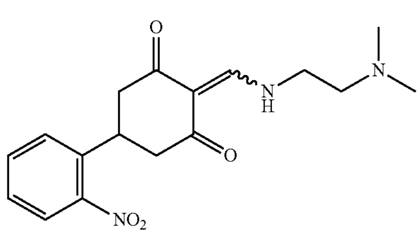 [SMILES: CN(C)CCNC=C1C(=O)CC(c2ccccc2[N+](=O)[O-])CC1=O] | 3-(((2-(dimethylamino)ethyl)amino)methylene)-6-(2-nitrophenyl)piperidine-2,4-dione | ¹H NMR (400 MHz, CDCl₃) δ 10.70 (s, 1H), 8.09 (d, J = 14.3 Hz, 1H), 7.96 (d, J = 8.0 Hz, 1H), 7.70 (t, J = 7.8 Hz, 1H), 7.64 (t, J = 7.6 Hz, 1H), 7.47 (t, J = 7.5 Hz, 1H), 5.65 (s, 1H), 5.35 (d, J = 8.3 Hz, 1H), 3.47 (dd, J = 6.7, 5.8 Hz, 2H), 3.17-3.03 (m, 1H), 2.70 (dd, J = 6.7, 6.9 Hz, 1H), 2.53 (t, J = 6.1 Hz, 2H), 2.28 (s, 6H). |

TABLE 7-continued

Compounds 119-355

| # | Structure | Name | Proton NMR(¹HNMR),<br>Mass Spectrum(MS) |
|---|---|---|---|
| 340 | 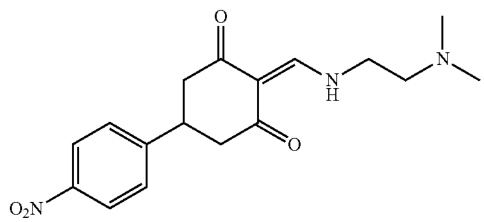 [SMILES: CN(C)CCNC=C1C(=O)CC(c2ccc([N+](=O)[O-])cc2)CC1=O] | 2-(((2-(dimethylamino)ethyl)amino)methylene)-5-(4-nitrophenyl)cyclohexane-1,3-dione | ¹H NMR (400 MHz, CDCl₃) δ 11.21 (s, 1H), 8.20 (dd, J = 11.7, 6.2 Hz, 3H), 7.40 (d, J = 8.5 Hz, 2H), 3.56-3.43 (m, 3H), 2.82-2.62 (m, 4H), 2.54 (t, J = 6.0 Hz, 2H), 2.29 (s, 6H). |
| 341 | 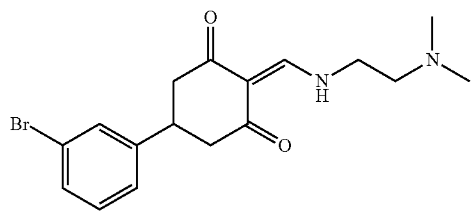 [SMILES: CN(C)CCNC=C1C(=O)CC(c2cccc(Br)c2)CC1=O] | 5-(3-bromophenyl)-2-(((2-(dimethylamino)ethyl)amino)methylene)cyclohexane-1,3-dione | ¹H NMR (400 MHz, CDCl₃) δ 11.18 (s, 1H), 8.16 (d, J = 14.4 Hz, 1H), 7.37 (dd, J = 4.7, 1.4 Hz, 2H), 7.17 (dt, J = 19.2, 7.8 Hz, 2H), 3.48 (q, J = 6.0 Hz, 2H), 3.37-3.26 (m, 1H), 2.77-2.56 (m, 4H), 2.52 (t, J = 6.1 Hz, 2H), 2.27 (s, 6H). |
| 342 | 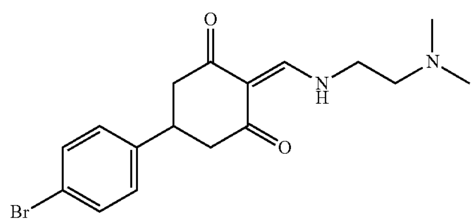 [SMILES: CN(C)CCNC=C1C(=O)CC(c2ccc(Br)cc2)CC1=O] | 5-(4-bromophenyl)-2-(((2-(dimethylamino)ethyl)amino)methylene)cyclohexane-1,3-dione | ¹H NMR (400 MHz, CDCl₃) δ 11.21 (s, 1H), 8.18 (d, J = 14.4 Hz, 1H), 7.47 (d, J = 8.4 Hz, 2H), 7.12 (d, J = 8.3 Hz, 2H), 3.51 (q, J = 6.0 Hz, 2H), 3.34 (ddd, J = 15.9, 11.1, 4.6 Hz, 1H), 2.80-2.58 (m, 4H), 2.55 (t, J = 6.1 Hz, 2H), 2.29 (s, 6H). |
| 343 | 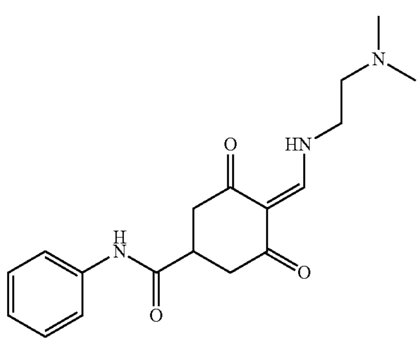 [SMILES: CN(C)CCNC=C1C(=O)CC(C(=O)Nc2ccccc2)CC1=O] | 4-(((2-(dimethylamino)ethyl)amino)methylene)-3,5-dioxo-N-phenylcyclohexane-1-carboxamide | ¹H NMR (400 MHz, CDCl₃) δ 11.16 (s, 1H), 8.12 (d, J = 14.6 Hz, 1H), 7.92 (s, 1H), 7.56 (d, J = 7.8 Hz, 2H), 7.32 (t, J = 7.8 Hz, 2H), 7.11 (t, J = 7.5 Hz, 1H), 3.45 (d, J = 6.0 Hz, 2H), 3.03-2.76 (m, 3H), 2.69 (d, J = 17.1 Hz, 2H), 2.51 (t, J = 6.1 Hz, 2H), 2.25 (s, 6H). |
| 344 | 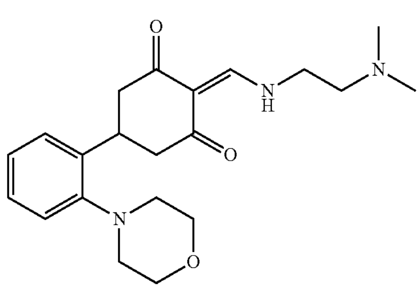 [SMILES: CN(C)CCNC=C1C(=O)CC(c2ccccc2N2CCOCC2)CC1=O] | 2-(((2-(dimethylamino)ethyl)amino)methylene)-5-(2-morpholinophenyl)cyclohexane-4,3-dione | ¹H NMR (400 MHz, CDCl₃) δ 11.21 (s, 1H), 8.21 (d, J = 14.4 Hz, 1H), 7.27-7.12 (m, 4H), 3.96 (dd, J = 9.8, 5.9 Hz, 1H), 3.88-3.72 (m, 4H), 3.52 (q, J = 6.0 Hz, 2H), 2.85 (s, 4H), 2.78-2.61 (m, 4H), 2.55 (t, J = 6.1 Hz, 2H), 2.29 (s, 6H). |

TABLE 7-continued

Compounds 119-355

| # | Structure | Name | Proton NMR(¹HNMR), Mass Spectrum(MS) |
|---|---|---|---|
| 345 | 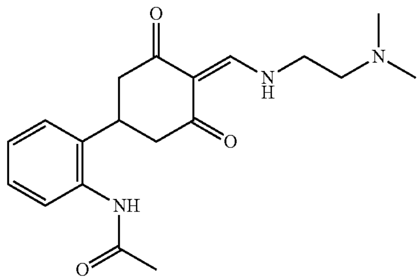 [SMILES: CC(=O)Nc1ccccc1C1CC(=O)C(=CNCCN(C)C)C(=O)C1] | N-(2-(4-(((2-(dimethylamino)ethyl)amino)methylene)-3,5-dioxocyclohexyl)phenyl)acetamide | ¹H NMR (400 MHz, CDCl₃) δ 11.15 (s, 1H), 8.12 (d, J = 14.3 Hz, 1H), 7.66 (s, 1H), 7.57 (d, J = 7.4 Hz, 1H), 7.25 (d, J = 4.9 Hz, 3H), 3.51 (t, J = 17.7 Hz, 3H), 2.64 (dd, J = 24.2, 10.9 Hz, 4H), 2.53 (t, J = 5.9 Hz, 2H), 2.27 (s, 6H), 2.18 (s, 3H). |
| 346 | 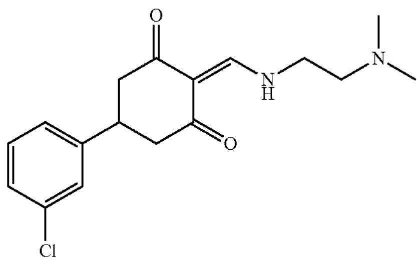 | 5-(3-chlorophenyl)-2-(((2-(dimethylamino)ethyl)amino)methylene)cyclohexane-1,3-dione | ¹H NMR (400 MHz, CDCl₃) δ 11.21 (s, 1H), 8.18 (d, J = 14.4 Hz, 1H), 7.26-7.19 (m, 3H), 7.11 (d, J = 7.3 Hz, 1H), 3.53-3.47 (m, 2H), 3.39-3.28 (m, 1H), 2.70 (dt, J = 33.1, 12.1 Hz, 4H), 2.54 (t, J = 6.1 Hz, 2H), 2.28 (s, 6H). |
| 347 | 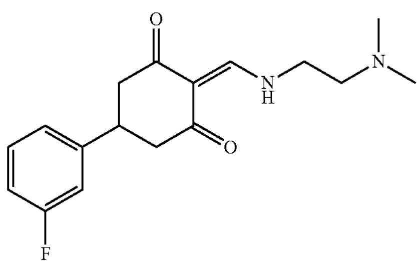 [SMILES: CN(C)CCNC=C1C(=O)CC(c2cccc(F)c2)CC1=O] | 2-(((2-(dimethylamino)ethyl)amino)methylene)-5-(3-fluorophenyl)cyclohexane-1,3-dione | ¹H NMR (400 MHz, CDCl₃) δ 11.21 (s, 1H), 8.18 (d, J = 14.4 Hz, 1H), 7.31 (dd, J = 9.5, 7.0 Hz, 1H), 7.01 (d, J = 7.7 Hz, 1H), 6.97-6.91 (m, 2H), 3.51 (q, J = 6.0 Hz, 2H), 3.41-3.31 (m, 1H), 2.79-2.59 (m, 4H), 2.55 (t, J = 6.1 Hz, 2H), 2.29 (s, 6H). |
| 349 | 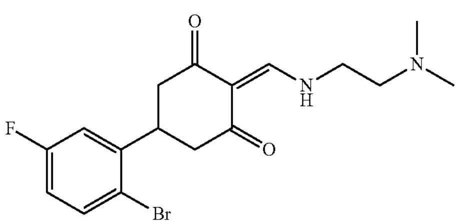 [SMILES: CN(C)CCNC=C1C(=O)CC(c2cc(F)ccc2Br)CC1=O] | 5-(2-bromo-5-fluorophenyl)-2-(((2-(dimethylamino)ethyl)amino)methylene)cyclohexane-1,3-dione | ¹H NMR (400 MHz, CDCl₃) δ 11.21 (s, 1H), 8.20 (d, J = 14.4 Hz, 1H), 7.53 (dd, J = 8.8, 5.5 Hz, 1H), 6.97 (dd, J = 9.8, 2.9 Hz, 1H), 6.89-6.81 (m, 1H), 3.84-3.73 (m, 1H), 3.52 (q, J = 6.0 Hz, 2H), 2.77 (dd, J = 16.5, 3.8 Hz, 2H), 2.67-2.50 (m, 4H), 2.29 (s, 6H). |
| 350 | 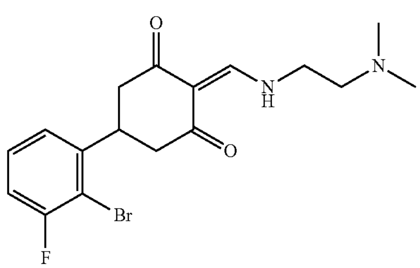 [SMILES: CN(C)CCNC=C1C(=O)CC(c2cccc(F)c2Br)CC1=O] | 5-(2-bromo-3-fluorophenyl)-2-(((2-(dimethylamino)ethyl)amino)methylene)cyclohexane-1,3-dione | ¹H NMR (400 MHz, CDCl₃) δ 11.21 (s, 1H), 8.20 (d, J = 14.4 Hz, 1H), 7.32-7.27 (m, 1H), 7.03 (t, J = 7.2 Hz, 2H), 3.85 (ddd, J = 15.7, 7.8, 4.1 Hz, 1H), 3.52 (q, J = 6.0 Hz, 2H), 2.81-2.59 (m, 4H), 2.56 (t, J = 6.1 Hz, 2H), 2.29 (s, 6H). |
| 351 | 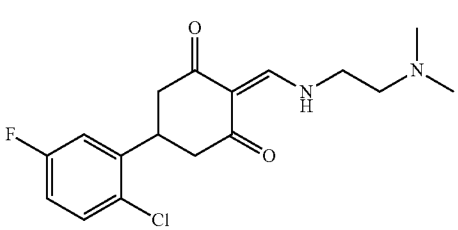 [SMILES: CN(C)CCNC=C1C(=O)CC(c2cc(F)ccc2Cl)CC1=O] | 5-(2-chloro-5-fluorophenyl)-2-(((2-(dimethylamino)ethyl)amino)methylene)cyclohexane-1,3-dione | ¹H NMR (400 MHz, CDCl₃) δ 11.22 (s, 1H), 8.20 (d, J = 14.4 Hz, 1H), 7.34 (dd, J = 8.8, 5.3 Hz, 1H), 6.99-6.88 (m, 2H), 3.86-3.76 (m, 1H), 3.52 (q, J = 6.0 Hz, 2H), 2.76 (dd, J = 16.6, 3.3 Hz, 2H), 2.68-2.52 (m, 4H), 2.29 (s, 6H). |

TABLE 7-continued

Compounds 119-355

| # | Name | Proton NMR(¹HNMR), Mass Spectrum(MS) |
|---|------|---------------------------------------|
| 352 | 2-(((2-(4-(2-hydroxyethyl)piperazin-1-yl)ethyl)amino)methylene)cycloheptane-1,3-dione | ¹H NMR (400 MHz, CD₃OD) δ 8.08 (s, 1H), 3.72 (t, J = 5.9 Hz, 2H), 3.55 (t, J = 5.9 Hz, 2H), 2.87-2.52 (m, 15H), 1.90-1.75 (m, 4H). MS: 310.2 [M + 1]. |
| 353 | 2-(((2-(4-(2-hydroxyethyl)piperazin-1-yl)ethyl)amino)methylene)-5-(3-phenyl-1H-indol-4-yl)cyclohexane-1,3-dione | ¹H NMR (400 MHz, CD₃OD) δ 8.10 (s, 1H), 7.39 (dd, J = 8.2, 1.3 Hz, 2H), 7.30 (m, 3H), 7.22 (m, 1H), 7.15-7.09 (m, 2H), 6.94 (d, J = 7.3 Hz, 1H), 3.81-3.76 (m, 2H), 3.74 (m, 1H), 3.55 (t, J = 5.8 Hz, 2H), 2.97 (m, 6H), 2.76-2.57 (m, 8H), 2.48 (m, 2H). MS: 487.2 [M + 1]. |
| 354 | 3-(((2-(4-(2-hydroxyethyl)piperazin-1-yl)ethyl)amino)methylene)-7-(trifluoromethyl)quinoline-2,4(1H,3H)-dione | ¹H NMR (400 MHz, CD₃OD) δ 8.54 (m, 1H), 8.19 (d, J = 8.0 Hz, 1H), 7.48 (s, 1H), 7.39 (d, J = 7.8 Hz, 1H), 3.81-3.68 (m, 4H), 2.88 (d, J = 34.6 Hz, 6H), 2.72 (s, 6H). MS: 413.1 [M + 1]. |
| 355 | 2-(((1-oxoisoindolin-4-yl)amino)methylene)-5-phenylcyclohexane-1,3-dione | ¹H NMR (400 MHz, DMSO-d6) δ 12.87 (s, 1H), 8.73 (s, 1H), 8.63 (m, 1H), 7.86 (m, 1H), 7.56 (s, 2H), 7.33 (s, 4H), 7.24-7.18 (m, 1H), 4.50 (s, 2H), 3.43-3.39 (m, 1H), 2.97-2.89 (m, 1H), 2.86-2.77 (m, 1H), 2.65 (m, 2H). MS: 347.1 [M + 1] |
| 356 | 5-(2,3-dichlorophenyl)-2-(((2-(dimethylamino)ethyl)amino)methylene)cyclohexane-1,3-dione | ¹H NMR (400 MHz, CDCl₃) δ 11.20 (s, 1H), 8.19 (d, J = 14.4 Hz, 1H), 7.38 (dd, J = 7.7, 1.3 Hz, 1H), 7.19 (dt, J = 7.8, 7.1 Hz, 2H), 3.95-3.84 (m, 1H), 3.51 (q, J = 6.0 Hz, 2H), 2.77 (m, 2H), 2.63 (m, 2H), 2.54 (t, J = 6.1 Hz, 2H), 2.28 (s, 6H). |
| 357 | 5-(2,5-dichlorophenyl)-2-(((2-(dimethylamino)ethyl)amino)methylene)cyclohexane-1,3-dione | ¹H NMR (400 MHz, CDCl₃) δ 11.20 (s, 1H), 8.20 (d, J = 14.4 Hz, 1H), 7.32 (d, J = 8.5 Hz, 1H), 7.23 (d, J = 2.3 Hz, 1H), 7.17 (dd, J = 8.4, 2.2 Hz, 1H), 3.80 (m, 1H), 3.51 (q, J = 6.0 Hz, 2H), 2.79-2.51 (m, 6H), 2.29 (s, 6H). |

TABLE 7-continued

Compounds 119-355

| # | Structure | Name | Proton NMR($^1$HNMR), Mass Spectrum(MS) |
|---|---|---|---|
| 358 | 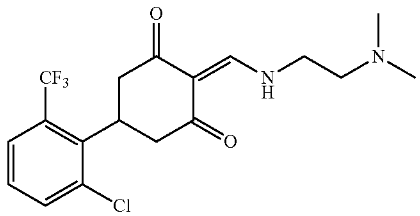 [SMILES: CN(C)CCNC=C1C(=O)CC(c2c(Cl)cccc2C(F)(F)F)CC1=O] | 5-(2-chloro-6-(trifluoromethyl)phenyl)-2-(((2-(dimethylamino)ethyl)amino)methylene)cyclohexane-1,3-dione | $^1$H NMR (400 MHz, CDCl$_3$) δ 11.27 (s, 1H), 8.22 (d, J = 14.4 Hz, 1H), 7.63 (d, J = 7.8 Hz, 1H), 7.56 (d, J = 7.9 Hz, 1H), 7.31 (t, J = 8.0 Hz, 1H), 3.96 (m, 1H), 3.75-3.56 (m, 2H), 3.51 (q, J = 6.1 Hz, 2H), 2.61-2.41 (m, 4H), 2.29 (s, 6H). |
| 359 | 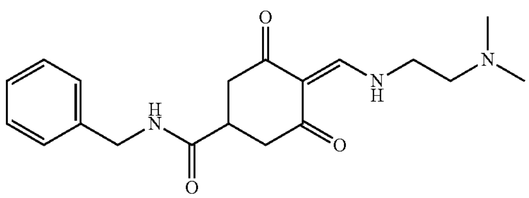 [SMILES: CN(C)CCNC=C1C(=O)CC(C(=O)NCc2ccccc2)CC1=O] | N-benzyl-4-(((2-(dimethylamino)ethyl)amino)methylene)-3,5-dioxocyclohexane-1-carboxamide | $^1$H NMR (400 MHz, CDCl$_3$) δ 11.15 (s, 1H), 8.12 (d, J = 14.5 Hz, 1H), 7.36-7.26 (m, 3H), 7.24 (s, 2H), 5.84 (s, 1H), 4.45 (d, J = 5.5 Hz, 2H), 3.49 (dd, J = 12.1, 6.0 Hz, 2H), 2.89-2.50 (m, 7H), 2.29 (s, 6H). |
| 360 | 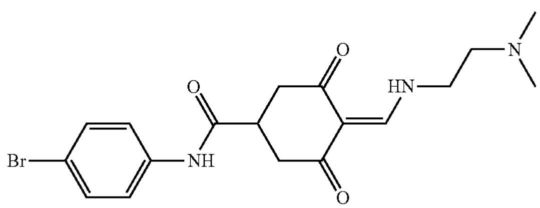 [SMILES: CN(C)CCNC=C1C(=O)CC(C(=O)Nc2ccc(Br)cc2)CC1=O] | N-(4-bromophenyl)-4-(((2-(dimethylamino)ethyl)amino)methylene)-3,5-dioxocyclohexane-1-carboxamide | $^1$H NMR (400 MHz, DMSO-d6) δ 10.89 (d, J = 14.7 Hz, 1H), 10.13 (s, 1H), 8.09 (d, J = 14.7 Hz, 1H), 7.57 (d, J = 8.9 Hz, 2H), 7.51-7.44 (m, 2H), 3.54 (dt, J = 14.5, 7.3 Hz, 2H), 3.15-3.04 (m, 1H), 2.64 (m, 1H), 2.55 (m, 3H), 2.42 (t, J = 5.8 Hz, 2H), 2.17 (s, 6H). |
| 361 | 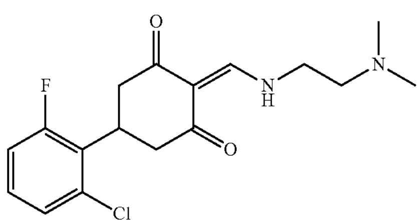 | 5-(2-chloro-6-fluorophenyl)-2-(((2-(dimethylamino)ethyl)amino)methylene)cyclohexane-1,3-dione | $^1$H NMR (400 MHz, CDCl$_3$) δ 11.22 (s, 1H), 8.21 (d, J = 14.4 Hz, 1H), 7.17 (dd, J = 7.5, 5.1 Hz, 2H), 7.01-6.94 (m, 1H), 4.02 (t, J = 13.3 Hz, 1H), 3.51 (q, J = 6.1 Hz, 2H), 3.22-3.02 (m, 2H), 2.56 (m, 4H), 2.29 (s, 6H). |
| 362 | 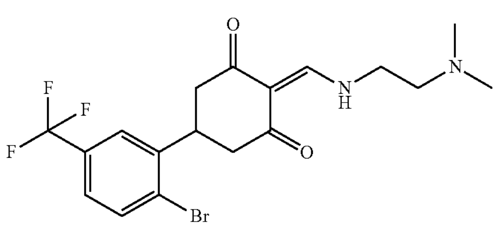 [SMILES: CN(C)CCNC=C1C(=O)CC(c2cc(C(F)(F)F)ccc2Br)CC1=O] | 5-(2-bromo-5-(trifluoromethyl)phenyl)-2-(((2-(dimethylamino)ethyl)amino)methylene)cyclohexane-1,3-dione | $^1$H NMR (400 MHz, CDCl$_3$) δ 11.21 (s, 1H), 8.20 (d, J = 14.4 Hz, 1H), 7.71 (d, J = 8.2 Hz, 1H), 7.48 (s, 1H), 7.38 (d, J = 8.3 Hz, 1H), 3.86 (s, 1H), 3.52 (q, J = 6.0 Hz, 2H), 2.79 (m, 2H), 2.74-2.60 (m, 2H), 2.57 (m, 2H), 2.30 (s, 6H). |
| 363 | 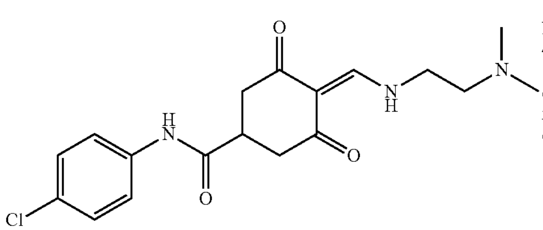 | N-(4-chlorophenyl)-4-(((2-(dimethylamino)ethyl)amino)methylene)-3,5-dioxocyclohexane-1-carboxamide | $^1$H NMR (400 MHz, CDCl$_3$) δ 11.17 (s, 1H), 8.38 (s, 1H), 8.12 (d, J = 14.4 Hz, 1H), 7.54 (d, J = 8.5 Hz, 2H), 7.28 (s, 1H), 3.51-3.42 (m, 2H), 3.00-2.76 (m, 3H), 2.68 (m, 2H), 2.52 (t, J = 6.0 Hz, 2H), 2.25 (s, 6H). |

TABLE 7-continued

Compounds 119-355

| # | Structure | Name | Proton NMR(¹HNMR), Mass Spectrum(MS) |
|---|---|---|---|
| 364 | 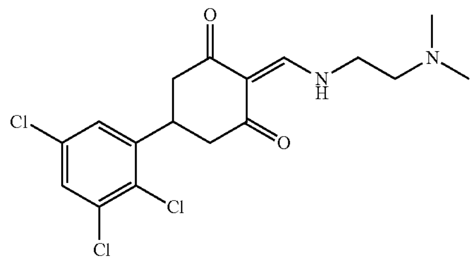 [SMILES: CN(C)CCNC=C1C(=O)CC(c2cc(Cl)cc(Cl)c2Cl)CC1=O] | 2-(((2-(dimethylamino)ethyl)amino)methylene)-5-(2,3,5-trichlorophenyl)cyclohexane-1,3-dione | ¹H NMR (400 MHz, CDCl₃) δ 11.20 (s, 1H), 8.19 (d, J = 14.5 Hz, 1H), 7.40 (d, J = 2.3 Hz, 1H), 7.15 (d, J = 2.3 Hz, 1H), 3.86 (s, 1H), 3.51 (q, J = 5.9 Hz, 2H), 2.84-2.69 (m, 2H), 2.69-2.48 (m, 4H), 2.29 (s, 6H). |
| 365 | 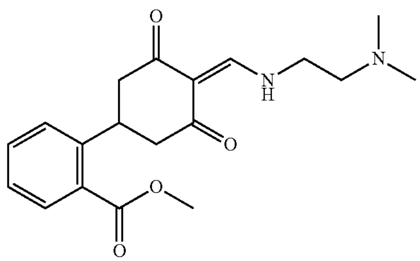 [SMILES: COC(=O)c1ccccc1C1CC(=O)C(=CNCCN(C)C)C(=O)C1] | methyl 2-(4-(((2-(dimethylamino)ethyl)amino)methylene)-3,5-dioxocyclohexyl)benzoate | ¹H NMR (400 MHz, CDCl₃) δ 11.18 (s, 1H), 8.18 (d, J = 14.3 Hz, 1H), 7.85 (d, J = 7.7 Hz, 1H), 7.51 (t, J = 7.6 Hz, 1H), 7.39 (d, J = 7.7 Hz, 1H), 7.31 (d, J = 7.6 Hz, 1H), 4.35-4.25 (m, 1H), 3.88 (s, 3H), 3.50 (q, J = 6.1 Hz, 2H), 2.80-2.71 (m, 2H), 2.71-2.60 (m, 2H), 2.54 (t, J = 6.1 Hz, 2H), 2.28 (s, 6H). |
| 366 | 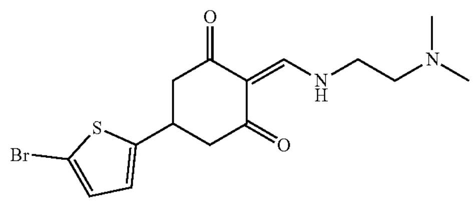 [SMILES: CN(C)CCNC=C1C(=O)CC(c2ccc(Br)s2)CC1=O] | 5-(5-bromothiophen-2-yl)-2-(((2-(dimethylamino)ethyl)amino)methylene)cyclohexane-1,3-dione | ¹H NMR (400 MHz, CDCl₃) δ 11.19 (s, 1H), 8.15 (d, J = 14.4 Hz, 1H), 6.87 (d, J = 3.7 Hz, 1H), 6.61 (d, J = 3.7 Hz, 1H), 3.55 (td, J = 10.6, 5.4 Hz, 1H), 3.48 (q, J = 6.0 Hz, 2H), 2.90-2.80 (m, 2H), 2.66 (m, 2H), 2.53 (t, J = 6.1 Hz, 2H), 2.27 (s, 6H). |
| 367 | 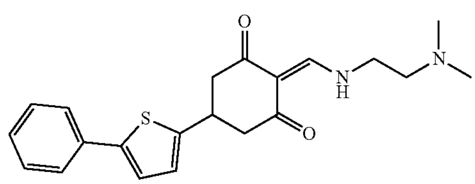 [SMILES: CN(C)CCNC=C1C(=O)CC(c2ccc(-c3ccccc3)s2)CC1=O] | 2-(((2-(dimethylamino)ethyl)amino)methylene)-5-(5-phenylthiophen-2-yl)cyclohexane-1,3-dione | ¹H NMR (400 MHz, CDCl₃) δ 11.19 (s, 1H), 8.17 (d, J = 14.4 Hz, 1H), 7.58-7.52 (m, 2H), 7.35 (t, J = 7.6 Hz, 2H), 7.27 (s, 1H), 7.13 (d, J = 3.6 Hz, 1H), 6.82 (dd, J = 3.6, 0.8 Hz, 1H), 3.63 (m, 1H), 3.49 (q, J = 6.1 Hz, 2H), 2.96-2.87 (m, 2H), 2.74 (m, 2H), 2.53 (m, 2H), 2.28 (s, 6H). |
| 368 | 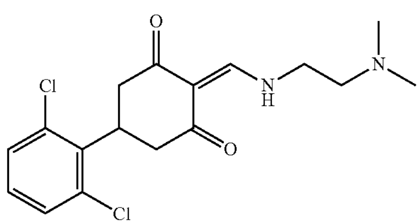 [SMILES: CN(C)CCNC=C1C(=O)CC(c2c(Cl)cccc2Cl)CC1=O] | 5-(2,6-dichlorophenyl)-2-(((2-(dimethylamino)ethyl)amino)methylene)cyclohexane-1,3-dione | ¹H NMR (400 MHz, CDCl₃) δ 11.25 (s, 1H), 8.22 (d, J = 14.4 Hz, 1H), 7.32 (s, 2H), 7.12 (t, J = 8.0 Hz, 1H), 4.37 (m, 1H), 3.65-3.47 (m, 4H), 2.56 (t, J = 6.1 Hz, 2H), 2.53-2.49 (m, 1H), 2.49-2.45 (m, 1H), 2.30 (s, 6H). |
| 369 | 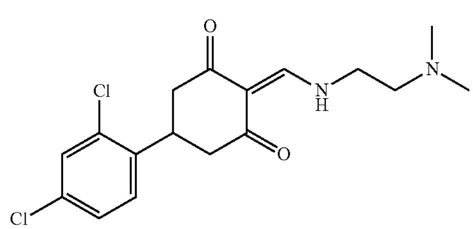 [SMILES: CN(C)CCNC=C1C(=O)CC(c2ccc(Cl)cc2Cl)CC1=O] | 5-(2,4-dichlorophenyl)-2-(((2-(dimethylamino)ethyl)amino)methylene)cyclohexane-1,3-dione | ¹H NMR (400 MHz, CDCl₃) δ 11.21 (s, 1H), 8.19 (d, J = 14.4 Hz, 1H), 7.40 (d, J = 2.1 Hz, 1H), 7.25 (dd, J = 8.4, 2.1 Hz, 1H), 7.18 (d, J = 8.4 Hz, 1H), 3.80 (m, 1H), 3.51 (q, J = 6.0 Hz, 2H), 2.78-2.70 (m, 2H), 2.69-2.58 (m, 2H), 2.55 (t, J = 6.0 Hz, 2H), 2.29 (s, 6H). |

TABLE 7-continued

Compounds 119-355

| # | Structure | Name | Proton NMR($^1$HNMR), Mass Spectrum(MS) |
|---|---|---|---|
| 370 | 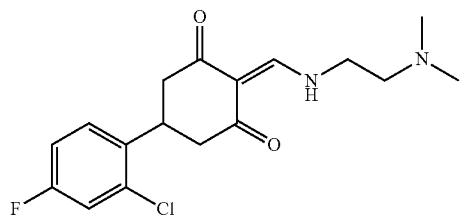 [SMILES: CN(C)CCNC=C1C(=O)CC(c2ccc(F)cc2Cl)CC1=O] | 5-(2-chloro-4-fluorophenyl)-2-(((2-(dimethylamino)ethyl)amino)methylene)cyclohexane-1,3-dione | $^1$H NMR (400 MHz, CDCl$_3$) δ 11.21 (s, 1H), 8.19 (d, J = 14.4 Hz, 1H), 7.22 (dd, J = 8.7, 5.9 Hz, 1H), 7.14 (dd, J = 8.5, 2.7 Hz, 1H), 6.99 (td, J = 8.3, 2.7 Hz, 1H), 3.80 (m, 1H), 3.51 (q, J = 6.1 Hz, 2H), 2.79-2.70 (m, 2H), 2.69-2.58 (m, 2H), 2.55 (t, J = 6.1 Hz, 2H), 2.29 (s, 6H). |
| 371 | 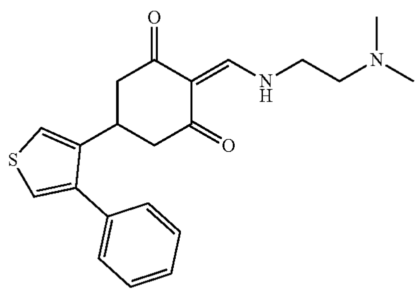 [SMILES: CN(C)CCNC=C1C(=O)CC(c2cscc2-c2ccccc2)CC1=O] | 2-(((2-(dimethylamino)ethyl)amino)methylene)-5-(4-phenylthiophen-3-yl)cyclohexane-1,3-dione | $^1$H NMR (400 MHz, CDCl$_3$) δ 11.12 (s, 1H), 8.10 (d, J = 14.4 Hz, 1H), 7.38 (dd, J = 7.8, 6.2 Hz, 2H), 7.34 (dd, J = 5.1, 3.6 Hz, 1H), 7.32-7.27 (m, 2H), 7.16 (d, J = 3.2 Hz, 1H), 7.13-7.09 (m, 1H), 3.56-3.48 (m, 1H), 3.45 (m, 2H), 2.70-2.61 (m, 2H), 2.58 (m, 2H), 2.50 (dd, J = 7.3, 4.9 Hz, 2H), 2.25 (s, 6H). |
| 372 | 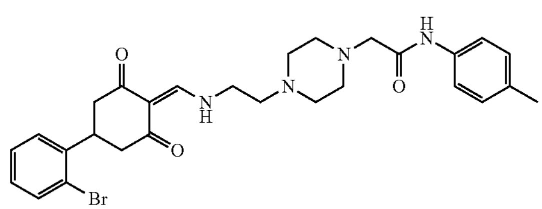 [SMILES: Cc1ccc(NC(=O)CN2CCN(CCNC=C3C(=O)CC(c4ccccc4Br)CC3=O)CC2)cc1] | 2-(4-(2-(((4-(2-bromophenyl)-2,6-dioxocyclohexylidene)methyl)amino)ethyl)piperazin-1-yl)-N-(p-tolyl)acetainide | $^1$H NMR (400 MHz, CD$_3$OD) δ 8.28 (s, 1H), 7.60 (d, J = 7.8 Hz, 1H), 7.40 (m, 4H), 7.13 (m, 3H), 3.80 (m, 1H), 3.62 (m, 2H), 3.16 (s, 2H), 2.65 (m, 13H), 2.29 (s, 3H). |
| 373 | 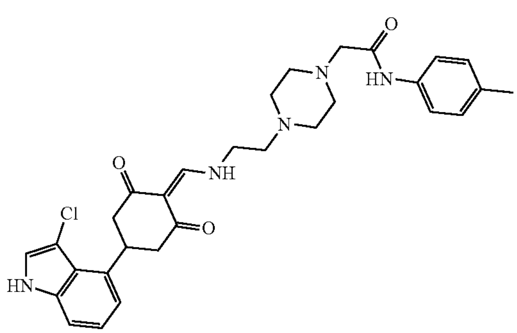 [SMILES: Cc1ccc(NC(=O)CN2CCN(CCNC=C3C(=O)CC(c4cccc5[nH]cc(Cl)c45)CC3=O)CC2)cc1] | 2-(4-(2-(((4-(3-chloro-1H-indol-4-yl)-2,6-dioxocyclohexylidene)methyl)amino)ethyl)piperazin-1-yl)-N-(p-tolyl)acetamide | $^1$H NMR (400 MHz, CD$_3$OD) δ 8.27 (s, 1H), 7.43 (d, J = 8.4 Hz, 2H), 7.30-7.20 (m, 2H), 7.11 (t, J = 7.8 Hz, 3H), 6.95 (d, J = 7.3 Hz, 1H), 4.54 (m, 1H), 3.62 (t, J = 5.8 Hz, 2H), 3.16 (s, 2H), 2.83 (m, 4H), 2.65 (s, 9H), 2.29 (s, 3H). |
| 374 | 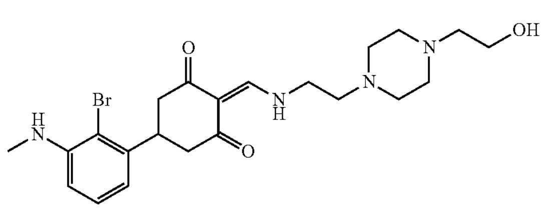 [SMILES: CNc1cccc(C2CC(=O)C(=CNCCN3CCN(CCO)CC3)C(=O)C2)c1Br] | 5-(2-bromo-3-(methylamino)phenyl)-2-(((2-(4-(2-hydroxyethyl)piperazin-1-yl)ethyl)amino)methylene)cyclohexane-1,3-dione | $^1$H NMR (400 MHz, CD$_3$OD) δ 8.26 (s, 1H), 7.19 (t, J = 7.9 Hz, 1H), 6.61 (dd, J = 24.0, 7.7 Hz, 2H), 3.79 (m, 1H), 3.73 (t, J = 5.8 Hz, 2H), 3.62 (t, J = 5.8 Hz, 2H), 3.35 (s, 1H), 2.86 (s, 3H), 2.70 (m, 15H). |

TABLE 7-continued

Compounds 119-355

| # | Structure | Name | Proton NMR($^1$HNMR), Mass Spectrum(MS) |
|---|---|---|---|
| 375 | 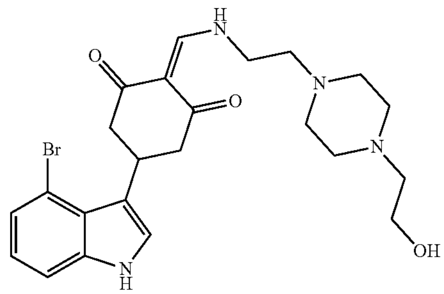 | 5-(4-bromo-1H-indol-3-yl)-2-(((2-(4-(2-hydroxyethyl)piperazin-1-yl)ethyl)amino)methylene)cyclohexane-1,3-dione | $^1$H NMR (400 MHz, CD$_3$OD) δ 8.26 (s, 1H), 7.34 (dd, J = 8.1, 0.7 Hz, 1H), 7.21-7.14 (m, 2H), 6.96 (t, J = 7.9 Hz, 1H), 4.28 (m, 1H), 3.78 (t, J = 5.6 Hz, 2H), 3.61 (t, J = 5.7 Hz, 2H), 2.91 (m, 8H), 2.71 (m, 8H). |
| 376 | 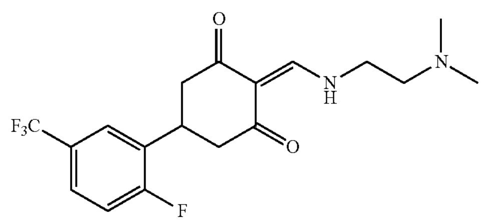 [SMILES: CN(C)CCNC=C1C(=O)CC(c2cc(C(F)(F)F)ccc2F)CC1=O] | 2-(((2-(dimethylamino)ethyl)amino)methylene)-5-(2-fluoro-5-(trifluoromethyl)phenyl)cyclohexane-1,3-dione | $^1$H NMR (400 MHz, CDCl$_3$) δ 11.22 (s, 1H), 8.20 (d, J = 14.4 Hz, 1H), 7.56-7.45 (m, 2H), 7.19 (s, 1H), 3.69 (ddd, J = 16.3, 10.8, 5.8 Hz, 1H), 3.52 (q, J = 6.0 Hz, 2H), 2.74 (td, J = 10.9, 6.3 Hz, 4H), 2.55 (t, J = 6.1 Hz, 2H), 2.29 (s, 6H). |
| 377 | 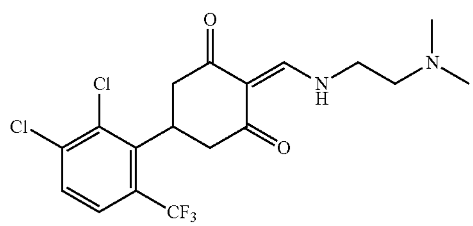 | 5-(2,3-dichloro-6-(trifluoromethyl)phenyl)-2-(((2-(dimethylamino)ethyl)amino)methylene)cyclohexane-1,3-dione | $^1$H NMR (400 MHz, CDCl$_3$) δ 11.28 (s, 1H), 8.23 (d, J = 14.4 Hz, 1H), 7.55 (q, J = 8.6 Hz, 2H), 4.00 (dd, J = 11.2, 6.8 Hz, 1H), 3.75-3.57 (m, 2H), 3.52 (q, J = 6.0 Hz, 2H), 2.56 (t, J = 6.1 Hz, 2H), 2.49 (d, J = 15.5 Hz, 2H), 2.30 (s, 6H). |
| 378 | 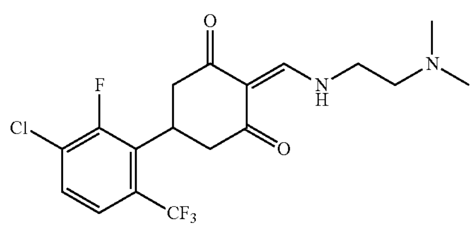 | 5-(3-chloro-2-fluoro-6-(trifluoromethyl)phenyl)-2-(((2-(dimethylamino)ethyl)amino)methylene)cyclohexane-1,3-dione | $^1$H NMR (400 MHz, CDCl$_3$) δ 11.24 (s, 1H), 8.22 (d, J = 14.4 Hz, 1H), 7.48-7.41 (m, 2H), 3.77 (t, J = 13.2 Hz, 1H), 3.52 (q, J = 6.0 Hz, 2H), 3.20-3.01 (m, 2H), 2.64-2.60 (m, 1H), 2.59-2.53 (m, 3H), 2.29 (s, 6H). |
| 379 | 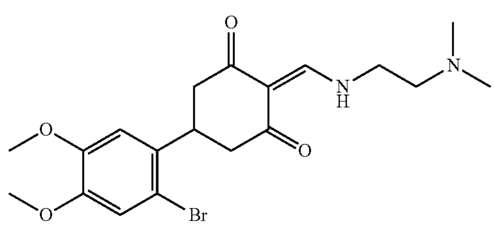 | 5-(2-bromo-4,5-dimethoxyphenyl)-2-(((2-(dimethylamino)ethyl)amino)methylene)cyclohexane-1,3-dione | $^1$H NMR (400 MHz, CDCl$_3$) δ 11.20 (s, 1H), 8.19 (d, J = 14.4 Hz, 1H), 7.04 (s, 1H), 6.73 (s, 1H), 3.86 (d, J = 1.9 Hz, 6H), 3.74 (tt, J = 11.9, 4.1 Hz, 1H), 3.51 (q, J = 6.1 Hz, 2H), 2.80-2.70 (m, 2H), 2.69-2.58 (m, 2H), 2.55 (t, J = 6.1 Hz, 2H), 2.29 (s, 6H). |
| 380 | 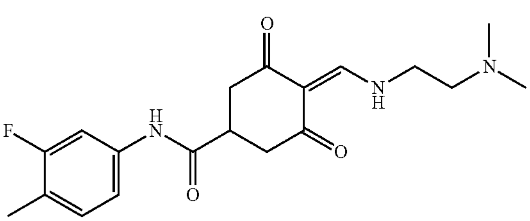 | 4-(((2-(dimethylamino)ethyl)amino)methylene)-N-(3-fluoro-4-methylphenyl)-3,5-dioxocyclohexane-1-carboxamide | $^1$H NMR (400 MHz, CDCl$_3$) δ 11.24-11.12 (m, 1H), 8.16-8.06 (m, 2H), 7.44 (d, J = 13.2 Hz, 1H), 7.15-7.05 (m, 2H), 3.50-3.41 (m, 2H), 2.97-2.75 (m, 3H), 2.72-2.62 (m, 2H), 2.51 (t, J = 6.0 Hz, 2H), 2.25 (s, 6H), 2.22 (d, J = 1.5 Hz, 3H). |

TABLE 7-continued

Compounds 119-355

| # | Structure | Name | Proton NMR(¹HNMR), Mass Spectrum(MS) |
|---|---|---|---|
| 381 | 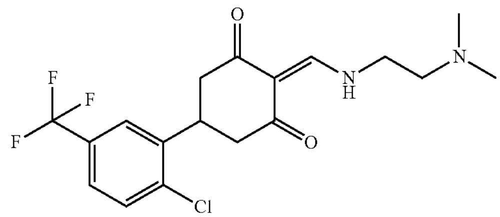 [SMILES: CN(C)CCNC=C1C(=O)CC(c2cc(C(F)(F)F)ccc2Cl)CC1=O] | 5-(2-chloro-5-(trifluoromethyl)phenyl)-2-(((2-(dimethylamino)ethyl)amino)methylene)cyclohexane-1,3-dione | ¹H NMR (400 MHz, CDCl₃) δ 11.22 (s, 1H), 8.20 (d, J = 14.5 Hz, 1H), 7.49 (dt, J = 8.4, 7.5 Hz, 3H), 3.93-3.84 (m, 1H), 3.52 (q, J = 6.1 Hz, 2H), 2.71 (tdd, J = 19.8, 12.2, 4.2 Hz, 4H), 2.56 (t, J = 6.1 Hz, 2H), 2.30 (s, 6H). |
| 382 | 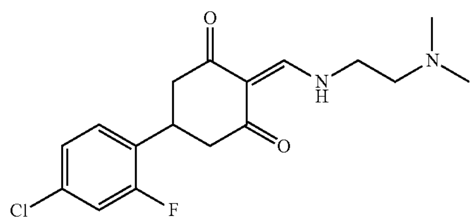 [SMILES: CN(C)CCNC=C1C(=O)CC(c2ccc(Cl)cc2F)CC1=O] | 5-(4-chloro-2-fluorophenyl)-2-(((2-(dimethylamino)ethyl)amino)methylene)cyclohexane-1,3-dione | ¹H NMR (400 MHz, CDCl₃) δ 11.20 (s, 1H), 8.18 (d, J = 14.4 Hz, 1H), 7.11 (dd, J = 18.1, 8.6 Hz, 3H), 3.62 (s, 1H), 3.51 (q, J = 6.0 Hz, 2H), 2.70 (dd, J = 14.9, 9.5 Hz, 4H), 2.55 (t, J = 6.1 Hz, 2H), 2.29 (s, 6H). |
| 383 | 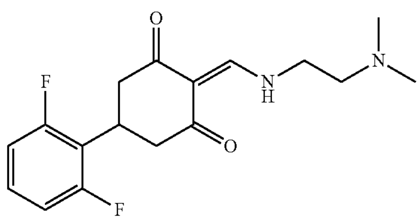 [SMILES: CN(C)CCNC=C1C(=O)CC(c2c(F)cccc2F)CC1=O] | 5-(2,6-difluorophenyl)-2-(((2-(dimethylamino)ethyl)amino)methylene)cyclohexane-1,3-dione | ¹H NMR (400 MHz, cdcl₃) δ 11.21 (s, 1H), 8.19 (d, J = 14.4 Hz, 1H), 7.23-7.10 (m, 1H), 6.87 (t, J = 8.5 Hz, 2H), 3.80 (s, 1H), 3.50 (q, J = 6.1 Hz, 2H), 3.05 (ddd, J = 30.5, 16.9, 13.5 Hz, 2H), 2.65-2.50 (m, 4H), 2.28 (s, 6H). |
| 384 | 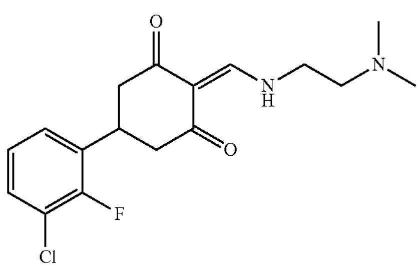 | 5-(3-chloro-2-fluorophenyl)-2-(((2-(dimethylamino)ethyl)amino)methylene)cyclohexane-1,3-dione | ¹H NMR (400 MHz, CDCl₃) δ 11.21 (s, 1H), 8.19 (d, J = 14.4 Hz, 1H), 7.30 (d, J = 7.5 Hz, 1H), 7.15-7.02 (m, 2H), 3.68 (s, 1H), 3.51 (q, J = 6.0 Hz, 2H), 2.72 (dd, J = 14.7, 9.5 Hz, 4H), 2.54 (t, J = 6.1 Hz, 2H), 2.28 (s, 6H). |
| 385 | 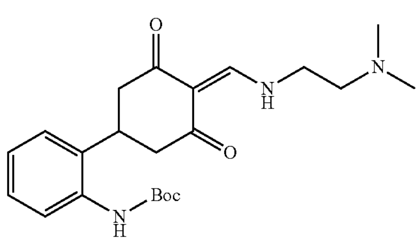 [SMILES: CN(C)CCNC=C1C(=O)CC(c2ccccc2NC(=O)OC(C)(C)C)CC1=O] | tert-butyl (2-(4-(((2-(dimethylamino)ethyl)amino)methylene)-3,5-dioxocyclohexyl)phenyl)carbamate | ¹H NMR (400 MHz, CDCl₃) δ 11.19 (s, 1H), 8.19 (d, J = 14.4 Hz, 1H), 7.62 (d, J = 7.2 Hz, 1H), 7.23 (t, J = 7.3 Hz, 2H), 7.16 (t, J = 6.9 Hz, 1H), 6.27 (s, 1H), 3.51 (dd, J = 11.9, 5.9 Hz, 3H), 2.73-2.60 (m, 4H), 2.54 (t, J = 6.1 Hz, 2H), 2.28 (s, 6H), 1.50 (s, 9H). |
| 386 | 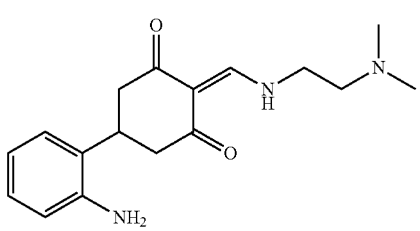 [SMILES: CN(C)CCNC=C1C(=O)CC(c2ccccc2N)CC1=O] | 5-(2-aminophenyl)-2-(((2-(dimethylamino)ethyl)amino)methylene)cyclohexane-1,3-dione | ¹H NMR (400 MHz, CDCl₃) δ 11.20 (s, 1H), 8.18 (d, J = 14.4 Hz, 1H), 7.07 (t, J = 7.8 Hz, 2H), 6.79 (t, J = 7.5 Hz, 1H), 6.70 (d, J = 7.9 Hz, 1H), 3.64 (s, 2H), 3.50 (dd, J = 12.0, 6.0 Hz, 2H), 3.38-3.28 (m, 1H), 2.81-2.50 (m, 6H), 2.28 (s, 6H). |

TABLE 7-continued

Compounds 119-355

| # | Structure | Name | Proton NMR(¹HNMR), Mass Spectrum(MS) |
|---|---|---|---|
| 387 | 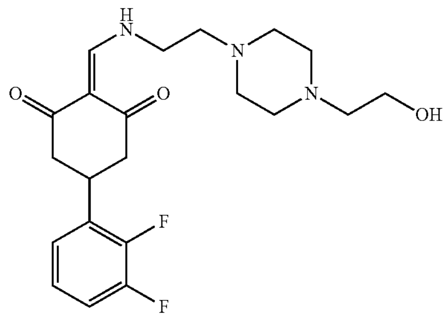 [SMILES: O=C1CC(c2cccc(F)c2F)CC(=O)C1=CNCCN1CCN(CCO)CC1] | 5-(2,3-difluorophenyl)-2-(((2-(4-(2-ethoxyl)piperazin-1-yl)ethyl)amino)methylene)cyclohexane-1,3-dione | ¹H NMR (400 MHz, CDCl₃) δ 11.18 (s, 1H), 8.20 (d, J = 14.5 Hz, 1H), 7.13-7.01 (m, 2H), 6.96 (s, 1H), 3.69 (s, 1H), 3.62 (t, J = 5.3 Hz, 2H), 3.56-3.47 (m, 2H), 2.73 (dd, J = 15.9, 9.4 Hz, 4H), 2.68-2.34 (m, 13H). |
| 388 | 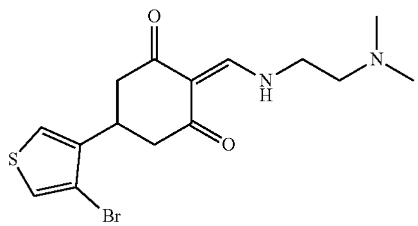 [SMILES: CN(C)CCNC=C1C(=O)CC(c2cscc2Br)CC1=O] | 5-(4-bromothiophen-3-yl)-2-(((2-(dimethylamino)ethyl)amino)methylene)cyclohexane-1,3-dione | ¹H NMR (400 MHz, CDCl₃) δ 11.20 (s, 1H), 8.18 (d, J = 14.3 Hz, 1H), 7.28 (d, J = 3.3 Hz, 1H), 7.00 (d, J = 3.0 Hz, 1H), 3.50 (t, J = 5.9 Hz, 3H), 2.84 (t, J = 10.5 Hz, 2H), 2.60 (ddd, J = 22.3, 14.3, 8.4 Hz, 4H), 2.29 (s, 6H). |
| 389 | 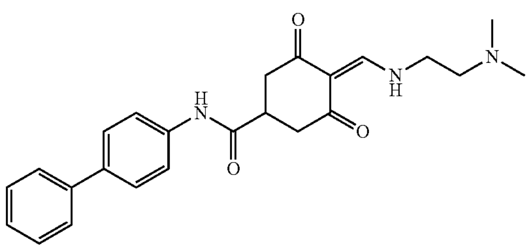 [SMILES: CN(C)CCNC=C1C(=O)CC(C(=O)Nc2ccc(-c3ccccc3)cc2)CC1=O] | N-([1,1'-biphenyl]-4-yl)-4-((((2-(dimethylamino)ethyl)amino)methylene)-3,5-dioxocyclohexane-1-carboxamide | ¹H NMR (400 MHz, DMSO-d6) δ 10.88 (s, 1H), 10.11 (s, 1H), 8.10 (d, J = 14.5 Hz, 1H), 7.74-7.57 (m, 6H), 7.43 (t, J = 7.4 Hz, 2H), 7.33 (d, J = 7.3 Hz, 1H), 3.55 (d, J = 5.6 Hz, 2H), 3.13 (s, 1H), 2.56 (d, J = 5.1 Hz, 4H), 2.43 (s, 2H), 2.18 (s, 6H). |
| 390 | 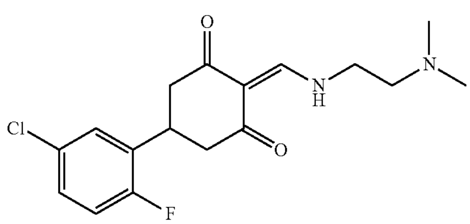 [SMILES: CN(C)CCNC=C1C(=O)CC(c2cc(Cl)ccc2F)CC1=O] | 5-(5-chloro-2-fluorophenyl)-2-(((2-(dimethylamino)ethyl)amino)methylene)cyclohexane-1,3-dione | ¹H NMR (400 MHz, CDCl₃) δ 11.20 (s, 1H), 8.19 (d, J = 14.4 Hz, 1H), 7.19 (t, J = 6.7 Hz, 2H), 6.99 (t, J = 9.1 Hz, 1H), 3.61 (s, 1H), 3.51 (dd, J = 12.0, 6.0 Hz, 2H), 2.70 (dd, J = 17.2, 10.2 Hz, 4H), 2.55 (t, J = 6.0 Hz, 2H), 2.29 (s, 6H). |
| 391 | 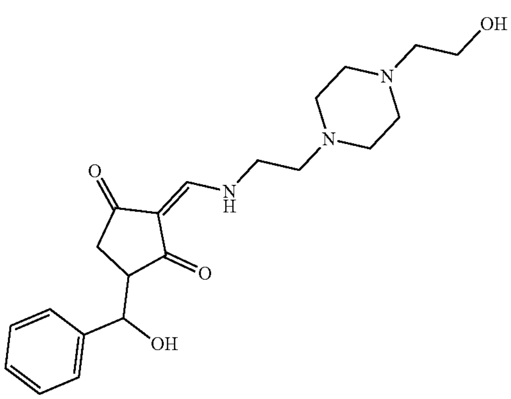 [SMILES: O=C1CC(C(O)c2ccccc2)C(=O)/C1=C\NCCN1CCN(CCO)CC1] | 4-(hydroxy(phenyl)methyl)-2-(((2-(4-(2-ethoxyl)piperazin-1-yl)ethyl)amino)methylene)cyclopentane-1,3-dione | ¹HNMR (400 MHz, CD₃OD) δ 7.77 (s, 1H), 7.26 (m, 5H), 5.13 (d, J = 6.0 Hz, 1H), 3.69 (t, J = 6.0 Hz, 2H), 3.55 (t, J = 5.7 Hz, 2H), 3.13 (m, 1H), 2.69-2.46 (m, 12H), 2.33 (m, 2H); MS: 388.2 [M + 1]. |

TABLE 7-continued

Compounds 119-355

| # | Structure | Name | Proton NMR($^1$HNMR), Mass Spectrum(MS) |
|---|---|---|---|
| 392 | 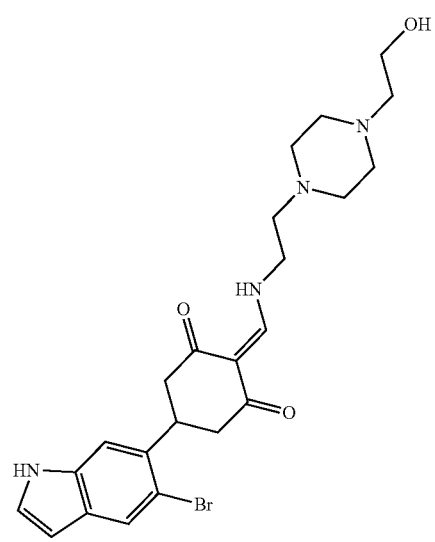 [SMILES: O=C1CC(c2cc3[nH]ccc3cc2Br)CC(=O)C1=CNCCN1CCN(CCO)CC1] | 5-(5-bromo-1H-indol-6-yl)-2-(((2-(4-(2-ethoxyl)piperazin-1-yl)ethyl)amino)methylene)cyclohexane-1,3-dione | $^1$H NMR (400 MHz, CD$_3$OD) δ 8.27 (s, 1H), 7.78 (s, 1H), 7.37 (s, 1H), 7.25 (d, J = 3.2 Hz, 1H), 6.38 (d, J = 2.4 Hz, 1H), 3.90-3.81 (m, 1H), 3.72 (t, J = 5.9 Hz, 2H), 3.62 (t, J = 5.6 Hz, 2H), 2.72 (m, 16H); MS: 491.1 [M + 1]. |
| 393 | 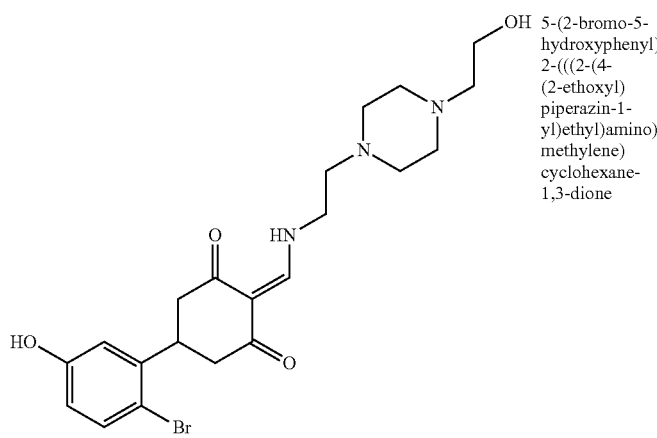 | 5-(2-bromo-5-hydroxyphenyl)-2-(((2-(4-(2-ethoxyl)piperazin-1-yl)ethyl)amino)methylene)cyclohexane-1,3-dione | $^1$H NMR (400 MHz, CD$_3$OD) δ 8.27 (s, 1H), 7.36 (d, J = 8.6 Hz, 1H), 6.78 (d, J = 2.9 Hz, 1H), 6.60 (dd, J = 8.7, 2.8 Hz, 1H), 3.80-3.57 (m, 4H), 2.77 (m, 13H); MS: 467.0 [M + 1]. |
| 394 | 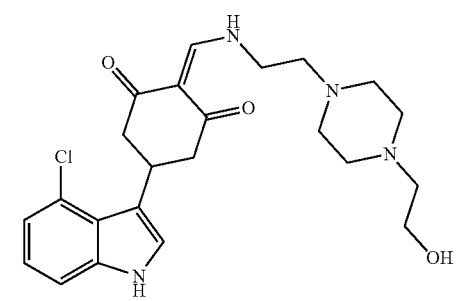 [SMILES: O=C1CC(c2c[nH]c3cccc(Cl)c23)CC(=O)C1=CNCCN1CCN(CCO)CC1] | 5-(4-chloro-1H-indol-3-yl)-2-(((2-(4-(2-ethoxyl)piperazin-1-yl)ethyl)amino)methylene)cyclohexane-1,3-dione | $^1$H NMR (400 MHz, CD$_3$OD) δ 8.27 (s, 1H), 7.36-7.26 (m, 1H), 7.14 (s, 1H), 7.03 (m, 2H), 4.22-4.12 (m, 1H), 3.77 (t, J = 5.7 Hz, 2H), 3.63 (m, 2H), 3.03-2.63 (m, 16H); MS: 445.1 [M + 1]. |
| 395 | 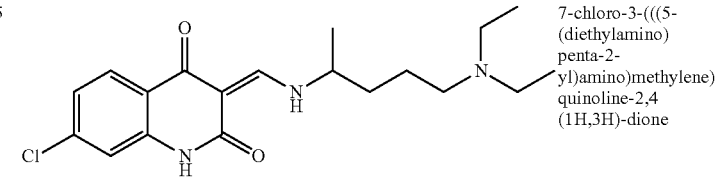 | 7-chloro-3-(((5-(diethylamino)penta-2-yl)amino)methylene)quinoline-2,4(1H,3H)-dione | $^1$H NMR (400 MHz, CD$_3$OD) δ 8.55 (s, 1H), 7.97 (d, J = 8.5 Hz, 1H), 7.18 (d, J = 1.7 Hz, 1H), 7.12 (dd, J = 8.5, 1.8 Hz, 1H), 3.81 (s, 1H), 3.06 (m, 6H), 1.75 (d, J = 5.6 Hz, 4H), 1.43 (d, J = 6.6 Hz, 3H), 1.30-1.18 (m, 6H); MS: 364.1 [M + 1]. |

TABLE 7-continued

Compounds 119-355

| # | Structure | Name | Proton NMR(¹HNMR), Mass Spectrum(MS) |
|---|---|---|---|
| 396 | 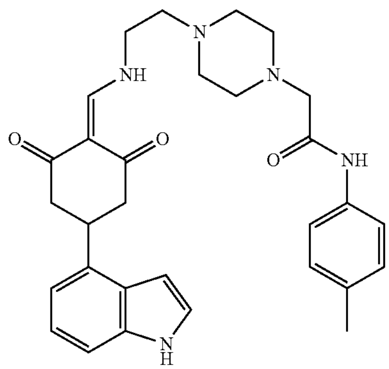 [SMILES: Cc1ccc(NC(=O)CN2CCN(CCNC=C3C(=O)CC(c4cccc5[nH]ccc45)CC3=O)CC2)cc1] | 2-(4-(2-(((4-(1H-indol-4-yl)-2,6-dioxocyclohexylidene)methyl)amino)ethyl)piperazin-1-yl)-N-(p-tolyl)acetamide | ¹H NMR (400 MHz, CD₃OD) δ 8.28 (s, 1H), 7.43 (d, J = 8.4 Hz, 2H), 7.26 (dd, J = 14.2, 5.7 Hz, 2H), 7.13 (d, J = 8.0 Hz, 2H), 7.06 (t, J = 7.7 Hz, 1H), 6.88 (d, J = 7.3 Hz, 1H), 6.53 (d, J = 2.6 Hz, 1H), 3.79 (m, 1H), 3.63 (m, 2H), 3.16 (s, 2H), 2.99-2.85 (m, 2H), 2.82 (m, 2H), 2.65 (s, 9H), 2.29 (s, 3H). |
| 397 | 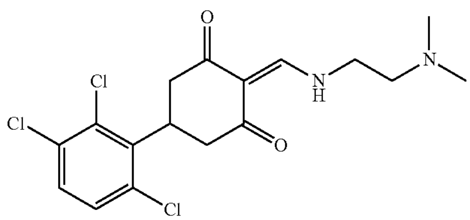 [SMILES: CN(C)CCNC=C1C(=O)CC(c2c(Cl)ccc(Cl)c2Cl)CC1=O] | 2-(((2-(dimethylamino)ethyl)amino)methylene)-5-(2,3,6-trichlorophenyl)cyclohexane-1,3-dione | ¹H NMR (400 MHz, CDCl₃) δ 11.25 (s, 1H), 8.21 (d, J = 14.4 Hz, 1H), 7.31 (s, 1H), 7.25-7.17 (m, 1H), 4.41 (s, 1H), 3.68-3.43 (m, 4H), 2.58 (t, J = 5.9 Hz, 2H), 2.48 (d, J = 16.7 Hz, 2H), 2.31 (s, 6H). |
| 398 | 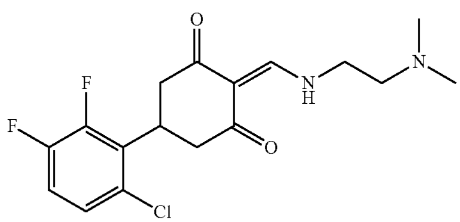 [SMILES: CN(C)CCNC=C1C(=O)CC(c2c(Cl)ccc(F)c2F)CC1=O] | 5-(6-chloro-2,3-difluorophenyl)-2-(((2-(dimethylamino)ethyl)amino)methylene)cyclohexane-1,3-dione | ¹H NMR (400 MHz, CDCl₃) δ 11.24 (s, 1H), 8.22 (d, J = 14.4 Hz, 1H), 7.15 (ddd, J = 9.0, 4.6, 2.0 Hz, 1H), 7.04 (dd, J = 17.4, 9.0 Hz, 1H), 4.06-3.93 (m, 1H), 3.53 (q, J = 6.0 Hz, 2H), 3.20-3.02 (m, 2H), 2.66-2.54 (m, 4H), 2.30 (s, 6H). |
| 399 | 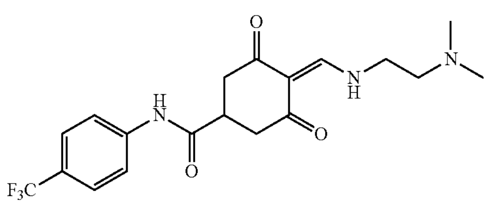 [SMILES: CN(C)CCNC=C1C(=O)CC(C(=O)Nc2ccc(C(F)(F)F)cc2)CC1=O] | 4-(((2-(dimethylamino)ethyl)amino)methylene)-3,5-dioxo-N-(4-(trifluoromethyl)phenyl)cyclohexane-1-carboxamide | ¹H NMR (400 MHz, CDCl₃) δ 11.16 (s, 1H), 8.14 (d, J = 14.5 Hz, 2H), 7.70 (d, J = 8.3 Hz, 2H), 7.57 (d, J = 8.7 Hz, 2H), 3.49 (d, J = 6.1 Hz, 2H), 2.97-2.66 (m, 5H), 2.53 (t, J = 6.0 Hz, 2H), 2.26 (s, 6H). |
| 400 | 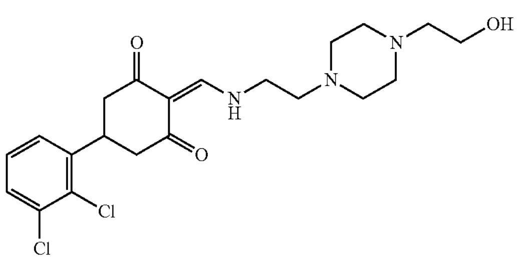 [SMILES: O=C1CC(c2cccc(Cl)c2Cl)CC(=O)C1=CNCCN1CCN(CCO)CC1] | 5-(2,3-dichlorophenyl)-2-(((2-(4-(2-ethoxyl)piperazin-1-yl)ethyl)amino)methylene)cyclohexane-1,3-dione | ¹H NMR (400 MHz, CDCl₃) δ 11.17 (s, 1H), 8.20 (d, J = 14.4 Hz, 1H), 7.40-7.36 (m, 1H), 7.24-7.14 (m, 2H), 3.95-3.85 (m, 1H), 3.62 (t, J = 5.3 Hz, 2H), 3.52 (dd, J = 11.9, 6.0 Hz, 2H), 2.78 (dt, J = 18.6, 4.2 Hz, 2H), 2.71-2.45 (m, 14H). |
| 401 | 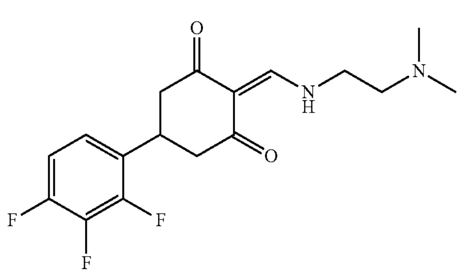 [SMILES: CN(C)CCNC=C1C(=O)CC(c2ccc(F)c(F)c2F)CC1=O] | 2-(((2-(dimethylamino)ethyl)amino)methylene)-5-(2,3,4-trifluorophenyl)cyclohexane-1,3-dione | ¹H NMR (400 MHz, CDCl₃) δ 11.21 (s, 1H), 8.19 (d, J = 14.4 Hz, 1H), 6.94 (dd, J = 8.4, 6.0 Hz, 2H), 3.68-3.59 (m, 1H), 3.52 (q, J = 6.0 Hz, 2H), 2.70 (m, 4H), 2.56 (t, J = 6.1 Hz, 2H). |

TABLE 7-continued

Compounds 119-355

| # | Structure | Name | Proton NMR($^1$HNMR), Mass Spectrum(MS) |
|---|---|---|---|
| 402 | 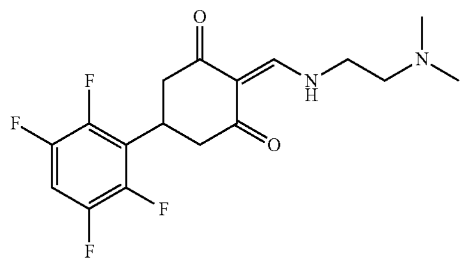 [SMILES: CN(C)CCNC=C1C(=O)CC(c2c(F)c(F)cc(F)c2F)CC1=O] | 2-(((2-(dimethylamino)ethyl)amino)methylene)-5-(2,3,5,6-tetrafluorophenyl)cyclohexane-1,3-dione | $^1$H NMR (400 MHz, CDCl$_3$) δ 11.23 (s, 1H), 8.21 (d, J = 14.4 Hz, 1H), 7.04-6.94 (m, 1H), 3.84 (m, 1H), 3.54 (q, J = 6.0 Hz, 2H), 3.12-2.94 (m, 2H), 2.67-2.53 (m, 4H), 2.31 (s, 6H). |
| 403 | 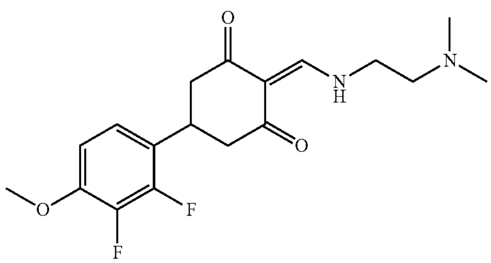 | 5-(2,3-difluoro-4-methoxyphenyl)-2-(((2-(dimethylamino)ethyl)amino)methylene)cyclohexane-1,3-dione | $^1$H NMR (400 MHz, CDCl$_3$) δ 11.21 (s, 1H), 8.18 (d, J = 14.4 Hz, 1H), 6.86 (t, J = 8.2 Hz, 1H), 6.71 (t, J = 7.6 Hz, 1H), 3.89 (s, 3H), 3.64-3.54 (m, 1H), 3.50 (q, J = 6.0 Hz, 2H), 2.70 (m, 4H), 2.54 (t, J = 6.1 Hz, 2H), 2.28 (s, 6H). |
| 404 | 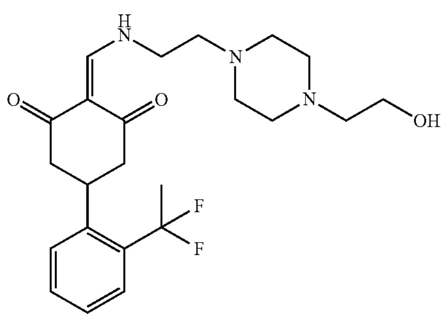 [SMILES: CC(F)(F)c1ccccc1C1CC(=O)C(=CNCCN2CCN(CCO)CC2)C(=O)C1] | 5-(2-(1,1-difluoroethyl)phenyl)-2-(((2-(4-(2-ethoxyl)piperazin-1-yl)ethyl)amino)methylene)cyclohexane-1,3-dione | $^1$H NMR (400 MHz, CD$_3$OD) δ 8.28 (s, 1H), 7.60 (d, J = 8.0 Hz, 1H), 7.53 (d, J = 7.7 Hz, 1H), 7.48 (t, J = 7.7 Hz, 1H), 7.32 (t, J = 7.7 Hz, 1H), 3.85 (t, J = 12.7 Hz, 1H), 3.77 (t, J = 5.7 Hz, 2H), 3.63 (t, J = 5.7 Hz, 2H), 3.07-2.59 (m, 14H), 2.54 (dd, J = 17.0, 3.6 Hz, 2H), 1.98 (t, J = 18.6 Hz, 3H). |
| 405 | 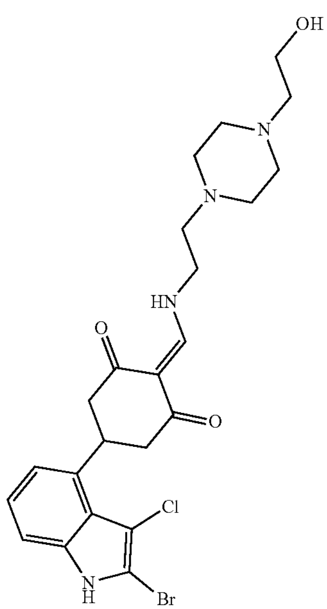 [SMILES: O=C1CC(c2cccc3[nH]c(Br)c(Cl)c23)CC(=O)C1=CNCCN1CCN(CCO)CC1] | 5-(2-bromo-3-chloro-1H-indol-4-yl)-2-(((2-(4-(2-ethoxyl)piperazin-1-yl)ethyl)amino)methylene)cyclohexane-1-1,3-dione | $^1$H NMR (400 MHz, DMSO-d6) δ 12.37 (s, 1H), 10.95 (m, 1H), 8.13 (d, J = 14.6 Hz, 1H), 7.23 (d, J = 8.2 Hz, 1H), 7.12 (t, J = 7.8 Hz, 1H), 6.98 (d, J = 7.3 Hz, 1H), 4.29 (m, 1H), 3.57 (m, 3H), 3.16 (m, 3H), 2.84-2.50 (m, 15H). |

TABLE 7-continued

Compounds 119-355

| # | Structure | Name | Proton NMR(¹HNMR), Mass Spectrum(MS) |
|---|---|---|---|
| 406 | 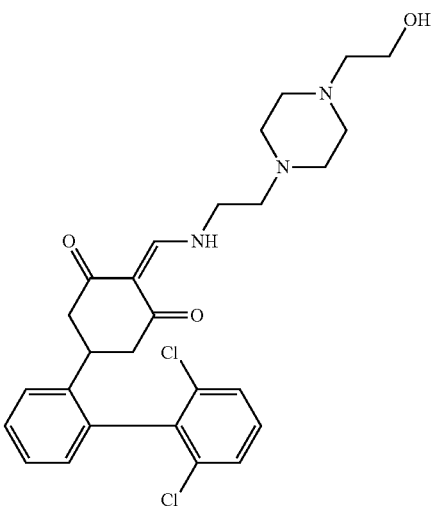 [SMILES: O=C1CC(c2ccccc2-c2c(Cl)cccc2Cl)CC(=O)C1=CNCCN1CCN(CCO)CC1] | 5-(2',6'-dichloro-[1,1'-biphenyl]-2-yl)-2-(((2-(4-(2-ethoxyl)piperazin-1-yl)ethyl)amino)methylene)cyclohexane-1,3-dione | ¹H NMR (400 MHz, CD$_3$OD) δ 8.17 (s, 1H), 7.55 (d, J = 7.6 Hz, 1H), 7.47 (m, 3H), 7.39-7.30 (m, 2H), 7.09-7.02 (m, 1H), 3.75 (t, J = 5.7 Hz, 2H), 3.56 (t, J = 5.9 Hz, 2H), 2.97-2.72 (m, 9H), 2.62 (m, 6H), 2.53 (dd, J = 16.3, 3.1 Hz, 2H). |
| 407 | 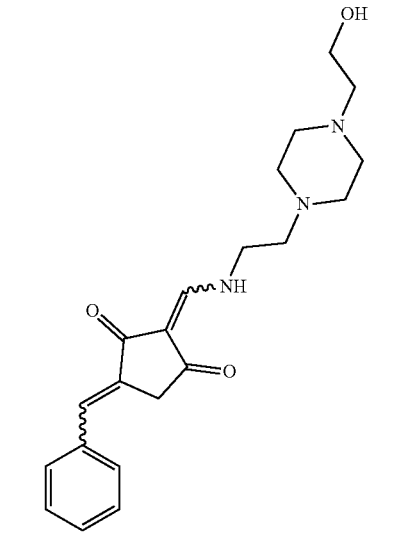 [SMILES: O=C1CC(=Cc2ccccc2)C(=O)C1=CNCCN1CCN(CCO)CC1] | 4-benzylidene-2-(((2-(4-(2-ethoxyl)piperazin-1-yl)ethyl)amino)methylene)cyclopentane-1,3-dione | ¹H NMR (400 MHz, CD$_3$OD) δ 8.08 (d, J = 0.5 Hz, 1H), 7.57 (d, J = 7.7 Hz, 2H), 7.40 (m, 4H), 3.97-3.86 (m, 4H), 3.39 (m, 10H), 3.28-3.13 (m, 4H). |
| 408 | 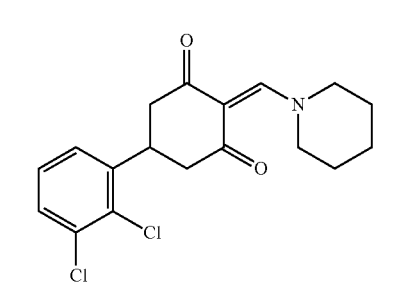 [SMILES: O=C1CC(c2cccc(Cl)c2Cl)CC(=O)C1=CN1CCCCC1] | 5-(2,3-dichlorophenyl)-2-(piperidine-1-ylmethylene)cyclohexane-1,3-dione | ¹H NMR (400 MHz, CDCl$_3$) δ 8.04 (s, 1H), 7.37 (dd, J = 7.5, 1.9 Hz, 1H), 7.23-7.11 (m, 2H), 3.91-3.80 (m, 1H), 3.80-3.55 (m, 4H), 2.77 (m, 2H), 2.60 (m, 2H), 1.84 (m, 4H), 1.74 (m, 2H). |

TABLE 7-continued

Compounds 119-355

| # | Structure | Name | Proton NMR(¹HNMR), Mass Spectrum(MS) |
|---|---|---|---|
| 409 | 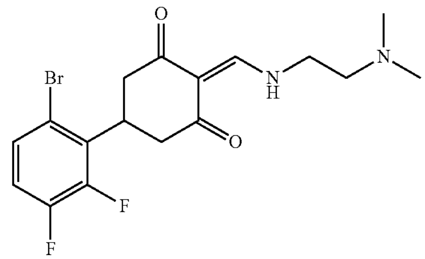 [SMILES: CN(C)CCNC=C1C(=O)CC(c2c(Br)ccc(F)c2F)CC1=O] | 5-(6-bromo-2,3-difluorophenyl)-2-((((2-(dimethylamino)ethyl)amino)methylene)cyclohexane-1,3-dione | ¹H NMR (400 MHz, CDCl₃) δ 11.24 (s, 1H), 8.22 (d, J = 14.4 Hz, 1H), 7.37-7.31 (m, 1H), 6.98 (dd, J = 17.5, 9.0 Hz, 1H), 3.96 (t, J = 13.6 Hz, 1H), 3.53 (q, J = 6.1 Hz, 2H), 3.19-2.99 (m, 2H), 2.67-2.53 (m, 4H), 2.30 (s, 6H). |
| 410 | 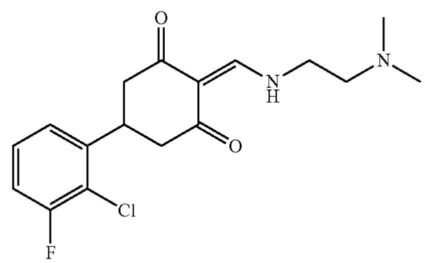 [SMILES: CN(C)CCNC=C1C(=O)CC(c2cccc(F)c2Cl)CC1=O] | 5-(2-chloro-3-fluorophenyl)-2-((((2-(dimethylamino)ethyl)amino)methylene)cyclohexane-1,3-dione | ¹H NMR (400 MHz, CDCl₃) δ 11.22 (s, 1H), 8.20 (d, J = 14.4 Hz, 1H), 7.26-7.20 (m, 1H), 7.06 (t, J = 7.8 Hz, 2H), 3.86 (td, J = 11.6, 5.8 Hz, 1H), 3.52 (q, J = 6.0 Hz, 2H), 2.80-2.60 (m, 4H), 2.56 (t, J = 6.1 Hz, 2H), 2.30 (s, 6H). |
| 411 | 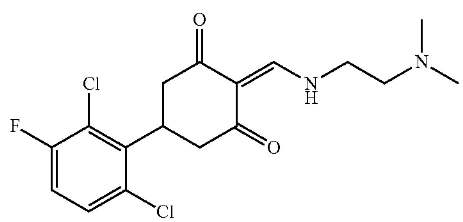 [SMILES: CN(C)CCNC=C1C(=O)CC(c2c(Cl)ccc(F)c2Cl)CC1=O] | 5-(2,6-dichloro-3-fluorophenyl)-2-(((2-(dimethylamino)ethyl)amino)methylene)cyclohexane-1,3-dione | ¹H NMR (400 MHz, CDCl₃) δ 11.25 (s, 1H), 8.22 (d, J = 14.4 Hz, 1H), 7.32 (s, 1H), 7.04 (dd, J = 8.8, 8.0 Hz, 1H), 4.35 (s, 1H), 3.66-3.45 (m, 4H), 2.55 (t, J = 6.1 Hz, 2H), 2.48 (m, 2H), 2.29 (s, 6H). |
| 412 | 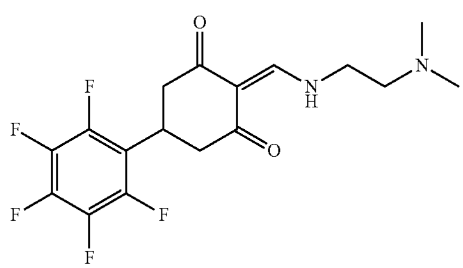 [SMILES: CN(C)CCNC=C1C(=O)CC(c2c(F)c(F)c(F)c(F)c2F)CC1=O] | 2-(((2-(dimethylamino)ethyl)amino)methylene)-5-(perfluorophenyl)cyclohexane-1,3-dione | ¹H NMR (400 MHz, CDCl₃) δ 11.23 (s, 1H), 8.21 (d, J = 14.5 Hz, 1H), 3.84-3.73 (m, 1H), 3.51 (q, J = 5.9 Hz, 2H), 3.09-2.90 (m, 2H), 2.61 (dd, J = 16.6, 2.1 Hz, 2H), 2.54 (t, J = 6.0 Hz, 2H), 2.29 (s, 6H). |
| 413 | 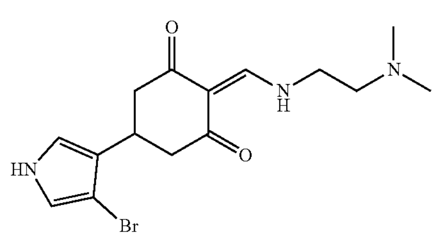 [SMILES: CN(C)CCNC=C1C(=O)CC(c2c[nH]cc2Br)CC1=O] | 5-(4-bromo-1H-pyrrole-3-yl)-2-(((2-(dimethylamino)ethyl)amino)methylene)cyclohexane-1,3-dione | ¹H NMR (400 MHz, CD₃OD) δ 8.23 (s, 1H), 6.72 (d, J = 1.8 Hz, 1H), 6.54 (d, J = 1.9 Hz, 1H), 3.61 (t, J = 6.2 Hz, 2H), 3.26 (m, 1H), 2.74 (m, 2H), 2.62 (t, J = 6.2 Hz, 4H), 2.32 (s, 6H). |

TABLE 7-continued

Compounds 119-355

| # | Structure | Name | Proton NMR($^1$HNMR), Mass Spectrum(MS) |
|---|---|---|---|
| 414 | 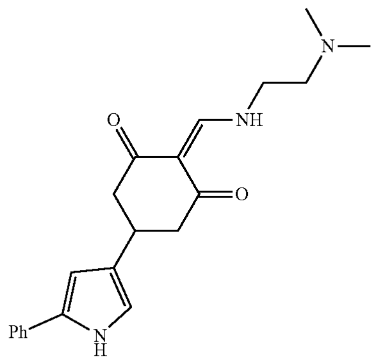 [SMILES: CN(C)CCNC=C1C(=O)CC(c2c[nH]c(-c3ccccc3)c2)CC1=O] | 2-(((2-(dimethylamino)ethyl)amino)methylene)-5-(5-phenyl-1H-pyrrole-3-yl)cyclohexane-1,3-dione | $^1$H NMR (400 MHz, CDCl$_3$) δ 11.26-11.10 (m, 1H), 8.52 (s, 1H), 8.14 (d, J = 14.3 Hz, 1H), 7.49-7.40 (m, 2H), 7.34 (t, J = 7.8 Hz, 2H), 7.19 (t, J = 7.4 Hz, 1H), 6.65 (s, 1H), 6.45-6.38 (m, 1H), 3.45 (q, J = 6.1 Hz, 2H), 3.35 (m, 1H), 2.84 (m, 2H), 2.66 (m, 2H), 2.51 (t, J = 6.2 Hz, 2H), 2.26 (s, 6H). |

Example 35: Synthesis of Compounds 415-452

The compounds 415-452 were synthesized by the same procedures as Example 4 or Example 8 (e.g., Compounds 3 and 8) except for using corresponding substituted cyclohexane-1,3-dione, as shown in Table 8.

TABLE 8

Compounds 415-452

| # | Structure | Name | Proton NMR($^1$H NMR), Mass Spectrum( MS) |
|---|---|---|---|
| 415 | 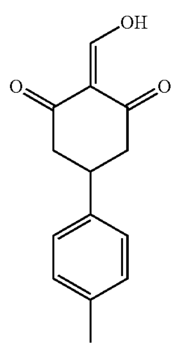 [SMILES: Cc1ccc(C2CC(=O)C(=CO)C(=O)C2)cc1] | 2-(hydroxymethylene)-5-(4-methylphenyl)cyclohexane-1,3-dione | $^1$H NMR (400 MHz, DMSO-d$_6$) δ 9.52 (s, 1H), 7.22 (d, J = 8.1 Hz, 2H), 7.14 (d, J = 8.0 Hz, 2H), 3.46-3.38 (m, 1H), 2.99-2.86 (m, 2H), 2.71-2.59 (m, 2H), 2.27 (s, 3H); MS: 229.1 [M − 1]. |
| 416 | 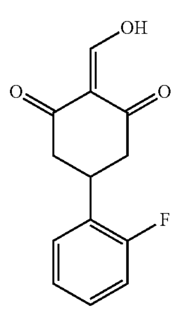 [SMILES: O=C1CC(c2ccccc2F)CC(=O)C1=CO] | 2-(hydroxymethylene)-5-(2-fluorophenyl)cyclohexane-1,3-dione | $^1$H NMR (400 MHz, DMSO-d$_6$) δ 9.52 (s, 1H), 7.42 (td, J = 8.0, 1.7 Hz, 1H), 7.37-7.29 (m, 1H), 7.25-7.16 (m, 2H), 3.78-3.70 (m, 1H), 3.01-2.94 (m, 2H), 2.70-2.64 (m, 2H); MS: 235.1 [M + 1]. |

TABLE 8-continued

Compounds 415-452

| # | Structure | Name | Proton NMR(¹H NMR), Mass Spectrum( MS) |
|---|---|---|---|
| 417 | 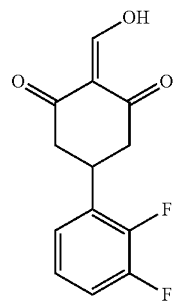 [SMILES: O=C1CC(c2cccc(F)c2F)CC(=O)C1=CO] | 2-(hydroxymethylene)-5-(2,3-difluorophenyl)cyclohexane-1,3-dione | ¹H NMR (400 MHz, DMSO-d₆) δ 9.51 (s, 1H), 7.39-7.32 (m, 1H), 7.29-7.19 (m, 2H), 3.85-3.71 (m, 1H), 3.03-2.95 (m, 2H), 2.71-2.66 (m, 2H); MS: 253.1 [M + 1]. |
| 418 | 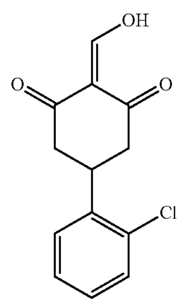 [SMILES: O=C1CC(c2ccccc2Cl)CC(=O)C1=CO] | 2-(hydroxymethylene)-5-(2-chlorophenyl)cyclohexane-1,3-dione | ¹H NMR (400 MHz, DMSO-d₆) δ 9.51 (s, 1H), 7.48 (t, J = 6.9 Hz, 2H), 7.38 (t, J = 7.6 Hz, 1H), 7.31 (m, 1H), 3.88-3.78 (m, 1H), 3.07-2.93 (m, 2H), 2.67 (m, 2H); MS: 249.1 [M − 1]. |
| 419 | 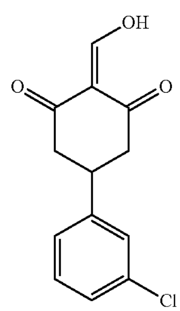 [SMILES: O=C1CC(c2cccc(Cl)c2)CC(=O)C1=CO] | 2-(hydroxymethylene)-5-(3-chlorophenyl)cyclohexane-1,3-dione | ¹H NMR (400 MHz, DMSO-d₆) δ 9.52 (s, 1H), 7.45 (s, 1H), 7.35 (m, 3H), 3.50 (m, 1H), 3.03-2.92 (m, 2H), 2.67 (d, J = 13.5 Hz, 2H); MS: 249.1 [M − 1]. |
| 420 | 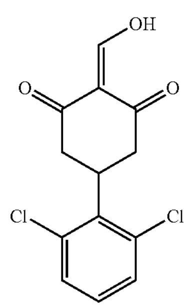 [SMILES: O=C1CC(c2c(Cl)cccc2Cl)CC(=O)C1=CO] | 2-(hydroxymethylene)-5-(2,6-dichlorophenyl)cyclohexane-1,3-dione | ¹H NMR (400 MHz, DMSO-d₆) δ 9.51 (s, 1H), 7.51 (t, J = 6.9 Hz, 1H), 7.33 (m, 2H), 4.02-3.89 (m, 1H), 3.27-3.13 (m, 2H), 2.67 (m, 2H); MS: 283.1 [M − 1]. |
| 421 | 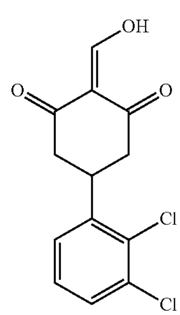 [SMILES: O=C1CC(c2cccc(Cl)c2Cl)CC(=O)C1=CO] | 2-(hydroxymethylene)-5-(2,3-dichlorophenyl)cyclohexane-1,3-dione | ¹H NMR (400 MHz, CDCl3) δ 15.89 (s, 1H), 9.66 (s, 1H), 7.43 (dd, J = 8.0, 1.5 Hz, 1H), 7.25 (t, J = 7.9 Hz, 1H), 7.16 (dd, J = 7.8, 1.4 Hz, 1H), 4.01-3.93 (m, 1H), 3.00-2.94 (m, 1H), 2.91-2.75 (m, 2H), 2.71-2.64 (m, 1H); MS: 285.0 [M + 1]. |

TABLE 8-continued

Compounds 415-452

| # | Structure | Name | Proton NMR($^1$H NMR), Mass Spectrum(MS) |
|---|---|---|---|
| 422 | 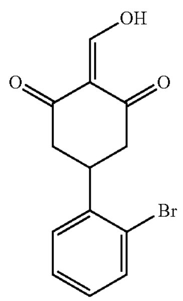 [SMILES: O=C1CC(c2ccccc2Br)CC(=O)C1=CO] | 2-(hydroxymethylene)-5-(2-bromophenyl)cyclohexane-1,3-dione | $^1$H NMR (400 MHz, DMSO-$d_6$) δ 9.52 (s, 1H), 7.65 (d, J = 7.2 Hz, 1H), 7.52-7.47 (m, 1H), 7.43 (t, J = 7.3 Hz, 1H), 7.27-7.20 (m, 1H), 3.81-3.73 (m, 2H), 3.05-2.91 (m, 2H), 2.70-2.65 (m, 2H); MS: 293.0 [M − 1]. |
| 423 | 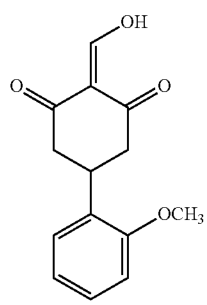 [SMILES: COc1ccccc1C1CC(=O)C(=CO)C(=O)C1] | 2-(hydroxymethylene)-5-(2-methoxyphenyl)cyclohexane-1,3-dione | $^1$H NMR (400 MHz, CDCl$_3$) δ 15.90 (s, 1H), 9.68 (s, 1H), 7.31-7.27 (m, 0.8H), 7.26-7.24 (m, 0.2H), 7.15-7.10 (m, 1H), 6.99-6.88 (m, 2H), 3.85 (s, 3H), 3.79-3.69 (m, 1H), 3.05-2.94 (m, 1H), 2.93-2.67 (m, 3H); MS: 247.1 [M + 1]. |
| 424 | 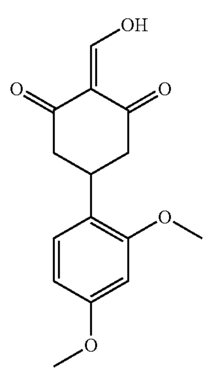 [SMILES: COc1ccc(C2CC(=O)C(=CO)C(=O)C2)c(OC)c1] | 2-(hydroxymethylene)-5-(2,4-dimethoxyphenyl)cyclohexane-1,3-dione | $^1$H NMR (400 MHz, CD$_3$OD) δ 9.63 (s, 1H), 7.08 (d, J = 8.8 Hz, 1H), 6.53-6.55 (m, 1H), 6.51-6.45 (m, 1H), 5.49 (s, 1H), 3.82 (d, J = 2.4 Hz, 3H), 3.78 (d, J = 2.4 Hz, 3H), 3.69-3.53 (m, 1H), 3.00-2.83 (m, 1H), 2.80-2.62 (m, 2H), 2.60-2.46 (m, 1H); MS: 277.1 [M + 1]. |
| 425 | 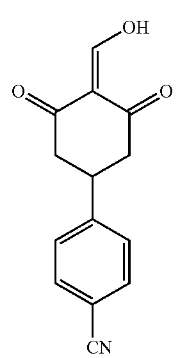 [SMILES: N#Cc1ccc(C2CC(=O)C(=CO)C(=O)C2)cc1] | 2-(hydroxymethylene)-5-(4-cyanophenyl)cyclohexane-1,3-dione | $^1$H NMR (400 MHz, DMSO-$d_6$) δ 9.52 (s, 1H), 7.83 (d, J = 8.0 Hz, 2H), 7.58 (d, J = 8.0 Hz, 2H), 3.65-3.55 (m, 1H), 3.05-2.96 (m, 2H), 2.73-2.64 (m, 2H); MS: 242.0 [M + 1]. |

TABLE 8-continued

Compounds 415-452

| # | Structure | Name | Proton NMR($^1$H NMR), Mass Spectrum( MS) |
|---|---|---|---|
| 426 | 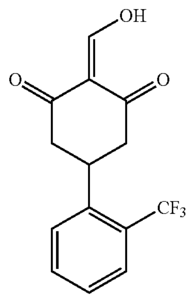 [SMILES: O=C1CC(c2ccccc2C(F)(F)F)CC(=O)C1=CO] | 2-(hydroxymethylene)-5-(2-trifluoromethylphenyl)cyclohexane-1,3-dione | $^1$H NMR (400 MHz, DMSO-d$_6$): δ 9.52 (s, 1H), 7.87 (d, J = 8.2 Hz, 1H), 7.79-7.68 (m, 2H), 7.50 (t, J = 7.7 Hz, 1H), 3.75-3.61 (m, 1H), 3.25-3.06 (m, 2H), 2.56 (d, J = 3.8 Hz, 1H). MS: 283.1 [M − 1]. |
| 427 | 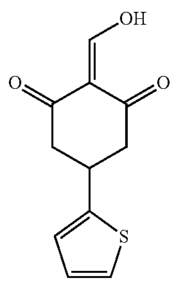 [SMILES: O=C1CC(c2cccs2)CC(=O)C1=CO] | 2-(hydroxymethylene)-5-(2-thiophen)cyclohexane-1,3-dione | $^1$H NMR (400 MHz, CDCl3) δ 15.87 (s, 1H), 9.64 (s, 1H), 7.23 (dd, J = 5.1, 1.1 Hz, 1H), 6.98-6.96 (m, 1H), 6.89 (dt, J = 3.5, 1.0 Hz, 1H), 3.79-3.68 (m, 1H), 3.10-3.04 (m, 1H), 2.99-2.88 (m, 2H), 2.76-2.69 (m, 1H); MS: 221.1 [M − 1]. |
| 428 | 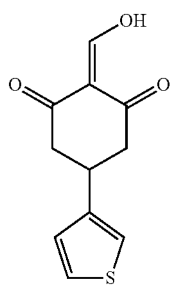 [SMILES: O=C1CC(c2ccsc2)CC(=O)C1=CO] | 2-(hydroxymethylene)-5-(3-thiophen)cyclohexane-1,3-dione | $^1$H NMR (400 MHz, CDCl$_3$) δ 15.86 (s, 1H), 9.63 (s, 1H), 7.35 (dd, J = 4.8, 2.0 Hz, 1H), 7.06-7.03 (m, 1H), 7.00 (dd, J = 5.2, 1.2 Hz, 1H), 3.59-3.50 (m, 1H), 3.05-2.96 (m, 1H), 2.93-2.81 (m, 2H), 2.72-2.62 (m, 1H); MS: 223.0 [M + 1]. |
| 429 | 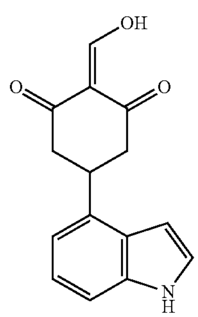 [SMILES: O=C1CC(c2cccc3[nH]ccc23)CC(=O)C1=CO] | 2-(hydroxymethylene)-5-(1H-indol-4-yl)cyclohexane-1,3-dione | $^1$H NMR (400 MHz, DMSO-d$_6$) δ 11.17 (s, 1H), 9.55 (s, 1H), 7.35 (t, J = 2.8 Hz, 1H), 7.30 (d, J = 8.0 Hz, 1H), 7.05 (t, J = 7.7 Hz, 1H), 6.89 (d, J = 7.2 Hz, 1H), 6.61 (s, 1H), 3.94-3.81 (m, 1H), 3.14-3.00 (m, 2H), 2.7-2.73 (m, 2H); MS: 254.1 [M − H]. |
| 430 | 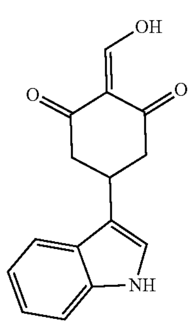 [SMILES: O=C1CC(c2c[nH]c3ccccc23)CC(=O)C1=CO] | 2-(hydroxymethylene)-5-(1H-indol-3-yl)cyclohexane-1,3-dione | $^1$H NMR (400 MHz, DMSO-d$_6$) δ 9.55 (s, 1H), 7.37 (s, 1H), 7.30-7.05 (m, 4H), 3.96-3.83 (m, 1H), 3.15-3.01 (m, 2H), 2.71-2.74 (m, 2H); MS: 254.1 [M − H]. |

TABLE 8-continued

Compounds 415-452

| # | Structure | Name | Proton NMR ($^1$H NMR), Mass Spectrum (MS) |
|---|---|---|---|
| 431 | 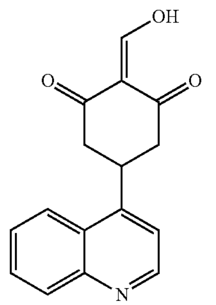 [SMILES: O=C1CC(c2ccnc3ccccc23)CC(=O)C1=CO] | 2-(hydroxymethylene)-5-(4-quinoline)cyclohexane-1,3-dione | $^1$H NMR (400 MHz, DMSO-d$_6$): δ 9.56 (s, 1H) 8.91 (d, J = 4.6 Hz, 1H), 8.34 (d, J = 8.1 Hz, 1H), 8.07 (d, J = 8.4 Hz, 1H), 7.81 (t, J = 7.0 Hz, 1H), 7.68 (t, J = 7.0 Hz, 1H), 7.55 (d, J = 4.7 Hz, 1H), 4.51-4.39 (m, 1H), 3.15-3.01 (m, 2H), 2.82-2.70 (m, 2H). MS: 266.1 [M − 1] |
| 432 | 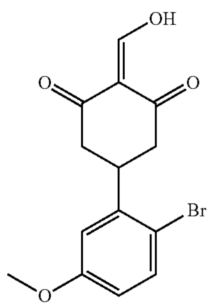 [SMILES: COc1ccc(Br)c(C2CC(=O)C(=CO)C(=O)C2)c1] | 2-(hydroxymethylene)-5-(2-bromo-5-methoxyphenyl)cyclohexane-1,3-dione | $^1$H NMR (400 MHz, DMSO-d$_6$) δ 9.51 (s, 1H), 7.52 (d, J = 8.8 Hz, 1H), 7.06 (d, J = 3.0 Hz, 1H), 6.83 (dd, J = 8.8, 3.0 Hz, 1H), 3.81-3.66 (m, 4H), 3.03-2.96 (m, 2H), 2.66-2.60 (m, 2H). MS: 325.0 [M − 1]. |
| 433 | 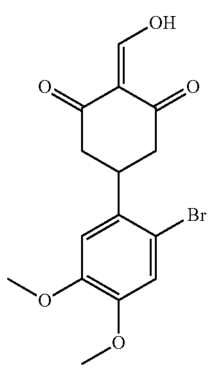 [SMILES: COc1cc(Br)c(C2CC(=O)C(=CO)C(=O)C2)cc1OC] | 2-(hydroxymethylene)-5-(2-bromo-4,5-dimethoxyphenyl)cyclohexane-1,3-dione | $^1$H NMR (400 MHz, DMSO-d$_6$) δ 9.53 (s, 1H), 7.14 (s, 1H), 7.08 (s, 1H), 3.78 (s, 3H), 3.76 (s, 3H), 3.70-3.65 (m, 1H), 3.08-2.98 (m, 2H), 2.58-2.55 (m, 2H). MS: 357.1 [M + 1]. |
| 434 | 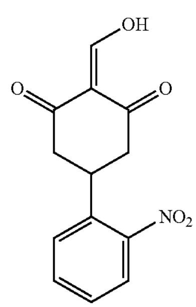 [SMILES: O=C1CC(c2ccccc2[N+](=O)[O-])CC(=O)C1=CO] | 2-(hydroxymethylene)-5-(2-nitrophenyl)cyclohexane-1,3-dione | $^1$H NMR (400 MHz, DMSO-d$_6$) δ 9.53 (s, 1H), 7.91 (s, 1H), 7.80-7.66 (m, 3H), 3.66-3.56 (m, 1H), 3.06-2.95 (m, 2H), 2.76-2.70 (m, 2H). MS: 260.1 [M − 1]. |

TABLE 8-continued

Compounds 415-452

| # | Structure | Name | Proton NMR(¹H NMR), Mass Spectrum( MS) |
|---|---|---|---|
| 435 | 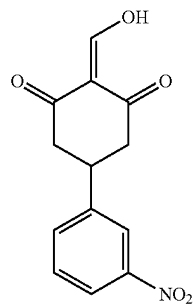 [SMILES: O=C1CC(c2cccc([N+](=O)[O-])c2)CC(=O)C1=CO] | 2-(hydroxymethylene)-5-(3-nitrophenyl)cyclohexane-1,3-dione | ¹H NMR (400 MHz, DMSO-d₆) δ 9.55 (s, 1H), 7.88 (s, 1H), 7.83-7.62 (m, 3H), 3.67-3.57 (m, 1H), 3.07-2.96 (m, 2H), 2.75-2.69 (m, 2H). MS: 260.1 [M − 1]. |
| 436 | 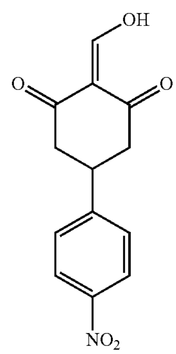 [SMILES: O=C1CC(c2ccc([N+](=O)[O-])cc2)CC(=O)C1=CO] | 2-(hydroxymethylene)-5-(4-nitrophenyl)cyclohexane-1,3-dione | ¹H NMR (400 MHz, DMSO-d₆) δ 9.55 (s, 1H), 7.82 (d, J = 8.1 Hz, 2H), 7.69 (d, J = 8.4 Hz, 2H), 3.67-3.57 (m, 1H), 3.07-2.96 (m, 2H), 2.75-2.69 (m, 2H). MS: 260.1 [M − 1]. |
| 437 | 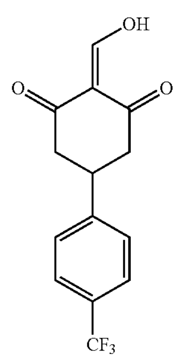 [SMILES: O=C1CC(c2ccc(C(F)(F)F)cc2)CC(=O)C1=CO] | 2-(hydroxymethylene)-5-(4-trifluoromethylphenyl)cyclohexane-1,3-dione | ¹H NMR (400 MHz, DMSO-d₆) δ 9.53 (s, 1H), 7.72 (d, J = 8.1 Hz, 2H), 7.59 (d, J = 8.4 Hz, 2H), 3.65-3.55 (m, 1H), 3.05-2.94 (m, 2H), 2.73-2.67 (m, 2H). MS: 283.1 [M − 1]. |
| 438 | 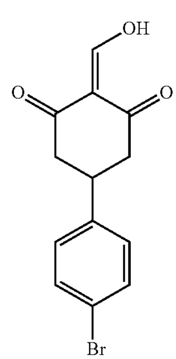 [SMILES: O=C1CC(c2ccc(Br)cc2)CC(=O)C1=CO] | 2-(hydroxymethylene)-5-(4-bromophenyl)cyclohexane-1,3-dione | ¹H NMR (400 MHz, DMSO-d₆) δ 9.55 (s, 1H), 7.68-7.75 (m, 2H), 7.47-7.40 (m, 2H), 3.81-3.73 (m, 1H), 3.08-2.94 (m, 2H), 2.73-2.68 (m, 2H); MS: 293.0 [M − 1]. |

TABLE 8-continued

Compounds 415-452

| # | Structure | Name | Proton NMR($^1$H NMR), Mass Spectrum(MS) |
|---|---|---|---|
| 439 | 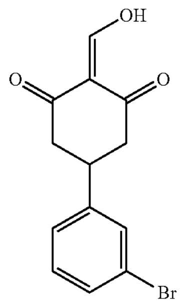 [SMILES: O=C1CC(c2cccc(Br)c2)CC(=O)C1=CO] | 2-(hydroxymethylene)-5-(3-bromophenyl)cyclohexane-1,3-dione | $^1$H NMR (400 MHz, DMSO-$d_6$) δ 9.52 (s, 1H), 7.65 (s, 1H), 7.65-7.58 (m, 3H), 3.81-3.73 (m, 1H), 3.07-2.91 (m, 2H), 2.70-2.62 (m, 2H); M: 293.0 [M − 1]. |
| 440 | 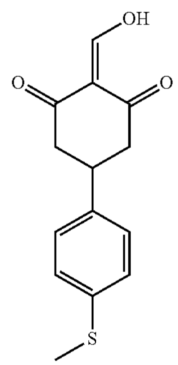 [SMILES: CSc1ccc(C2CC(=O)C(=CO)C(=O)C2)cc1] | 5-(4-methylthiophenyl)-2-(hydroxymethylene)cyclohexane-1,3-dione | $^1$H NMR (400 MHz, CDCl3) δ 9.68 (s, 1H), 7.28 (d, J = 8.5 Hz, 2H), 7.18 (d, J = 8.3 Hz, 2H), 3.45-3.80 (m, 1H), 2.91 (d, J = 8.3 Hz, 2H), 2.81-2.76 (m, 1H), 2.71-2.64 (m, 1H), 2.51 (s, 3H); MS: 263.1 [M + 1]. |
| 441 | 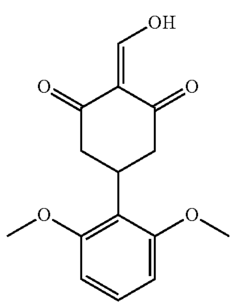 | 2-(hydroxymethylene)-5-(2,6-dimethoxyphenyl)cyclohexane-1,3-dione | $^1$H NMR (400 MHz, CDCl$_3$) δ 9.65 (s, 1H), 7.31-7.10 (m, 3H), 3.88 (s, 3H), 3.86 (s, 3H), 3.79-3.69 (m, 1H), 3.05-2.94 (m, 1H), 2.93-2.67 (m, 3H); MS: 277.1 [M + 1]. |
| 442 | 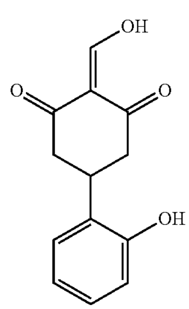 [SMILES: O=C1CC(c2ccccc2O)CC(=O)C1=CO] | 2-(hydroxymethylene)-5-(2-hydroxyphenyl)cyclohexane-1,3-dione | $^1$H NMR (400 MHz, CDCl3) δ 9.68 (s, 1H), 7.36-7.11 (m, 4H), 3.75-3.62 (m, 1H), 2.81 (m, 1H), 2.68-2.36 (m, 3H); MS: 233.1 [M + 1]. |

TABLE 8-continued

Compounds 415-452

| # | Structure | Name | Proton NMR($^1$H NMR), Mass Spectrum(MS) |
|---|---|---|---|
| 443 | 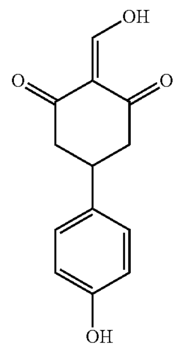 | 2-(hydroxymethylene)-5-(4-hydroxyphenyl)cyclohexane-1,3-dione | $^1$H NMR (400 MHz, CDCl3) δ 9.68 (s, 1H), 7.36 (d, J = 8.5 Hz, 2H), 7.29 (d, J = 8.3 Hz, 2H), 3.55-3.80 (m, 1H), 2.81 (d, J = 8.3 Hz, 2H), 2.71-2.65 (m, 1H), 2.60-2.56 (m, 1H); MS: 233.1 [M + 1]. |
| 444 | 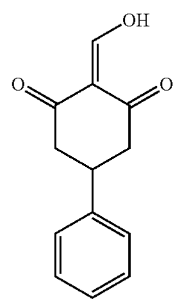 [SMILES: O=C1CC(c2ccccc2)CC(=O)C1=CO] | 2-(hydroxymethylene)-5-phenylcyclohexane-1,3-dione | $^1$H NMR (400 MHz, CDCl3) δ 15.86 (s, 1H), 9.67 (s, 1H), 7.39-7.35 (m, 2H), 7.32-7.27 (m, 1H), 7.25-7.21 (m, 2H), 3.49-3.38 (m, 1H), 2.95-2.89 (m, 2H), 2.82-2.63 (m, 2H); MS: 217.1 [M + 1]. |
| 445 | 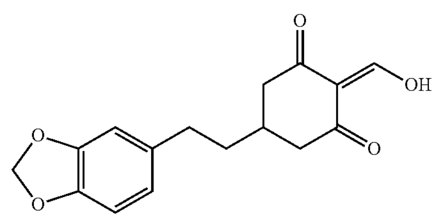 [SMILES: O=C1CC(CCc2ccc3c(c2)OCO3)CC(=O)C1=CO] | 2-(hydroxymethylene)-5-(2-(benzo[d][1,3]dioxo-5-yl)ethyl)-cyclohexane-1,3-dione | $^1$H NMR (400 MHz, DMSO-d$_6$) δ 9.48 (s, 1H), 6.86-6.73 (m, 2H), 6.66 (dd, J = 7.9, 1.5 Hz, 1H), 5.95 (s, 2H), 2.69-2.52 (m, 4H), 2.48-2.30 (m, 2H), 2.13-2.01 (m, 1H), 1.64-1.59 (m, 2H); MS: 289.1 [M + 1]. |
| 446 | 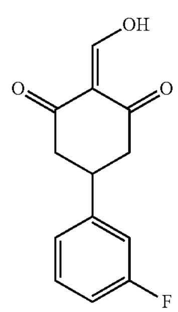 [SMILES: O=C1CC(c2cccc(F)c2)CC(=O)C1=CO] | 2-(hydroxymethylene)-5-(3-fluorophenyl)cyclohexane-1,3-dione | $^1$H NMR (400 MHz, CDCl3) δ 15.88 (s, 1H), 9.66 (s, 1H), 7.37-7.27 (m, 1H), 7.06-6.89 (m, 3H), 3.48-3.40 (m, 1H), 2.92-2.89 (m, 2H), 2.83-2.74 (m, 1H), 2.70-2.62 (m, 1H); MS: 235.1 [M + 1]. |
| 447 | 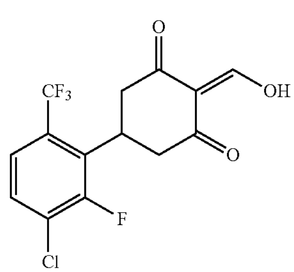 [SMILES: O=C1CC(c2c(C(F)(F)F)ccc(Cl)c2F)CC(=O)C1=CO] | 2-(hydroxymethylene)-5-((2-fluoro-3-chloro-6-trifluoromethyl)phenyl)cyclohexane-1,3-dione | $^1$H NMR (400 MHz, CDCl3) δ 15.93 (s, 1H), 9.69 (s, 1H), 7.55-7.45 (m, 2H), 3.87-3.75 (m, 1H), 3.39-3.31 (m, 1H), 3.11-3.03 (m, 1H), 2.78-2.63 (m, 2H); MS: 337.0 [M + 1]. |

TABLE 8-continued

Compounds 415-452

| # | Structure | Name | Proton NMR($^1$H NMR), Mass Spectrum(MS) |
|---|---|---|---|
| 448 | 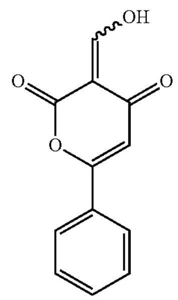 [SMILES: O=C1C=C(c2ccccc2)OC(=O)C1=CO] | 3-(hydroxymethylene)-6-phenyl-2H-pyran-2,4(3H)-dione | $^1$H NMR (400 MHz, CDCl3) δ 14.46 (s, 1H), 9.97 (s, 1H), 7.94-7.85 (m, 2H), 7.61-7.50 (m, 3H), 6.59 (s, 1H); MS: 217.1 [M + 1]. |
| 449 | 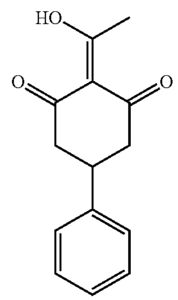 [SMILES: CC(O)=C1C(=O)CC(c2ccccc2)CC1=O] | 2-(1-hydroxyethylidene)-5-phenylcyclohexane-1,3-dione | $^1$H NMR (400 MHz, DMSO-$d_6$) δ 18.06 (s, 1H), 7.37-7.30 (m, 4H), 7.29-7.21 (m, 1H), 3.44-3.37 (m, 1H), 2.96 (br, 2H), 2.71 (br, 2H), 2.55 (s, 3H); MS: 231.1 [M + 1]. |
| 450 | 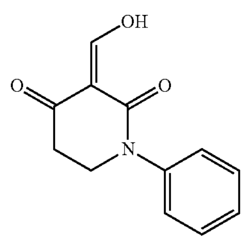 [SMILES: O=C1CCN(c2ccccc2)C(=O)/C1=C\O] | 3-(hydroxymethylene)-N-phenylpiperidine-2,4-dione | $^1$H NMR (400 MHz, DMSO-$d_6$) δ 10.00 (s, 1H), 8.03 (t, J = 14.5 Hz, 1H), 7.40-7.32 (m, 2H), 7.29 (t, J = 7.4 Hz, 2H), 7.17 (q, J = 14.0, 7.3 Hz, 1H), 3.83-3.73 (m, 2H), 3.46-3.34 (m, 2H), 2.59 (t, J = 6.5 Hz, 1H), 2.54 (t, J = 6.6 Hz, 1H). |
| 451 | 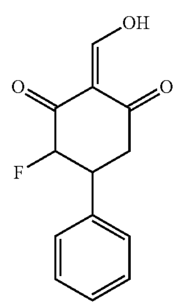 [SMILES: O=C1CC(c2ccccc2)C(F)C(=O)/C1=C/O] | 2-(hydroxymethylene)-4-fluoro-5-(phenyl)cyclohexane-1,3-dione | $^1$H NMR (400 MHz, DMSO-$d_6$) δ 8.26-8.07 (m, 1H), 7.40-7.12 (m, 4H), 5.29-5.04 (m, 1H), 3.83-3.69 (m, 1H), 2.92-2.63 (m, 2H). |
| 452 | 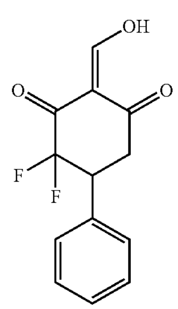 [SMILES: O=C1CC(c2ccccc2)C(F)(F)C(=O)/C1=C/O] | 2-(hydroxymethylene)-4,4-difluoro-5-(phenyl)cyclohexane-1,3-dione | $^1$H NMR (400 MHz, CD$_3$OD) δ 9.84 (s, 1H), 7.58 (s, 1H), 7.41-7.29 (m, 5H), 3.79-3.64 (m, 1H), 3.12-3.02 (m, 1H), 2.72-2.63 (m, 1H); MS: 253.1 [M + 1]$^+$ |

Example 36: Synthesis of Compound 5-(((2-(4-(2-hydroxyethyl)piperazin-1-yl)ethyl)amino)methylene)thiazolidine-2,4-dione (Compound 200)

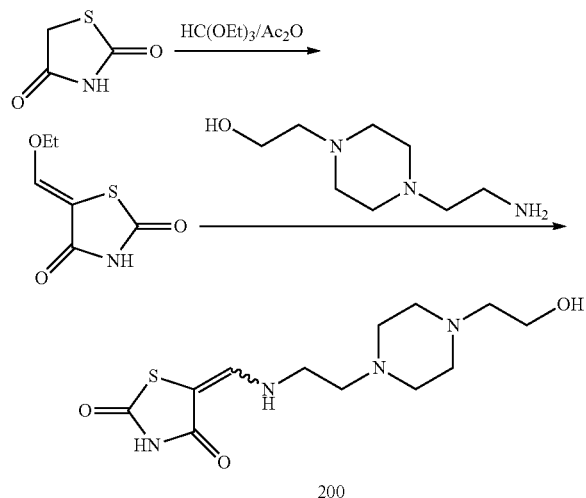

Step 1: Synthesis of Compound 5-(ethoxymethylene)thiazolidine-2,4-dione

The mixture of thiazolidine-2,4-dione (2.8 g, 23.93 mmol), triethoxymethane (4 mL) and acetic anhydride (6 mL) was heated under reflux overnight. After the reaction was completed, the reaction mixture was cooled to RT to precipitate solid and then filtered. The filtrate was collected and concentrated to give a crude product of the desired compound, which can be directly used in the next step without further purification.

Step 2: Synthesis of Compound 5-(((2-(4-(2-hydroxyethyl)piperazin-1-yl)ethyl)amino)methylene)thiazolidine-2,4-dione The operation procedures were the same as Example 2 (Compound 1).

Example 37: Synthesis of Compound 4-((dimethylamino)methylene)-2-methyl-2-phenylcyclobutane-1,3-dione (Compound 201)

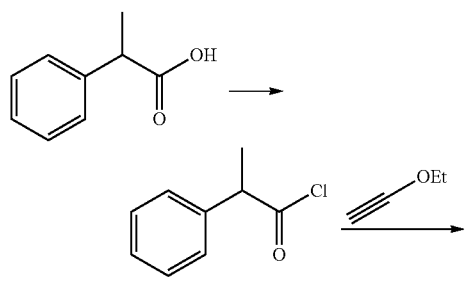

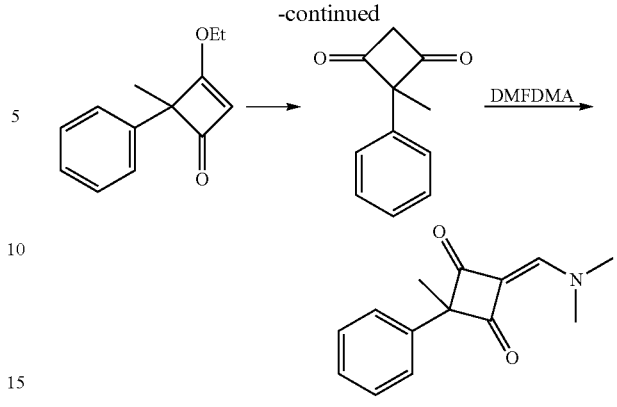

Step 1: Synthesis of 2-phenylpropanoyl Chloride

Under the protection of nitrogen atmosphere, $SOCl_2$ (4.8 g, 40.3 mmol) was added dropwise at 0° C. into the solution of 2-phenylpropanoic acid (2 g, 13.3 mmol) in DCM (20 mL). After the addition, a catalytic amount of DMF was added. The mixture was refluxed and reacted for 2 hrs and concentrated to give a crude product of 2-phenylpropanoyl chloride, which can be directly used in the next step.

Step 2: Synthesis of Compound 3-ethoxy-4-methyl-4-phenylcyclobut-2-en-1-one

Under the protection of nitrogen atmosphere, ethoxyacetylene (3.72 g, 26.6 mmol, 50% w/w of hexane solution) was added dropwise into the solution of 2-phenylpropanoyl chloride (13.3 mmol) in ether (40 mL). The above mixture was added dropwise with TEA (2 g, 19.8 mmol), then stirred at RT for 30 min. The suspension was heated to reflux and reacted for 24 hrs. After the reaction was completed, the resulting mixture was cooled and filtrated. The filtrate was concentrated, separated and purified by column chromatography to give 600 mg of the desired product.

Step 3: Synthesis of Compound 2-methyl-2-phenylcyclobutane-1,3-dione

The compound 3-ethoxy-4-methyl-4-phenylcyclobut-2-en-1-one (350 mg, 1.73 mmol) was dissolved in the mixed solution of 2M hydrochloric acid (5 mL) and THF (3 mL), stirred vigorously at RT for 48 hrs. After the reaction was completed, the reaction mixture was extracted with DCM. The combined organic layers were dried and concentrated to give 250 mg of the crude product, which can be directly used in the next step.

Step 4: Synthesis of Compound 4-((dimethylamino)methylene)-2-methyl-2-phenylcyclobutane-1,3-dione (compound 201)

The operation procedures were the same as Example 8 (compound 8). Compound 201: $^1H$ NMR (400 MHz, $CDCl_3$) δ 7.56-7.48 (m, 2H), 7.31 (m, 2H), 7.21 (m, 1H), 7.04 (s, 1H), 3.64 (s, 3H), 3.27 (s, 3H), 1.59 (s, 3H).

Example 38: Synthesis of Compound Chloride-(2-(((2-(dimethylamino)ethyl)amino)methylene)-5-phenylcyclohexane-1,3-dione) nickel (II) Complex

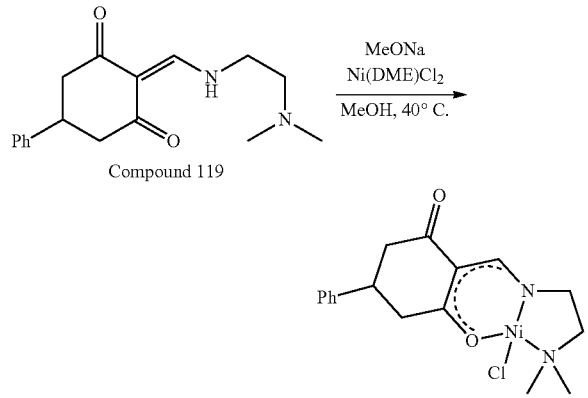

The solution compound 119 (2.86 g, 10 mmol) in MeOH (7.5 mL) was added dropwise to a solution of sodium (264 mg, 11 mmol) in MeOH (20 mL), stirred at room temperature for 10 min, followed by adding nickel (II) chloride-1,2-dimethoxyethane (2.63 g, 12 mmol) in MeOH (10 mL) into the mixed solution. The mixture was heated to 40° C. and stirred for 2 h. Then concentrated and the concentrated crude product was diluted with acetone and refluxed for 1 h, then cooled, the solid substance was filtered off, the residue was washed with acetone and dried to give 1.1 g of the desired compound with a yield of 29%. MS (ESI): [M−Cl]$^+$: 343.3; [M+Cl]$^-$: 413.2

Example 39: Synthesis of 2-(hydroxymethylene)-5-phenylcyclohexane-1,3-dione Sodium Salt (Compound 463)

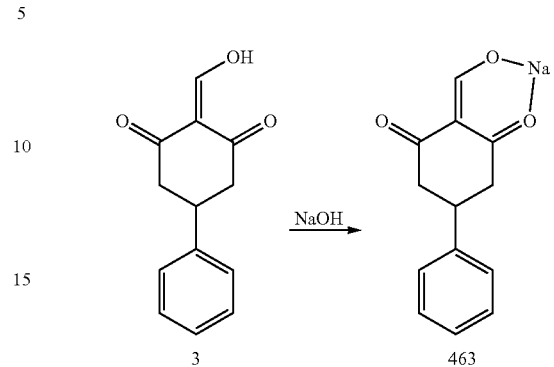

Compound 3 (294 mg) was added into water (8 ml), followed by adding NaOH solid (57 mg), stirred at RT overnight. The reaction solution was concentrated and beat with ether, then filtrated to give a yellow solid product: Compound 463 (267 mg, yield 83%).

The coordination bond of Na with carbonyl was formed in Compound 463.

Example 40: Synthesis of Compounds 453-462 and 464

Compounds 453-462 and 464 were synthesized by the same procedures as Example 39, except for using corresponding diketone compounds and alkali, as shown in table 9.

TABLE 9

Compounds 453-464

| # | Structure | Name | Proton NMR($^1$HNMR), Mass Spectrum (MS) |
|---|---|---|---|
| 453 | (structure shown) | 2-(hydroxymethylene)-5-(2-thiophen)cyclohexane-1,3-dione lithium salt | $^1$H NMR (400 MHz, DMSO-d$_6$) δ 9.43 (s, 1H), 7.35 (d, J = 5.0, 1H), 6.97-6.93 (m, 1H), 6.92-6.91 (m, 1H), 3.58-3.49 (m, 1H), 2.65-2.51 (m, 4H); MS: 221.1 [M-Li]. |
| 454 | (structure shown) | 2-(hydroxymethylene)-5-(2-thiophen)cyclohexane-1,3-dione sodium salt | $^1$H NMR (400 MHz, DMSO-d$_6$) δ 9.59 (s, 1H), 7.33 (d, J = 4.9 Hz, 1H), 6.97-6.92 (m, 1H), 6.91-6.90 (m, 1H), 3.51-3.43 (m, 1H), 2.54-2.40 (m, 4H, Part of the peak is contained in solvent residual peak of DMSO-d6); MS: 221.1 [M-Na]. |

TABLE 9-continued

Compounds 453-464

| # | Structure | Name | Proton NMR($^1$HNMR), Mass Spectrum (MS) |
|---|---|---|---|
| 455 | 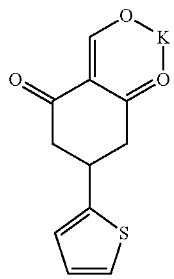 | 2-(hydroxy-methylene)-5-(2-thiophen)cyclo-hexane-1,3-dione potassium salt | $^1$H NMR (400 MHz, DMSO-$d_6$) δ 9.65 (s, 1H), 7.32 (dd, 5.1, 1.2 Hz, 1H), 6.94 (dd, J = 5.1, 3.5 Hz, 1H), 6.89 (dt, J = 3.5, 1.1 Hz, 1H), 3.47-3.38 (m, 1H), 2.48-2.33 (m, 4H); MS: 221.1 [M-K]. |
| 456 | 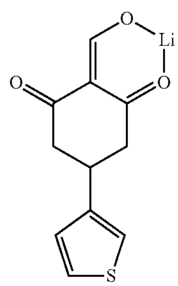 | 2-(hydroxy-methylene)-5-(3-thiophen)cyclo-hexane-1,3-dione lithium salt | $^1$H NMR (400 MHz, DMSO-$d_6$) δ 9.43 (s, 1H), 7.49-7.45 (m, 1H), 7.24-7.20 (m, 1H), 7.14-7.10 (m, 1H), 3.34-3.25 (m, 1H), 2.52-2.48 (m, 4H); MS: 223.0 [M + 1]. |
| 457 | 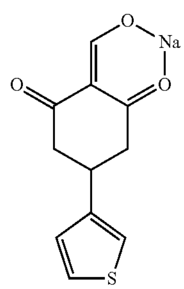 | 2-(hydroxy-methylene)-5-(3-thiophen)cyclo-hexane-1,3-dione sodium salt | $^1$H NMR (400 MHz, DMSO-$d_6$) δ 9.59 (s, 1H), 7.47-7.44 (m, 1H), 7.20 (d, J = 2.8 Hz, 1H), 7.12-7.09 (m, 1H), 3.30-3.21 (m, 1H), 2.46-2.40 (m, 4H); MS: 223.0 [M + 1]. |
| 458 | 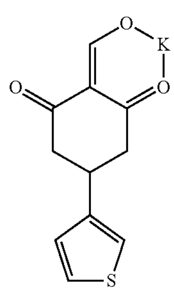 | 2-(hydroxy-methylene)-5-(3-thiophen)cyclo-hexane-1,3-dione potassium salt | $^1$H NMR (400 MHz, DMSO-$d_6$) δ 9.64 (s, 1H), 7.47-7.42 (m, 1H), 7.20-7.17 (m, 1H), 7.10-7.06 (m, 1H), 3.28-3.16 (m, 1H), 2.42-2.30 (m, 4H); MS: 223.0 [M + 1]. |
| 459 | 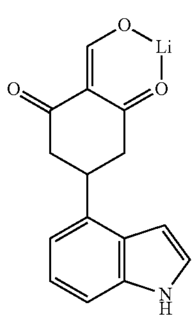 | 2-(hydroxy-methylene)-5-(1H-indol-4-yl)cyclo-hexane-1,3-dione lithium salt | $^1$H NMR (400 MHz, DMSO-$d_6$) δ 9.35 (s, 1H), 7.45 (t, J = 2.8 Hz, 1H), 7.50 (d, J = 8.0 Hz, 1H), 7.15 (t, J = 7.7 Hz, 1H), 7.09 (d, J = 7.2 Hz, 1H), 6.71 (s, 1H), 3.74-3.56 (m, 1H), 2.50-2.46 (m, 4H): MS: 254.1 [M-H]. |

TABLE 9-continued

Compounds 453-464

| # | Structure | Name | Proton NMR (¹HNMR), Mass Spectrum (MS) |
|---|---|---|---|
| 460 | 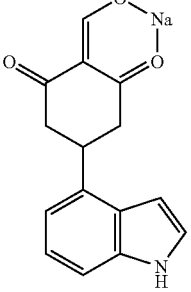 | 2-(hydroxy-methylene)-5-(1H-indol-4-yl)cyclohexane-1,3-dione sodium salt | ¹H NMR (400 MHz, DMSO-d$_6$) δ 9.51 (s, 1H), 7.47 (t, J = 2.8 Hz, 1H), 7.34 (d, J = 8.0 Hz, 1H), 7.09 (t, J = 7.7 Hz, 1H), 6.93 (d, J = 7.2 Hz, 1H), 6.65 (s, 1H), 3.66-3.53 (m, 1H), 2.44-2.40 (m, 4H); MS: 254.1 [M-H]. |
| 461 | 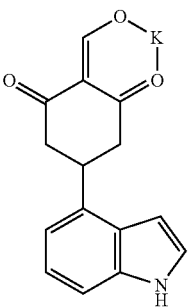 | 2-(hydroxy-methylene)-5-(1H-indol-4-yl)cyclohexane-1,3-dione potassium salt | ¹H NMR (400 MHz, DMSO-d$_6$) δ 9.56 (s, 1H), 7.45 (t, J = 2.8 Hz, 1H), 7.44 (d, J = 8.0 Hz, 1H), 7.09 (t, J = 7.7 Hz, 1H), 6.93 (d, J = 7.2 Hz, 1H), 6.65 (s, 1H), 3.63-3.50 (m, 1H), 2.40-2.36 (m, 4H); MS: 254.1 [M-H]. |
| 462 | 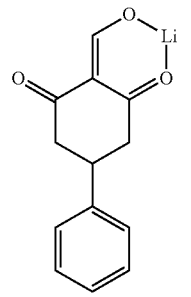 | 2-(hydroxy-methylene)-5-phenylcyclohexane-1,3-dione lithium salt | ¹H NMR (400 MHz, DMSO-d$_6$) δ 9.45 (s, 1H), 7.35-7.26 (m, 4H), 7.25-7.17 (m, 1H), 3.29-3.14 (m, 1H), 2.67-2.53 (m, 2H), 2.46-2.33 (m, 2H). |
| 463 | 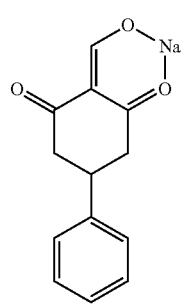 | 2-(hydroxy-methylene)-5-phenylcyclohexane-1,3-dione sodium salt | ¹H NMR (400 MHz, DMSO-d$_6$) δ 9.61 (s, 1H), 7.35-7.25 (m, 4H), 7.22-7.14 (m, 1H), 3.24-3.12 (m, 1H), 2.56-2.45 (m, 2H), 2.37-2.25 (m, 2H). |
| 464 | 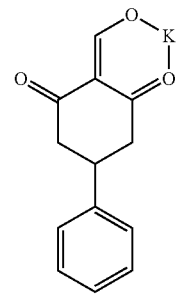 | 2-(hydroxy-methylene)-5-phenylcyclohexane-1,3-dione potassium salt | ¹H NMR (400 MHz, DMSO-d$_6$) δ 9.66 (s, 1H), 7.33-7.24 (m, 4H), 7.22-7.13 (m, 1H), 3.17-3.09 (m, 1H), 2.48-2.37 (m, 2H), 2.31-2.22 (m, 2H). |

The coordination bonds of Li, Na or K with carbonyl were formed in the above compounds.

Example 41

The compounds of the present invention for regulating the autophagy-related protein LC3B were tested by Fluorescence Polarization (FP) Assay.

Fluorescence Polarization (FP) Assay Test

The histone GST-LC3B (final concentration, 180 nM) (SEQ ID NO:1) and N-terminal FITC-labeled peptide ((SEQ ID NO:2, Sequence: FITC-GGDDDWTHLSSKEVD-NH2; final concentration, 18 nM) were placed in the FP buffer solution (50 mM HEPES pH 7.5, 0.1 mg/ml BSA, 1 mM DTT), into which the compound serially diluted by the FP buffer was added, then the above mixture was incubated in the dark at 25° C. Fluorescence polarization values were monitored (PerkinElmer Envision, wavelength of the emission light, 480 nm; wavelength of the absorption light, 535 nm) and $IC_{50}$ values were calculated by the GraphPad Prism 6.0 program. The test results were listed in table 8.

Representation of $IC_{50}$ value of the compounds: Compound with "100 μM<$IC_{50}$≤1 mM" is considered as having low activity (+) against LC3B. Compound with "15 μM<$IC_{50}$≤100 μM" is considered as having moderate activity (++) against LC3B. Compound with "3 μM<$IC_{50}$≤15 μM" is considered as having high activity (+++) against LC3B. Compound with "$IC_{50}$≤3 μM" is considered as having higher activity (++++) against LC3B. $IC_{50}$ values of the compounds of the present inventions are shown in Table 10.

TABLE 10

$IC_{50}$ values of the compounds

| No. | $IC_{50}$ (μM) | ID. | $IC_{50}$ (μM) | ID. | $IC_{50}$ (μM) | ID. | $IC_{50}$ (μM) | ID. | $IC_{50}$ (μM) | ID. | $IC_{50}$ (μM) |
|---|---|---|---|---|---|---|---|---|---|---|---|
| 1 | + | 2 | +++ | 4A | +++ | 7 | +++ | 8 | ++++ | 9 | + |
| 10 | + | 11 | + | 12 | + | 14 | + | 15 | +++ | 17 | +++ |
| 18 | +++ | 19 | ++ | 20 | + | 21 | ++ | 22 | + | 23 | +++ |
| 24 | ++++ | 25 | + | 26 | ++ | 27 | ++ | 28 | +++ | 29 | + |
| 30 | + | 31 | +++ | 32 | +++ | 33 | ++ | 34 | ++++ | 35 | ++ |
| 36 | + | 37 | ++++ | 39 | ++++ | 40 | ++++ | 41 | +++ | 42 | +++ |
| 43 | +++ | 44 | ++ | 45 | ++ | 46 | ++++ | 47 | +++ | 48 | ++++ |
| 49 | ++++ | 50 | ++++ | 51 | ++ | 52 | ++ | 53 | ++ | 54 | ++++ |
| 55 | ++ | 56 | +++ | 57 | ++ | 58 | ++ | 59 | + | 61 | ++++ |
| 62 | +++ | 63 | ++ | 64 | + | 65 | + | 66 | ++++ | 67 | + |
| 68 | ++++ | 69 | ++ | 70 | + | 71 | ++ | 72 | ++++ | 73 | ++++ |
| 74 | ++++ | 75 | +++ | 76 | ++ | 77 | ++ | 78 | ++ | 79 | + |
| 80 | ++ | 81 | ++ | 82 | ++ | 83 | ++ | 84 | ++ | 85 | ++ |
| 86 | ++ | 87 | ++ | 88 | +++ | 89 | + | 90 | + | 91 | ++ |
| 92 | ++ | 93 | +++ | 94 | ++ | 95 | ++ | 96 | + | 97 | ++ |
| 99 | + | 100 | ++ | 101 | ++ | 102 | ++ | 103 | ++ | 104 | ++ |
| 106 | + | 107 | ++ | 108 | + | 109 | + | 110 | + | 111 | + |
| 112 | ++ | 113 | + | 114 | + | 115 | +++ | 116 | ++++ | 119 | ++++ |
| 120 | ++++ | 121 | ++ | 122 | + | 123 | + | 124 | + | 125 | + |
| 126 | ++ | 127 | ++ | 128 | + | 129 | ++ | 131 | ++ | 132 | + |
| 133 | + | 134 | + | 135 | + | 136 | + | 137 | +++ | 138 | + |
| 139 | + | 140 | ++ | 141 | +++ | 142 | ++ | 143 | ++ | 145 | + |
| 146 | ++ | 147 | ++ | 148 | ++++ | 149 | ++++ | 150 | ++++ | 155 | ++ |
| 156 | +++ | 158 | + | 160 | ++ | 161 | + | 162 | ++ | 163 | + |
| 164 | +++ | 165 | + | 169 | +++ | 170 | +++ | 171 | +++ | 172 | +++ |
| 173 | ++ | 174 | ++ | 175 | +++ | 176 | + | 177 | + | 178 | ++ |
| 180 | + | 182 | + | 183 | + | 184 | + | 185 | ++++ | 186 | +++ |
| 187 | ++++ | 188 | +++ | 189 | ++++ | 190 | ++ | 191 | ++++ | 192 | +++ |
| 193 | ++ | 194 | ++ | 195 | +++ | 196 | +++ | 197 | ++++ | 198 | ++ |
| 200 | + | 201 | + | 202 | ++ | 203 | +++ | 204 | + | 205 | + |
| 206 | ++ | 207 | ++ | 208 | ++ | 209 | ++++ | 210 | ++ | 211 | ++++ |
| 212 | ++++ | 213 | ++++ | 214 | ++++ | 215 | ++++ | 216 | ++++ | 217 | +++ |
| 218 | ++++ | 219 | ++++ | 220 | +++ | 221 | ++++ | 222 | ++++ | 223 | +++ |
| 224 | ++++ | 225 | ++++ | 226 | ++++ | 227 | + | 228 | ++++ | 229 | ++++ |
| 230 | ++++ | 231 | ++++ | 232 | ++++ | 233 | ++++ | 236 | +++ | 237 | +++ |
| 238 | ++++ | 239 | ++++ | 240 | ++++ | 241 | ++++ | 242 | +++ | 245 | ++++ |
| 246 | ++++ | 247 | ++ | 248 | ++++ | 249 | ++++ | 251 | ++++ | 252 | ++++ |
| 253 | ++++ | 254 | ++++ | 255 | ++++ | 256 | ++++ | 257 | ++ | 258 | ++++ |
| 259 | ++++ | 260 | ++++ | 262 | ++++ | 263 | ++++ | 264 | ++++ | 265 | +++ |
| 266 | +++ | 267 | +++ | 268 | +++ | 269 | +++ | 270 | +++ | 271 | ++++ |
| 272 | +++ | 273 | ++ | 274 | ++ | 276 | ++ | 277 | ++++ | 278 | ++++ |
| 279 | +++ | 280 | ++++ | 281 | ++++ | 282 | ++++ | 283 | ++++ | 284 | +++ |
| 285 | +++ | 286 | ++++ | 287 | +++ | 288 | +++ | 289 | +++ | 290 | +++ |
| 291 | +++ | 293 | +++ | 294 | ++++ | 295 | +++ | 296 | ++++ | 297 | ++++ |
| 298 | ++++ | 299 | +++ | 300 | ++++ | 301 | ++++ | 302 | ++++ | 303 | ++++ |
| 304 | ++++ | 305 | ++++ | 306 | ++++ | 307 | +++ | 308 | +++ | 309 | ++++ |
| 310 | ++++ | 311 | ++++ | 315 | ++++ | 317 | +++ | 318 | ++++ | 320 | ++++ |
| 321 | +++ | 322 | ++++ | 323 | +++ | 324 | +++ | 325 | ++ | 326 | + |
| 327 | ++++ | 328 | +++ | 329 | ++++ | 330 | +++ | 331 | +++ | 332 | +++ |
| 333 | ++ | 334 | +++ | 335 | +++ | 336 | +++ | 337 | ++++ | 338 | ++++ |
| 339 | ++ | 340 | ++++ | 341 | ++++ | 342 | ++++ | 343 | +++ | 344 | +++ |
| 345 | +++ | 346 | ++++ | 347 | ++++ | 349 | ++++ | 350 | ++++ | 351 | ++++ |
| 352 | + | 353 | ++++ | 354 | ++++ | 355 | ++++ | 356 | ++++ | 357 | ++++ |
| 358 | ++++ | 359 | ++ | 360 | +++ | 361 | ++++ | 362 | ++++ | 363 | +++ |

TABLE 10-continued

IC$_{50}$ values of the compounds

| No. | IC$_{50}$ (μM) | ID. | IC$_{50}$ (μM) | ID. | IC$_{50}$ (μM) | ID. | IC$_{50}$ (μM) | ID. | IC$_{50}$ (μM) | ID. | IC$_{50}$ (μM) |
|---|---|---|---|---|---|---|---|---|---|---|---|
| 364 | ++++ | 365 | ++++ | 366 | ++++ | 367 | ++++ | 368 | ++++ | 369 | ++++ |
| 370 | ++++ | 371 | ++++ | 372 | ++++ | 373 | ++++ | 374 | ++++ | 375 | ++++ |
| 376 | ++++ | 377 | ++++ | 378 | ++++ | 379 | ++++ | 380 | +++ | 381 | ++++ |
| 382 | ++++ | 383 | ++++ | 384 | ++++ | 385 | ++++ | 386 | ++++ | 387 | ++++ |
| 388 | ++++ | 389 | ++++ | 390 | ++++ | 391 | ++ | 392 | ++++ | 393 | ++++ |
| 394 | ++++ | 395 | +++ | 396 | ++++ | 397 | ++++ | 398 | ++++ | 399 | +++ |
| 400 | ++++ | 401 | ++++ | 402 | ++++ | 403 | ++++ | 404 | ++++ | 405 | ++++ |
| 406 | ++++ | 407 | ++ | 408 | +++ | 409 | ++++ | 410 | ++++ | 411 | ++++ |
| 412 | ++++ | 413 | +++ | 414 | +++ | 415 | +++ | 416 | ++++ | 417 | ++++ |
| 418 | ++++ | 419 | ++++ | 420 | ++++ | 421 | ++++ | 422 | ++++ | 423 | +++ |
| 424 | +++ | 425 | ++ | 426 | ++++ | 427 | +++ | 428 | +++ | 429 | ++++ |
| 430 | ++++ | 431 | +++ | 432 | ++++ | 433 | ++++ | 434 | +++ | 435 | +++ |
| 436 | +++ | 437 | +++ | 438 | +++ | 439 | +++ | 440 | +++ | 441 | ++ |
| 442 | ++ | 443 | ++ | 444 | +++ | 445 | ++ | 446 | +++ | 447 | ++++ |
| 448 | +++ | 449 | ++ | 450 | ++ | 451 | +++ | 452 | +++ | 453 | +++ |
| 454 | +++ | 455 | +++ | 456 | +++ | 457 | +++ | 458 | +++ | 459 | ++++ |
| 460 | ++++ | 461 | ++++ | 462 | +++ | 463 | +++ | 464 | +++ | | |

The compounds of the present invention show activities against LC3B, and some compounds have higher activities against LC3B. These compounds also have activities against other mammalian homologues of ATG8. Thus, these compounds can regulate LC3B and other mammalian homologues of ATG8 to treat autophagy related deceases.

It will be apparent to those skilled in the art that various modifications and variations can be made in the present invention without deviating from the essence or scope of the invention. Thus, it is intended that the present invention cover the modifications and variations of this invention provided they come within the scope of the appended claims and their equivalents.

What is claimed is:

1. A compound of general formula (IVd), or pharmaceutically acceptable salts thereof:

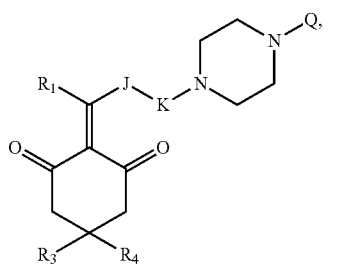
(IVa)

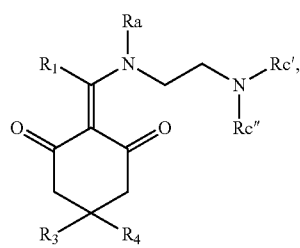
(IVb)

-continued

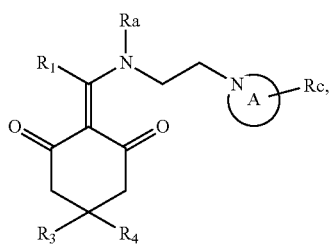
(IVc)

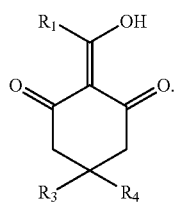
(IVd)

wherein:

R₁ is selected from the group consisting of H deuterium, and C1-6 hydroxyalkyl;

R₃ is selected from the group consisting of

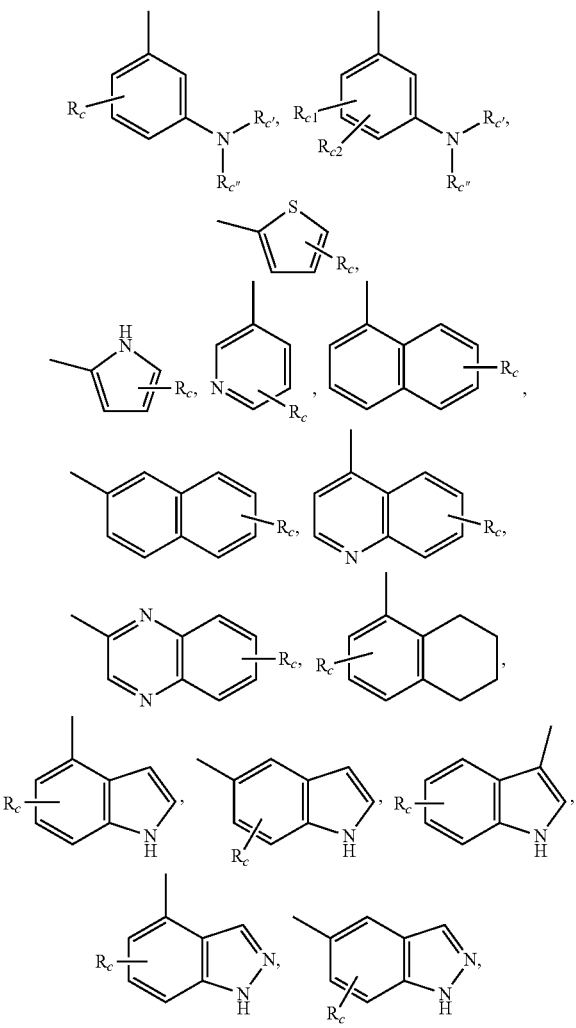

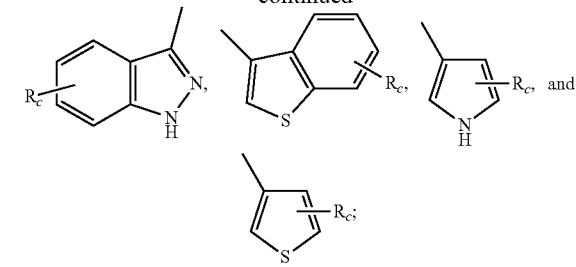

wherein, $R_c$, $R_{c1}$, $R_{c2}$, $R_c'$ and $R_c''$ are each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; and $R_a$ and $R_a'$ are each independently H or C1-6 alkyl;

or

R₃ is

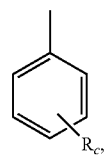

$R_c$ is -hydroxyl, amino group, NRaRa', halogen, cyano, nitro, carboxyl, formyl, amide group, ester group, C1-6 haloalkyl, C1-6 hydroxyalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl, or C1-6 alkyl 5-10 membered heteroaryl, and Ra and Ra' are each independently H or C1-6 alkyl;

or

R₃ is selected from the following groups:

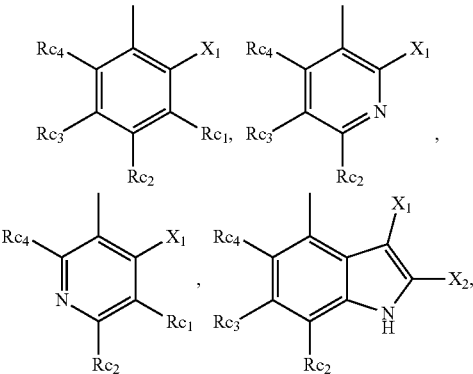

-continued

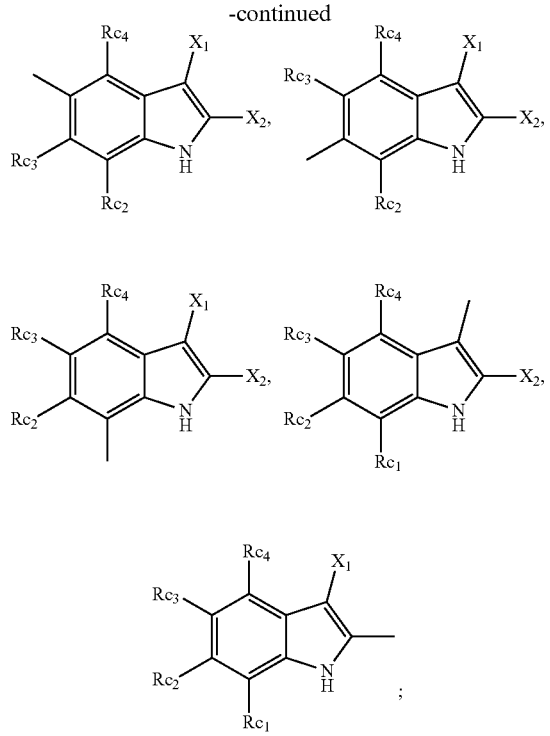

wherein, $X_1$ is F, Cl, Br, I or trifluoromethyl; $X_2$ is H, F, Cl, Br, or I;

$R_{c1}$, $R_{c2}$, $R_{c3}$, or $R_{c4}$ is each independently selected from the group consisting of H, hydroxyl, amino group, NRaRa', halogen, cyano, nitro, carboxyl, formyl, amide group, ester group, C1-6 haloalkyl, C1-6 hydroxyalkyl, C1-6 alkoxy, C1-6 alkoxyalkyl, C2-6 alkenyl, C2-6 alkynyl, C6-10 aryl, 5-10 membered heteroaryl, C3-10 cycloalkyl, 3-10 membered heterocycloalkyl, 3-7 membered heterocycloalkenyl, C1-6 alkyl C6-10 aryl, 5-10 membered heteroaryl C1-6 alkyl or C1-6 alkyl 5-10 membered heteroaryl; and $R_a$ and $R_a'$ are each independently H or C1-6 alkyl; and $R_4$ is H;

unsubstituted or substituted means that the group is unsubstituted or substituted by one or more substituents selected from the group consisting of hydroxyl, amino group, cyano, nitro, carboxyl, halogen, C1-6 alkyl, C1-6 haloalkyl or C1-6 hydroxyalkyl, or two adjacent substituents may be bonded to form a C6-10 aryl group, a C5-10 heteroaryl group, a C3-10 cycloalkyl group or a C3-10 heterocycloalkyl group.

2. A pharmaceutical composition, comprising the compounds or pharmaceutically acceptable salts thereof according to claim 1.

3. A compound selected from the group consisting of following compounds or pharmaceutically acceptable salts thereof:

| No. | Structures |
|-----|------------|
| 415 | 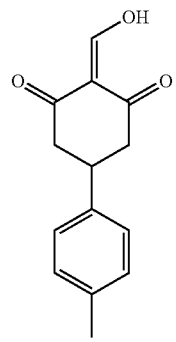 |
| 416 | 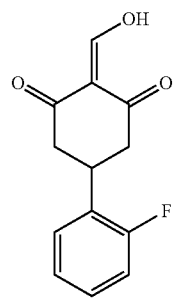 |

| No. | Structures |
|---|---|
| 417 | 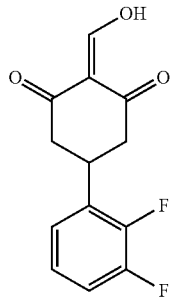 [SMILES: O=C1CC(c2cccc(F)c2F)CC(=O)C1=CO] |
| 418 | 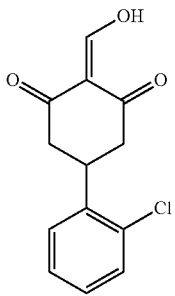 |
| 419 | 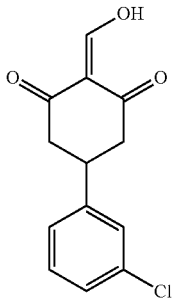 |
| 420 | 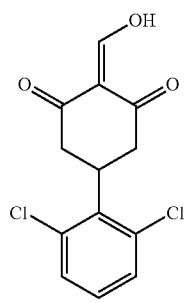 [SMILES: O=C1CC(c2c(Cl)cccc2Cl)CC(=O)C1=CO] |
| 421 | 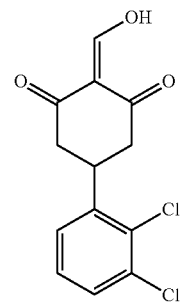 |

| No. | Structures |
|---|---|
| 422 | 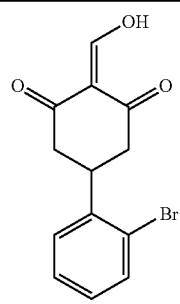 |
| 423 | 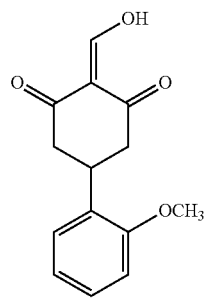 [SMILES: COc1ccccc1C1CC(=O)C(=CO)C(=O)C1] |
| 424 | 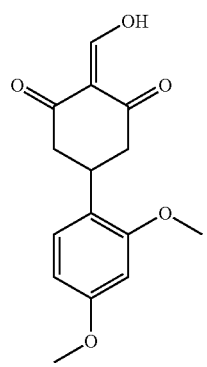 [SMILES: COc1ccc(C2CC(=O)C(=CO)C(=O)C2)c(OC)c1] |
| 425 | 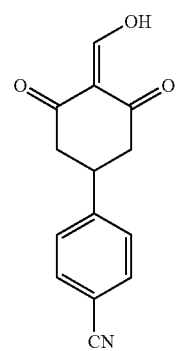 [SMILES: N#Cc1ccc(C2CC(=O)C(=CO)C(=O)C2)cc1] |
| 426 | 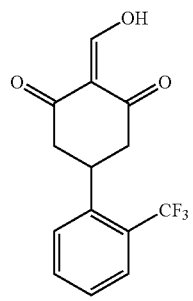 [SMILES: O=C1CC(c2ccccc2C(F)(F)F)CC(=O)C1=CO] |

-continued
| No. | Structures |
|---|---|
| 427 | 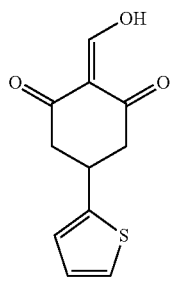 [SMILES: O=C1CC(c2cccs2)CC(=O)C1=CO] |
| 428 | 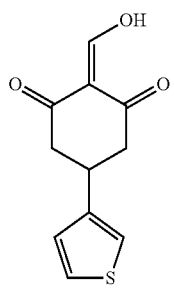 |
| 429 | 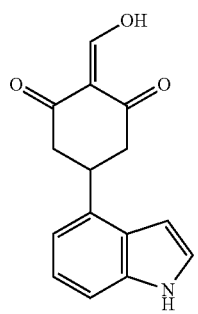 [SMILES: O=C1CC(c2cccc3[nH]ccc23)CC(=O)C1=CO] |
| 430 | 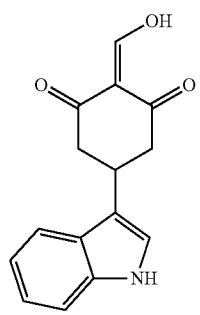 [SMILES: O=C1CC(c2c[nH]c3ccccc23)CC(=O)C1=CO] |
| 431 | 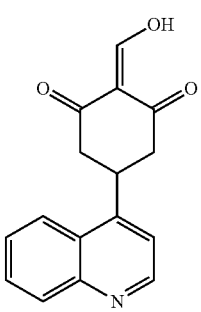 [SMILES: O=C1CC(c2ccnc3ccccc23)CC(=O)C1=CO] |

| No. | Structures |
|---|---|
| 432 | 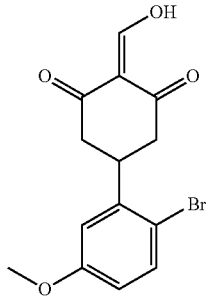 [SMILES: COc1ccc(Br)c(C2CC(=O)C(=CO)C(=O)C2)c1] |
| 433 | 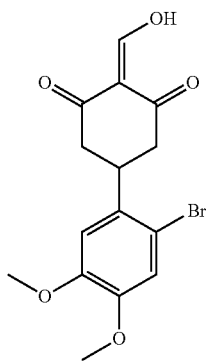 [SMILES: COc1cc(Br)c(C2CC(=O)C(=CO)C(=O)C2)cc1OC] |
| 434 | 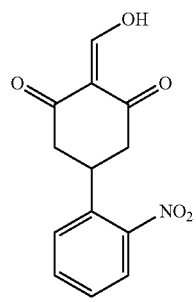 |
| 435 | 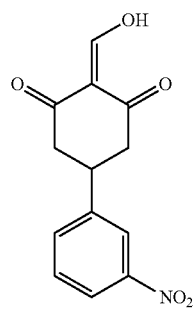 [SMILES: O=C1CC(c2cccc([N+](=O)[O-])c2)CC(=O)C1=CO] |

-continued
| No. | Structures |
|---|---|
| 436 | 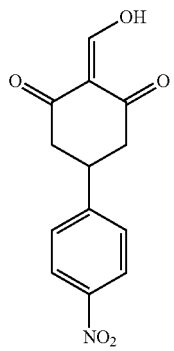 [SMILES: O=C1CC(c2ccc([N+](=O)[O-])cc2)CC(=O)C1=CO] |
| 437 | 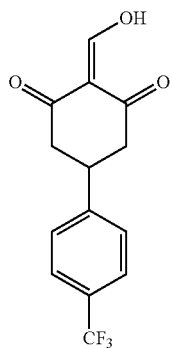 [SMILES: O=C1CC(c2ccc(C(F)(F)F)cc2)CC(=O)C1=CO] |
| 438 | 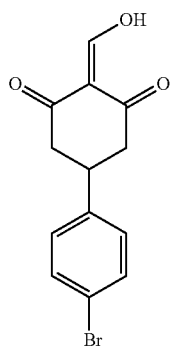 [SMILES: O=C1CC(c2ccc(Br)cc2)CC(=O)C1=CO] |
| 439 | 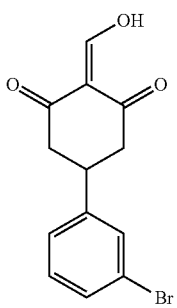 |

-continued
| No. | Structures |
|-----|------------|
| 440 | 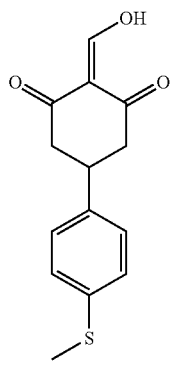 [SMILES: CSc1ccc(C2CC(=O)C(=CO)C(=O)C2)cc1] |
| 441 | 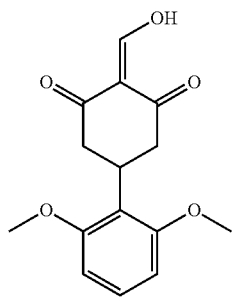 |
| 442 | 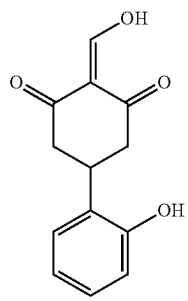 [SMILES: O=C1CC(c2ccccc2O)CC(=O)C1=CO] |
| 443 | 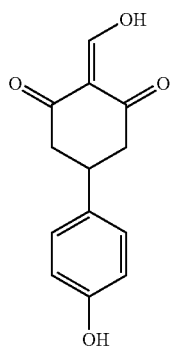 [SMILES: O=C1CC(c2ccc(O)cc2)CC(=O)C1=CO] |

| No. | Structures |
|---|---|
| 446 | 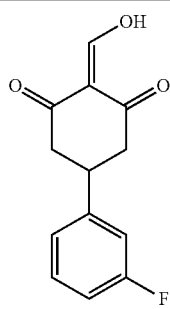 |
| 447 | 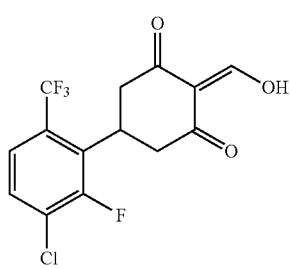 [SMILES: O=C1CC(c2c(C(F)(F)F)ccc(Cl)c2F)CC(=O)C1=CO] |
| 453 | 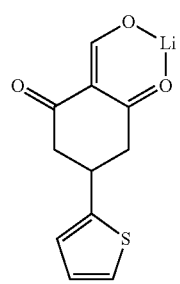 |
| 454 | 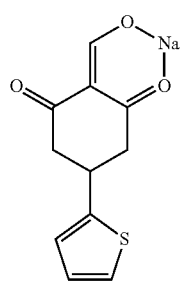 |
| 455 | 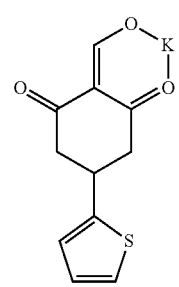 |

| No. | Structures |
|---|---|
| 456 | 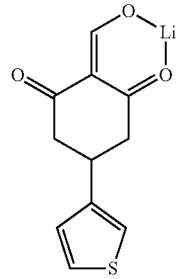 |
| 457 | 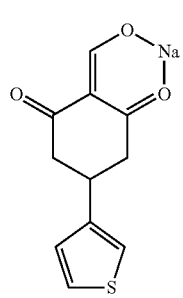 |
| 458 | 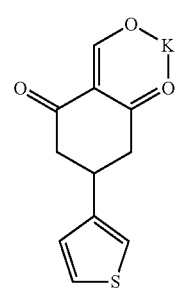 |
| 459 | 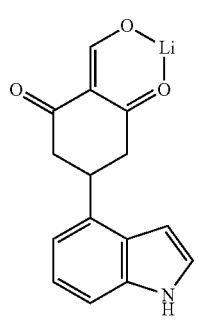 |
| 460 | 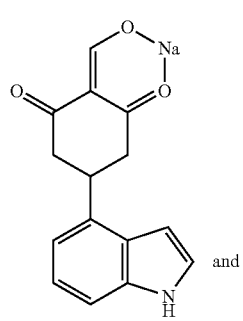 and |

| No. | Structures |
|---|---|
| 461 | 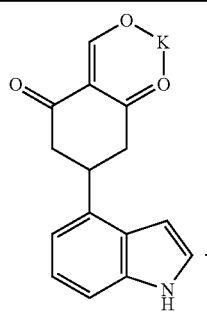 |
4. A compound selected from the group consisting of following compounds or pharmaceutically acceptable salts thereof:
| No. | Structures |
|---|---|
| 8 | 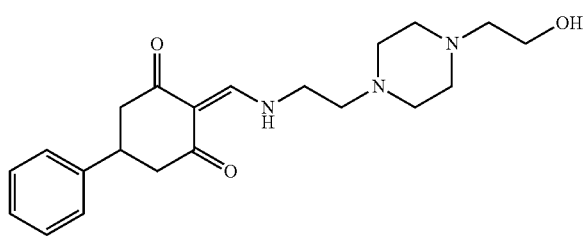 |
| 17 | 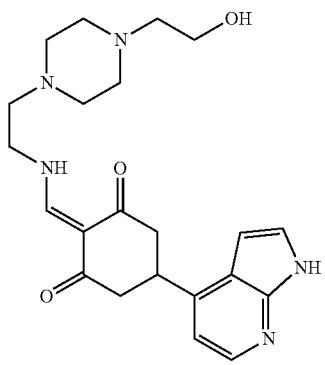 [SMILES: O=C1CC(c2ccnc3[nH]ccc23)CC(=O)C1=CNCCN1CCN(CCO)CC1] |
| 18 | 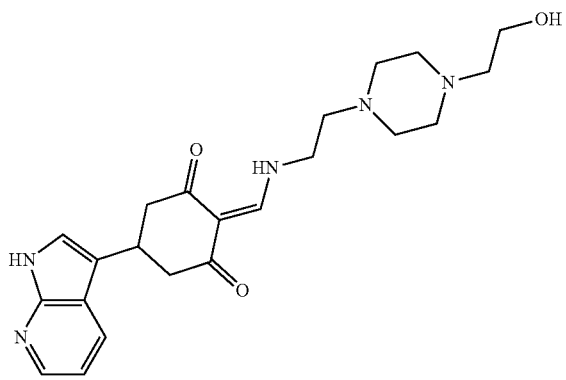 [SMILES: O=C1CC(c2c[nH]c3ncccc23)CC(=O)C1=CNCCN1CCN(CCO)CC1] |

| No. | Structures |
|---|---|
| 19 | 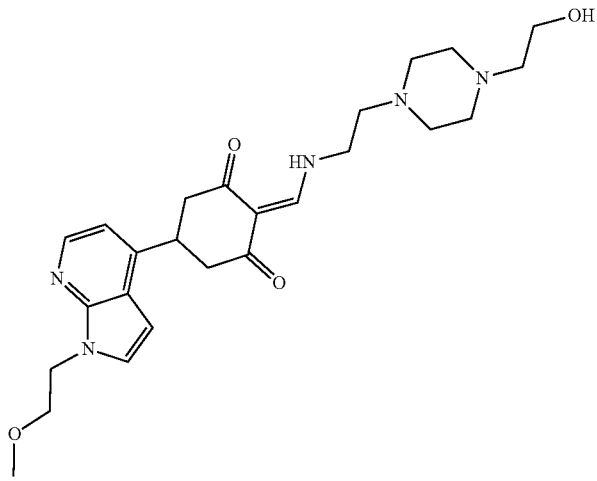 [SMILES: COCCn1ccc2c(C3CC(=O)C(=CNCCN4CCN(CCO)CC4)C(=O)C3)ccnc21] |
| 20 | 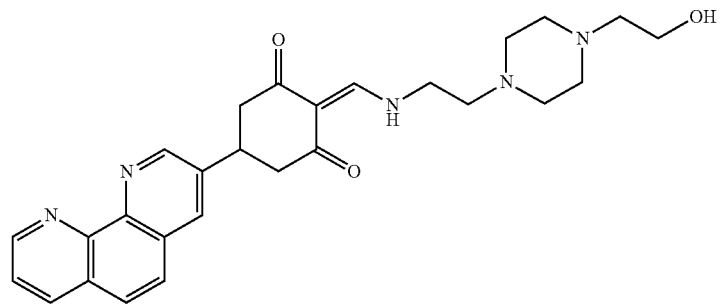 [SMILES: O=C1CC(c2cnc3c(ccc4cccnc43)c2)CC(=O)C1=CNCCN1CCN(CCO)CC1] |
| 21 | 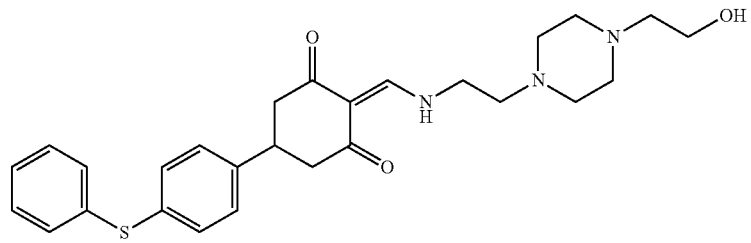 [SMILES: O=C1CC(c2ccc(Sc3ccccc3)cc2)CC(=O)C1=CNCCN1CCN(CCO)CC1] |
| 22 | 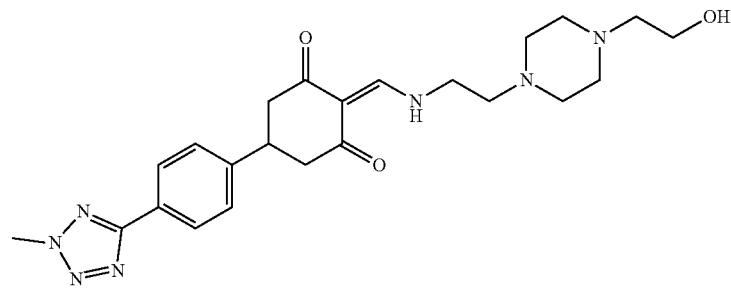 [SMILES: Cn1nnc(-c2ccc(C3CC(=O)C(=CNCCN4CCN(CCO)CC4)C(=O)C3)cc2)n1] |
| 23 | 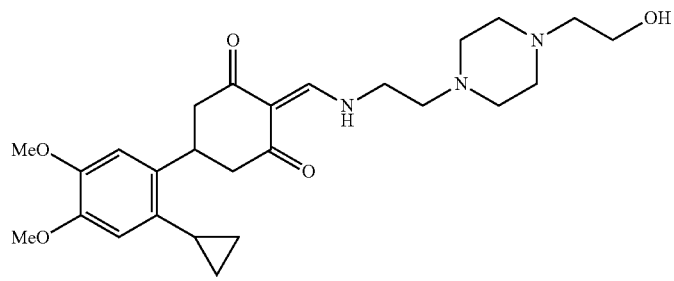 [SMILES: COc1cc(C2CC2)c(C2CC(=O)C(=CNCCN3CCN(CCO)CC3)C(=O)C2)cc1OC] |

| No. | Structures |
|---|---|
| 24 | 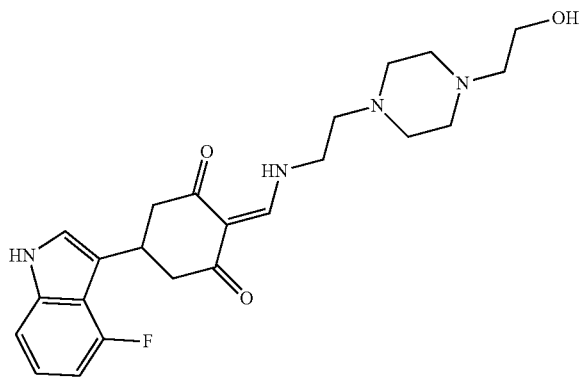 [SMILES: O=C1CC(c2c[nH]c3cccc(F)c23)CC(=O)C1=CNCCN1CCN(CCO)CC1] |
| 25 | 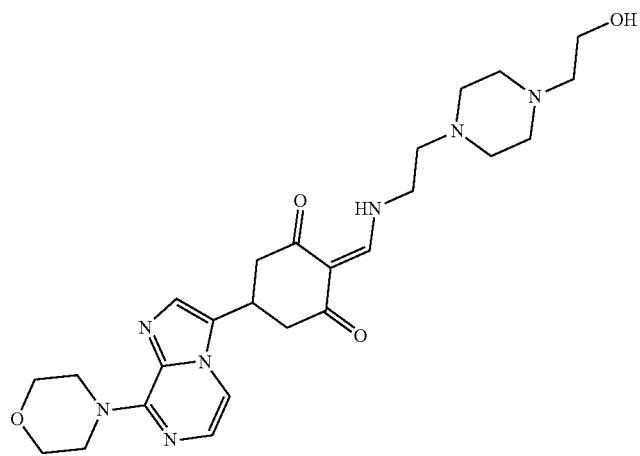 [SMILES: O=C1CC(c2cnc3c(N4CCOCC4)nccn23)CC(=O)C1=CNCCN1CCN(CCO)CC1] |
| 26 | 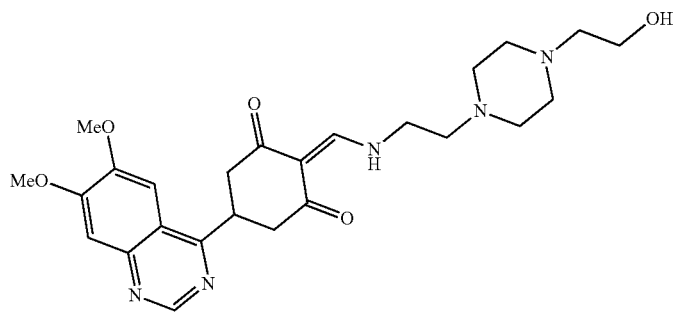 [SMILES: COc1cc2ncnc(C3CC(=O)C(=CNCCN4CCN(CCO)CC4)C(=O)C3)c2cc1OC] |
| 27 | 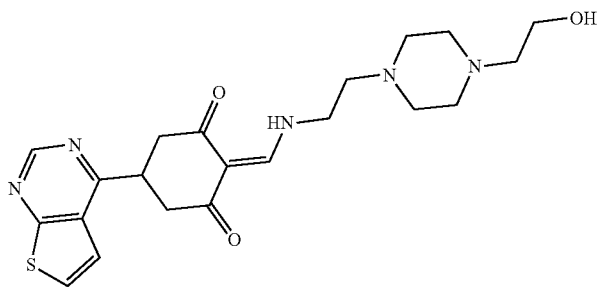 [SMILES: O=C1CC(c2ncnc3sccc23)CC(=O)C1=CNCCN1CCN(CCO)CC1] |

| No. | Structures |
|---|---|
| 28 | 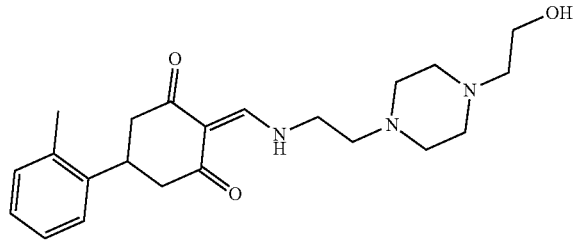 [SMILES: Cc1ccccc1C1CC(=O)C(=CNCCN2CCN(CCO)CC2)C(=O)C1] |
| 29 | 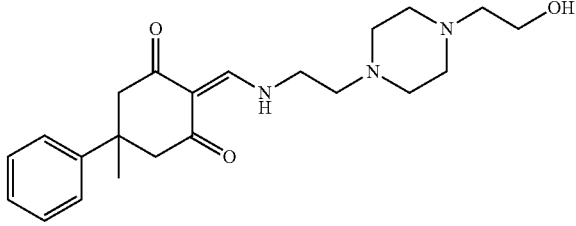 [SMILES: CC1(c2ccccc2)CC(=O)C(=CNCCN2CCN(CCO)CC2)C(=O)C1] |
| 33 | 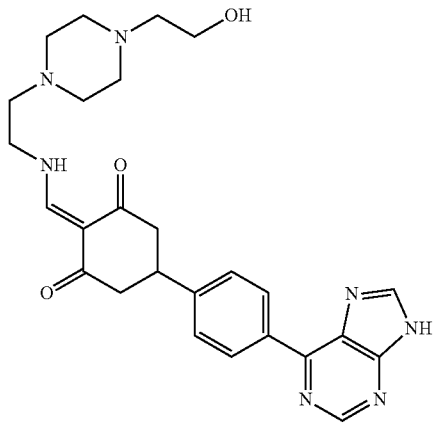 [SMILES: O=C1CC(c2ccc(-c3ncnc4[nH]cnc34)cc2)CC(=O)C1=CNCCN1CCN(CCO)CC1] |
| 34 | 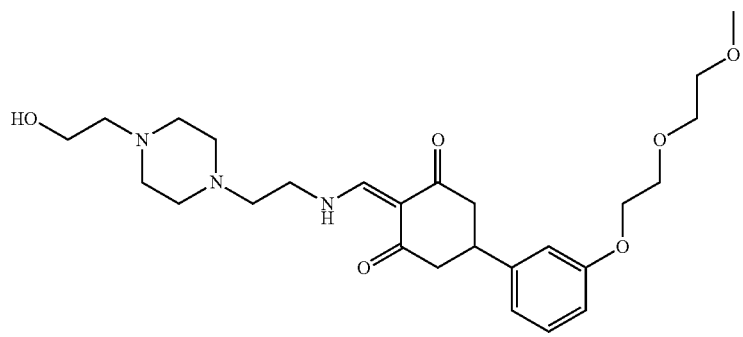 [SMILES: COCCOCCOc1cccc(C2CC(=O)C(=CNCCN3CCN(CCO)CC3)C(=O)C2)c1] |
| 35 | 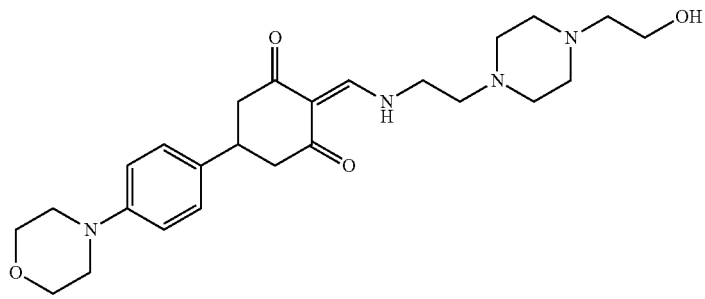 [SMILES: O=C1CC(c2ccc(N3CCOCC3)cc2)CC(=O)C1=CNCCN1CCN(CCO)CC1] |

-continued
| No. | Structures |
|---|---|
| 36 | 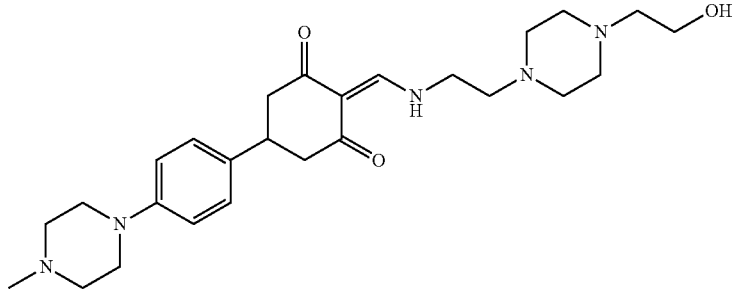 [SMILES: CN1CCN(c2ccc(C3CC(=O)C(=CNCCN4CCN(CCO)CC4)C(=O)C3)cc2)CC1] |
| 37 | 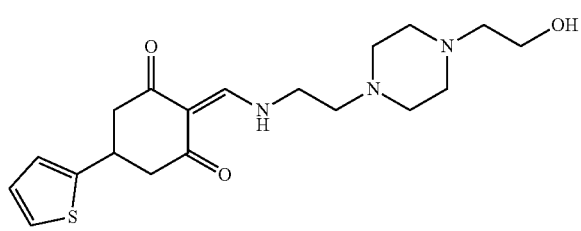 |
| 39 | 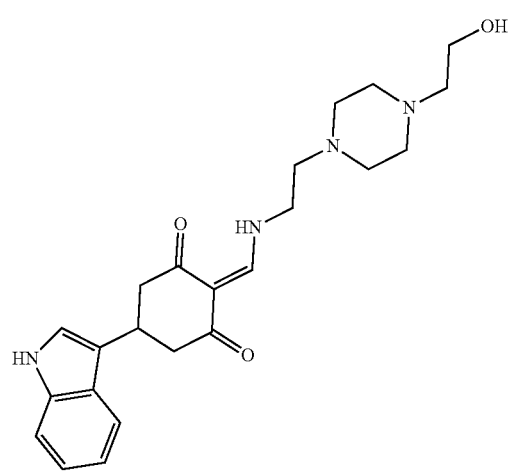 [SMILES: O=C1CC(c2c[nH]c3ccccc23)CC(=O)C1=CNCCN1CCN(CCO)CC1] |
| 40 | 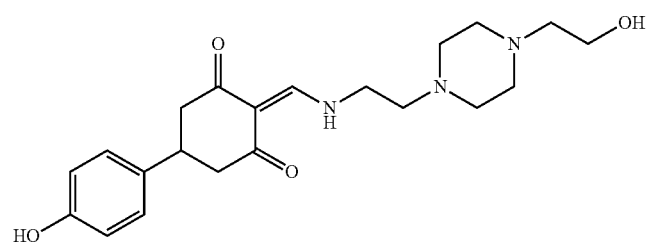 |
| 41 | 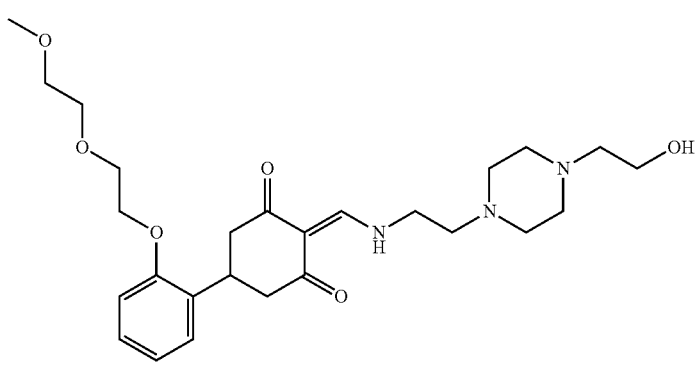 [SMILES: COCCOCCOc1ccccc1C1CC(=O)C(=CNCCN2CCN(CCO)CC2)C(=O)C1] |

-continued
| No. | Structures |
|---|---|
| 42 | 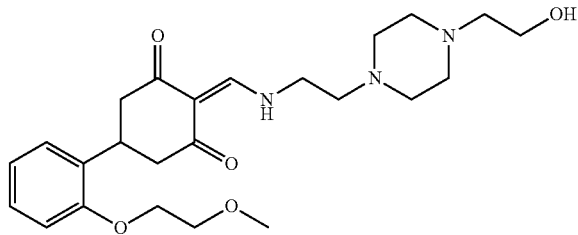 [SMILES: COCCOc1ccccc1C1CC(=O)C(=CNCCN2CCN(CCO)CC2)C(=O)C1] |
| 43 | 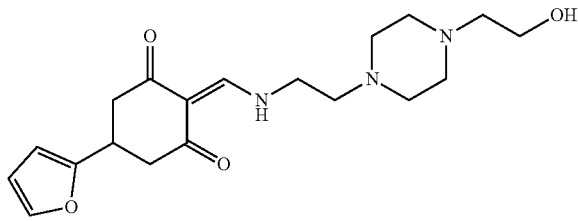 |
| 44 | 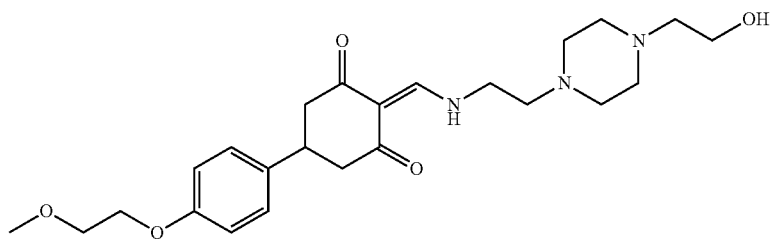 [SMILES: COCCOc1ccc(C2CC(=O)C(=CNCCN3CCN(CCO)CC3)C(=O)C2)cc1] |
| 45 | 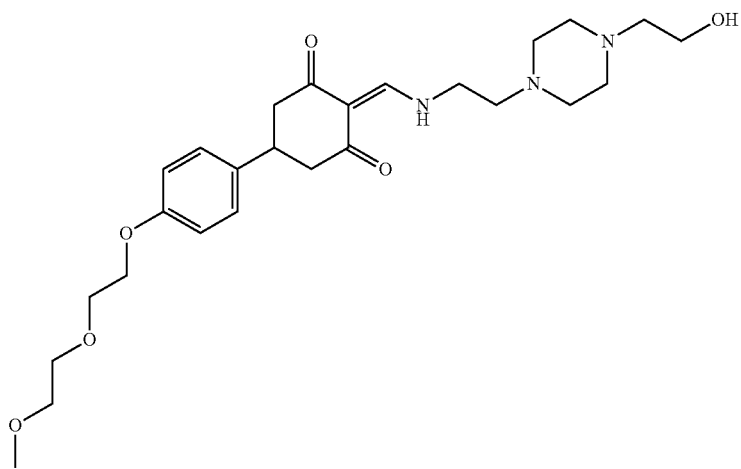 [SMILES: COCCOCCOc1ccc(C2CC(=O)C(=CNCCN3CCN(CCO)CC3)C(=O)C2)cc1] |
| 46 | 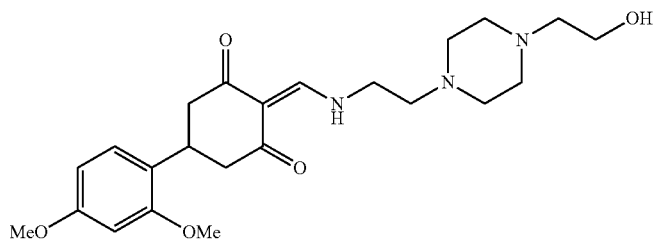 [SMILES: COc1ccc(C2CC(=O)C(=CNCCN3CCN(CCO)CC3)C(=O)C2)c(OC)c1] |

-continued
| No. | Structures |
|---|---|
| 48 | 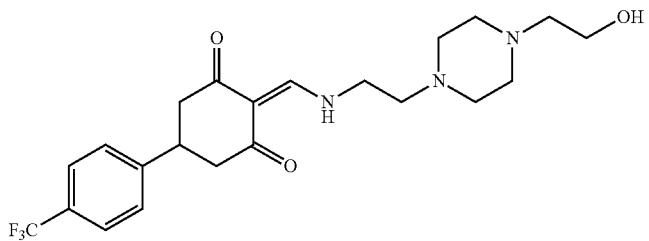 [SMILES: O=C1CC(c2ccc(C(F)(F)F)cc2)CC(=O)C1=CNCCN1CCN(CCO)CC1] |
| 49 | 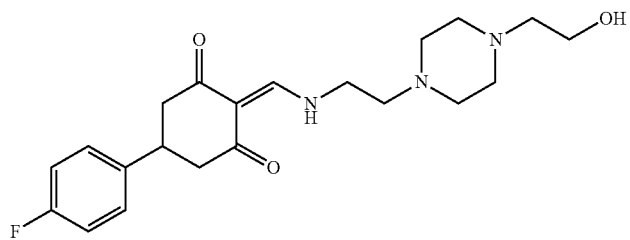 [SMILES: O=C1CC(c2ccc(F)cc2)CC(=O)C1=CNCCN1CCN(CCO)CC1] |
| 50 | 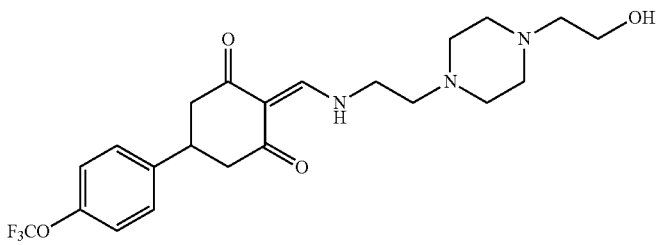 [SMILES: O=C1CC(c2ccc(OC(F)(F)F)cc2)CC(=O)C1=CNCCN1CCN(CCO)CC1] |
| 51 | 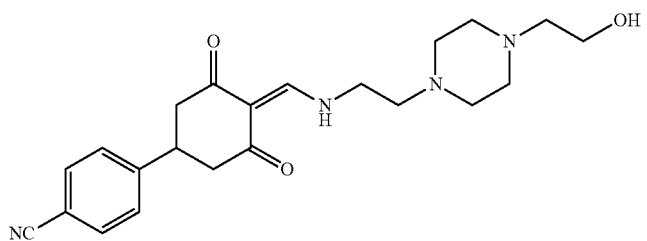 [SMILES: N#Cc1ccc(C2CC(=O)C(=CNCCN3CCN(CCO)CC3)C(=O)C2)cc1] |
| 52 | 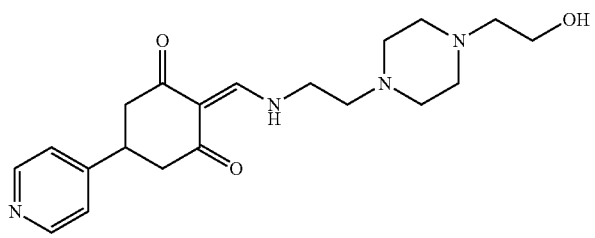 [SMILES: O=C1CC(c2ccncc2)CC(=O)C1=CNCCN1CCN(CCO)CC1] |
| 53 | 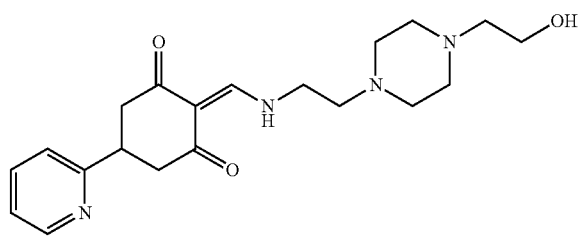 [SMILES: O=C1CC(c2ccccn2)CC(=O)C1=CNCCN1CCN(CCO)CC1] |

-continued
| No. | Structures |
|---|---|
| 54 | 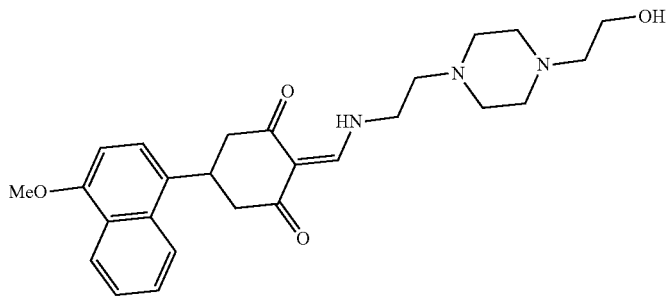 [SMILES: COc1ccc(C2CC(=O)C(=CNCCN3CCN(CCO)CC3)C(=O)C2)c2ccccc12] |
| 55 | 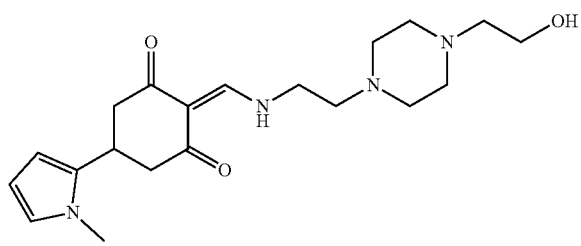 [SMILES: Cn1cccc1C1CC(=O)C(=CNCCN2CCN(CCO)CC2)C(=O)C1] |
| 56 | 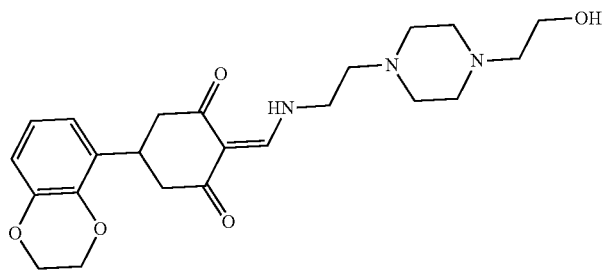 [SMILES: O=C1CC(c2cccc3c2OCCO3)CC(=O)C1=CNCCN1CCN(CCO)CC1] |
| 57 | 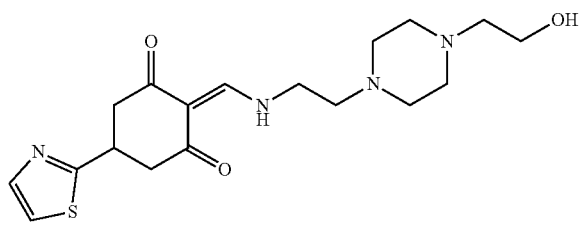 [SMILES: O=C1CC(c2nccs2)CC(=O)C1=CNCCN1CCN(CCO)CC1] |
| 58 | 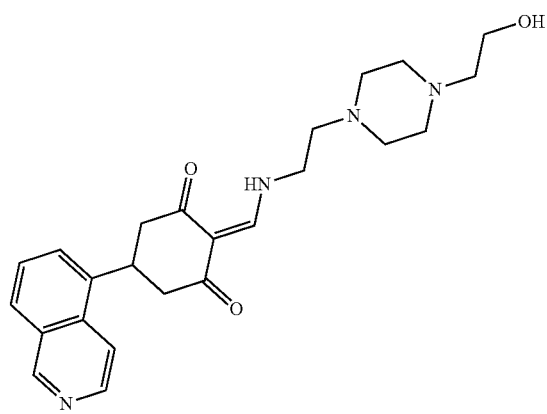 [SMILES: O=C1CC(c2cccc3cnccc23)CC(=O)C1=CNCCN1CCN(CCO)CC1] |

| No. | Structures |
|---|---|
| 59 | (5-(1H-imidazol-4-yl)-2-(((2-(4-(2-hydroxyethyl)piperazin-1-yl)ethyl)amino)methylene)cyclohexane-1,3-dione) |
| 61 | (5-(anthracen-9-yl)-2-(((2-(4-(2-hydroxyethyl)piperazin-1-yl)ethyl)amino)methylene)cyclohexane-1,3-dione) |
| 62 | (2-(((2-(4-(2-hydroxyethyl)piperazin-1-yl)ethyl)amino)methylene)-5-(quinolin-4-yl)cyclohexane-1,3-dione) |
| 65 | (2-(((2-(4-(2-hydroxyethyl)piperazin-1-yl)ethyl)amino)methylene)-5-(4-(methylsulfonyl)phenyl)cyclohexane-1,3-dione) |
| 66 | (5-(benzo[b]thiophen-3-yl)-2-(((2-(4-(2-hydroxyethyl)piperazin-1-yl)ethyl)amino)methylene)cyclohexane-1,3-dione) |

-continued
| No. | Structures |
|---|---|
| 68 | 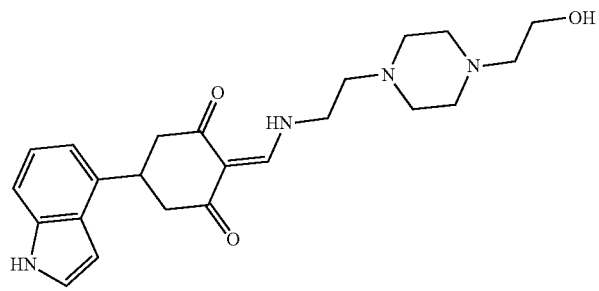 [SMILES: O=C1CC(c2cccc3[nH]ccc23)CC(=O)C1=CNCCN1CCN(CCO)CC1] |
| 72 | 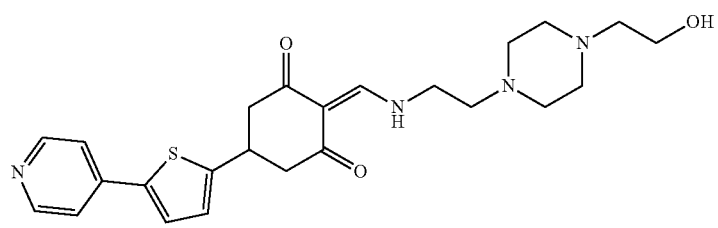 [SMILES: O=C1CC(c2ccc(-c3ccncc3)s2)CC(=O)C1=CNCCN1CCN(CCO)CC1] |
| 73 | 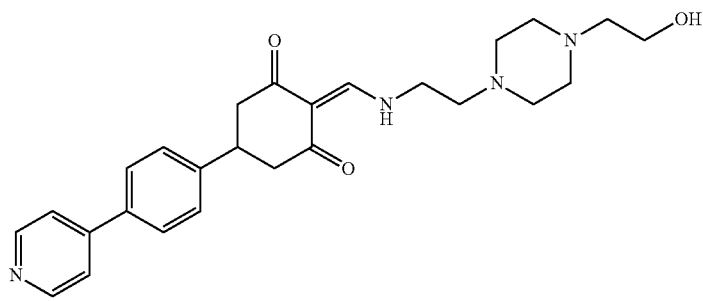 [SMILES: O=C1CC(c2ccc(-c3ccncc3)cc2)CC(=O)C1=CNCCN1CCN(CCO)CC1] |
| 74 | 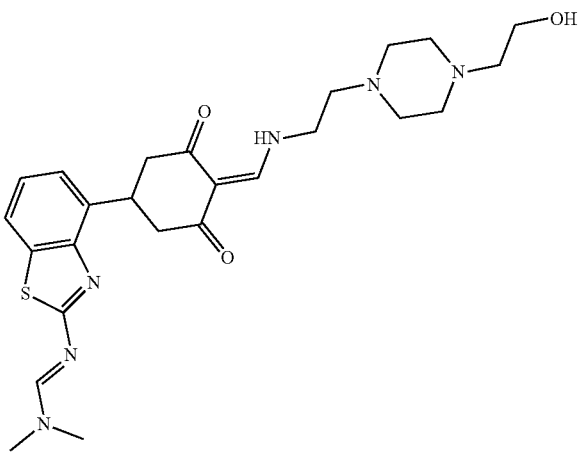 [SMILES: CN(C)/C=N/c1nc2c(C3CC(=O)C(=CNCCN4CCN(CCO)CC4)C(=O)C3)cccc2s1] |
| 75 | 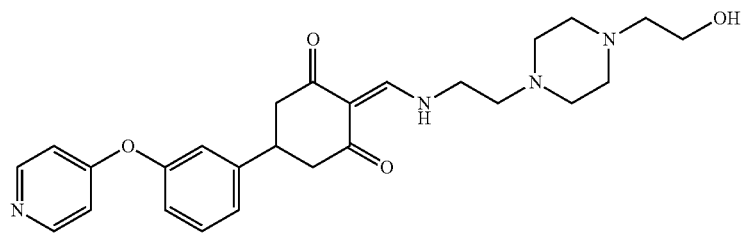 [SMILES: O=C1CC(c2cccc(Oc3ccncc3)c2)CC(=O)C1=CNCCN1CCN(CCO)CC1] |

-continued
| No. | Structures |
|---|---|
| 76 | 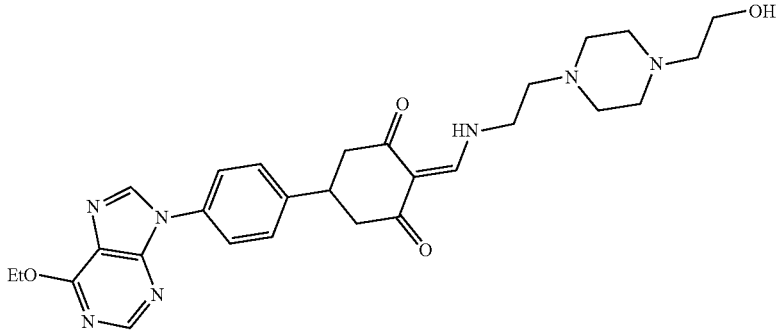 [SMILES: CCOc1ncnc2c1ncn2-c1ccc(C2CC(=O)C(=CNCCN3CCN(CCO)CC3)C(=O)C2)cc1] |
| 77 | 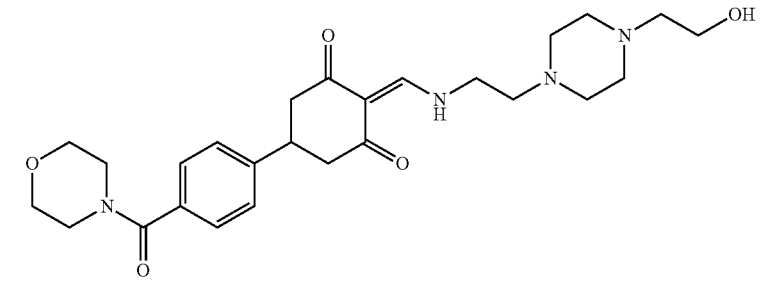 [SMILES: O=C1CC(c2ccc(C(=O)N3CCOCC3)cc2)CC(=O)C1=CNCCN1CCN(CCO)CC1] |
| 79 | 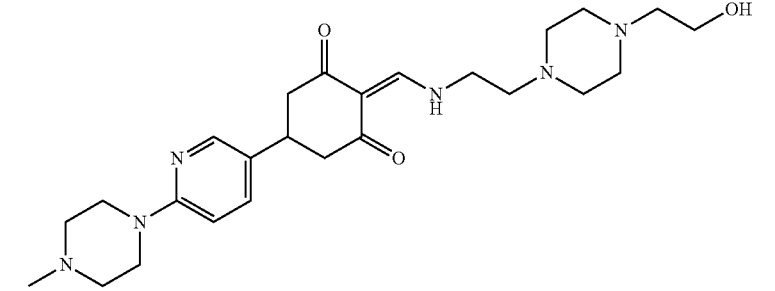 [SMILES: CN1CCN(c2ccc(C3CC(=O)C(=CNCCN4CCN(CCO)CC4)C(=O)C3)cn2)CC1] |
| 80 | 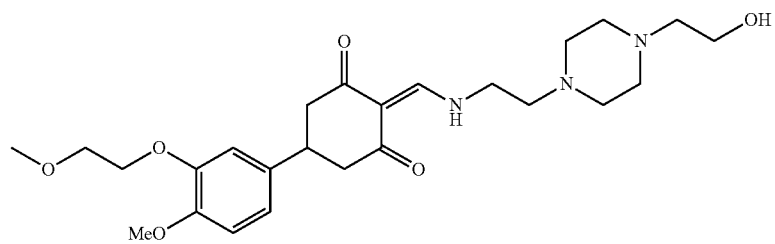 [SMILES: COCCOc1cc(C2CC(=O)C(=CNCCN3CCN(CCO)CC3)C(=O)C2)ccc1OC] |
| 81 | 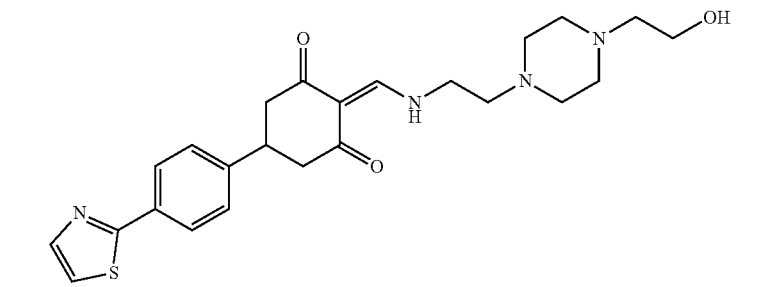 [SMILES: O=C1CC(c2ccc(-c3nccs3)cc2)CC(=O)C1=CNCCN1CCN(CCO)CC1] |

| No. | Structures |
|---|---|
| 82 | 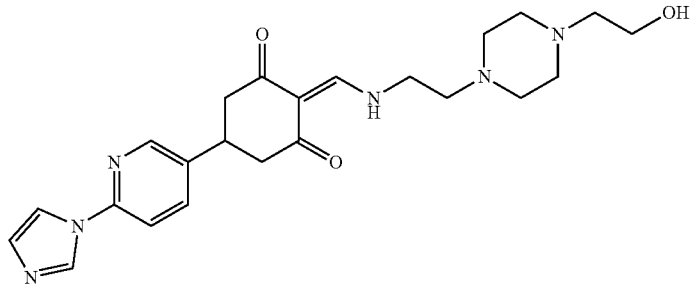 [SMILES: O=C1CC(c2ccc(-n3ccnc3)nc2)CC(=O)C1=CNCCN1CCN(CCO)CC1] |
| 83 | 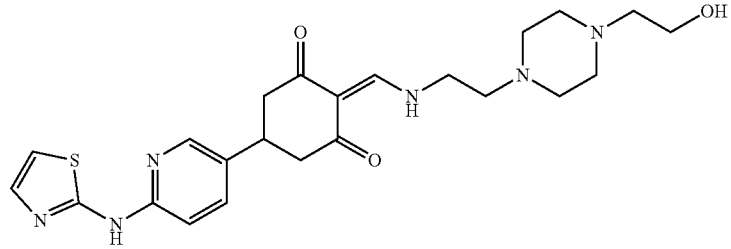 [SMILES: O=C1CC(c2ccc(Nc3nccs3)nc2)CC(=O)C1=CNCCN1CCN(CCO)CC1] |
| 84 | 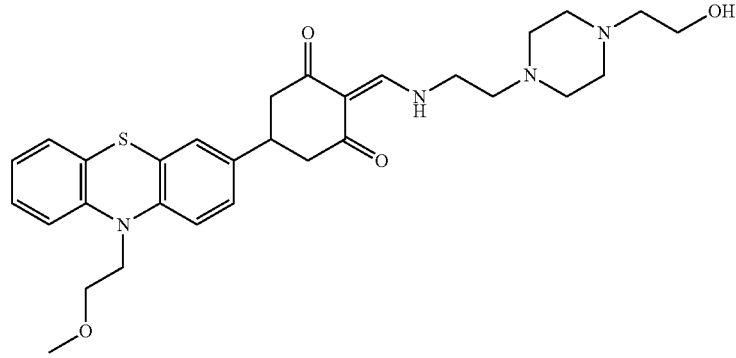 [SMILES: COCCN1c2ccccc2Sc2cc(C3CC(=O)C(=CNCCN4CCN(CCO)CC4)C(=O)C3)ccc21] |
| 85 | 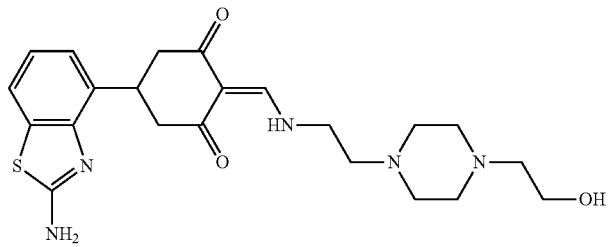 [SMILES: Nc1nc2c(C3CC(=O)C(=CNCCN4CCN(CCO)CC4)C(=O)C3)cccc2s1] |
| 87 | 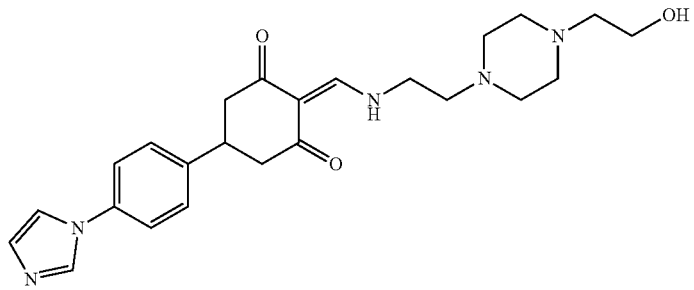 [SMILES: O=C1CC(c2ccc(-n3ccnc3)cc2)CC(=O)C1=CNCCN1CCN(CCO)CC1] |

-continued
| No. | Structures |
|---|---|
| 88 | 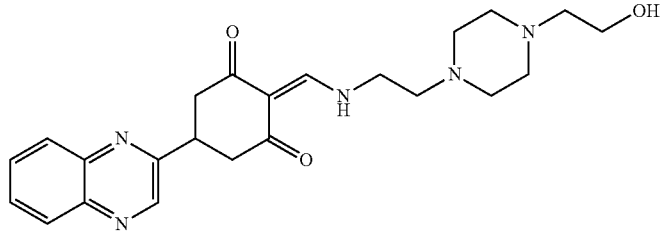 [SMILES: O=C1CC(c2cnc3ccccc3n2)CC(=O)C1=CNCCN1CCN(CCO)CC1] |
| 89 | 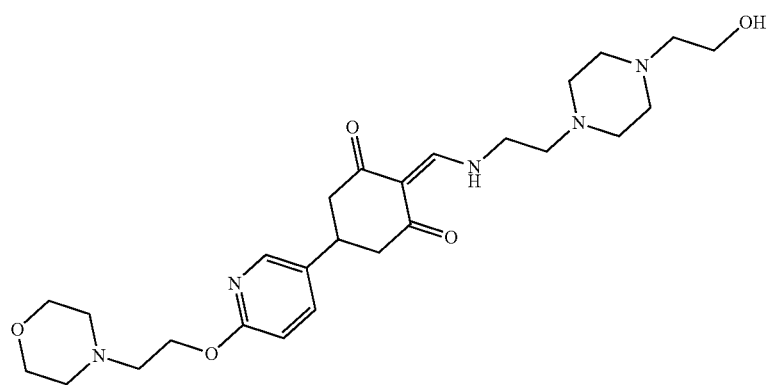 [SMILES: O=C1CC(c2ccc(OCCN3CCOCC3)nc2)CC(=O)C1=CNCCN1CCN(CCO)CC1] |
| 90 | 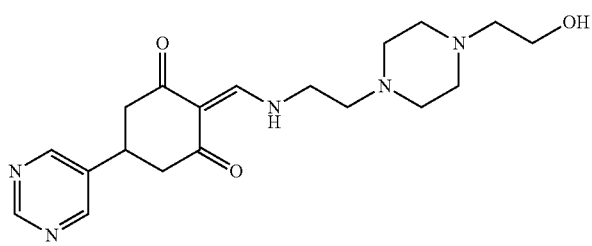 [SMILES: O=C1CC(c2cncnc2)CC(=O)C1=CNCCN1CCN(CCO)CC1] |
| 91 | 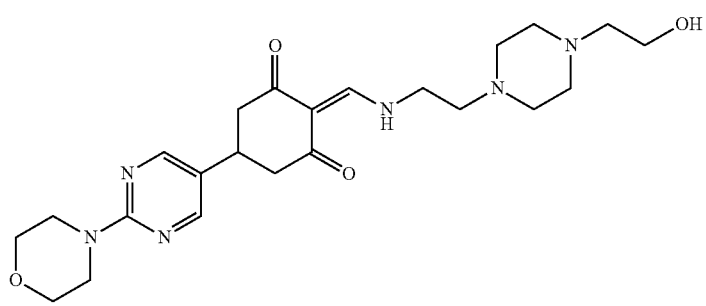 |
| 92 | 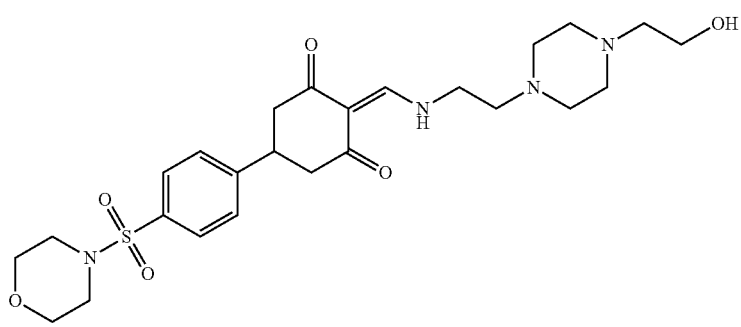 [SMILES: O=C1CC(c2ccc(S(=O)(=O)N3CCOCC3)cc2)CC(=O)C1=CNCCN1CCN(CCO)CC1] |

-continued

| No. | Structures |
|---|---|
| 93 | 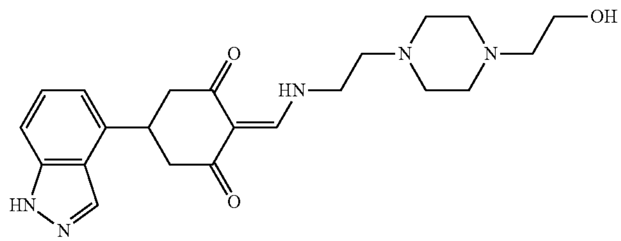 [SMILES: O=C1CC(c2cccc3[nH]ncc23)CC(=O)C1=CNCCN1CCN(CCO)CC1] |
| 108 | 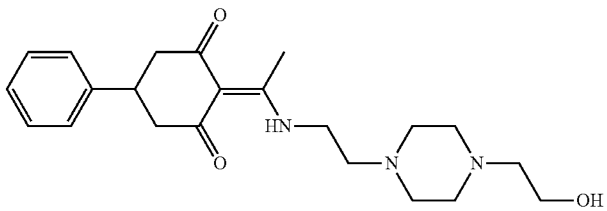 [SMILES: CC(NCCN1CCN(CCO)CC1)=C1C(=O)CC(c2ccccc2)CC1=O] |
| 109 | 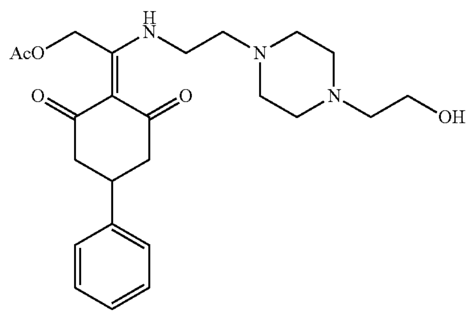 [SMILES: CC(=O)OCC(NCCN1CCN(CCO)CC1)=C1C(=O)CC(c2ccccc2)CC1=O] |
| 110 | 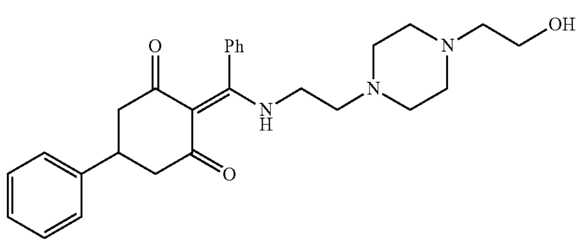 [SMILES: O=C1CC(c2ccccc2)CC(=O)C1=C(NCCN1CCN(CCO)CC1)c1ccccc1] |
| 139 | 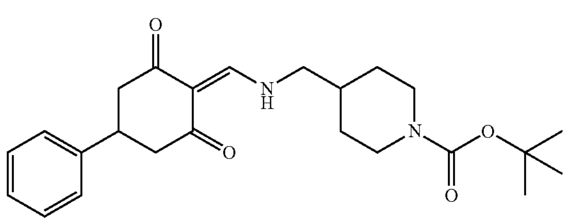 [SMILES: CC(C)(C)OC(=O)N1CCC(CNC=C2C(=O)CC(c3ccccc3)CC2=O)CC1] |
| 161 | 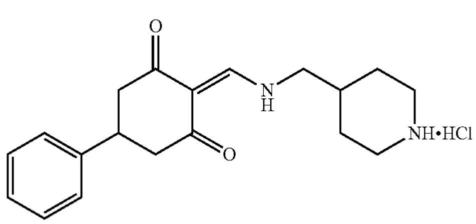 |

-continued

| No. | Structures |
|---|---|
| 171 | 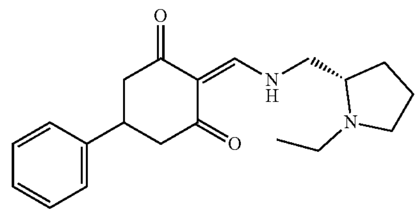 [SMILES: CCN1CCC[C@H]1CNC=C1C(=O)CC(c2ccccc2)CC1=O] |
| 184 | 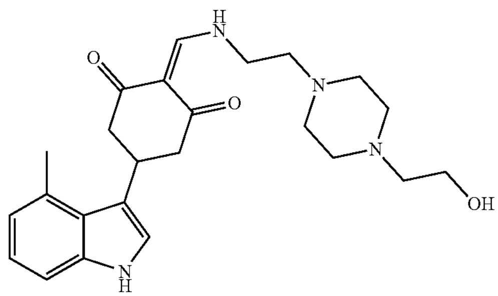 [SMILES: Cc1cccc2[nH]cc(C3CC(=O)C(=CNCCN4CCN(CCO)CC4)C(=O)C3)c12] |
| 185 | 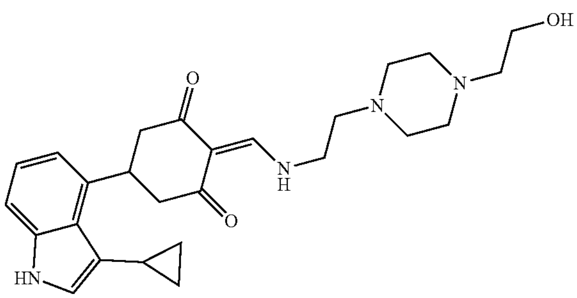 [SMILES: O=C1CC(c2cccc3[nH]cc(C4CC4)c23)CC(=O)C1=CNCCN1CCN(CCO)CC1] |
| 186 | 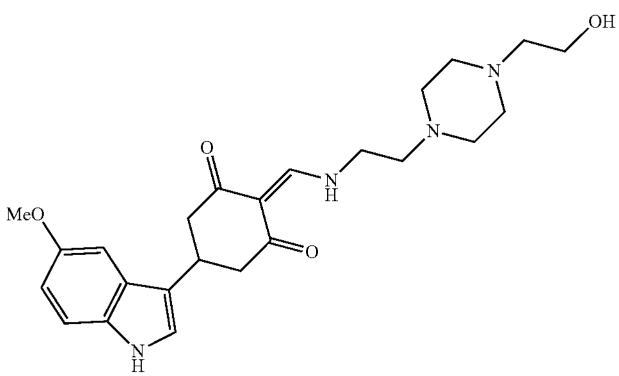 [SMILES: COc1ccc2[nH]cc(C3CC(=O)C(=CNCCN4CCN(CCO)CC4)C(=O)C3)c2c1] |
| 187 | 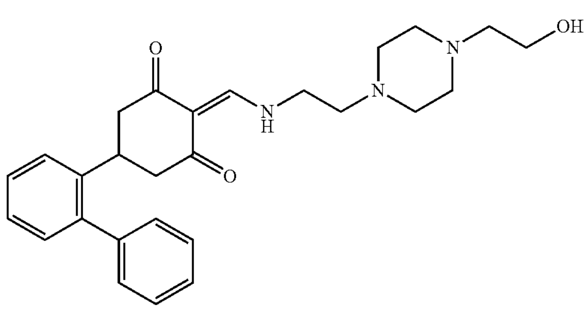 [SMILES: O=C1CC(c2ccccc2-c2ccccc2)CC(=O)C1=CNCCN1CCN(CCO)CC1] |

-continued
| No. | Structures |
|---|---|
| 188 | 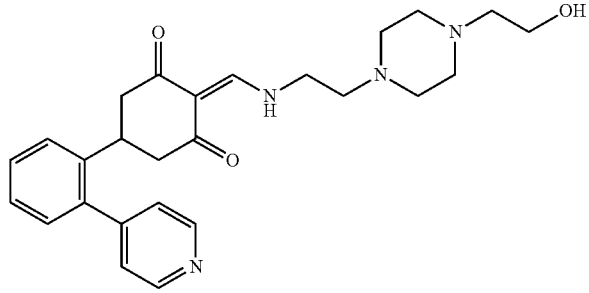 [SMILES: O=C1CC(c2ccccc2-c2ccncc2)CC(=O)C1=CNCCN1CCN(CCO)CC1] |
| 189 | 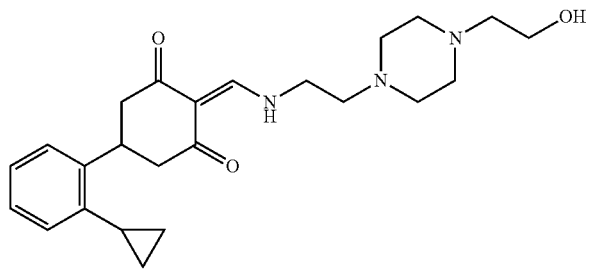 [SMILES: O=C1CC(c2ccccc2C2CC2)CC(=O)C1=CNCCN1CCN(CCO)CC1] |
| 211 | 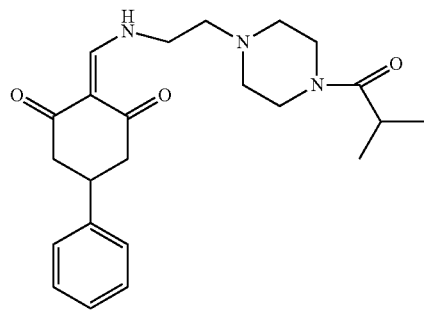 |
| 212 | 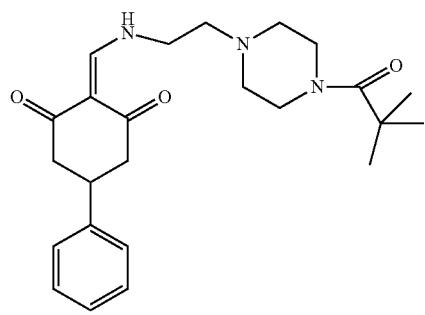 [SMILES: CC(C)(C)C(=O)N1CCN(CCNC=C2C(=O)CC(c3ccccc3)CC2=O)CC1] |
| 213 | 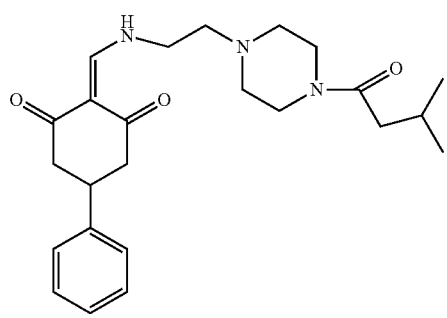 [SMILES: CC(C)CC(=O)N1CCN(CCNC=C2C(=O)CC(c3ccccc3)CC2=O)CC1] |

-continued

| No. | Structures |
|---|---|
| 214 | 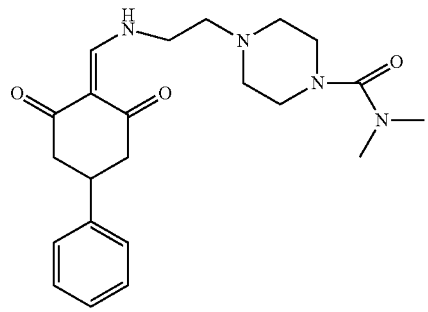 |
| 215 | 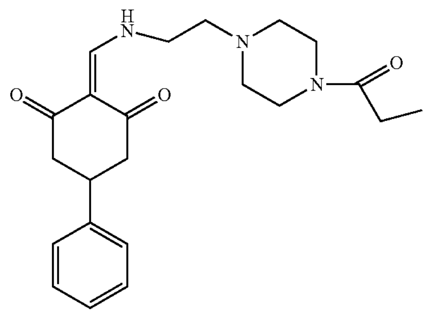 [SMILES: CCC(=O)N1CCN(CCNC=C2C(=O)CC(c3ccccc3)CC2=O)CC1] |
| 216 | 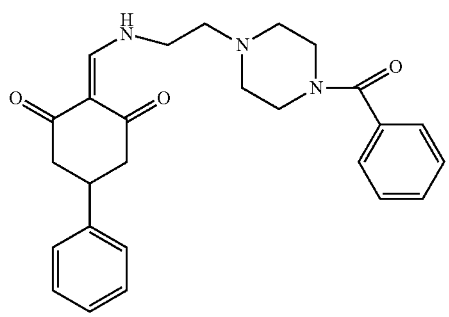 [SMILES: O=C1CC(c2ccccc2)CC(=O)C1=CNCCN1CCN(C(=O)c2ccccc2)CC1] |
| 217 | 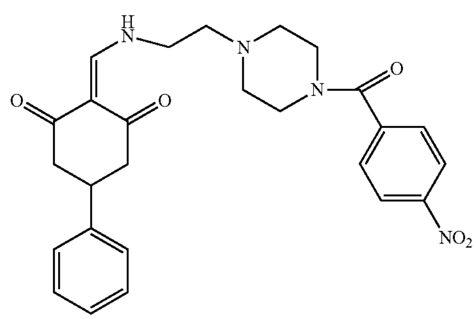 [SMILES: O=C1CC(c2ccccc2)CC(=O)C1=CNCCN1CCN(C(=O)c2ccc([N+](=O)[O-])cc2)CC1] |
| 218 | 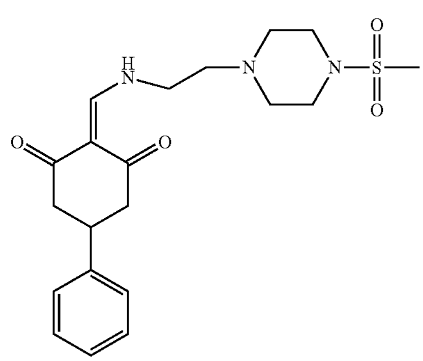 [SMILES: CS(=O)(=O)N1CCN(CCNC=C2C(=O)CC(c3ccccc3)CC2=O)CC1] |

| No. | Structures |
|---|---|
| 219 | 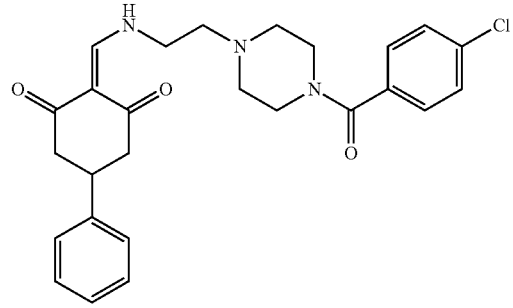 [SMILES: O=C1CC(c2ccccc2)CC(=O)C1=CNCCN1CCN(C(=O)c2ccc(Cl)cc2)CC1] |
| 220 | 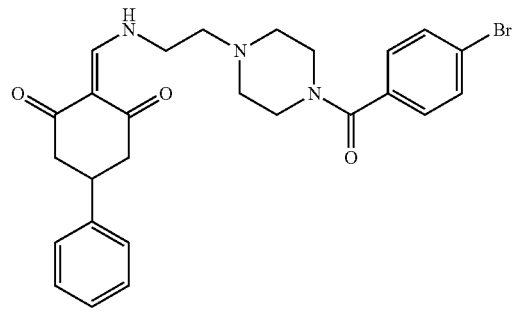 [SMILES: O=C1CC(c2ccccc2)CC(=O)C1=CNCCN1CCN(C(=O)c2ccc(Br)cc2)CC1] |
| 222 | 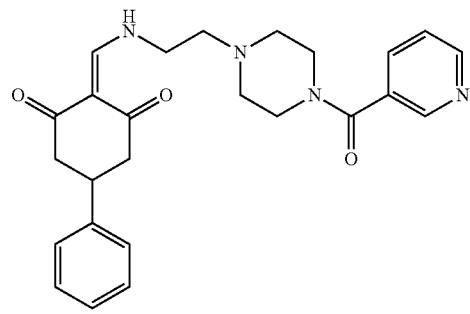 [SMILES: O=C1CC(c2ccccc2)CC(=O)C1=CNCCN1CCN(C(=O)c2cccnc2)CC1] |
| 223 | 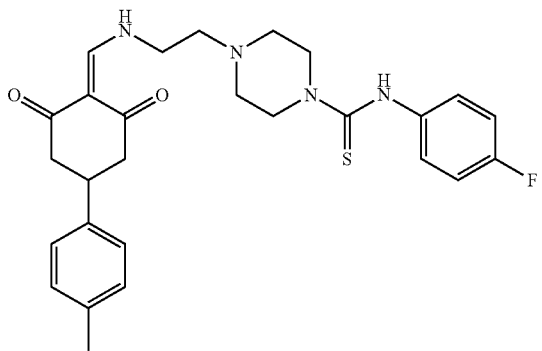 [SMILES: Cc1ccc(C2CC(=O)C(=CNCCN3CCN(C(=S)Nc4ccc(F)cc4)CC3)C(=O)C2)cc1] |

| No. | Structures |
|---|---|
| 224 | 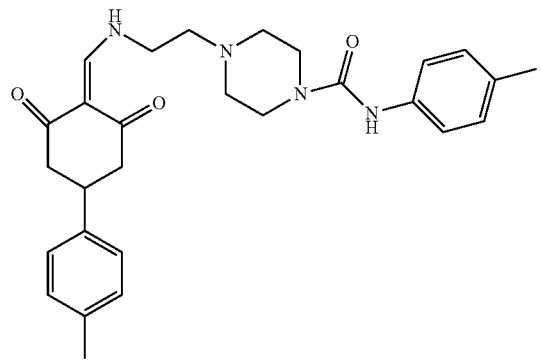 [SMILES: Cc1ccc(NC(=O)N2CCN(CCNC=C3C(=O)CC(c4ccc(C)cc4)CC3=O)CC2)cc1] |
| 225 | 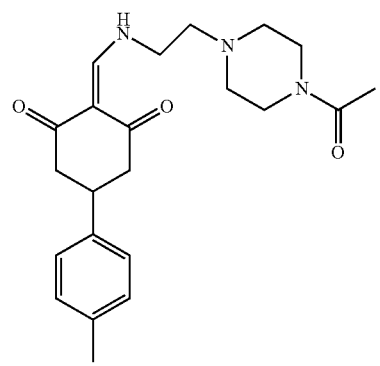 [SMILES: CC(=O)N1CCN(CCNC=C2C(=O)CC(c3ccc(C)cc3)CC2=O)CC1] |
| 226 | 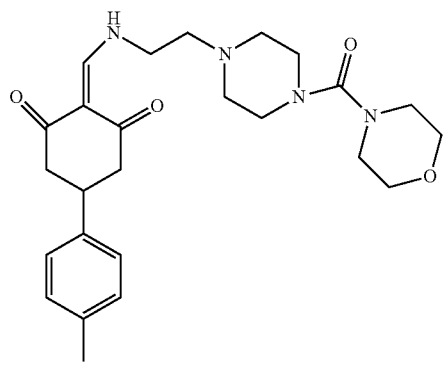 [SMILES: Cc1ccc(C2CC(=O)C(=CNCCN3CCN(C(=O)N4CCOCC4)CC3)C(=O)C2)cc1] |
| 227 | 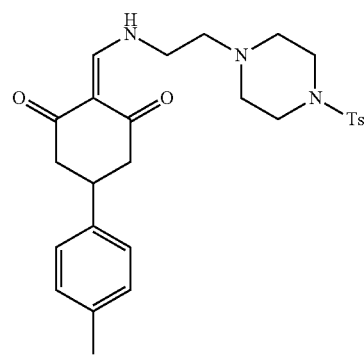 [SMILES: Cc1ccc(C2CC(=O)C(=CNCCN3CCN(S(=O)(=O)c4ccc(C)cc4)CC3)C(=O)C2)cc1] |

| No. | Structures |
|---|---|
| 228 | 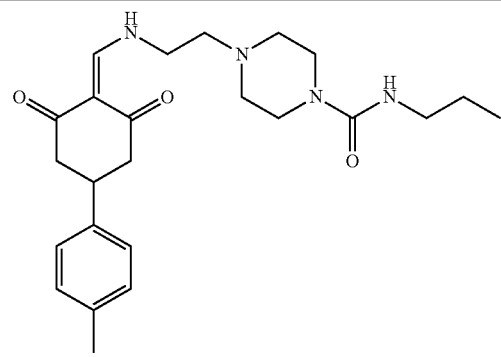 [SMILES: CCCNC(=O)N1CCN(CCNC=C2C(=O)CC(c3ccc(C)cc3)CC2=O)CC1] |
| 229 | 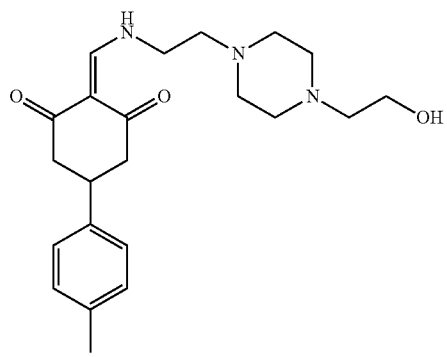 [SMILES: Cc1ccc(C2CC(=O)C(=CNCCN3CCN(CCO)CC3)C(=O)C2)cc1] |
| 230 | 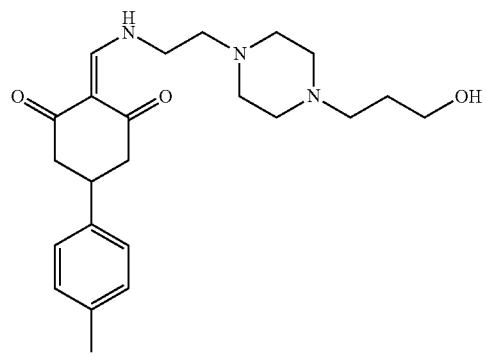 [SMILES: Cc1ccc(C2CC(=O)C(=CNCCN3CCN(CCCO)CC3)C(=O)C2)cc1] |
| 231 | 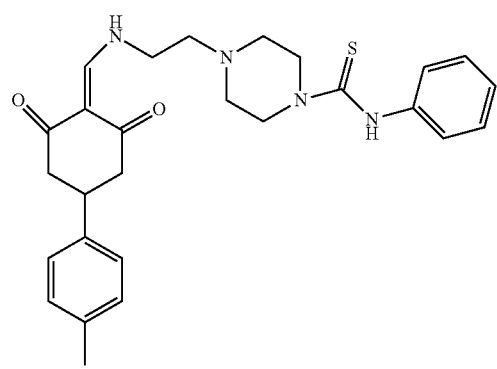 [SMILES: Cc1ccc(C2CC(=O)C(=CNCCN3CCN(C(=S)Nc4ccccc4)CC3)C(=O)C2)cc1] |

-continued
| No. | Structures |
|---|---|
| 232 | 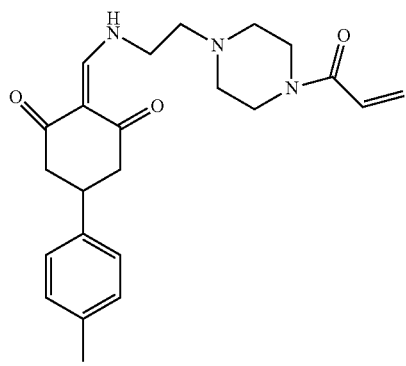 [SMILES: C=CC(=O)N1CCN(CCNC=C2C(=O)CC(c3ccc(C)cc3)CC2=O)CC1] |
| 233 | 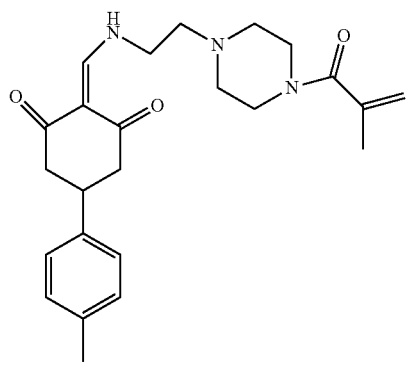 [SMILES: C=C(C)C(=O)N1CCN(CCNC=C2C(=O)CC(c3ccc(C)cc3)CC2=O)CC1] |
| 236 | 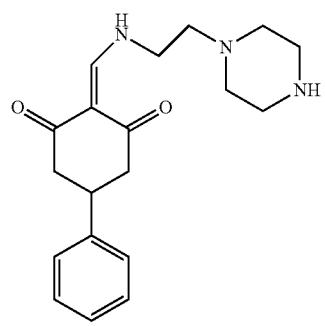 [SMILES: O=C1CC(c2ccccc2)CC(=O)C1=CNCCN1CCNCC1] |
| 237 | 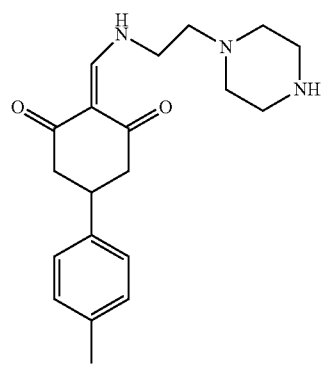 [SMILES: Cc1ccc(C2CC(=O)C(=CNCCN3CCNCC3)C(=O)C2)cc1] |

| No. | Structures |
|-----|------------|
| 238 | 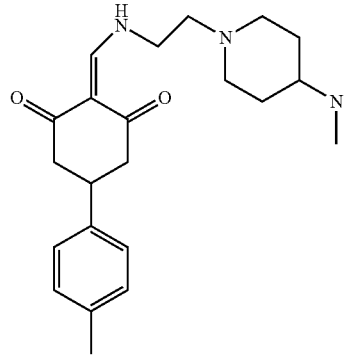 [SMILES: CNC1CCN(CCNC=C2C(=O)CC(c3ccc(C)cc3)CC2=O)CC1] |
| 239 | 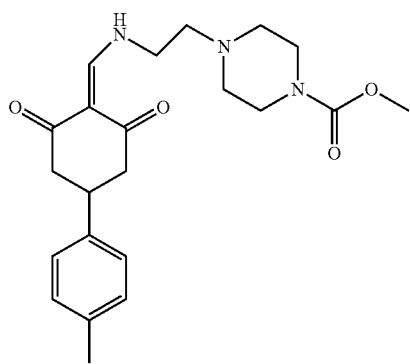 [SMILES: COC(=O)N1CCN(CCNC=C2C(=O)CC(c3ccc(C)cc3)CC2=O)CC1] |
| 240 | 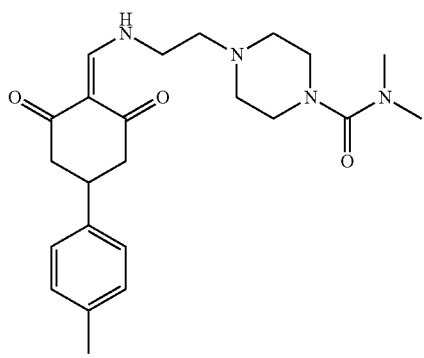 [SMILES: Cc1ccc(C2CC(=O)C(=CNCCN3CCN(C(=O)N(C)C)CC3)C(=O)C2)cc1] |
| 245 | 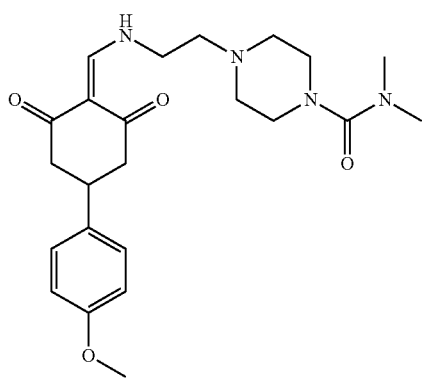 [SMILES: COc1ccc(C2CC(=O)C(=CNCCN3CCN(C(=O)N(C)C)CC3)C(=O)C2)cc1] |

| No. | Structures |
|---|---|
| 246 | 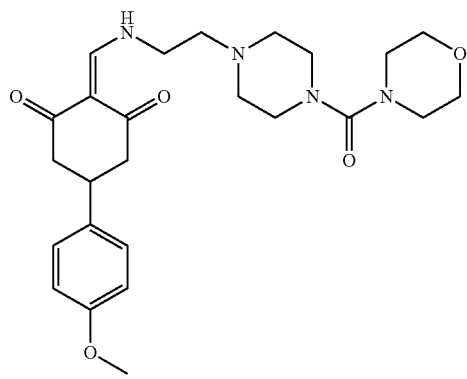 [SMILES: COc1ccc(C2CC(=O)C(=CNCCN3CCN(C(=O)N4CCOCC4)CC3)C(=O)C2)cc1] |
| 248 | 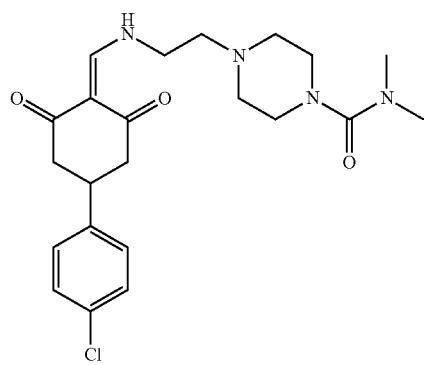 [SMILES: CN(C)C(=O)N1CCN(CCNC=C2C(=O)CC(c3ccc(Cl)cc3)CC2=O)CC1] |
| 249 | 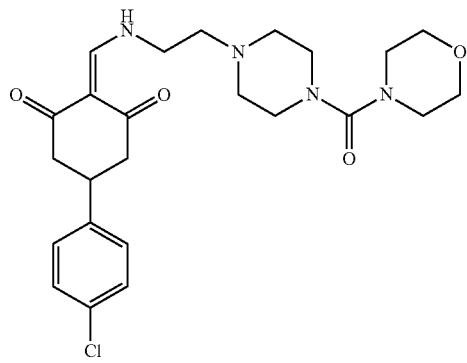 [SMILES: O=C1CC(c2ccc(Cl)cc2)CC(=O)C1=CNCCN1CCN(C(=O)N2CCOCC2)CC1] |
| 258 | 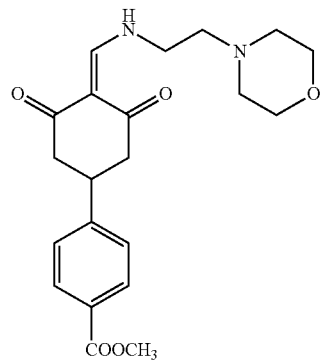 |

| No. | Structures |
|---|---|
| 260 | 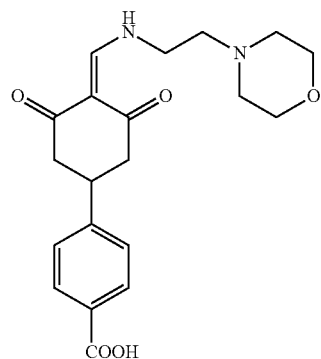 |
| 263 | 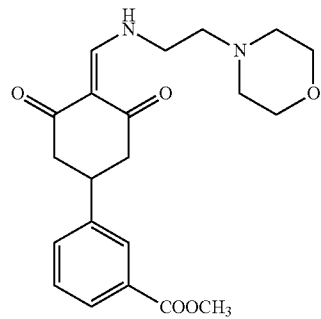 |
| 315 | 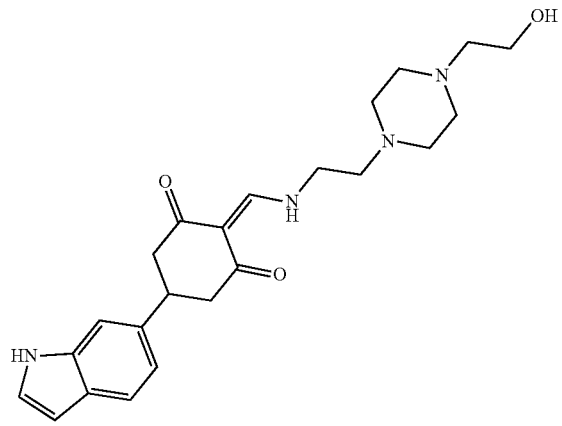 [SMILES: O=C1CC(c2ccc3cc[nH]c3c2)CC(=O)C1=CNCCN1CCN(CCO)CC1] |
| 320 | 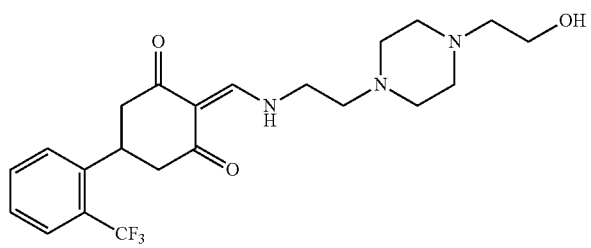 [SMILES: O=C1CC(c2ccccc2C(F)(F)F)CC(=O)C1=CNCCN1CCN(CCO)CC1] |

-continued
| No. | Structures |
|---|---|
| 322 | 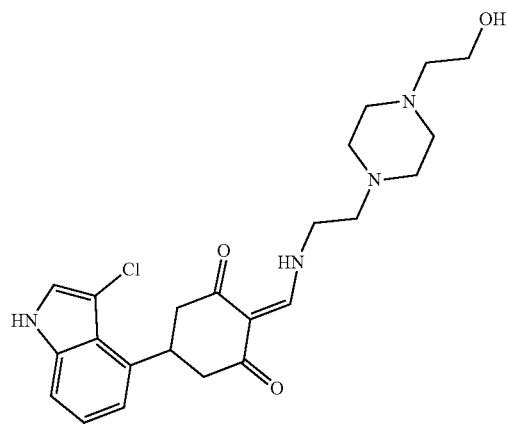 [SMILES: O=C1CC(c2cccc3[nH]cc(Cl)c23)CC(=O)C1=CNCCN1CCN(CCO)CC1] |
| 329 | 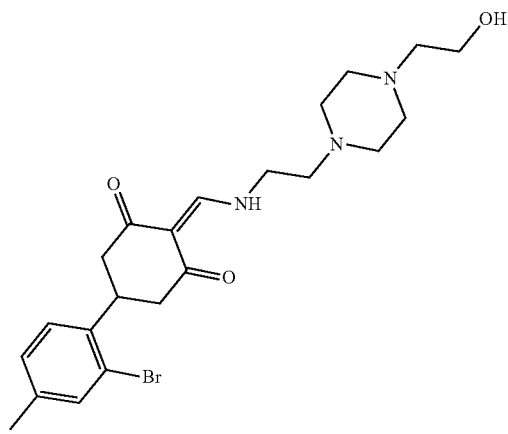 [SMILES: Cc1ccc(C2CC(=O)C(=CNCCN3CCN(CCO)CC3)C(=O)C2)c(Br)c1] |
| 332 | 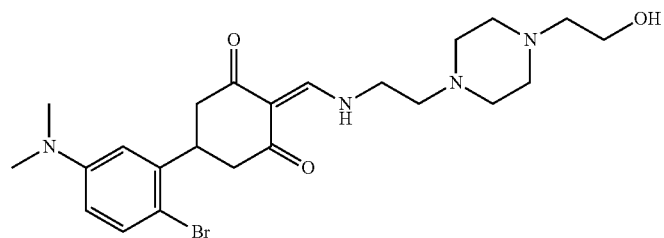 [SMILES: CN(C)c1ccc(Br)c(C2CC(=O)C(=CNCCN3CCN(CCO)CC3)C(=O)C2)c1] |
| 353 | 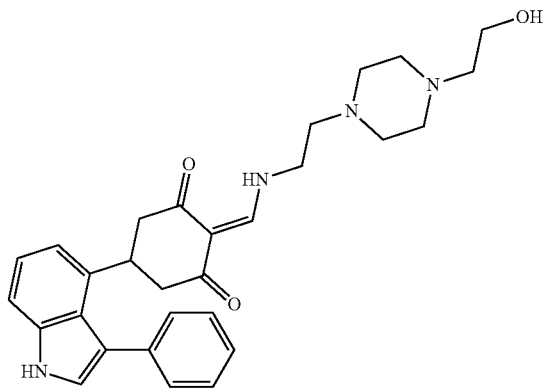 [SMILES: O=C1CC(c2cccc3[nH]cc(-c4ccccc4)c23)CC(=O)C1=CNCCN1CCN(CCO)CC1] |

-continued
| No. | Structures |
|---|---|
| 372 | 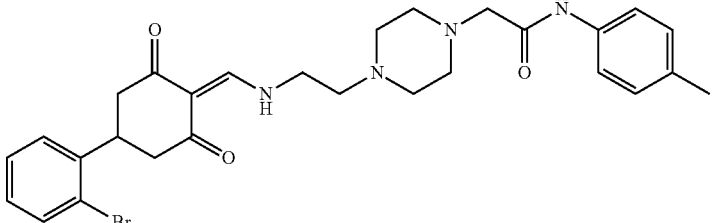 |
| 373 | 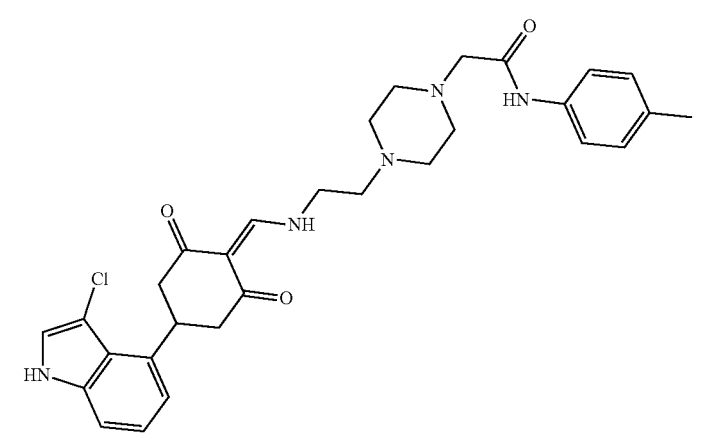 [SMILES: Cc1ccc(NC(=O)CN2CCN(CCNC=C3C(=O)CC(c4cccc5[nH]cc(Cl)c45)CC3=O)CC2)cc1] |
| 374 | 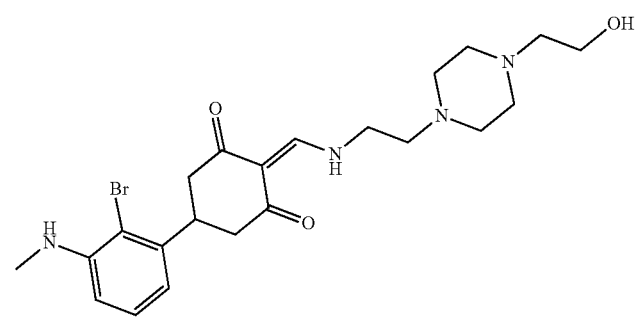 [SMILES: CNc1cccc(C2CC(=O)C(=CNCCN3CCN(CCO)CC3)C(=O)C2)c1Br] |
| 375 | 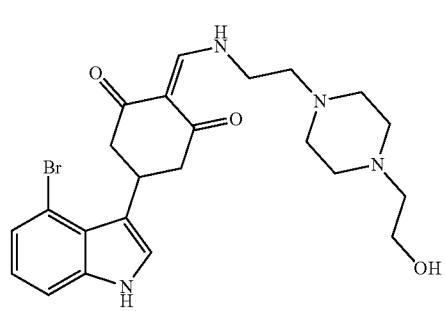 |
| 387 | 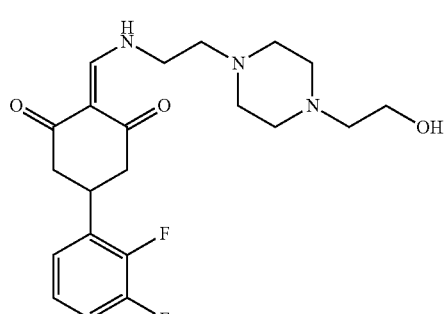 |

-continued
| No. | Structures |
|---|---|
| 392 | 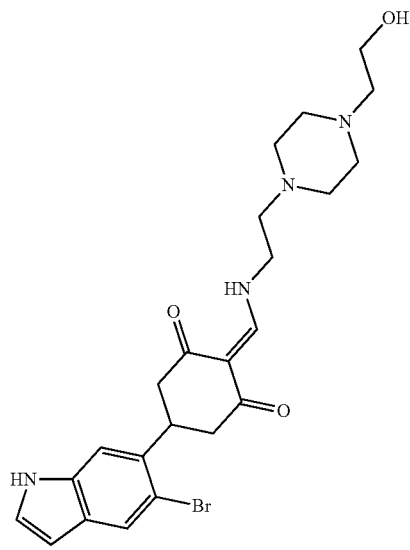 [SMILES: O=C1CC(c2cc3[nH]ccc3cc2Br)CC(=O)C1=CNCCN1CCN(CCO)CC1] |
| 393 | 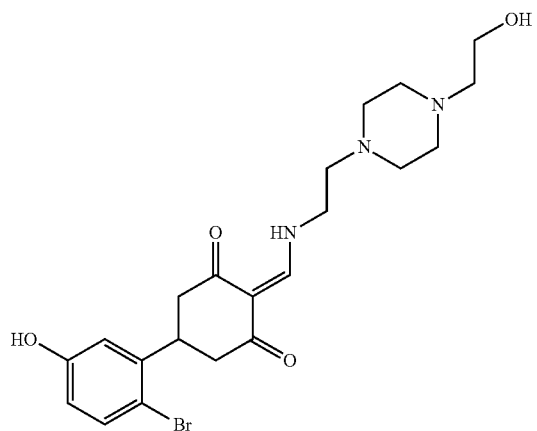 [SMILES: O=C1CC(c2cc(O)ccc2Br)CC(=O)C1=CNCCN1CCN(CCO)CC1] |
| 394 | 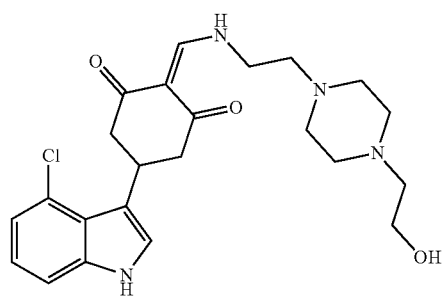 |

-continued

| No. | Structures |
|---|---|
| 396 | 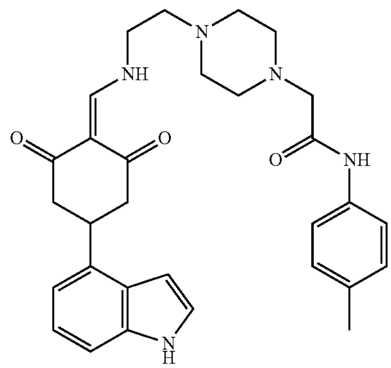 [SMILES: Cc1ccc(NC(=O)CN2CCN(CCNC=C3C(=O)CC(c4cccc5[nH]ccc45)CC3=O)CC2)cc1] |
| 400 | 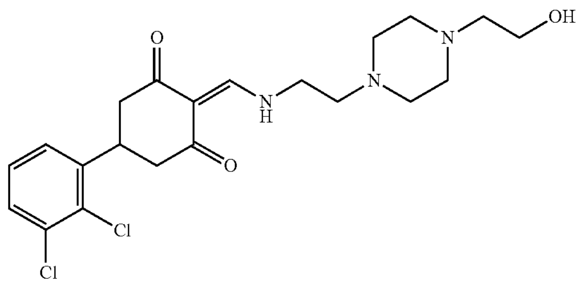 [SMILES: O=C1CC(c2cccc(Cl)c2Cl)CC(=O)C1=CNCCN1CCN(CCO)CC1] |
| 404 | 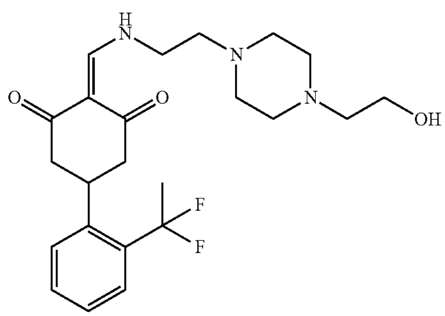 [SMILES: CC(F)(F)c1ccccc1C1CC(=O)C(=CNCCN2CCN(CCO)CC2)C(=O)C1] |
| 405 | and |

| No. | Structures |
|---|---|
| 406 | 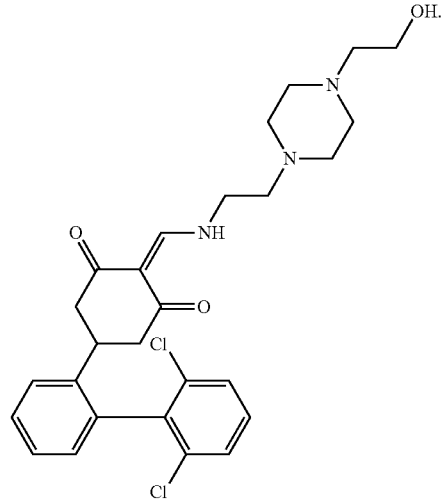 [SMILES: O=C1CC(c2ccccc2-c2c(Cl)cccc2Cl)CC(=O)C1=CNCCN1CCN(CCO)CC1] |
5. A pharmaceutical composition, comprising the compounds or pharmaceutically acceptable salts thereof according to claim 3.
6. A pharmaceutical composition, comprising the compounds or pharmaceutically acceptable salts thereof according to claim 4.
* * * * *

```
                        SEQUENCE LISTING

<160> NUMBER OF SEQ ID NOS: 2

<210> SEQ ID NO 1
<211> LENGTH: 356
<212> TYPE: PRT
<213> ORGANISM: Artificial Sequence
<220> FEATURE:
<223> OTHER INFORMATION: GST-LC3B

<400> SEQUENCE: 1

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125
```

```
Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
210                 215                 220

Phe Gln Gly Pro Leu Gly Ser Met Pro Ser Glu Lys Thr Phe Lys Gln
225                 230                 235                 240

Arg Arg Thr Phe Glu Gln Arg Val Glu Asp Val Arg Leu Ile Arg Glu
                245                 250                 255

Gln His Pro Thr Lys Ile Pro Val Ile Ile Glu Arg Tyr Lys Gly Glu
            260                 265                 270

Lys Gln Leu Pro Val Leu Asp Lys Thr Lys Phe Leu Val Pro Asp His
        275                 280                 285

Val Asn Met Ser Glu Leu Ile Lys Ile Ile Arg Arg Arg Leu Gln Leu
290                 295                 300

Asn Ala Asn Gln Ala Phe Phe Leu Leu Val Asn Gly His Ser Met Val
305                 310                 315                 320

Ser Val Ser Thr Pro Ile Ser Glu Val Tyr Glu Ser Glu Lys Asp Glu
                325                 330                 335

Asp Gly Phe Leu Tyr Met Val Tyr Ala Ser Gln Glu Thr Phe Gly Met
            340                 345                 350

Lys Leu Ser Val
        355

<210> SEQ ID NO 2
<211> LENGTH: 15
<212> TYPE: PRT
<213> ORGANISM: Artificial Sequence
<220> FEATURE:
<223> OTHER INFORMATION: N-terminal FITC-labeled peptide

<400> SEQUENCE: 2

Gly Gly Asp Asp Asp Trp Thr His Leu Ser Ser Lys Glu Val Asp
1               5                   10                  15
```